United States Patent
Horiguchi et al.

(10) Patent No.: US 11,261,378 B2
(45) Date of Patent: *Mar. 1, 2022

(54) POLYMERIZABLE COMPOUND AND OPTICALLY ANISOTROPIC OBJECT

(71) Applicant: DIC CORPORATION, Tokyo (JP)

(72) Inventors: Masahiro Horiguchi, Saitama (JP); Sayaka Nose, Saitama (JP); Akihiro Koiso, Saitama (JP)

(73) Assignee: DIC CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/539,666

(22) PCT Filed: Dec. 17, 2015

(86) PCT No.: PCT/JP2015/085342
§ 371 (c)(1),
(2) Date: Jun. 23, 2017

(87) PCT Pub. No.: WO2016/104317
PCT Pub. Date: Jun. 30, 2016

(65) Prior Publication Data
US 2017/0369783 A1    Dec. 28, 2017

(30) Foreign Application Priority Data

Dec. 25, 2014   (JP) .............................. JP2014-261949

(51) Int. Cl.
*C09K 19/54*    (2006.01)
*C07C 69/753*   (2006.01)
(Continued)

(52) U.S. Cl.
CPC .............. *C09K 19/54* (2013.01); *C07C 69/75* (2013.01); *C07C 69/753* (2013.01); *C07C 69/757* (2013.01); *C07C 69/76* (2013.01); *C07C 69/94* (2013.01); *C07C 245/08* (2013.01); *C07C 251/18* (2013.01); *C07C 251/24* (2013.01); *C07C 251/78* (2013.01); *C07C 251/86* (2013.01); *C07C 251/88* (2013.01); *C07C 323/21* (2013.01); *C07C 327/48* (2013.01); *C07D 207/452* (2013.01); *C07D 209/12* (2013.01); *C07D 209/40* (2013.01); *C07D 209/88* (2013.01); *C07D 213/74* (2013.01); *C07D 249/04* (2013.01); *C07D 249/06* (2013.01); *C07D 265/16* (2013.01); *C07D 277/64* (2013.01); *C07D 277/82* (2013.01); *C07D 303/48* (2013.01); *C07D 305/06* (2013.01); *C07D 307/66* (2013.01); *C07D 333/22* (2013.01); *C07D 333/36* (2013.01); *C07D 333/76* (2013.01); *C07D 339/06* (2013.01); *C07D 339/08* (2013.01); *C07D 403/04* (2013.01); *C07D 403/12* (2013.01); *C07D 407/12* (2013.01); *C07D 409/06* (2013.01); *C07D 409/12* (2013.01); *C07D 409/14* (2013.01); *C07D 413/12* (2013.01); *C07D 417/04* (2013.01); *C07D 417/06* (2013.01); *C07D 417/12* (2013.01); *C07D 495/04* (2013.01); *C07D 513/04* (2013.01); *C08F 20/10* (2013.01); *C09K 19/32* (2013.01); *C09K 19/322* (2013.01); *C09K 19/3405* (2013.01); *C09K 19/348* (2013.01); *C09K 19/3477* (2013.01); *C09K 19/3491* (2013.01); *C09K 19/3494* (2013.01); *C09K 19/3497* (2013.01); *C09K 19/38* (2013.01);
(Continued)

(58) Field of Classification Search
CPC ....................................................... C09K 19/54
See application file for complete search history.

(56) References Cited

U.S. PATENT DOCUMENTS 5,445,854 A   8/1995  Newsham et al.
6,465,060 B1  10/2002 Wingen et al.
(Continued)

FOREIGN PATENT DOCUMENTS

CN    103664868 A    3/2014
CN    103772335 A    5/2014
(Continued)

OTHER PUBLICATIONS

Calvin, J. et al. "Rhodium-Catalyzed adn Zinc(II)-Triflate-Promoted Asymmetric Hydrogenation of Tetrasubstituted α,β—Unsaturated Ketones." Organic Letters 2012. vol. 14, No. 4, pp. 1038-1041.
Szelinski, H. et al. "Porphyrins Linked to High Acceptor Strength Cyano Quinones as Models for the Photosynthetic Reaction Center." Tetrahedron, 1996, vol. 52, No. 25, pp. 8497-8516.
(Continued)

*Primary Examiner* — Chanceity N Robinson
(74) *Attorney, Agent, or Firm* — McDermott Will & Emery LLP

(57) ABSTRACT

The present invention aims to provide a polymerizable compound that has high storage stability without causing crystal precipitation when added to a polymerizable composition and to provide a polymerizable composition containing the polymerizable compound. A polymer film produced by polymerization of the polymerizable composition has a low haze, high thickness uniformity, low occurrence of nonuniform orientation, high surface hardness, high adhesiveness, and good appearances and fewer orientation defects even after ultraviolet irradiation. The present invention also aims to provide a polymer produced by polymerization of the polymerizable composition and an optically anisotropic body produced from the polymer.

7 Claims, No Drawings

(51) Int. Cl.

| | |
|---|---|
| *C07C 69/76* | (2006.01) |
| *C07D 333/22* | (2006.01) |
| *C07D 339/06* | (2006.01) |
| *C07D 339/08* | (2006.01) |
| *C07D 407/12* | (2006.01) |
| *C07D 409/12* | (2006.01) |
| *C07C 323/21* | (2006.01) |
| *C07D 413/12* | (2006.01) |
| *C07D 417/04* | (2006.01) |
| *C07D 417/06* | (2006.01) |
| *C07D 249/06* | (2006.01) |
| *C07C 327/48* | (2006.01) |
| *C07C 251/24* | (2006.01) |
| *C07D 207/452* | (2006.01) |
| *C07C 251/86* | (2006.01) |
| *C07C 251/88* | (2006.01) |
| *C07D 209/12* | (2006.01) |
| *C07D 277/82* | (2006.01) |
| *C07D 513/04* | (2006.01) |
| *C08F 20/10* | (2006.01) |
| *G02B 5/30* | (2006.01) |
| *C07C 69/94* | (2006.01) |
| *C07C 69/75* | (2006.01) |
| *C09K 19/34* | (2006.01) |
| *C07D 409/14* | (2006.01) |
| *C07D 305/06* | (2006.01) |
| *C07C 251/78* | (2006.01) |
| *C07D 403/04* | (2006.01) |
| *C07D 209/40* | (2006.01) |
| *C07D 303/48* | (2006.01) |
| *C09K 19/32* | (2006.01) |
| *C07D 495/04* | (2006.01) |
| *C07C 69/757* | (2006.01) |
| *C07C 245/08* | (2006.01) |
| *C07D 333/36* | (2006.01) |
| *C07D 307/66* | (2006.01) |
| *C07D 403/12* | (2006.01) |
| *C07D 417/12* | (2006.01) |
| *C07D 265/16* | (2006.01) |
| *C07D 249/04* | (2006.01) |
| *C07D 213/74* | (2006.01) |
| *C07C 251/18* | (2006.01) |
| *C07D 409/06* | (2006.01) |
| *C07D 333/76* | (2006.01) |
| *C07D 277/64* | (2006.01) |
| *C07D 209/88* | (2006.01) |
| *C09K 19/38* | (2006.01) |
| *G02F 1/13363* | (2006.01) |
| *C09K 19/04* | (2006.01) |
| *C08F 220/30* | (2006.01) |

(52) U.S. Cl.
CPC ............. *G02B 5/30* (2013.01); *G02F 1/13363* (2013.01); *C07C 2601/14* (2017.05); *C07C 2603/18* (2017.05); *C08F 220/303* (2020.02); *C09K 2019/0448* (2013.01); *G02B 5/3083* (2013.01)

(56) References Cited

U.S. PATENT DOCUMENTS

| | | | |
|---|---|---|---|
| 10,647,662 B2 | 5/2020 | Kadomoto et al. | |
| 2007/0176145 A1* | 8/2007 | Nishikawa | C09K 19/18 |
| | | | 252/299.01 |
| 2009/0189120 A1 | 7/2009 | Takeuchi | |
| 2009/0268143 A1 | 10/2009 | Takeuchi et al. | |
| 2011/0237768 A1 | 9/2011 | Katoh et al. | |
| 2012/0224245 A1 | 9/2012 | Adlem et al. | |
| 2014/0107247 A1 | 4/2014 | Sakamoto et al. | |
| 2014/0142266 A1* | 5/2014 | Sakamoto | C07D 215/38 |
| | | | 526/257 |
| 2014/0200320 A1 | 7/2014 | Sakamoto et al. | |
| 2014/0309396 A1 | 10/2014 | Sakamoto et al. | |
| 2015/0115199 A1* | 4/2015 | Choi | G02F 1/133784 |
| | | | 252/299.61 |
| 2015/0175564 A1* | 6/2015 | Sakamoto | C07D 277/84 |
| | | | 526/257 |
| 2015/0183902 A1 | 7/2015 | Sakamoto et al. | |
| 2015/0274647 A1* | 10/2015 | Sakamoto | C08F 222/1006 |
| | | | 526/263 |
| 2015/0274872 A1 | 10/2015 | Sakamoto et al. | |
| 2015/0277006 A1* | 10/2015 | Takasago | G02B 1/12 |
| | | | 349/194 |
| 2015/0277007 A1 | 10/2015 | Matsuyama et al. | |
| 2015/0277010 A1 | 10/2015 | Aimatsu et al. | |
| 2015/0285979 A1 | 10/2015 | Aimatsu | |
| 2016/0002374 A1 | 1/2016 | Sakamoto et al. | |
| 2016/0200841 A1 | 7/2016 | Sakamoto | |
| 2016/0257659 A1 | 9/2016 | Sakamoto et al. | |
| 2016/0280672 A1 | 9/2016 | Sakamoto et al. | |
| 2017/0008833 A1 | 1/2017 | Sakamoto et al. | |
| 2017/0260150 A1 | 9/2017 | Nose et al. | |
| 2017/0369783 A1 | 12/2017 | Horiguchi et al. | |
| 2018/0002276 A1 | 1/2018 | Kadomoto et al. | |
| 2018/0002459 A1 | 1/2018 | Endo et al. | |
| 2018/0002460 A1 | 1/2018 | Endo et al. | |
| 2018/0016502 A1 | 1/2018 | Endo et al. | |
| 2018/0031738 A1 | 2/2018 | Ishii et al. | |
| 2018/0037817 A1 | 2/2018 | Kuwana et al. | |
| 2018/0066189 A1 | 3/2018 | Ishii et al. | |
| 2018/0112022 A1 | 4/2018 | Ishii et al. | |
| 2018/0319755 A1 | 11/2018 | Teng et al. | |

FOREIGN PATENT DOCUMENTS

| | | |
|---|---|---|
| JP | 2001-206884 A | 7/2001 |
| JP | 2005-289980 A | 10/2005 |
| JP | 2007-328053 A | 12/2007 |
| JP | 2009-029795 A | 2/2009 |
| JP | 2009-062508 A | 3/2009 |
| JP | 2009-173893 A | 8/2009 |
| JP | 2009-179563 A | 8/2009 |
| JP | 2009-265317 A | 11/2009 |
| JP | 2010-031223 A | 2/2010 |
| JP | 2010-100541 A | 5/2010 |
| JP | 2010-163482 A | 7/2010 |
| JP | 2011-006361 A | 1/2011 |
| JP | 2011-162678 A | 8/2011 |
| JP | 2011-207765 A | 10/2011 |
| JP | 2011-207941 A | 10/2011 |
| JP | 2011207765 A * | 10/2011 |
| JP | 2011-246381 A | 12/2011 |
| JP | 2012-077055 A | 4/2012 |
| JP | 2012-136641 A | 7/2012 |
| JP | 2013-509458 A | 3/2013 |
| JP | 2015-200877 A | 11/2015 |
| JP | 2016-113583 A | 6/2016 |
| JP | 6066252 B2 | 1/2017 |
| JP | 6172556 B2 | 8/2017 |
| JP | 6172557 B2 | 8/2017 |
| JP | 6213797 B2 | 10/2017 |
| WO | 2005/112540 A2 | 12/2005 |
| WO | 2012/141245 A1 | 10/2012 |
| WO | 2012/147904 A1 | 11/2012 |
| WO | 2012/176679 A1 | 12/2012 |
| WO | 2013/157888 A1 | 10/2013 |
| WO | 2013/180217 A1 | 12/2013 |
| WO | 2014/010325 A1 | 1/2014 |
| WO | 2014/061709 A1 | 4/2014 |
| WO | 2014/065176 A1 | 5/2014 |
| WO | 2014/065243 A1 | 5/2014 |
| WO | 2014069515 A1 | 5/2014 |
| WO | 2014/126113 A1 | 8/2014 |
| WO | 2014/132978 A1 | 9/2014 |

(56) References Cited

FOREIGN PATENT DOCUMENTS

| WO | WO-2014132978 A1 * | 9/2014 | ........... G02B 5/3083 |
|---|---|---|---|
| WO | 2015/025793 A1 | 2/2015 | |
| WO | 2015/064698 A1 | 5/2015 | |
| WO | 2015/122384 A1 | 8/2015 | |
| WO | 2015/122385 A1 | 8/2015 | |
| WO | 2016/56542 A1 | 4/2016 | |
| WO | 2016/056542 A1 | 4/2016 | |
| WO | 2016/088749 A1 | 6/2016 | |
| WO | 2016/104317 A1 | 6/2016 | |
| WO | 2016/114252 A1 | 7/2016 | |
| WO | 2016/114253 A1 | 7/2016 | |
| WO | 2016/114254 A1 | 7/2016 | |
| WO | 2016/114255 A1 | 7/2016 | |
| WO | 2016/114348 A1 | 7/2016 | |
| WO | 2017/038265 A1 | 3/2017 | |
| WO | 2017/038266 A1 | 3/2017 | |
| WO | 2017/038267 A1 | 3/2017 | |
| WO | 2017/068860 A1 | 4/2017 | |
| WO | 2017057020 A1 | 4/2017 | |

OTHER PUBLICATIONS

Kallitsis, J. et al., "Soluble Polymers with Laterally Attached Oligophenyl Units for Potential Use as Blue Luminescent Materials." Macromolecules, 1997, vol. 30. No. 10, pp. 2989-2996.

Benbow, J. et al. "An Approach to Dibenzofuran Heterocycles. 1. Electron-Transfer Processes en Route to Dibenzofuran-1, 4-diones." J. Org. Chem., 1997, vol. 62, No. 26, pp. 9345-9347.

Yu, S. et al. "Self-Assembled Electroluminescent Polymers Derived from Terpyridine-Based Moieties." Advanced Materials, 2003, vol. 15, No. 19, pp. 1643-1647.

Benbow, J. et al. "Biaryl Formation Using the Suzuki Protocol: Considerations of Base, Halide, and Protecting Group." Tetrahedron Letters, 1996, vol. 37, No. 49, pp. 8829-8832.

Macdonald, D. et al. "Substituted 2,2-bisaryl-bicycloheptanes as novel and potent inhibitors of 5-lipxygenase activating protein." Bioorganic and Medicinal Chemistry Letters, 2008, vol. 18, pp. 2023-2027.

International Search Report and Written Opinion issued in International Patent Application No. PCT/JP2015/085342, dated Feb. 16, 2016; with partial English translation.

International Search Report issued in corresponding International Application No. PCT/JP2016/050322, dated Apr. 12, 2016, with English translation.

Scifinder CAS search Apr. 14, 2019 pp. 1-5.

International Search Report dated Jan. 26, 2016, issued in counterpart International Application No. PCT/JP2015/083728.

Notification of Reasons for Refusal dated Jan. 31, 2017, issued in counterpart Japanese Patent Application No. 2016-562632, w/English translation.

Office Action dated Jan. 17, 2019, issued in counterpart to Japanese Application No. 2018-052601, with English translation (13 pages).

International Search Report dated Aug. 12, 2016, issued in counterpart International Application No. PCT/CN2015/094100 (3 pages).

Office Action dated Nov. 15, 2016, issued in counterpart Japanese Application No. 2015-240161, with Engiish translation (35 pages).

* cited by examiner

POLYMERIZABLE COMPOUND AND OPTICALLY ANISOTROPIC OBJECT

RELATED APPLICATIONS

This application is the U.S. National Phase under 35 U.S.C. § 371 of International Patent Application No. PCT/JP2015/085342, filed on Dec. 17, 2015, which in turn claims the benefit of Japanese Application No. 2014-261949, filed on Dec. 25, 2014, the disclosures of which Applications are incorporated by reference herein.

TECHNICAL FIELD

The present invention relates to a compound having a polymerizable group, a polymerizable composition containing the compound, a polymerizable liquid crystal composition containing the compound, and an optically anisotropic body produced from the polymerizable liquid crystal composition.

BACKGROUND ART

Compounds having a polymerizable group (polymerizable compounds) are used for various optical materials. For example, a polymerizable composition containing a polymerizable compound can be arranged in a liquid crystal state and polymerized to produce a polymer with uniform orientation. Such a polymer can be used for a polarizing plate or a retardation plate necessary for displays. In many instances, a polymerizable composition containing two or more polymerizable compounds is used to satisfy required optical characteristics, rate of polymerization, solubility, melting point, glass transition temperature, transparency of polymer, mechanical strength, surface hardness, heat resistance, and light resistance. Such polymerizable compounds should impart good physical properties to the polymerizable composition without adversely affecting other characteristics.

In order to improve the viewing angle of a liquid crystal display, it is necessary to reduce or reverse the wavelength dispersion characteristics of the birefringence index of a retardation film. A polymerizable compound used for this purpose preferably has high storage stability with less crystal precipitation when added to a polymerizable composition. Furthermore, a polymer film produced by polymerization of a polymerizable composition containing a polymerizable compound preferably has a low haze, high thickness uniformity, low occurrence of nonuniform orientation, high surface hardness, and high adhesiveness. A retardation film for use in onboard equipment or mobile devices requires high durability under ultraviolet light. Thus, preferably, a polymer film irradiated with ultraviolet light is rarely discolored and separated from a substrate and has fewer orientation defects.

CITATION LIST

Patent Literature

PTL 1: Japanese Unexamined Patent Application Publication No. 2007-328053

SUMMARY OF INVENTION

Technical Problem

The present invention aims to provide a polymerizable compound that has high storage stability without causing crystal precipitation when added to a polymerizable composition and to provide a polymerizable composition containing the polymerizable compound. A polymer film produced by polymerization of the polymerizable composition has a low haze, high thickness uniformity, low occurrence of nonuniform orientation, high surface hardness, high adhesiveness, and good appearances and fewer orientation defects even after ultraviolet irradiation. The present invention also aims to provide a polymer produced by polymerization of the polymerizable composition and an optically anisotropic body produced from the polymer.

Solution to Problem

The present inventors have extensively studied to achieve these objects and have developed a compound represented by the following general formula (I). More specifically, the present invention provides a compound represented by the general formula (I) and also provides a polymerizable composition containing the compound, a resin, resin additive agent, oil, filter, bonding agent, adhesive, fat or oil, ink, pharmaceutical agent, cosmetic, detergent, building material, packaging material, liquid crystal material, organic EL material, organic semiconductor material, electronic material, display device, electronic device, communication device, automotive component, aircraft component, mechanical component, agrochemical, and food produced from the compound, as well as a product produced therefrom, a polymerizable liquid crystal composition, a polymer produced by polymerization of the polymerizable liquid crystal composition, and an optically anisotropic body produced from the polymer.

[Chem. 1]

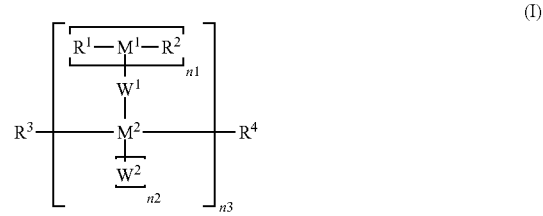

(I)

(wherein $R^1$, $R^2$, $R^3$, and $R^4$ independently denote a hydrogen atom or a hydrocarbon group having 1 to 80 carbon atoms, the group may have a substituent, and any of the carbon atoms may be substituted by a heteroatom, $W^1$ and $W^2$ independently denote a single bond or a group containing a conjugated system having 2 to 100 π electrons, $M^1$ and $M^2$ independently denote a group containing a mesogenic group, n1 and n2 are independently 0 or 1, provided that when both n1 and n2 are 0 the corresponding groups denote a hydrogen atom, n3 is an integer in the range of 1 to 1000, $W^1$, $W^2$, $M^1$, and $M^2$ may independently have a substituent L, L denotes a fluorine atom, a chlorine atom, a bromine atom, an iodine atom, a pentafluorosulfuranyl group, a nitro group, a cyano group, an isocyano group, an amino group, a hydroxy group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms with one —$CH_2$— or nonadjacent two or more —$CH_2$—'s optionally independently substituted by —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, any hydrogen atom of the alkyl group may be substituted by a fluorine atom, or L may denote a group represented by $P^L$-$(S^L$-$X^L)_{kL}$-, $P^L$ denotes a polymerizable group, $S^L$ denotes a spacer group or a single bond, a plurality of $S^L$'s, if present at all, may be the same or different, $X^L$ denotes —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond, a plurality of $X^L$'s, if present at all, may be the same or different, (provided that the $P^L$-$(S^L$-$X^L)_{kL}$- has no —O—O— bond), a plurality of L's, if present at all, in the compound may be the same or different, and kL is an integer in the range of 0 to 10, and $M^1$-$W^1$, $W^1$-$M^2$, and/or $M^2$-$W^2$ may independently form a conjugated system)

Advantageous Effects of Invention

A compound according to the present invention has high storage stability when constituting a polymerizable composition and is useful as a constituent of a polymerizable composition. An optically anisotropic body produced from a polymerizable liquid crystal composition containing a compound according to the present invention has less nonuniformity and is useful as an optical material, such as a retardation film.

DESCRIPTION OF EMBODIMENTS

The present invention provides a reverse dispersion compound represented by the general formula (I) and also provides a polymerizable composition containing the compound, a resin, resin additive agent, oil, filter, bonding agent, adhesive, fat or oil, ink, pharmaceutical agent, cosmetic, detergent, building material, packaging material, liquid crystal material, organic EL material, organic semiconductor material, electronic material, display device, electronic device, communication device, automotive component, aircraft component, mechanical component, agrochemical, and food produced from the compound, as well as a product produced therefrom, a polymerizable liquid crystal composition, a polymer produced by polymerization of the polymerizable liquid crystal composition, and an optically anisotropic body produced from the polymer.

In a graph with the horizontal axis representing the wavelength λ of light incident on a retardation film and the vertical axis representing the birefringence index Δn, if the birefringence index Δn decreases with decreasing wavelength λ, the film is generally referred to as "reverse wavelength dispersion" or "reverse dispersion" by a person skilled in the art. In the present invention, a compound constituting a reverse dispersion retardation film is referred to as a reverse dispersion compound.

<<$R^1$, $R^2$, $R^3$, $R^4$>>

In the general formula (I), $R^1$, $R^2$, $R^3$, and $R^4$ independently denote a hydrogen atom or a hydrocarbon group having 1 to 80 carbon atoms, the group may have a substituent, and any of the carbon atoms may be substituted by a heteroatom. $R^1$, $R^2$, $R^3$, and $R^4$ independently denote a hydrogen atom or a hydrocarbon group having 1 to 20 carbon atoms, the group may have a substituent, and any of the carbon atoms may be substituted by a heteroatom. More specifically, preferably, $R^1$, $R^2$, $R^3$, and $R^4$ independently denote a hydrogen atom, a fluorine atom, a chlorine atom, a bromine atom, an iodine atom, a pentafluorosulfuranyl group, a cyano group, a nitro group, an isocyano group, a thioisocyano group, or a linear or branched alkyl group having 1 to 20 carbon atoms with one —CH$_2$— or nonadjacent two or more —CH$_2$—'s optionally independently substituted by —O—, —S—, —CO—, —COO—, —OCO—, —CO—S—, —S—CO—, —O—CO—O—, —CO—NH—, —NH—CO—, —C=C—, or —C≡C— (any hydrogen atom of the alkyl group may be substituted by a fluorine atom), or a group having a polymerizable group.

In $R^1$, $R^2$, $R^3$, and $R^4$ of the general formula (I), at least one of present $R^1$, present $R^2$, $R^3$, and $R^4$ preferably denotes a group having a polymerizable group.

The group having a polymerizable group is preferably a group represented by the general formula (I-R).

[Chem. 2]

$$P^1\text{-}(S^1\text{-}X^1)_k \quad \text{(I-R)}$$

(wherein $P^1$ denotes a polymerizable group, $S^1$ denotes a spacer group or a single bond, a plurality of $S^1$'s, if present at all, may be the same or different, $X^1$ denotes —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond, a plurality of $X^1$'s, if present at all, may be the same or different (provided that $P^1$-$(S^1$-$X^1)_k$- has no —O—O— bond), and k is an integer in the range of 0 to 10)

$P^1$ in the general formula (I-R) denotes a polymerizable group, preferably a group selected from the following formulae (P-1) to (P-20), and these polymerizable groups are polymerized by radical polymerization, radical addition polymerization, cationic polymerization, and anionic polymerization.

[Chem. 3]

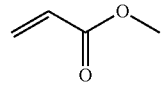

(P-1)

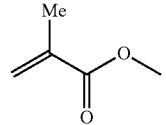

(P-2)

-continued

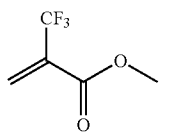 (P-3)

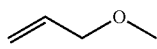 (P-4)

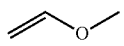 (P-5)

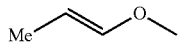 (P-6)

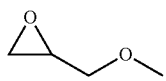 (P-7)

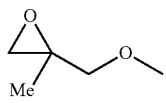 (P-8)

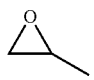 (P-9)

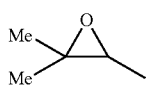 (P-10)

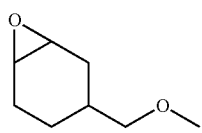 (P-11)

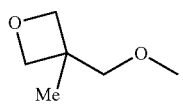 (P-12)

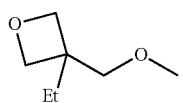 (P-13)

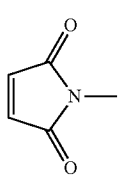 (P-14)

 (P-15)

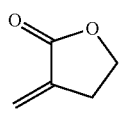 (P-16)

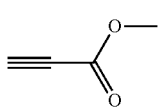 (P-17)

-continued

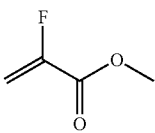 (P-18)

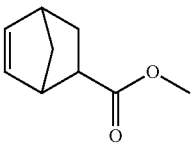 (P-19)

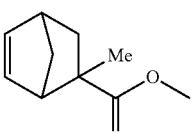 (P-20)

In particular, when ultraviolet polymerization is performed as a polymerization method, the formula (P-1), (P-2), (P-3), (P-4), (P-5), (P-7), (P-11), (P-13), (P-15), or (P-18) is preferred, the formula (P-1), (P-2), (P-7), (P-11), or (P-13) is more preferred, the formula (P-1), (P-2), or (P-3) is still more preferred, and the formula (P-1) or (P-2) is particularly preferred.

$S^1$ in the general formula (I-R) denotes a spacer group or a single bond, and a plurality of $S^1$'s, if present at all, may be the same or different. The spacer group is preferably an alkylene group having 1 to 20 carbon atoms with one —CH$_2$— or nonadjacent two or more —CH$_2$—'s optionally independently substituted by —O—, —COO—, —OCO—, —OCO—O—, —CO—NH—, —NH—CO—, —CH=CH—, or —C≡C—. From the perspective of the availability of raw materials and the ease of synthesis, more preferably, a plurality of $S^1$'s, if present at all, may be the same or different and independently denote an alkylene group having 1 to 10 carbon atoms with one —CH$_2$— or nonadjacent two or more —CH$_2$—'s optionally independently substituted by —O—, —COO—, or —OCO—, or a single bond, still more preferably independently denote an alkylene group having 1 to 10 carbon atoms or a single bond, and, particularly preferably, a plurality of $S^1$'s, if present at all, may be the same or different and independently denote an alkylene group having 1 to 8 carbon atoms.

$X^1$ in the general formula (I-R) denotes —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond, and a plurality of $X^1$'s, if present at all, may be the same or different (provided that P$^1$-(S$^1$-X$^1$)$_k$- has no —O—O— bond). From the perspective of the availability of raw materials and the ease of synthesis, preferably, a plurality of $X^1$'s, if present at all, may be the same or different and independently denote —O—, —S—, —OCH$_2$—, —CH$_2$O—, —COO—, —OCO—, —CO—S—, —S—CO—, —O—CO—O—, —CO—NH—, —NH—CO—, —COO—CH$_2$CH$_2$—, —OCO—CH$_2$CH$_2$—, —CH$_2$CH$_2$—COO—, —CH$_2$CH$_2$—OCO—, or a single bond, more preferably, X$^1$'s independently denote —O—, —OCH$_2$—, —CH$_2$O—, —COO—, —OCO—, —COO—CH$_2$CH$_2$—, —OCO—CH$_2$CH$_2$—, —CH$_2$CH$_2$—COO—, —CH$_2$CH$_2$—, or a single bond, and, particularly preferably, a plurality of X$^1$'s, if present at all, may be the same or different and independently denote —O—, —COO—, —OCO—, or a single bond.

k in the general formula (I-R) is an integer in the range of 0 to 10, preferably an integer in the range of 0 to 5, more preferably an integer in the range of 0 to 2, particularly preferably 1.

If R$^1$, R$^2$, R$^3$, and R$^4$ of the general formula (I) denote a group other than the groups having a polymerizable group, R$^1$, R$^2$, R$^3$, and R$^4$ preferably denote a group selected from R$^5$ (wherein R$^5$ denotes a hydrogen atom, a fluorine atom, a chlorine atom, a bromine atom, an iodine atom, a pentafluorosulfuranyl group, a nitro group, a cyano group, an isocyano group, an amino group, a hydroxy group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms with one —CH$_2$— or nonadjacent two or more —CH$_2$—'s optionally independently substituted by —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and any hydrogen atom of the alkyl group may be substituted by a fluorine atom).

From the perspective of liquid crystallinity, inverse dispersibility, the ease of synthesis, and storage stability, the group represented by R$^5$ more preferably denotes a hydrogen atom, a fluorine atom, a chlorine atom, a cyano group, or a linear or branched alkyl group having 1 to 20 carbon atoms with one —CH$_2$— or nonadjacent two or more —CH$_2$—'s optionally independently substituted by —O—, —COO—, —OCO—, —O—CO—O—, —CO—NH—, or —NH—CO— and with any hydrogen atom optionally substituted by a fluorine atom, still more preferably a hydrogen atom, a fluorine atom, a chlorine atom, or a linear alkyl group having 1 to 10 carbon atoms with one —CH$_2$— or nonadjacent two or more —CH$_2$—'s optionally independently substituted by —O—, —COO—, —OCO—, or —O—CO—O— and with any hydrogen atom optionally substituted by a fluorine atom, still more preferably a linear alkyl group having 1 to 10 carbon atoms with one —CH$_2$— or nonadjacent two or more —CH$_2$—'s optionally independently substituted by —O—, particularly preferably a linear alkyl group having 1 to 5 carbon atoms.

<<Substituent L>>

A compound represented by the general formula (I) may be unsubstituted or substituted by a substituent L. The substituent L denotes a fluorine atom, a chlorine atom, a bromine atom, an iodine atom, a pentafluorosulfuranyl group, a nitro group, a cyano group, an isocyano group, an amino group, a hydroxy group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms with one —CH$_2$— or nonadjacent two or more —CH$_2$—'s optionally independently substituted by —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, any hydrogen atom of the alkyl group may be substituted by a fluorine atom, or L may denote a group represented by P$^L$—(S$^L$-X$^L$)$_{kL}$—, P$^L$ denotes a polymerizable group, S$^L$ denotes a spacer group or a single bond, a plurality of S$^L$'s, if present at all, may be the same or different, X$^L$ denotes —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond, a plurality of X$^L$'s, if present at all, may be the same or different, (provided that the P$^L$-(S$^L$-X$^L$)$_{kL}$— has no —O—O— bond), kL is an integer in the range of 0 to 10, kL is preferably 1, and a plurality of L's, if present at all, in the compound may be the same or different. From the perspective of the availability of raw materials and the ease of synthesis, preferably, a plurality of L's, if present at all, may be the same or different and denote a fluorine atom, a chlorine atom, a nitro group, a cyano group, or a linear or branched alkyl group having 1 to 20 carbon atoms with one —CH$_2$— or nonadjacent two or more —CH$_2$—'s optionally independently substituted by —O—, —COO—, or —OCO— and with any hydrogen atom optionally substituted by a fluorine atom. More preferably, a plurality of L's, if present at all, may be the same or different and denote a fluorine atom, a chlorine atom, a nitro group, a cyano group, or a linear alkyl group having 1 to 12 carbon atoms with one —CH$_2$— or nonadjacent two or more —CH$_2$—'s optionally independently substituted by —O—. Particularly preferably, a plurality of L's, if present at all, may be the same or different and denote a fluorine atom, a cyano group, a methyl group, or a methoxy group.

<<W$^1$, W$^2$>>

W$^1$ and W$^2$ in the general formula (I) independently denote a single bond or a group containing a conjugated system having 2 to 100 π electrons. From the perspective of the availability of raw materials and the ease of synthesis, W$^1$ and W$^2$ preferably denote a group having a single bond or a carbon group or hydrocarbon group having 2 to 80 π electrons with any carbon atom optionally substituted by a heteroatom and having a single bond or an aromatic and/or non-aromatic hydrocarbon ring having 5 to 80 carbon atoms optionally substituted by one or more substituents L's with any carbon atom optionally substituted by a heteroatom.

In the general formula (I), preferably, W$^1$ is represented by the following general formula (I-W1), and W$^2$ is represented by the following general formula (I-W2).

[Chem. 4]

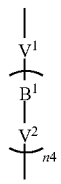

(I-W1)

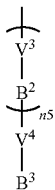
(I-W2)

In the formula, $V^1$, $V^2$, $V^3$, and $V^4$ independently denote a single bond or a divalent linking group, $B^1$, $B^2$, and $B^3$ independently denote a single bond or an optionally substituted aromatic and/or non-aromatic hydrocarbon ring having 5 to 80 carbon atoms, any carbon atom of the carbon ring or hydrocarbon ring may be substituted by a heteroatom, these groups may be unsubstituted or substituted by one or more substituents L's, these groups are bonded to a hydrogen atom or a group represented by the substituent L when $B^3$ denotes a single bond, and n4 and n5 are independently an integer in the range of 0 to 10.

In the formula, $V^1$, $V^2$, $V^3$, and $V^4$ independently denote the following formulae (V-1) to (V-15).

[Chem. 5]

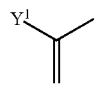 (V-1)

 (V-2)

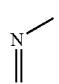 (V-3)

 (V-4)

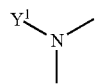 (V-5)

 (V-6)

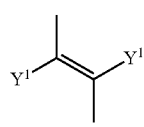 (V-7)

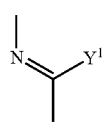 (V-8)

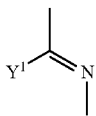 (V-9)

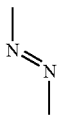 (V-10)

 (V-11)

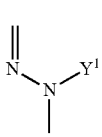 (V-12)

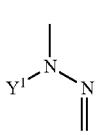 (V-13)

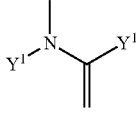 (V-14)

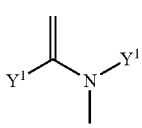 (V-15)

(In the formula $Y^1$ denotes a hydrogen atom, a fluorine atom, a chlorine atom, a bromine atom, an iodine atom, a pentafluorosulfuranyl group, a nitro group, a cyano group, an isocyano group, an amino group, a hydroxy group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms with one —$CH_2$— or nonadjacent two or more —$CH_2$—'s optionally independently substituted by —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, any hydrogen atom of the alkyl group may be substituted by a fluorine atom, a plurality of $Y^1$'s, if present at all, may be the same or different, or $Y^1$ may denote a group represented by $P^Y\text{-}(S^Y\text{-}X^Y)_j\text{-}$, $P^Y$ denotes a polymerizable group, preferably a group selected from the formulae (P-1) to (P-20), and these polymerizable groups are polymerized by radical polymerization, radical addition polymerization, cationic polymerization, and anionic polymerization. In particular, when ultraviolet polymerization is performed as a polymerization method, the formula (P-1), (P-2), (P-3), (P-4), (P-5), (P-7), (P-11), (P-13), (P-15), or (P-18) is preferred, the formula (P-1), (P-2), (P-7), (P-11), or (P-13) is more preferred, the formula (P-1), (P-2), or (P-3) is still more preferred, and the formula (P-1) or (P-2) is particularly preferred, and $S^Y$ denotes a spacer group or a single bond, and a plurality of $S^Y$'s, if present at all, may be the same or different. From the perspective of liquid crystallinity, the availability of raw materials, and the ease of synthesis, preferably, a plurality of $S^Y$'s, if present at all, may be the same or different and independently denote an alkylene group having 1 to 20 carbon atoms with one —CH$_2$— or nonadjacent two or more —CH$_2$—'s optionally independently substituted by —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH═CH—COO—, —CH═CH—OCO—, —COO—CH═CH—, —OCO—CH═CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH═CH—, —N═N—, —CH═N—N═CH—, —CF═CF—, or —C≡C—. More preferably, a plurality of S's, if present at all, may be the same or different and independently denote a linear alkylene group having 1 to 20 carbon atoms with one —CH$_2$— or nonadjacent two or more —CH$_2$—'s optionally independently substituted by —O—, —COO—, —OCO—, or —OCO—O—. Still more preferably, a plurality of $S^Y$'s, if present at all, may be the same or different and independently denote a linear alkylene group having 1 to 12 carbon atoms with one —CH$_2$— or nonadjacent two or more —CH$_2$—'s optionally independently substituted by —O—. From the perspective of liquid crystallinity and solubility in solvent, particularly preferably, $S^Y$ denotes a linear alkylene group having 1 to 12 carbon atoms with one —CH$_2$— or nonadjacent two or more —CH$_2$—'s optionally independently substituted by —O—. $X^Y$ denotes —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH═CH—COO—, —CH═CH—OCO—, —COO—CH═CH—, —OCO—CH═CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH═CH—, —N═N—, —CH═N—N═CH—, —CF═CF—, —C≡C—, or a single bond, a plurality of $X^Y$'s, if present at all, may be the same or different (provided that $P^Y$-$(S^Y$-$X^Y)_j$- has no —O—O— bond). From the perspective of the availability of raw materials and the ease of synthesis, preferably, a plurality of $X^Y$'s, if present at all, may be the same or different and independently denote —O—, —S—, —OCH$_2$—, —CH$_2$O—, —COO—, —OCO—, —CO—S—, —S—CO—, —O—CO—O—, —COO—CH$_2$CH$_2$—, —OCO—CH$_2$CH$_2$—, —CH$_2$CH$_2$—COO—, —CH$_2$CH$_2$—OCO—, or a single bond, more preferably $X^Y$'s independently denote —O—, —COO—, —OCO—, or a single bond, particularly preferably $X^Y$'s independently denote a single bond. j is an integer in the range of 0 to 10 and, from the perspective of liquid crystallinity and the availability of raw materials, is preferably an integer in the range of 1 to 3. From the perspective of the cure shrinkage of a film, j is particularly preferably 1.

In the formulae (V-1) to (V-15), if a group represented by $P^Y$-$(S^Y$-$X^Y)_j$- is bonded to a N atom, a group directly bonded to the N atom is preferably —CH$_2$—, from the perspective of the ease of synthesis.

In the formulae (V-1) to (V-15), a group represented by $P^Y$-$(S^Y$-$X^Y)_j$- preferably denotes a group selected from the following formulae (PY-1), (PY-2), and (PY-3), from the perspective of phase difference, temporal stability of inverse wavelength dispersibility, and detachment due to prolonged ultraviolet irradiation.

[Chem. 6]

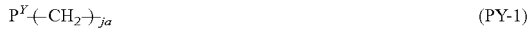  (PY-1)

  (PY-2)

  (PY-3)

(wherein ja is an integer in the range of 2 to 20, and jb is an integer in the range of 1 to 6)

In the formula (PY-1), from the perspective of liquid crystallinity, ja is more preferably an integer in the range of 2 to 12, particularly preferably an integer in the range of 2 to 8. In the formulae (PY-2) and (PY-3), from the perspective of liquid crystallinity, jb is more preferably an integer in the range of 1 to 3, particularly preferably 1 or 2.

In the formulae (V-1) to (V-15), preferably, if $Y^1$ denotes a group other than the groups represented by $P^Y$-$(S^Y$-$X^Y)_j$-, $Y^1$ denotes a linear or branched alkyl group having 1 to 20 carbon atoms with one —CH$_2$— or nonadjacent two or more —CH$_2$—'s optionally independently substituted by —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF—, or —C≡C—, any hydrogen atom of the alkyl group may be substituted by a fluorine atom, and a plurality of $Y^1$'s, if present at all, may be the same or different. In this case, from the perspective of liquid crystallinity, the availability of raw materials, and the ease of synthesis, more preferably, a plurality of $Y^1$'s, if present at all, may be the same or different and denote a linear or branched alkyl group having 1 to 20 carbon atoms with any hydrogen atom optionally substituted by a fluorine atom and with one —CH$_2$— or nonadjacent two or more —CH$_2$—'s optionally independently substituted by —O—, —CO—, —COO—, —OCO—, —O—CO—O—, —CH═CH—, —CF═CF—, or —C≡C—, still more preferably, a plurality of $Y^1$'s, if present at all, may be the same or different and denote a linear alkyl group having 1 to 20 carbon atoms with any hydrogen atom optionally substituted by a fluorine atom and with one —CH$_2$— or nonadjacent two or more —CH$_2$—'s optionally independently substituted by —O—, and particularly preferably, a plurality of $Y^1$'s, if present at all, may be the same or different and denote a linear alkyl group having 1 to 10 carbon atoms with one —CH$_2$— or nonadjacent two or more —CH$_2$—'s optionally independently substituted by —O—. From the perspective of solubility in various solvents and adhesiveness to various substrates (or alignment films), preferably, $Y^1$ denotes a group selected from the groups represented by $H_3C—(O—(CH_2)_{j1})_{j2}$— (wherein j1 is an integer in the range of 2 to 10, and j2 is an integer in the range of 1 to 10, preferably, j1 is an integer in the range of 2 to 6, and j2 is an integer in the range of 1 to 4, more preferably, j1 is 2 or 3, and j2 is an integer in the range of 1 to 3, particularly preferably, j1 is 2, and j2 is 2 or 3), a single bond, a double bond, —O—, —S—, —OCH$_2$—, —CH$_2$O—, —CO—, —CH$_2$—, —COO—, —OCO—, —CO—S—, —S—CO—, —O—CO—O—, —CO—NH—, —NH—CO—, —CS—NH—, —NH—CS—, —SCH$_2$—, —CH$_2$S—, —CF$_2$O—, —OCF$_2$—, —CF$_2$S—, —SCF$_2$—, —CH═CH—COO—, —CH═CH—OCO—, —COO—CH═CH—, —OCO—CH═CH—, —CH$_2$CH$_2$—, —COO—CH$_2$CH$_2$—, —OCO—

CH$_2$CH$_2$—, —CH$_2$CH$_2$—COO—, —CH$_2$CH$_2$—OCO—, —COO—CH$_2$—, —OCO—CH$_2$—, —CH$_2$—COO—, and —CH$_2$—OCO—. At least one of present M$^1$-V$^1$, V$^1$-B$^1$, B$^2$-V$^2$, V$^2$-M$^2$, M$^2$-V$^3$, V$^3$-B$^2$, B$^2$-V$^4$, and V$^4$-B$^3$ in the formulae (I-W1) and (I-W2) forms a conjugated system.

From the perspective of inverse dispersibility, the availability of raw materials, and the ease of synthesis, V, V$^2$, V$^3$, and V$^4$ more preferably independently denote a group selected from the groups represented by the formulae (V-1) to (V-15), a single bond, a double bond, —O—, —S—, —CH$_2$—, —COO—, —OCO—, —CO—S—, —S—CO—, —CO—NH—, —NH—CO—, —CS—NH—, —NH—CS—, —CH═CH—COO—, —CH═CH—OCO—, —COO—CH═CH—, —OCO—CH═CH—, —CH$_2$CH$_2$—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, and —CH$_2$—OCO—, still more preferably a group selected from the groups represented by the formulae (V-1) to (V-15), a single bond, a double bond, —S—, —CH$_2$—, —COO—, —OCO—, —CO—NH—, —NH—CO—, —CS—NH—, —NH—CS—, and —CH$_2$CH$_2$—, still more preferably a group selected from the groups represented by the formulae (V-1) to (V-15), a single bond, a double bond, —CH$_2$—, —COO—, —OCO—, and —CH$_2$CH$_2$—, particularly preferably a group selected from the groups represented by the formulae (V-1) to (V-15), a single bond, and a double bond. At least one of present M$^1$-V$^1$, V$^1$-B$^1$, B$^1$-V$^2$, V$^2$-M$^2$, M$^2$-V$^3$, V$^3$-B$^2$, B$^2$-V$^4$, and V$^4$-B$^3$ in the formulae (I-W1) and (I-W2) forms a conjugated system.

From the perspective of the availability of raw materials and the ease of synthesis, if Y$^1$ is bonded to a carbon atom, Y$^1$ preferably denotes a hydrogen atom, a fluorine atom, a chlorine atom, a nitro group, a cyano group, or a linear or branched alkyl group having 1 to 20 carbon atoms with one —CH$_2$— or nonadjacent two or more —CH$_2$—'s optionally independently substituted by —O—, —COO—, or —OCO— and with any hydrogen atom optionally substituted by a fluorine atom, more preferably a hydrogen atom, a fluorine atom, a chlorine atom, a nitro group, a cyano group, or a linear alkyl group having 1 to 12 carbon atoms, still more preferably a hydrogen atom, a fluorine atom, a cyano group, or a linear alkyl group having 1 to 8 carbon atoms, particularly preferably a hydrogen atom. If Y$^1$ is bonded to a nitrogen atom, Y$^1$ preferably denotes a hydrogen atom or a linear or branched alkyl group having 1 to 20 carbon atoms with one —CH$_2$— or nonadjacent two or more —CH$_2$—'s optionally independently substituted by —O—, —COO—, or —OCO— and with any hydrogen atom optionally substituted by a fluorine atom, more preferably a hydrogen atom or a linear or branched alkyl group having 1 to 20 carbon atoms, still more preferably a hydrogen atom or a linear alkyl group having 1 to 8 carbon atoms, particularly preferably a hydrogen atom.

In the formula, present B$^1$, present B$^2$, and B$^3$ preferably independently denote the following formulae (B-1) to (B-21) or a single bond.

[Chem. 7]

(B-1)

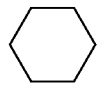
(B-2)

(B-3)

(B-4)

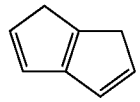
(B-5)

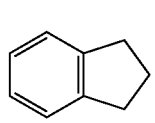
(B-6)

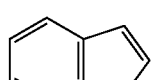
(B-7)

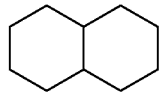
(B-8)

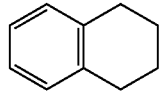
(B-9)

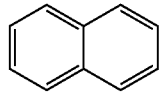
(B-10)

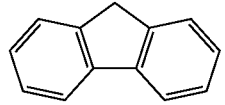
(B-11)

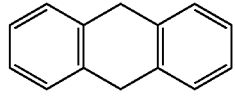
(B-12)

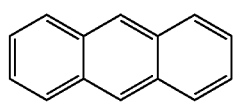
(B-13)

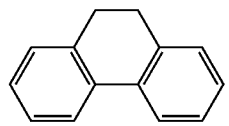
(B-14)

(B-15)

-continued

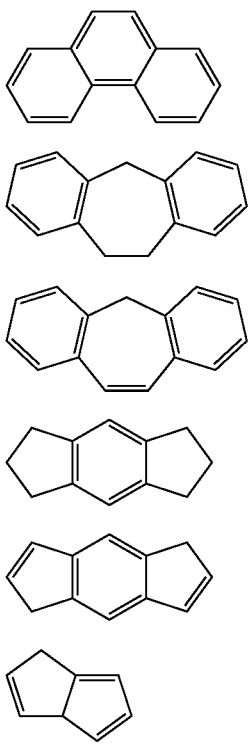

(B-16)

(B-17)

(B-18)

(B-19)

(B-20)

(B-21)

(In the formula, the ring structure may have a bonding arm at any position, any —CH= may independently be substituted by —N=, and —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included. The phrase "may have a bonding arm at any position" means that, for example, B$^1$ is a divalent group and therefore has two bonding arms at any position (the phrase "may have a bonding arm at any position" hereinafter has this meaning). These groups may be unsubstituted or substituted by one or more substituents L's, and these groups are bonded to a hydrogen atom or a group represented by the substituent L when B$^3$ denotes a single bond.)

From the perspective of the availability of raw materials, the ease of synthesis, and inverse dispersibility, B$^1$, B$^2$, and B$^3$ preferably independently denote a group selected from the formulae (B-3), (B-4), (B-5), (B-6), (B-7), (B-8), (B-10), (B-11), (B-12), (B-13), (B-17), (B-18), (B-19), (B-20), and (B-21) and a single bond.

The group represented by the formula (B-3) preferably denotes a group selected from the following formulae (B-3-1) to (B-3-7), more preferably a group selected from the formulae (B-3-2), (B-3-4), (B-3-5), (B-3-6), and (B-3-7).

[Chem. 8]

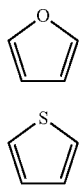
(B-3-1)

(B-3-2)

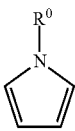
(B-3-3)

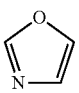
(B-3-4)

(B-3-5)

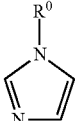
(B-3-6)

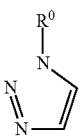
(B-3-7)

(wherein the ring structure may have a bonding arm at any position, R$^0$ denotes a hydrogen atom or an alkyl group having 1 to 20 carbon atoms, and these groups may be unsubstituted or substituted by one or more substituents L's)

The group represented by the formula (B-4) preferably denotes a group selected from the following formulae (B-4-1) to (B-4-8), more preferably a group represented by the formula (B-4-1).

[Chem. 9]

(B-4-1)

(B-4-2)

(B-4-3)

(B-4-4)

(B-4-5)

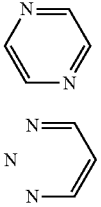
(B-4-6)

-continued

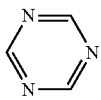 (B-4-7)

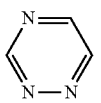 (B-4-8)

(wherein the ring structure may have a bonding arm at any position, and these groups may be unsubstituted or substituted by one or more substituents L's)

The group represented by the formula (B-5) preferably denotes a group selected from the following formulae (B-5-1) to (B-5-6).

[Chem. 10]

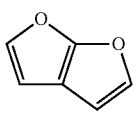 (B-5-1)

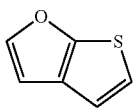 (B-5-2)

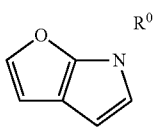 (B-5-3)

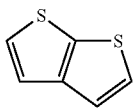 (B-5-4)

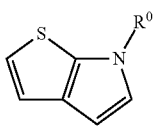 (B-5-5)

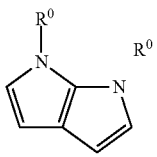 (B-5-6)

(wherein the ring structure may have a bonding arm at any position, $R^0$ denotes a hydrogen atom or an alkyl group having 1 to 20 carbon atoms, and these groups may be unsubstituted or substituted by one or more substituents L's)

The group represented by the formula (B-6) preferably denotes a group selected from the following formulae (B-6-1) to (B-6-9).

[Chem. 11]

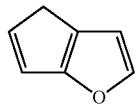 (B-6-1)

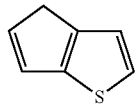 (B-6-2)

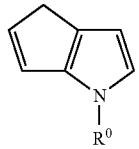 (B-6-3)

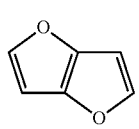 (B-6-4)

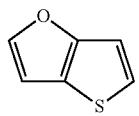 (B-6-5)

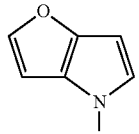 (B-6-6)

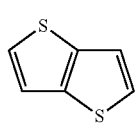 (B-6-7)

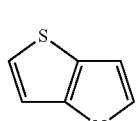 (B-6-8)

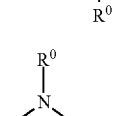 (B-6-9)

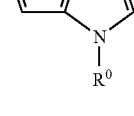

(wherein the ring structure may have a bonding arm at any position, $R^0$ denotes a hydrogen atom or an alkyl group having 1 to 20 carbon atoms, and these groups may be unsubstituted or substituted by one or more substituents L's)

The group represented by the formula (B-7) preferably denotes a group selected from the following formulae (B-7-1) to (B-7-12), more preferably a group selected from the formulae (B-7-8), (B-7-9), (B-7-10), (B-7-11), and (B-7-12), still more preferably a group represented by the formula (B-7-11).

[Chem. 12]

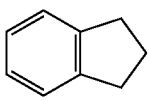 (B-7-1)

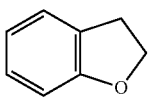 (B-7-2)

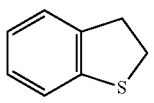 (B-7-3)

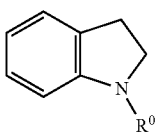 (B-7-4)

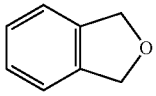 (B-7-5)

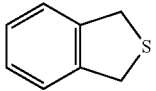 (B-7-6)

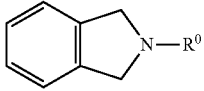 (B-7-7)

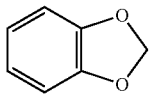 (B-7-8)

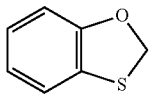 (B-7-9)

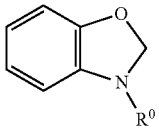 (B-7-10)

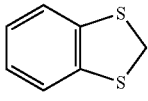 (B-7-11)

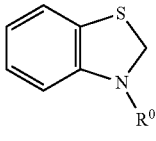 (B-7-12)

(wherein the ring structure may have a bonding arm at any position, $R^0$ denotes a hydrogen atom or an alkyl group having 1 to 20 carbon atoms, and these groups may be unsubstituted or substituted by one or more substituents L's)

The group represented by the formula (B-8) preferably denotes a group selected from the following formulae (B-8-1) to (B-8-8), more preferably a group selected from the formulae (B-8-2), (B-8-3), (B-8-4), (B-8-6), (B-8-7), and (B-8-8).

[Chem. 13]

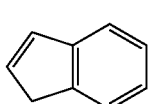 (B-8-1)

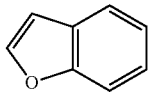 (B-8-2)

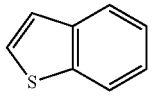 (B-8-3)

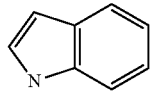 (B-8-4)

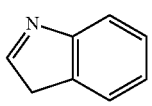 (B-8-5)

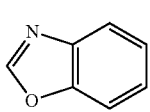 (B-8-6)

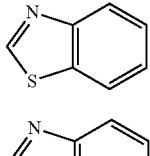 (B-8-7)

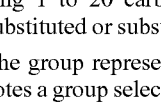 (B-8-8)

(wherein the ring structure may have a bonding arm at any position, $R^0$ denotes a hydrogen atom or an alkyl group having 1 to 20 carbon atoms, and these groups may be unsubstituted or substituted by one or more substituents L's)

The group represented by the formula (B-10) preferably denotes a group selected from the following formulae (B-10-1) to (B-10-19).

[Chem. 14]

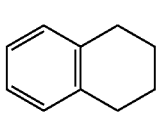 (B-10-1)

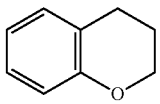 (B-10-2)

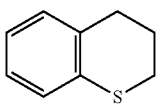 (B-10-3)

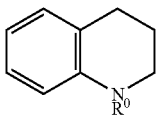 (B-10-4)

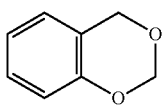 (B-10-5)

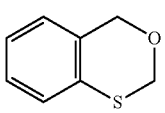 (B-10-6)

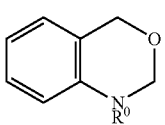 (B-10-7)

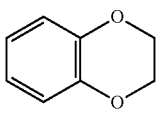 (B-10-8)

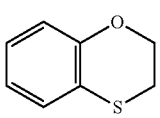 (B-10-9)

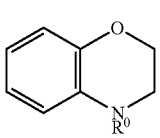 (B-10-10)

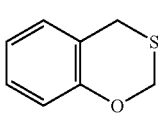 (B-10-11)

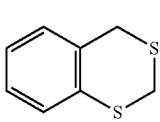 (B-10-12)

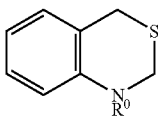 (B-10-13)

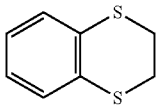 (B-10-14)

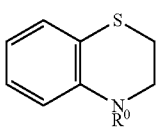 (B-10-15)

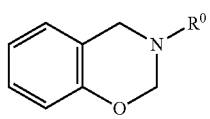 (B-10-16)

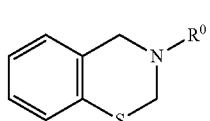 (B-10-17)

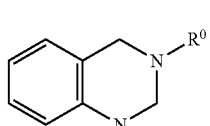 (B-10-18)

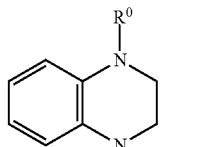 (B-10-19)

(wherein the ring structure may have a bonding arm at any position, $R^0$ denotes a hydrogen atom or an alkyl group having 1 to 20 carbon atoms, and these groups may be unsubstituted or substituted by one or more substituents L's)

The group represented by the formula (B-11) preferably denotes a group selected from the following formulae (B-11-1) to (B-11-7), more preferably a group selected from the formulae (B-11-1), (B-11-2), and (B-11-7).

[Chem. 15]

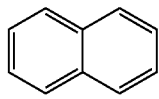 (B-11-1)

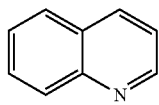 (B-11-2)

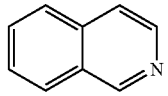 (B-11-3)

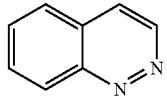 (B-11-4)

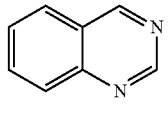 (B-11-5)

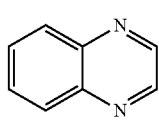 (B-11-6)

-continued

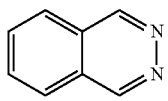
(B-11-7)

(wherein the ring structure may have a bonding arm at any position, R⁰ denotes a hydrogen atom or an alkyl group having 1 to 20 carbon atoms, and these groups may be unsubstituted or substituted by one or more substituents L's)

The group represented by the formula (B-12) preferably denotes a group selected from the following formulae (B-12-1) to (B-12-4), preferably a group selected from the formulae (B-12-1) and (B-12-4).

[Chem. 16]

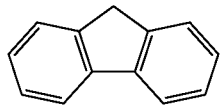
(B-12-1)

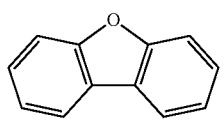
(B-12-2)

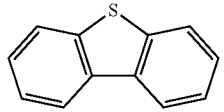
(B-12-3)

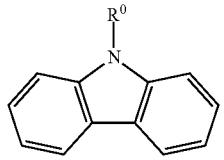
(B-12-4)

(wherein the ring structure may have a bonding arm at any position, R⁰ denotes a hydrogen atom or an alkyl group having 1 to 20 carbon atoms, and these groups may be unsubstituted or substituted by one or more substituents L's)

The group represented by the formula (B-13) preferably denotes a group selected from the following formulae (B-13-1) to (B-13-10).

[Chem. 17]

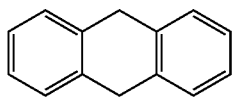
(B-13-1)

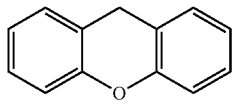
(B-13-2)

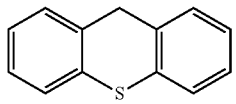
(B-13-3)

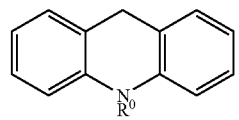
(B-13-4)

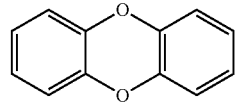
(B-13-5)

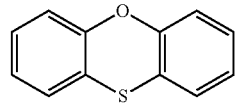
(B-13-6)

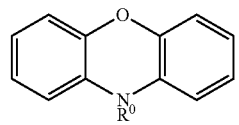
(B-13-7)

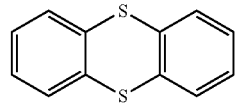
(B-13-8)

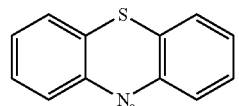
(B-13-9)

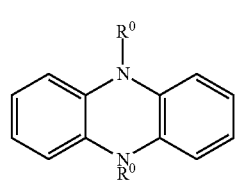
(B-13-10)

(wherein the ring structure may have a bonding arm at any position, R⁰ denotes a hydrogen atom or an alkyl group having 1 to 20 carbon atoms, and these groups may be unsubstituted or substituted by one or more substituents L's)

The group represented by the formula (B-17) preferably denotes a group selected from the following formulae (B-17-1) to (B-17-18).

[Chem. 18]

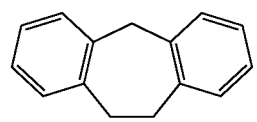
(B-17-1)

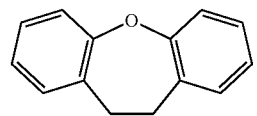
(B-17-2)

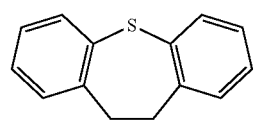
(B-17-3)

(B-17-4)
(B-17-5)
(B-17-6)
(B-17-7)
(B-17-8)
(B-17-11)
(B-17-12)
(B-17-13)
(B-17-14)
(B-17-15)
(B-17-16)

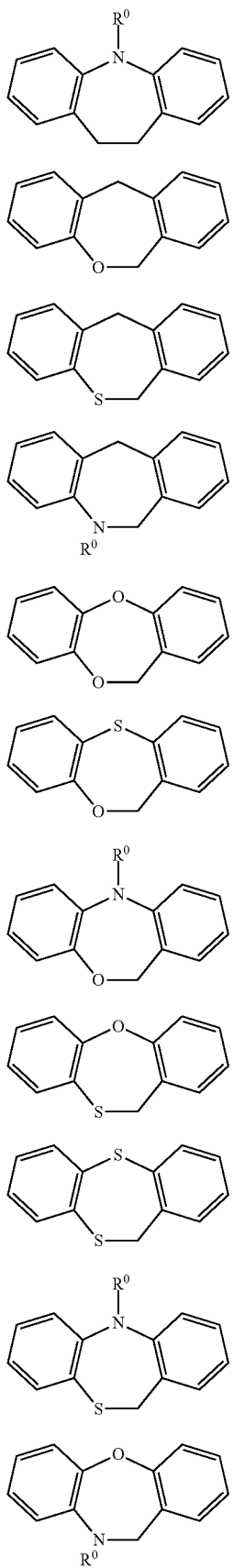

(B-17-17)
(B-17-18)

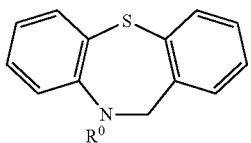
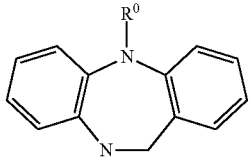

(wherein the ring structure may have a bonding arm at any position, $R^0$ denotes a hydrogen atom or an alkyl group having 1 to 20 carbon atoms, and these groups may be unsubstituted or substituted by one or more substituents L's)

The group represented by the formula (B-18) preferably denotes a group selected from the following formulae (B-18-1) to (B-18-4).

[Chem. 15]

(B-18-1)
(B-18-2)
(B-18-3)
(B-18-4)

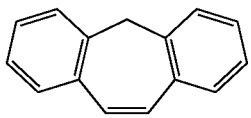
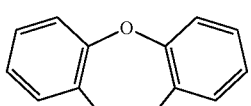
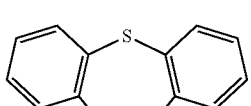
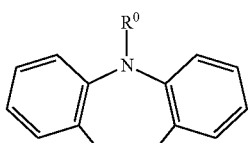

(wherein the ring structure may have a bonding arm at any position, $R^0$ denotes a hydrogen atom or an alkyl group having 1 to 20 carbon atoms, and these groups may be unsubstituted or substituted by one or more substituents L's)

The group represented by the formula (B-19) preferably denotes a group selected from the following formulae (B-19-1) to (B-19-16).

[Chem. 20]

(B-19-1)

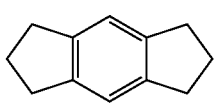

(B-19-2) 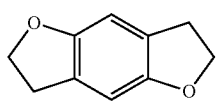
(B-19-3) 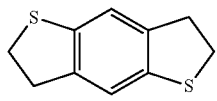
(B-19-4) 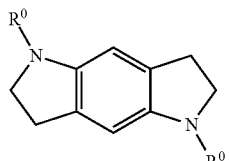
(B-19-5) 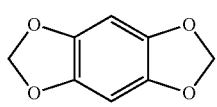
(B-19-6) 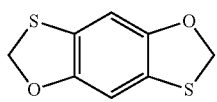
(B-19-7) 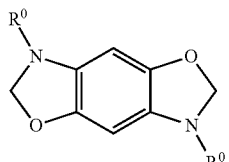
(B-19-8) 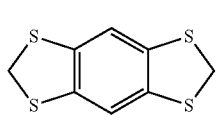
(B-19-9) 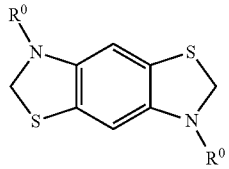
(B-19-10) 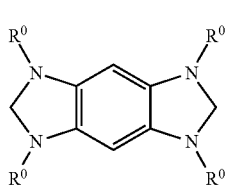
(B-19-11) 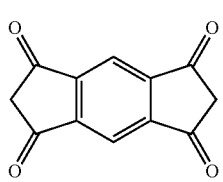
(B-19-12) 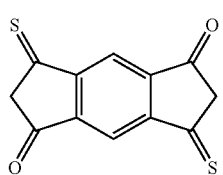
(B-19-13) 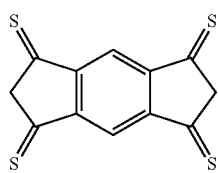
(B-19-14) 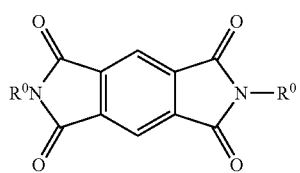
(B-19-15) 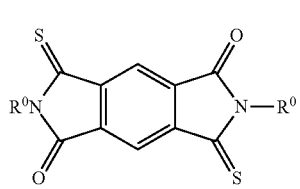
(B-19-16) 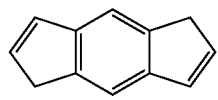
(wherein the ring structure may have a bonding arm at any position, $R^0$ denotes a hydrogen atom or an alkyl group having 1 to 20 carbon atoms, and these groups may be unsubstituted or substituted by one or more substituents L's)
The group represented by the formula (B-20) preferably denotes a group selected from the following formulae (B-20-1) to (B-20-12).
[Chem. 21]
(B-20-1) 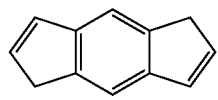
(B-20-2) 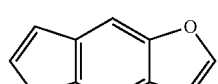
(B-20-3) 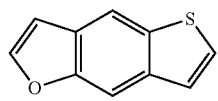
(B-20-4) 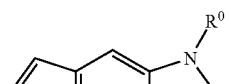
(B-20-5) 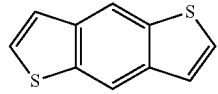

-continued (B-20-6)
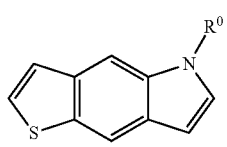

(B-20-7)
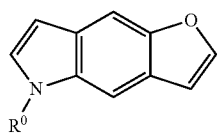

(B-20-8)
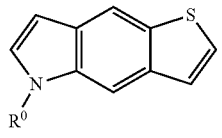

(B-20-9)
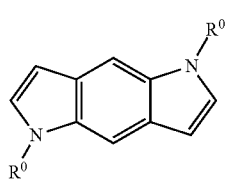

(B-20-10)
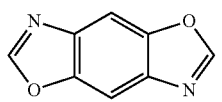

(B-20-11)
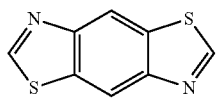

(B-20-12)
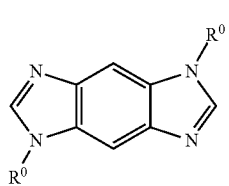

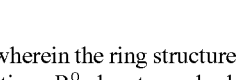

(wherein the ring structure may have a bonding arm at any position, $R^0$ denotes a hydrogen atom or an alkyl group having 1 to 20 carbon atoms, and these groups may be unsubstituted or substituted by one or more substituents L's)

The group represented by the formula (B-21) preferably denotes a group selected from the following formulae (B-21-1) to (B-21-13).

[Chem. 22]

(B-21-1)
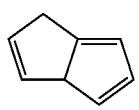

(B-21-2)
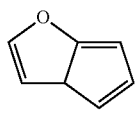

-continued (B-21-3)
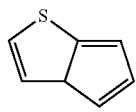

(B-21-4)
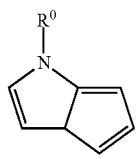

(B-21-5)
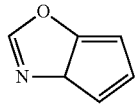

(B-21-6)
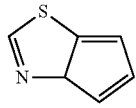

(B-21-7)
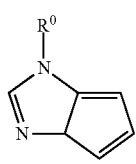

(B-21-8)
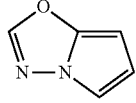

(B-21-9)
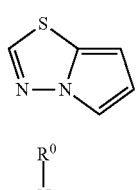

(B-21-10)
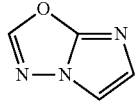

(B-21-11)
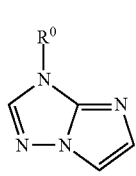

(B-21-12)
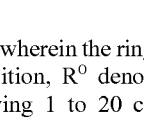

(B-21-13)

(wherein the ring structure may have a bonding arm at any position, $R^0$ denotes a hydrogen atom or an alkyl group having 1 to 20 carbon atoms, and these groups may be unsubstituted or substituted by one or more substituents L's)

<<M¹, M²>>

In the general formula (I), M¹ and M² independently denote a group containing a mesogenic group.

More specifically, M¹ preferably denotes a group represented by the following formula (I-M1), and M² preferably denotes a group represented by the following formula (I-M2).

[Chem. 23]

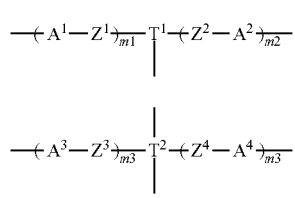

(I-M1)

(I-M2)

(wherein A¹, A², A³, and A⁴ independently denote a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, these groups may be unsubstituted or substituted by one or more substituents L's, a plurality of A¹'s, A²'s, A³'s, and/or A⁴'s, if present at all, may be the same or different, Z¹, Z², Z³, and Z⁴ independently denote —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C—, or a single bond, a plurality of Z¹'s, Z²'s, Z³'s, and/or Z⁴'s, if present at all, may be the same or different, T¹ denotes an optionally substituted trivalent group, T² denotes an optionally substituted trivalent group when n2 is 0 or an optionally substituted tetravalent group when n2 is 1, and m1, m2, m3, and m4 are independently an integer in the range of 0 to 5)

From the perspective of the availability of raw materials and the ease of synthesis, A¹, A², A³, and A⁴ preferably independently denote a 1,4-phenylene group, a 1,4-cyclohexylene group, or a naphthalene-2,6-diyl group optionally substituted by one or more substituents L's, more preferably a group selected from the following formulae (A-1) to (A-11), still more preferably a group selected from the formulae (A-1) to (A-8), particularly preferably a group selected from the formulae (A-1) to (A-4).

[Chem. 24]

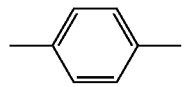
(A-1)

(A-2)

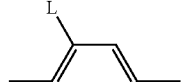
(A-3)

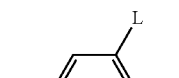
(A-4)

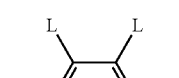
(A-5)

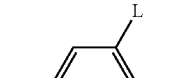
(A-6)

(A-7)

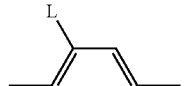
(A-8)

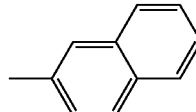
(A-9)

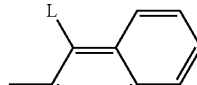
(A-10)

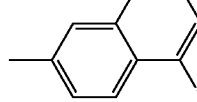
(A-11)

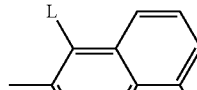

From the perspective of the liquid crystallinity, the availability of raw materials, and the ease of synthesis of the compound, Z¹, Z², Z³, and Z⁴ preferably independently denote a single bond, —OCH$_2$—, —CH$_2$O—, —COO—, —OCO—, —CF$_2$—, —OCF$_2$—, —CH$_2$CH$_2$—, —CF$_2$CF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —CH═CH—, —CF═CF—, —C≡C—, or a single bond, more preferably —OCH$_2$—, —CH$_2$O—, —CH$_2$CH$_2$—, —COO—, —OCO—, —COO—CH$_2$CH$_2$—, —OCO—CH$_2$CH$_2$—, —CH$_2$CH$_2$—COO—, —CH$_2$CH$_2$—OCO—, —CH═CH—, —C≡C—, or a single bond, still more preferably —CH$_2$CH$_2$—, —COO—, —OCO—, —COO—CH$_2$CH$_2$—, —OCO—CH$_2$CH$_2$—, —CH$_2$CH$_2$—COO—, —CH$_2$CH$_2$—OCO—, or a single bond, particularly preferably —COO—, —OCO—, or a single bond.

Each of m1, m2, m3, and m4 is an integer in the range of 0 to 5 and, from the perspective of liquid crystallinity, the ease of synthesis, and storage stability, is preferably an integer in the range of 1 to 4, more preferably an integer in the range of 1 to 3, particularly preferably 1 or 2. Each of m1+m2 and m3+m4 is preferably an integer in the range of 1 to 4, particularly preferably 2, 3, or 4.

T$^1$ and T$^2$ in the formulae (I-M1) and (I-M2) preferably independently denote a group selected from the following formulae (T-1) to (T-22).

[Chem. 25]

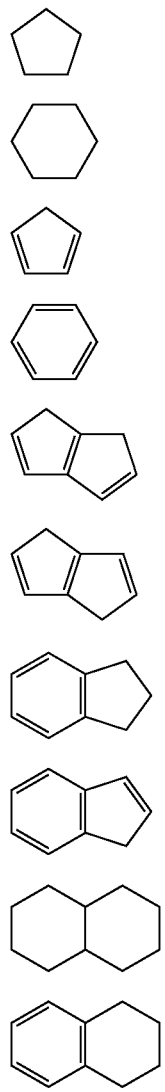

(T-1)
(T-2)
(T-3)
(T-4)
(T-5)
(T-6)
(T-7)
(T-8)
(T-9)
(T-10)

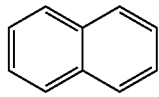 (T-11)

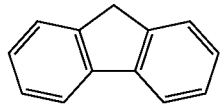 (T-12)

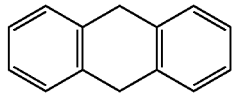 (T-13)

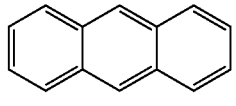 (T-14)

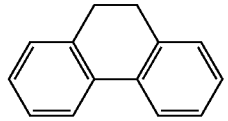 (T-15)

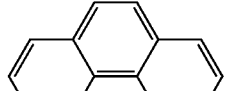 (T-16)

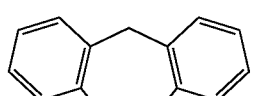 (T-17)

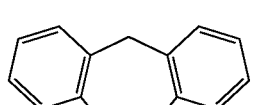 (T-18)

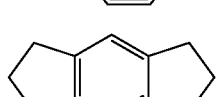 (T-19)

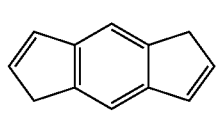 (T-20)

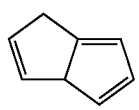 (T-21)

 (T-22)

(wherein the group may have a bonding arm at any position, any —CH═ may independently be substituted by —N═, —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more L's, and k1 is an integer in the range of 1 to 20)

<<n1, n2, n3>> n1 and n2 are independently 0 or 1. When n1 is 0, the group bonded to $W^1$ described later denotes a hydrogen atom. When n2 is 0, the group bonded to $M^2$ described later denotes a hydrogen atom.

n3 is an integer in the range of 1 to 1000, preferably an integer in the range of 1 to 10, more preferably an integer in the range of 1 to 5, still more preferably an integer in the range of 1 to 3, particularly preferably 1 or 2.

Although each of n1, n2, and n3 is an integer as described above,

A: <n1 and n2 are 0, and n3 is 1>,
B: <n1 is 1, n2 is 0, and n3 is 1>,
C: <n1 is 0, and n2 and n3 are 1>, or
D: <n1 and n2 are 0, and n3 ranges from 2 to 1000> is particularly preferred in terms of good inverse dispersibility.

Each group will be described below for each of the particularly preferred A to D.

Compound in which <<n1 and n2 are 0, and n3 is 1>>
<$W^1$-A11>

For a compound in which <n1 and n2 are 0, and n3 is 1>, in careful consideration of the appearances after ultraviolet irradiation and the surface hardness of a polymer film produced from the compound, $W^1$ in the general formula (I) preferably denotes a group represented by the following formula (I-W11).

[Chem. 26]

(I-W11)

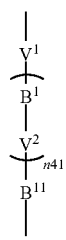

(wherein $V^1$ and present $V^2$ independently denote a single bond or a divalent linking group, present $B^1$ and $B^{11}$ independently denote a group selected from the formulae (B-1) to (B-21) and a single bond, and n41 is an integer in the range of 0 to 5)

[Chem. 27]

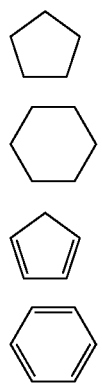

(B-1)

(B-2)

(B-3)

(B-4)

-continued

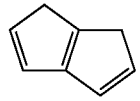 (B-5)

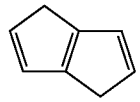 (B-6)

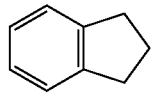 (B-7)

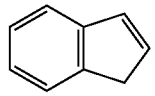 (B-8)

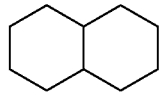 (B-9)

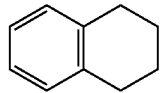 (B-10)

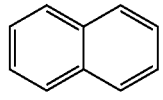 (B-11)

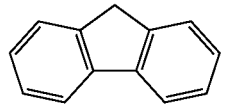 (B-12)

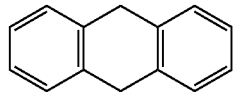 (B-13)

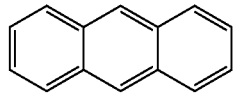 (B-14)

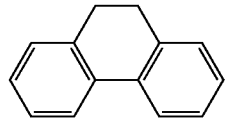 (B-15)

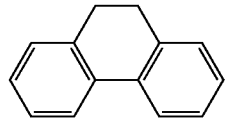 (B-16)

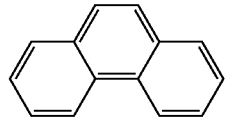 (B-17)

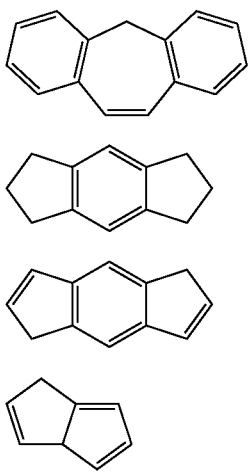

(B-18)

(B-19)

(B-20)

(B-21)

(wherein the group may have a bonding arm at any position, any —CH= may independently be substituted by —N=, —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more substituents L's)

V$^1$ and V$^2$ preferably independently denote a group represented by one of the formulae (V-1) to (V-15) described in <<W$^1$, W$^2$>> (wherein Y$^1$ if present at all, preferably denotes a group selected from the perspective of the availability of the raw materials described in <<W$^1$, W$^2$>> and the ease of synthesis), a single bond, a double bond, —O—, —S—, —OCH$_2$—, —CH$_2$O—, —CO—, —CH$_2$—, —COO—, —OCO—, —CO—S—, —S—CO—, —O—CO—O—, —CO—NH—, —NH—CO—, —CS—NH—, —NH—CS—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —CH$_2$CH$_2$—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, or —CH$_2$—OCO—, more preferably a group selected from the formulae (V-5), (V-6), (V-8), (V-9), and (V-10), a single bond, and a double bond, particularly preferably a single bond.

B$^1$ and B$^{11}$ preferably independently denote a group selected from the formulae (B-3), (B-4), (B-8), (B-13), and (B-16) and a single bond, more preferably a group selected from the formulae (B-3), (B-4), and (B-8) and a single bond, more specifically, specifically preferably a group selected from the formulae (B-3-1), (B-3-2), (B-3-5), (B-3-7), (B-4-1), (B-8-4), (B-8-7), (B-13-7), and (B-13-8) described in <<W$^1$, W$^2$>> and a single bond, specifically preferably a group selected from the formulae (B-3-7), (B-4-1), and (B-8-4).

n41 is more preferably 0, 1, or 2, still more preferably 0 or 1, still more preferably 1.

<W$^1$-A12>

For a compound in which <n1 and n2 are 0, and n3 is 1>, in careful consideration of the storage stability of the polymerizable composition and orientation defects after ultraviolet irradiation and nonuniform orientation of a polymer film produced from the polymerizable composition, W in the general formula (I) preferably denotes a group represented by the following formula (I-W12).

[Chem. 28]

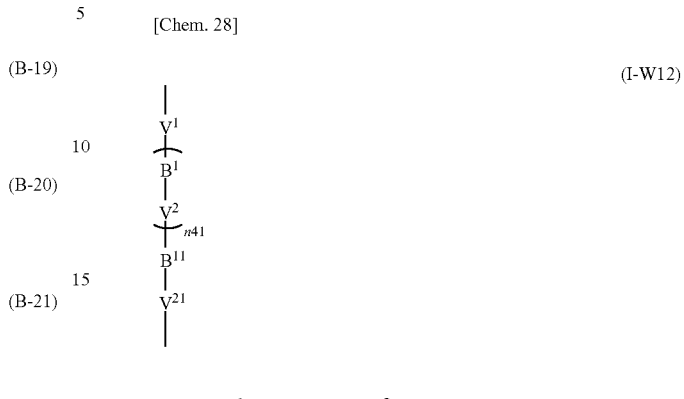

(I-W12)

(wherein V$^1$ and present V$^2$ independently denote a single bond or a divalent linking group, V$^{21}$ denotes —NR$^0$—, —CR$^0$=, =CR$^0$—, —N=, or =N— (wherein R$^0$ independently denotes a hydrogen atom or an alkyl group having 1 to 8 carbon atoms), present B$^1$ and B$^{11}$ independently denote a group selected from the formulae (B-1) to (B-21) and a single bond, and n41 is an integer in the range of 0 to 5)

[Chem. 29]

(B-1)

(B-2)

(B-3)


(B-4)

(B-5)

(B-6)

(B-7)

(B-8)

-continued (B-9) 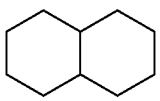

(B-10) 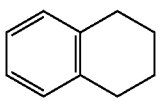

(B-11) 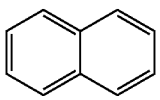

(B-12) 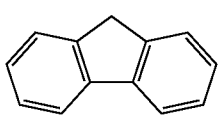

(B-13) 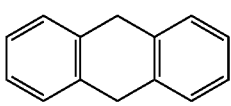

(B-14) 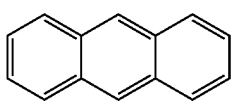

(B-15) 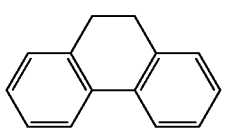

(B-16) 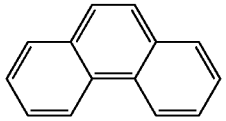

(B-17) 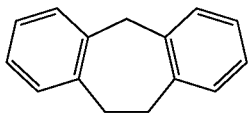

(B-18) 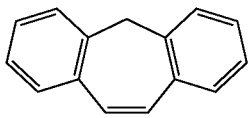

(B-19) 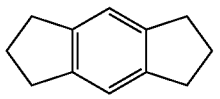

(B-20) 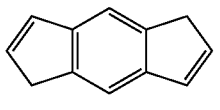

(B-21) 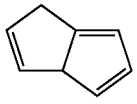

(wherein the group may have a bonding arm at any position, any —CH= may independently be substituted by —N=, —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more substituents L's)

V$^{21}$ more preferably denotes a group selected from —NR$^0$—, —N=, and =N— (wherein R$^0$ independently denotes a hydrogen atom or an alkyl group having 1 to 8 carbon atoms), still more preferably —NH—.

V$^1$ and present V$^2$ more preferably independently denote a group represented by one of the formulae (V-1) to (V-15) (wherein Y$^1$ if present at all, preferably denotes a group selected from the perspective of the availability of the raw materials described in <<W$^1$, W$^2$>> and the ease of synthesis), a single bond, a double bond, —O—, —S—, —OCH$_2$—, —CH$_2$O—, —CO—, —CH$_2$—, —COO—, —OCO—, —CO—S—, —S—CO—, —O—CO—O—, —CO—NH—, —NH—CO—, —CS—NH—, —NH—CS—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —CH$_2$CH$_2$—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, or —CH$_2$—OCO—, still more preferably the formula (V-1), (V-2), (V-5), (V-6), (V-8), or (V-9), a single bond, —S—, or —CH$_2$CH$_2$—, still more preferably the formula (V-5) or a single bond.

B$^1$ and B$^{11}$ preferably independently denote a group selected from the formulae (B-3), (B-4), (B-6), (B-7), (B-8), (B-10), (B-11), and (B-21) and a single bond, preferably a group selected from the formulae (B-3), (B-4), (B-8), and (B-21), more specifically, preferably a group selected from the formulae (B-3-2), (B-3-5), (B-3-7), (B-4-1), (B-4-2), (B-4-3), (B-4-4), (B-4-5), (B-6-7), (B-7-8), (B-7-11), (B-7-12), (B-8-3), (B-8-4), (B-10-11), (B-10-16), (B-11-6), and (B-21-12) described in <<W$^1$, W$^2$>>, more preferably a group selected from the formulae (B-3-7), (B-4-1), (B-4-2), (B-4-3), (B-8-4), and (B-21-12).

n41 is more preferably 0, 1, or 2, still more preferably 0 or 1.

<W$^1$-A13>

For a compound in which <n1 and n2 are 0, and n3 is 1>, in careful consideration of the thickness uniformity and adhesiveness of a polymer film produced from the compound, W in the general formula (I) preferably denotes a group represented by the following formula (I-W13).

[Chem. 30]

$$\begin{array}{c} | \\ V^1 \\ | \\ B^1 \\ | \\ V^2 \\ | \\ B^{11} \\ | \\ V^{21} \\ | \end{array} \Bigg\}_{n41}$$

(I-W13)

(wherein V$^1$ and present V$^2$ independently denote a single bond or a divalent linking group, V$^{21}$ denotes —CR$^0$=CR$^0$—, —C≡C—, —CR$^0$=N—, —N=CR$^0$—, —NR$^0$—CR$^0$=, =CR$^0$—NR$^0$—, —NR$^0$—N=, =N—NR⁰—, —N=N—, or =N—N= (wherein R⁰ independently denotes a hydrogen atom or an alkyl group having 1 to 8 carbon atoms), and present B¹ and B¹¹ independently denote a group selected from the formulae (B-1) to (B-21) and a single bond, and n41 is an integer in the range of 0 to 5)

[Chem. 31]

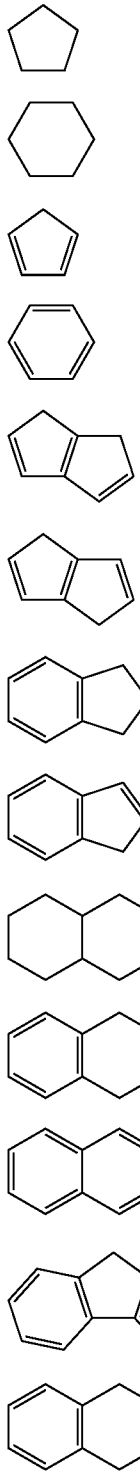

(B-1)
(B-2)
(B-3)
(B-4)
(B-5)
(B-6)
(B-7)
(B-8)
(B-9)
(B-10)
(B-11)
(B-12)
(B-13)

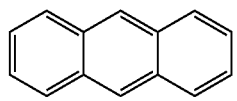

(B-14)

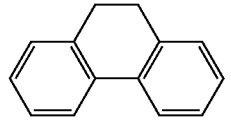

(B-15)

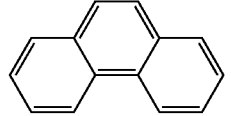

(B-16)

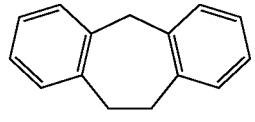

(B-17)

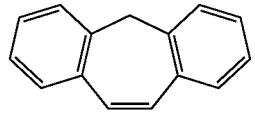

(B-18)

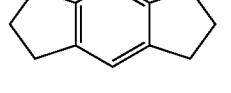

(B-19)

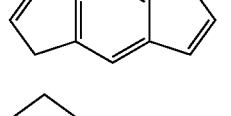

(B-20)

(B-21)

(wherein the group may have a bonding arm at any position, any —CH= may independently be substituted by —N=, —CH₂— may independently be substituted by —O—, —S—, —NR⁰— (wherein R⁰ denotes a hydrogen atom or an alkyl group having 1 to 20 carbon atoms), —CS—, or —CO—, provided that no —O—O— bond is included, and these groups may be unsubstituted or substituted by one or more substituents L's)

$V^{21}$ more preferably denotes a group selected from —CR⁰=CR⁰—, —C≡C—, —CR⁰=N—, —N=CR⁰—, —NR⁰—CR⁰=, =CR⁰—NR⁰—, —N=N—, and =N—N= (wherein R⁰ independently denotes a hydrogen atom or an alkyl group having 1 to 8 carbon atoms), still more preferably a group selected from —CH=CH—, —CH=N—, —N=CH—, and —N=N—, still more preferably a group selected from —CH=CH—, —CH=N—, and —N=CH—. $V^1$ and $V^2$ more preferably independently denote a group represented by one of the formulae (V-1) to (V-15) (wherein $Y^1$ if present at all, preferably denotes a group selected from the perspective of the availability of the raw materials described in <<W¹, W²>> and the ease of synthesis), a single bond, a double bond, —O—, —S—, —OCH₂—, —CH₂O—, —CO—, —CH₂—, —COO—, —OCO—, —CO—S—, —S—CO—, —O—CO—O—, —CO—NH—, —NH—CO—, —CS—NH—, —NH—

CS—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —CH$_2$CH$_2$—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, or —CH$_2$—OCO—, still more preferably the formula (V-1), (V-2), (V-3), (V-4), (V-5), or (V-10), —CH$_2$CH$_2$—, or a single bond, still more preferably the formula (V-1), (V-2), (V-3), or (V-4), or a single bond. B$^1$ and B$^{11}$ preferably independently denote a group selected from the formulae (B-3), (B-4), (B-5), (B-6), (B-7), (B-8), (B-10), (B-11), (B-12), (B-13), (B-17), and (B-18) and a single bond, more preferably a group selected from the formulae (B-3), (B-4), (B-7), (B-8), (B-10), (B-12), and (B-13) and a single bond, more specifically, preferably a group selected from the formulae (B-3-2), (B-3-5), (B-4-1), (B-7-11), (B-8-7), (B-10-11), (B-12-3), (B-12-4), and (B-13-6) described in <<W$^1$, W$^2$>> and a single bond, more preferably a group selected from (B-3-2), (B-3-5), (B-4-1), (B-7-11), (B-8-7), (B-12-4), and a single bond, still more preferably a group selected from the formulae (B-3-2), (B-4-1), (B-8-7), and (B-12-4) and a single bond.

n41 is more preferably 0, 1, or 2, still more preferably 0 or 1, still more preferably 1.

<W$^1$-A14>

For a compound in which <n1 and n2 are 0, and n3 is 1>, in careful consideration of storage stability when added to a polymerizable composition and orientation defects after ultraviolet irradiation and the haze of a polymer film produced from the compound, W$^1$ in the general formula (I) preferably denotes a group represented by the following formula (I-W14).

[Chem. 32]

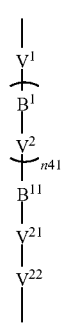

(I-W14)

(herein V$^1$ and present V$^2$ independently denote a single bond or a divalent linking group, V$^{21}$ denotes —CR$^0$=CR$^0$—, —C≡C—, —CR$^0$=N—, —N=CR$^0$—, —NR$^0$—CR$^0$=, =CR$^0$—NR$^0$—, —NR$^0$—N=, =N—NR$^0$—, —N=N—, or =N—N=, V$^{22}$ denotes —NR$^0$—, —CR$^0$=, =CR$^0$—, —N=, or =N— (wherein R$^0$ independently denotes a hydrogen atom or an alkyl group having 1 to 8 carbon atoms), present B$^1$ and B$^{11}$ independently denote a group selected from the formulae (B-1) to (B-21) and a single bond, and n41 is an integer in the range of 0 to 5)

[Chem. 33]

 (B-1)

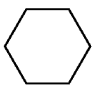 (B-2)

 (B-3)

 (B-4)

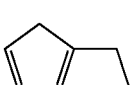 (B-5)

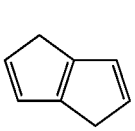 (B-6)

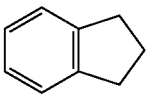 (B-7)

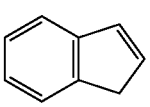 (B-8)

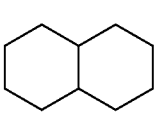 (B-9)

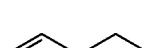 (B-10)

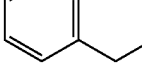 (B-11)

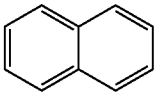 (B-12)

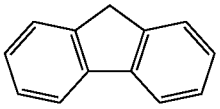 (B-13)

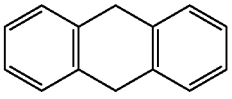 (B-14)

(B-15)

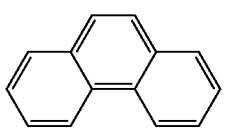
(B-16)

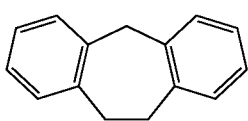
(B-17)

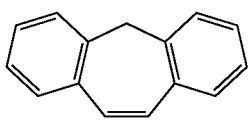
(B-18)

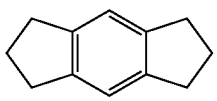
(B-19)

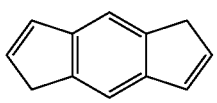
(B-20)

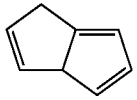
(B-21)

(wherein the group may have a bonding arm at any position, any —CH═ may independently be substituted by —N═, —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more substituents L's)

V$^{21}$ more preferably denotes a group selected from —CR$^0$═N—, —N═CR$^0$—, —NR$^0$—CR$^0$═, ═CR$^0$—NR$^0$—, —NR$^0$—N═, ═N—NR$^0$—, and ═N—N═ (wherein R$^0$ independently denotes a hydrogen atom or an alkyl group having 1 to 8 carbon atoms), still more preferably a group selected from —CH═N—, —N═CH—, —NH—CH═, ═CH—NH—, —NH—N═, ═N—NH—, and ═N—N═. V$^{22}$ more preferably denotes a group selected from —NR$^0$—, —N═, and ═N— (wherein R$^0$ independently denotes a hydrogen atom or an alkyl group having 1 to 8 carbon atoms), still more preferably a group selected from —NH—, —N═, and ═N—. V$^1$ and present V$^2$ more preferably independently denote a group represented by one of the formulae (V-1) to (V-15) (wherein Y$^1$, if present at all, preferably denotes a group selected from the perspective of the availability of the raw materials described in <<W$^1$, W$^2$>> and the ease of synthesis), a single bond, a double bond, —O—, —S—, —OCH$_2$—, —CH$_2$O—, —CO—, —CH$_2$—, —COO—, —OCO—, —CO—S—, —S—CO—, —O—CO—O—, —CO—NH—, —NH—CO—, —CS—NH—, —NH—CS—, —SCH$_2$—, —CH$_2$S—, —CF$_2$O—, —OCF$_2$—, —CF$_2$S—, —SCF$_2$—, —CH═CH—COO—, —CH═CH—OCO—, —COO—CH═CH—, —OCO—CH═CH—, —CH$_2$CH$_2$—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, or —CH$_2$—OCO—, still more preferably the formula (V-5), (V-6), (V-8), or (V-9), a single bond, or —CH$_2$CH$_2$—, still more preferably a single bond. Present B$^1$ and B$^{11}$ preferably independently denote a group selected from the formulae (B-3), (B-4), (B-7), (B-8), (B-10), (B-11), and (B-12) and a single bond, more preferably a group selected from the formulae (B-4), (B-7), and (B-8) and a single bond, more specifically, preferably a group selected from the formulae (B-3-1), (B-3-2), (B-3-5), (B-3-7), (B-4-1), (B-4-3), (B-4-6), (B-7-11), (B-8-4), (B-8-7), (B-10-11), (B-11-1), and (B-12-4) described in <<W$^1$, W$^2$>> and a single bond, more preferably a group selected from the formulae (B-4-1), (B-7-11), and (B-8-7) and a single bond.

n41 is more preferably 0, 1, or 2, still more preferably 0 or 1, still more preferably 0.

<W$^1$-A15>

For a compound in which <n1 and n2 are 0, and n3 is 1>, in careful consideration of the haze and the thickness uniformity of a polymer film produced from the compound, W$^1$ in the general formula (I) preferably denotes a group represented by the following formula (I-W18).

[Chem. 34]

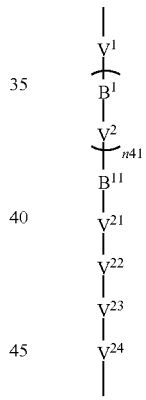
(I-W18)

(wherein V$^1$ and present V$^2$ independently denote a single bond or a divalent linking group, V$^{21}$, V$^{22}$, V$^{23}$, and V$^{24}$ denote —CR$^0$═CR$^0$—, —C≡C—, —CR$^0$═N—, —N═CR$^0$—, —NR$^0$—CR$^0$═, ═CR$^0$—NR$^0$—, —NR$^0$—N═, ═N—NR$^0$—, —N═N—, ═N—N—, —NR$^0$—, —CR$^0$═, ═CR$^0$—, —N═, or ═N— (wherein R$^0$ independently denotes a hydrogen atom or an alkyl group having 1 to 8 carbon atoms), and present B$^1$ and B$^{11}$ independently denote a group selected from the formulae (B-1) to (B-21) and a single bond, and n41 is an integer in the range of 0 to 5)

[Chem. 35]

(B-1)

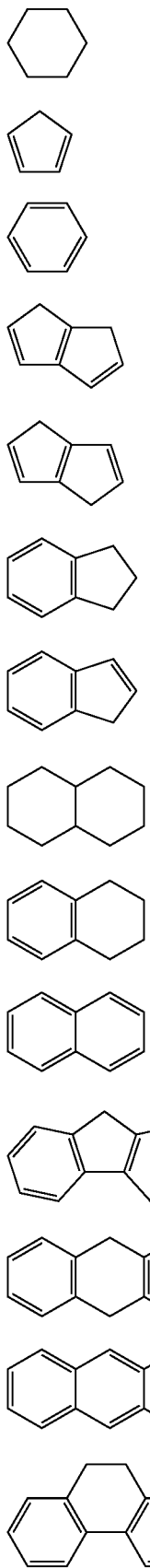
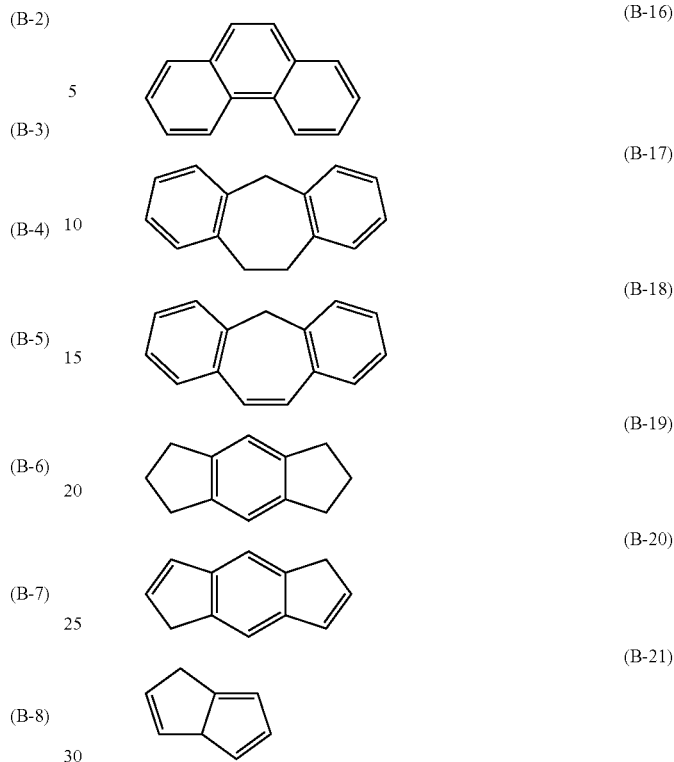

(wherein the group may have a bonding arm at any position, any —CH= may independently be substituted by —N=, —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more substituents L's)

V$^{21}$, V$^{22}$, V$^{23}$, and V$^{24}$ preferably denote —CR$^0$=CR$^0$—, —C≡C—, —CR$^0$=N—, —N=CR$^0$—, —NR$^0$—CR$^0$=, =CR$^0$—NR$^0$—, —NR$^0$—N=, =N—NR$^0$—, —NR$^0$—, —CR$^0$=, =CR$^0$—, —N=, or =N— (wherein R$^0$ independently denotes a hydrogen atom or an alkyl group having 1 to 8 carbon atoms), more preferably —CR$^0$=CR$^0$—, —C≡C—, —CR$^0$=N—, —N=CR$^0$—, —NR$^0$—N=, =N—NR$^0$—, —NR$^0$—, —CR$^0$=, or =CR$^0$— (wherein R$^0$ independently denotes a hydrogen atom or an alkyl group having 1 to 8 carbon atoms), still more preferably —CR$^0$=N— or —N=CR$^0$— (wherein R$^0$ independently denotes a hydrogen atom or an alkyl group having 1 to 8 carbon atoms), still more preferably —CH=N— or —N=CH—. V$^1$ and present V$^2$ more preferably independently denote a group represented by one of the formulae (V-1) to (V-15) (wherein Y$^1$, if present at all, preferably denotes a group selected from the perspective of the availability of the raw materials described in <<W$^1$, W$^2$>> and the ease of synthesis), a single bond, a double bond, —O—, —S—, —OCH$_2$—, —CH$_2$O—, —CO—, —CH$_2$—, —COO—, —OCO—, —CO—S—, —S—CO—, —O—CO—O—, —CO—NH—, —NH—CO—, —CS—NH—, —NH—CS—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —CH$_2$CH$_2$—, —COO—CH$_2$CH$_2$—, —OCO—CH$_2$CH$_2$—, —CH$_2$CH$_2$—COO—, —CH$_2$CH$_2$—

OCO—, —COO—CH$_2$—, —OCO—CH$_2$—, —CH$_2$—COO—, or —CH$_2$—OCO—, still more preferably the formula (V-6), a single bond, or —CH$_2$CH$_2$—, still more preferably a group selected from the formula (V-6) and a single bond. Present B$^1$ and B$^{11}$ preferably independently denote a group selected from the formulae (B-3), (B-4), (B-7), (B-8), (B-10), (B-11), and (B-12) and a single bond, more preferably a group selected from the formulae (B-4), (B-8), and (B-12) and a single bond, more specifically, preferably a group selected from the formulae (B-3-2), (B-3-5), (B-4-1), (B-7-11), (B-8-7), (B-10-11), (B-11-1), and (B-12-4) described in <<W$^1$, W$^2$>> and a single bond, more preferably a group selected from the formulae (B-4-1), (B-8-7), and (B-12-4) and a single bond, still more preferably a group selected from the formula (B-4-1) and a single bond.

n41 is more preferably 0, 1, or 2, still more preferably 0 or 1, still more preferably 1.

<M$^2$-A1>

For a compound in which <n1 and n2 are 0, and n3 is 1>, in careful consideration of storage stability when added to a polymerizable composition and the haze, thickness uniformity, nonuniform orientation, and surface hardness of a polymer film produced from the compound, M$^2$ in the general formula (I) is preferably represented by the following formula (I-M21), and

[Chem. 36]

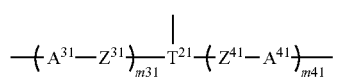
(I-M21)

(wherein present A$^{31}$ and present A$^{41}$ independently denote a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, these groups may be unsubstituted or substituted by one or more substituents L's, a plurality of A$^{31}$'s and/or A$^{41}$'s, if present at all, may be the same or different, present Z$^{31}$ and present Z$^{41}$ independently denote —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C—, or a single bond, a plurality of Z$^{31}$'s and/or Z$^{41}$'s, if present at all, may be the same or different, and m31 and m41 are independently an integer in the range of 0 to 5)

T$^{21}$ denotes a group selected from the following formulae (T2-1) to (T2-10), these groups may be unsubstituted or substituted by one or more substituents L's, and m31+m41 preferably ranges from 1 to 6.

[Chem. 37]

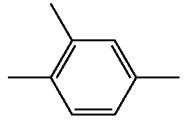
(T2-1)

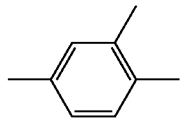
(T2-2)

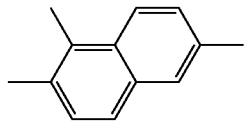
(T2-3)

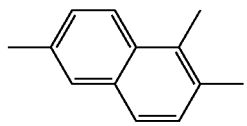
(T2-4)

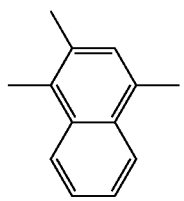
(T2-5)

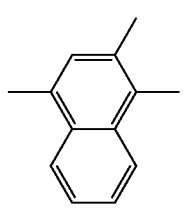
(T2-6)

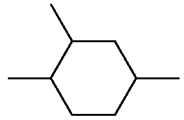
(T2-7)

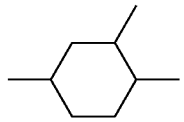
(T2-8)

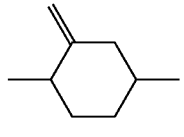
(T2-9)

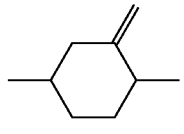
(T2-10)

From the perspective of the availability of raw materials and the ease of synthesis, A$^{31}$ and A$^{41}$ preferably independently denote a 1,4-phenylene group, a 1,4-cyclohexylene group, or a naphthalene-2,6-diyl group optionally substituted by one or more substituents L's, more preferably a group selected from the following formulae (A-A1-1) to (A-A1-11), still more preferably a group selected from the formulae (A-A1-1) to (A-A1-8), particularly preferably a group selected from the formulae (A-A1-1) to (A-A1-4).

[Chem. 38]

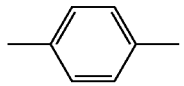 (A-A1-1)

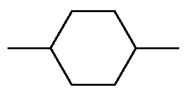 (A-A1-2)

 (A-A1-3)

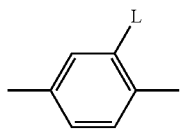 (A-A1-4)

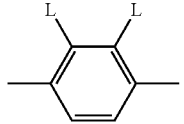 (A-A1-5)

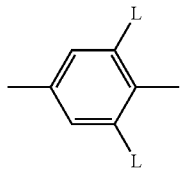 (A-A1-6)

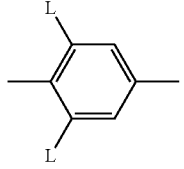 (A-A1-7)

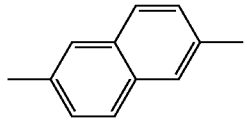 (A-A1-8)

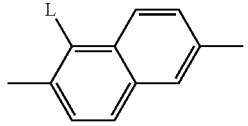 (A-A1-9)

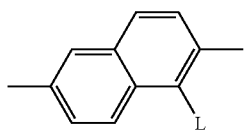 (A-A1-10)

-continued

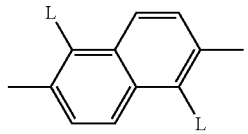 (A-A1-11)

From the perspective of the liquid crystallinity, the availability of raw materials, and the ease of synthesis of the compound, $Z^{31}$ and $Z^{41}$ preferably independently denote a single bond, —OCH$_2$—, —CH$_2$O—, —COO—, —OCO—, —CF$_2$O—, —OCF$_2$—, —CH$_2$CH$_2$—, —CF$_2$CF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —CH=CH—, —CF=CF—, —C≡C—, or a single bond, more preferably —OCH$_2$—, —CH$_2$O—, —CH$_2$CH$_2$—, —COO—, —OCO—, —COO—CH$_2$CH$_2$—, —OCO—CH$_2$CH$_2$—, —CH$_2$CH$_2$—COO—, —CH$_2$CH$_2$—OCO—, —CH=CH—, —C≡C—, or a single bond, still more preferably —CH$_2$CH$_2$—, —COO—, —OCO—, —COO—CH$_2$CH$_2$—, —OCO—CH$_2$CH$_2$—, —CH$_2$CH$_2$—COO—, —CH$_2$CH$_2$—OCO—, or a single bond, particularly preferably —COO—, —OCO—, or a single bond.

From the perspective of liquid crystallinity, the ease of synthesis, and storage stability, m31 and m41 are preferably independently an integer in the range of 1 to 4, more preferably an integer in the range of 1 to 3, particularly preferably 1 or 2. m31+m41 is preferably an integer in the range of 1 to 4, particularly preferably 2, 3, or 4.

$T^{21}$ more preferably denotes a group represented by one of the formulae (T2-1) to (T2-6), still more preferably a group represented by the formula (T2-1) or (T2-2).

If $M^2$ denotes a group represented by the formula (I-M21), $W^1$ preferably denotes a group selected from <$W^1$-A11> to <$W^1$-A15>, more preferably <$W^1$-A11>, <$W^1$-A12>, or <$W^1$-A14>.

<$M^2$-A2>

For a compound in which <n1 and n2 are 0, and n3 is 1>, in careful consideration of the appearances and orientation defects after ultraviolet irradiation of a polymer film produced from the compound, $M^2$ in the general formula (I) is preferably represented by the following formula (I-M22), and

[Chem. 39]

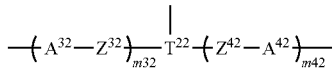 (I-M22)

(wherein present $A^{32}$ and present $A^{42}$ independently denote a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, these groups may be unsubstituted or substituted by one or more substituents L's, a plurality of $A^{32}$'s and/or $A^{42}$'s, if present at all, may be the same or different, present $Z^{32}$ and present $Z^{42}$ independently denote —O—, —S—, —OCH$_2$—, —CH$_2$O—, —CH$_2$CH$_2$—, —CO—, —COO—, —OCO—, —CO—S—, —S—CO—, —O—CO—O—, —CO—

NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C—, or a single bond, a plurality of Z$^{32}$'s and/or Z$^{42}$'s, if present at all, may be the same or different, T$^{22}$ denotes an optionally substituted trivalent group, and m32 and m42 are independently an integer in the range of 0 to 5)

in the formula (I-M22), T$^{22}$ preferably denotes a group selected from the following formulae (T2-11) to (T2-27),

[Chem. 40]

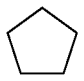 (T2-11)

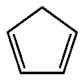 (T2-12)

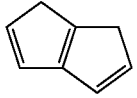 (T2-13)

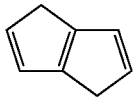 (T2-14)

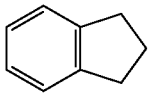 (T2-15)

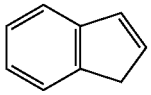 (T2-16)

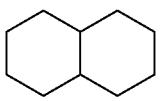 (T2-17)

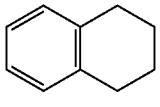 (T2-18)

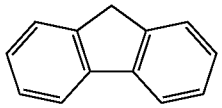 (T2-19)

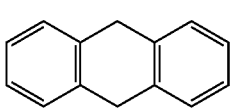 (T2-20)

-continued

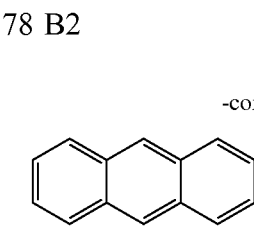 (T2-21)

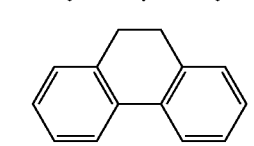 (T2-22)

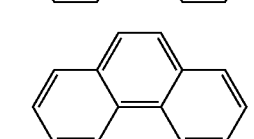 (T2-23)

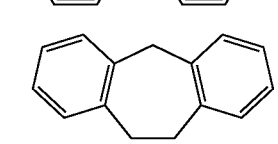 (T2-24)

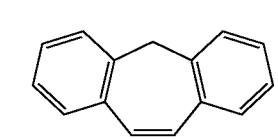 (T2-25)

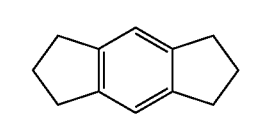 (T2-26)

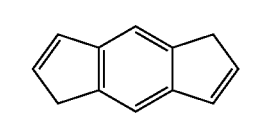 (T2-27)

(wherein the group may have a bonding arm at any position, any —CH= may independently be substituted by —N=, —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more L's)

the following formulae (T2-28) to (T2-31),

[Chem. 41]

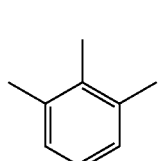 (T2-28)

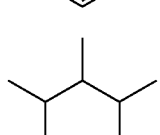 (T2-28)

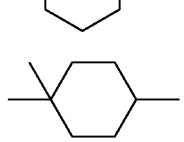 (T2-30)

(T2-31)

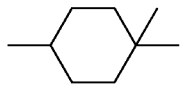

(wherein any —CH= may independently be substituted by —N=, —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more L's)

the following formula (T2-32), and

[Chem. 42]

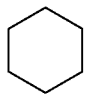

(T2-32)

(wherein the group may have a bonding arm at any position, at least one —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more L's)

the following formula (T2-33) or (T2-34), and

[Chem. 43]

(T2-33)

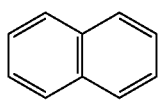

(T2-34)

(wherein the group may have a bonding arm at any position, at least one —CH= may independently be substituted by —N=, and these groups may be unsubstituted or substituted by one or more L's)

m32+m42 is preferably an integer in the range of 1 to 6.

M$^2$ is preferably represented by the following formula (I-M222),

[Chem. 44]

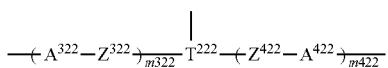

(I-M222)

(wherein A$^{322}$ and A$^{422}$ independently denote a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, these groups may be unsubstituted or substituted by one or more substituents L's, a plurality of A$^{322}$'s and/or A$^{422}$'s, if present at all, may be the same or different, Z$^{322}$ and Z$^{422}$ independently denote —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C—, or a single bond, a plurality of Z$^{322}$'s and/or Z$^{422}$'s, if present at all, may be the same or different, and T$^{222}$ denotes an optionally substituted trivalent group)

in the formula (I-M222), T$^{222}$ preferably denotes a group selected from the following formulae (T2-35) to (T2-41), and

[Chem. 45]

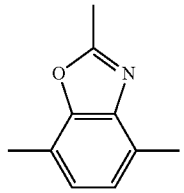

(T2-35)

(T2-36)

(T2-37)

(T2-38)

(T2-39)

(T2-40)

(T2-41)

(wherein R⁰ denotes a hydrogen atom or an alkyl group having 1 to 20 carbon atoms)

m322 and m422 are preferably independently 1 or 2.

From the perspective of the availability of raw materials and the ease of synthesis, $A^{322}$ and $A^{22}$ preferably independently denote a 1,4-phenylene group, a 1,4-cyclohexylene group, or a naphthalene-2,6-diyl group optionally substituted by one or more substituents L's, more preferably a group selected from the following formulae (A-A2-1) to (A-A2-11), still more preferably a group selected from the formulae (A-A2-1) to (A-A2-8), particularly preferably a group selected from the formulae (A-A2-1) to (A-A2-4).

[Chem. 46]

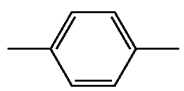
(A-A2-1)

(A-A2-2)

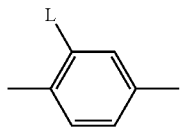
(A-A2-3)

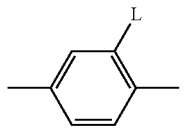
(A-A2-4)

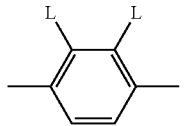
(A-A2-5)

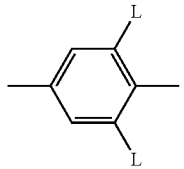
(A-A2-6)

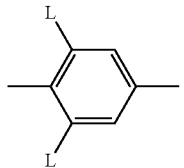
(A-A2-7)

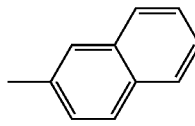
(A-A2-8)

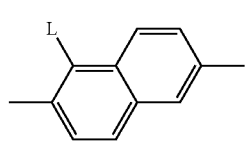
(A-A2-9)

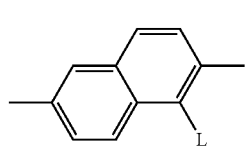
(A-A2-10)

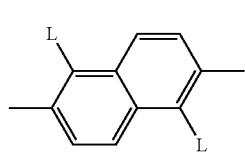
(A-A2-11)

From the perspective of the liquid crystallinity, the availability of raw materials, and the ease of synthesis of the compound, $Z^{322}$ and $Z^{422}$ preferably independently denote a single bond, —OCH₂—, —CH₂O—, —COO—, —OCO—, —CF₂O—, —OCF₂—, —CH₂CH₂—, —CF₂CF₂—, —CH=CH—COO—, —CH=CH—OCO—, —COO—CH=CH—, —OCO—CH=CH—, —COO—CH₂CH₂—, —OCO—CH₂CH₂—, —CH₂CH₂—COO—, —CH₂CH₂—OCO—, —CH=CH—, —CF=CF—, —C≡C—, or a single bond, more preferably —OCH₂—, —CH₂O—, —CH₂CH₂—, —COO—, —OCO—, —COO—CH₂CH₂—, —OCO—CH₂CH₂—, —CH₂CH₂—COO—, —CH₂CH₂—OCO—, —CH=CH—, —C≡C—, or a single bond, still more preferably —CH₂CH₂—, —COO—, —OCO—, —COO—CH₂CH₂—, —OCO—CH₂CH₂—, —CH₂CH₂—COO—, —CH₂CH₂—OCO—, or a single bond, particularly preferably —COO—, —OCO—, or a single bond.

$T^{222}$ preferably denotes a group represented by the formula (T2-36), (T2-38), (T2-39), (T2-40), or (T2-41).

<W¹-A2>

For a compound in which <n1 and n2 are 0, and n3 is 1>, in careful consideration of the appearances and orientation defects after ultraviolet irradiation of a polymer film produced from the compound, W¹ in the general formula (I) preferably denotes a group selected from the following formula (I-W19).

[Chem. 47]

(I-W19)

(wherein V¹ and V² independently denote a single bond or a divalent linking group, B¹ independently denotes a group selected from the formulae (B-1) to (B-21) and a single bond, and n4 is an integer in the range of 0 to 5)

[Chem. 48]

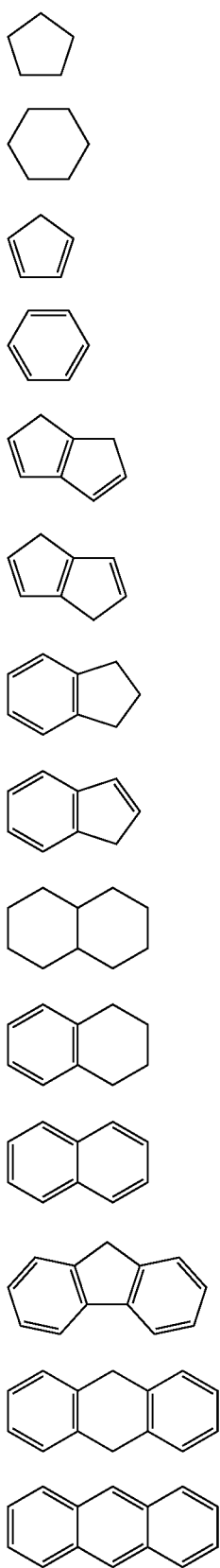
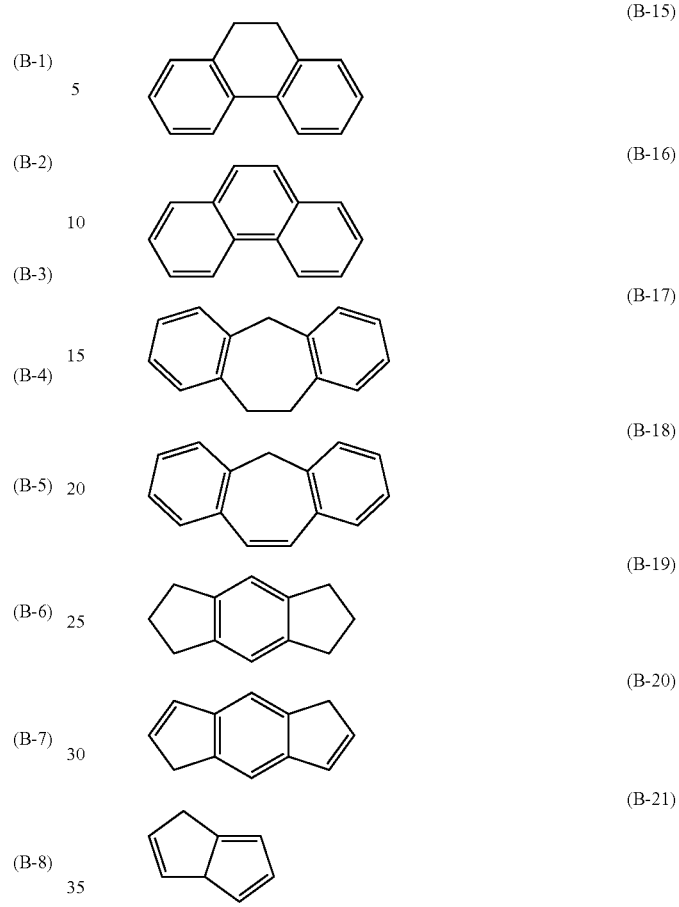

(wherein the group may have a bonding arm at any position, any —CH= may independently be substituted by —N=, —CH₂— may independently be substituted by —O—, —S—, —NR⁰— (wherein R⁰ denotes a hydrogen atom or an alkyl group having 1 to 20 carbon atoms), —CS—, or —CO—, provided that no —O—O— bond is included, and these groups may be unsubstituted or substituted by one or more substituents L's)

$V^1$ and $V^2$ preferably independently denote a group represented by one of the formulae (V-1) to (V-15) described in <<$W^1$, $W^2$>> (wherein $Y^1$, if present at all, preferably denotes a group selected from the perspective of the availability of the raw materials described in <<$W^1$, $W^2$>> and the ease of synthesis), a single bond, a double bond, —O—, —S—, —OCH₂—, —CH₂O—, —CO—, —CH₂—, —COO—, —OCO—, —CO—S—, —S—CO—, —O—CO—O—, —CO—NH—, —NH—CO—, —CS—NH—, —NH—CS—, —SCH₂—, —CH₂S—, —CF₂O—, —OCF₂—, —CF₂S—, —SCF₂—, —CH=CH—COO—, —CH=CH—OCO—, —COO—CH=CH—, —OCO—CH=CH—, —CH₂CH₂—, —COO—CH₂CH₂—, —OCO—CH₂CH₂—, —CH₂CH₂—COO—, —CH₂CH₂—OCO—, —COO—CH₂—, —OCO—CH₂—, —CH₂COO—, or —CH₂—OCO—, more preferably a group selected from the formulae (V-1), (V-2), (V-5), (V-6), (V-7), (V-8), (V-9), (V-12), and (V-13), —COO—, and —OCO—, still more preferably a group selected from the formulae (V-5), (V-6), (V-7), (V-8), (V-9), (V-12), and (V-13), —COO—, and —OCO—.

$B^1$ preferably independently denotes a group selected from the formulae (B-4), (B-8), (B-11), and (B-12) and a single bond, more specifically, preferably a group selected from the formulae (B-4-1), (B-8-7), (B-11-1), and (B-12-4) described in <<$W^1$, $W^2$>> and a single bond, more preferably a group selected from the formulae (B-4-1), (B-8-7), and (B-12-4) and a single bond.

n4 preferably ranges from 0 to 8, more preferably 0 to 6.

If $T^{222}$ denotes a group selected from the formulae (T2-35) and (T2-36), then in the formula (I-W19), preferably, $B^1$ denotes a single bond, n4 ranges from 1 to 6, and $V^1$ and $V^2$ denote a group other than a single bond.

<$M^2$-A3>

For a compound in which <n1 and n2 are 0, and n3 is 1>, in careful consideration of storage stability when added to a polymerizable composition and orientation defects after ultraviolet irradiation and the thickness uniformity of a polymer film produced from the compound, $M^2$ in the general formula (I) is preferably represented by the following formula (I-M23), and

[Chem. 49]

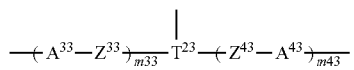

(I-M23)

(wherein present $A^{33}$ and present $A^{43}$ independently denote a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, these groups may be unsubstituted or substituted by one or more substituents L's, a plurality of $A^{33}$'s and/or $A^{43}$'s, if present at all, may be the same or different, present $Z^{33}$ and present $Z^{43}$ independently denote —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C—, or a single bond, a plurality of $Z^{33}$'s and/or $Z^{43}$'s, if present at all, may be the same or different, $T^{23}$ denotes an optionally substituted trivalent group, and m33 and m43 are independently an integer in the range of 0 to 5)

in the formula (I-M23), $T^{23}$ preferably denotes an optionally substituted noncyclic group having 1 to 80 carbon atoms, any carbon atom of the noncyclic group may be substituted by a heteroatom, and m33+m43 is preferably an integer in the range of 1 to 6.

$M^2$ is preferably represented by the following formula (I-M232),

[Chem. 50]

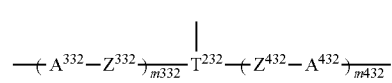

(I-M232)

(wherein present $A^{332}$ and present $A^{432}$ independently denote a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, these groups may be unsubstituted or substituted by one or more substituents L's, a plurality of $A^{332}$'s and/or $A^{432}$'s, if present at all, may be the same or different, present $Z^{332}$ and present $Z^{432}$ independently denote —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C—, or a single bond, a plurality of $Z^{332}$'s and/or $Z^{432}$'s, if present at all, may be the same or different, $T^{232}$ denotes an optionally substituted trivalent group, and m332 and m432 are independently an integer in the range of 0 to 5) in the formula (I-M232), $T^{232}$ preferably denotes a group represented by the formula (T-22), and

[Chem. 51]

 (T-22)

(wherein the group may have a bonding arm at any position, any —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more L's, and k1 is an integer in the range of 1 to 20)

m332+m432 is preferably an integer in the range of 1 to 6.

From the perspective of the availability of raw materials and the ease of synthesis, $A^{33}$ and $A^{432}$ preferably independently denote a 1,4-phenylene group, a 1,4-cyclohexylene group, or a naphthalene-2,6-diyl group optionally substituted by one or more substituents L's, more preferably a group selected from the following formulae (A-A2-1) to (A-A2-11), still more preferably a group selected from the formulae (A-A3-1) to (A-A3-8), particularly preferably a group selected from the formulae (A-A3-1) to (A-A3-4).

[Chem. 52]

(A-A3-1)
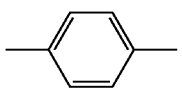

(A-A3-2)
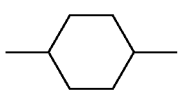

(A-A3-3)
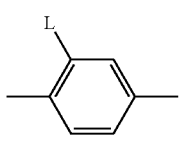

(A-A3-4)
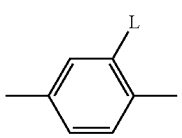

(A-A3-5)
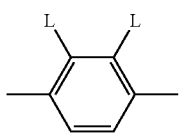

(A-A3-6)
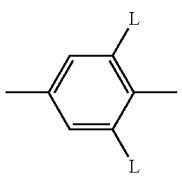

(A-A3-7)
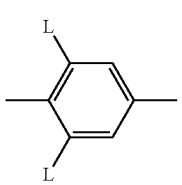

(A-A3-8)
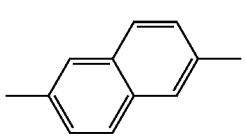

(A-A3-9)
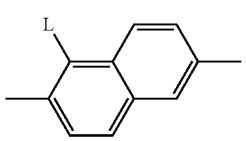

(A-A3-10)
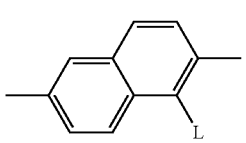

(A-A3-11)
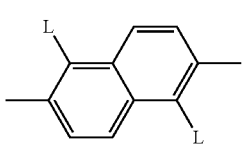

From the perspective of the liquid crystallinity, the availability of raw materials, and the ease of synthesis of the compound, $Z^{332}$ and $Z^{432}$ preferably independently denote a single bond, —OCH$_2$—, —CH$_2$O—, —COO—, —OCO—, —CF$_2$O—, —OCF$_2$—, —CH$_2$CH$_2$—, —CF$_2$CF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —CH=CH—, —CF=CF—, —C≡C—, or a single bond, more preferably —OCH$_2$—, —CH$_2$O—, —CH$_2$CH$_2$—, —COO—, —OCO—, —COO—CH$_2$CH$_2$—, —OCO—CH$_2$CH$_2$—, —CH$_2$CH$_2$—COO—, —CH$_2$CH$_2$—OCO—, —CH=CH—, —C≡C—, or a single bond, still more preferably —CH$_2$CH$_2$—, —COO—, —OCO—, —COO—CH$_2$CH$_2$—, —OCO—CH$_2$CH$_2$—, —CH$_2$CH$_2$—COO—, —CH$_2$CH$_2$—OCO—, or a single bond, particularly preferably —COO—, —OCO—, or a single bond.

From the perspective of liquid crystallinity, the ease of synthesis, and storage stability, m332 and m432 are preferably independently an integer in the range of 1 to 4, more preferably an integer in the range of 1 to 3, particularly preferably 1 or 2. m31+m41 is preferably an integer in the range of 1 to 4, particularly preferably 2, 3, or 4.

$T^{232}$ preferably denotes a group selected from the following formulae (T-22-1) and (T-22-2), more preferably the formula (T-22-1). Particularly preferably, k131 and k132 in the formula (T-22-1) are 1.

[Chem. 53]

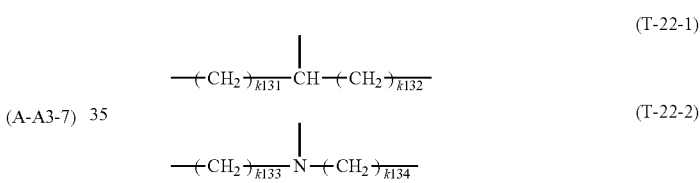

(T-22-1)

(T-22-2)

(wherein any —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more L's, and k131 to k134 are independently an integer in the range of 0 to 20)

<W$^1$-A3>

For a compound in which <n1 and n2 are 0, and n3 is 1>, in careful consideration of storage stability when added to a polymerizable composition and orientation defects after ultraviolet irradiation and the thickness uniformity of a polymer film produced from the compound, W$^1$ in the general formula (I) preferably denotes a group selected from the following formula (I-W20).

[Chem. 54]

(I-W20)

(wherein $V^1$ and present $V^2$ independently denote a single bond or a divalent linking group, present $B^1$ independently denotes a group selected from the formulae (B-1) to (B-21) and a single bond, and n4 is an integer in the range of 0 to 5)

[Chem. 55]

 (B-1)

 (B-2)

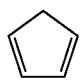 (B-3)

 (B-4)

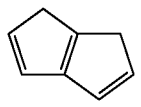 (B-5)

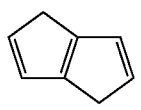 (B-6)

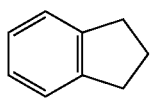 (B-7)

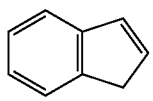 (B-8)

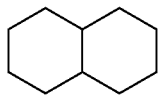 (B-9)

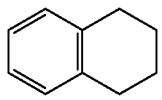 (B-10)

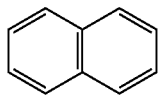 (B-11)

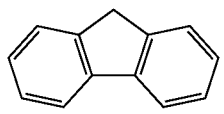 (B-12)

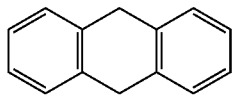 (B-13)

-continued

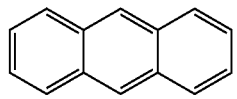 (B-14)

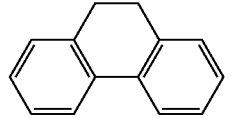 (B-15)

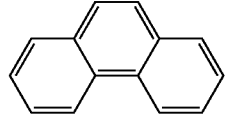 (B-16)

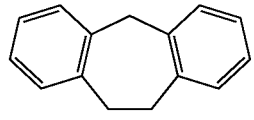 (B-17)

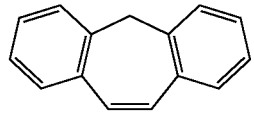 (B-18)

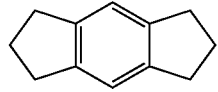 (B-19)

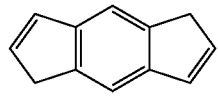 (B-20)

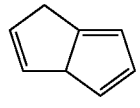 (B-21)

(wherein the group may have a bonding arm at any position, any —CH= may independently be substituted by —N=, —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more substituents L's)

$V^1$ and $V^2$ preferably independently denote a group represented by one of the formulae (V-1) to (V-15) described in <<W$^1$, W$^2$>> (wherein Y$^1$, if present at all, preferably denotes a group selected from the perspective of the availability of the raw materials described in <<W$^1$, W$^2$>> and the ease of synthesis), a single bond, a double bond, —O—, —S—, —OCH$_2$—, —CH$_2$O—, —CO—, —CH$_2$—, —COO—, —OCO—, —CO—S—, —S—CO—, —O—CO—O—, —CO—NH—, —NH—CO—, —CS—NH—, —NH—CS—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —CH$_2$CH$_2$—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, or —CH$_2$—OCO—, more preferably a group selected from the formulae (V-5), (V-6), (V-8), (V-9), and (V-10) and a single bond, still more preferably a group selected from the formulae (V-5), (V-6), (V-8), and (V-9). From the perspective of the ease of synthesis, among the groups represented by $V^2$, a group directly bonded to $T^{232}$ is preferably a group other than the groups represented by the formula (V-6).

$B^1$ preferably independently denotes a group selected from the formulae (B-4), (B-8), and (B-11) and a single bond, more specifically, preferably a group selected from the formulae (B-4-1), (B-8-7), and (B-11-1) described in <<$W^1$, $W^2$>> and a single bond, more preferably a group selected from the formula (B-4-1) and a single bond.

<$R^3$ and $R^4$>

In a compound in which <n1 and n2 are 0, and n3 is 1>, $M^2$ and $W^1$ described above are preferably appropriately selected, and $R^3$ and $R^4$ preferably denote the following groups.

$R^3$ preferably denotes a group represented by the formula (I-R),

[Chem. 56]

$$P^1\text{-}(S^1\text{-}X^1)_k \quad \text{(I-R)}$$

(wherein $P^1$ denotes a polymerizable group, $S^1$ denotes a spacer group or a single bond, a plurality of $S^{13}$ s, if present at all, may be the same or different, $X^1$ denotes —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond, a plurality of $X^1$'s, if present at all, may be the same or different (provided that $P^1$-($S^1$-$X^1$)$_k$- has no —O—O— bond), and k is an integer in the range of 0 to 10)

$R^4$ preferably denotes a group selected from the groups represented by the formula (I-R) and $R^5$ (wherein $R^5$ denotes a hydrogen atom, a fluorine atom, a chlorine atom, a bromine atom, an iodine atom, a pentafluorosulfuranyl group, a nitro group, a cyano group, an isocyano group, an amino group, a hydroxy group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms with one —CH$_2$— or nonadjacent two or more —CH$_2$—'s optionally independently substituted by —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and any hydrogen atom of the alkyl group may be substituted by a fluorine atom), $R^3$ and $R^4$ particularly preferably denote a group represented by the formula (I-R), and in this case, $P^1$, $S^1$, $X^1$, and k are selected from the preferred groups and numerical values described in <<$R^1$, $R^2$, $R^3$, $R^4$>>.

Compound in which <<n1 is 1, n2 is 0, and n3 is 1>>

<$W^1$-B11>

For a compound in which <n1 is 1, n2 is 0, and n3 is 1>, in careful consideration of the nonuniform orientation and surface hardness of a polymer film produced from the compound, $W^1$ in the general formula (I) preferably denotes a group represented by the following formula (I-W15).

[Chem. 57]

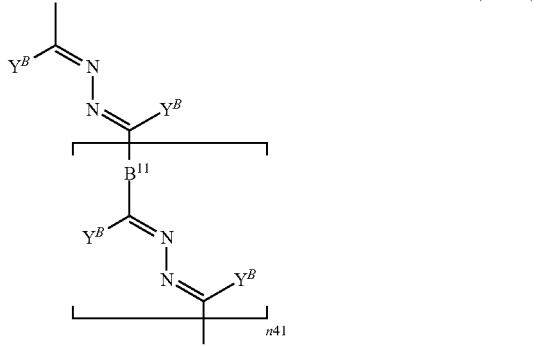

(I-W15)

(wherein $Y^B$ denotes a hydrogen atom, a fluorine atom, a chlorine atom, a bromine atom, an iodine atom, a pentafluorosulfuranyl group, a nitro group, a cyano group, an isocyano group, an amino group, a hydroxy group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms with one —CH$_2$— or nonadjacent two or more —CH$_2$—'s optionally independently substituted by —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, any hydrogen atom of the alkyl group may be substituted by a fluorine atom, a plurality of $Y^B$'s, if present at all, may be the same or different, or $Y^B$ may denote a group represented by P-(S-X)$_j$-, P denotes a polymerizable group, S denotes a spacer group or a single bond, a plurality of S's, if present at all, may be the same or different, X denotes —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond, a plurality of X's, if present at all, may be the same or different (provided that P-(S-X)$_j$- has no —O—O— bond), and j is an integer in the range of 0 to 10, and $B^{11}$ denotes a group selected from the formulae (B-1) to (B-21) and a single bond, and n41 is an integer in the range of 0 to 5)

[Chem. 58]

(B-1)

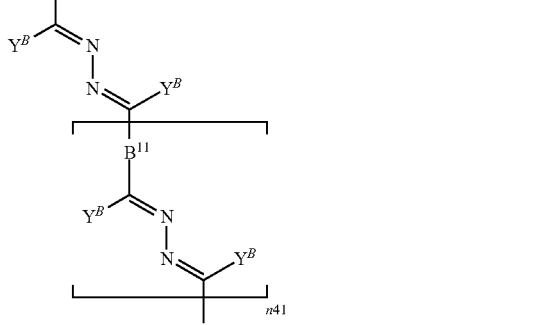

(B-2)

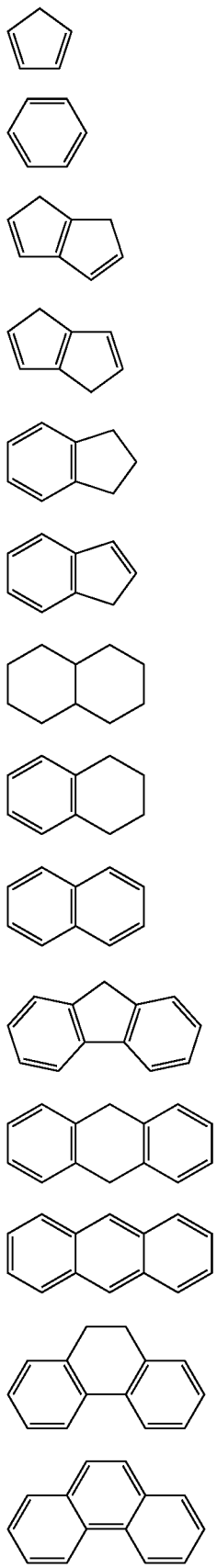

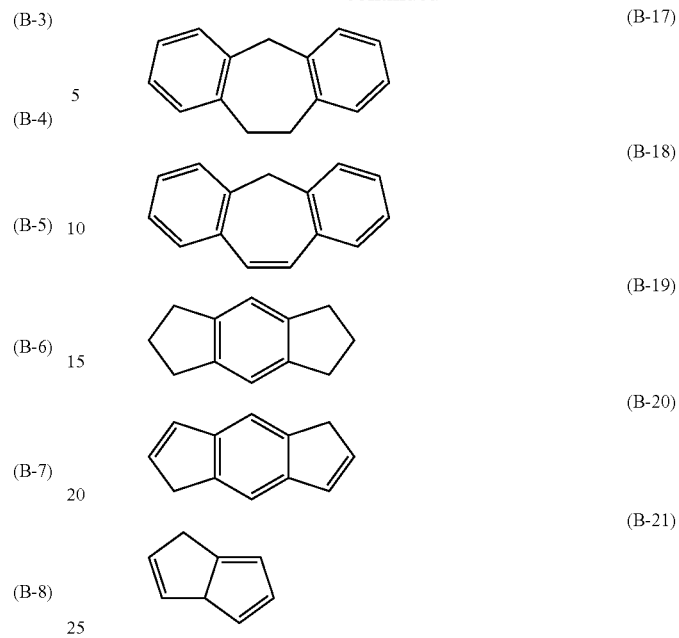

(wherein the group may have a bonding arm at any position, any —CH= may independently be substituted by —N=, —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more substituents L's)

Y$^B$ more preferably denotes a hydrogen atom, a fluorine atom, a chlorine atom, a nitro group, a cyano group, or a linear or branched alkyl group having 1 to 20 carbon atoms with one —CH$_2$— or nonadjacent two or more —CH$_2$—'s optionally substituted by —O—, still more preferably a hydrogen atom or a methyl group, still more preferably a hydrogen atom, B$^{11}$ preferably independently denotes a group selected from the formulae (B-4) and (B-11), more specifically, specifically preferably a group selected from the formulae (B-4-1) and (B-11-1) described in <<W$^1$, W$^2$>>, and n41 is more preferably 0, 1, or 2, still more preferably 0 or 1, still more preferably 0.

<W$^1$-B2>

For a compound in which <n1 is 1, n2 is 0, and n3 is 1>, in careful consideration of the surface hardness and adhesiveness of a polymer film produced from the compound, W in the general formula (I) preferably denotes a group selected from the following formula (I-W21).

[Chem. 59]

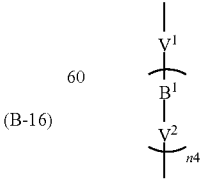

(I-W21)

(wherein V$^1$ and V$^2$ independently denote a single bond or a divalent linking group, B$^1$ independently denotes a group selected from the formulae (B-1) to (B-21) and a single bond, and n4 is an integer in the range of 0 to 5)

[Chem. 60]

(wherein the group may have a bonding arm at any position, any —CH= may independently be substituted by =N—, —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more substituents L's)

V$^1$ and V$^2$ preferably independently denote a group represented by one of the formulae (V-1) to (V-15) described in <<W$^1$, W$^2$>> (wherein Y$^1$, if present at all, preferably denotes a group selected from the perspective of the availability of the raw materials described in <<W$^1$, W$^2$>> and the ease of synthesis), a single bond, a double bond, —O—, —S—, —OCH$_2$—, —CH$_2$O—, —CO—, —CH$_2$—, —COO—, —OCO—, —CO—S—, —S—CO—, —O—CO—O—, —CO—NH—, —NH—CO—, —CS—NH—, —NH—CS—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —CH$_2$CH$_2$—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$COO—, or —CH$_2$—OCO—, more preferably a group selected from the formulae (V-1), (V-2), (V-5), (V-6), (V-7), (V-8), and (V-9), a single bond, —COO—, —OCO—, —CO—NH—, —NH—CO—, and —CH$_2$CH$_2$—, still more preferably a group selected from the formulae (V-1), (V-2), (V-5), and (V-7), a single bond, —COO—, —OCO—, —CO—NH—, —NH—CO—, and —CH$_2$CH$_2$—, still more preferably a group selected from the formulae (V-1) and (V-2), —COO—, —OCO—, —CO—NH—, —NH—CO—, and —CH$_2$CH$_2$—.

B$^1$ preferably independently denotes a group selected from the formulae (B-4) and (B-20) and a single bond, more specifically, specifically preferably a group selected from the formulae (B-4-1) and (B-20-2) described in <<W$^1$, W$^2$>> and a single bond.

<W$^1$-B3>

For a compound in which <n1 is 1, n2 is 0, and n3 is 1>, in careful consideration of the appearances after ultraviolet irradiation and adhesiveness of a polymer film produced from the compound, W$^1$ in the general formula (I) preferably denotes a group selected from the following formula (I-W22).

[Chem. 61]

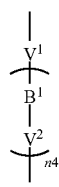

(I-W22)

(wherein V$^1$ and V$^2$ independently denote a single bond or a divalent linking group, B$^1$ independently denotes a group selected from the formulae (B-1) to (B-21) and a single bond, and n4 is an integer in the range of 0 to 5)

[Chem. 62]

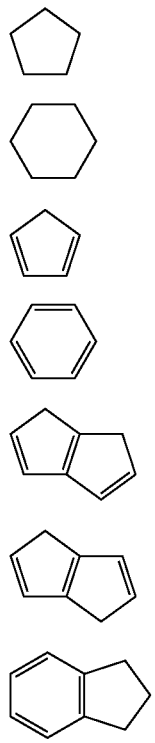

(B-1)

(B-2)

(B-3)

(B-4)

(B-5)

(B-6)

(B-7)

-continued

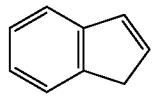 (B-8)

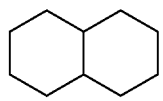 (B-9)

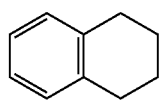 (B-10)

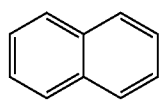 (B-11)

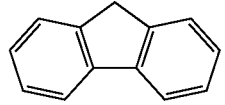 (B-12)

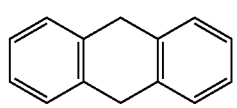 (B-13)

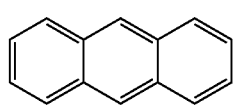 (B-14)

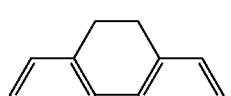 (B-15)

 (B-16)

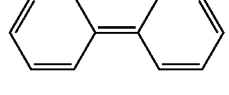 (B-17)

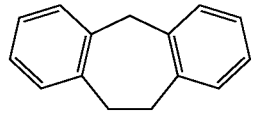 (B-18)

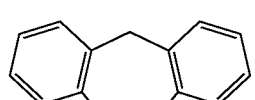 (B-19)

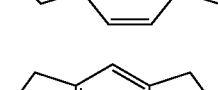 (B-20)

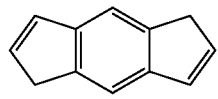

-continued

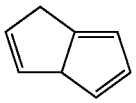
(B-21)

(wherein the group may have a bonding arm at any position, any —CH= may independently be substituted by —N=, —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more substituents L's)

V$^1$ and V$^2$ preferably independently denote a group represented by one of the formulae (V-1) to (V-15) described in <<W$^1$, W$^2$>> (wherein Y$^1$, if present at all, preferably denotes a group selected from the perspective of the availability of the raw materials described in <<W$^1$, W$^2$>> and the ease of synthesis), a single bond, a double bond, —O—, —S—, —OCH$_2$—, —CH$_2$O—, —CO—, —CH$_2$—, —COO—, —OCO—, —CO—S—, —S—CO—, —O—CO—O—, —CO—NH—, —NH—CO—, —CS—NH—, —NH—CS—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —CH$_2$CH$_2$—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, or —CH$_2$—OCO—, more preferably the formula (V-6), (V-7), (V-8), (V-9), or (V-10), a single bond, —COO—, —OCO—, —CS—NH—, or —NH—CS—, still more preferably the formula (V-8) or (V-9), —COO—, or —OCO—.

B$^1$ preferably independently denotes a group selected from the formulae (B-4) and (B-11) and a single bond, more preferably a group selected from the formula (B-4) and a single bond, more specifically, preferably a group selected from the formulae (B-4-1) and (B-11-1) described in <<W$^1$, W$^2$>> and a single bond, more preferably a group selected from the formula (B-4-1) and a single bond.

<M$^1$-B, M$^2$-B>

Because of the structure of a compound in which <n1 is 1, n2 is 0, and n3 is 1>, a polymer film produced from the compound has less nonuniform orientation, high surface hardness, or high adhesiveness. Thus, in the general formula (I), preferably, M1 is represented by the following formula (I-M14), and M$^2$ is represented by the following formula (I-M24), and

[Chem. 63]

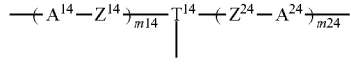
(I-M14)

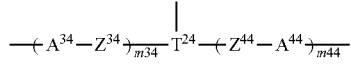
(I-M24)

(wherein A$^{14}$, A$^{24}$, A$^{34}$, and A$^{44}$ independently denote a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, these groups may be unsubstituted or substituted by one or more substituents L's, a plurality of A$^{14}$'s, A$^{24}$'s, A$^{34}$'s, and/or A$^{44}$'s, if present at all, may be the same or different, Z$^{14}$, Z$^{24}$, Z$^{34}$, and Z$^{44}$ independently denote —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C—, or a single bond, a plurality of Z$^{14}$'s, Z$^{24}$'s, Z$^{34}$'s, and/or Z$^{44}$'s, if present at all, may be the same or different, and m14, m24, m34, and m44 are independently an integer in the range of 1 to 5)

T$^{14}$ and T$^{24}$ in the formulae (I-M14) and (I-M24) independently denote a group selected from the following formulae (T-1) to (T-22).

[Chem. 64]

(T-1)

(T-2)

(T-3)

(T-4)

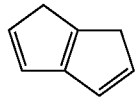
(T-5)

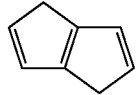
(T-6)

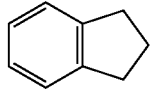
(T-7)

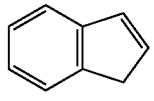
(T-8)

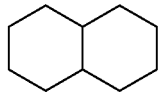
(T-9)

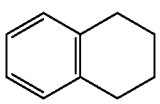 (T-10)

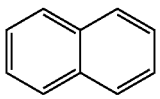 (T-11)

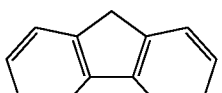 (T-12)

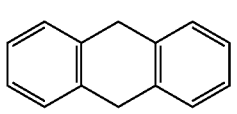 (T-13)

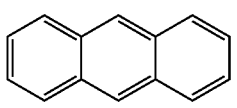 (T-14)

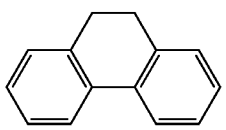 (T-15)

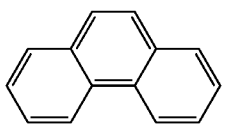 (T-16)

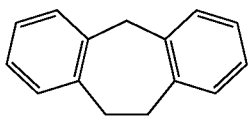 (T-17)

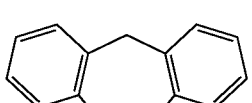 (T-18)

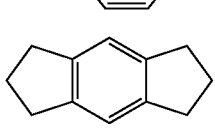 (T-19)

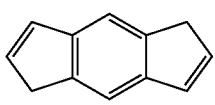 (T-20)

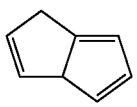 (T-21)

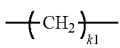 (T-22)

(wherein the group may have a bonding arm at any position, any —CH═ may independently be substituted by —N═, —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more L's, and k1 is an integer in the range of 1 to 20)

T$^{14}$ and T$^{24}$ preferably independently denote a group selected from the formulae (T-1) to (T-22). More preferably, T$^{14}$ and T$^{24}$ denote the same group.

From the perspective of the availability of raw materials and the ease of synthesis, A$^{14}$, A$^{24}$, A$^{34}$, and A$^{44}$ preferably independently denote a 1,4-phenylene group, a 1,4-cyclohexylene group, or a naphthalene-2,6-diyl group optionally substituted by one or more substituents L's, more preferably a group selected from the following formulae (A-A2-1) to (A-A2-11), still more preferably a group selected from the formulae (A-A3-1) to (A-A3-8), particularly preferably a group selected from the formulae (A-A3-1) to (A-A3-4).

[Chem. 65]

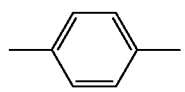 (A-A3-1)

 (A-A3-2)

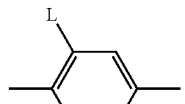 (A-A3-3)

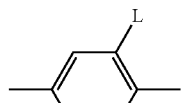 (A-A3-4)

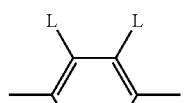 (A-A3-5)

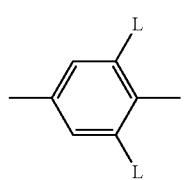 (A-A3-6)

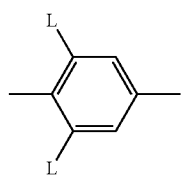 (A-A3-7)

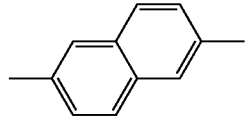 (A-A3-8)

-continued (A-A3-9)

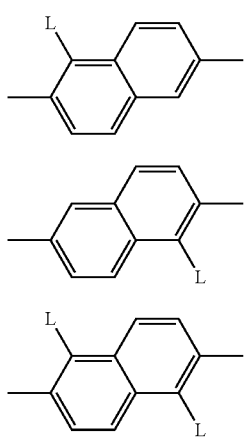

(A-A3-10)

(A-A3-11)

From the perspective of the liquid crystallinity, the availability of raw materials, and the ease of synthesis of the compound, $Z^{14}$, $Z^{24}$, $Z^{34}$, and $Z^{44}$ preferably independently denote a single bond, —OCH$_2$—, —CH$_2$O—, —COO—, —OCO—, —CF$_2$O—, —OCF$_2$—, —CH$_2$CH$_2$—, —CF$_2$CF$_2$—, —CH═CH—COO—, —CH═CH—OCO—, —COO—CH═CH—, —OCO—CH═CH—, —COO—CH$_2$CH$_2$—, —OCO—CH$_2$CH$_2$—, —CH$_2$CH$_2$—COO—, —CH$_2$CH$_2$—OCO—, —CH═CH—, —CF═CF—, —C≡C—, or a single bond, more preferably —OCH$_2$—, —CH$_2$O—, —CH$_2$CH$_2$—, —COO—, —OCO—, —COO—CH$_2$CH$_2$—, —OCO—CH$_2$CH$_2$—, —CH$_2$CH$_2$—COO—, —CH$_2$CH$_2$—OCO—, —CH═CH—, —C≡C—, or a single bond, still more preferably —CH$_2$CH$_2$—, —COO—, —OCO—, —COO—CH$_2$CH$_2$—, —OCO—CH$_2$CH$_2$—, —CH$_2$CH$_2$—COO—, —CH$_2$CH$_2$—OCO—, or a single bond, particularly preferably —COO—, —OCO—, or a single bond.

From the perspective of liquid crystallinity, the ease of synthesis, and storage stability, m14, m24, m34, and m44 are preferably independently an integer in the range of 1 to 4, more preferably an integer in the range of 1 to 3, particularly preferably 1 or 2. Each of m14+m24 and m34+m44 is preferably an integer in the range of 1 to 4, particularly preferably 2, 3, or 4.

<M$^1$-B11, M$^2$-B11>

In careful consideration of the nonuniform orientation and surface hardness of a polymer film produced from the compound, $T^{14}$ in the formula (I-M14) preferably denotes the one described above, $T^{24}$ in the formula (I-M24) preferably denotes a group selected from the following formulae (T2-1) to (T2-10), and these groups may be unsubstituted or substituted by one or more substituents L's.

[Chem. 66]

(T2-1)

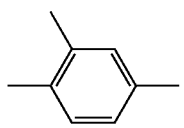

(T2-2)

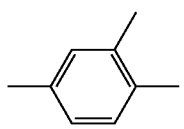

(T2-3)

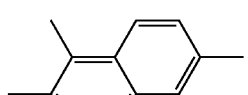

(T2-4)

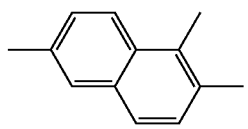

(T2-5)

(T2-6)

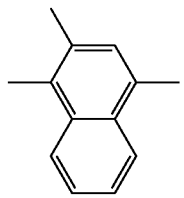

(T2-7)

(T2-8)

(T2-9)

(T2-10)

$T^{24}$ more preferably denotes a group represented by one of the formulae (T2-1) to (T2-6), still more preferably a group represented by the formula (T2-1) or (T2-2). More preferably, $T^{14}$ denotes a group selected from the following formulae (T1-1) to (T1-10), these groups may be unsubstituted or substituted by one or more substituents L's, and $T^{24}$ denotes a group selected from the formulae (T2-1) to (T2-10), and these groups may be unsubstituted or substituted by one or more substituents L's. Still more preferably, $T^{14}$ denotes a group selected from the formulae (T1-1) to (T1-6), and $T^{24}$ denotes a group selected from the formulae (T2-1) to (T2-6). Still more preferably, $T^{14}$ denotes a group selected from the formulae (T1-1) and (T1-2), and $T^{24}$ denotes a group selected from the formulae (T2-1) and (T2-2).

[Chem. 67]
(T1-1) 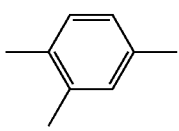
(T1-2) 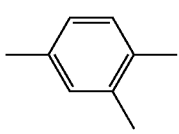
(T1-3) 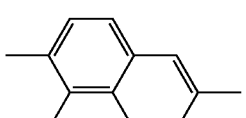
(T1-4) 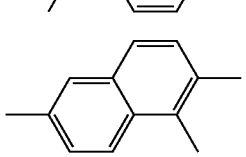
(T1-5) 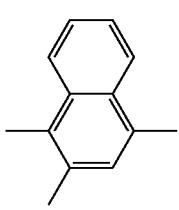
(T1-6) 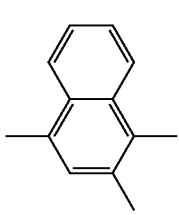
(T1-7) 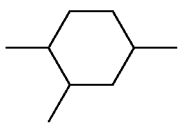
(T1-8) 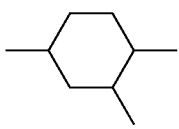
(T1-9) 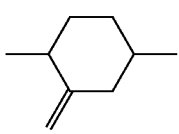
(T1-10) 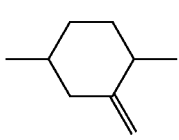
<M¹-B2>
In careful consideration of the surface hardness and adhesiveness of a polymer film produced from the compound, preferably, $T^{14}$ in the formula (I-M14) denotes the one described in <M1-B, M²-B>, and $T^{24}$ in the formula (I-M24) denotes a group selected from the following formulae (T2-11) to (T2-27),
[Chem. 68]
(T2-11) 
(T2-12) 
(T2-13) 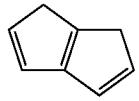
(T2-14) 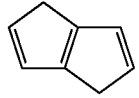
(T2-15) 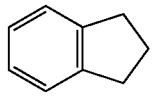
(T2-16) 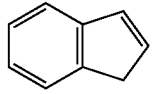
(T2-17) 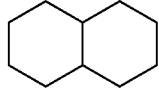
(T2-18) 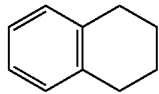
(T2-19) 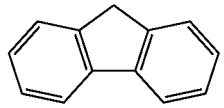
(T2-20) 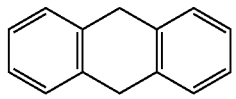
(T2-21) 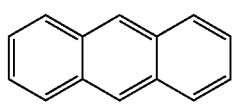
(T2-22) 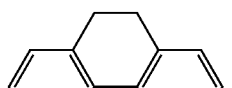
(T2-23) 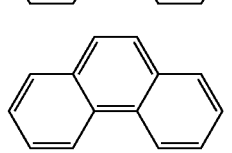

-continued (T2-24)
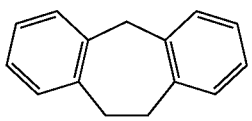

(T2-25)
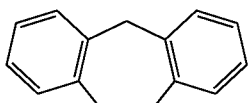

(T2-26)
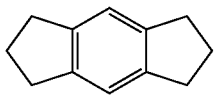

(T2-27)
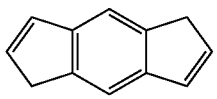

(wherein the group may have a bonding arm at any position, any —CH═ may independently be substituted by —N═, —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more L's)

the following formulae (T2-28) to (T2-31),

[Chem. 69]

(T2-28)
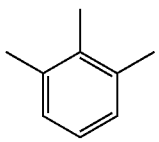

(T2-28)
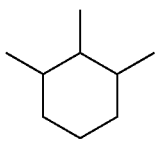

(T2-30)

(T2-31)

(wherein any —CH═ may independently be substituted by —N═, —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more L's)

the following formula (T2-32), and

[Chem. 70]

(T2-32)

(wherein the group may have a bonding arm at any position, at least one —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more L's)

the following formula (T2-33) or (T2-34), and

[Chem. 71]

(T2-33)

(T2-34)
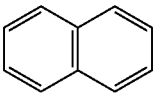

(wherein the group may have a bonding arm at any position, at least one —CH═ may independently be substituted by —N—, and these groups may be unsubstituted or substituted by one or more L's)

m34+m44 is an integer in the range of 1 to 6, and

T$^{24}$ in the formula (I-M24) particularly preferably denotes a group selected from the following formulae (T2-35) to (T2-41).

[Chem. 72]

(T2-35)
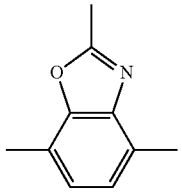

(T2-36)
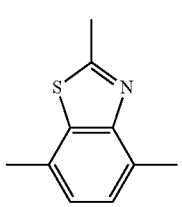

-continued (T2-37)
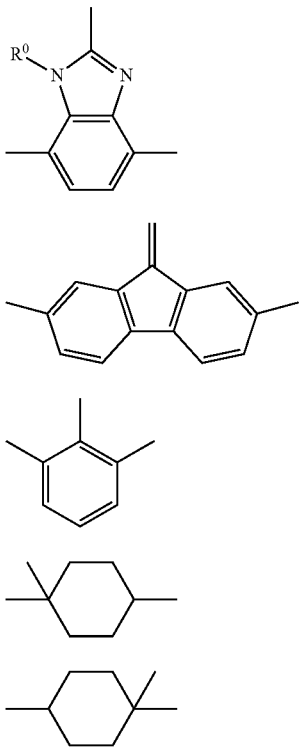
(T2-38)

(T2-39)

(T2-40)

(T2-41)

(wherein R⁰ denotes a hydrogen atom or an alkyl group having 1 to 20 carbon atoms)

More preferably, $T^{14}$ in the formula (I-M14) denotes a group selected from the following formulae (T1-11) to (T1-27),

[Chem. 73]

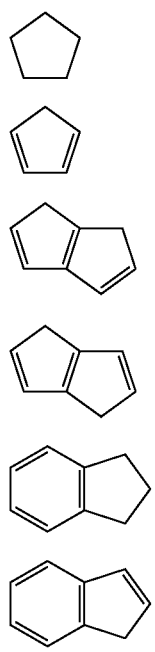

(T1-11)

(T1-12)

(T1-13)

(T1-14)

(T1-15)

(T1-16)

-continued

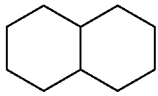 (T1-17)

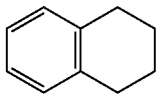 (T1-18)

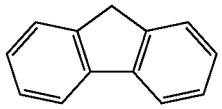 (T1-19)

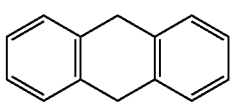 (T1-20)

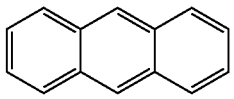 (T1-21)

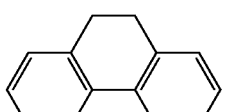 (T1-22)

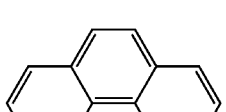 (T1-23)

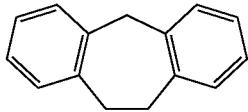 (T1-24)

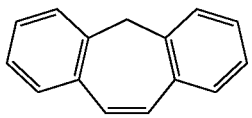 (T1-25)

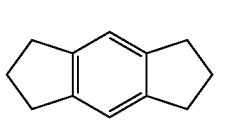 (T1-26)

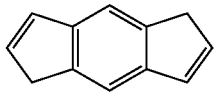 (T1-27)

(wherein the group may have a bonding arm at any position, any —CH= may independently be substituted by —N=, —CH₂— may independently be substituted by —O—, —S—, —NR⁰— (wherein R⁰ denotes a hydrogen atom or an alkyl group having 1 to 20 carbon atoms), —CS—, or —CO—, provided that no —O—O— bond is included, and these groups may be unsubstituted or substituted by one or more L's)

the following formulae (T1-28) to (T1-31),

[Chem. 74]

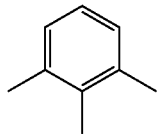
(T1-28)

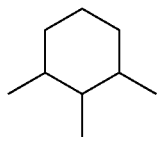
(T1-28)

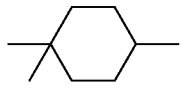
(T1-30)

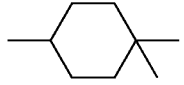
(T1-31)

(wherein any —CH= may independently be substituted by —N=, —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more L's)

the following formula (T1-32), and

[Chem. 75]

(T1-32)

(wherein the group may have a bonding arm at any position, at least one —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more L's)

the following formula (T1-33) or (T1-34), and

[Chem. 76]

(T1-33)

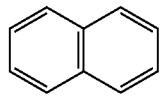
(T1-34)

(wherein the group may have a bonding arm at any position, at least one —CH= may independently be substituted by —N=, and these groups may be unsubstituted or substituted by one or more L's)

T$^{24}$ in the formula (I-M24) denotes a group selected from the formulae (T2-11) to (T2-41). Still more preferably, T$^{14}$ in the formula (I-M14) denotes a group selected from the following formulae (T1-35) to (T1-41), and T$^{24}$ in the formula (I-M24) denotes a group selected from the formulae (T2-35) to (T2-41).

[Chem. 77]

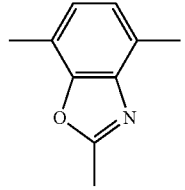
(T1-35)

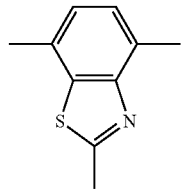
(T1-36)

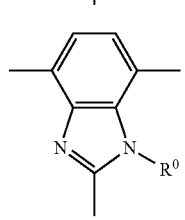
(T1-37)

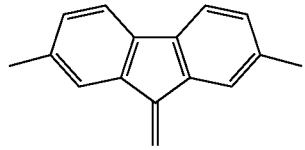
(T1-38)

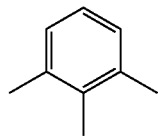
(T1-39)

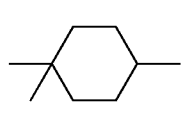
(T1-40)

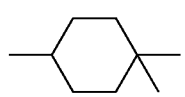
(T1-41)

(wherein $R^0$ denotes a hydrogen atom or an alkyl group having 1 to 20 carbon atoms)

If $T^{14}$ denotes a group selected from the formulae (T1-40) and (T1-41), and $T^{24}$ denotes a group selected from the formulae (T2-40) and (T2-41), then $V^1$ and $V^2$ in the formula (I-W21) preferably denote a group other than the groups represented by the formula (V-6).

<$M^1$-B3>

In careful consideration of the appearances after ultraviolet irradiation and the adhesiveness of a polymer film produced from the compound, preferably, $T^{14}$ in the formula (I-M14) denotes the one described above, $T^{24}$ denotes an optionally substituted noncyclic group having 1 to 80 carbon atoms, and any carbon atom of the noncyclic group may be substituted by a heteroatom.

$T^{24}$ preferably denotes a group represented by the formula (T-22),

[Chem. 78]

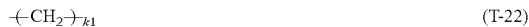
(T-22)

(wherein the group may have a bonding arm at any position, any —$CH_2$— may independently be substituted by —O—, —S—, —$NR^0$— (wherein $R^0$ denotes a hydrogen atom or an alkyl group having 1 to 20 carbon atoms), —CS—, or —CO—, provided that no —O—O— bond is included, and these groups may be unsubstituted or substituted by one or more L's, and k1 is an integer in the range of 1 to 20)

preferably a group selected from the following formulae (T-22-1) and (T-22-2),

[Chem. 79]

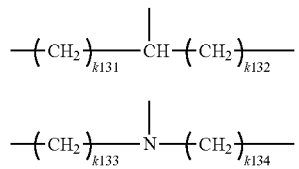
(T-22-1)

(T-22-2)

(wherein any —$CH_2$— may independently be substituted by —O—, —S—, —$NR^0$— (wherein $R^0$ denotes a hydrogen atom or an alkyl group having 1 to 20 carbon atoms), —CS—, or —CO—, provided that no —O—O— bond is included, and these groups may be unsubstituted or substituted by one or more L's, and k131 to k134 are independently an integer in the range of 0 to 20)

more preferably the formula (T-22-1), and k131 and k132 in the formula (T-22-1) are 1. If in the formula (T-22-1), k131 is 0 and k132 is 1, or k131 is 1 and k132 is 0, then the group represented by $V^2$ in the formula (I-W22) directly bonded to $T^{14}$ and $T^{24}$ preferably denotes a group other than the formula (V-6) and a single bond. Both $T^{14}$ and $T^{24}$ preferably denote a group represented by the formula (T-22), more preferably a group represented by the formula (T-22-1) or (T-22-2), still more preferably the formula (T-22-1).

<$R^1$, $R^2$, $R^3$, $R^4$>

Because of the structure of a compound in which <n1 is 1, n2 is 0, and n3 is 1>, a polymer film produced from the compound has less nonuniform orientation, high surface hardness, or high adhesiveness. Thus, in the general formula (I), $M^1$, $M^2$, and W1 described above are preferably appropriately selected, and $R^1$ to $R^4$ are preferably the following groups.

$R^2$ and $R^3$ preferably denote a group represented by the formula (I-R), and

[Chem. 80]

(I-R)

(wherein P denotes a polymerizable group, S denotes a spacer group or a single bond, a plurality of S's, if present at all, may be the same or different, X denotes —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C—, or a single bond, a plurality of X's, if present at all, may be the same or different (provided that P-(S-X)$_k$- has no —O—O— bond), and k is an integer in the range of 0 to 10)

$R^1$ and $R^4$ preferably denote a group selected from the groups represented by the formula (I-R) and $R^5$ (wherein $R^5$ denotes a hydrogen atom, a fluorine atom, a chlorine atom, a bromine atom, an iodine atom, a pentafluorosulfuranyl group, a nitro group, a cyano group, an isocyano group, an amino group, a hydroxy group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms with one —$CH_2$— or nonadjacent two or more —$CH_2$—'s optionally independently substituted by —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and any hydrogen atom of the alkyl group may be substituted by a fluorine atom).

For a compound in which <n1 is 1, n2 is 0, and n3 is 1>, in careful consideration of the nonuniform orientation and surface hardness of a polymer film produced from the compound, in the general formula (I), preferably, $R^2$ and $R^3$ denote a group represented by the formula (I-R), and $R^1$ and $R^4$ denote a group represented by $R^5$. In this case, P, S, X, k, and $R^5$ are selected from the preferred groups and numerical values described in <<$R^1$, $R^2$, $R^3$, $R^4$>>.

For a compound in which <n1 is 1, n2 is 0, and n3 is 1>, in careful consideration of the surface hardness and adhesiveness of a polymer film produced from the compound, or in careful consideration of the appearances after ultraviolet irradiation and the adhesiveness of a polymer film produced from the compound, $R^1$, $R^2$, $R^3$, and $R^4$ particularly preferably denote a group represented by the formula (I-R). In this case, P, S, X, and k are selected from the preferred groups and numerical values described in <<$R^1$, $R^2$, $R^3$, $R^4$>>.

Compound in which <<n1 is 0, and n2 and n3 are 1>>

<$M^2$-C>

Because of the structure of a compound in which <n1 is 0, and n2 and n3 are 1>, a polymer film produced from the compound has fewer orientation defects after ultraviolet irradiation, high thickness uniformity, and/or high surface hardness. Thus, $M^2$ in the general formula (I) is preferably represented by the following formula (I-M2C), and

[Chem. 81]

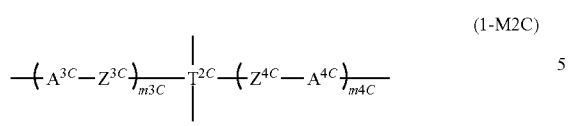

(1-M2C)

(wherein present $A^{3C}$ and present $A^{4C}$ independently denote a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, these groups may be unsubstituted or substituted by one or more substituents L's, a plurality of $A^{3C}$'s and/or $A^{4C}$'s, if present at all, may be the same or different, $Z^{3C}$ and $Z^{4C}$ independently denote —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C—, or a single bond, a plurality of $Z^{3C}$'s and/or $Z^{4C}$'s, if present at all, may be the same or different, and $m^{3C}$ and $m^{4C}$ are independently an integer in the range of 0 to 5)

in the formula (I-M2C), $T^{2C}$ preferably denotes a group selected from the following formulae (T-1) to (T-22), and these groups may be unsubstituted or substituted by one or more substituents L's.

[Chem. 82]

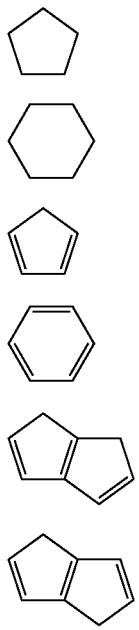

(T-1)

(T-2)

(T-3)

(T-4)

(T-5)

(T-6)

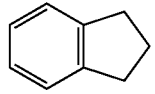

(T-7)

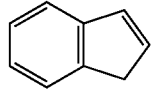

(T-8)

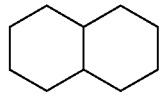

(T-9)

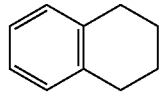

(T-10)

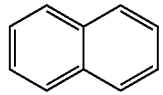

(T-11)

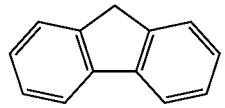

(T-12)

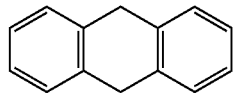

(T-13)

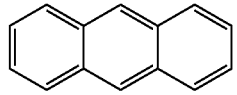

(T-14)

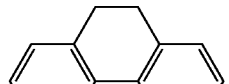

(T-15)

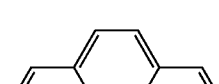

(T-16)

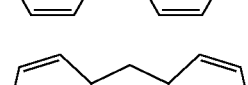

(T-17)

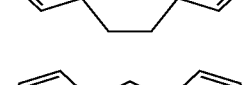

(T-18)

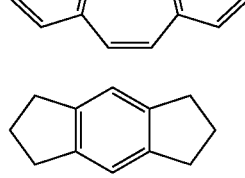

(T-19)

-continued (T-20)
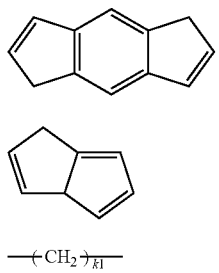

(T-21)

(T-22)
—(CH$_2$)$_{k1}$—

(wherein the group may have a bonding arm at any position, any —CH= may independently be substituted by —N=, —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more L's, and k1 is an integer in the range of 1 to 20)

From the perspective of the availability of raw materials and the ease of synthesis, $A^{3C}$ and $A^{4C}$ preferably independently denote a 1,4-phenylene group, a 1,4-cyclohexylene group, or a naphthalene-2,6-diyl group optionally substituted by one or more substituents L's, more preferably a group selected from the following formulae (A-C-1) to (A-C-11), still more preferably a group selected from the formulae (A-C-1) to (A-C-8), particularly preferably a group selected from the formulae (A-C-1) to (A-C-4)

[Chem. 83]

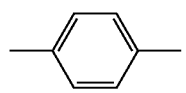 (A-C-1)

 (A-C-2)

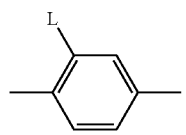 (A-C-3)

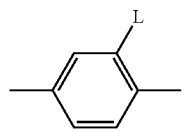 (A-C-4)

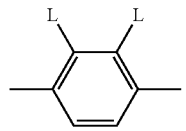 (A-C-5)

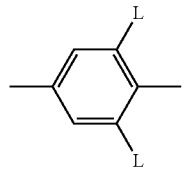 (A-C-6)

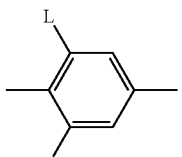 (A-C-7)

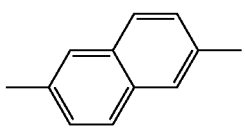 (A-C-8)

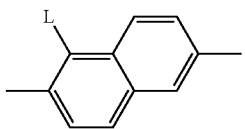 (A-C-9)

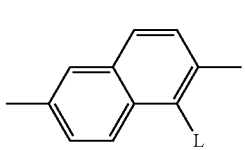 (A-C-10)

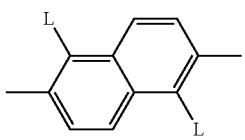 (A-C-11)

From the perspective of the liquid crystallinity, the availability of raw materials, and the ease of synthesis of the compound, $Z^{3C}$ and $Z^{4C}$ preferably independently denote a single bond, —OCH$_2$—, —CH$_2$O—, —COO—, —OCO—, —CF$_2$O—, —OCF$_2$—, —CH$_2$CH$_2$—, —CF$_2$CF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —CH=CH—, —CF=CF—, —C≡C—, or a single bond, more preferably —OCH$_2$—, —CH$_2$O—, —CH$_2$CH$_2$—, —COO—, —OCO—, —COO—CH$_2$CH$_2$—, —OCO—CH$_2$CH$_2$—, —CH$_2$CH$_2$—COO—, —CH$_2$CH$_2$—OCO—, —CH=CH—, —C≡C—, or a single bond, still more preferably —CH$_2$CH$_2$—, —COO—, —OCO—, —COO—CH$_2$CH$_2$—, —OCO—CH$_2$CH$_2$—, —CH$_2$CH$_2$—COO—, —CH$_2$CH$_2$—OCO—, or a single bond, particularly preferably —COO—, —OCO—, or a single bond.

From the perspective of liquid crystallinity, the ease of synthesis, and storage stability, $m^{3C}$ and $m^{4C}$ are preferably independently an integer in the range of 1 to 4, more preferably an integer in the range of 1 to 3, particularly preferably 1 or 2. $m^{3C}+m^{4C}$ is preferably independently an integer in the range of 1 to 4, more preferably 2, 3, or 4.

<M$^2$-C11, M$^2$-C12>

In careful consideration of the thickness uniformity of a polymer film produced from the compound, preferably, $T^{2C}$ in the formula (I-M2C) denotes a group selected from the following formulae (T2-C-1) to (T2-C-12), and these groups may be unsubstituted or substituted by one or more substituents L's.

[Chem. 84]

(T2-C-1) 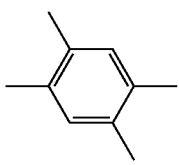

(T2-C-2) 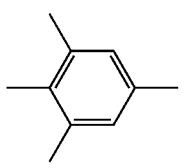

(T2-C-3) 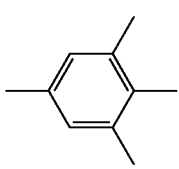

(T2-C-4) 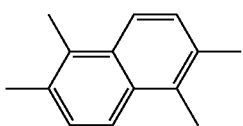

(T2-C-5) 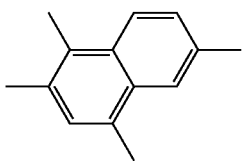

(T2-C-6) 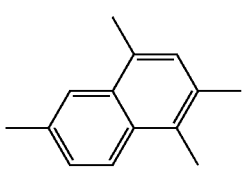

(T2-C-7) 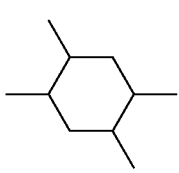

(T2-C-8) 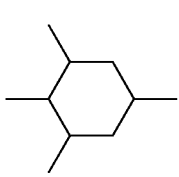

(T2-C-9) 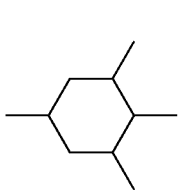

(T2-C-10) 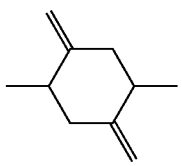

(T2-C-11) 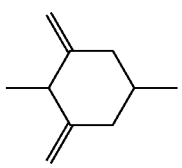

(T2-C-12) 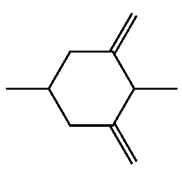

$T^{2C}$ more preferably denotes a group represented by one of the formulae (T2-C-1) to (T2-C-4), still more preferably a group represented by the formulae (T2-C-1) or (T2-C-4).

<M²-C2>

In careful consideration of the storage stability of the composition and orientation defects after ultraviolet irradiation of a polymer film produced from the compound, $T^{2C}$ in the formula (I-M2C) preferably denotes a group selected from one of the following formulae (T2-C-13) to (T2-C-42), more preferably a group selected from one of the formulae (T2-C-13), (T2-C-22), (T2-C-27), (T2-C-28), (T2-C-29), (T2-C-36), (T2-C-37), (T2-C-38), (T2-C-39), and (T2-C-41), still more preferably a group selected from one of the formulae (T2-C-13), (T2-C-27), and (T2-C-29), still more preferably the formula (T2-C-13).

[Chem. 85]

(T2-C-13) 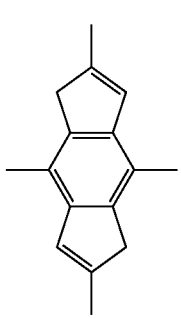

(T2-C-14) 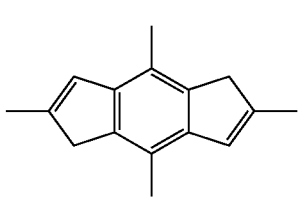

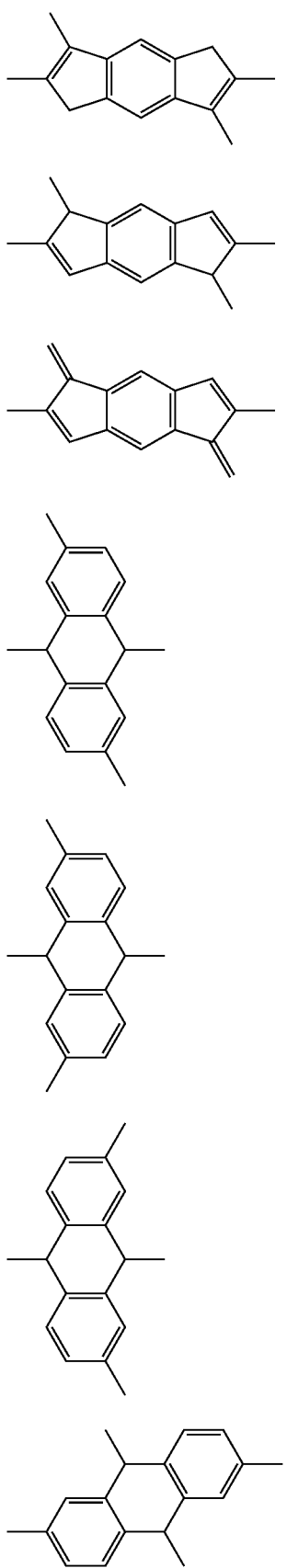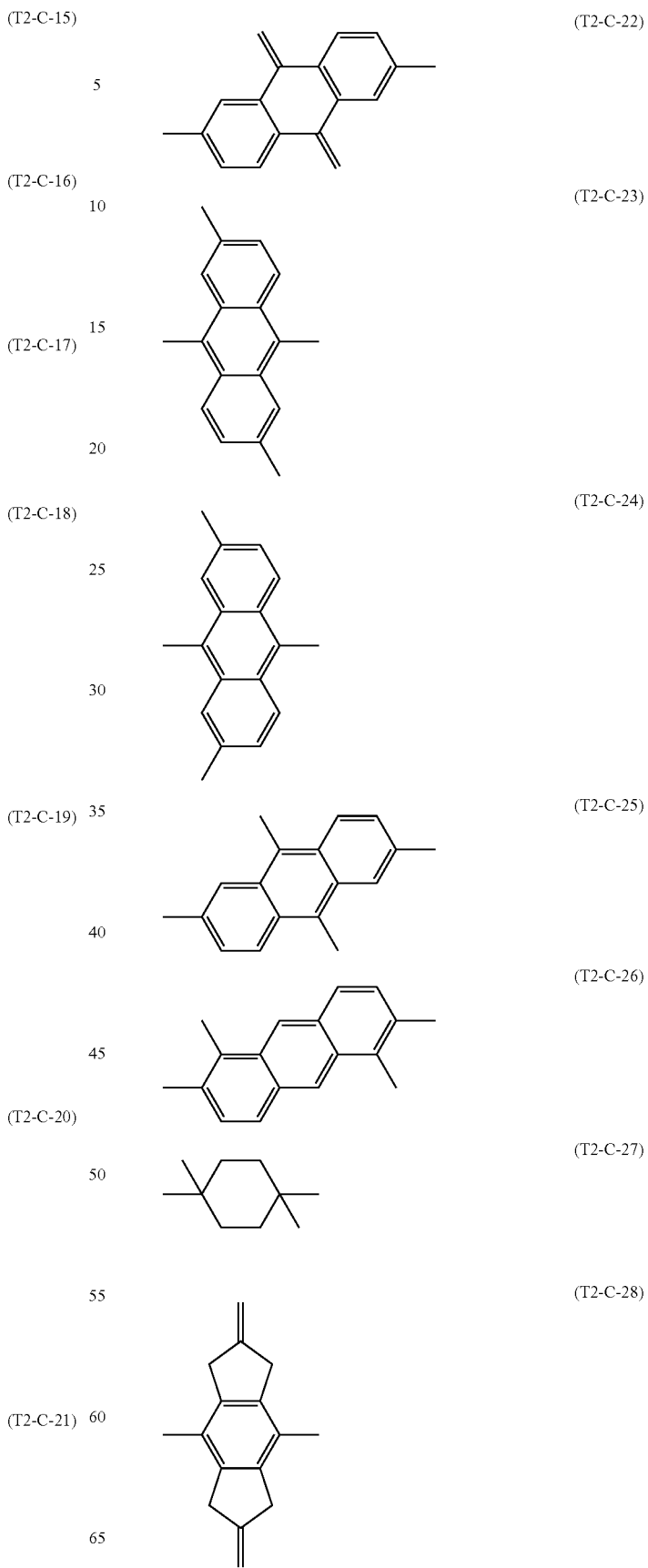

(T2-C-29)
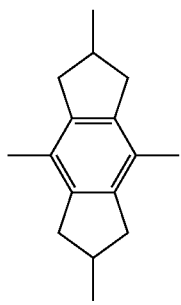
(T2-C-30)
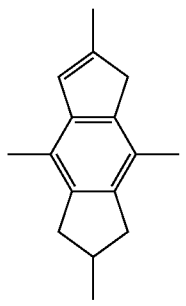
(T2-C-31)
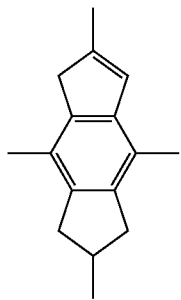
(T2-C-32)
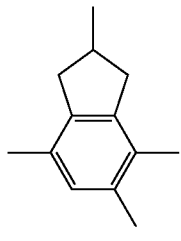
(T2-C-33)
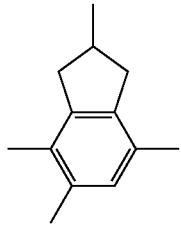
(T2-C-34)
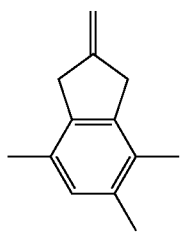
(T2-C-35)
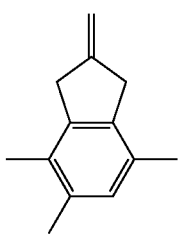
(T2-C-36)
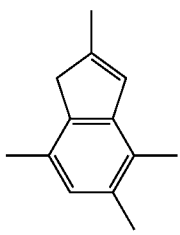
(T2-C-37)
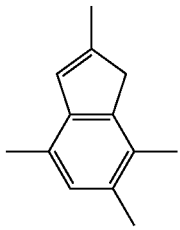
(T2-C-38)
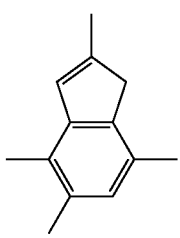
(T2-C-39)
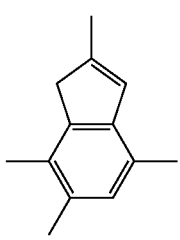
(T2-C-40)
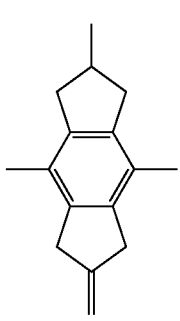

(T2-C-41)

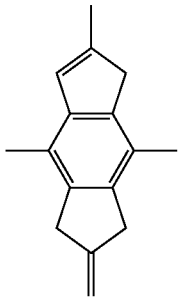

(T2-C-42)

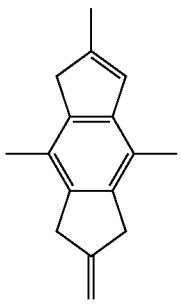

(wherein the group may have a bonding arm at any position, any —CH= may independently be substituted by —N=, —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more L's)

<M$^2$-C3>

In careful consideration of orientation defects after ultraviolet irradiation and the surface hardness of a polymer film produced from the compound, T$^{2C}$ in the formula (I-M2C) preferably denotes an optionally substituted noncyclic group having 1 to 80 carbon atoms, and any carbon atom of the noncyclic group may be substituted by a heteroatom.

T$^{2C}$ preferably denotes a group represented by the formula (T-22),

[Chem. 86]

—(CH$_2$)$_{k1}$—    (T-22)

(wherein the group may have a bonding arm at any position, any —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more L's, and k1 is an integer in the range of 1 to 20)

more preferably a group selected from the following formula (T-22-3). In the formula (T-22-3), k141 and k42 are still more preferably independently an integer in the range of 1 to 10, still more preferably an integer in the range of 1 to 4, particularly preferably 1.

[Chem. 87]

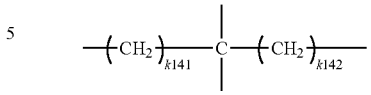

(T-22-3)

(wherein any —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more L's, and k141 and k142 are independently an integer in the range of 0 to 20)

<W$^1$-M$^2$-W$^2$C1>

Because of the structure of a compound in which <n1 is 0, and n2 and n3 are 1>, a polymer film produced from the compound has fewer orientation defects after ultraviolet irradiation, high thickness uniformity, and/or high surface hardness. Thus, in the general formula (I), M$^2$ preferably denotes a group described in <M2-C11, M2-C12>, and the group represented by W1-M$^2$-W$^2$ (M$^2$ is bonded to R$^3$ and R$^4$ at any position) preferably denotes a group selected from the following formulae (I-W16-1) and (I-W16-2).

[Chem. 88]

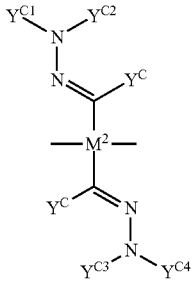

(I-W16-1)

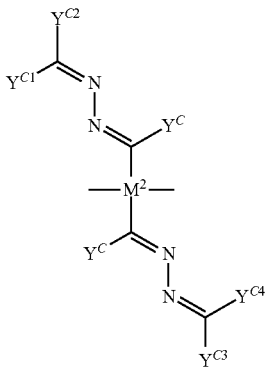

(I-W16-2)

(wherein Y$^{C1}$ and Y$^{C4}$ independently denote an optionally substituted group having 1 to 80 carbon atoms and having an aromatic and/or non-aromatic carbon ring or heterocycle, and any carbon atom of the carbon ring or heterocycle may be substituted by a heteroatom (provided that no oxygen atoms are directly bonded to each other), Y$^{C2}$ and Y$^{C3}$ independently denote a hydrogen atom or a linear or branched alkyl group having 1 to 20 carbon atoms with one —CH$_2$— or nonadjacent two or more —CH$_2$—'s optionally independently substituted by —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and any hydrogen atom of the alkyl group may be substituted by a fluorine atom, or $Y^{C2}$ and $Y^{C3}$ may denote a group having at least one aromatic group and having 5 to 30 carbon atoms, and the group may be unsubstituted or substituted by one or more substituents L's, and $Y^C$ denotes a hydrogen atom, a fluorine atom, a chlorine atom, a bromine atom, an iodine atom, a pentafluorosulfuranyl group, a nitro group, a cyano group, an isocyano group, an amino group, a hydroxy group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms with one —CH$_2$— or nonadjacent two or more —CH$_2$—'s optionally independently substituted by —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, any hydrogen atom of the alkyl group may be substituted by a fluorine atom, a plurality of $Y^C$'s, if present at all, may be the same or different, or $Y^C$ may denote a group represented by P-(S-X)$_j$-, P denotes a polymerizable group, S denotes a spacer group or a single bond, a plurality of S's, if present at all, may be the same or different, X denotes —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond, a plurality of X's, if present at all, may be the same or different (provided that P-(S-X)$_j$- has no —O—O— bond), j is an integer in the range of 0 to 10, $Y^{C1}$ and $Y^{C2}$ together may form a ring structure, and $Y^{C3}$ and $Y^{C4}$ together may form a ring structure)

From the perspective of liquid crystallinity and the ease of synthesis, $Y^C$ in the formula (I-W16-1) and (I-W16-2) preferably denotes a linear or branched alkyl group having 1 to 12 carbon atoms with any hydrogen atom optionally substituted by a fluorine atom and with one —CH$_2$— or nonadjacent two or more —CH$_2$—'s optionally independently substituted by —O—, —COO—, or —OCO—, more preferably a linear or branched alkyl group having 1 to 12 carbon atoms with any hydrogen atom optionally substituted by a fluorine atom, particularly preferably a linear alkyl group having 1 to 12 carbon atoms.

$Y^{C1}$ and $Y^{C4}$ in the formulae (I-W16-1) and (I-W16-2) preferably independently denote a group represented by one of the formulae (B-1) to (B-21).

[Chem. 89]

(B-1)

(B-2)

(B-3)

(B-4)

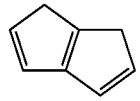
(B-5)

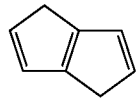
(B-6)

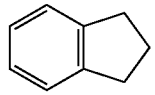
(B-7)

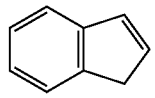
(B-8)

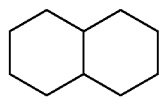
(B-9)

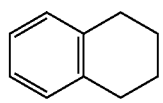
(B-10)

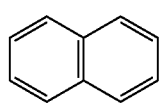
(B-11)

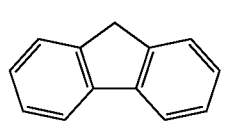
(B-12)

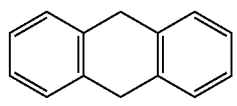
(B-13)

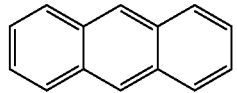
(B-14)

(B-15)

-continued

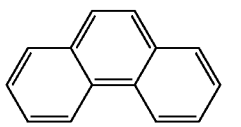
(B-16)

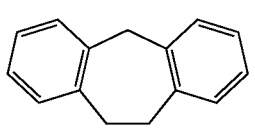
(B-17)

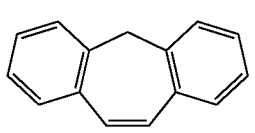
(B-18)

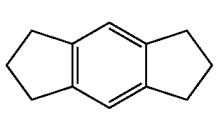
(B-19)

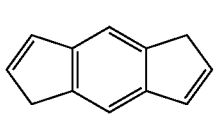
(B-20)

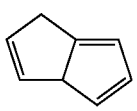
(B-21)

(wherein the group may have a bonding arm at any position, any —CH= may independently be substituted by —N=, —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more substituents L's)

Y$^{C1}$ and Y$^{C4}$ more preferably independently denote a group selected from the formulae (B-8) and (B-12), more specifically, preferably a group selected from the formulae (B-8-1) and (B-12-1) described in <<W$^1$, W$^2$>>.

From the perspective of the availability of raw materials and the ease of synthesis, if Y$^{C2}$ and Y$^{C3}$ in the formulae (I-W16-1) and (I-W16-2) independently denote a hydrogen atom or a linear or branched alkyl group having 1 to 20 carbon atoms with one —CH$_2$— or nonadjacent two or more —CH$_2$—'s optionally independently substituted by —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C— and with any hydrogen atom optionally substituted by a fluorine atom, then Y$^{C2}$ and Y$^{C3}$ preferably independently denote a hydrogen atom or a linear or branched alkyl group having 1 to 12 carbon atoms with one —CH$_2$— or nonadjacent two or more —CH$_2$—'s optionally independently substituted by —O—, —CO—, —COO—, or —OCO— and with any hydrogen atom optionally substituted by a fluorine atom, more preferably a hydrogen atom or a linear or branched alkyl group having 1 to 12 carbon atoms with one —CH$_2$— or nonadjacent two or more —CH$_2$—'s optionally independently substituted by —O—, —CO—, —COO—, or —OCO—, still more preferably a hydrogen atom or a linear alkyl group having 1 to 8 carbon atoms, still more preferably a hydrogen atom. From the perspective of the availability of raw materials and the ease of synthesis, if Y$^{C2}$ and Y$^{C3}$ denote a group having at least one aromatic group and having 5 to 30 carbon atoms, optionally substituted by one or more substituents L's, then Y$^{C2}$ and Y$^{C3}$ preferably independently denote a group represented by one of the formulae (B-1) to (B-21), more preferably a group selected from the formulae (B-8) and (B-12), more specifically, preferably a group selected from the formulae (B-8-1) and (B-12-1) described in <<W$^1$, W$^2$>>.

[Chem. 90]

(B-1)

(B-2)

(B-3)

(B-4)

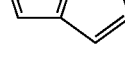
(B-5)

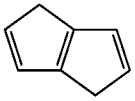
(B-6)

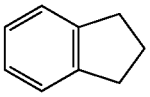
(B-7)

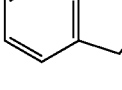
(B-8)

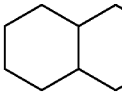
(B-9)

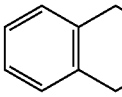
(B-10)

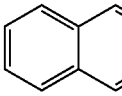
(B-11)

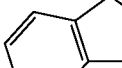
(B-12)

-continued (B-13)
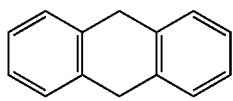

(B-14)
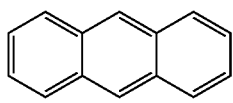

(B-15)
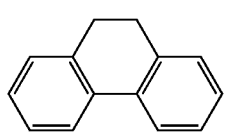

(B-16)
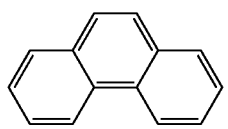

(B-17)
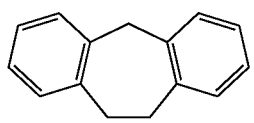

(B-18)
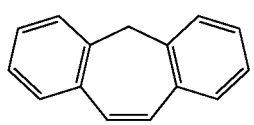

(B-19)
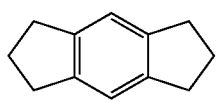

(B-20)
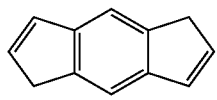

(B-21)
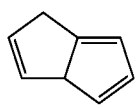

(wherein the group may have a bonding arm at any position, any —CH= may independently be substituted by —N=, —CH$_2$— may independently be substituted by —O—, —S—, —NR$^O$— (wherein R$^O$ denotes a hydrogen atom or an alkyl group having 1 to 20 carbon atoms), —CS—, or —CO—, provided that no —O—O— bond is included, and these groups may be unsubstituted or substituted by one or more substituents L's)

If Y$^{C1}$ and Y$^{C2}$ or Y$^{C3}$ and Y$^{C4}$ in the formula (I-W16-1) and (I-W16-2) together form a ring structure, a group selected from the following formulae (Y-C-1) to (Y-C-29) is preferred, and a group represented by the formula (Y-C-26) is more preferred.

[Chem. 91]

(Y-C-1)
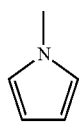

(Y-C-2)
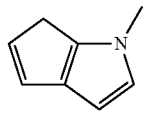

(Y-C-3)
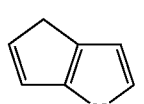

(Y-C-4)
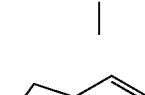

(Y-C-5)
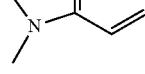

(Y-C-6)
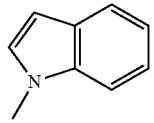

(Y-C-7)
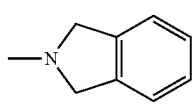

(Y-C-8)
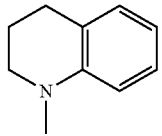

(Y-C-9)
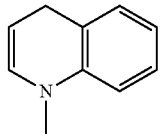

(Y-C-9)
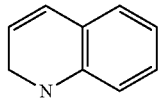

(Y-C-10)
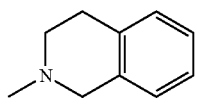

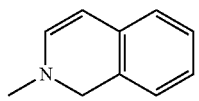

-continued (Y-C-11)

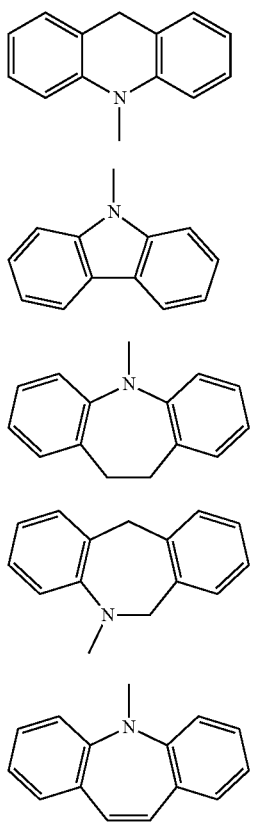

(Y-C-12)

(Y-C-13)

(Y-C-14)

[Chem. 92]

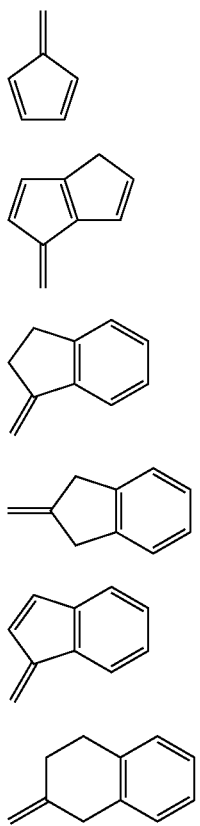

(Y-C-15)

(Y-C-16)

(Y-C-17)

(Y-C-18)

(Y-C-19)

(Y-C-20)

-continued

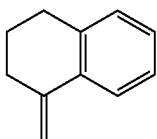 (Y-C-21)

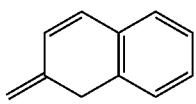 (Y-C-22)

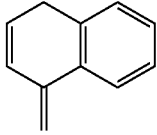 (Y-C-23)

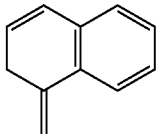 (Y-C-24)

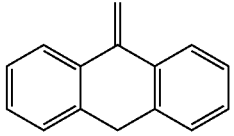 (Y-C-25)

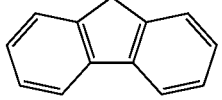 (Y-C-26)

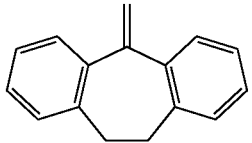 (Y-C-27)

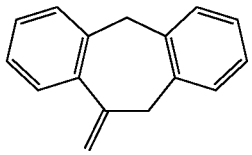 (Y-C-28)

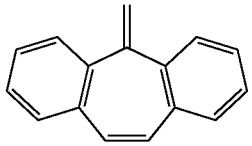 (Y-C-29)

(wherein any —CH= may independently be substituted by —N=, —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more substituents L's)

<W$^1$-M$^2$-W$^2$-C2>

For a compound in which <n1 is 0, and n2 and n3 are 1>, in careful consideration of the storage stability of the composition and orientation defects after ultraviolet irradiation of a polymer film produced from the compound, the groups represented by $W^1$ and $W^2$ are preferably groups selected from the general formulae (I-W1) and (I-W2) described in <<$W^1$, $W^2$>> from the perspective of the availability of raw materials and the ease of synthesis.

$V^1$, $V^2$, $V^3$, and $V^4$ in the general formulae (I-W1) and (I-W2) preferably independently denote a group represented by one of the formulae (V-1) to (V-15) described in <<$W^1$, $W^2$>> (wherein $Y^1$, if present at all, preferably denotes a group selected from the perspective of the availability of the raw materials described in <<$W^1$, $W^2$>> and the ease of synthesis), a single bond, a double bond, —O—, —S—, —OCH$_2$—, —CH$_2$O—, —CO—, —CH$_2$—, —COO—, —OCO—, —CO—S—, —S—CO—, —O—CO—O—, —CO—NH—, —NH—CO—, —CS—NH—, —NH—CS—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —CH$_2$CH$_2$—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, or —CH$_2$—OCO—, more preferably the formula (V-1), (V-2), (V-3), (V-4), (V-5), (V-6), (V-7), or (V-11), a single bond, or a double bond, still more preferably the formula (V-1), (V-2), (V-3), (V-4), or (V-5) or a single bond, still more preferably a single bond.

$B^1$, $B^2$, and $B^3$ in the general formulae (I-W1) and (I-W2) preferably independently denote a group selected from the formulae (B-1) to (B-21) and a single bond.

[Chem. 93]

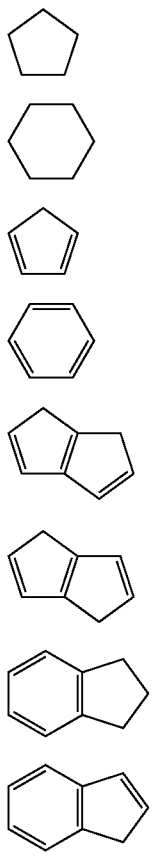

(B-1)
(B-2)
(B-3)
(B-4)
(B-5)
(B-6)
(B-7)
(B-8)

-continued

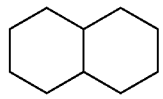 (B-9)

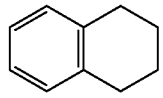 (B-10)

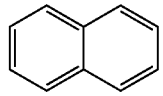 (B-11)

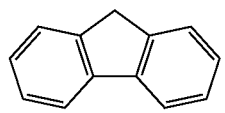 (B-12)

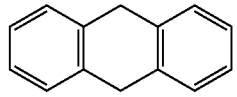 (B-13)

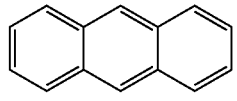 (B-14)

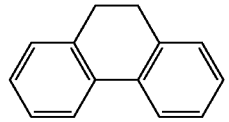 (B-15)

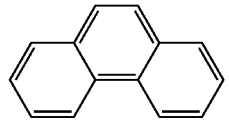 (B-16)

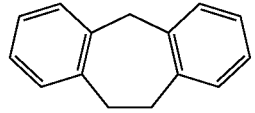 (B-17)

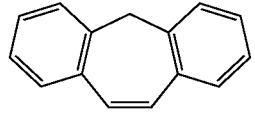 (B-18)

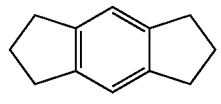 (B-19)

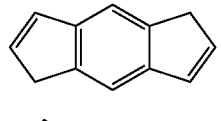 (B-20)

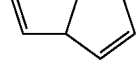 (B-21)

(wherein the group may have a bonding arm at any position, any —CH= may independently be substituted by —N=, —CH$_2$— may independently be substituted by —O—, —S—, —NR⁰— (wherein R⁰ denotes a hydrogen atom or an alkyl group having 1 to 20 carbon atoms), —CS—, or —CO—, provided that no —O—O— bond is included, and these groups may be unsubstituted or substituted by one or more substituents L's)

A group selected from the formulae (B-4), (B-8), (B-11), (B-12) and a single bond is preferred, a group selected from the formulae (B-4) and (B-8) and a single bond is more preferred, more specifically, a group selected from the formulae (B-4-1), (B-8-6), (B-8-7), (B-11-1), (B-11-2), (B-12-1), and (B-12-2) described in <<W¹, W²>> and a single bond is preferred, a group selected from the formulae (B-4-1), (B-8-6), and (B-8-7) and a single bond is more preferred, and a group selected from the formula (B-4-1) and a single bond is still more preferred.

<W¹-M²-W²-C3>

For a compound in which <n1 is 0, and n2 and n3 are 1>, in careful consideration of orientation defects after ultraviolet irradiation and the surface hardness of a polymer film produced from the compound, the groups represented by W¹ and W² are preferably groups selected from the perspective of the availability of the raw materials described in <<W¹, W²>> and the ease of synthesis.

V¹, V², V³, and V⁴ preferably independently denote a group represented by one of the formulae (V-1) to (V-15) described in <<W¹, W²>> (wherein Y¹, if present at all, preferably denotes a group selected from the perspective of the availability of the raw materials described in <<W¹, W²>> and the ease of synthesis), a single bond, a double bond, —O—, —S—, —OCH₂—, —CH₂O—, —CO—, —CH₂—, —COO—, —OCO—, —CO—S—, —S—CO—, —O—CO—O—, —CO—NH—, —NH—CO—, —CS—NH—, —NH—CS—, —SCH₂—, —CH₂S—, —CF₂O—, —OCF₂—, —CF₂S—, —SCF₂—, —CH=CH—COO—, —CH=CH—OCO—, —COO—CH=CH—, —OCO—CH=CH—, —CH₂CH₂—, —COO—CH₂CH₂—, —OCO—CH₂CH₂—, —CH₂CH₂—COO—, —CH₂CH₂—OCO—, —COO—CH₂—, —OCO—CH₂—, —CH₂—COO—, or —CH₂—OCO—, more preferably the formula (V-1), (V-2), (V-6), (V-8), (V-9), or (V-10), a single bond, —CH₂—, —COO—, —OCO—, —CS—NH—, —NH—CS—, or —CH₂CH₂—, still more preferably the formula (V-6), (V-8), or (V-9), —CH₂—, —COO—, or —OCO—, still more preferably the formula (V-8) or (V-9).

B¹, B², and B³ preferably independently denote a group selected from the formulae (B-1) to (B-21) and a single bond.

[Chem. 94]

(B-1)

(B-2)

(B-3)

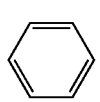
(B-4)

-continued

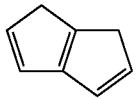
(B-5)

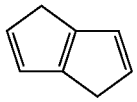
(B-6)

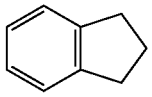
(B-7)

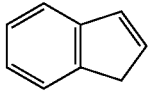
(B-8)

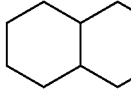
(B-9)

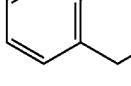
(B-10)

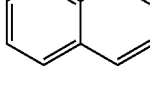
(B-11)

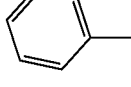
(B-12)

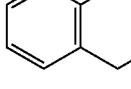
(B-13)

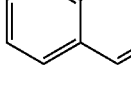
(B-14)

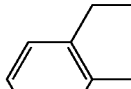
(B-15)

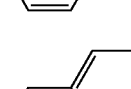
(B-16)

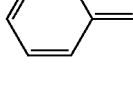
(B-17)

-continued

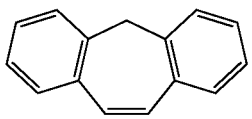

(B-18)

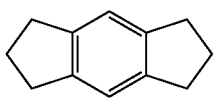

(B-19)

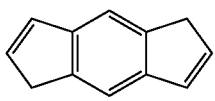

(B-20)

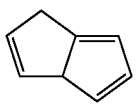

(B-21)

(wherein the group may have a bonding arm at any position, any —CH═ may independently be substituted by —N═, —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more substituents L's)

A group selected from the formulae (B-3), (B-4), (B-7), (B-11), and (B-12) and a single bond is preferred, a group selected from the formulae (B-4) and (B-12) and a single bond is more preferred, more specifically, a group selected from the formulae (B-3-2), (B-4-1), (B-7-9), (B-7-11), (B-11-1), and (B-12-4) described in <<W$^1$, W$^2$>> and a single bond is preferred, a group selected from the formulae (B-4-1) and (B-12-4) and a single bond is more preferred, and a group selected from the formula (B-4-1) and a single bond is still more preferred.

<R$^3$, R$^4$>

In a compound in which <n1 is 0, and n2 and n3 are 1>, M$^2$, W$^1$, and W$^2$ described above are preferably appropriately selected, and R$^3$ and R$^4$ are preferably the following groups.

R$^3$ preferably denotes a group represented by the formula (I-R),

[Chem. 95]

P—(S—X)$_k$       (I-R)

(wherein P denotes a polymerizable group, S denotes a spacer group or a single bond, a plurality of S's, if present at all, may be the same or different, X denotes —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH═CH—COO—, —CH═CH—OCO—, —COO—CH═CH—, —OCO—CH═CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH═CH—, —N═N—, —CH═N—N═CH—, —CF═CF—, —C≡C—, or a single bond, a plurality of X's, if present at all, may be the same or different (provided that P-(S-X)$_k$- has no —O—O— bond), and k is an integer in the range of 0 to 10)

R$^4$ preferably denotes a group selected from the groups represented by the formula (I-R) and R$^5$ (wherein R$^5$ denotes a hydrogen atom, a fluorine atom, a chlorine atom, a bromine atom, an iodine atom, a pentafluorosulfuranyl group, a nitro group, a cyano group, an isocyano group, an amino group, a hydroxy group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms with one —CH$_2$— or nonadjacent two or more —CH$_2$—'s optionally independently substituted by —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF—, or —C≡C—, and any hydrogen atom of the alkyl group may be substituted by a fluorine atom), and R$^3$ and R$^4$ particularly preferably denote a group represented by the formula (I-R), and in this case, P, S, X, and k are selected from the preferred groups and numerical values described in <<R$^1$, R$^2$, R$^3$, R$^4$>>.

Compound in which <<n1 and n2 are 0, and n3 Ranges from 2 to 1000>>

<W$^1$-D1>

Because of the structure of a compound in which <n1 and n2 are 0, and n3 is 2>, a polymer film produced from the compound has high thickness uniformity or adhesiveness. Thus, W$^1$ in the general formula (I) preferably denotes a group selected from the following formulae (I-W17-1) and (I-W17-2).

[Chem. 96]

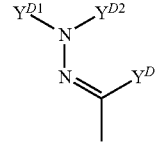

(I-W17-1)

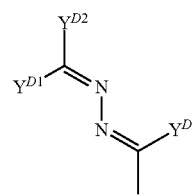

(I-W17-2)

(wherein Y$^{D1}$ denotes an optionally substituted group having 1 to 80 carbon atoms and having an aromatic and/or non-aromatic carbon ring or heterocycle, and any carbon atom of the carbon ring or heterocycle may be substituted by a heteroatom (provided that no oxygen atoms are directly bonded to each other), Y$^{D2}$ denotes a hydrogen atom or a linear or branched alkyl group having 1 to 20 carbon atoms with one —CH$_2$— or nonadjacent two or more —CH$_2$—'s optionally independently substituted by —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF—, or —C≡C—, and any hydrogen atom of the alkyl group may be substituted by a fluorine atom, or Y$^{D2}$ may denote a group having at least one aromatic group and having 2 to 30 carbon atoms, and the group may be unsubstituted or substituted by one or more substituents L's, and $Y^D$ denotes a hydrogen atom, a fluorine atom, a chlorine atom, a bromine atom, an iodine atom, a pentafluorosulfuranyl group, a nitro group, a cyano group, an isocyano group, an amino group, a hydroxy group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms with one —CH$_2$— or nonadjacent two or more —CH$_2$—'s optionally independently substituted by —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, any hydrogen atom of the alkyl group may be substituted by a fluorine atom, a plurality of $Y^D$'s, if present at all, may be the same or different, or $Y^D$ may denote a group represented by P-(S-X)$_j$-, P denotes a polymerizable group, S denotes a spacer group or a single bond, a plurality of S's, if present at all, may be the same or different, X denotes —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond, a plurality of X's, if present at all, may be the same or different (provided that P-(S-X)$_j$- has no —O—O— bond), j is an integer in the range of 0 to 10, and $Y^{D1}$ and $Y^{D2}$ together may form a ring structure)

From the perspective of liquid crystallinity and the ease of synthesis, $Y^D$ preferably denotes a linear or branched alkyl group having 1 to 12 carbon atoms with any hydrogen atom optionally substituted by a fluorine atom and with one —CH$_2$— or nonadjacent two or more —CH$_2$—'s optionally independently substituted by —O—, —COO—, or —OCO—, more preferably a linear or branched alkyl group having 1 to 12 carbon atoms with any hydrogen atom optionally substituted by a fluorine atom, particularly preferably a linear alkyl group having 1 to 12 carbon atoms.

$Y^{D1}$ preferably denotes a group represented by one of the following formulae (B-1) to (B-21).

[Chem. 97]

 (B-1)

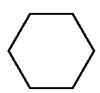 (B-2)

 (B-3)

 (B-4)

-continued

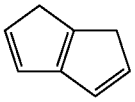 (B-5)

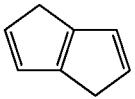 (B-6)

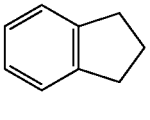 (B-7)

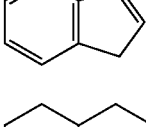 (B-8)

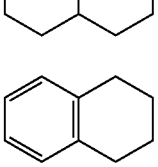 (B-9)

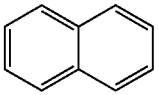 (B-10)

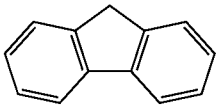 (B-11)

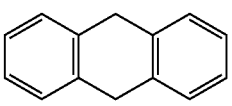 (B-12)

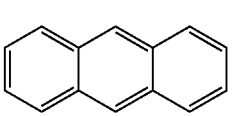 (B-13)

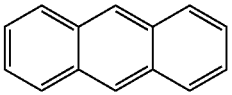 (B-14)

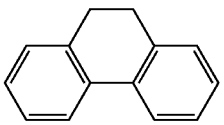 (B-15)

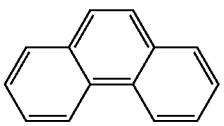 (B-16)

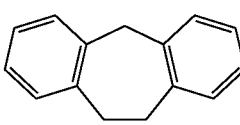 (B-17)

-continued

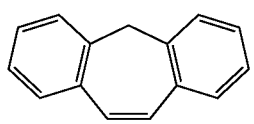
(B-18)

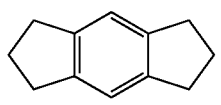
(B-19)

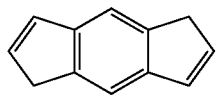
(B-20)

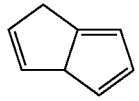
(B-21)

(wherein the group may have a bonding arm at any position, any —CH= may independently be substituted by —N=, —CH₂— may independently be substituted by —O—, —S—, —NR⁰— (wherein R⁰ denotes a hydrogen atom or an alkyl group having 1 to 20 carbon atoms), —CS—, or —CO—, provided that no —O—O— bond is included, and these groups may be unsubstituted or substituted by one or more substituents L's)

$Y^{D1}$ more preferably denotes a group selected from the formulae (B-3), (B-8), (B-11), and (B-12), more specifically, preferably a group selected from the formulae (B-3-5), (B-8-7), (B-11-1), and (B-12-1) described in <<W¹, W²>>, more preferably a group selected from the formulae (B-8-7) and (B-12-1), still more preferably a group represented by the formula (B-8-7).

From the perspective of the availability of raw materials and the ease of synthesis, if $Y^{D2}$ independently denotes a hydrogen atom or a linear or branched alkyl group having 1 to 20 carbon atoms with one —CH₂— or nonadjacent two or more —CH₂—'s optionally independently substituted by —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C— and with any hydrogen atom optionally substituted by a fluorine atom, then $Y^{D2}$ preferably independently denotes a hydrogen atom or a linear or branched alkyl group having 1 to 12 carbon atoms with one —CH₂— or nonadjacent two or more —CH₂—'s optionally independently substituted by —O—, —CO—, —COO—, or —OCO— and with any hydrogen atom optionally substituted by a fluorine atom, more preferably a hydrogen atom or a linear or branched alkyl group having 1 to 12 carbon atoms with one —CH₂— or nonadjacent two or more —CH₂—'s optionally independently substituted by —O—, —CO—, —COO—, or —OCO—, still more preferably a hydrogen atom or a linear alkyl group having 1 to 8 carbon atoms, still more preferably a hydrogen atom. From the perspective of the availability of raw materials and the ease of synthesis, if $Y^{D2}$ denotes a group having at least one aromatic group and having 5 to 30 carbon atoms, optionally substituted by one or more substituents L's, then $Y^{D2}$ preferably denotes a group represented by one of the formulae (B-1) to (B-21),

[Chem. 98]

(B-1)

(B-2)

(B-3)

(B-4)

(B-5)

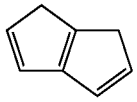
(B-6)

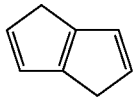
(B-7)

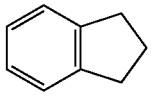
(B-8)

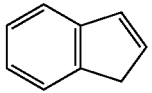
(B-9)

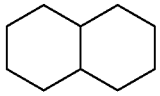
(B-10)

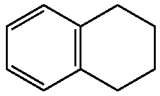
(B-11)

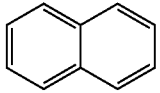
(B-12)

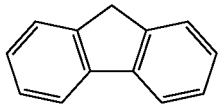
(B-13)

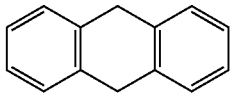
(B-14)

-continued

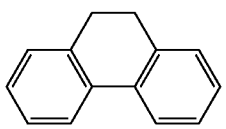 (B-15)

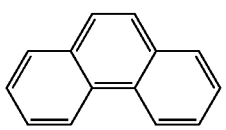 (B-16)

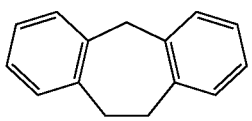 (B-17)

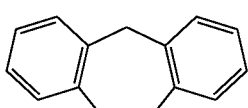 (B-18)

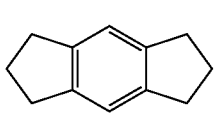 (B-19)

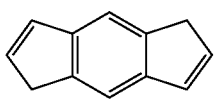 (B-20)

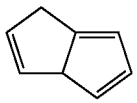 (B-21)

(wherein the group may have a bonding arm at any position, any —CH= may independently be substituted by —N=, —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more substituents L's)

Y$^{D2}$ more preferably denotes a group selected from the formulae (B-3), (B-8), (B-11), and (B-12), more specifically, preferably a group selected from the formulae (B-3-5), (B-8-7), (B-11-1), and (B-12-1) described in <<W$^1$, W$^2$>>, more preferably a group selected from the formulae (B-8-7) and (B-12-1), still more preferably a group represented by the formula (B-8-7).

If Y$^{D1}$ and Y$^{D2}$ together form a ring structure, a group selected from the following formulae (Y-D-1) to (Y-D-29) is preferred, and a group represented by the formula (Y-D-26) is more preferred.

[Chem. 99]

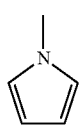 (Y-D-1)

-continued

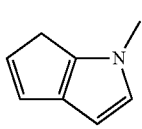 (Y-D-2)

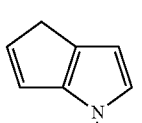 (Y-D-3)

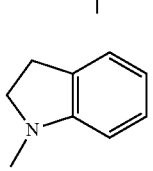 (Y-D-4)

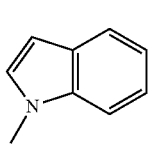 (Y-D-5)

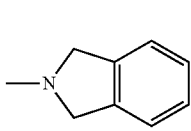 (Y-D-6)

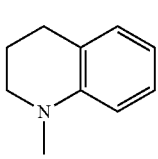 (Y-D-7)

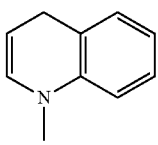 (Y-D-8)

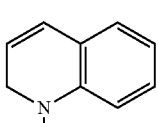 (Y-D-9)

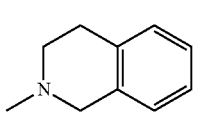 (Y-D-9)

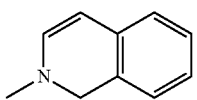 (Y-D-10)

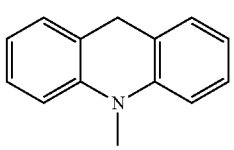 (Y-D-11)

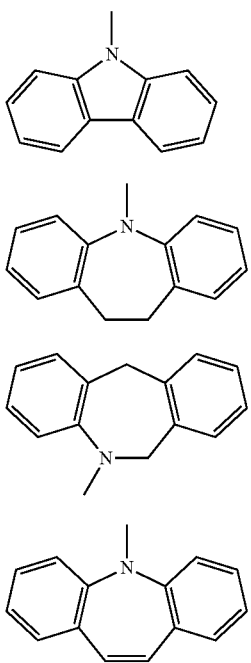

[Chem. 100]

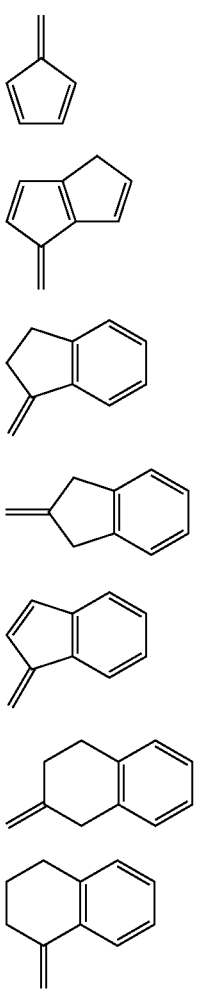

(Y-D-11)
(Y-D-12)
(Y-D-13)
(Y-D-14)
(Y-D-15)
(Y-D-16)
(Y-D-17)
(Y-D-18)
(Y-D-19)
(Y-D-20)
(Y-D-21)

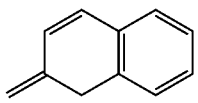
(Y-D-22)

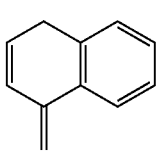
(Y-D-23)

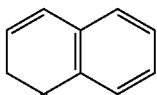
(Y-D-24)

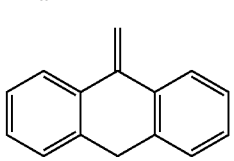
(Y-D-25)

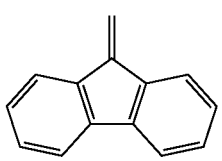
(Y-D-26)

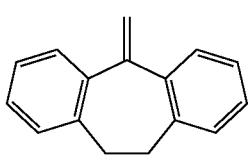
(Y-D-27)

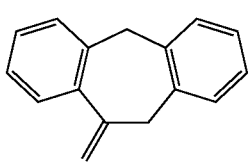
(Y-D-28)

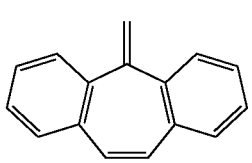
(Y-D-29)

(wherein any —CH= may independently be substituted by —N=, —CH₂— may independently be substituted by —O—, —S—, —NR⁰— (wherein R⁰ denotes a hydrogen atom or an alkyl group having 1 to 20 carbon atoms), —CS—, or —CO—, provided that no —O—O— bond is included, and these groups may be unsubstituted or substituted by one or more substituents L's)

<W¹-D2>

For a compound in which <n1 and n2 are 0, and n3 is 2>, in careful consideration of the haze and adhesiveness of a polymer film produced from the compound, the group represented by W¹ is preferably a group selected from the general formula (I-W1) described in <<W¹, W²>> from the perspective of the availability of raw materials and the ease of synthesis.

V¹ and V² in the general formula (I-W1) preferably independently denote a group represented by one of the formulae (V-1) to (V-15) described in <<W¹, W²>> (wherein Y¹, if present at all, preferably denotes a group selected from the perspective of the availability of the raw materials described in <<W¹, W²>> and the ease of synthesis), a single bond, a double bond, —O—, —S—, —OCH₂—, —CH₂O—, —CO—, —CH₂—, —COO—, —OCO—, —CO—S—, —S—CO—, —O—CO—O—, —CO—NH—, —NH—CO—, —CS—NH—, —NH—CS—, —SCH₂—, —CH₂S—, —CF₂O—, —OCF₂—, —CF₂S—, —SCF₂—, —CH═CH—COO—, —CH═CH—OCO—, —COO—CH═CH—, —OCO—CH═CH—, —CH₂CH₂—, —COO—CH₂CH₂—, —OCO—CH₂CH₂—, —CH₂CH₂—COO—, —CH₂CH₂—OCO—, —COO—CH₂—, —OCO—CH₂—, —CH₂—COO—, or —CH₂—OCO—, more preferably the formula (V-1), (V-2), (V-3), (V-4), (V-5), (V-6), (V-7), (V-8), or (V-9), a single bond, —COO—, or —OCO—, still more preferably the formula (V-5), (V-8), or (V-9) or a single bond, still more preferably a single bond.

B¹ in the general formula (I-W1) preferably independently denotes a group selected from the formulae (B-1) to (B-21) and a single bond.

[Chem. 101]

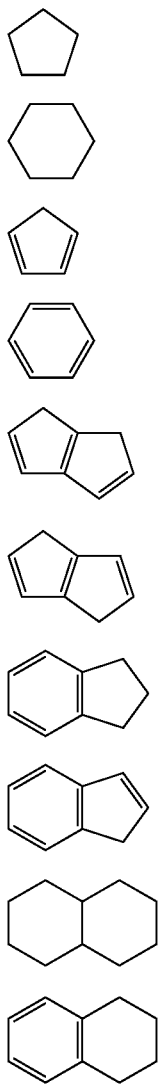

(B-1)
(B-2)
(B-3)
(B-4)
(B-5)
(B-6)
(B-7)
(B-8)
(B-9)
(B-10)

-continued

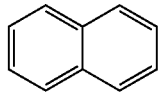 (B-11)

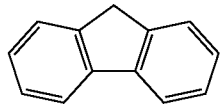 (B-12)

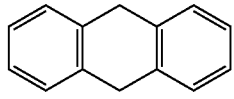 (B-13)

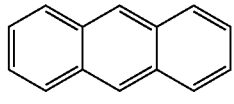 (B-14)

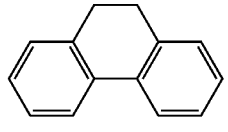 (B-15)

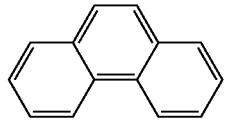 (B-16)

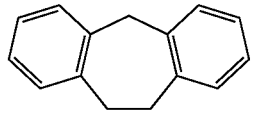 (B-17)

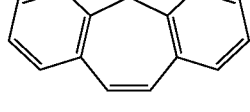 (B-18)

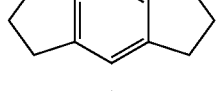 (B-19)

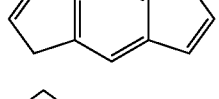 (B-20)

(B-21)

(wherein the group may have a bonding arm at any position, any —CH═ may independently be substituted by —N═, —CH₂— may independently be substituted by —O—, —S—, —NR⁰— (wherein R⁰ denotes a hydrogen atom or an alkyl group having 1 to 20 carbon atoms), —CS—, or —CO—, provided that no —O—O— bond is included, and these groups may be unsubstituted or substituted by one or more substituents L's)

A group selected from the formulae (B-4), (B-8), (B-11), and (B-12) and a single bond is preferred, a group selected from the formulae (B-8) and (B-12) and a single bond is more preferred, more specifically, a group selected from the formulae (B-4-1), (B-8-2), (B-8-7), (B-11-1), (B-12-1), and (B-12-4) described in <<W$^1$, W$^2$>> and a single bond is preferred, a group selected from the formulae (B-8-2) and (B-12-4) and a single bond is more preferred, and a group represented by the formula (B-8-2) is still more preferred.

<W$^1$-D3>

For a compound in which <n1 and n2 are 0, and n3 is 2>, in careful consideration of the haze and surface hardness of a polymer film produced from the compound, the groups represented by W$^1$ and W$^2$ are preferably a group selected from the general formula (I-W1) described in <<W$^1$, W$^2$>> from the perspective of the availability of raw materials and the ease of synthesis.

V$^1$ and V$^2$ in the general formula (I-W1) independently denote a group represented by one of the formulae (V-1) to (V-15) described in <<W$^1$, W$^2$>> (wherein Y$^1$, if present at all, preferably denotes a group selected from the perspective of the availability of the raw materials described in <<W$^1$, W$^2$>> and the ease of synthesis), a single bond, a double bond, —O—, —S—, —OCH$_2$—, —CH$_2$O—, —CO—, —CH$_2$—, —COO—, —OCO—, —CO—S—, —S—CO—, —O—CO—O—, —CO—NH—, —NH—CO—, —CS—NH—, —NH—CS—, —SCH$_2$—, —CH$_2$S—, —CF$_2$O—, —OCF$_2$—, —CF$_2$S—, —SCF$_2$—, —CH═CH—COO—, —CH═CH—OCO—, —COO—CH═CH—, —OCO—CH═CH—, —CH$_2$CH$_2$—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, or —CH$_2$—OCO—, more preferably the formula (V-5), (V-6), (V-7), (V-8), (V-9), or (V-10), a single bond, —COO—, —OCO—, —CS—NH—, or —NH—CS—, still more preferably the formula (V-6), (V-8), or (V-9), —COO—, or —OCO—.

B$^1$ in the general formula (I-W1) preferably independently denotes a group selected from the formulae (B-1) to (B-21) and a single bond.

[Chem. 102]

 (B-1)

 (B-2)

 (B-3)

 (B-4)

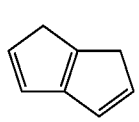 (B-5)

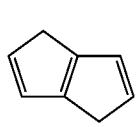 (B-6)

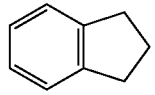 (B-7)

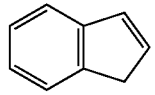 (B-8)

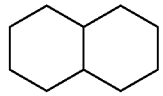 (B-9)

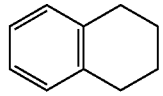 (B-10)

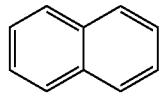 (B-11)

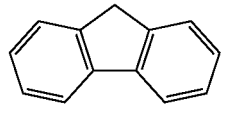 (B-12)

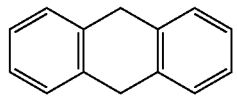 (B-13)

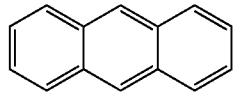 (B-14)

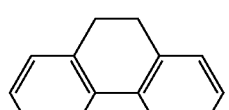 (B-15)

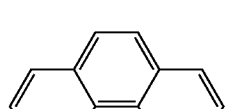 (B-16)

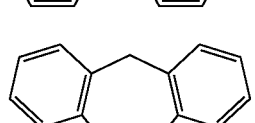 (B-17)

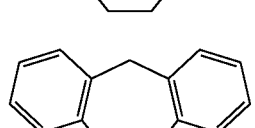 (B-18)

(B-19)

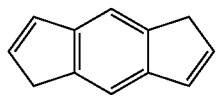
(B-20)

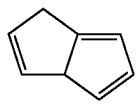
(B-21)

(wherein the group may have a bonding arm at any position, any —CH═ may independently be substituted by —N═, —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more substituents L's)

A group selected from the formulae (B-4), (B-8), and (B-11) and a single bond is preferred, a group selected from the formula (B-4) and a single bond is more preferred, more specifically, a group selected from the formulae (B-4-1), (B-8-6), (B-8-7), and (B-11-1) described in <<W$^1$, W$^2$>> and a single bond is preferred, and a group selected from the formula (B-4-1) and a single bond is more preferred.
<-(M$^2$)$_2$->

Because of the structure of a compound in which <n1 and n2 are 0, and n3 is 2>, a polymer film produced from the compound has a low haze, high thickness uniformity, or high adhesiveness. Thus, -(M$^2$)$_2$- in the general formula (I) is preferably a group represented by the following general formula (I-M3).

[Chem. 103]

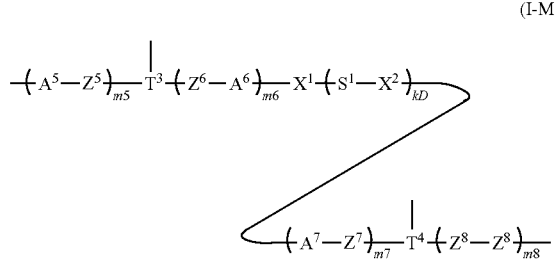
(I-M3)

(wherein present A$^5$, present A$^6$, present A$^7$, and present A$^8$ independently denote a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, these groups may be unsubstituted or substituted by one or more substituents L's, a plurality of A$^5$'s, A$^6$'s, A$^7$'s, and/or A$^8$'s, if present at all, may be the same or different, present Z$^5$, present Z$^6$, present Z$^7$, and present Z$^8$ independently denote —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —CH═CH—COO—, —CH═CH—OCO—, —COO—CH═CH—, —OCO—CH═CH—, —COO— CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH═CH—, —N═N—, —CH═N—, —N═CH—, —CH═N— N═CH—, —CF═CF—, —C≡C—, or a single bond, a plurality of Z$^5$'s, Z$^6$'s, Z$^7$'s, and/or Z$^8$'s, if present at all, may be the same or different, X$^1$ and X$^2$ denote —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH═CH—COO—, —CH═CH—OCO—, —COO— CH═CH—, —OCO—CH═CH—, —COO—CH$_2$CH$_2$—, —OCO—CH$_2$CH$_2$—, —CH$_2$CH$_2$—COO—, —CH$_2$CH$_2$— OCO—, —COO—CH$_2$—, —OCO—CH$_2$—, —CH$_2$— COO—, —CH$_2$—OCO—, —CH═CH—, —N═N—, —CH═N—N═CH—, —CF═CF—, —C≡C—, or a single bond, a plurality of X$^2$'s, if present at all, may be the same or different, S$^1$ denotes a single bond, or a linear or branched alkylene group having 1 to 20 carbon atoms with one —CH$_2$— or nonadjacent two or more —CH$_2$—'s optionally independently substituted by —O—, —COO—, —OCO—, —OCO—O—, —CO—NH—, —NH—CO—, —CH═CH—, or —C≡C—, a plurality of S$^1$'s, if present at all, may be the same or different (provided that X$^1$-S$^1$ and S$^1$-X$^2$ have no —O—O— bond), kD is an integer in the range of 0 to 8, m5, m6, m7, and m8 are independently an integer in the range of 0 to 5, and m5, m6, m7, and m8 range from 0 to 6 in total, T$^3$ and T$^4$ independently denote a group selected from the following formulae (T-1) to (T-22))

[Chem. 104]

(T-1)

(T-2)

(T-3)

(T-4)

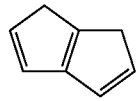
(T-5)

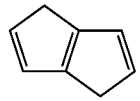
(T-6)

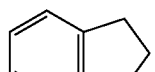
(T-7)

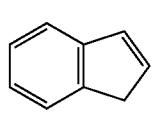
(T-8)

-continued (T-9) 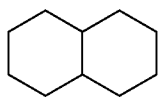

(T-10) 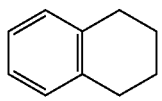

(T-11) 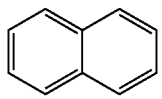

(T-12) 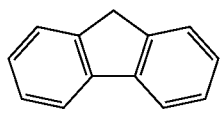

(T-13) 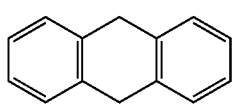

(T-14) 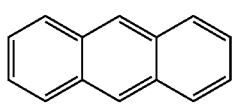

(T-15) 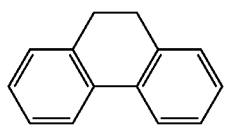

(T-16) 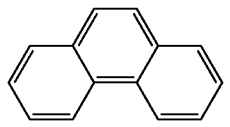

(T-17) 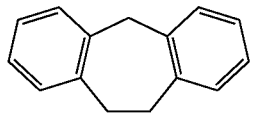

(T-18) 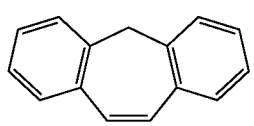

(T-19) 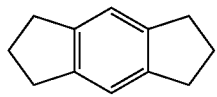

(T-20) 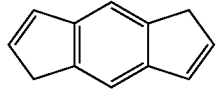

(T-21) 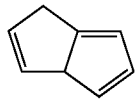

(T-22) 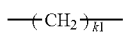

(wherein the group may have a bonding arm at any position, any —CH= may independently be substituted by —N=, —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more L's, and kD is an integer in the range of 1 to 20)

T$^3$ and T$^4$ preferably denote a group selected from the formulae (T-1) to (T-22). More preferably, T$^3$ and T$^4$ denote the same group.

From the perspective of the availability of raw materials and the ease of synthesis, A$^5$, A$^6$, A$^7$, and A$^8$ preferably independently denote a 1,4-phenylene group, a 1,4-cyclohexylene group, or a naphthalene-2,6-diyl group optionally substituted by one or more substituents L's, more preferably a group selected from the following formulae (A-D-1) to (A-D-11), still more preferably a group selected from the formulae (A-D-1) to (A-D-8), particularly preferably a group selected from the formulae (A-D-1) to (A-D-4).

[Chem. 105]

(A-D-1) 

(A-D-2) 

(A-D-3) 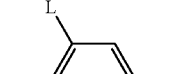

(A-D-4) 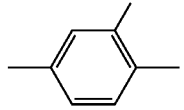

(A-D-5) 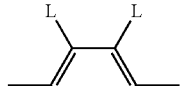

(A-D-6) 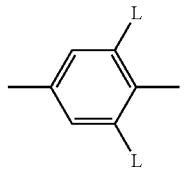

(A-D-7) 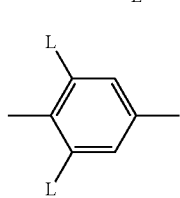

-continued

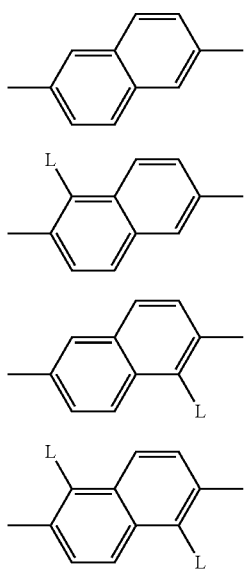

(A-D-8)

(A-D-9)

(A-D-10)

(A-D-11)

From the perspective of the liquid crystallinity, the availability of raw materials, and the ease of synthesis of the compound, $Z^5$, $Z^6$, $Z^7$, and $Z^8$ preferably independently denote a single bond, —OCH$_2$—, —CH$_2$O—, —COO—, —OCO—, —CF$_2$O—, —OCF$_2$—, —CH$_2$CH$_2$—, —CF$_2$CF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —CH=CH—, —CF=CF—, —C≡C—, or a single bond, more preferably —OCH$_2$—, —CH$_2$O—, —CH$_2$CH$_2$—, —COO—, —OCO—, —COO—CH$_2$CH$_2$—, —OCO—CH$_2$CH$_2$—, —CH$_2$CH$_2$—COO—, —CH$_2$CH$_2$—OCO—, —CH=CH—, —C≡C—, or a single bond, still more preferably —CH$_2$CH$_2$—, —COO—, —OCO—, —COO—CH$_2$CH$_2$—, —OCO—CH$_2$CH$_2$—, —CH$_2$CH$_2$—COO—, —CH$_2$CH$_2$—OCO—, or a single bond, particularly preferably —COO—, —OCO—, or a single bond.

From the perspective of liquid crystallinity, the ease of synthesis, and storage stability, m5, m6, m7, and m8 are preferably independently an integer in the range of 1 to 4, more preferably an integer in the range of 1 to 3, particularly preferably 1 or 2. The total of m5, m6, m7, and m8 is preferably independently an integer in the range of 2 to 4.

$S^1$ preferably independently denotes a linear alkylene group having 1 to 20 carbon atoms with one —CH$_2$— or nonadjacent two or more —CH$_2$—'s optionally independently substituted by —O—, —COO—, —OCO—, —OCO—O—, —CO—NH—, —NH—CO—, —CH=CH—, or —C≡C—, more preferably a linear alkylene group having 1 to 12 carbon atoms with one —CH$_2$— or nonadjacent two or more —CH$_2$—'s optionally independently substituted by —O—, —COO—, or —OCO—, still more preferably a linear alkylene group having 1 to 6 carbon atoms.

$X^1$ and $X^2$ preferably denote —O—, —CO—, —COO—, —OCO—, —CO—NH—, —NH—CO—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, or a single bond, more preferably —O—, —COO—, —OCO—, or a single bond.

kD is preferably an integer in the range of 0 to 4, more preferably an integer in the range of 0 to 2, still more preferably 1 or 2, still more preferably 1.

<-(M$^2$)$_2$-D1>

For a compound in which <n1 and n2 are 0, and n3 is 2>, in careful consideration of the storage stability of the composition and the appearances after ultraviolet irradiation and the adhesiveness of a polymer film produced from the compound, or in careful consideration of the thickness uniformity and nonuniform orientation of a polymer film produced from the compound, $T^3$ and $T^4$ in the general formula (I-M3) preferably independently denote a group selected from the formulae (T2-1) to (T2-10), and these groups may be unsubstituted or substituted by one or more substituents L's. More preferably, $T^3$ and $T^4$ independently denote a group selected from the formulae (T2-1) and (T2-2).

[Chem. 106]

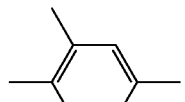

(T2-1)

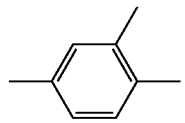

(T2-2)

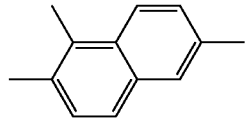

(T2-3)

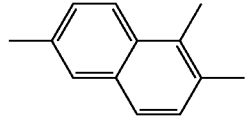

(T2-4)

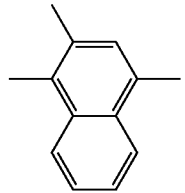

(T2-5)

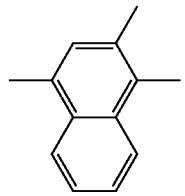

(T2-6)

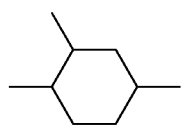

(T2-7)

-continued

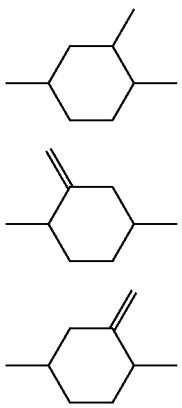

(T2-8)

(T2-9)

(T2-10)

$T^3$ and $T^4$ preferably denote a group selected from the formulae (T2-1) to (T2-10). More preferably, $T^3$ and $T^4$ denote the same group.

<-$(M^2)_2$-D2>

For a compound in which <n1 and n2 are 0, and n3 is 2>, in careful consideration of the haze and adhesiveness of a polymer film produced from the compound, $T^3$ in the general formula (I-M3) independently denotes a group selected from the following formulae (T2-11) to (T2-27),

[Chem. 107]

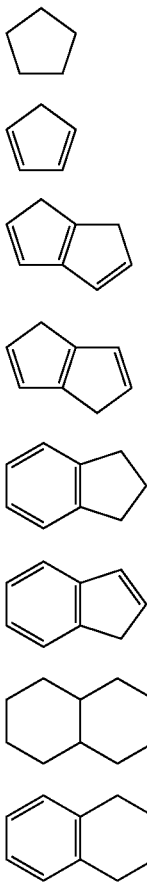

(T2-11)

(T2-12)

(T2-13)

(T2-14)

(T2-15)

(T2-16)

(T2-17)

(T2-18)

-continued

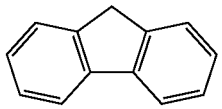

(T2-19)

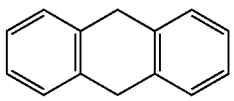

(T2-20)

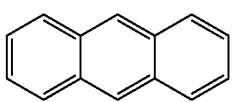

(T2-21)

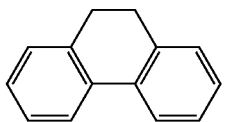

(T2-22)

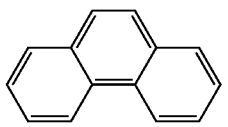

(T2-23)

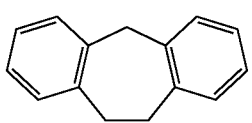

(T2-24)

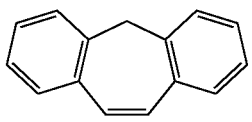

(T2-25)

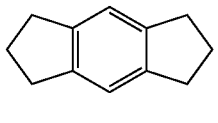

(T2-26)

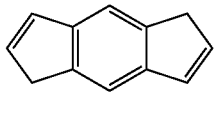

(T2-27)

(wherein the group may have a bonding arm at any position, any —CH= may independently be substituted by —N=, —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more L's), the following formulae (T2-28) to (T2-31),

[Chem. 108]

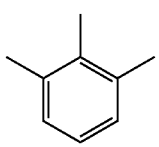

(T2-28)

-continued (T2-28)
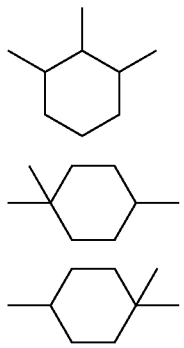

(T2-30)

(T2-31)

(wherein any —CH= may independently be substituted by —N=, —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more L's), the following formula (T2-32), and

[Chem. 109]

(T2-32)

(wherein the group may have a bonding arm at any position, at least one —CH$_2$— may independently be substituted by —O—, —S—, —NR$^0$— (wherein R$^0$ denotes a hydrogen atom or an alkyl group having 1 to 20 carbon atoms), —CS—, or —CO—, provided that no —O—O— bond is included, and these groups may be unsubstituted or substituted by one or more L's), the following formula (T2-33) or (T2-34), and

[Chem. 110]

(T2-33)

(T2-34)
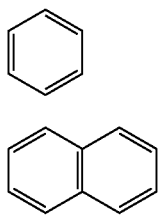

(wherein the group may have a bonding arm at any position, at least one —CH= may independently be substituted by —N=, and these groups may be unsubstituted or substituted by one or more L's)

T$^4$ in the general formula (I-M3) preferably denotes a group selected from the formulae (T2-1) to (T2-10) and (T2-11) to (T2-34).

T$^3$ more preferably denotes a group selected from the following formulae (T2-35) to (T2-41), still more preferably a group selected from the formulae (T2-36), (T2-40), and (T2-41), still more preferably the formula (T2-36).

[Chem. 111]

(T2-35)

(T2-36)

(T2-37)
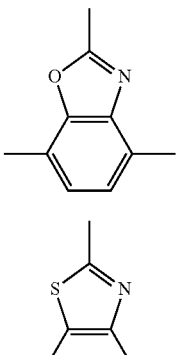

(T2-38)
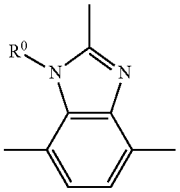

(T2-39)
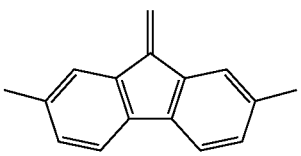

(T2-40)
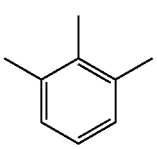

(T2-41)
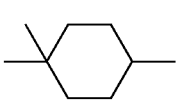

(wherein R$^0$ denotes a hydrogen atom or an alkyl group having 1 to 20 carbon atoms)

T$^3$ and T$^4$ preferably denotes a group selected from the formulae (T2-35) to (T2-41), more preferably a group selected from the formulae (T2-36), (T2-40), and (T2-41), still more preferably the formula (T2-36).

<-(M$^2$)$_2$-D3>

For a compound in which <n1 and n2 are 0, and n3 is 2>, in careful consideration of the haze and surface hardness of a polymer film produced from the compound, T$^3$ preferably denotes an optionally substituted noncyclic group having 1 to 80 carbon atoms, and any carbon atom of the noncyclic group may be substituted by a heteroatom.

T$^3$ in the general formula (I-M3) is preferably represented by the following formula (T-22),

[Chem. 112]

$-(-CH_2-)_{k1}$ (T-22)

(wherein the group may have a bonding arm at any position, any —$CH_2$— may independently be substituted by —O—, —S—, —$NR^0$— (wherein $R^0$ denotes a hydrogen atom or an alkyl group having 1 to 20 carbon atoms), —CS—, or —CO—, provided that no —O—O— bond is included, and these groups may be unsubstituted or substituted by one or more L's, and k1 is an integer in the range of 1 to 20)

preferably a group selected from the following formulae (T-22-1) and (T-22-2), more preferably the formula (T-22-1). Still more preferably, k131 and k132 in the formula (T-22-1) are 1.

[Chem. 113]

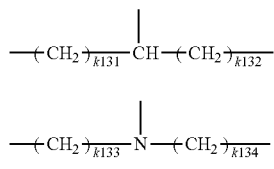

(T-22-1)

(T-22-2)

(wherein any —$CH_2$— may independently be substituted by —O—, —S—, —$NR^0$— (wherein $R^0$ denotes a hydrogen atom or an alkyl group having 1 to 20 carbon atoms), —CS—, or —CO—, provided that no —O—O— bond is included, and these groups may be unsubstituted or substituted by one or more L's, and k131 to k134 are independently an integer in the range of 0 to 20)

Both $T^3$ and $T^4$ preferably denote a group represented by the formula (T-22), more preferably a group represented by the formula (T-22-1) or (T-22-2), still more preferably the formula (T-22-1).

<$R^3$, $R^4$>

In a compound in which <n1 and n2 are 0, and n3 is 2>, $M^2$ and $W^1$ described above are preferably appropriately selected, and $R^3$ and $R^4$ preferably denote the following groups.

$R^3$ preferably denotes a group represented by the formula (I-R),

[Chem. 114]

P—(S-X)—$_k$     (I-R)

(wherein P denotes a polymerizable group, S denotes a spacer group or a single bond, a plurality of S's, if present at all, may be the same or different, X denotes —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C—, or a single bond, a plurality of X's, if present at all, may be the same or different (provided that P-(S-X)$_k$- has no —O—O— bond), and k is an integer in the range of 0 to 10)

$R^4$ preferably denotes a group selected from the groups represented by the formula (I-R) and $R^5$ (wherein $R^5$ denotes a hydrogen atom, a fluorine atom, a chlorine atom, a bromine atom, an iodine atom, a pentafluorosulfuranyl group, a nitro group, a cyano group, an isocyano group, an amino group, a hydroxy group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms with one —$CH_2$— or nonadjacent two or more —$CH_2$—'s optionally independently substituted by —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and any hydrogen atom of the alkyl group may be substituted by a fluorine atom), $R^3$ and $R^4$ particularly preferably denote a group represented by the formula (I-R), and in this case, P, S, X, and k are selected from the preferred groups and numerical values described in <<$R^1$, $R^2$, $R^3$, $R^4$>>.

Because of the structure of a compound having n3 in the range of 3 to 1000 out of the compounds in which <n1 and n2 are 0, and n3 ranges from 2 to 1000>, a polymer film produced from the compound has a low haze and good appearances and fewer orientation defects after ultraviolet irradiation. Thus, $W^1$ in the general formula (I) is selected from the preferred groups and numerical values described in <$W^1$-D1>, <$W^1$-D2>, and <$W^1$-D3>. Furthermore, -($M^2$)$_{n3}$- in the general formula (I) is selected from the preferred groups and numerical values described in <-($M^2$)$_2$-D1>, <-($M^2$)$_2$-D2>, and <-($M^2$)$_2$-D3>.

In careful consideration of inverse dispersibility, solubility in solvent, the ease of synthesis, the availability of raw materials, liquid crystallinity, and less cure shrinkage and curvature of a film produced from the compound, the compound represented by the general formula (I) is preferably a group represented by the following general formula (I-z1),

[Chem. 115]

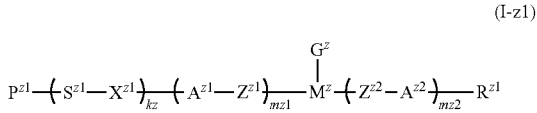

(I-z1)

(In the formula, $P^{z1}$ denotes a polymerizable group, preferably a group selected from the formulae (P-1) to (P-20), and these polymerizable groups are polymerized by radical polymerization, radical addition polymerization, cationic polymerization, and anionic polymerization. In particular, when ultraviolet polymerization is performed as a polymerization method, the formula (P-1), (P-2), (P-3), (P-4), (P-5), (P-7), (P-11), (P-13), (P-15), or (P-18) is preferred, the formula (P-1), (P-2), (P-7), (P-11), or (P-13) is more preferred, the formula (P-1), (P-2), or (P-3) is still more preferred, and the formula (P-1) or (P-2) is particularly preferred. $S^{z1}$ denotes a spacer group or a single bond, and a plurality of $S^{z1}$'s, if present at all, may be the same or different. From the perspective of liquid crystallinity, the availability of raw materials, and the ease of synthesis, preferably, a plurality of $S^{z1}$'s, if present at all, may be the same or different and independently denote an alkylene group having 1 to 20 carbon atoms with one —$CH_2$— or nonadjacent two or more —$CH_2$—'s optionally independently substituted by —O—, —S—, —$OCH_2$—, —$CH_2O$—, —CO—, —COO—, —OCO—, —CO—S—, —S—CO—, —O—CO—O—, —CO—NH—, —NH—

CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, or —C≡C—, or a single bond. More preferably, a plurality of $S^{z1}$'s, if present at all, may be the same or different and independently denote a linear alkylene group having 1 to 20 carbon atoms with one —CH$_2$— or nonadjacent two or more —CH$_2$—'s optionally independently substituted by —O—, —COO—, —OCO—, or —OCO—O—, or a single bond. Still more preferably, a plurality of $S^{z1}$'s, if present at all, may be the same or different and independently denote a linear alkylene group having 1 to 12 carbon atoms with one —CH$_2$— or nonadjacent two or more —CH$_2$—'s optionally independently substituted by —O—. A linear alkylene group having 1 to 12 carbon atoms with one —CH$_2$— or nonadjacent two or more —CH$_2$—'s optionally independently substituted by —O— is still more preferred. A linear alkylene group having 1 to 12 carbon atoms is particularly preferred. $X^{z1}$ denotes —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond, a plurality of X's, if present at all, may be the same or different (provided that $P^{z1}$-($S^{z1}$-$X^{z1}$)$_{kz}$- has no —O—O— bond). From the perspective of the availability of raw materials and the ease of synthesis, preferably, a plurality of $X^{z1}$'s, if present at all, may be the same or different and independently denote —O—, —S—, —OCH$_2$—, —CH$_2$O—, —COO—, —OCO—, —CO—S—, —S—CO—, —O—CO—O—, —CO—NH—, —NH—CO—, —COO—CH$_2$CH$_2$—, —OCO—CH$_2$CH$_2$—, —CH$_2$CH$_2$—COO—, —CH$_2$CH$_2$—OCO—, or a single bond, more preferably $X^{z1}$'s independently denote —O—, —OCH$_2$—, —CH$_2$O—, —COO—, —OCO—, —COO—CH$_2$CH$_2$—, —OCO—CH$_2$CH$_2$—, —CH$_2$CH$_2$—COO—, —CH$_2$CH$_2$—OCO—, or a single bond, and, particularly preferably, a plurality of $X^{z1}$'s, if present at all, may be the same or different and independently denote —O—, —COO—, —OCO—, or a single bond. $A^{z1}$ and $A^{z2}$ independently denote a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, these groups may be unsubstituted or substituted by one or more L's, a plurality of $A^{z1}$'s and/or $A^{z2}$'s, if present at all, may be the same or different. The preferred structures of $A^{z1}$ and $A^{z2}$ are the same as in A, $A^2$, $A^3$, and $A^4$. $Z^{z1}$ and $Z^{z2}$ independently denote —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C—, or a single bond, a plurality of $Z^{z1}$'s and/or $Z^{z2}$'s, if present at all, may be the same or different. From the perspective of the liquid crystallinity, the availability of raw materials, and the ease of synthesis of the compound, $Z^{z1}$ and $Z^{z2}$ preferably independently denote a single bond, —OCH$_2$—, —CH$_2$O—, —COO—, —OCO—, —CF$_2$O—, —OCF$_2$—, —CH$_2$CH$_2$—, —CF$_2$CF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —CH=CH—, —CF=CF—, —C≡C—, or a single bond, more preferably —OCH$_2$—, —CH$_2$O—, —CH$_2$CH$_2$—, —COO—, —OCO—, —COO—CH$_2$CH$_2$—, —OCO—CH$_2$CH$_2$—, —CH$_2$CH$_2$—COO—, —CH$_2$CH$_2$—OCO—, —CH=CH—, —C≡C—, or a single bond, still more preferably —OCH$_2$—, —CH$_2$O—, —CH$_2$CH$_2$—, —COO—, —OCO—, —COO—CH$_2$CH$_2$—, —OCO—CH$_2$CH$_2$—, —CH$_2$CH$_2$—COO—, —CH$_2$CH$_2$—OCO—, or a single bond, still more preferably —OCH$_2$—, —CH$_2$O—, —COO—, —OCO—, —COO—CH$_2$CH$_2$—, —OCO—CH$_2$CH$_2$—, —CH$_2$CH$_2$—COO—, —CH$_2$CH$_2$—OCO—, or a single bond, particularly preferably —OCH$_2$—, —CH$_2$O—, —COO—, —OCO—, or a single bond.

$M^z$ denotes a group selected from the following formulae (M-z-1) to (M-z-8), these groups may be unsubstituted or substituted by one or more $L^{Mz}$'s, $L^{Mz}$ denotes a fluorine atom, a chlorine atom, a bromine atom, an iodine atom, a pentafluorosulfuranyl group, a nitro group, a cyano group, an isocyano group, an amino group, a hydroxy group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms with one —CH$_2$— or nonadjacent two or more —CH$_2$—'s optionally independently substituted by —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, any hydrogen atom of the alkyl group may be substituted by a fluorine atom, and a plurality of $L^{Mz}$'s, if present at all, may be the same or different.

[Chem. 116]

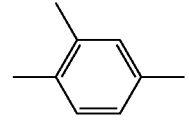

(M-z-1)

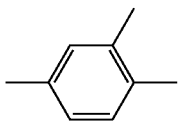
(M-z-2)

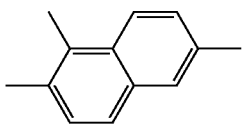
(M-z-3)

(M-z-4)

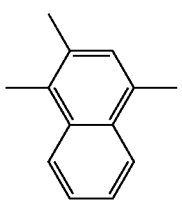
(M-z-5)

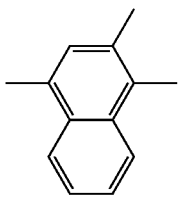
(M-z-6)

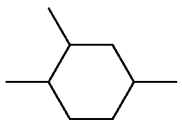
(M-z-7)

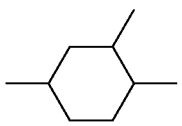
(M-z-8)

From the perspective of the availability of raw materials and the ease of synthesis, $M^z$ preferably independently denotes a group selected from the formulae (M-z-1) and (M-z-2) optionally substituted by one or more $L^{Mz}$'s or an unsubstituted group selected from the formulae (M-z-3) to (M-z-6), more preferably a group selected from the formulae (M-z-1) and (M-z-2) optionally substituted by one or more $L^{Mz}$'s, particularly preferably an unsubstituted group selected from the formulae (M-z-1) and (M-z-2).

$R^{z1}$ denotes a hydrogen atom, a fluorine atom, a chlorine atom, a bromine atom, an iodine atom, a pentafluorosulfuranyl group, a cyano group, a nitro group, an isocyano group, a thioisocyano group, or a linear or branched alkyl group having 1 to 20 carbon atoms with one —CH$_2$— or nonadjacent two or more —CH$_2$—'s optionally independently substituted by —O—, —S—, —CO—, —COO—, —OCO—, —CO—S—, —S—CO—, —O—CO—O—, —CO—NH—, —NH—CO—, —CH=CH—, —CF=CF—, or —C≡C—, and any hydrogen atom of the alkyl group may be substituted by a fluorine atom. From the perspective of liquid crystallinity and the ease of synthesis, $R^{z1}$ preferably denotes a hydrogen atom, a fluorine atom, a chlorine atom, a cyano group, or a linear or branched alkyl group having 1 to 12 carbon atoms with one —CH$_2$— or nonadjacent two or more —CH$_2$—'s optionally independently substituted by —O—, —COO—, —OCO—, or —O—CO—O—, more preferably a hydrogen atom, a fluorine atom, a chlorine atom, a cyano group, or a linear alkyl or alkoxy group having 1 to 12 carbon atoms, still more preferably a hydrogen atom or a linear alkyl or alkoxy group having 1 to 12 carbon atoms, particularly preferably a linear alkyl or alkoxy group having 1 to 12 carbon atoms.

$G^z$ denotes a group selected from the following formulae (G-z-1) and (G-z-2),

[Chem. 117]

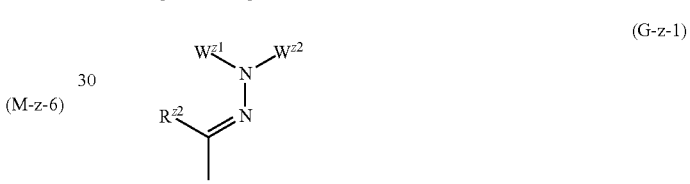
(G-z-1)

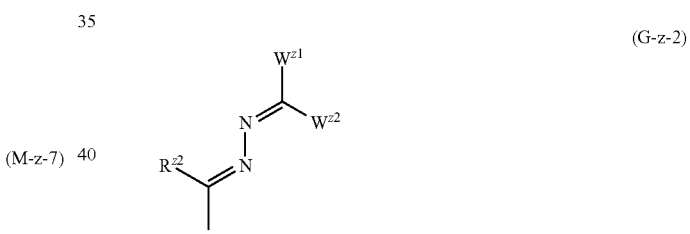
(G-z-2)

(In the formula, $R^{z2}$ denotes a hydrogen atom or a linear or branched alkyl group having 1 to 20 carbon atoms with one —CH$_2$— or nonadjacent two or more —CH$_2$—'s optionally independently substituted by —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and any hydrogen atom of the alkyl group may be substituted by a fluorine atom.

$W^{z1}$ denotes a group having at least one aromatic group and having 2 to 30 carbon atoms, and the group may be unsubstituted or substituted by one or more $L^{Wz}$'s. $L^{Wz}$ denotes a fluorine atom, a chlorine atom, a bromine atom, an iodine atom, a pentafluorosulfuranyl group, a nitro group, a cyano group, an isocyano group, an amino group, a hydroxy group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms with one —CH$_2$— or nonadjacent two or more —CH$_2$—'s optionally independently substituted by —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and any hydrogen atom of the alkyl group may be substituted by a fluorine atom. A plurality of L$^{Wz}$'s, if present at all, may be the same or different.

W$^{z2}$ denotes a hydrogen atom or a linear or branched alkyl group having 1 to 20 carbon atoms with one —CH$_2$— or nonadjacent two or more —CH$_2$—'s optionally independently substituted by —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and any hydrogen atom of the alkyl group may be substituted by a fluorine atom, or W$^{z2}$ may denote a group having at least one aromatic group and having 2 to 30 carbon atoms, the group may be unsubstituted or substituted by one or more substituents L$^{Wz}$'s, and W$^{z1}$ and W$^{z2}$ together may form a ring structure.)

kz is an integer in the range of 0 to 8. From the perspective of liquid crystallinity, the availability of raw materials, and the ease of synthesis, kz is preferably an integer in the range of 0 to 4, more preferably an integer in the range of 0 to 2, still more preferably 0 or 1, particularly preferably 1. mz1 and mz2 are independently an integer in the range of 0 to 5, and mz1+mz2 is an integer in the range of 1 to 5. From the perspective of liquid crystallinity, the ease of synthesis, and storage stability, mz1 and mz2 are preferably independently an integer in the range of 1 to 4, more preferably an integer in the range of 1 to 3, particularly preferably 1 or 2. mz1+mz2 is preferably an integer in the range of 1 to 4, particularly preferably 2 or 3.)

more preferably a compound selected from the following general formulae (I-z1-A) to (I-z1-D).

(wherein P$^{z1}$, S$^{z1}$, X$^{z1}$, kz, M$^z$, G$^z$, and R$^{z1}$ denote the same as in the general formula (I-z1), A$^{z11}$ and A$^{z12}$ independently denote the same as A$^{z1}$ in the general formula (I-z1), Z$^{z11}$ and Z$^{z12}$ independently denote the same as Z$^{z1}$ in the general formula (I-z1), A$^{z21}$ and A$^{z22}$ independently denote the same as A$^{z2}$ in the general formula (I-z1), and Z$^{z21}$ and Z$^{z22}$ independently denote the same as Z$^{z2}$ in the general formula (I-z1))

From the perspective of the balance between refractive index anisotropy and inverse dispersibility, A$^{z11}$ in the general formulae (I-z1-A) and (I-z1-B) more preferably denotes a 1,4-phenylene group optionally substituted by a substituent L. Still more preferably, in the general formulae (I-z1-C) and (I-z1-D), A$^{z11}$ denotes a 1,4-phenylene group optionally substituted by a substituent L, and A$^{z12}$ denotes a 1,4-cyclohexylene group optionally substituted by a substituent L. In the general formulae (I-z1-A) to (I-z1-D), still more preferably, A$^{z21}$ denotes a 1,4-phenylene or 1,4-cyclohexylene group optionally substituted by a substituent L, and A$^{z22}$ denotes a 1,4-cyclohexylene group optionally substituted by a substituent L. In the general formulae (I-z1-A) to (I-z1-D), from the perspective of liquid crystallinity, the ease of synthesis, and storage stability, compounds represented by the general formulae (I-z1-A) to (I-z1-C) are more preferred, and a compound represented by the general formula (I-z1-A) or (I-z1-C) is particularly preferred. When a higher transition temperature T$_{NI}$ from the nematic phase to the isotropic phase is required, a compound represented by the general formula (I-z1-C) is particularly preferred.

From the perspective of inverse dispersibility, solubility in solvent, the ease of synthesis, the availability of raw materials, and liquid crystallinity, more specifically, the compound represented by the general formula (I-z1) is still more preferably a compound selected from the following general formula (I-z1-A-1) to (I-z1-D-2).

[Chem. 118]

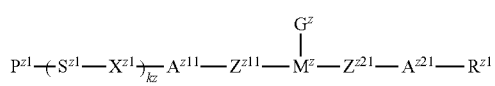

(I-z1-A)

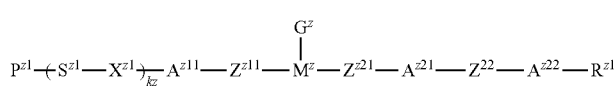

(I-z1-B)

(I-z1-C)

(I-z1-D)

[Chem. 119]
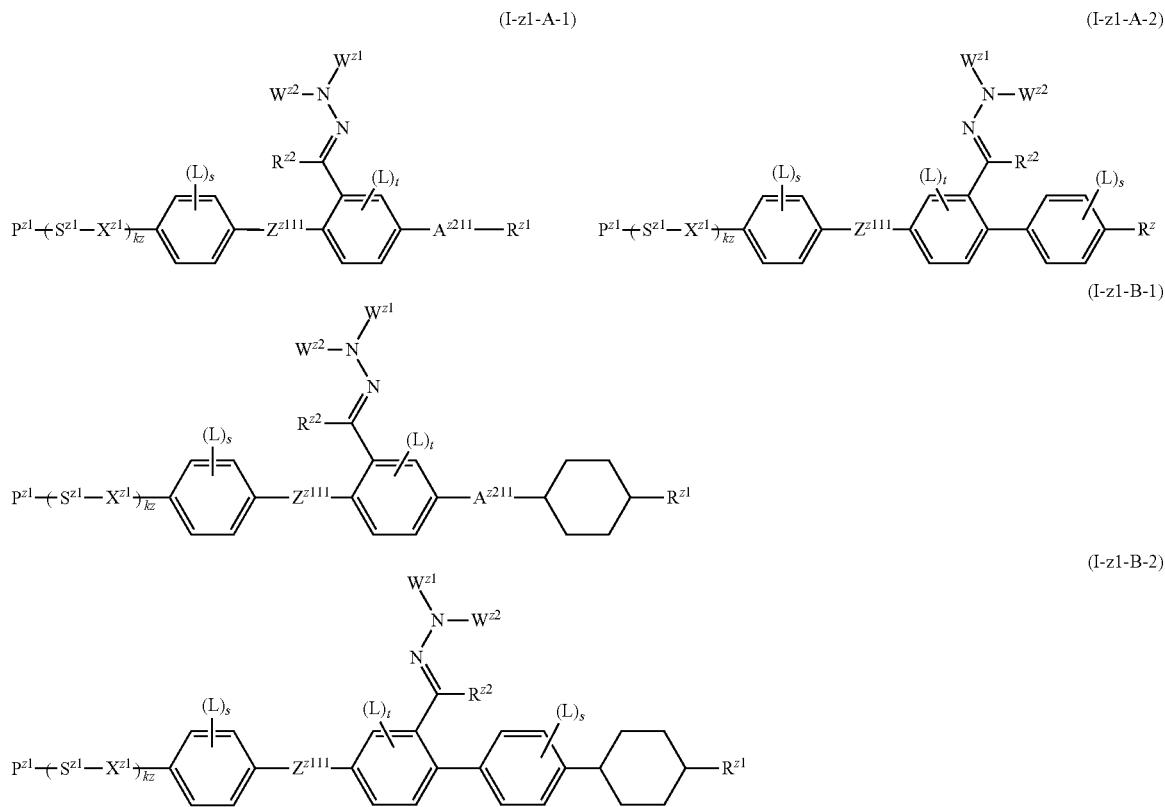
[Chem. 120]
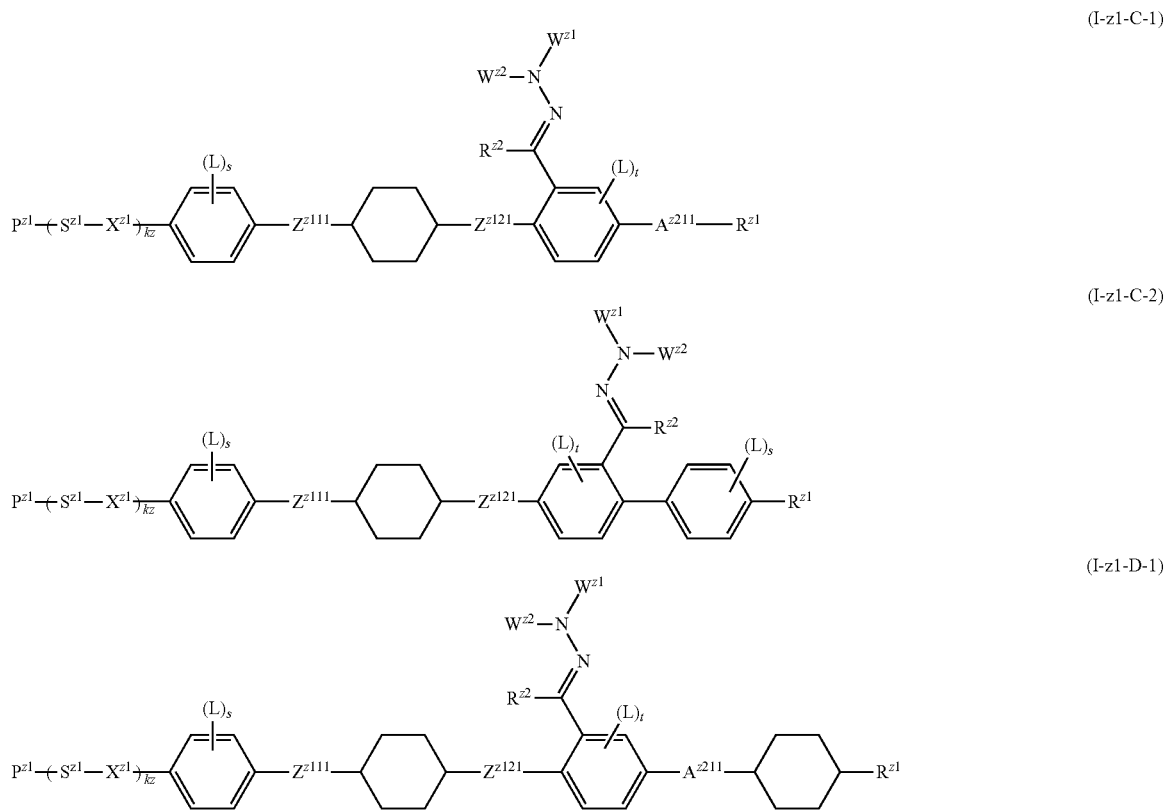

(I-z1-D-2)

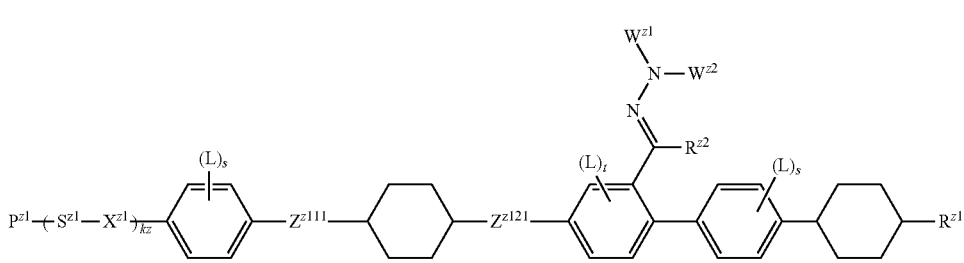

(In the formula, $P^{z1}$, $S^{z1}$, $X^{z1}$, kz, L, $R^{z2}$, $W^{z1}$, $W^{z2}$, and $R^{z1}$ denote the same as in the general formula (I-z1), s is an integer in the range of 0 to 4, t is an integer in the range of 0 to 3, $A^{z211}$ denotes the same as $A^{z2}$ in the general formula (I-z1), and $Z^{z111}$ and $Z^{z12}1$ independently denote the same as $Z^{z1}$ in the general formula (I-z1). The preferred structure of each group is the same as in the general formula (I-z1).)

In the general formulae (I-z1-A-1) to (I-z1-D-2), from the perspective of liquid crystallinity, the ease of synthesis, and storage stability, compounds represented by the general formulae (I-z1-A-1) to (I-z1-C-2) are more preferred, and a compound represented by the general formula (I-z1-A-1), (I-z1-A-2), (I-z1-C-1), or (I-z1-C-2) is particularly preferred. When inverse wavelength dispersibility on the short wavelength side is required, a compound represented by the general formula (I-z1-A-1) or (I-z1-C-1) is particularly preferred. When the balance between inverse wavelength dispersibility and refractive index anisotropy is required, a compound represented by the general formula (I-z1-A-2) or (I-z1-C-2) is particularly preferred. When a higher transition temperature $T_{NI}$ from the nematic phase to the isotropic phase is required, a compound represented by the general formula (I-z1-C-1) or (I-z1-C-2) is particularly preferred. When inverse wavelength dispersibility on the long wavelength side is required, a compound represented by the general formula (I-z1-C-1) is particularly preferred.

Particularly preferably, $W^{z1}$ denotes a group selected from the following formulae (W-a-1) to (W-a-6).

[Chem. 121]

(W-a-1)

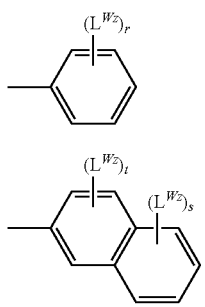

(W-a-2)

(W-a-3)

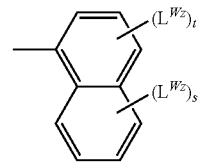

(W-a-4)

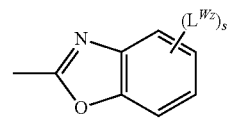

(W-a-5)

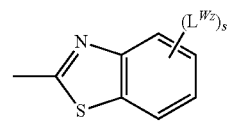

(W-a-6)

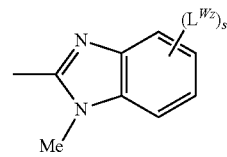

(wherein r is an integer in the range of 0 to 5, s is an integer in the range of 0 to 4, and t is an integer in the range of 0 to 3)

$R^{z2}$ preferably denotes a hydrogen atom or an alkyl group having 1 to 6 carbon atoms optionally substituted by one or more F's, particularly preferably a hydrogen atom.

In careful consideration of inverse dispersibility and liquid crystallinity, $W^{z2}$ preferably denotes a hydrogen atom.

In careful consideration of the resistance to deterioration of the compound dissolved in an organic solvent and stored for extended periods, the resistance to deterioration of the compound added to a composition and stored for extended periods, or the phase difference stability of a film produced from the compound, $W^{z2}$ preferably denotes a linear or branched alkyl group having 1 to 20 carbon atoms with a hydrogen atom optionally substituted by a fluorine atom and with one —$CH_2$— or nonadjacent two or more —$CH_2$—'s optionally independently substituted by —O—, —CO—, —COO—, or —OCO—, or a group represented by —($X^{z4}$-$S^{z4}$)$_{kz}$-$P^{z4}$ (wherein $P^{z4}$ denotes the same as $P^{z1}$, $S^{z4}$ denotes the same as $S^{z1}$, and $X^{z4}$ denotes the same as $X^{z1}$). Among these groups, $W^{z2}$ more preferably denotes a linear alkyl group having 1 to 12 carbon atoms with one —$CH_2$— or nonadjacent two or more —$CH_2$—'s optionally independently substituted by —O—, or a group represented by —($X^{z4}$-$S^{z4}$)$_{kz}$-$P^{z4}$. More specifically, from the perspective of the ease of synthesis, $W^{z2}$ more preferably denotes a linear or branched alkyl group having 1 to 20 carbon atoms with one —$CH_2$— or nonadjacent two or more —$CH_2$—'s optionally independently substituted by —O—, or a group represented by —($X^{z4}$-$S^{z4}$)$_{kz}$-$P^{z4}$, still more preferably a linear alkyl group having 1 to 12 carbon atoms with one —$CH_2$— or nonadjacent two or more —$CH_2$—'s optionally independently substituted by —O—, or a group represented by —($X^{z4}$-$S^{z4}$)$_{kz}$-$P^{z4}$.

In careful consideration of inverse dispersibility, high refractive index anisotropy, a good liquid crystallinity balance of the compound added to a composition, the resistance to deterioration of the compound dissolved in an organic solvent and stored for extended periods, the resistance to deterioration of the compound added to a composition and stored for extended periods, or the phase difference stability of a film produced from the compound, a compound represented by the following general formula (1-z2) is preferred.

[Chem. 122]

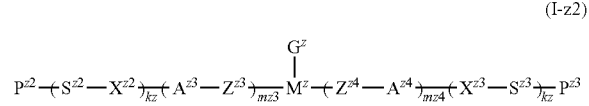

(I-z2)

(wherein kz, $M^z$, and $G^z$ denote the same as in the general formula (I-z1), $P^{z2}$ and $P^{z3}$ independently denote the same as $P^{z1}$ in the general formula (I-z1), $S^{z2}$ and $S^{z3}$ independently denote the same as $S^{z1}$ in the general formula (I-z1), $X^{z2}$ and $X^{z3}$ independently denote the same as $X^{z1}$ in the general formula (I-z1), $A^{z3}$ and $A^{z4}$ independently denote the same as $A^{z1}$ and $A^{z2}$ in the general formula (I-z1), $Z^{z3}$ and $Z^{z4}$ independently denote the same as $Z^{z1}$ and $Z^{z2}$ in the general formula (I-z1), mz3 and mz4 are independently an integer in the range of 0 to 5, and mz3+mz4 is an integer in the range of 1 to 5)

In careful consideration of inverse dispersibility, high refractive index anisotropy, and a good liquid crystallinity balance of the compound added to a composition, the following general formulae (I-z2-A) and (I-z2-B) are preferred.

[Chem. 123]

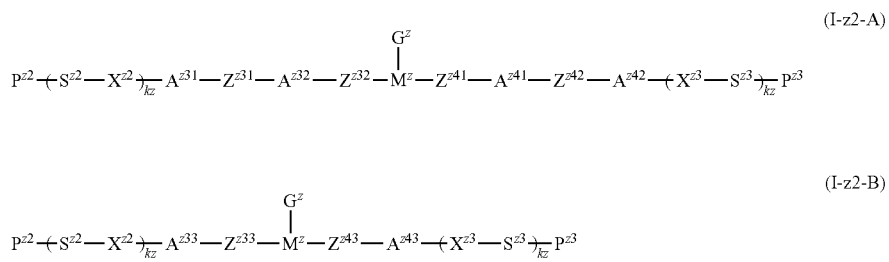

(wherein $P^{z2}$, $P^{z3}$, $S^{z2}$, $S^{z3}$, $M^z$, and $G^z$ denote the same as in the general formula (I-z2), $A^{z31}$, $A^{z42}$, $A^{z33}$, and $A^{z43}$ independently denote a 1,4-phenylene group, the group may be unsubstituted or substituted by one or more substituents $L^{z11}$'s, $L^{z11}$ denotes a fluorine atom, a chlorine atom, or a linear or branched alkyl group having 1 to 20 carbon atoms with one —$CH_2$— or nonadjacent two or more —$CH_2$—'s optionally independently substituted by —O—, —CO—, —COO—, or —OCO—, any hydrogen atom of the alkyl group may be substituted by a fluorine atom, a plurality of $L^{z11}$'s, if present at all, in the compound may be the same or different, $A^{z32}$ and $A^{z41}$ denote a 1,4-cyclohexylene group, $Z^{z31}$ and $Z^{z42}$ independently denote —$OCH_2$—, —$CH_2O$—, —COO—, —OCO—, or a single bond, $Z^{z32}$, $Z^{41}$, $Z^{z33}$ and $Z^{z43}$ independently denote —$OCH_2$—, —$CH_2O$—, —COO—$CH_2CH_2$—, —$CH_2CH_2$—OCO—, —COO—, or —OCO—, and at least one of $Z^{z32}$ and $Z^{41}$ and at least one of $Z^{z33}$ and $Z^{z43}$ denote a group selected from —$OCH_2$—, —$CH_2O$—, —COO—$CH_2CH_2$—, and —$CH_2CH_2$—OCO—).

In careful consideration of inverse dispersibility, high refractive index anisotropy, a good liquid crystallinity balance of the compound added to a composition, the resistance to deterioration of the compound dissolved in an organic solvent and stored for extended periods, the resistance to deterioration of the compound added to a composition and stored for extended periods, or the phase difference stability of a film produced from the compound, a compound represented by the following general formula (I-z2-A-1) is preferred.

[Chem. 124]

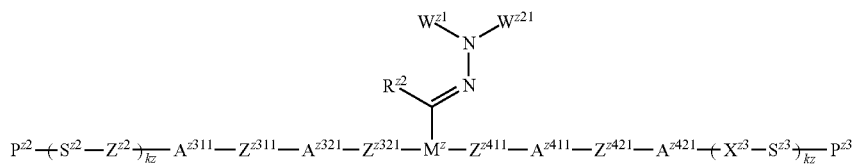

(I-z2-A-1)

(In the formula, $P^{z2}$, $P^{z3}$, $S^{z2}$, $S^{z3}$, $X^{z2}$, $X^{z3}$, $M^z$, $R^{z2}$, and $W^{z1}$ denote the same as in the general formula (I-z1), $A^{z311}$ and $A^{z421}$ independently denote a 1,4-phenylene group, the group may be unsubstituted or substituted by one or more substituents $L^{z11}$'s, $A^{z321}$ and $A^{z411}$ denote a 1,4-cyclohexylene group, $Z^{z311}$ and $Z^{z421}$ independently denote —OCH$_2$—, —CH$_2$O—, —COO—, or —OCO—, $Z^{z321}$ and $Z^{411}$ independently denote —OCH$_2$—, —CH$_2$O—, —COO—CH$_2$CH$_2$—, —CH$_2$CH$_2$—OCO—, —COO—, or —OCO—, and at least one of $Z^{z321}$ and $Z^{411}$ particularly preferably denotes a group selected from —OCH$_2$—, —CH$_2$O—, —COO—CH$_2$CH$_2$—, and —CH$_2$CH$_2$—OCO—.

$W^{z21}$ denotes a group selected from a linear or branched alkyl group having 1 to 20 carbon atoms with one —CH$_2$— or nonadjacent two or more —CH$_2$—'s optionally independently substituted by —O—, and a group represented by —(X$^{z4}$-S$^{z4}$)$_{kz}$-P$^{z4}$.)

The preferred structure of $W^{z1}$ is the same as described above.

More specifically, the compounds represented by the general formula (I) are preferably the compounds represented by the following formulae.

[Chem. 125]

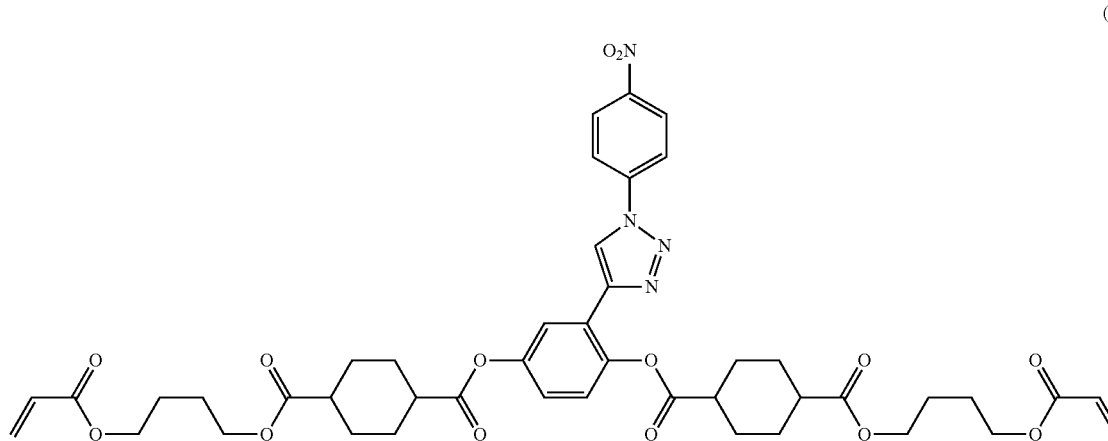

(A11-1)

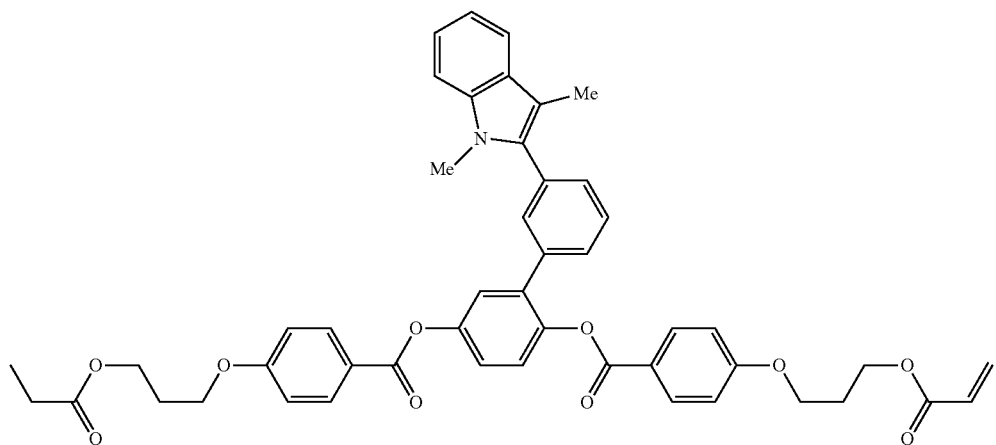

(A11-2)

-continued
(A11-3)
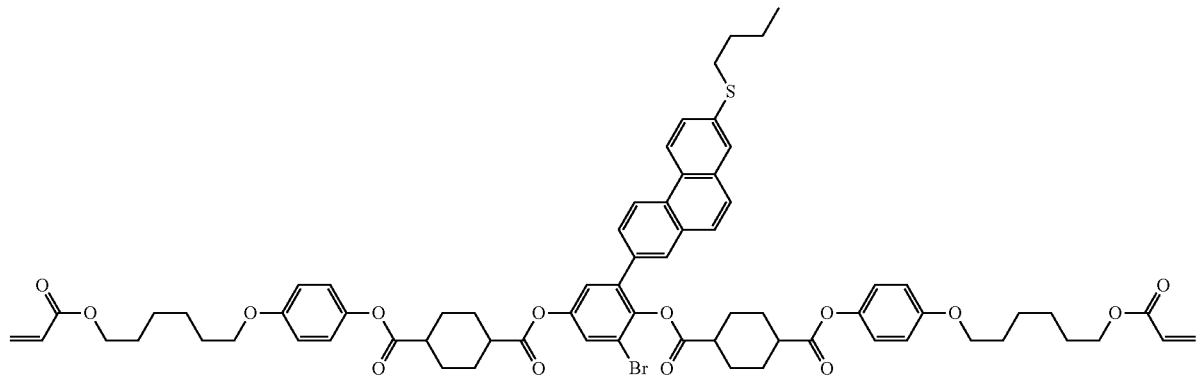
(A11-4)
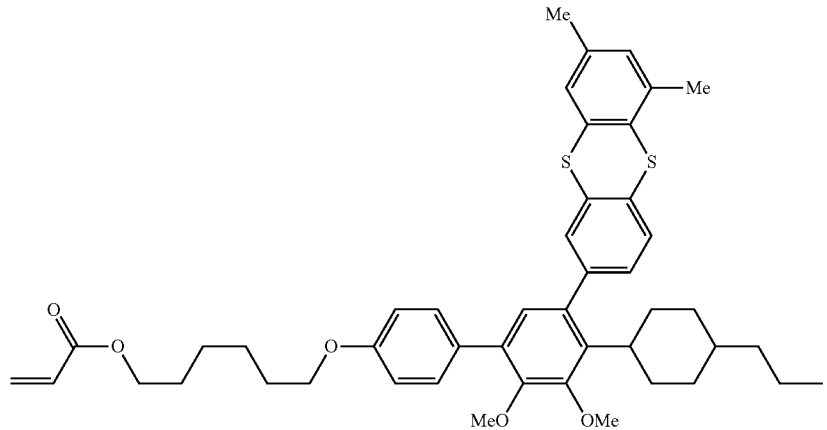
(A11-5)
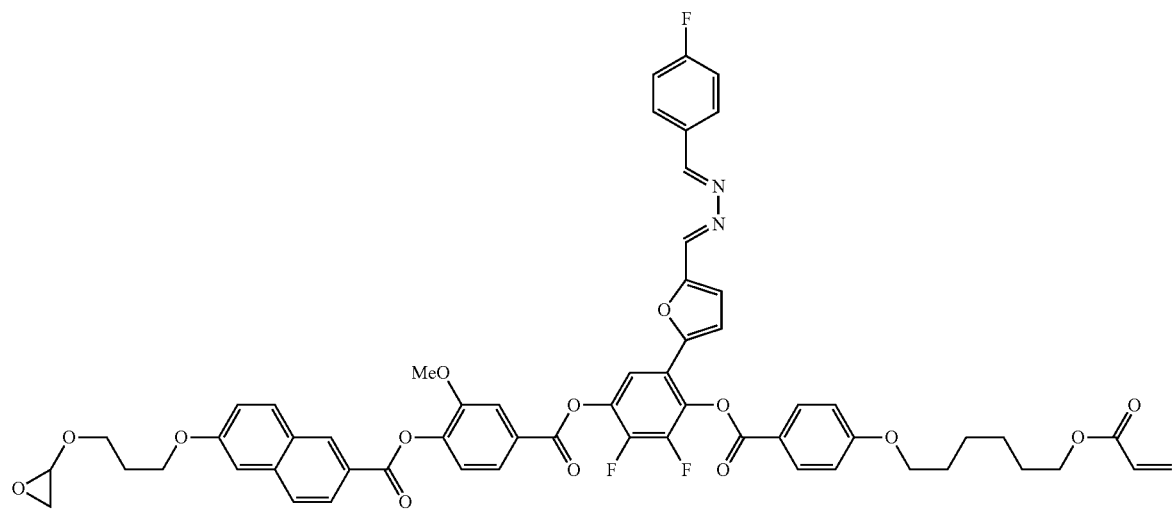

-continued
[Chem. 126]
(A11-6)
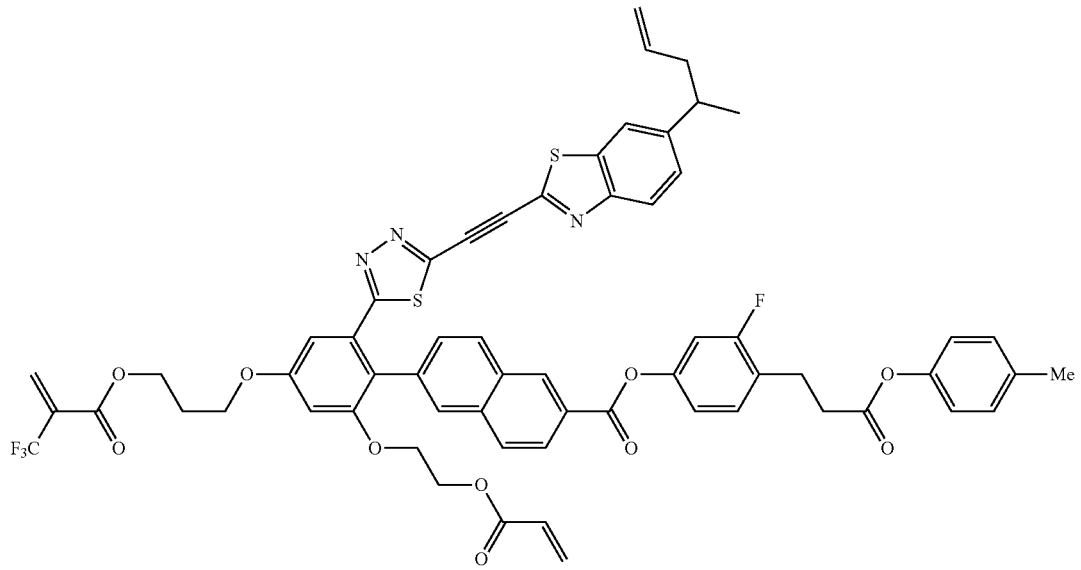
(A11-7)
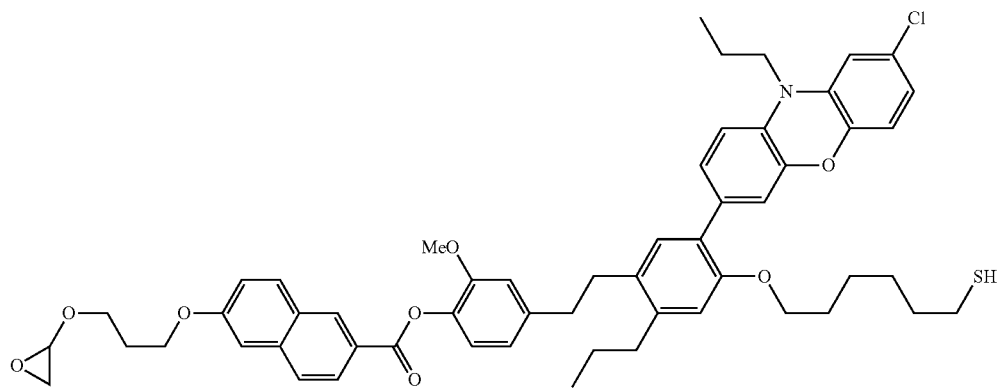
(A11-8)
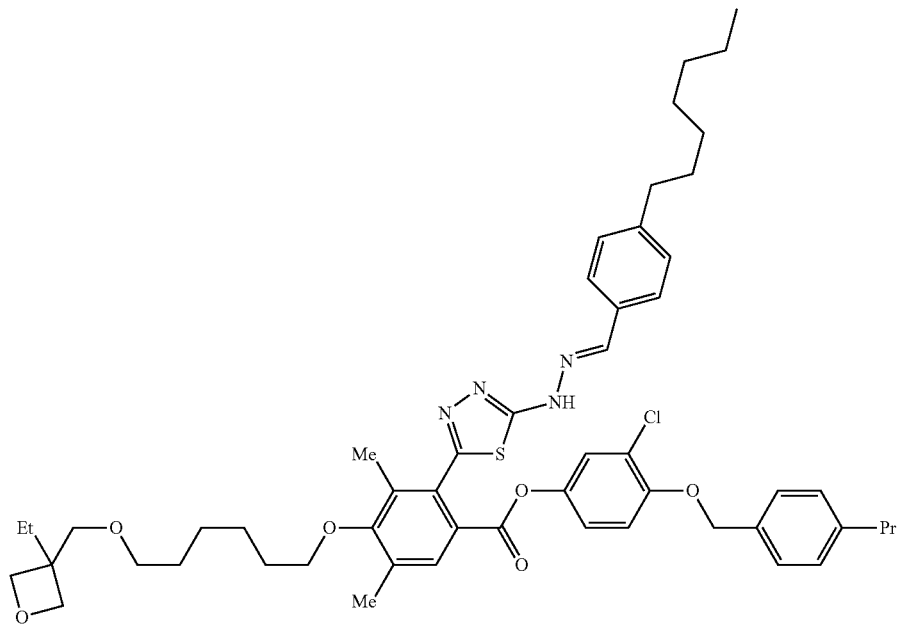

-continued
(A11-9)
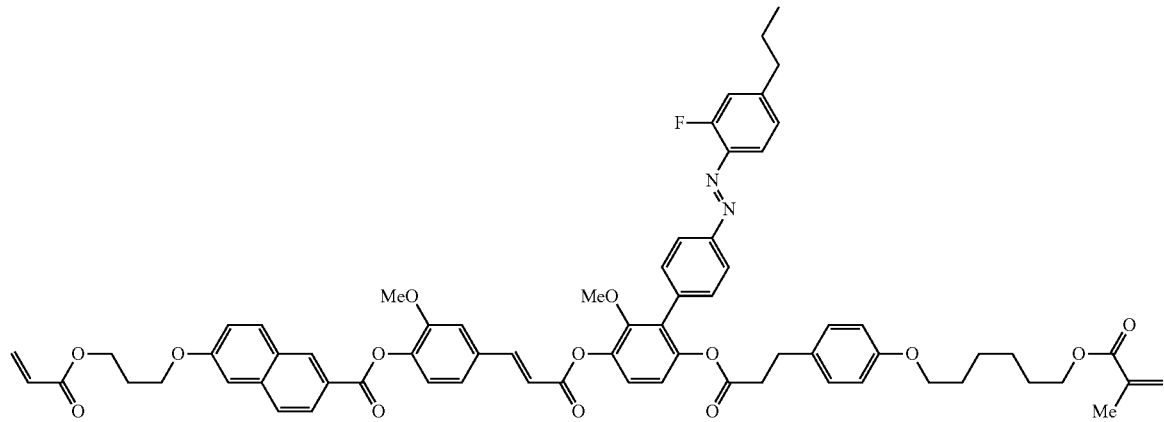
(A11-10)
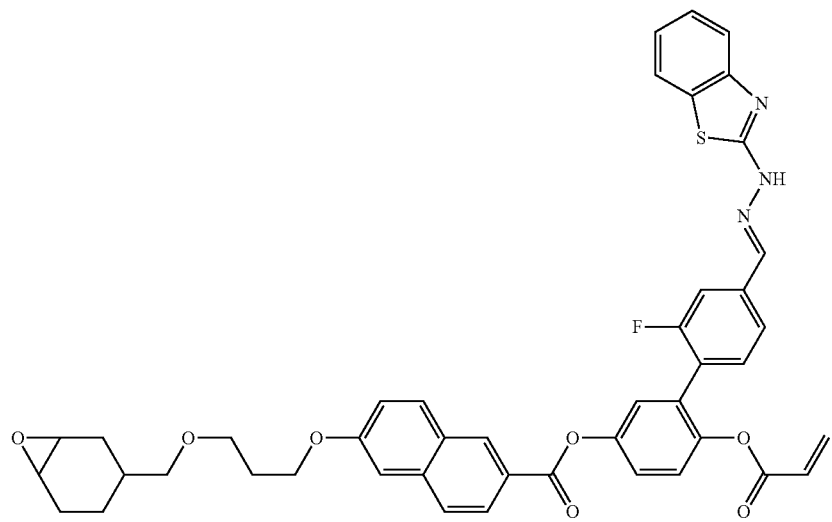
[Chem. 127]
(A11-11)
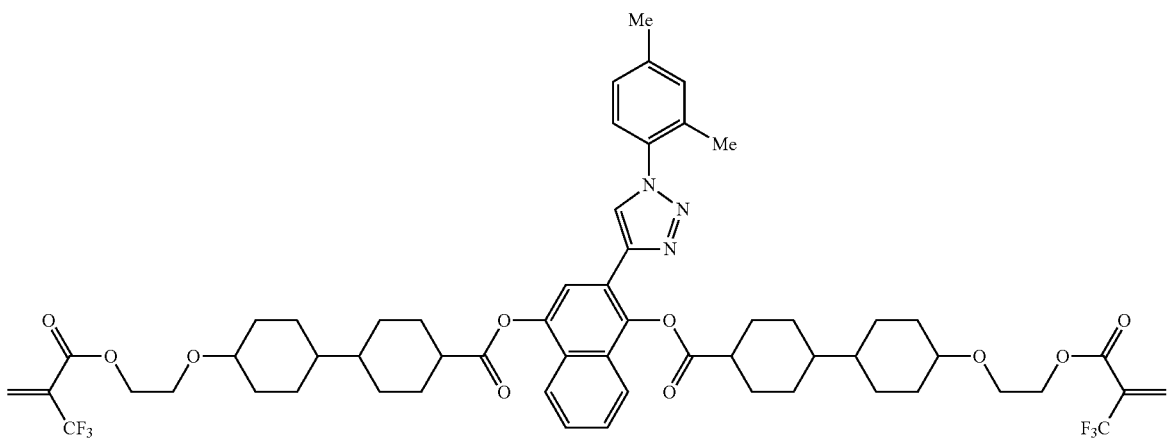

(A11-12)
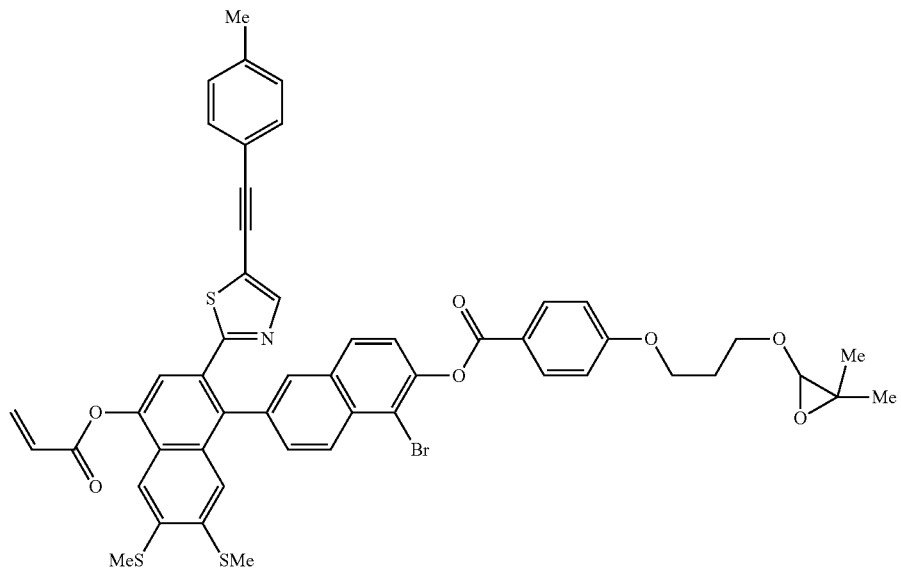
(A11-13)
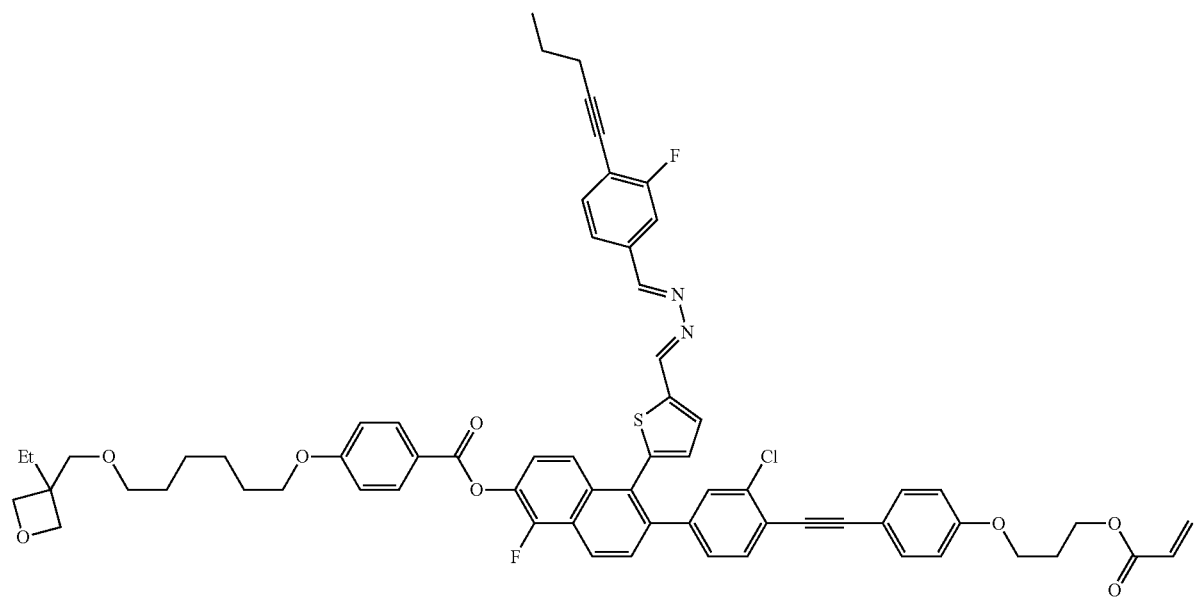
(A11-14)
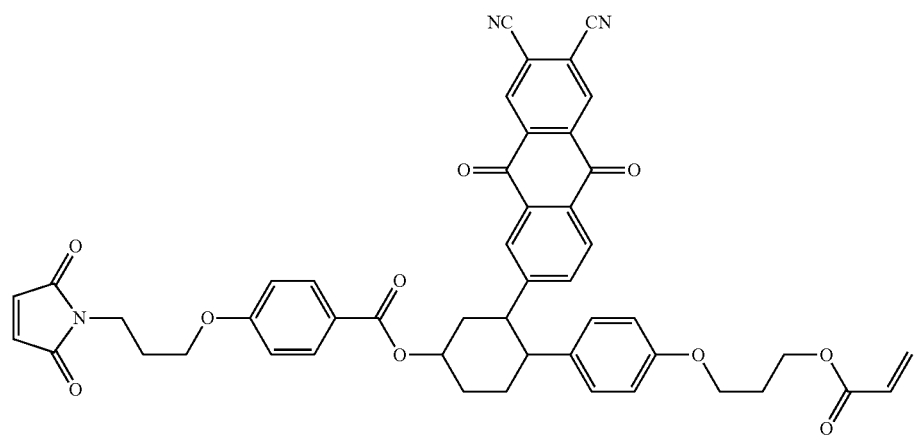

-continued
(A11-15)
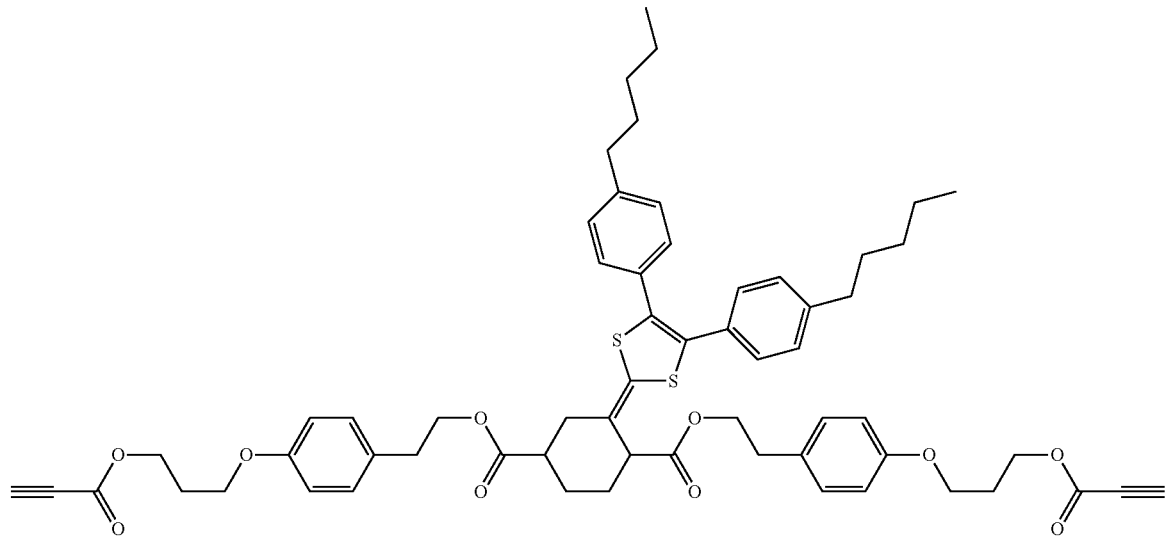
[Chem. 128]
(A12-1)
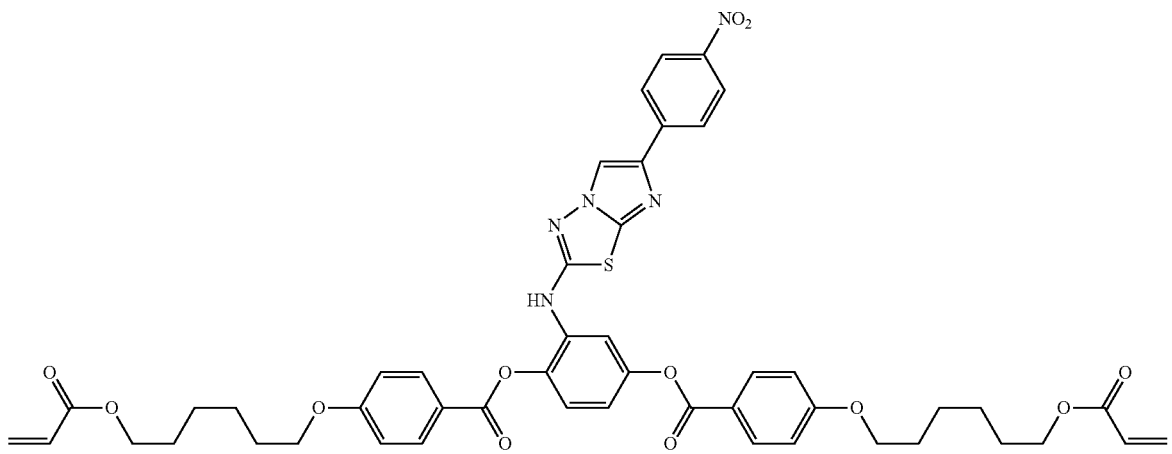
(A12-2)
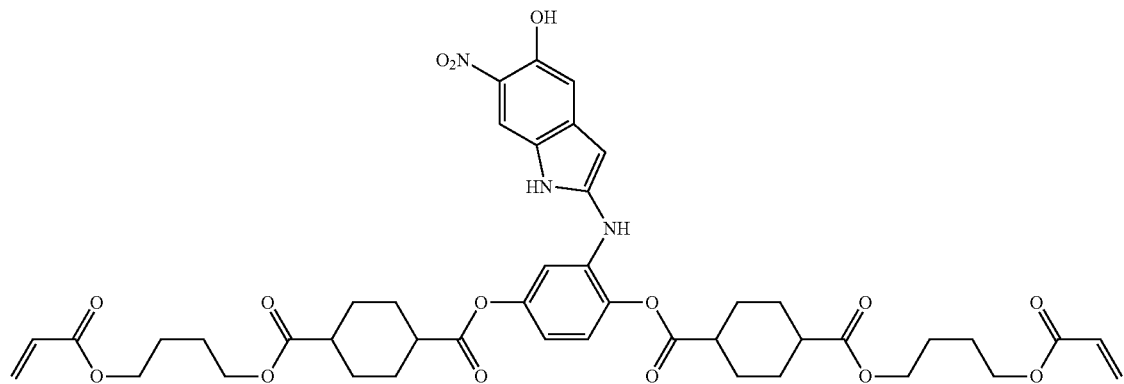

(A12-3)
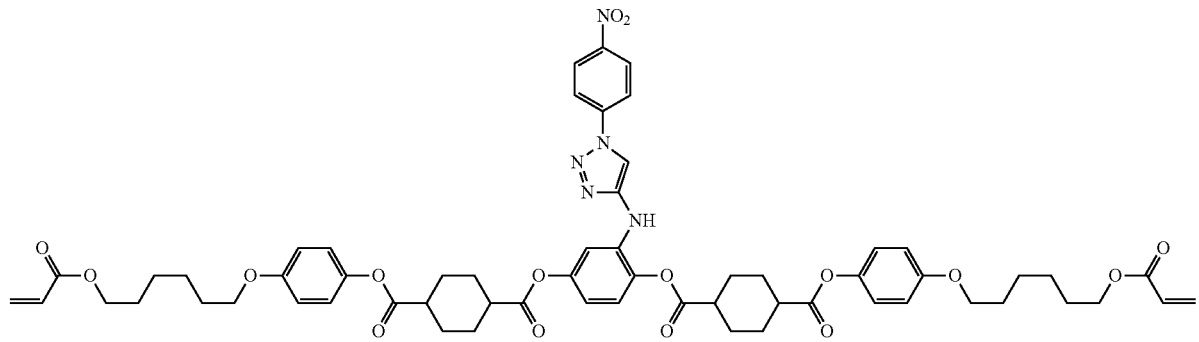
(A12-4)
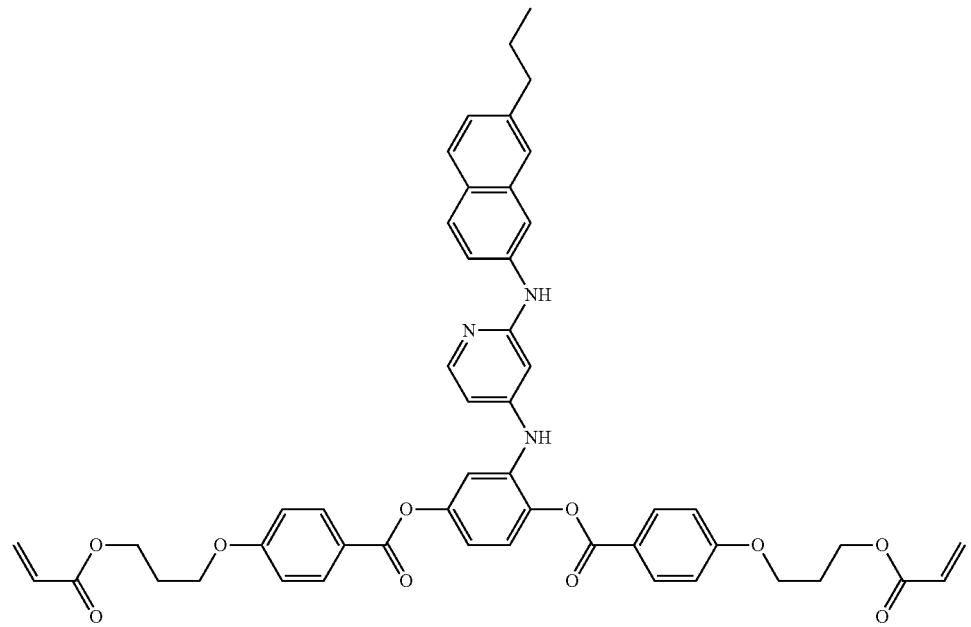
(A12-5)
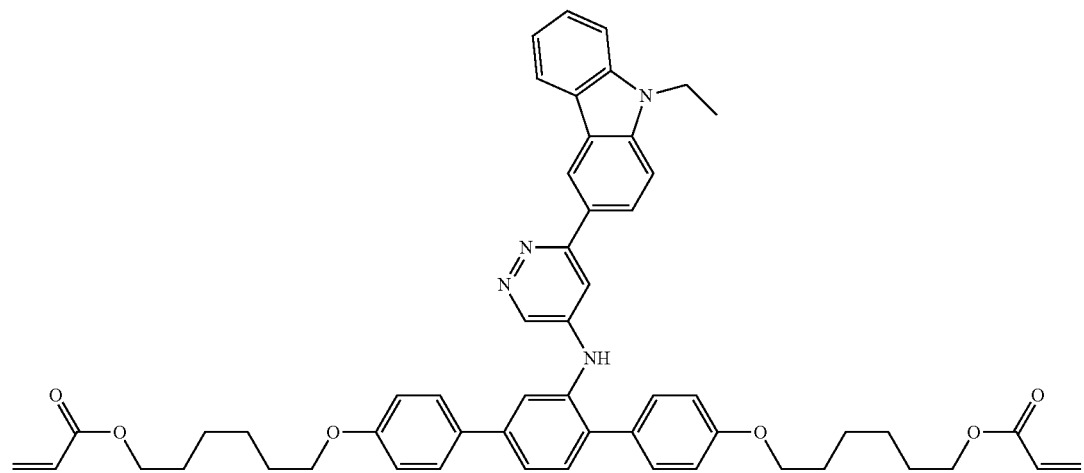

[Chem. 129]
(A12-6)
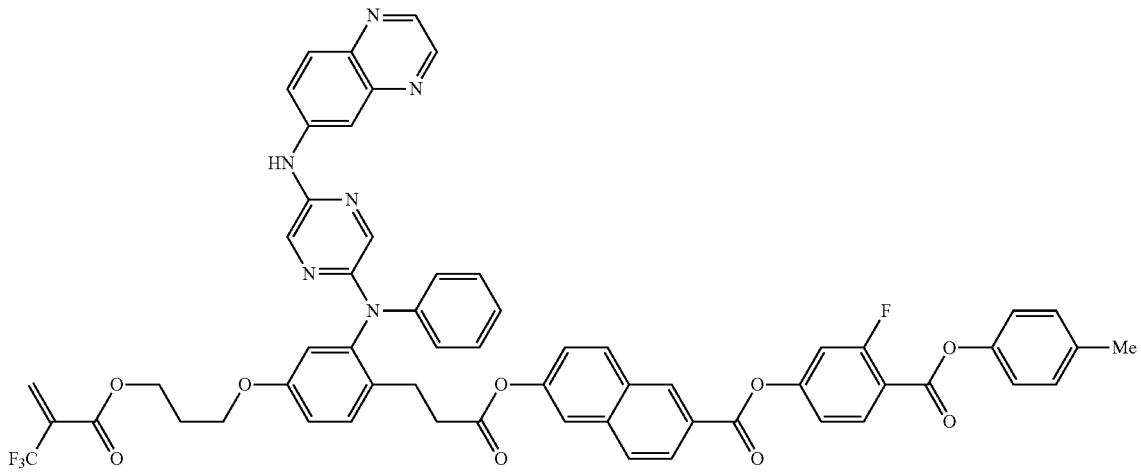
(A12-7)
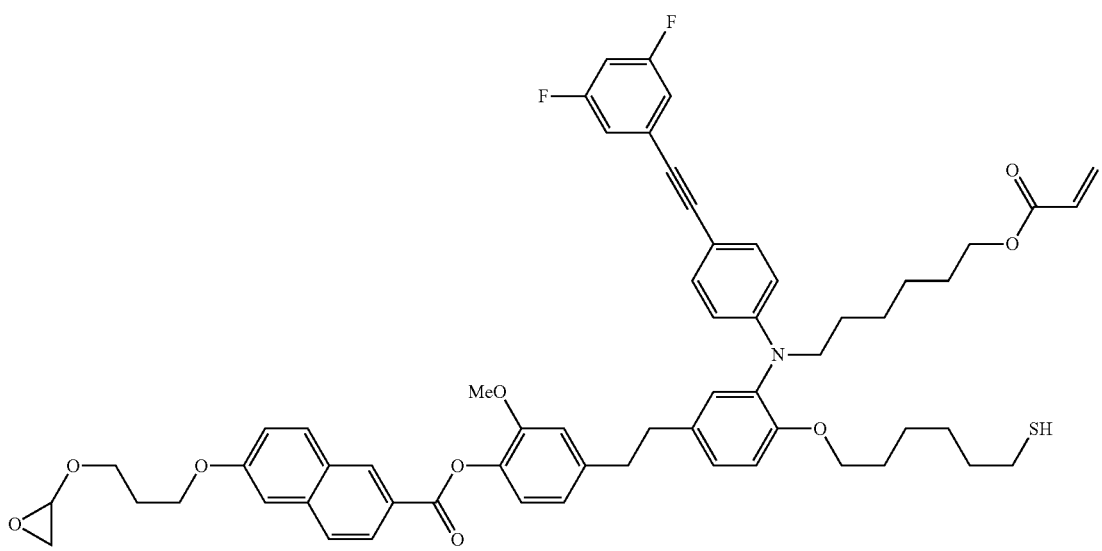
(A12-8)
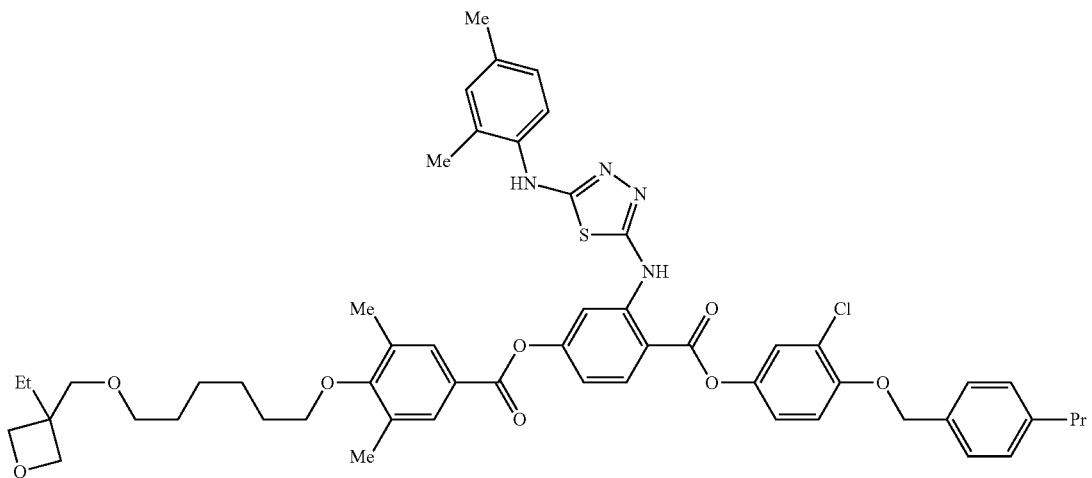

-continued
(A12-9)
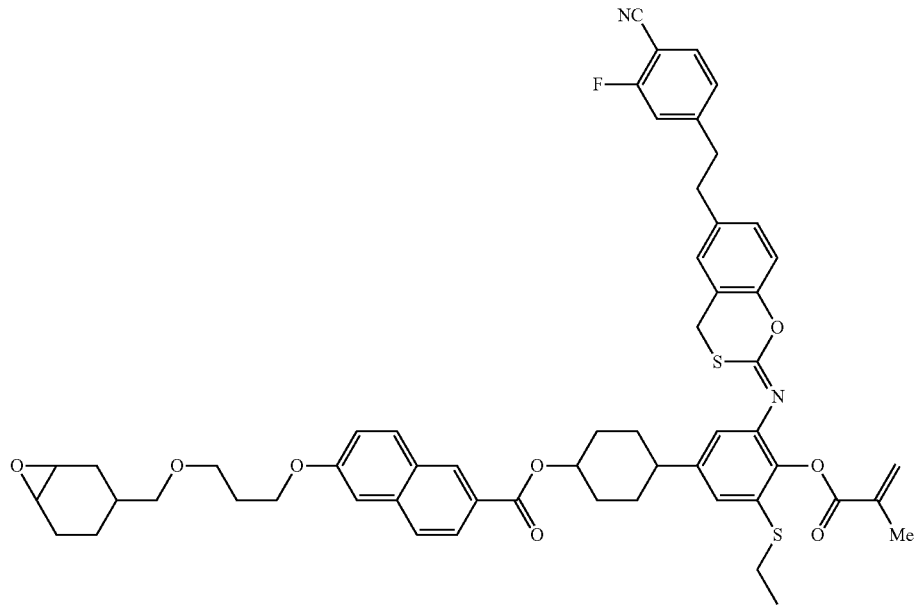
(A12-10)
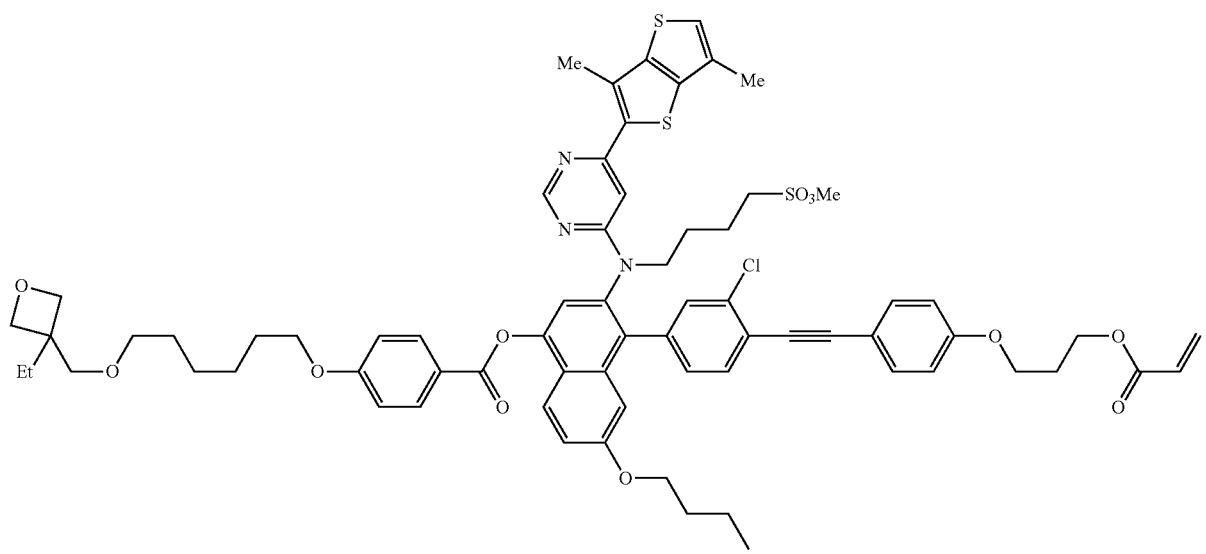
[Chem. 130]
(A12-11)
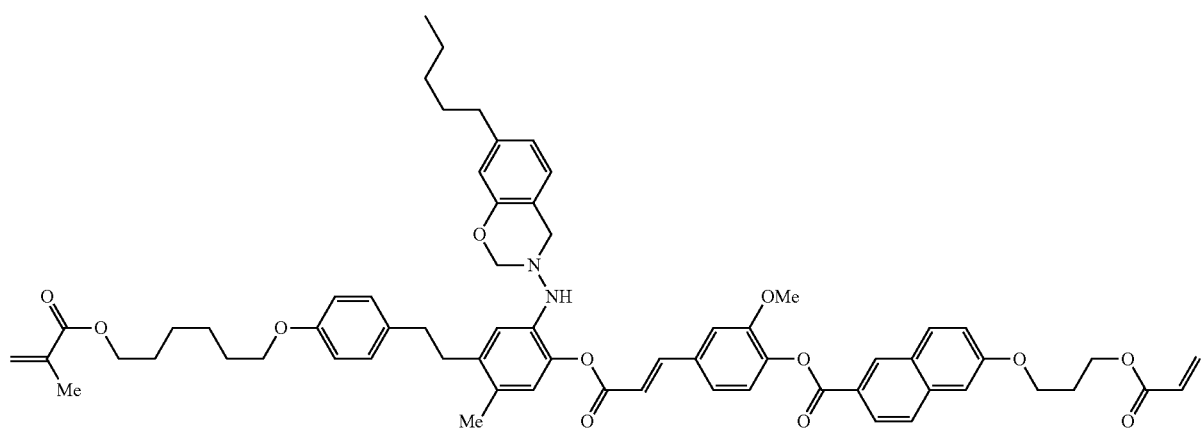

-continued
(A12-12)
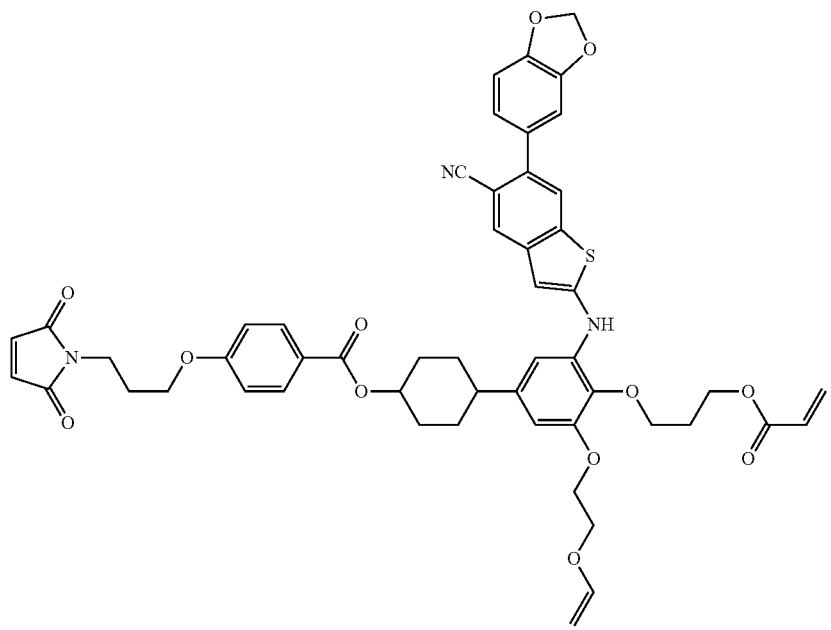
(A12-13)
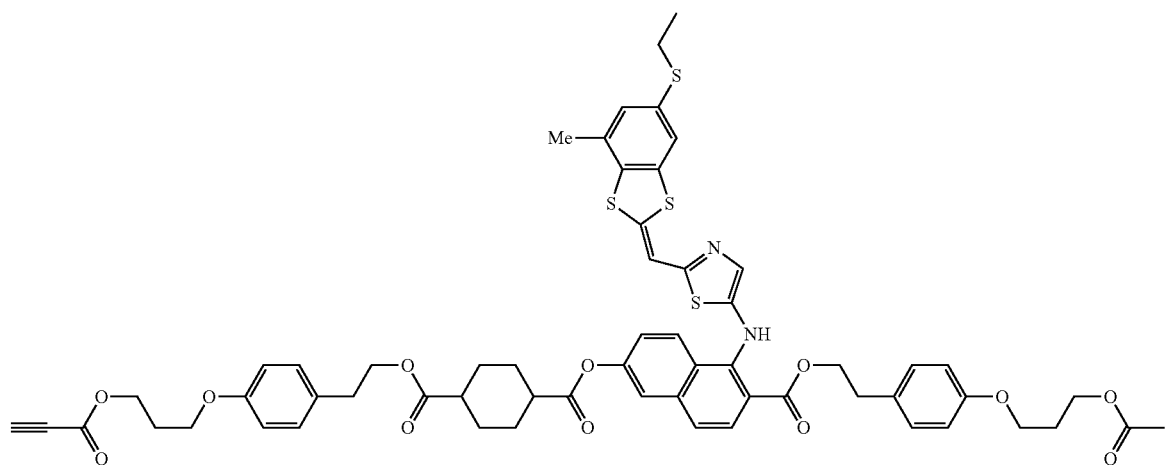
(A12-14)
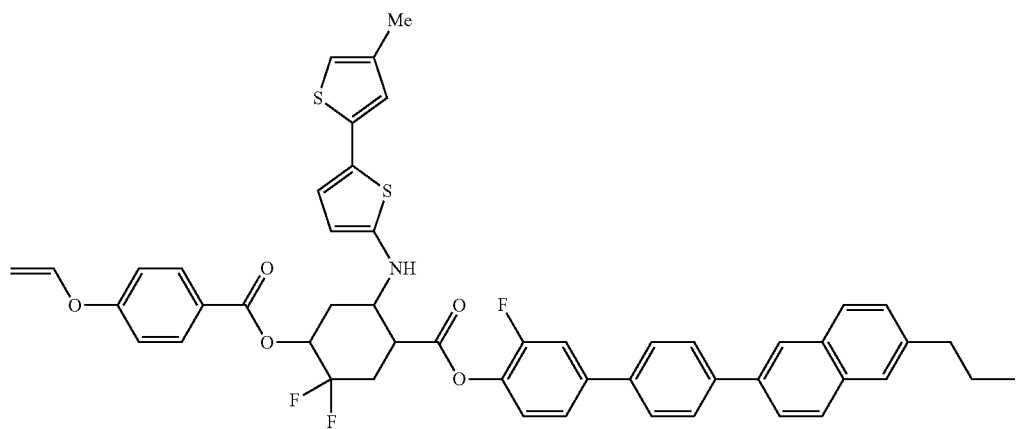

-continued
(A12-15)
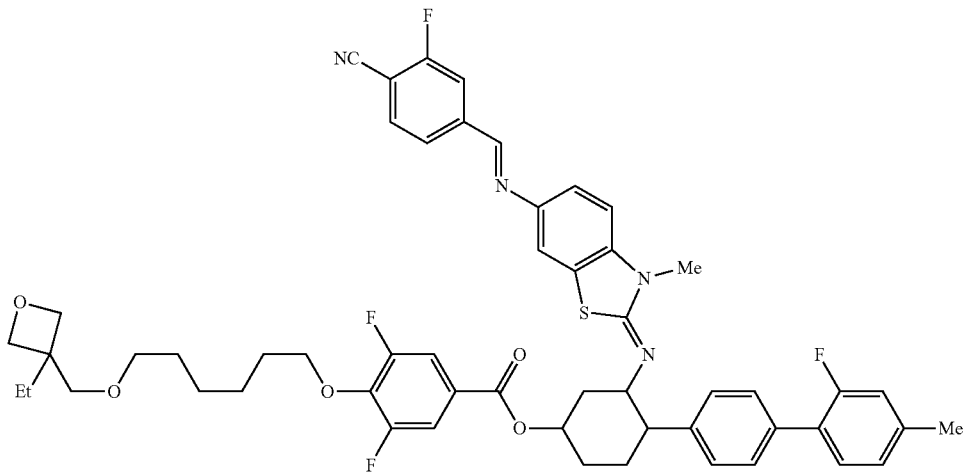
[Chem. 131]
(A12-16)
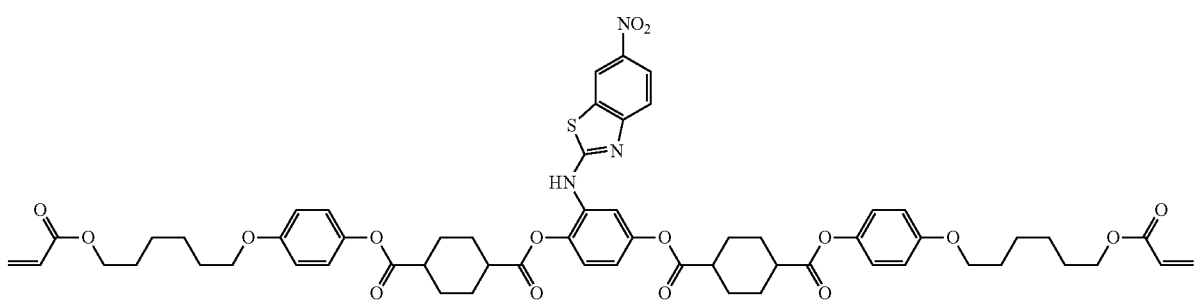
(A12-17)
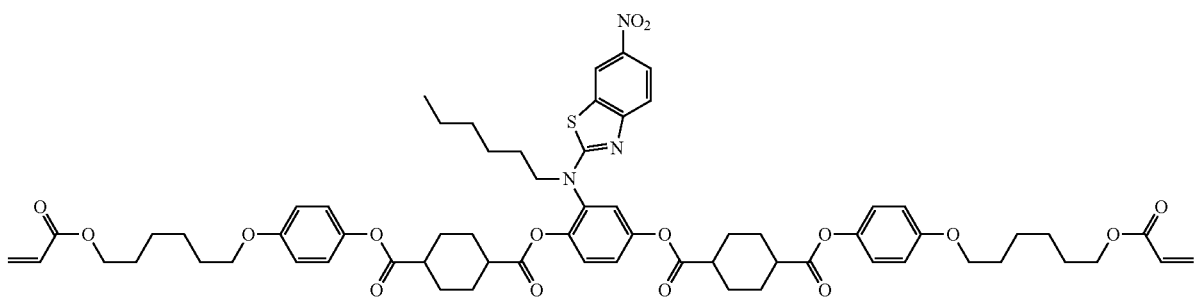
(A12-18)
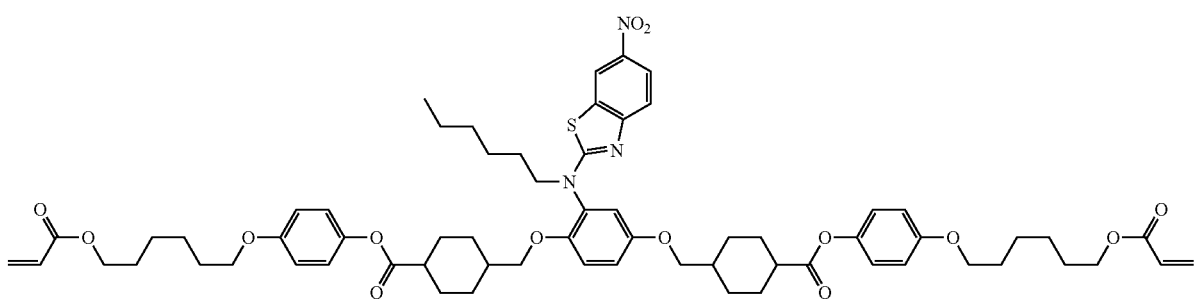

[Chem. 132]
(A13-1)
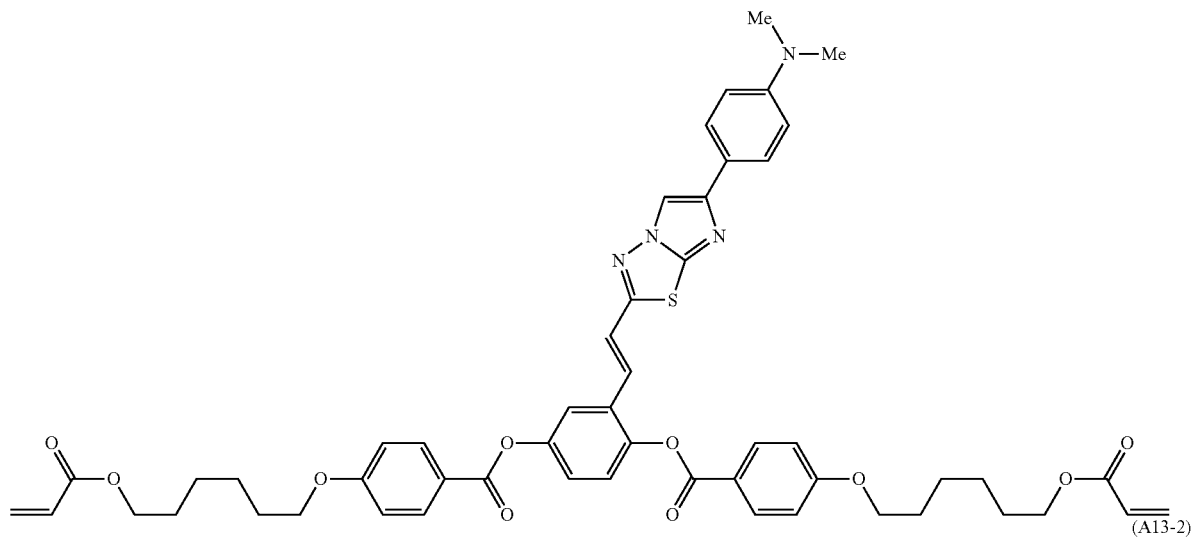
(A13-2)
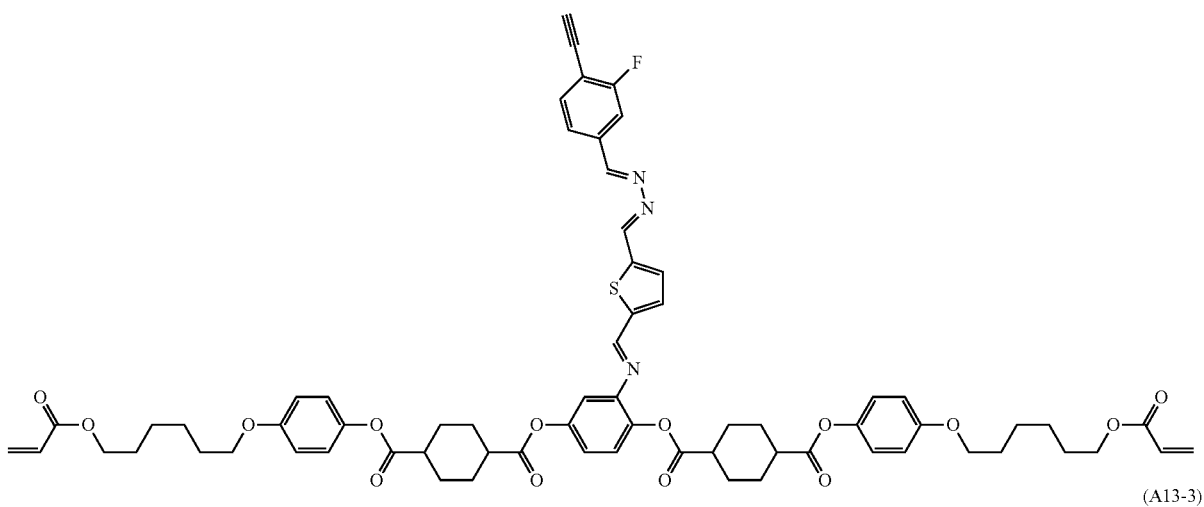
(A13-3)
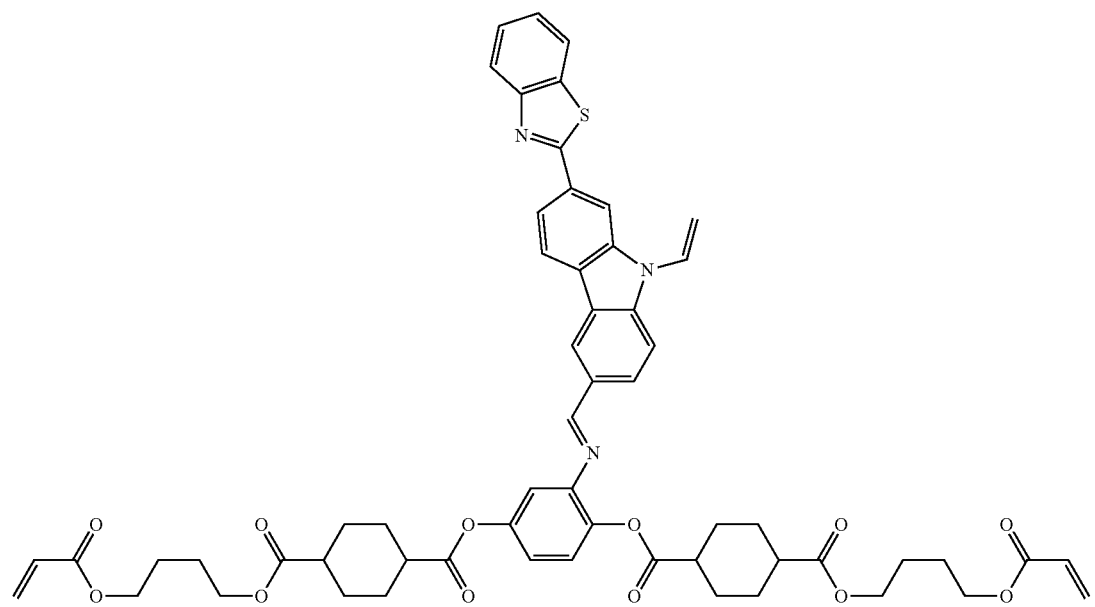

-continued
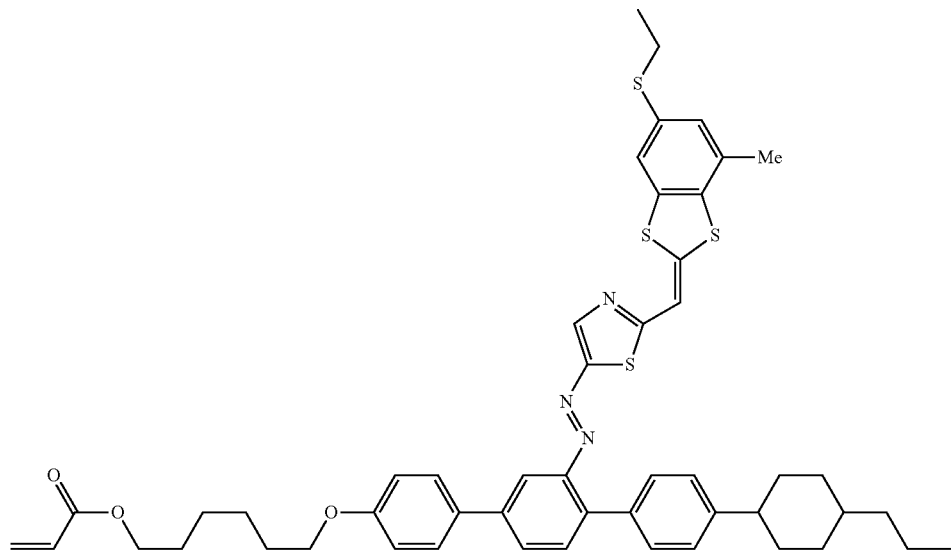
(A13-4)
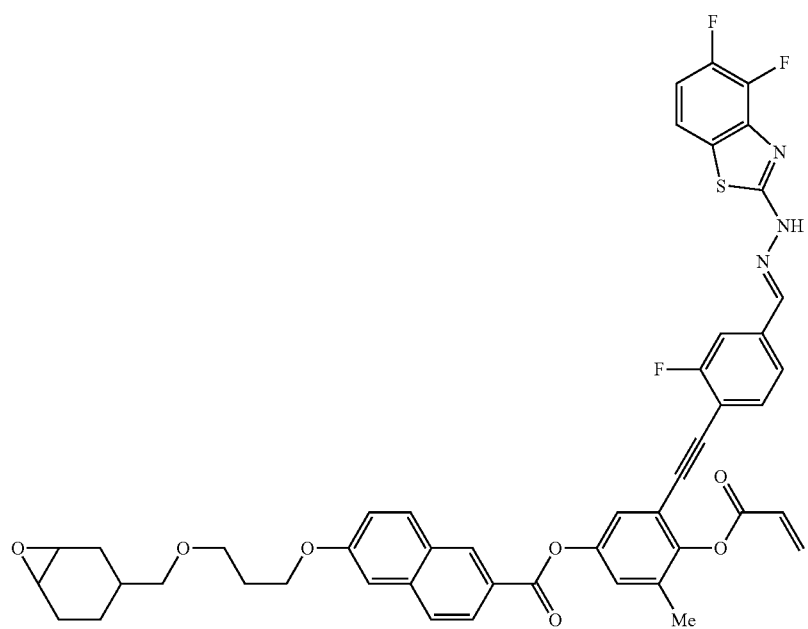
(A13-5)

-continued
(A13-6)
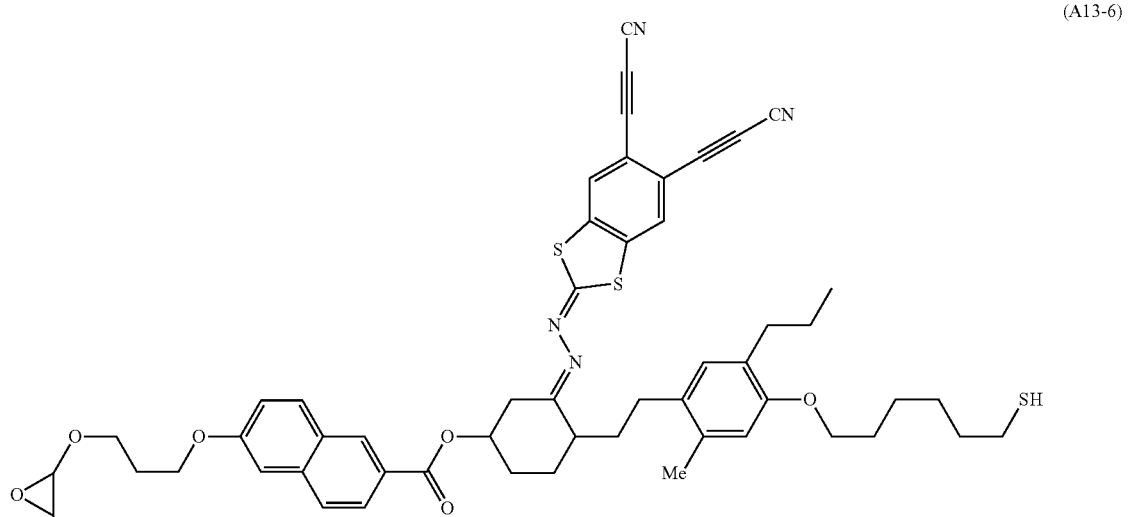
(A13-7)
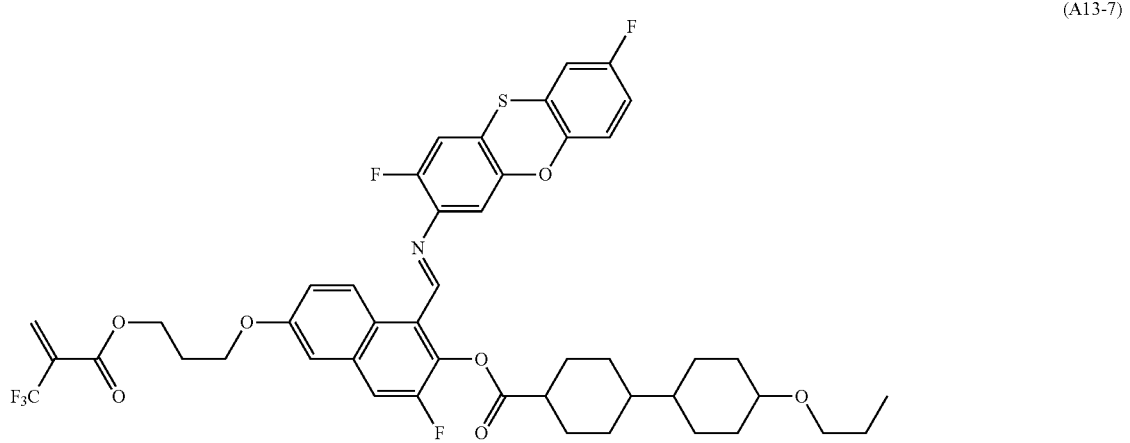
(A13-8)
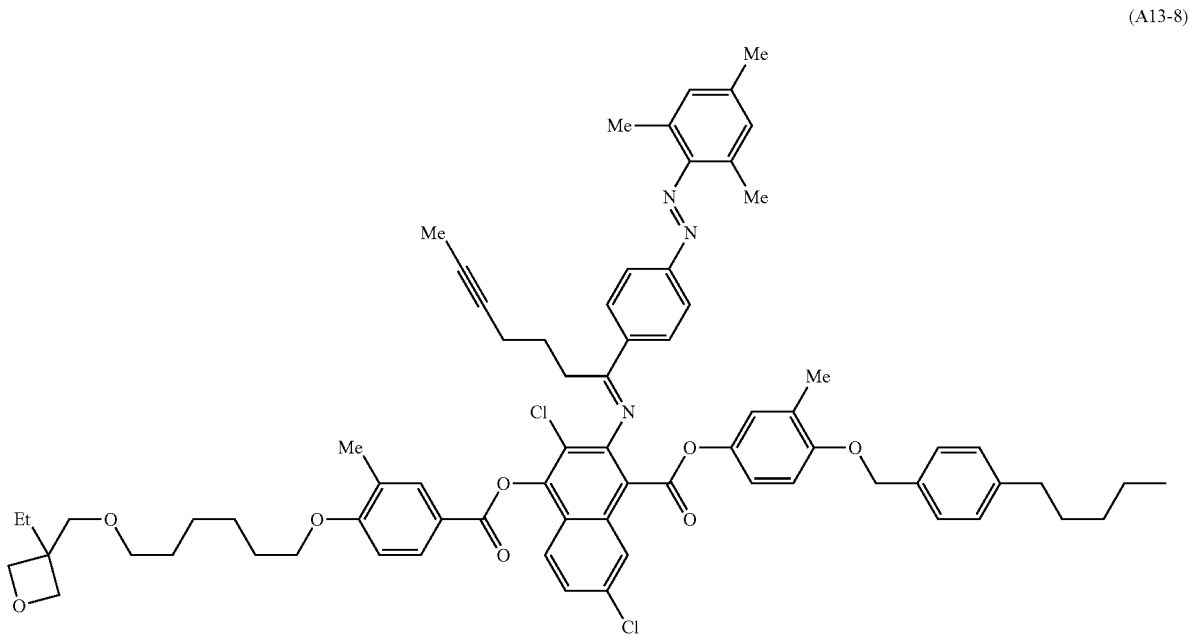

-continued
(A13-9)
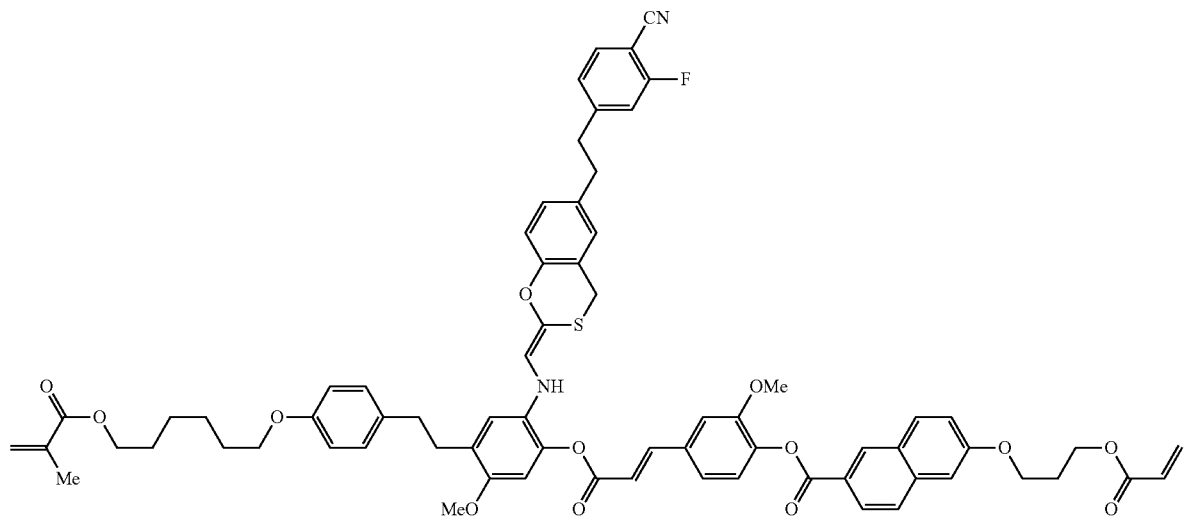
(A13-10)
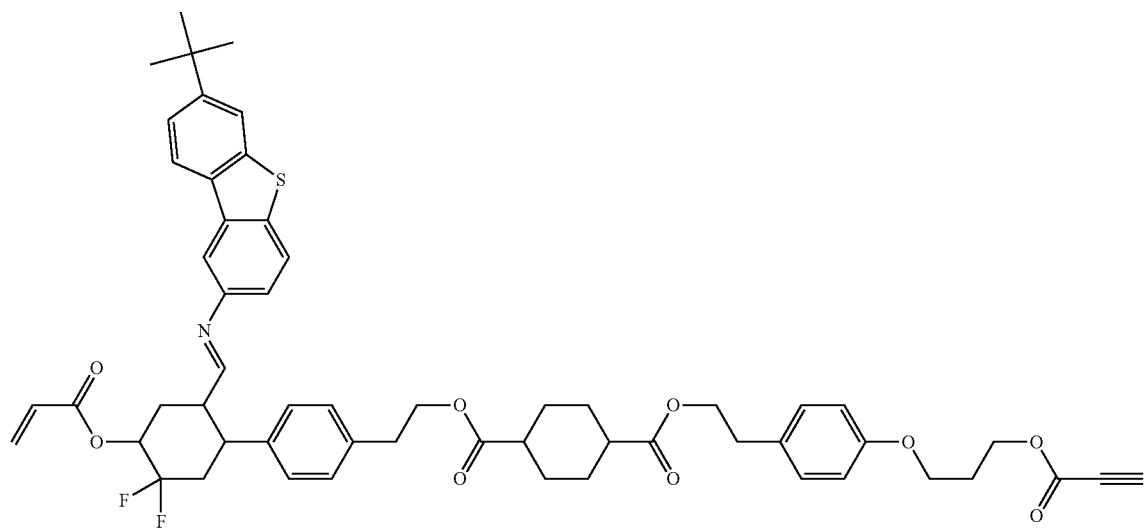
[Chem. 134]
(A14-1)
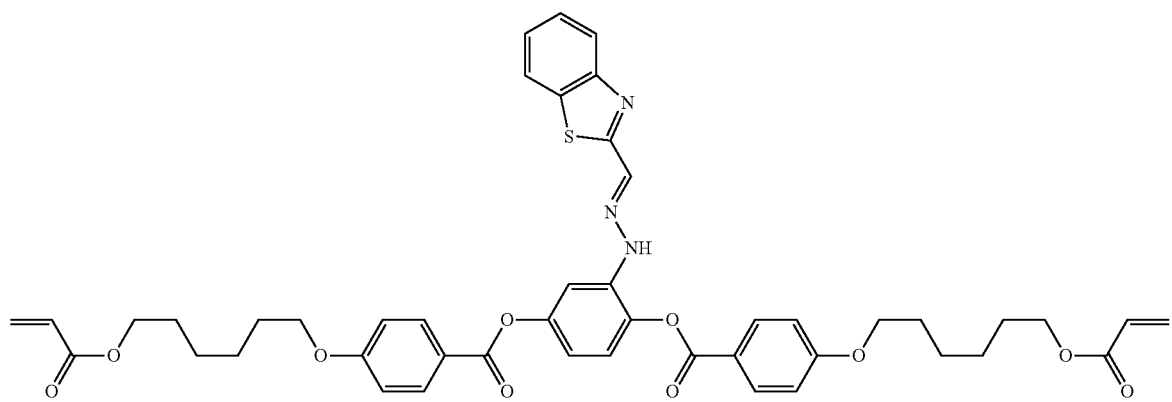

(A14-2)
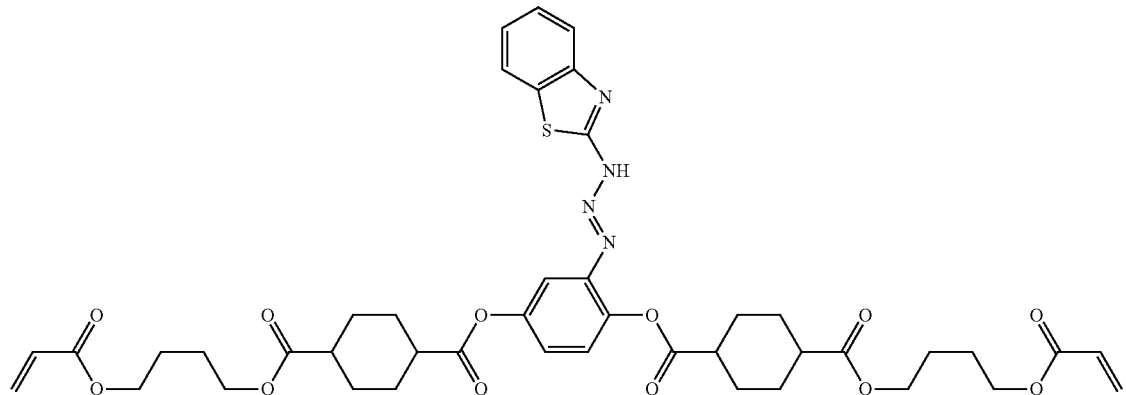
(A14-3)
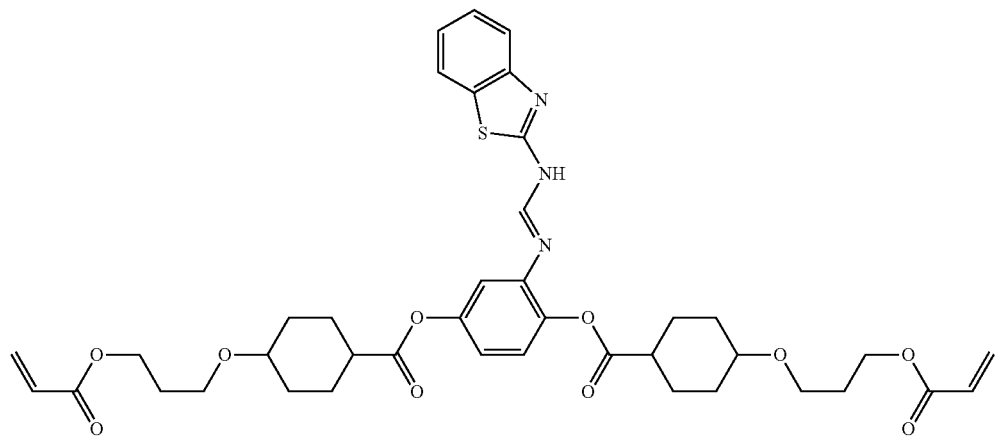
(A14-4)
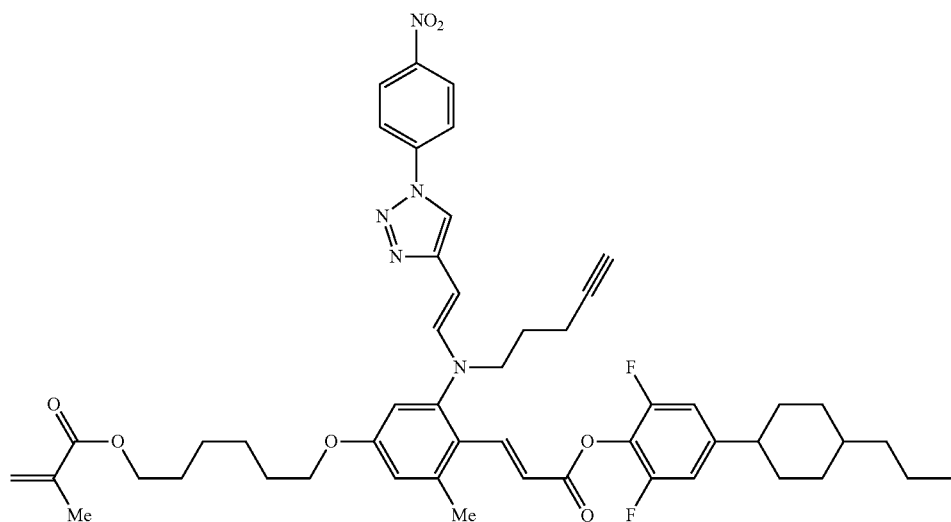

(A14-5)
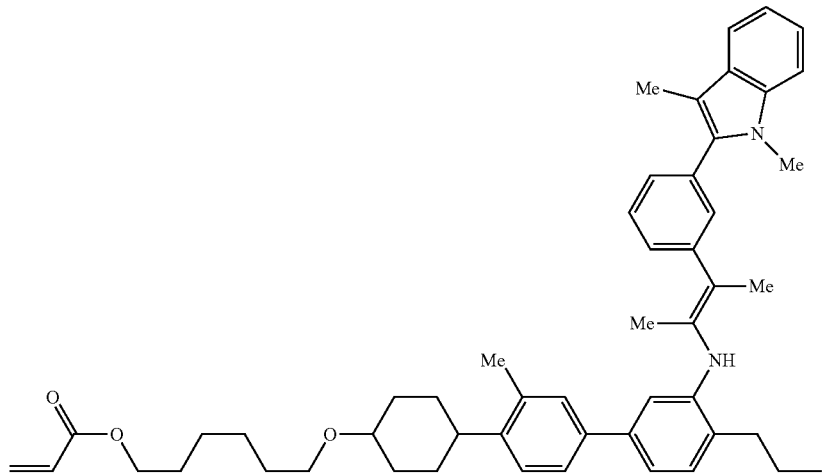
[Chem. 135]
(A14-6)
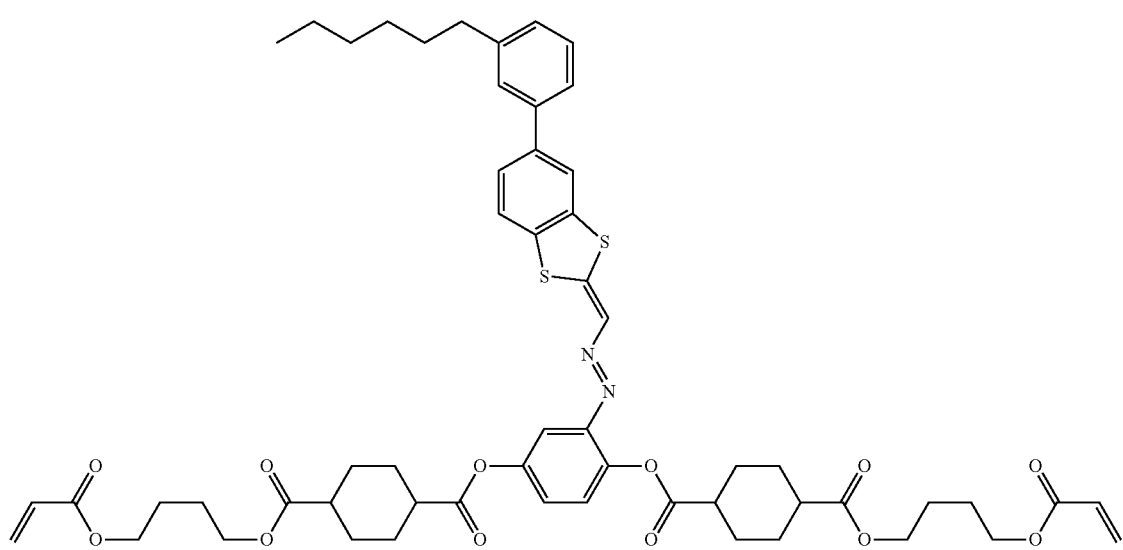
(A14-7)
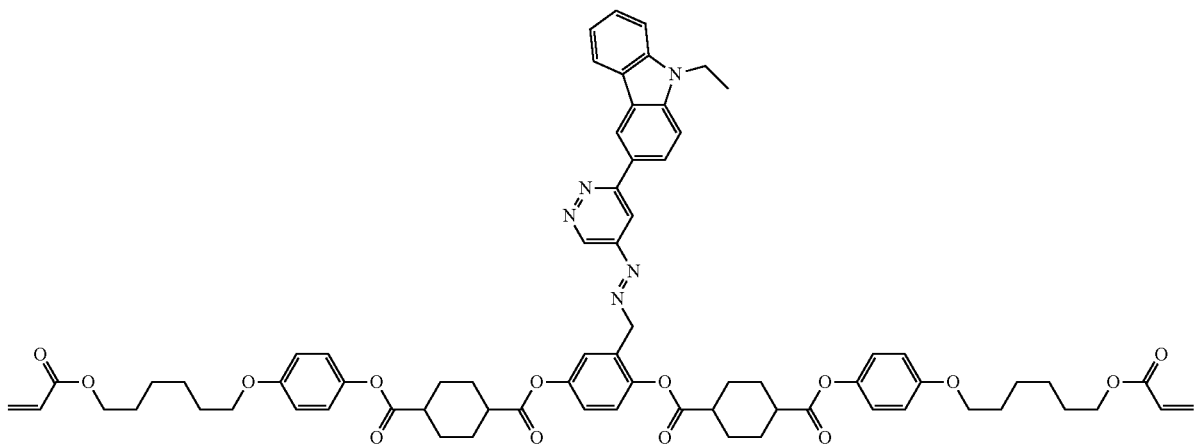

-continued
(A14-8)
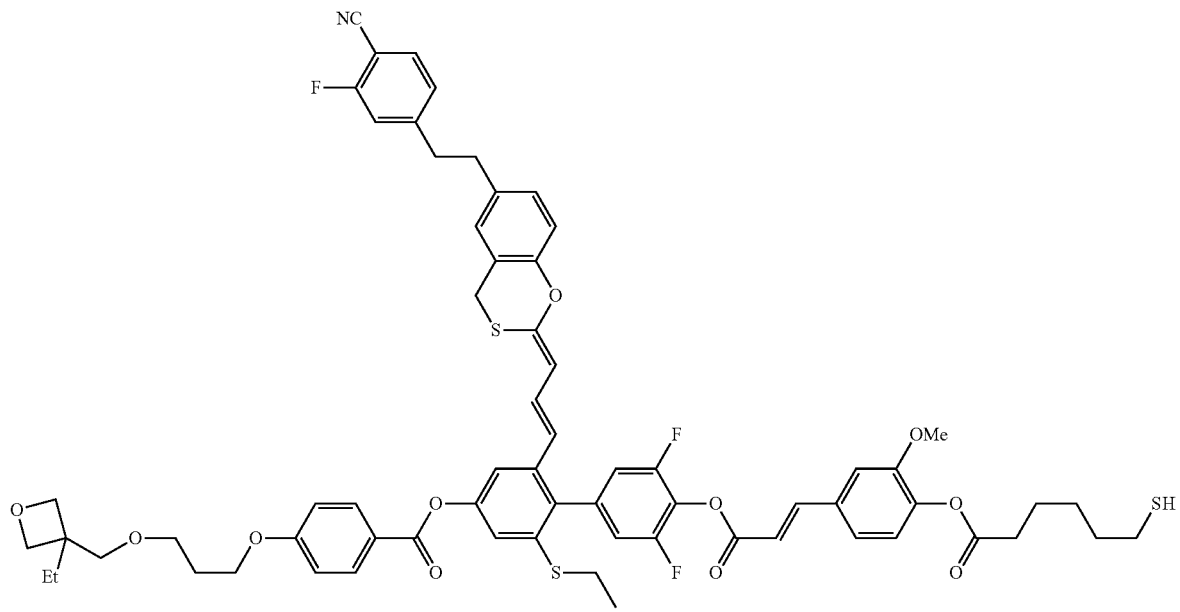
(A14-9)
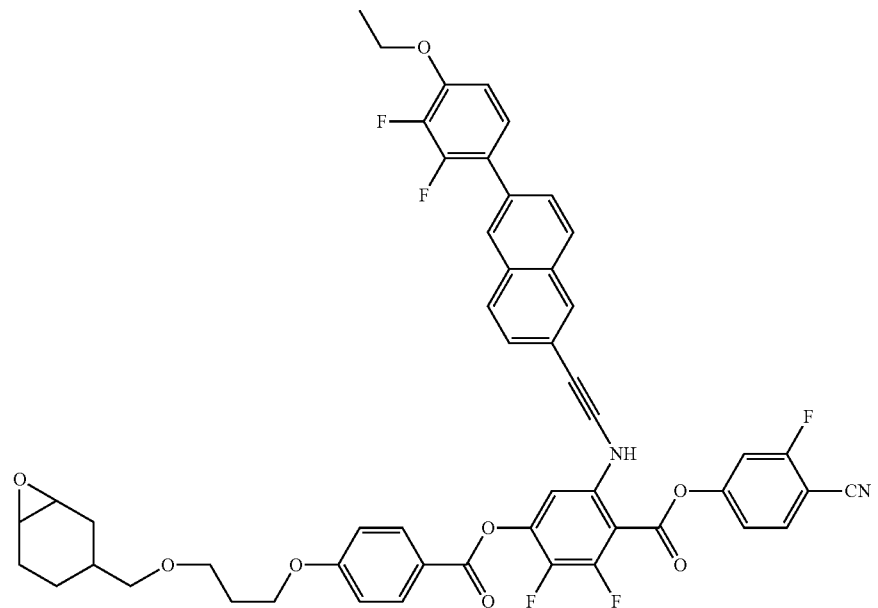

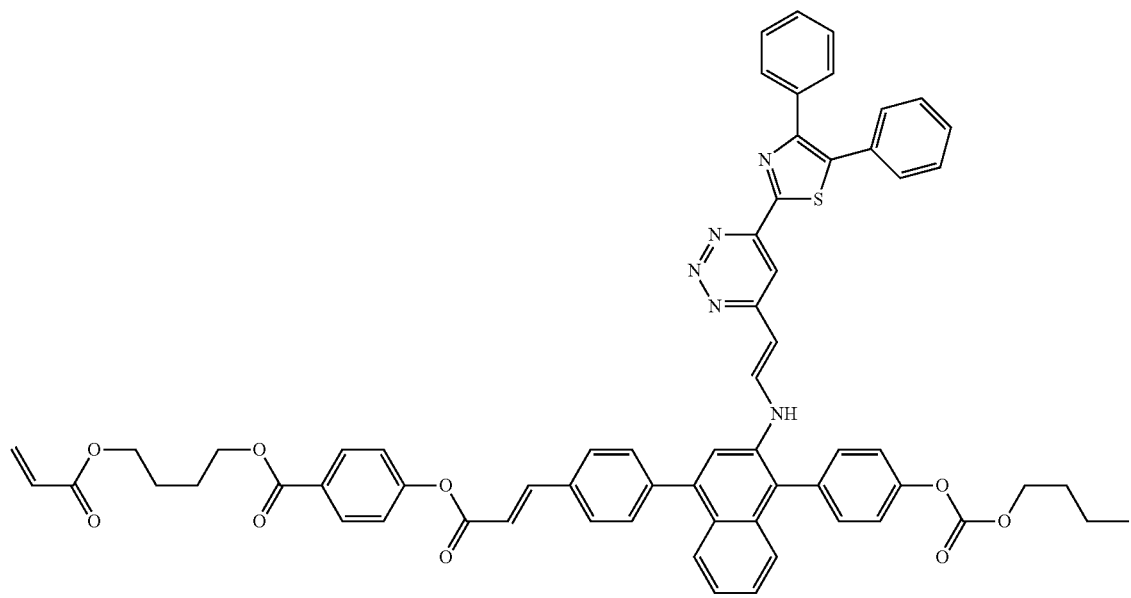
(A14-10)
[Chem. 136]
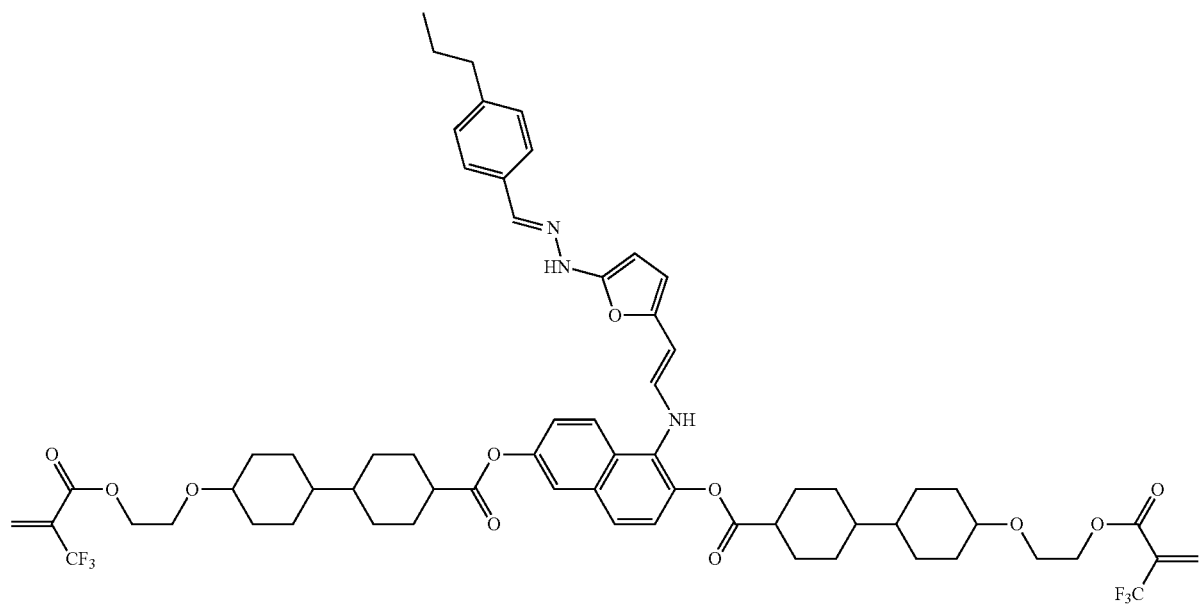
(A14-11)

-continued
(A14-12)
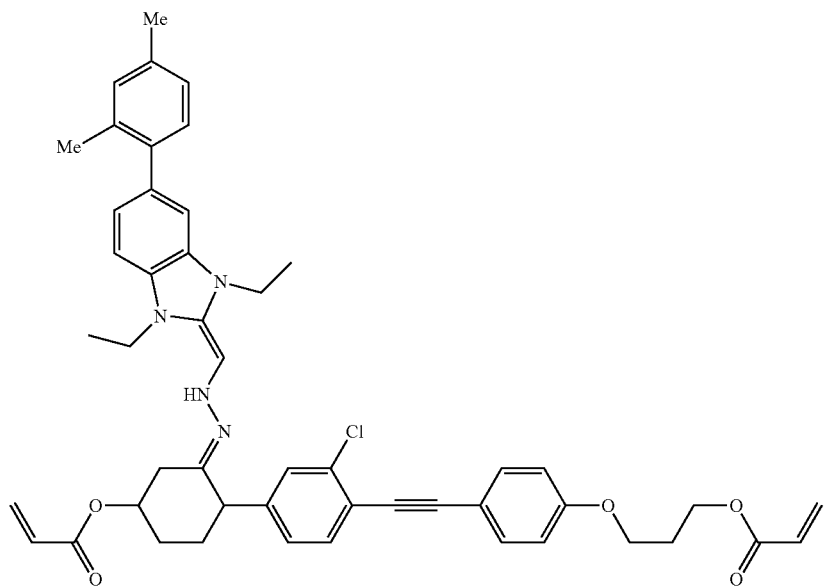
(A14-13)
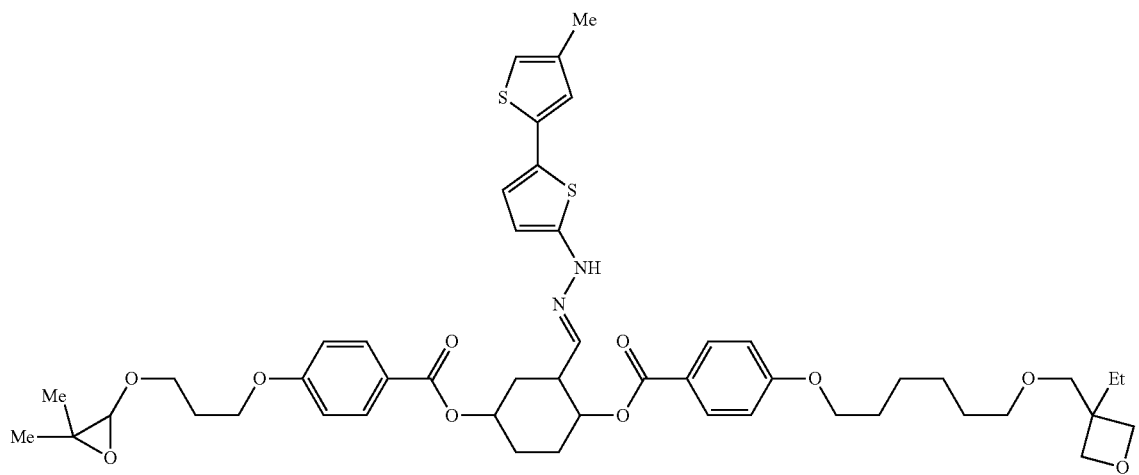
(A14-14)
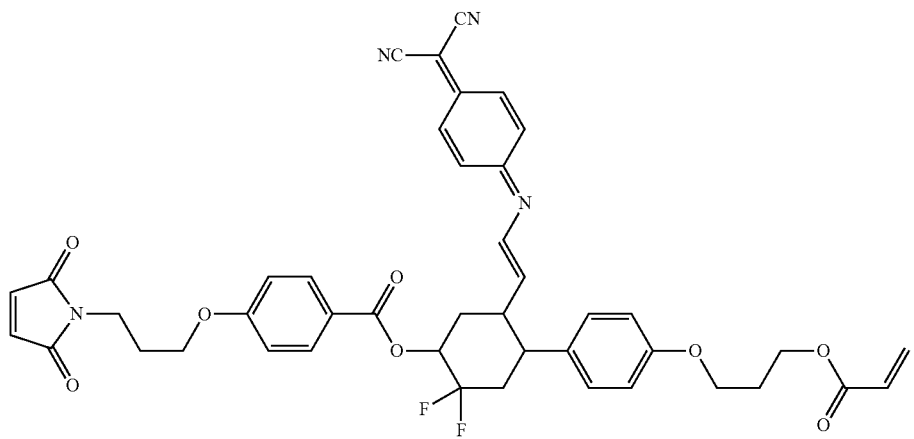

-continued
(A14-15)
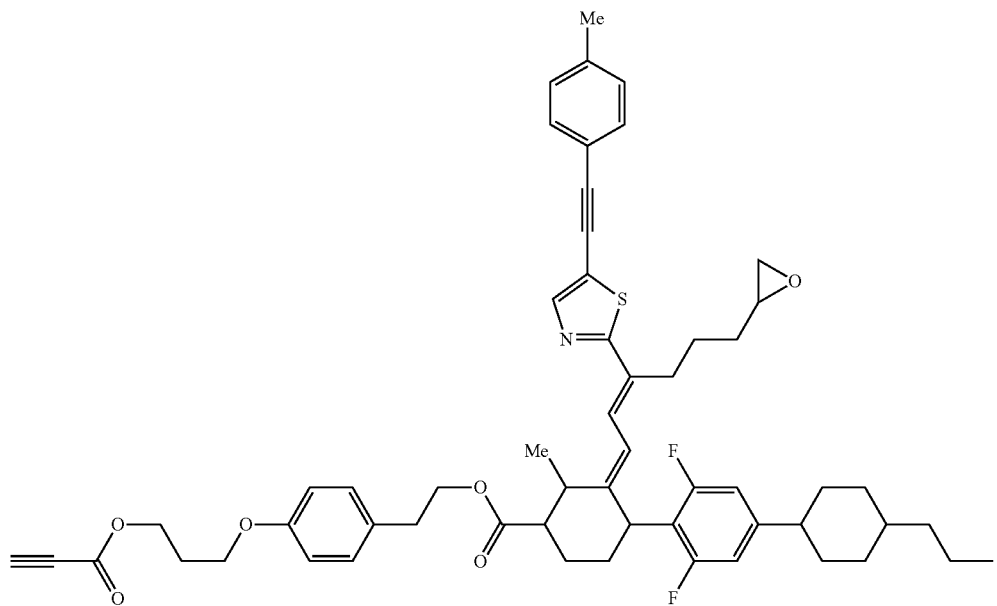
[Chem. 137]
(A141-1)
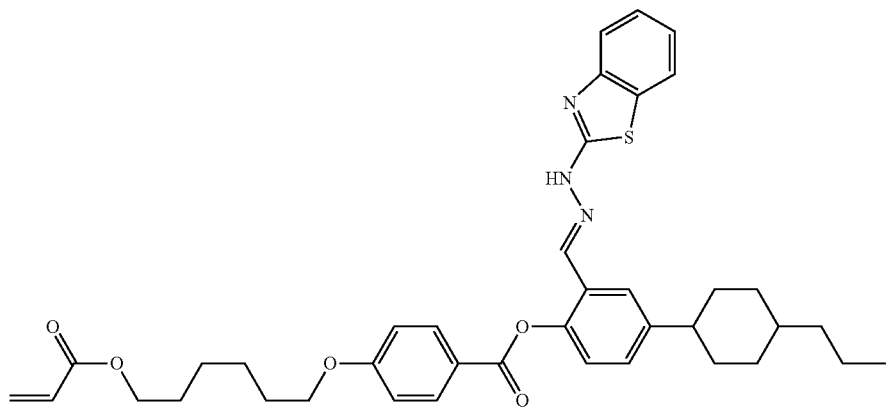
(A141-2)
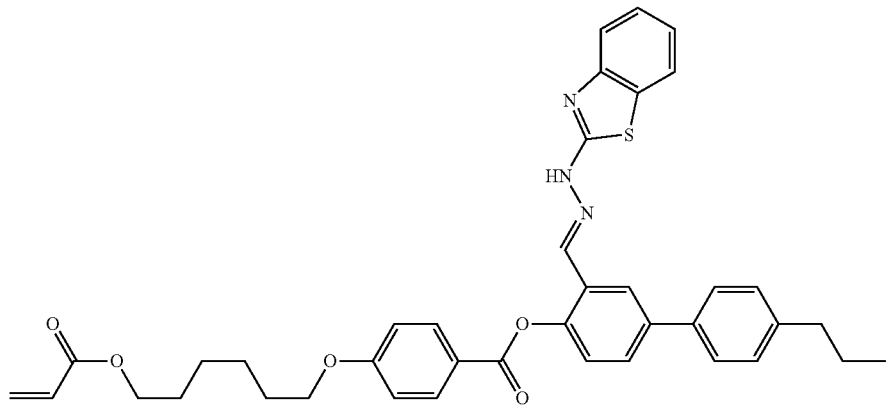

-continued
(A141-3)
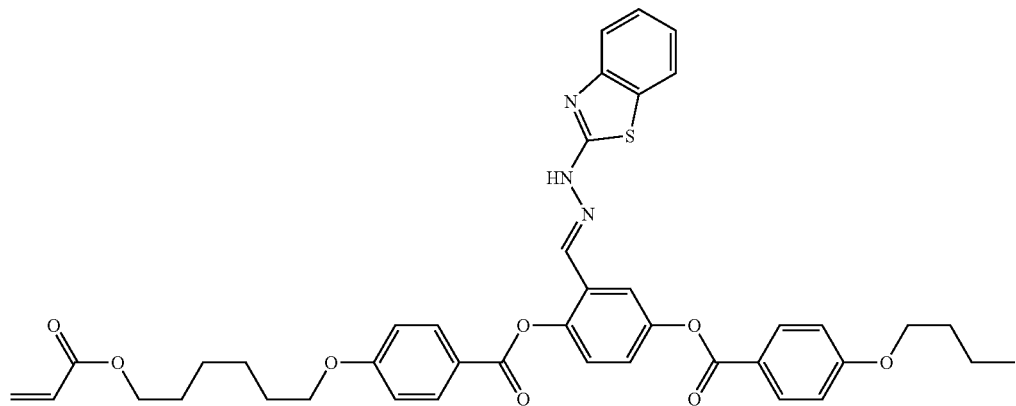
(A141-4)
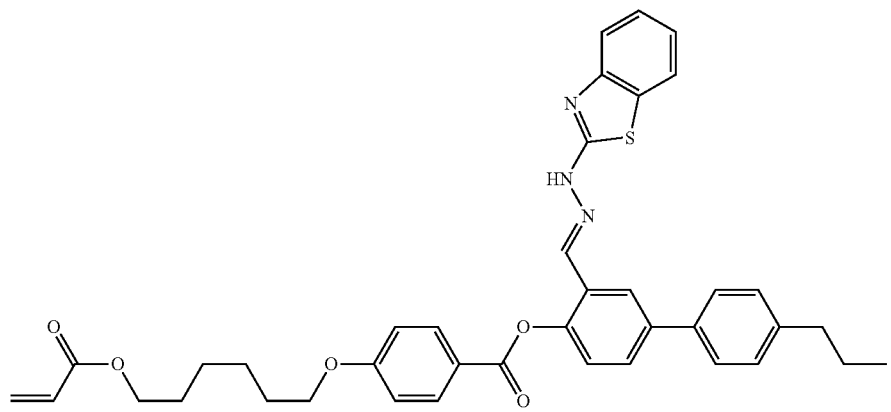
(A141-5)
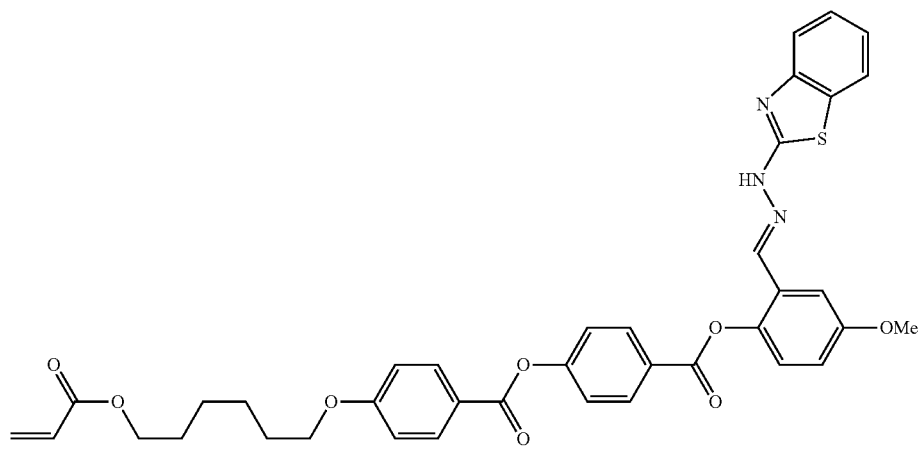

[Chem. 138]
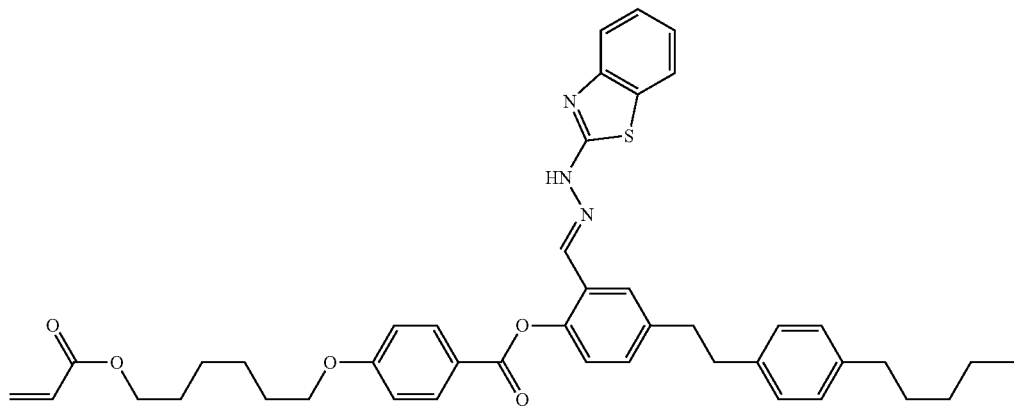
(A141-6)
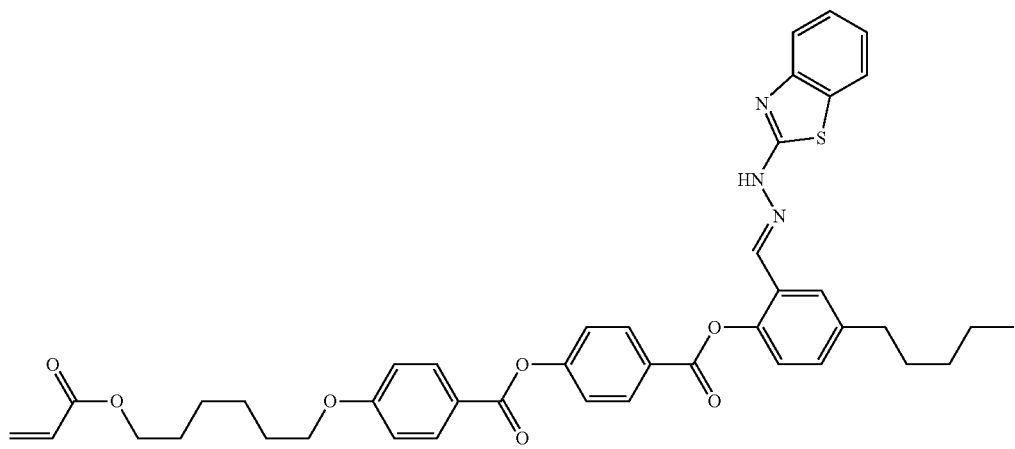
(A141-7)
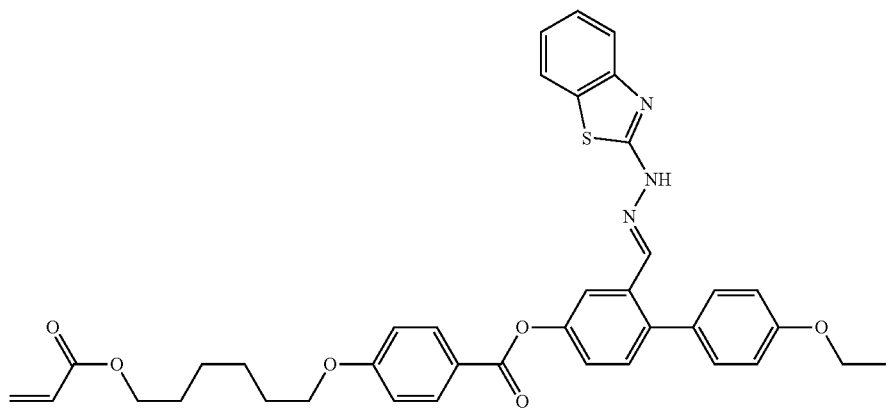
(A141-8)

(A141-9)
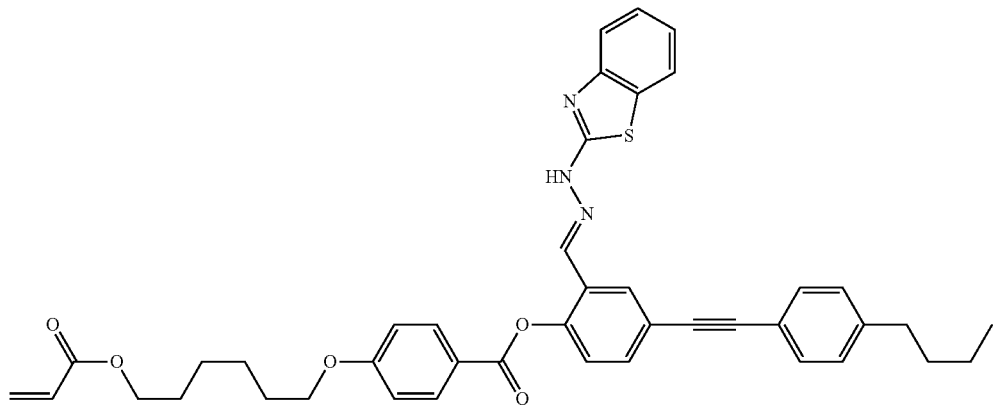
(A141-10)
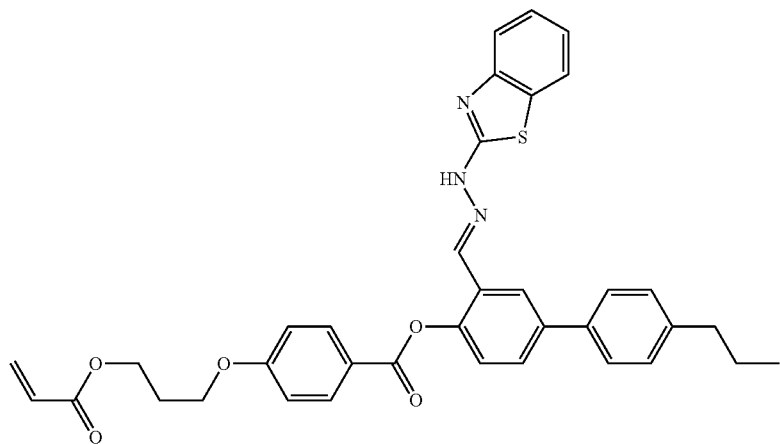
[Chem. 139]
(A141-11)
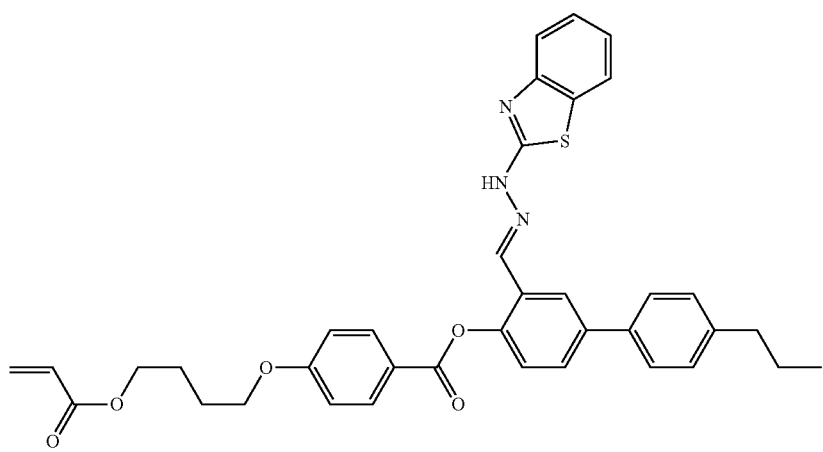

(A141-12)
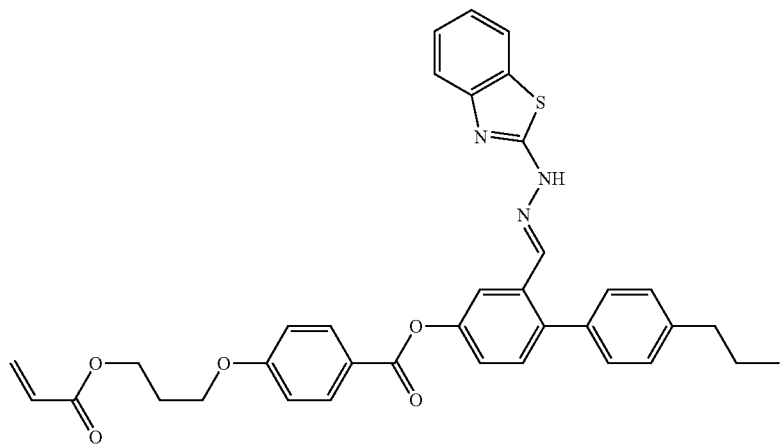
(A141-13)
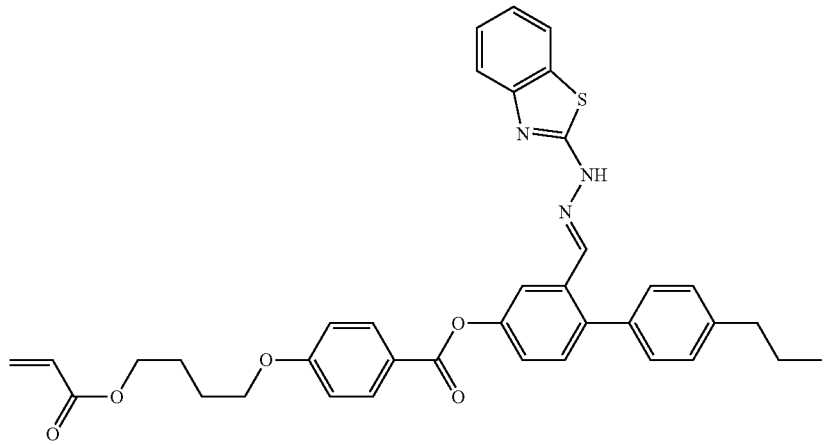
(A141-14)
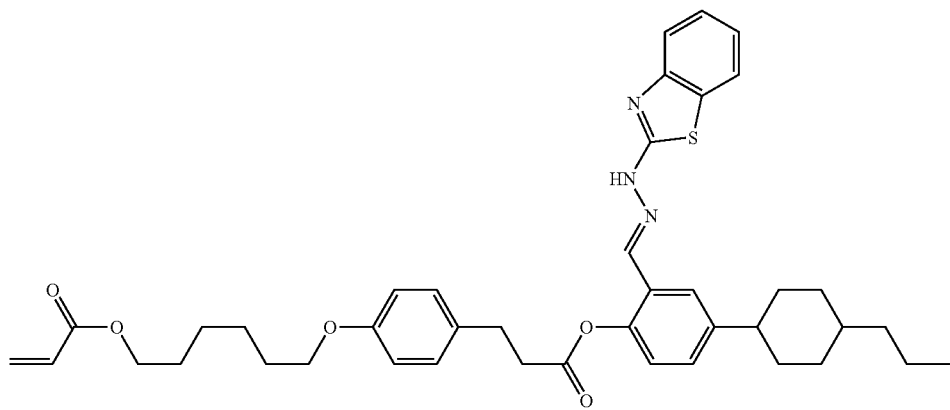

-continued
(A141-15)
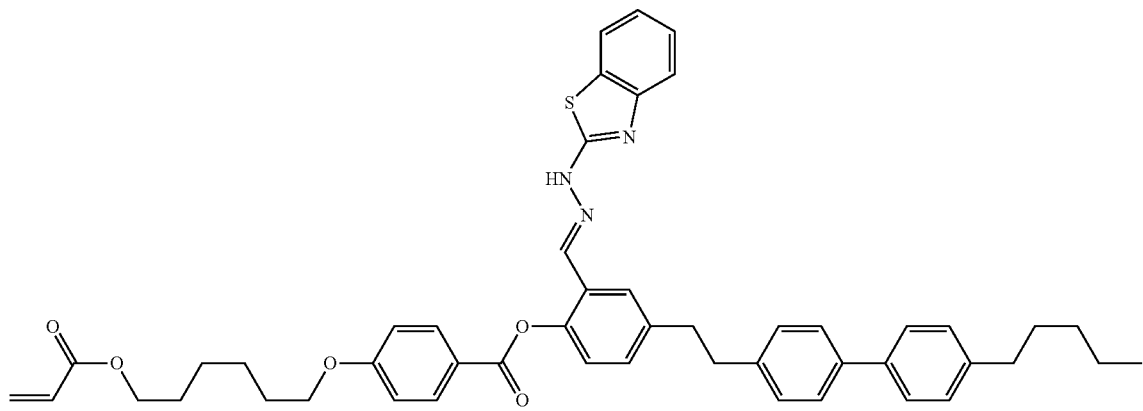
[Chem. 140]
(A141-16)
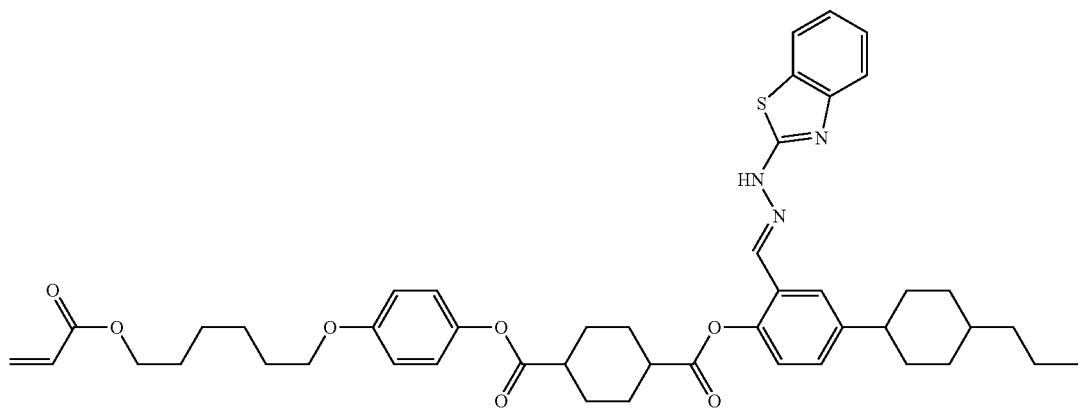
(A141-17)
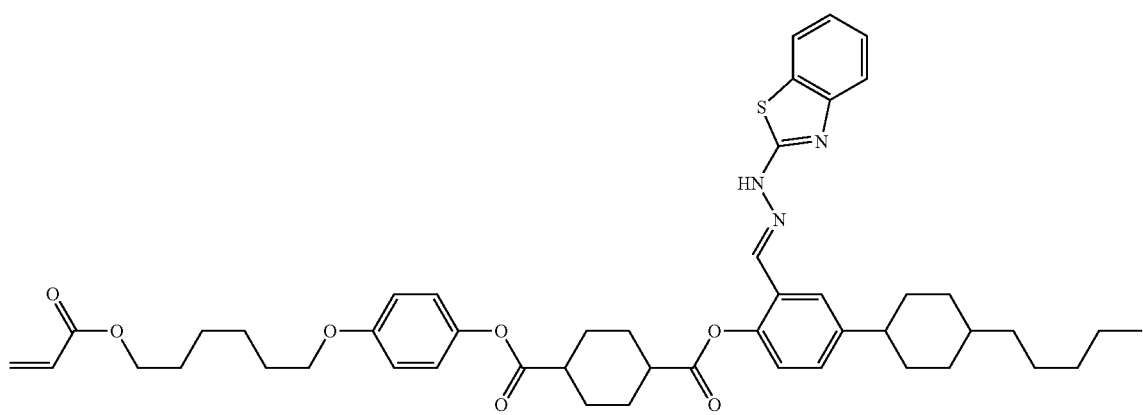

(A141-18)
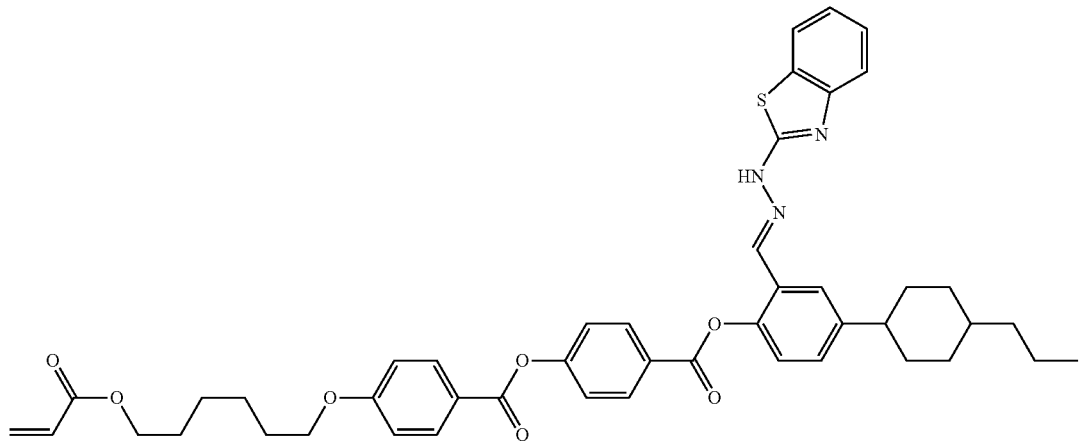
(A141-19)
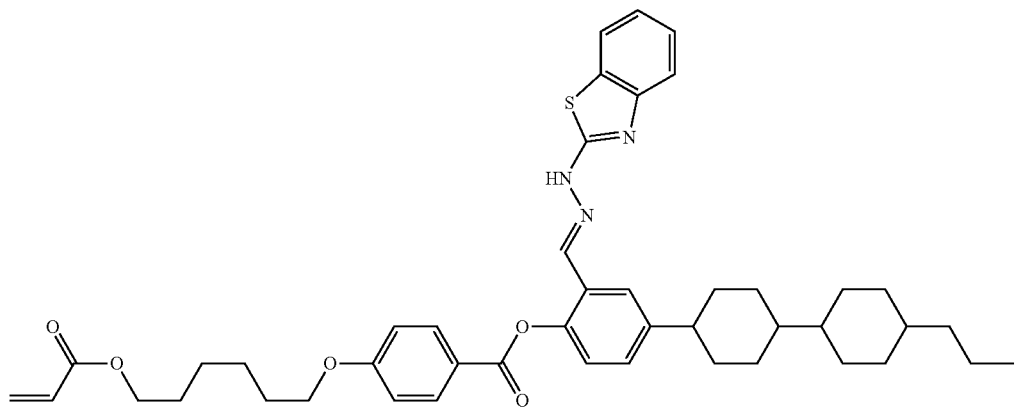
(A141-20)
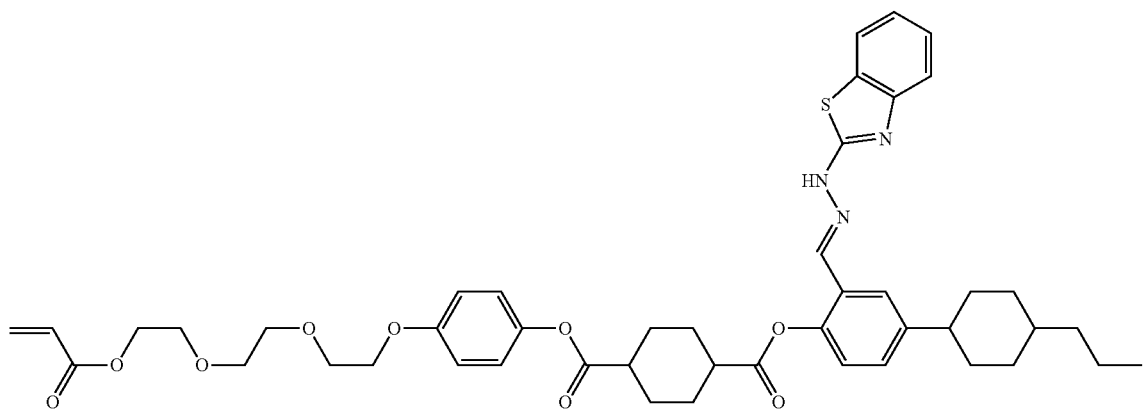

[Chem. 141]
(A141-21)
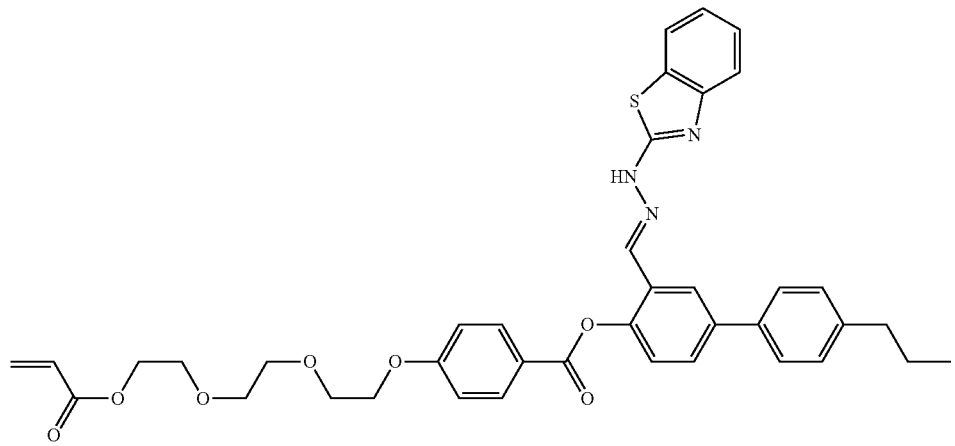
(A141-22)
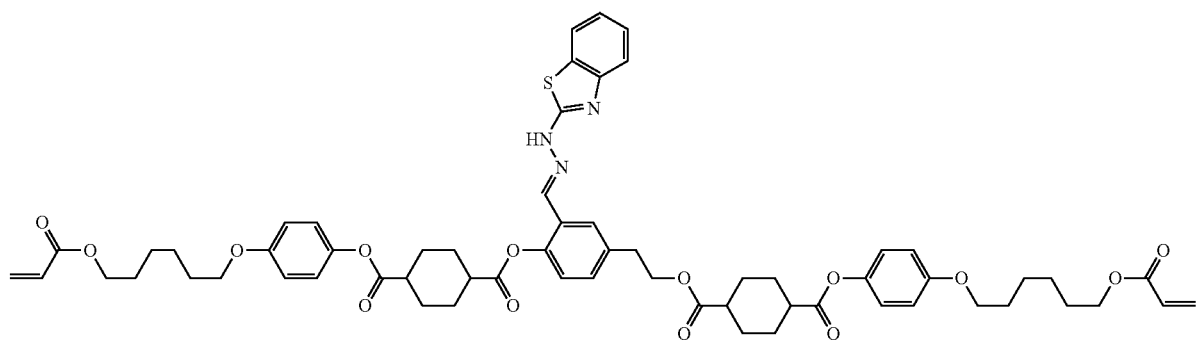
(A141-23)
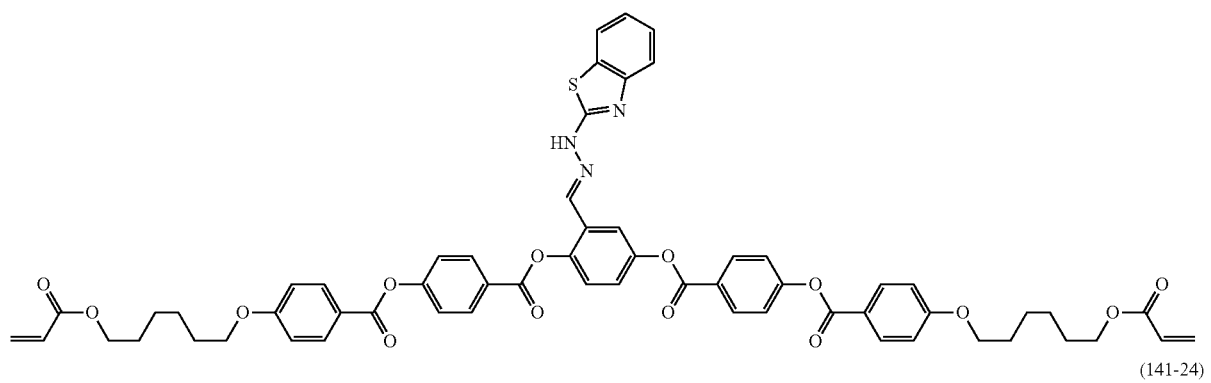
(141-24)
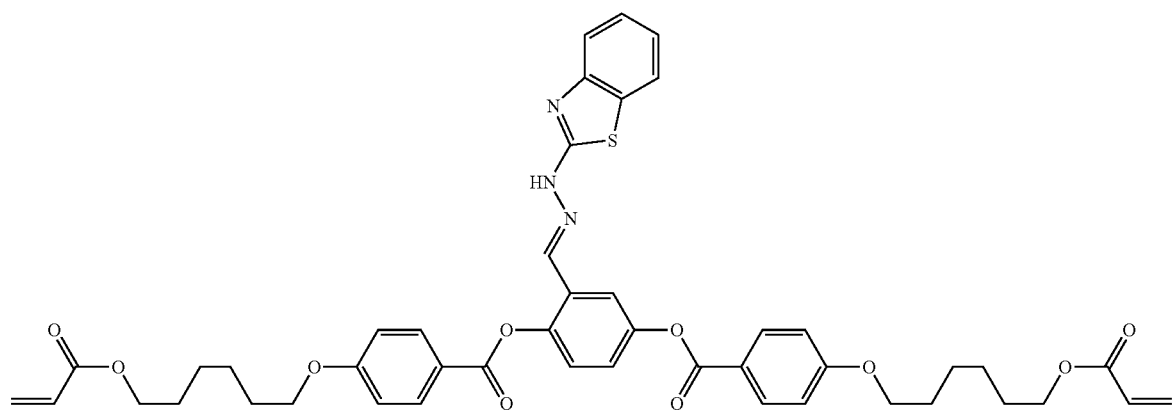

-continued
(A141-25)
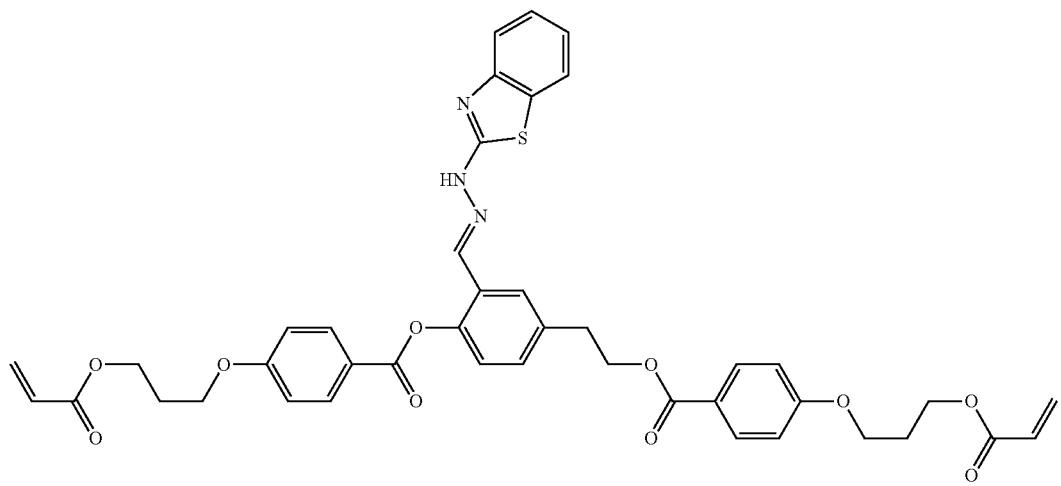
[Chem. 142]
(A141-26)
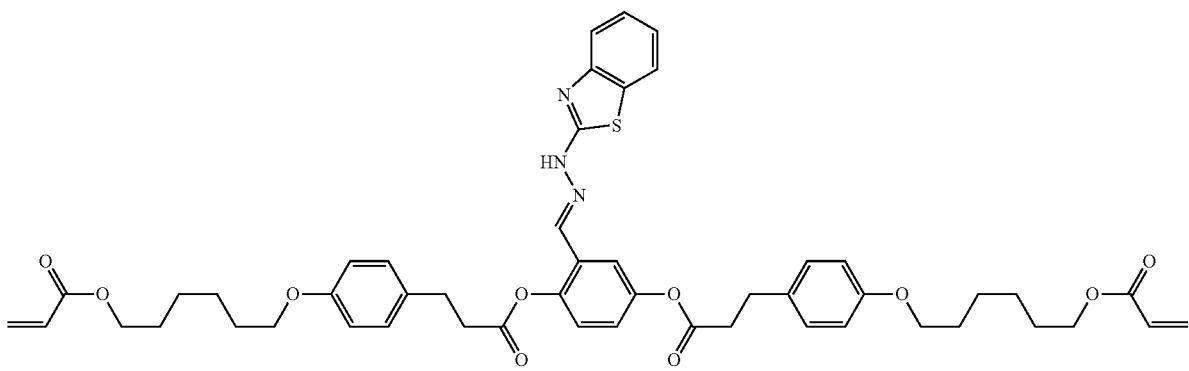
(A141-27)
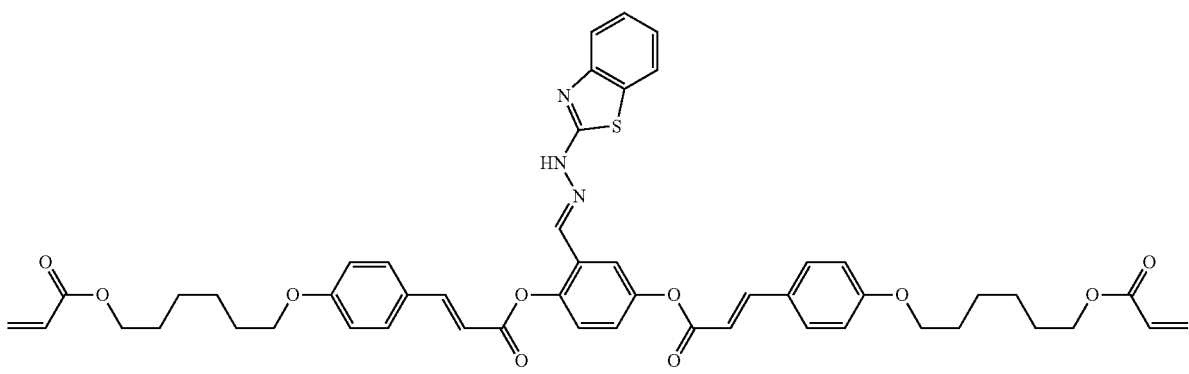
(A141-28)
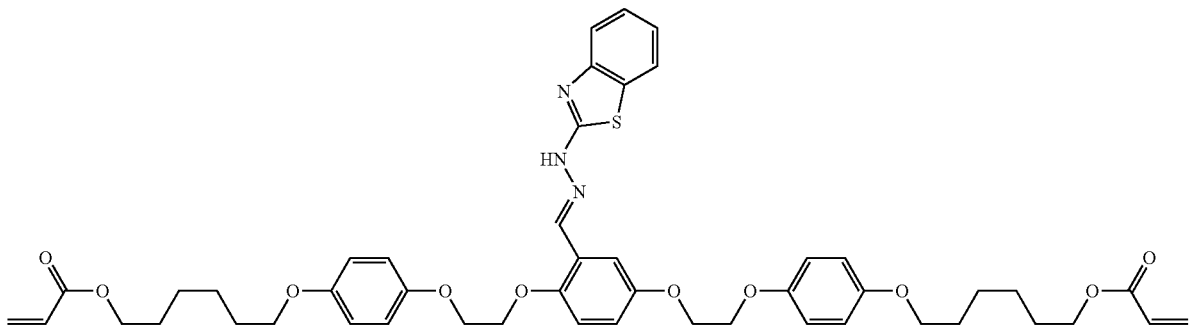

(A141-29)
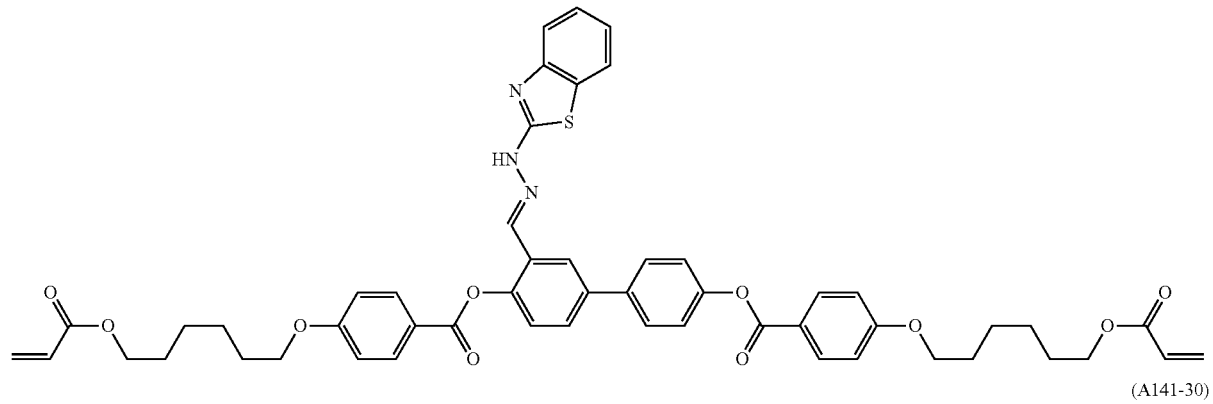
(A141-30)
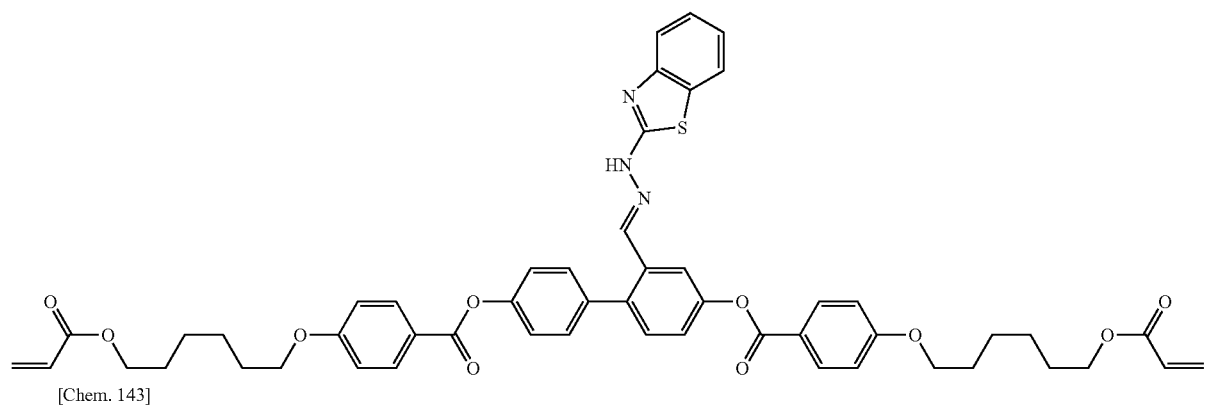
[Chem. 143]
(A141-31)
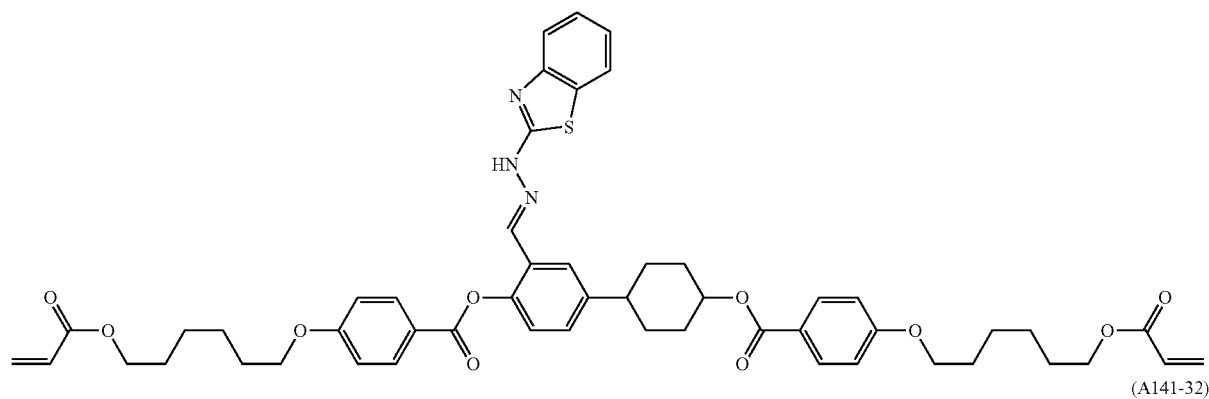
(A141-32)
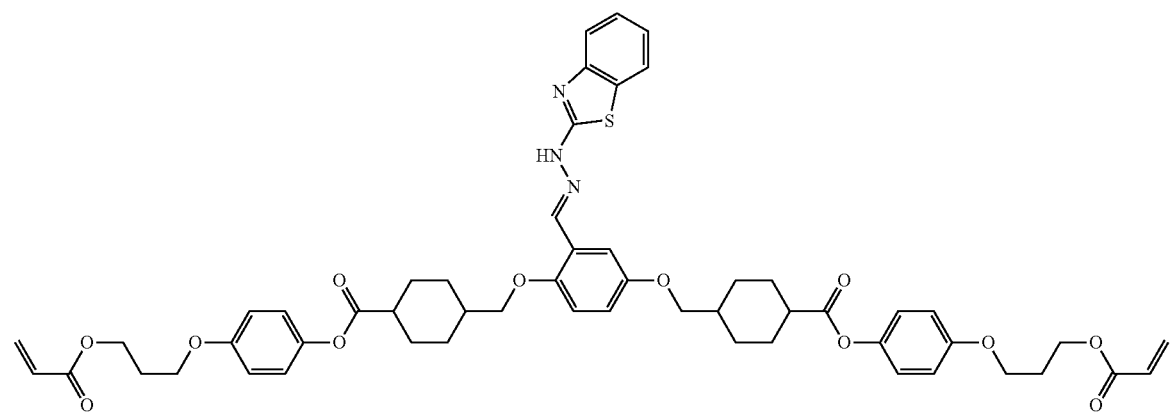

(A141-33)
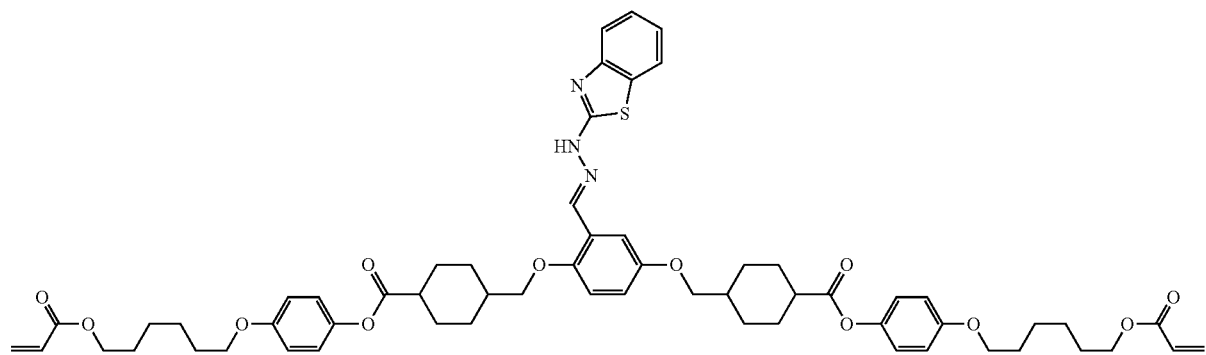
[Chem. 144]
(A142-1)
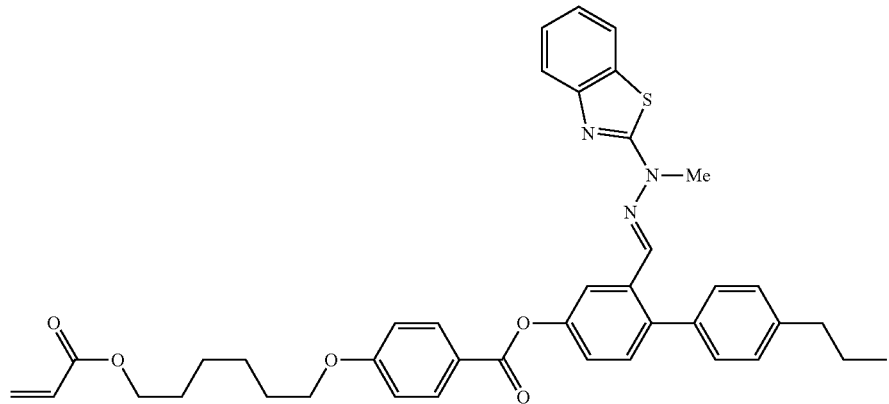
(A142-2)
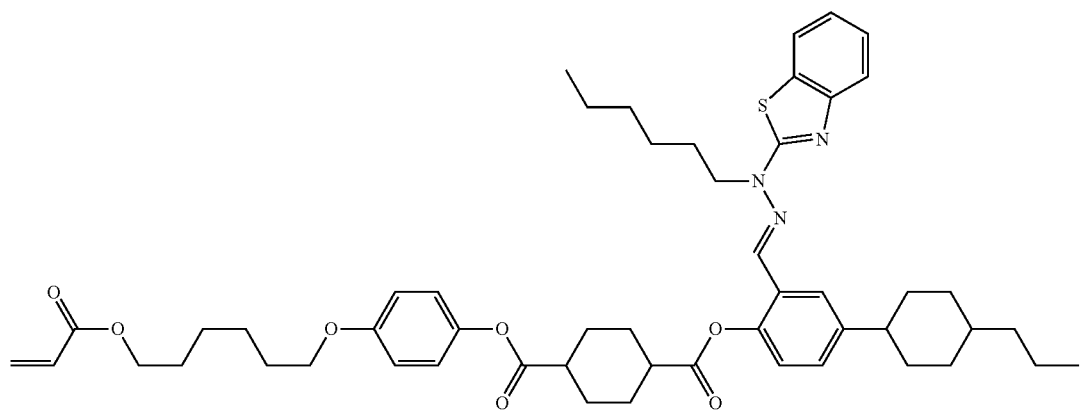

(A142-3)
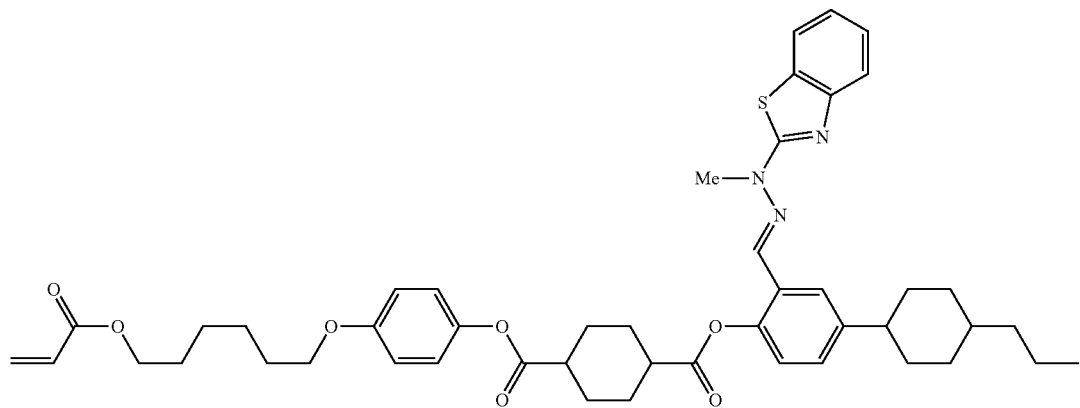
(A142-4)
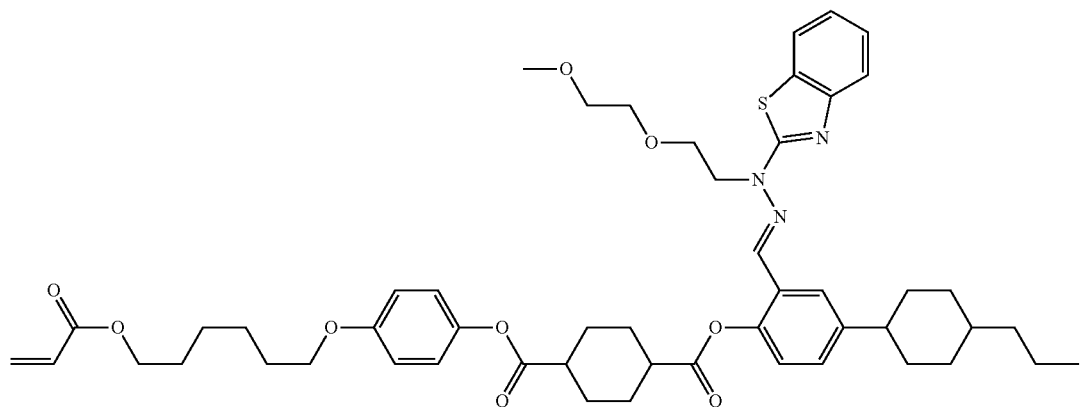
(A142-5)
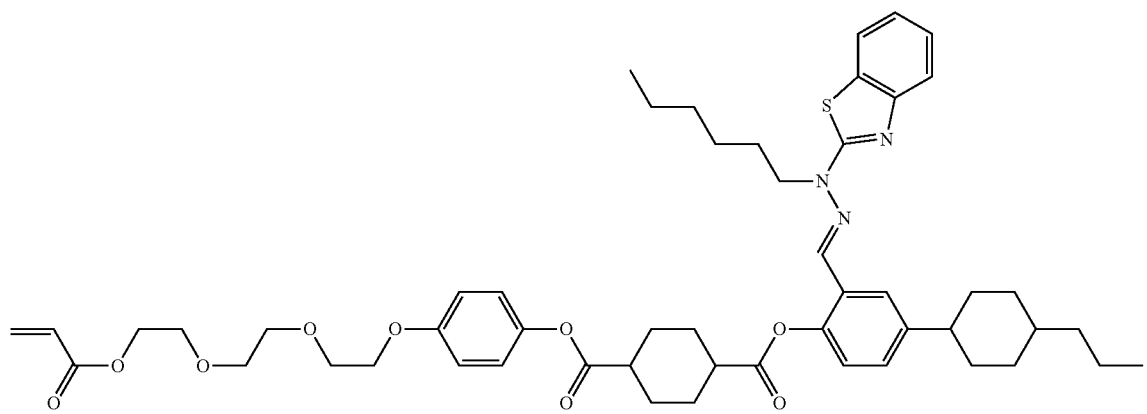

-continued
[Chem. 145]
(A142-6)
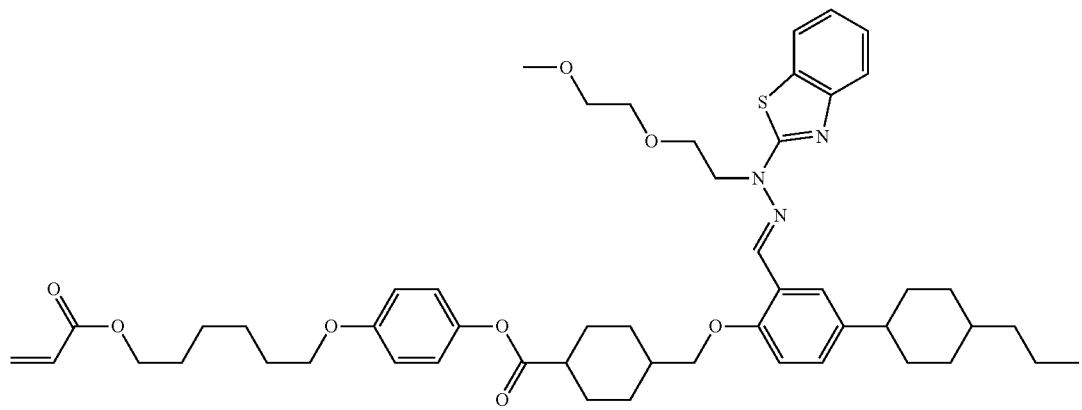
(A142-7)
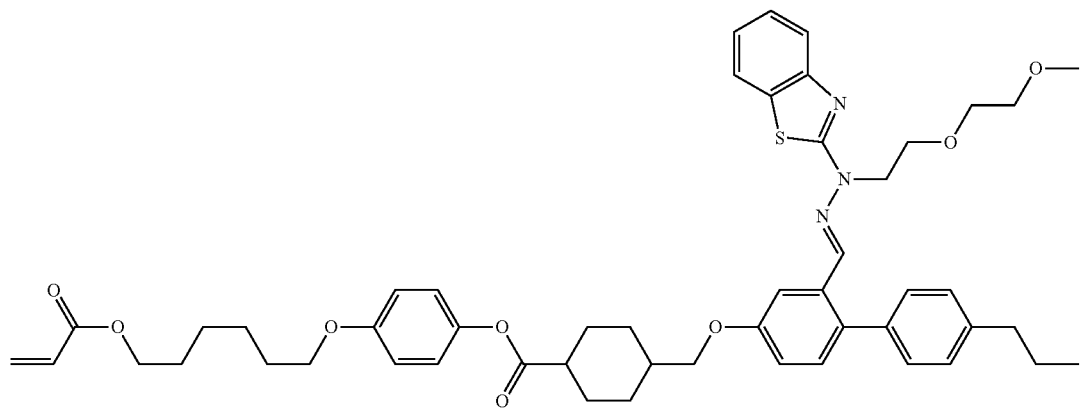
(A142-8)
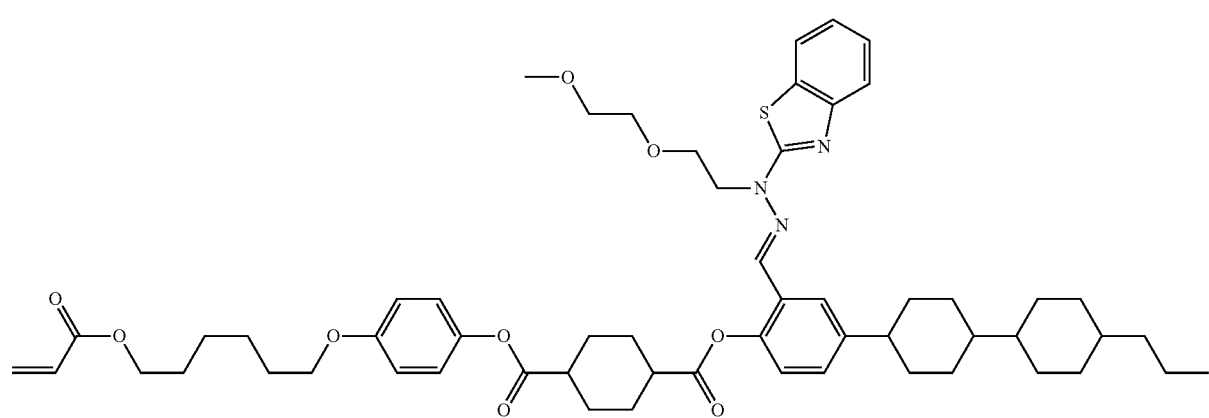

-continued
(A142-9)
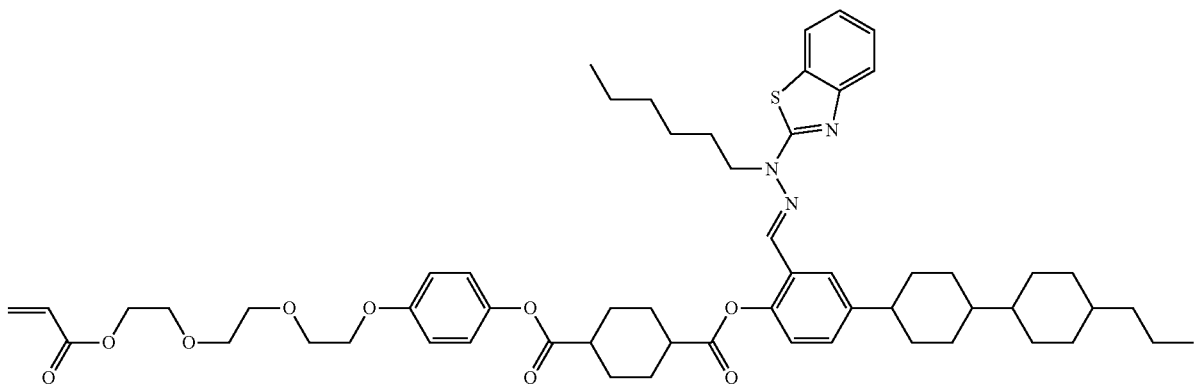
(A142-10)
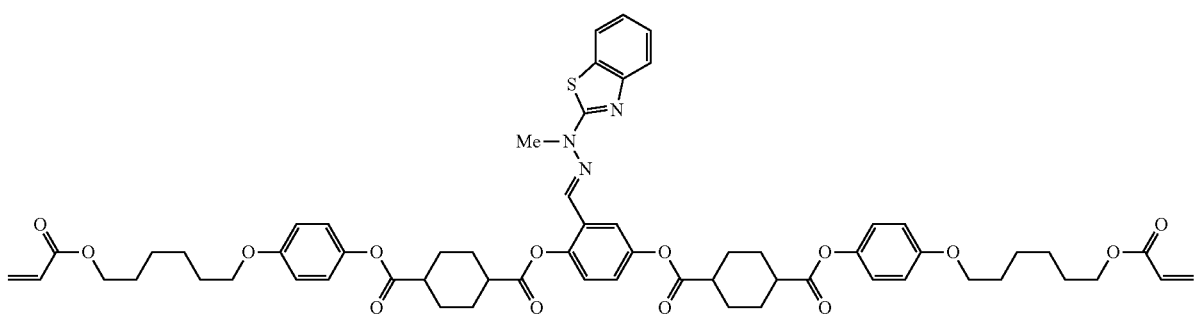
[Chem. 146]
(A142-11)
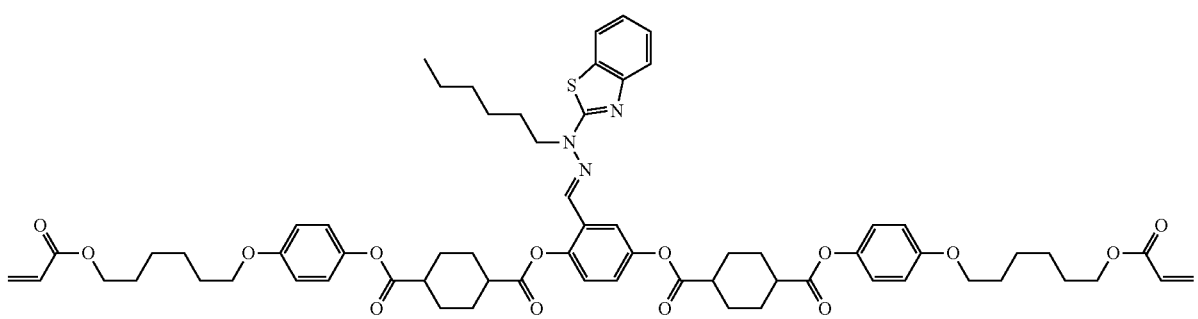
(A142-12)
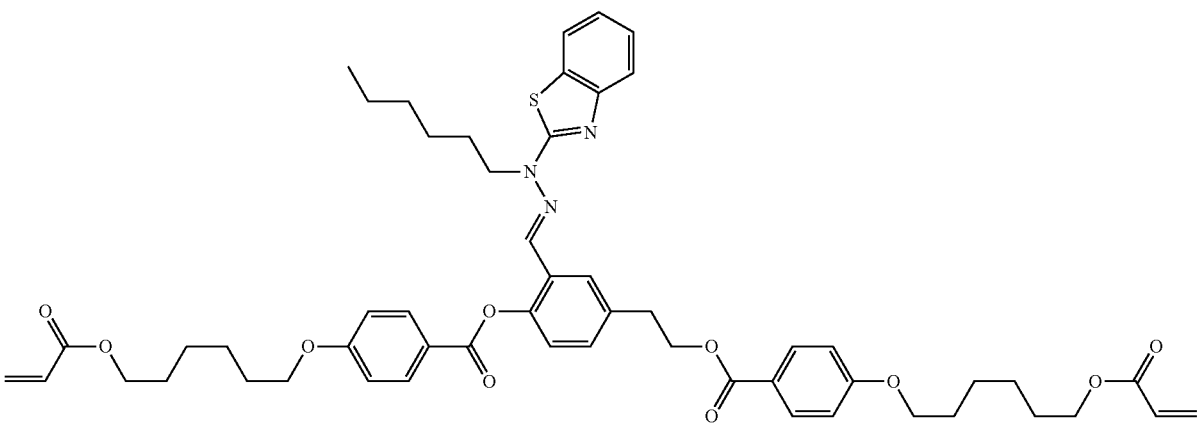

(A142-13)
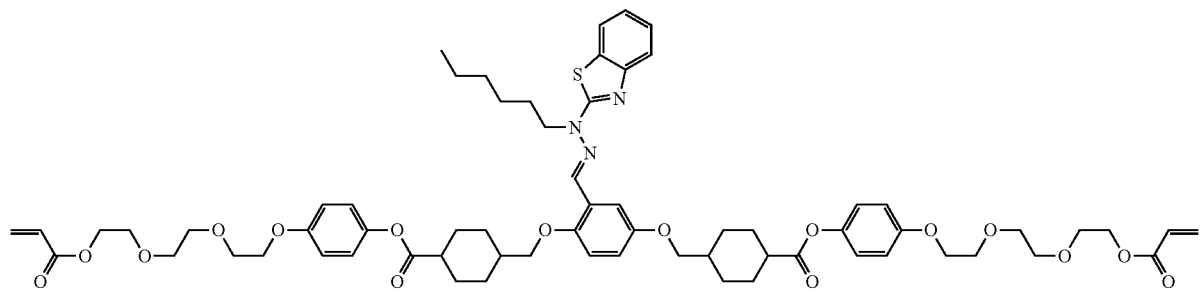
(A142-14)
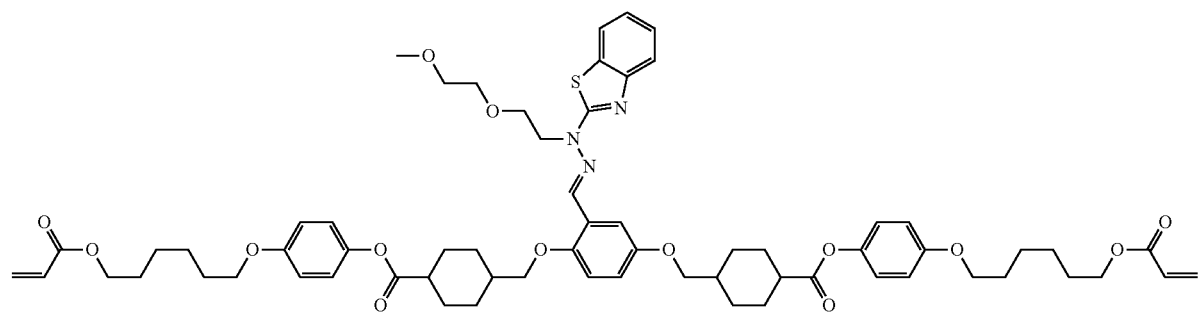
(A142-15)
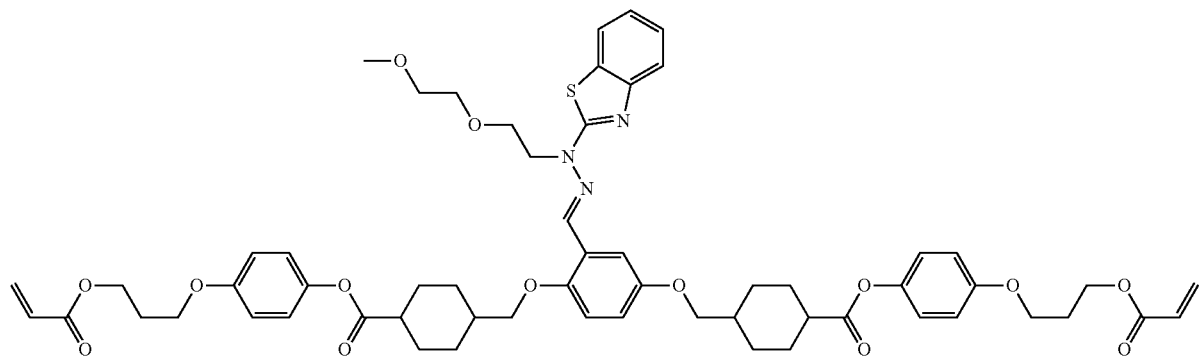
[Chem. 147]
(A143-1)
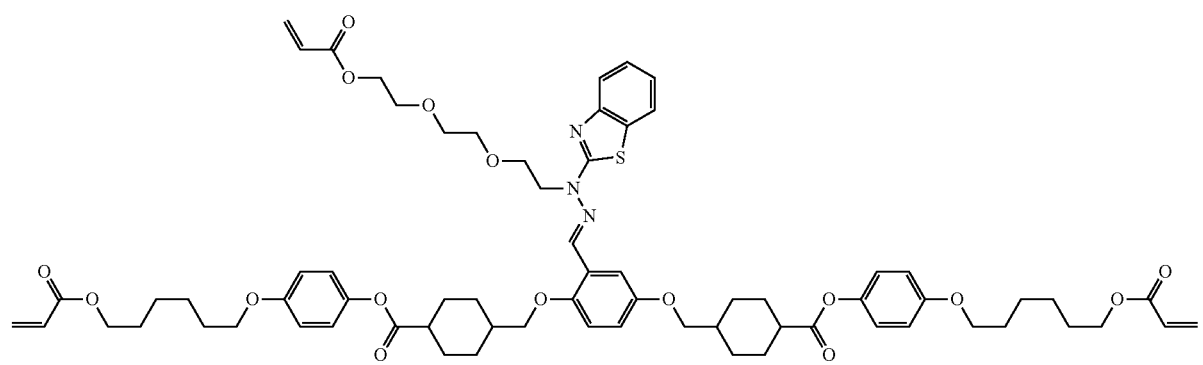

-continued
(A143-2)
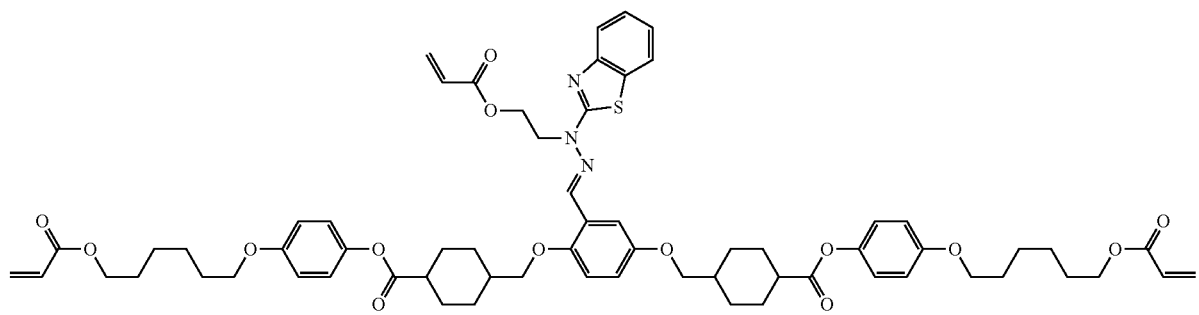
[Chem. 148]
(A144-1)
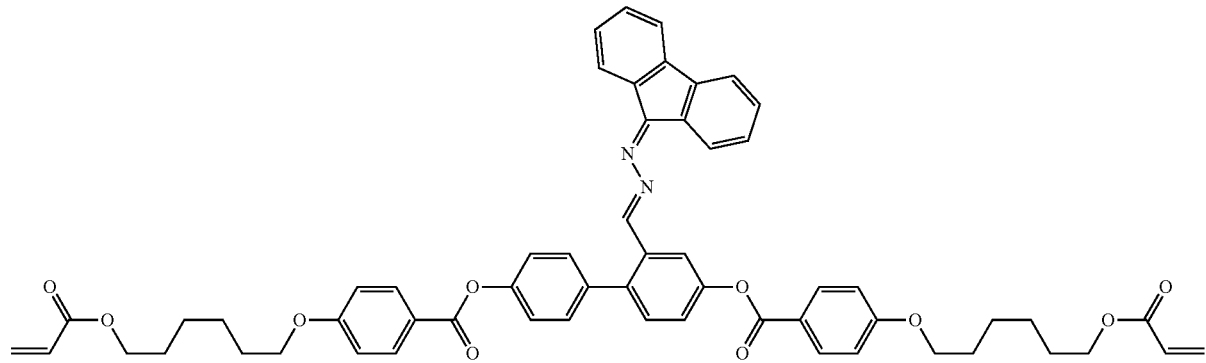
[Chem. 149]
(A15-1)
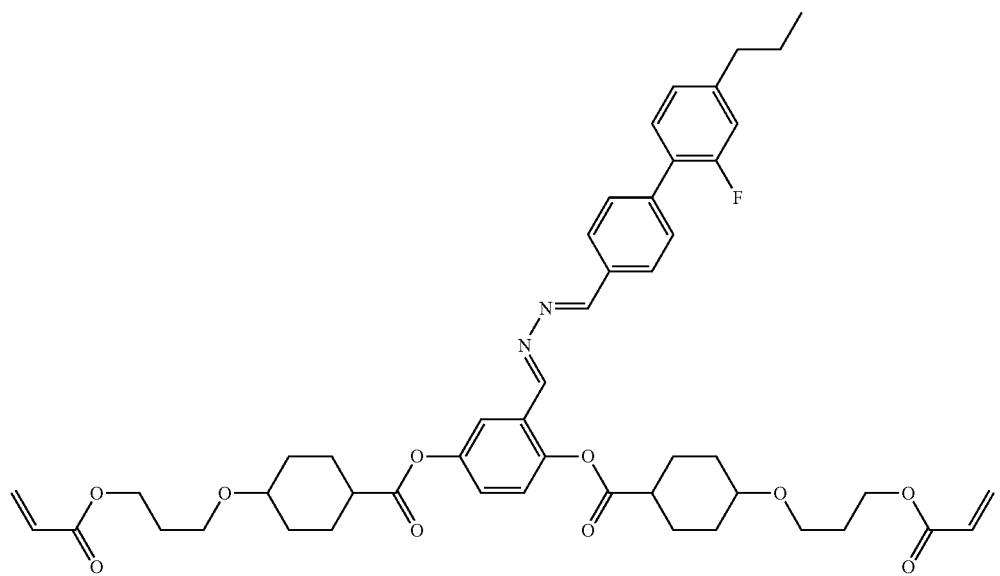

(A15-2)
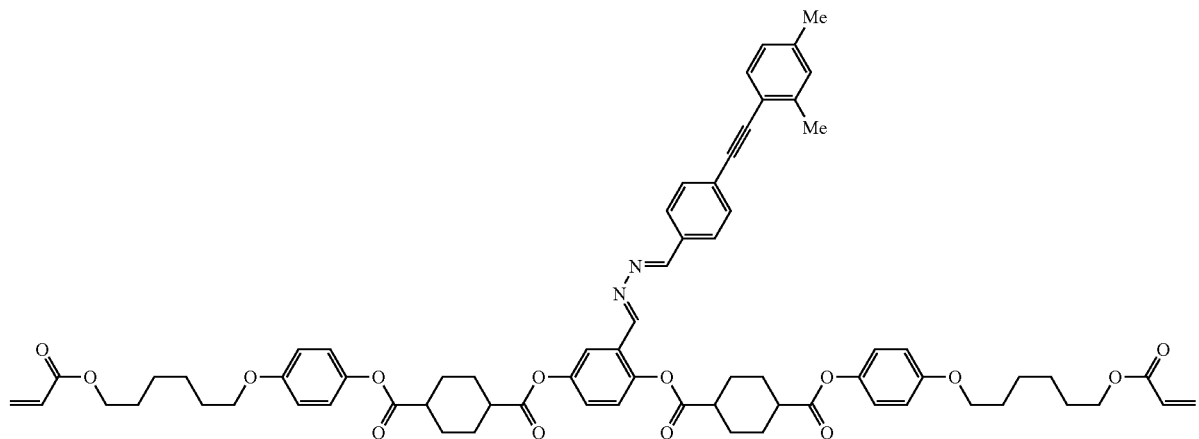
(A15-3)
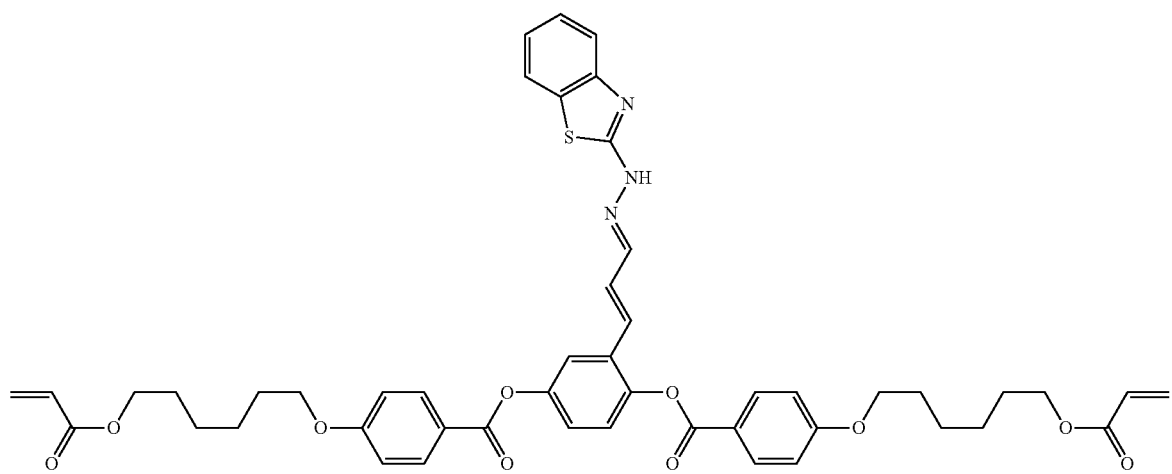
(A15-4)
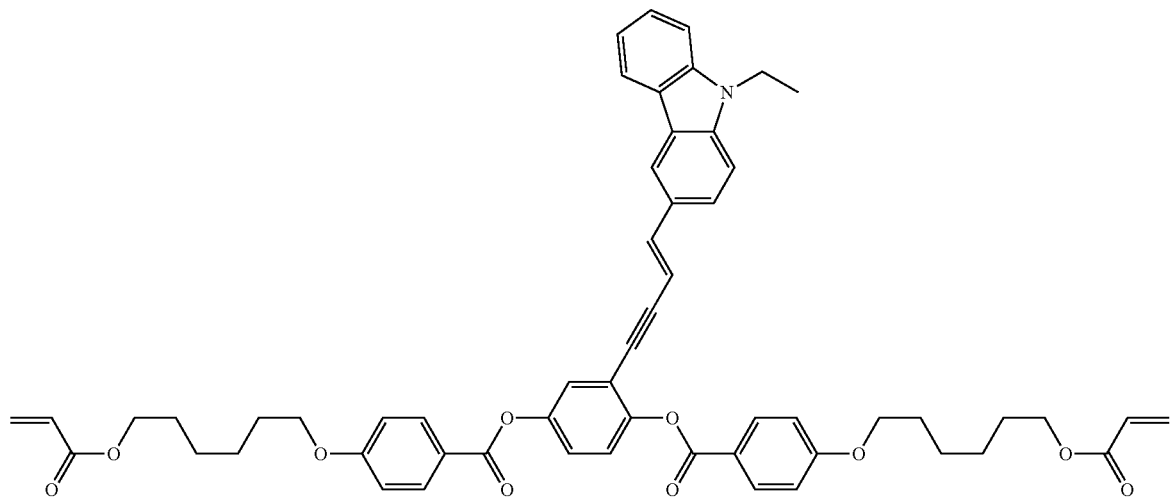

(A15-5)
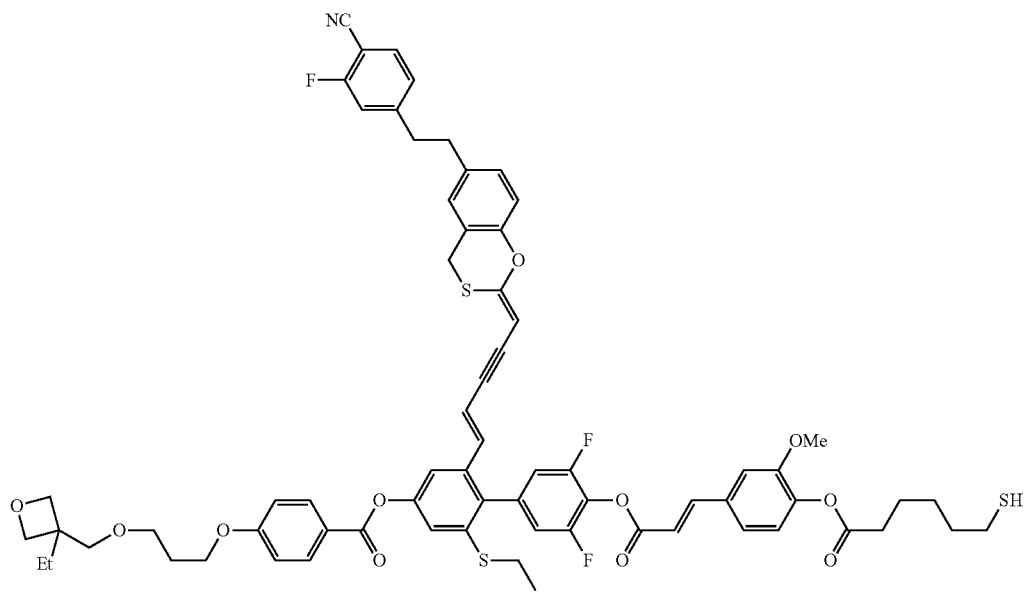
[Chem. 150]
(A15-6)
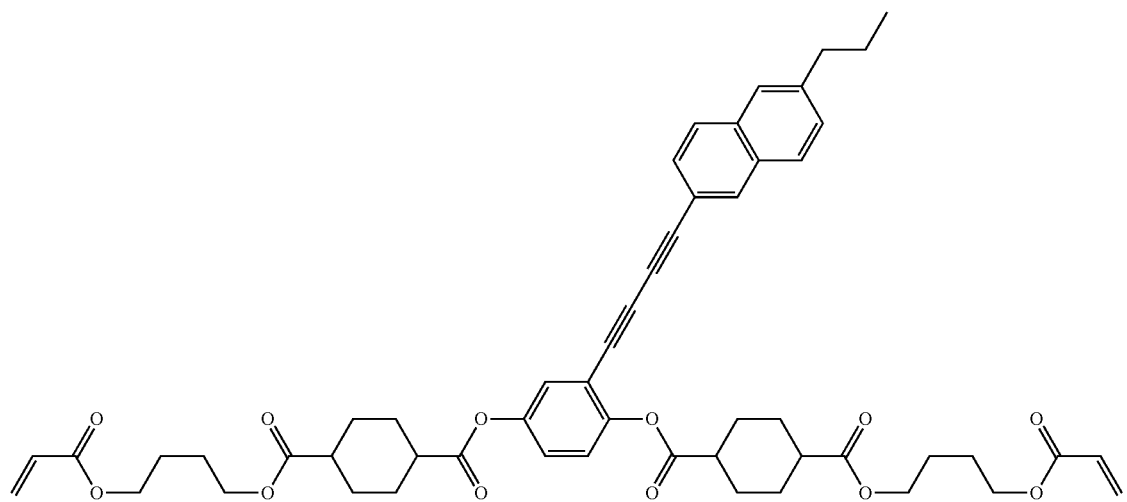

-continued
(A15-7)
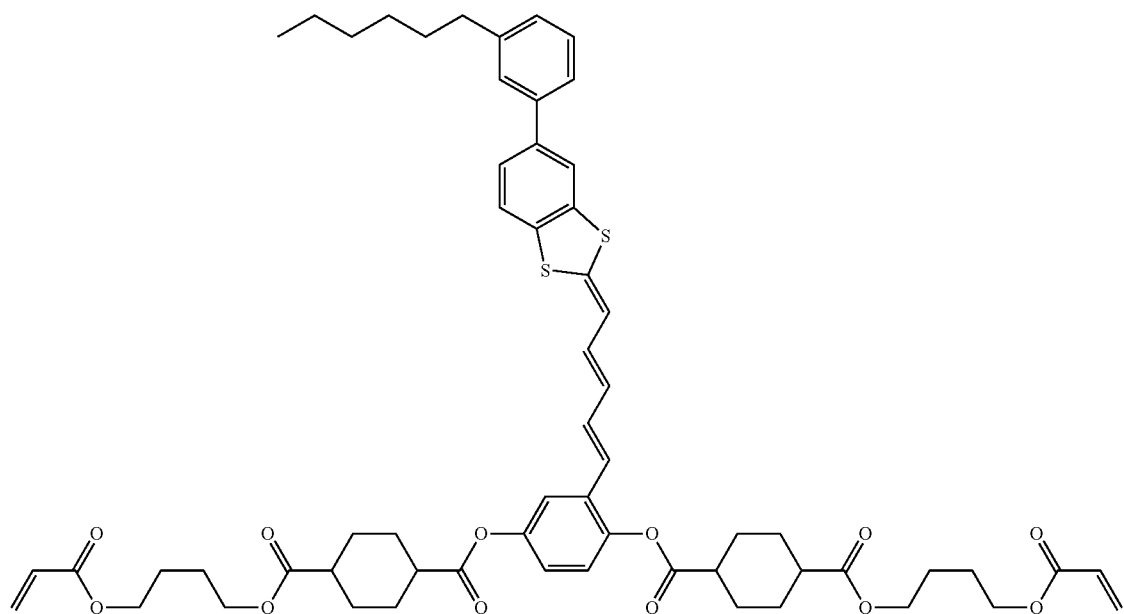
(A15-8)
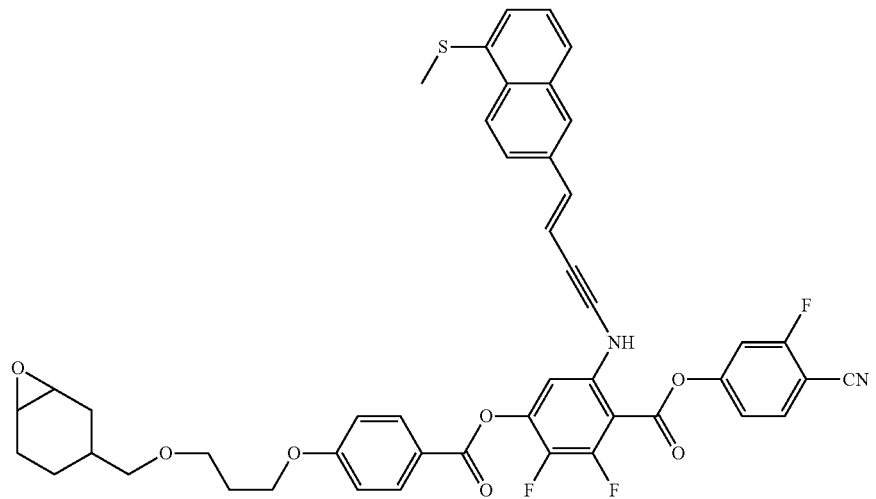

-continued
(A15-9)
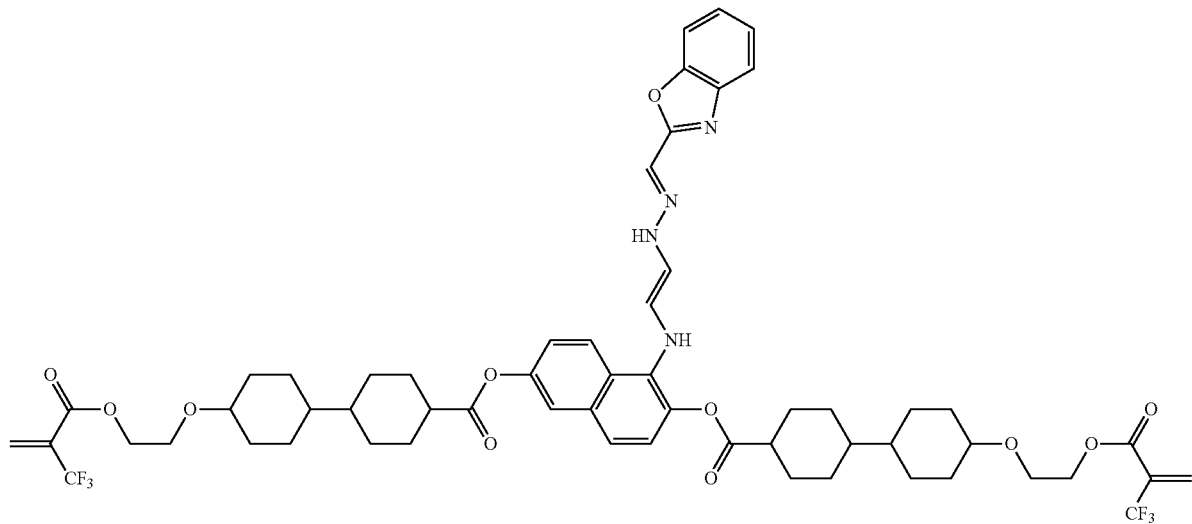
(A15-10)
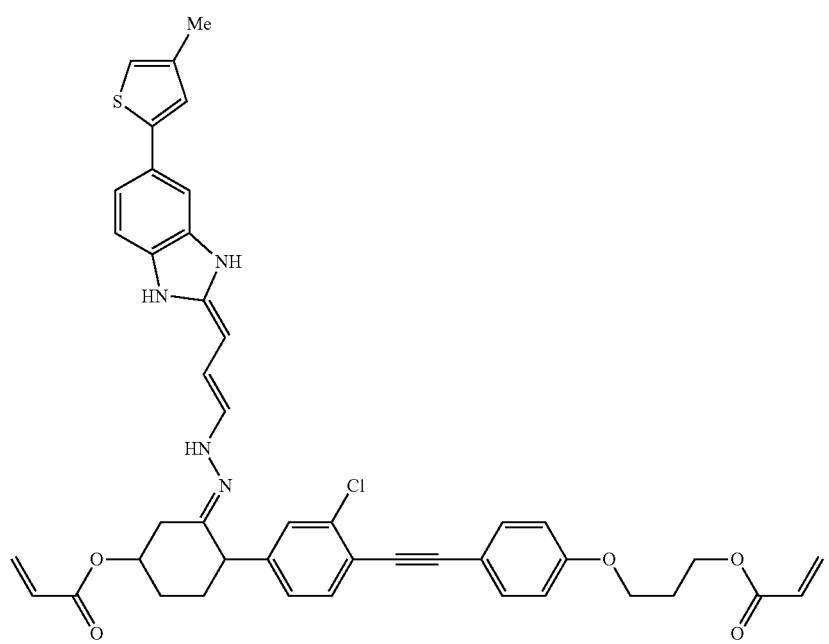

[Chem. 151]
(A15-11)
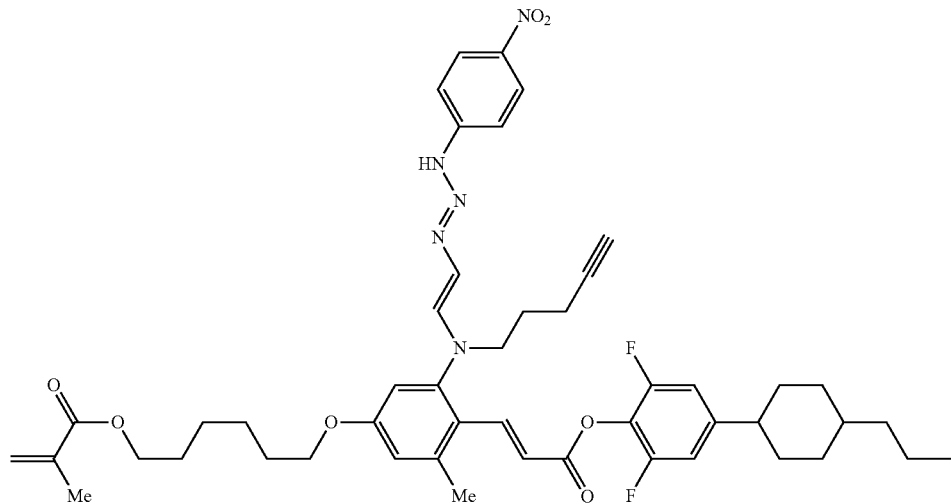
(A15-12)
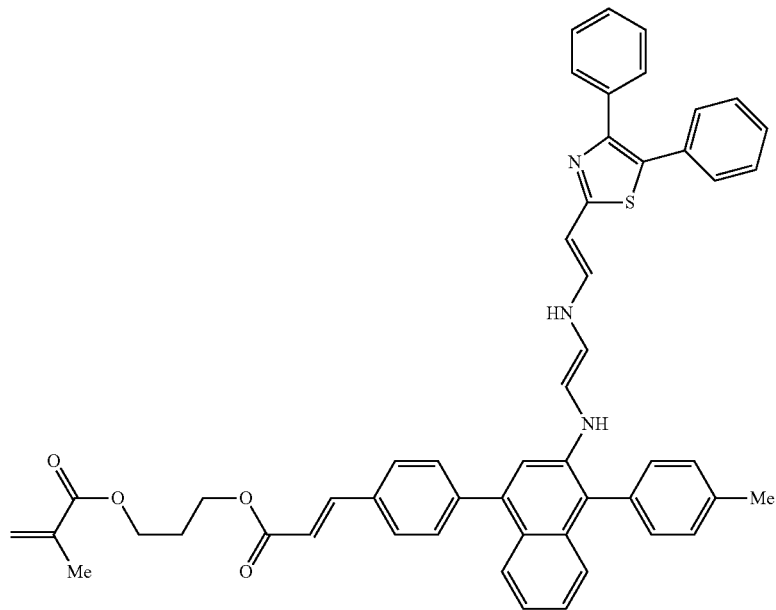
(A15-13)
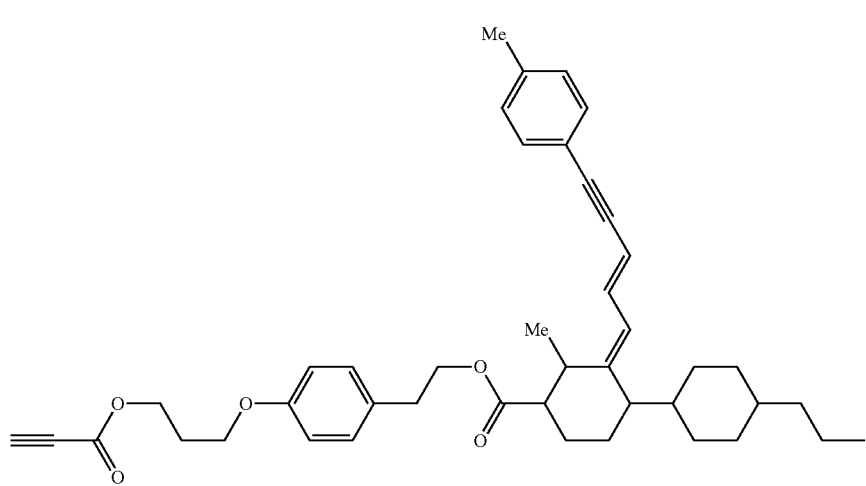

-continued
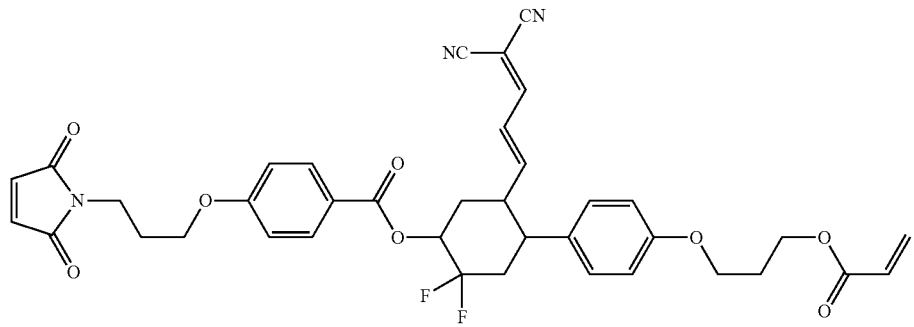
(A15-14)
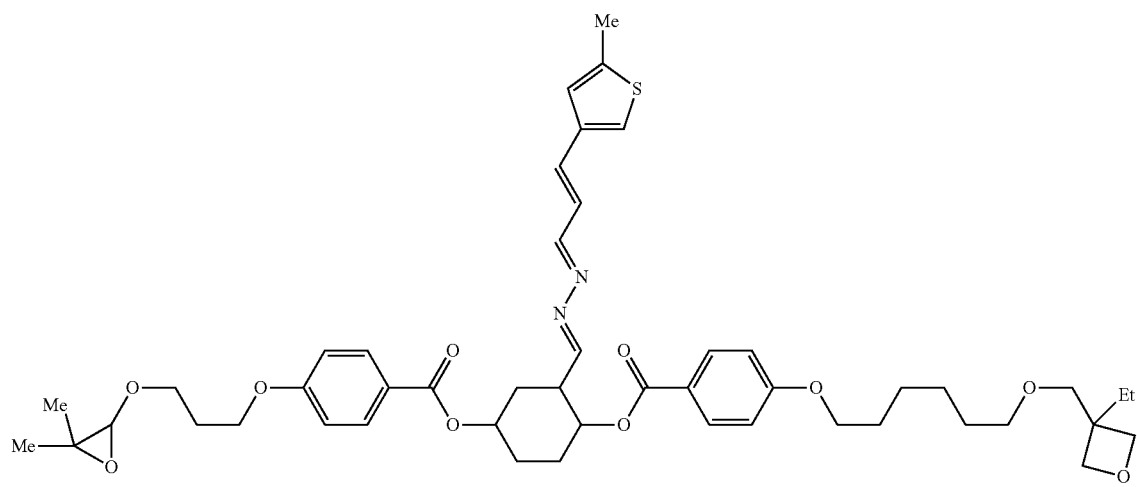
(A15-15)
[Chem. 152]
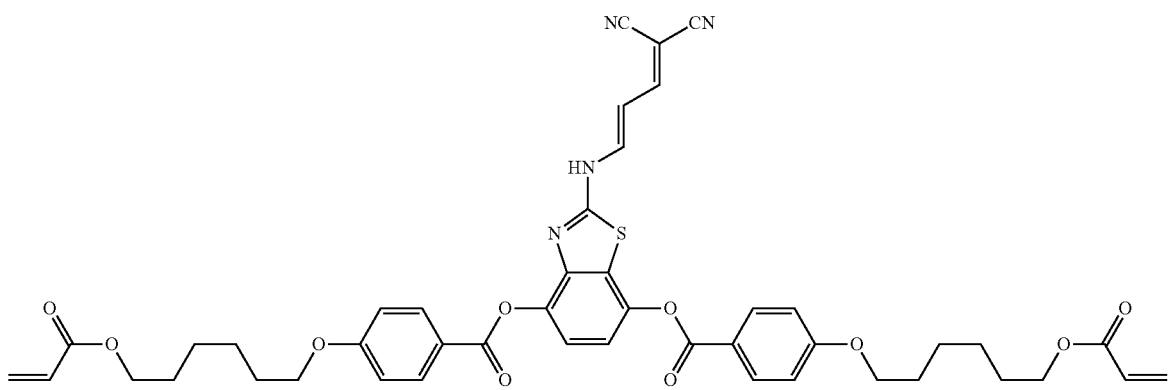
(A2-1)

-continued
(A2-2)
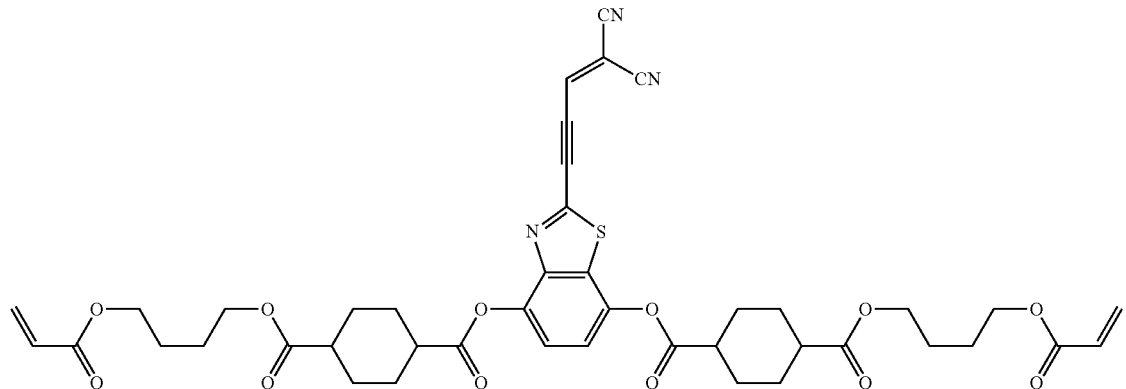
(A2-3)
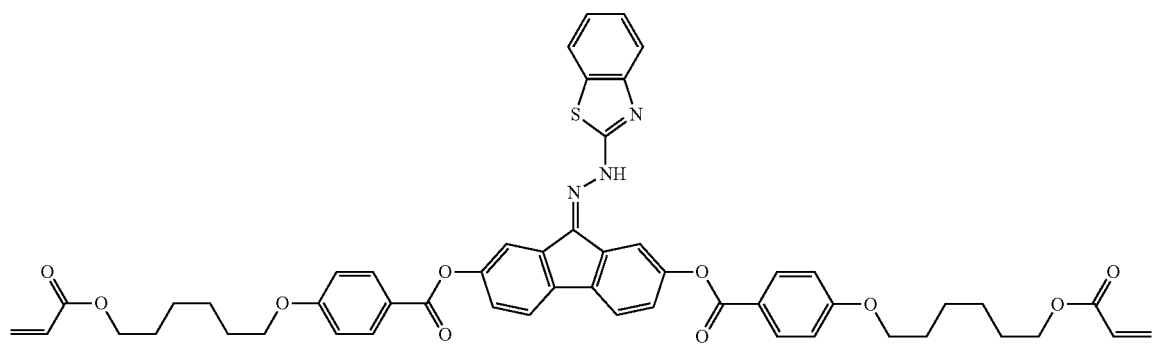
(A2-4)
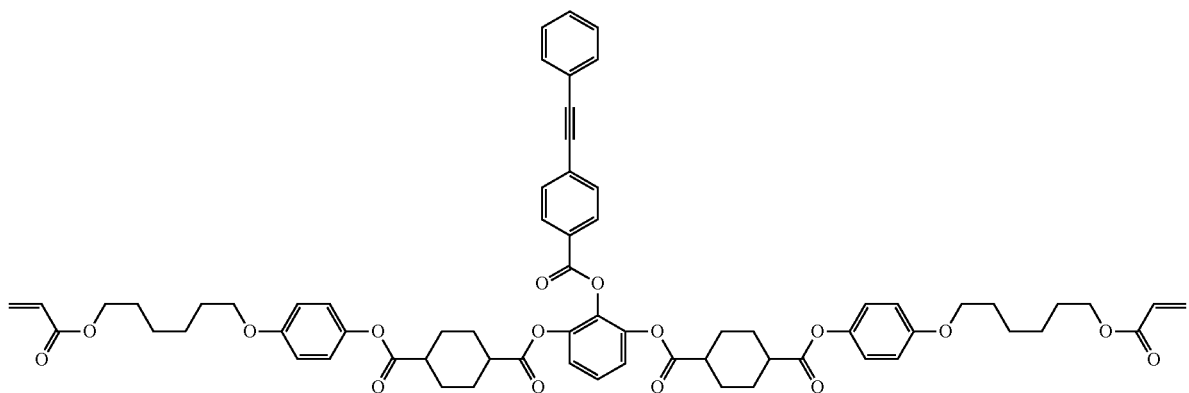

-continued
(A2-5)
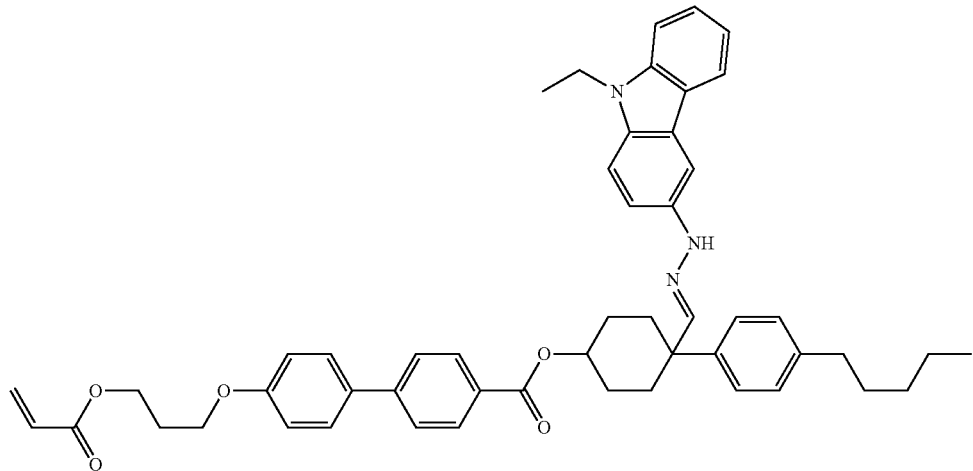
[Chem. 153]
(A2-6)
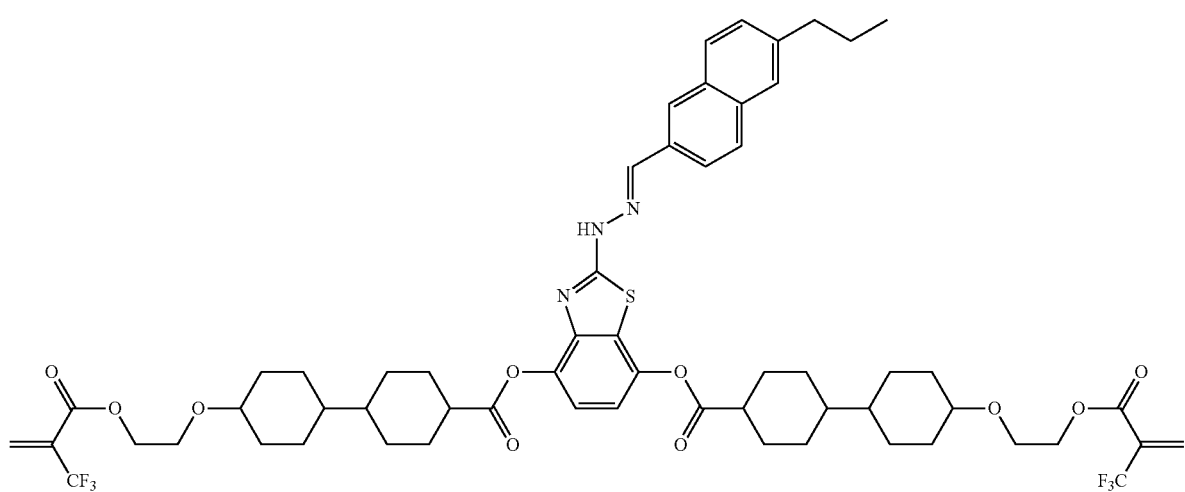
(A2-7)
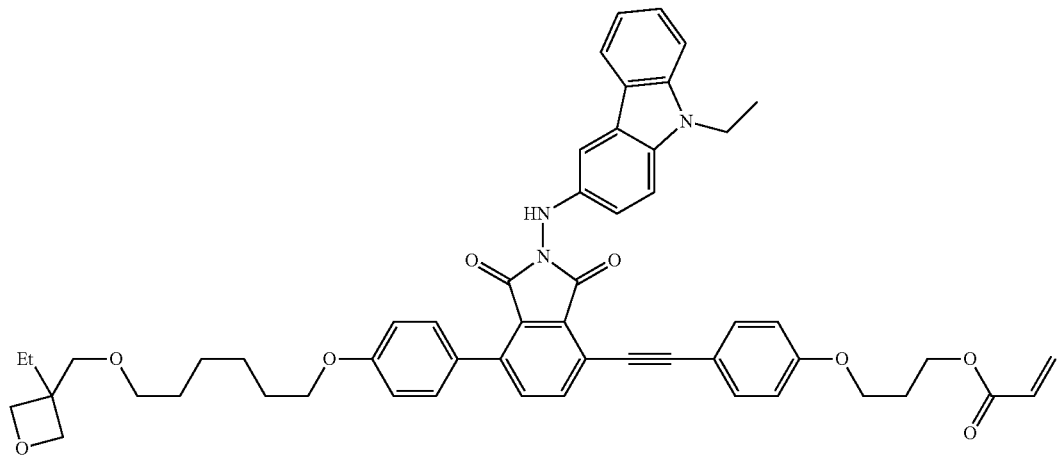

-continued
(A2-8)
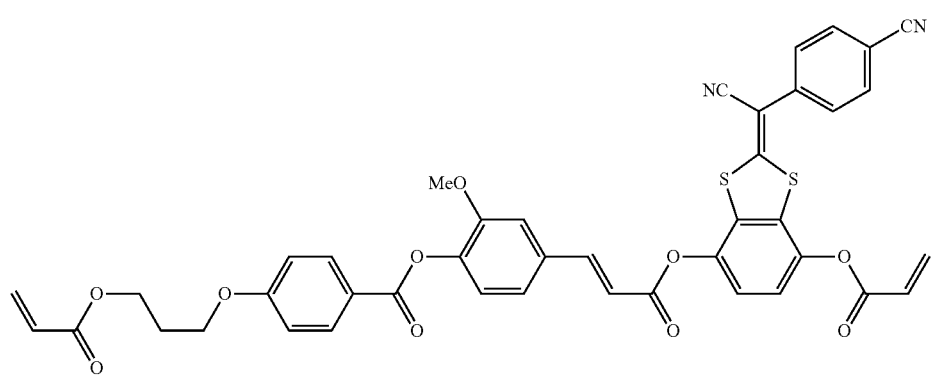
(A2-9)
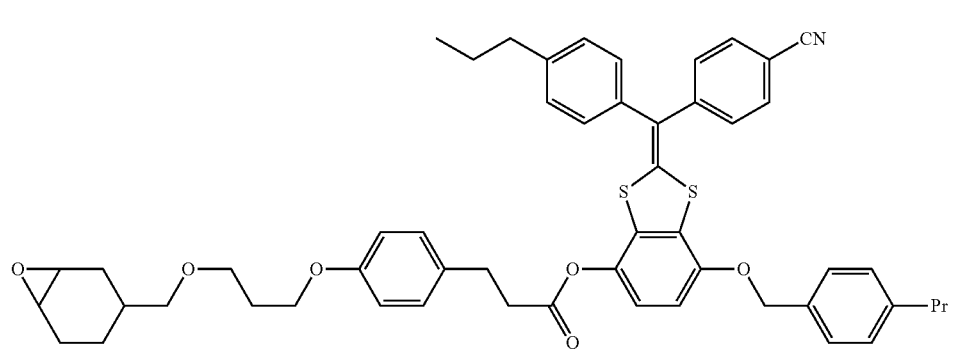
(A2-10)
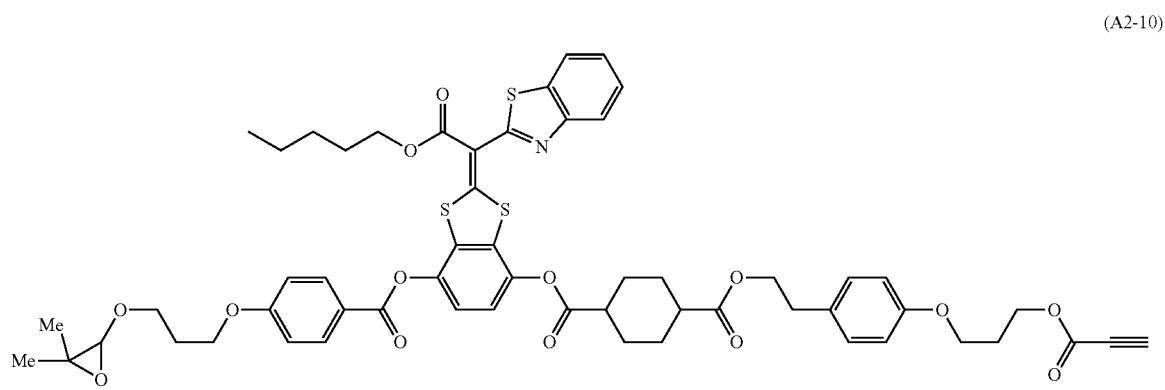
[Chem. 154]
(A3-1)
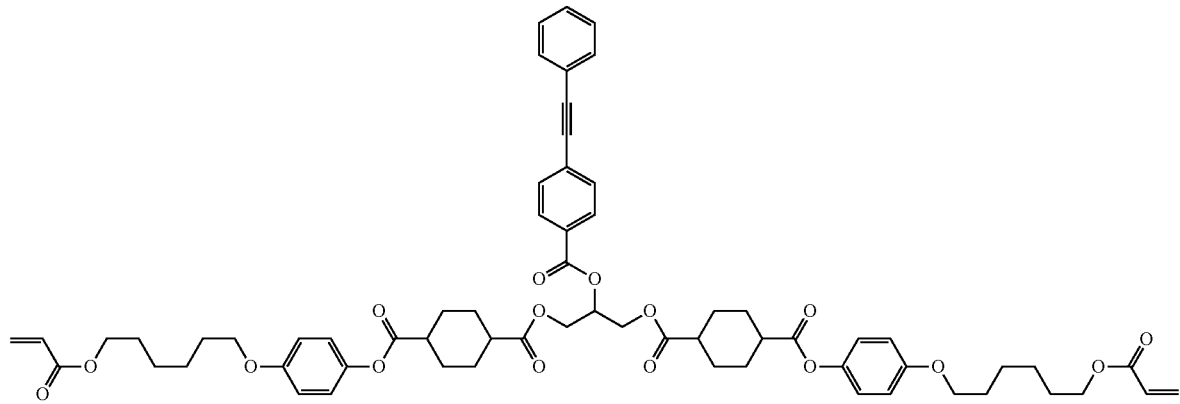

(A3-2)
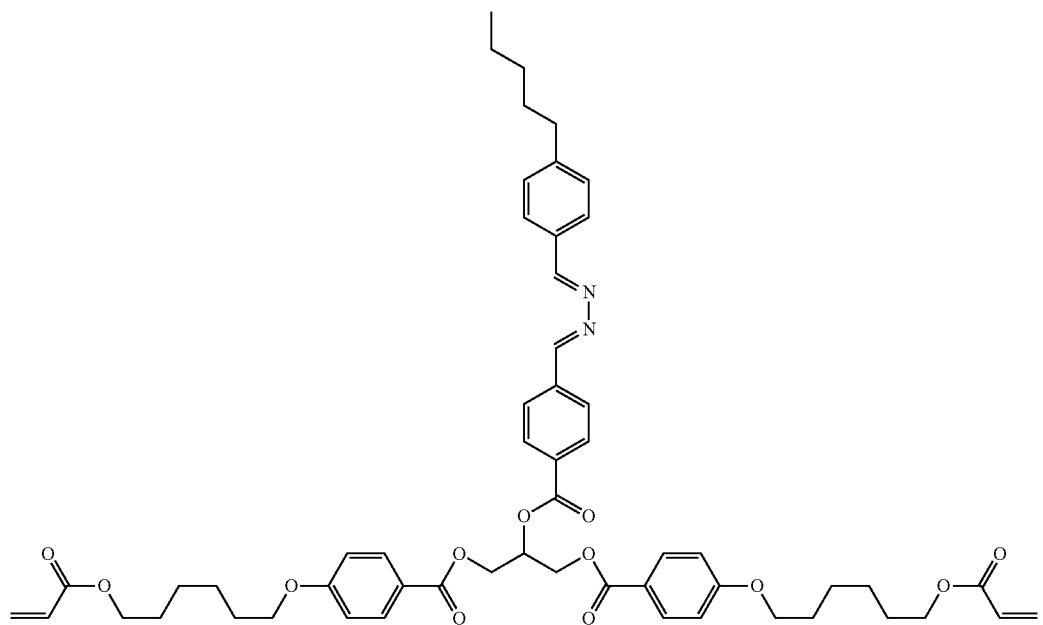
(A3-3)
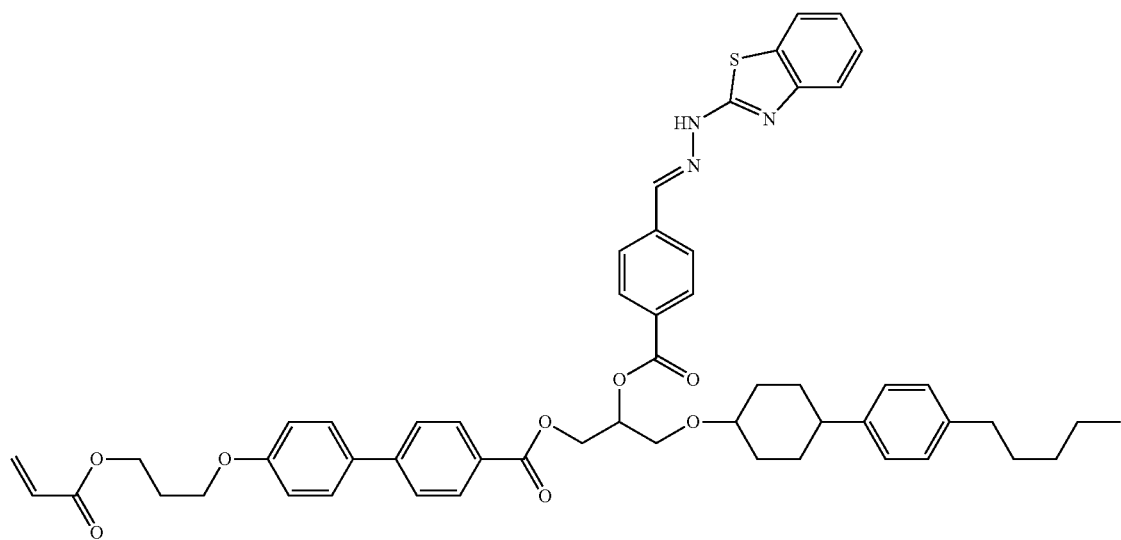

(A3-5)
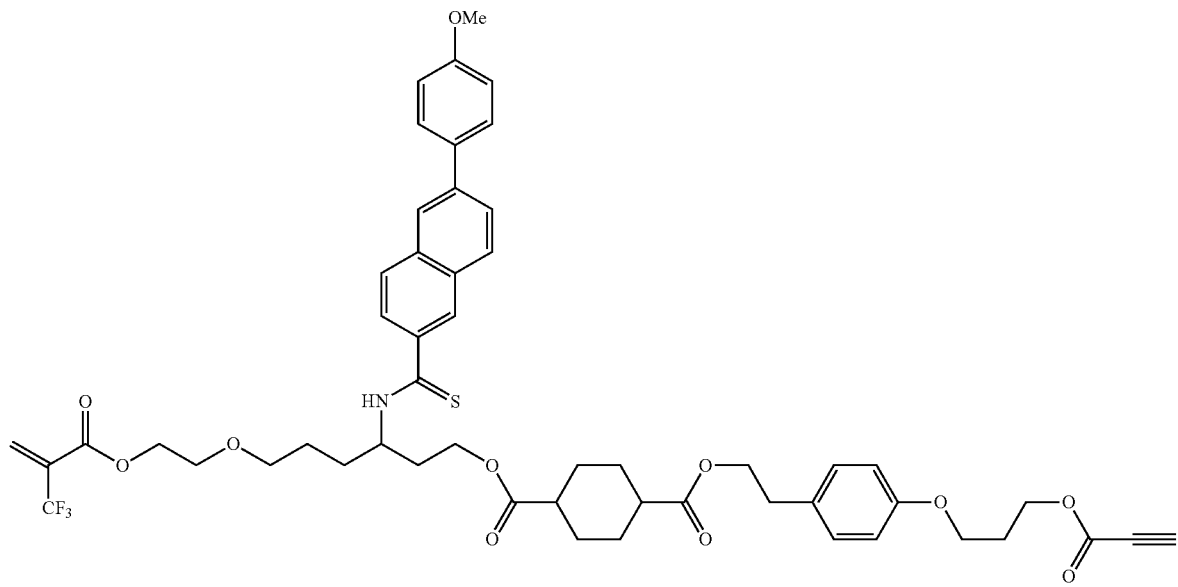
[Chem. 155]
(B11-1)
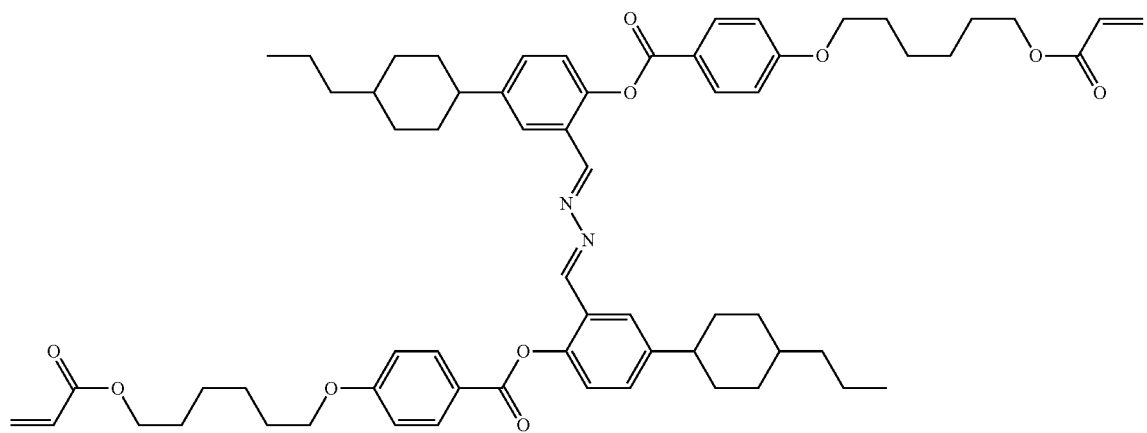
(B11-2)
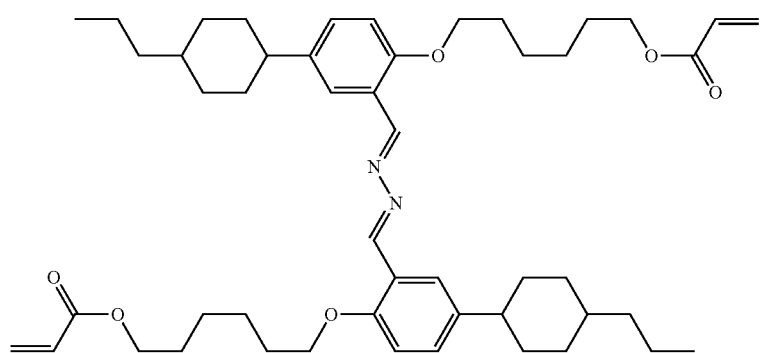

-continued
(B11-3)
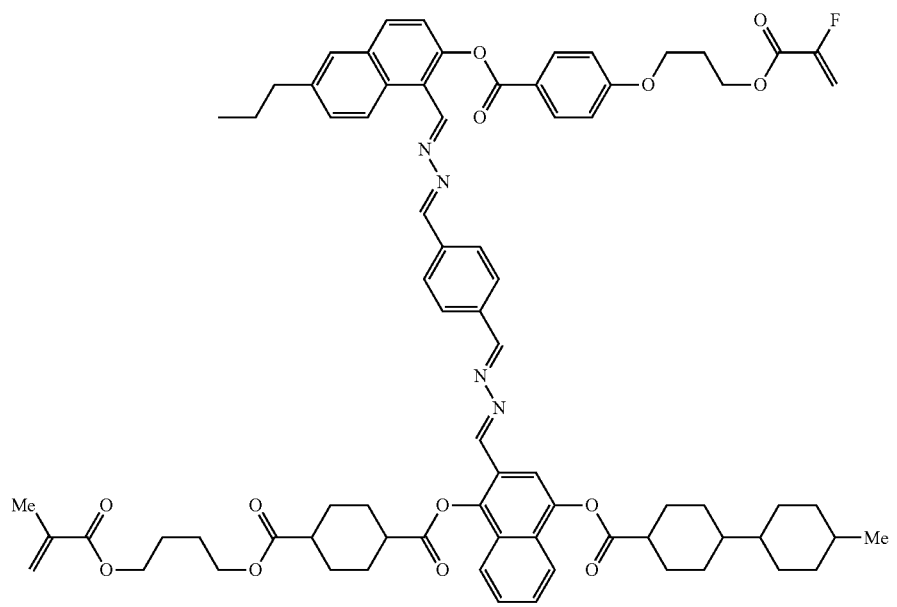
(B11-4)
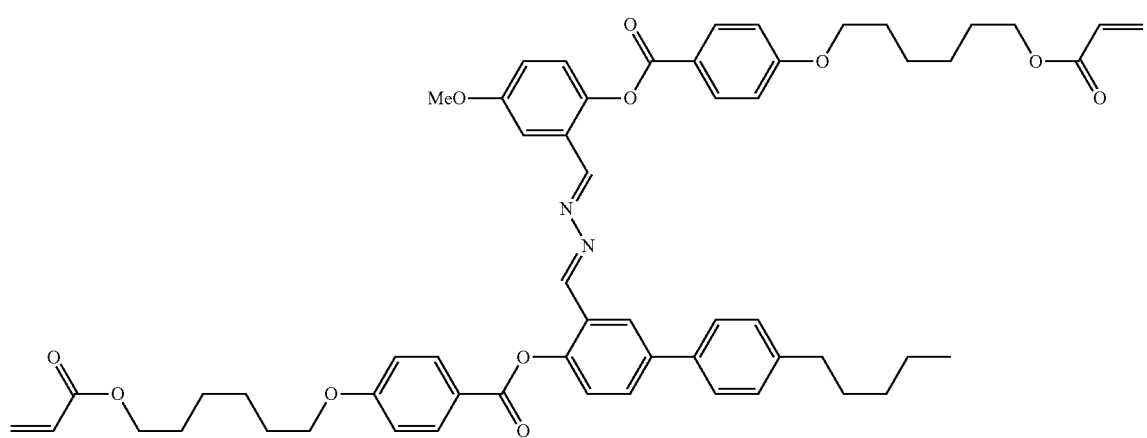

[Chem. 156]
(B11-5)
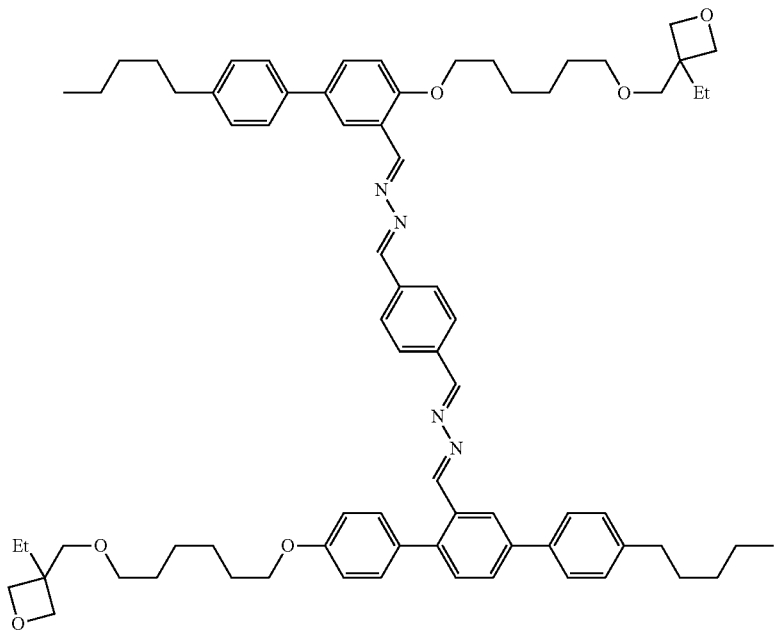
(B11-6)
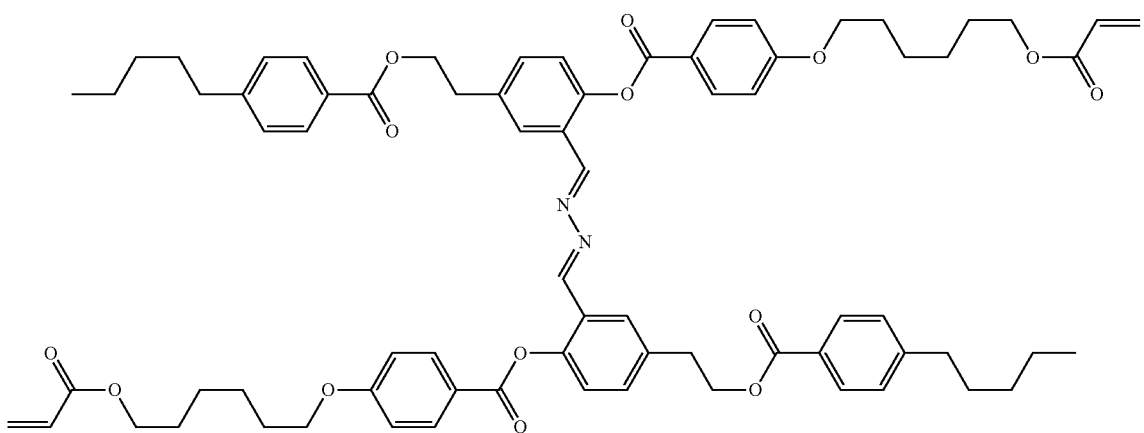
(B11-7)
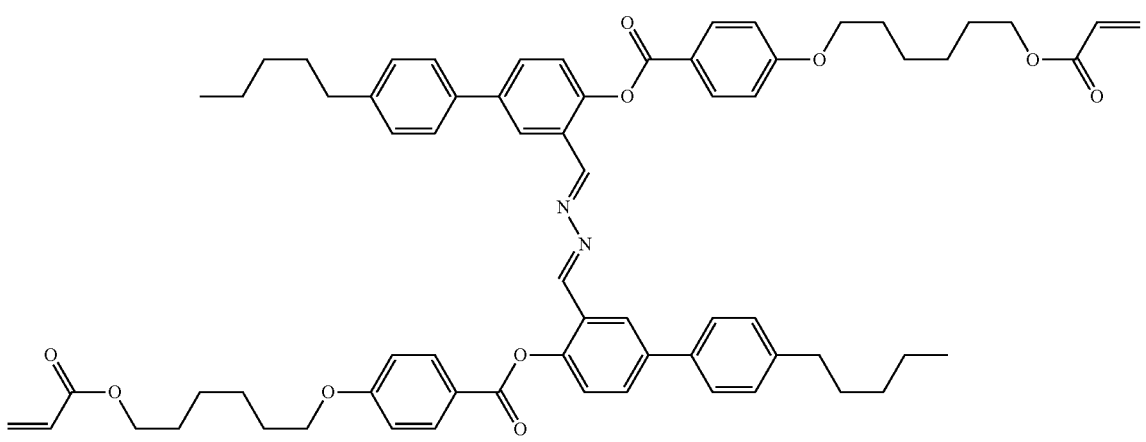

(B11-8)
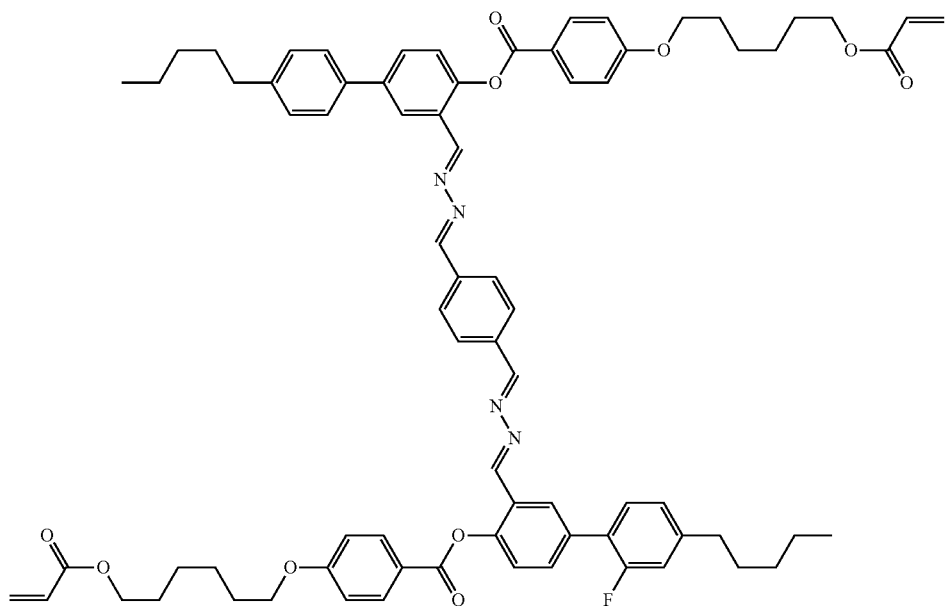
[Chem. 157]
(B11-9)
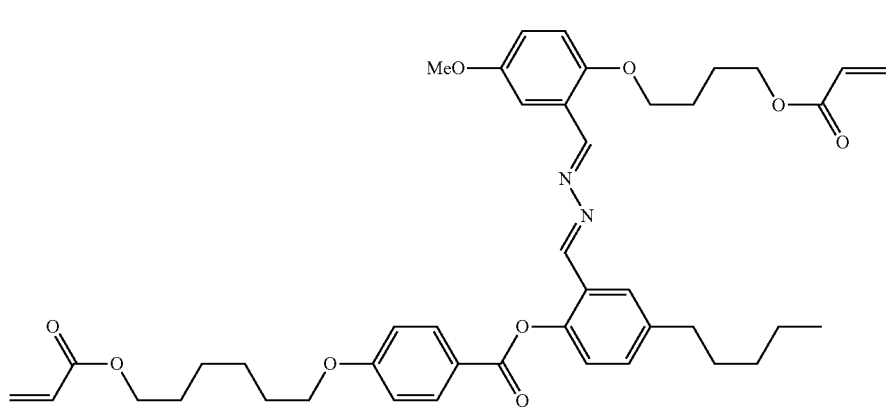
(B11-10)
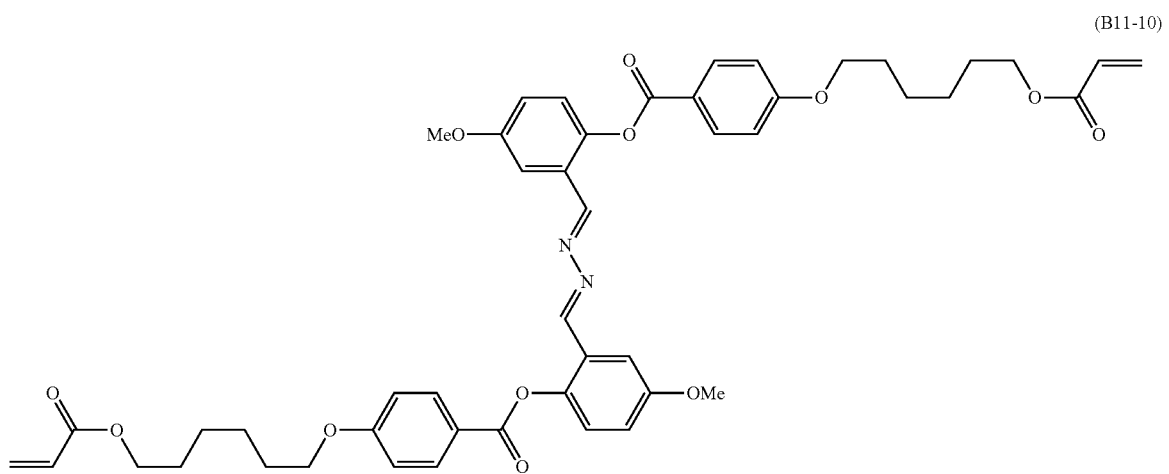

(B11-11)
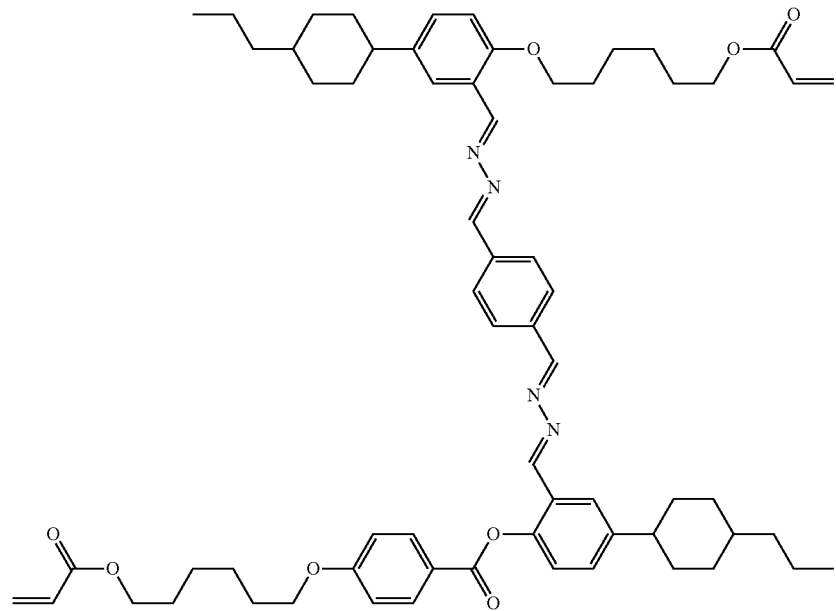
(B11-12)
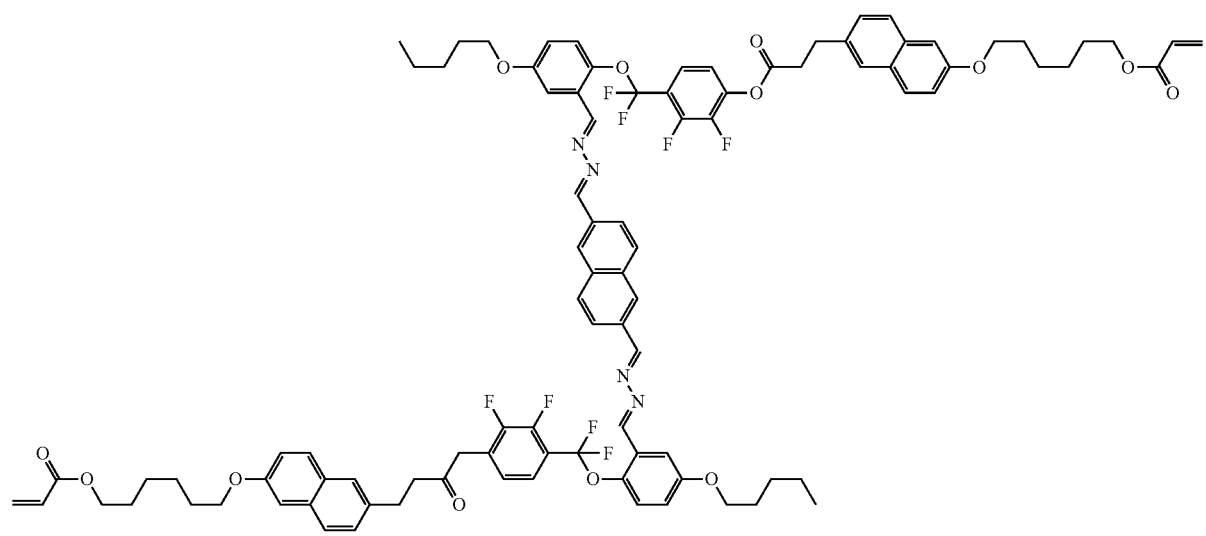

[Chem. 158]
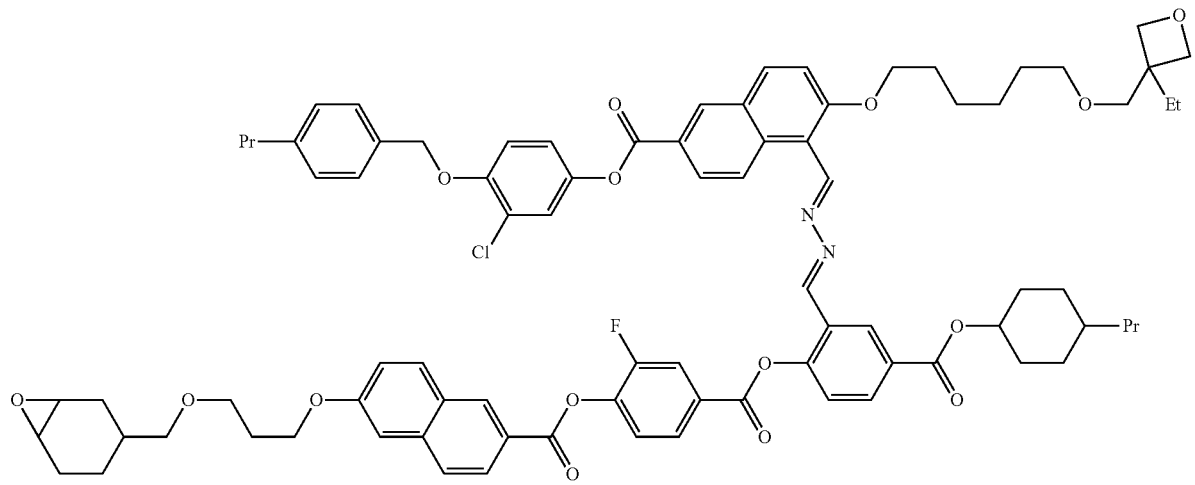
(B11-13)
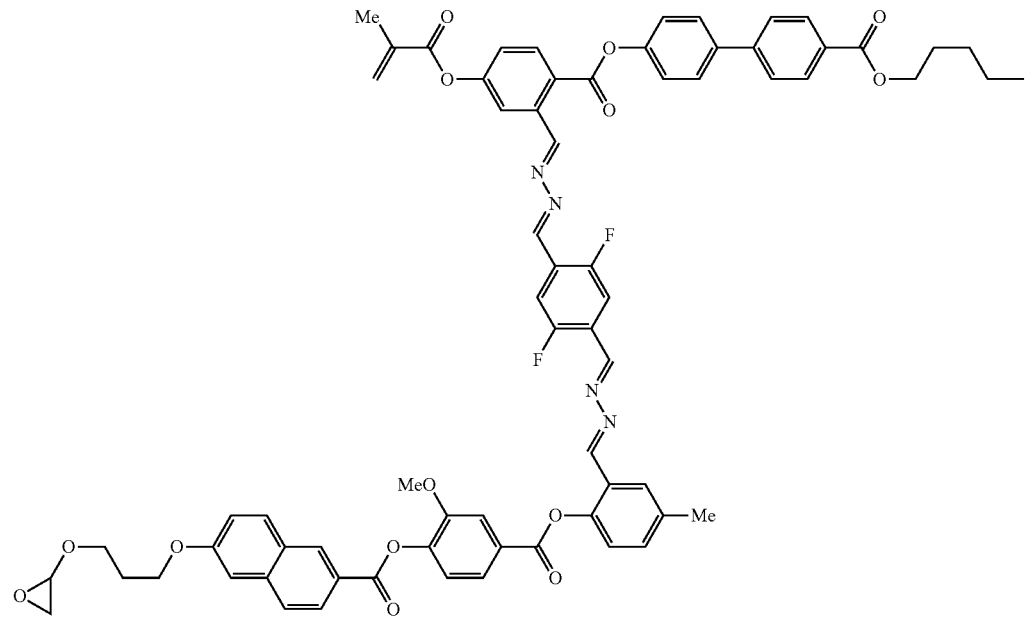
(B11-14)

(B11-15)
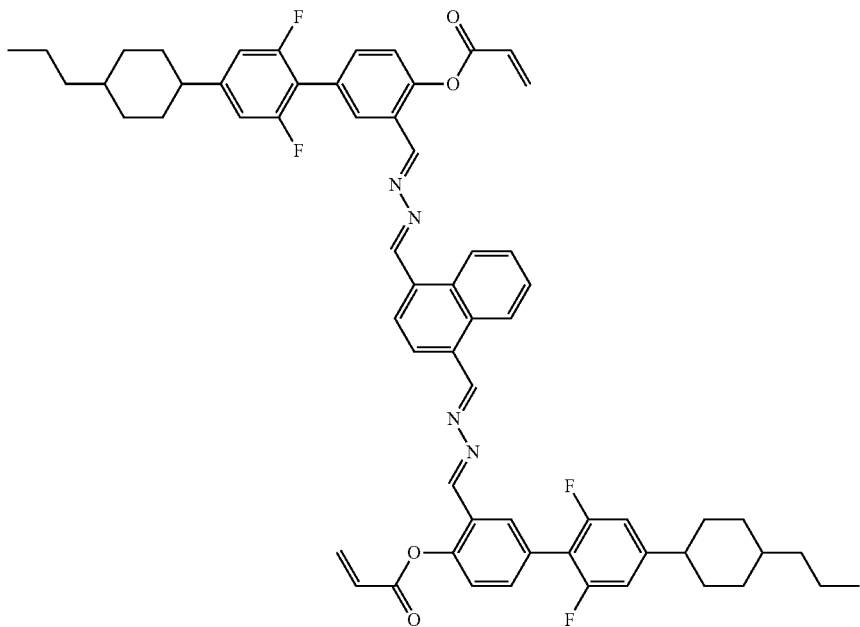
(B11-16)
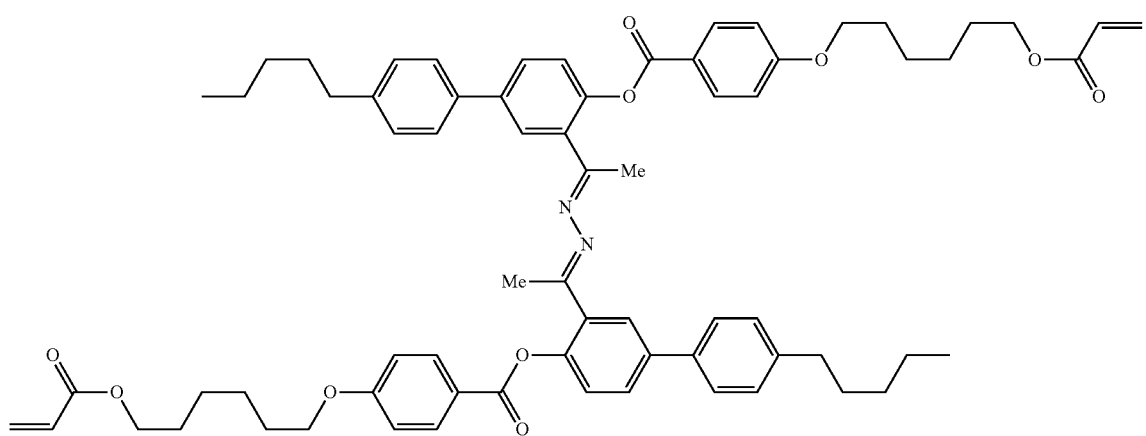

-continued
[Chem. 159]
(B2-1)
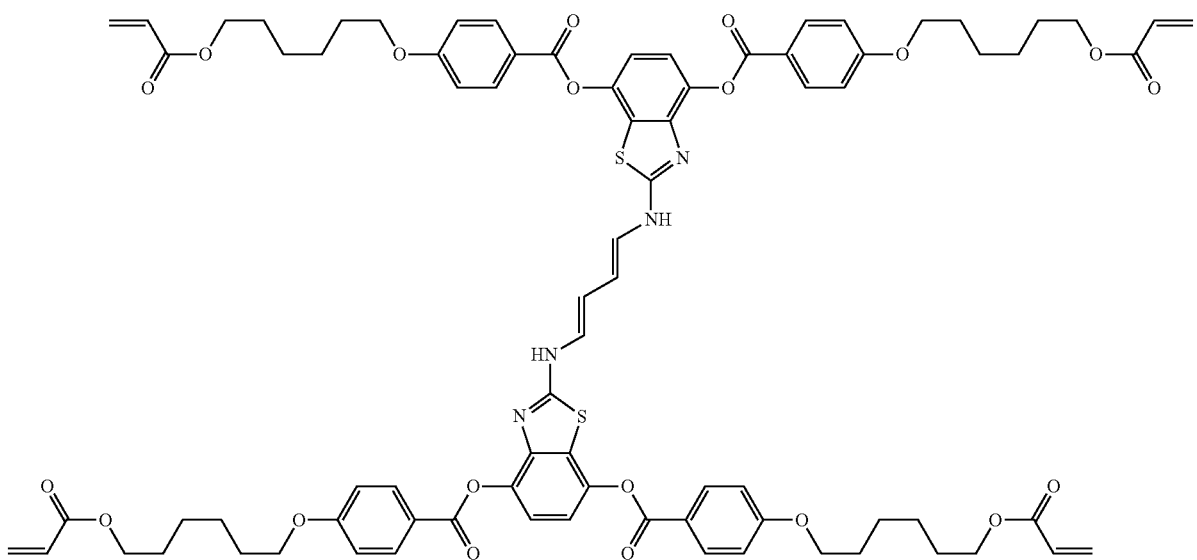
(B2-2)
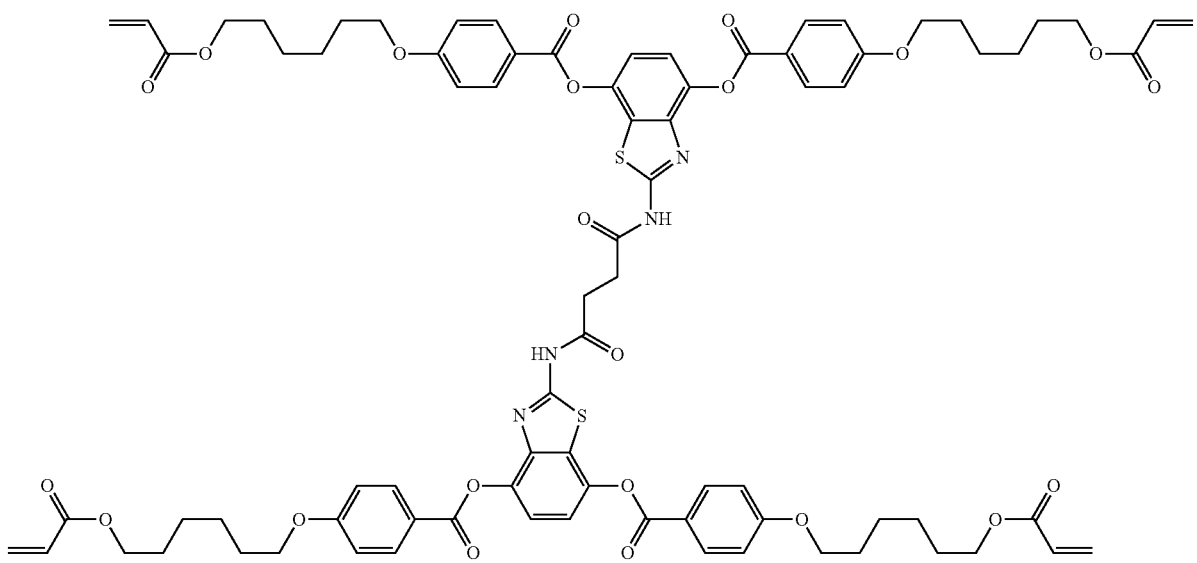

(B2-3)
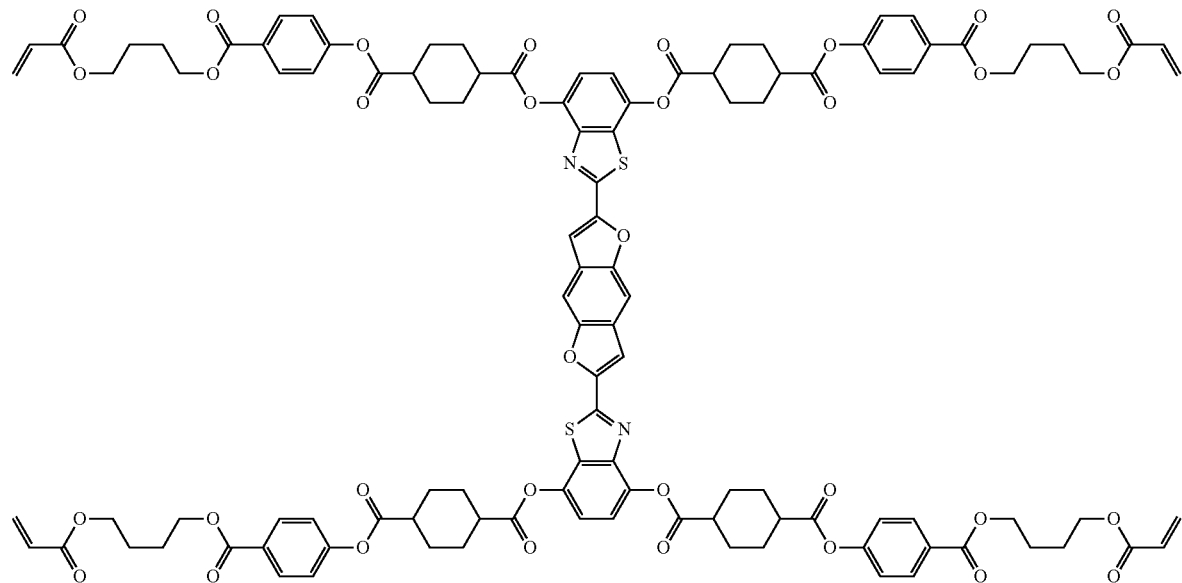
[Chem. 160]
(B2-4)
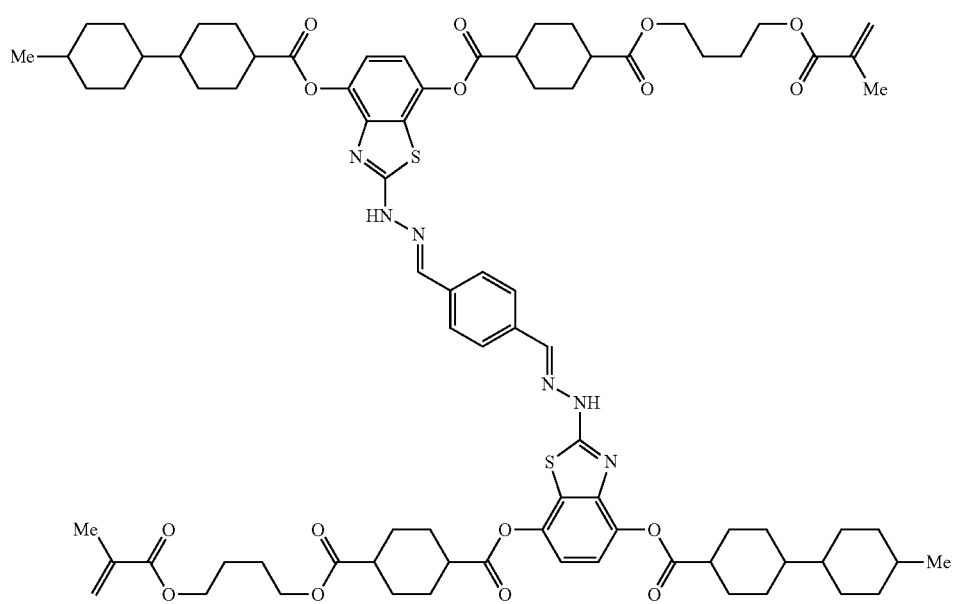

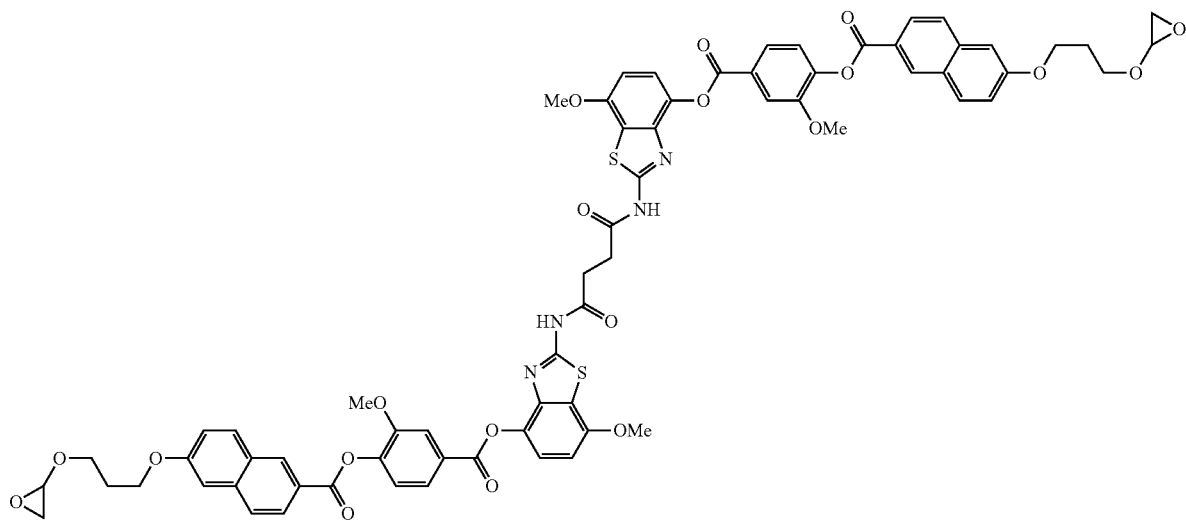
(B2-5)
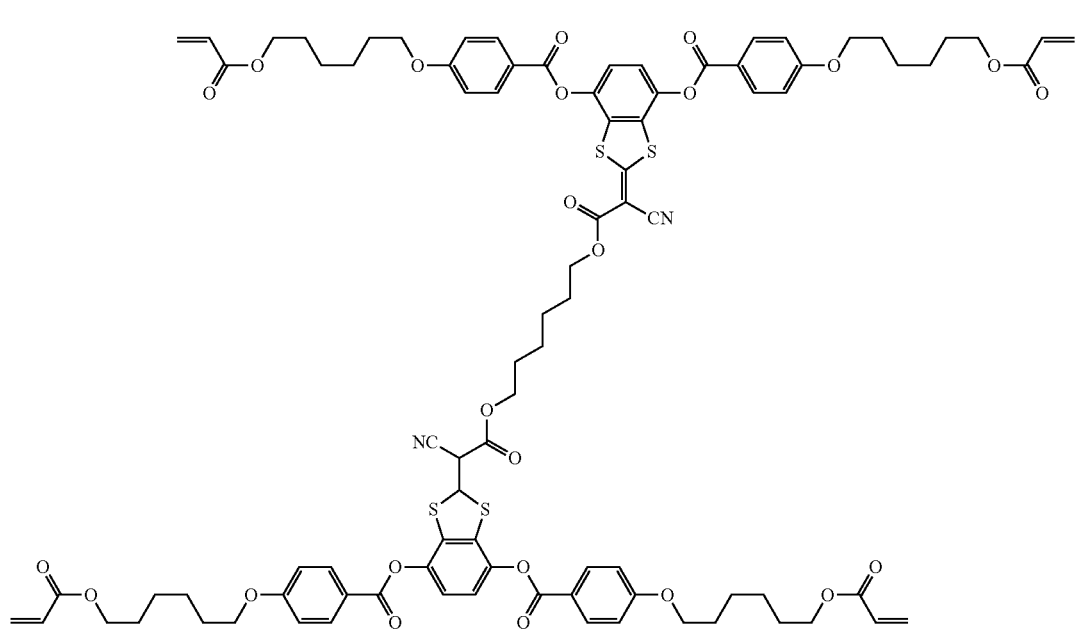
(B2-6)

-continued
[Chem. 161]
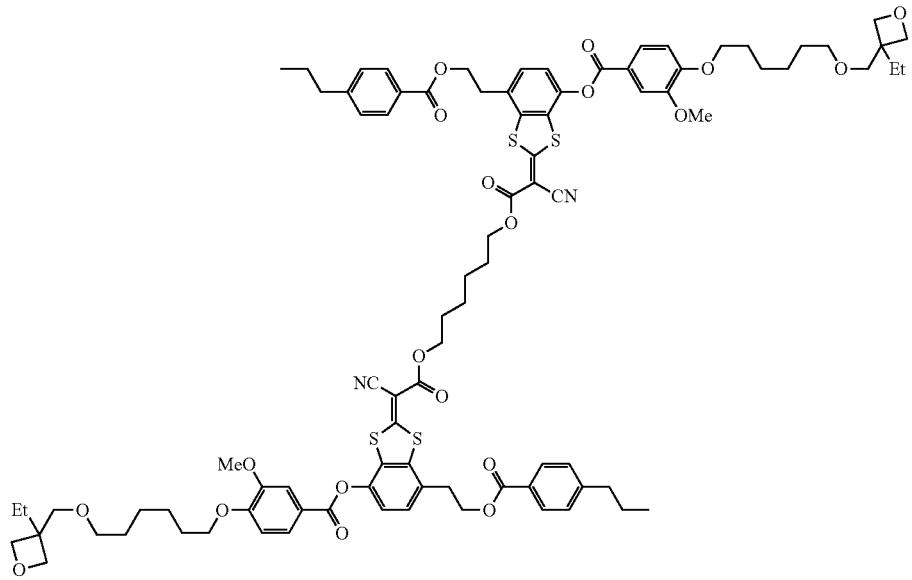
(B2-7)
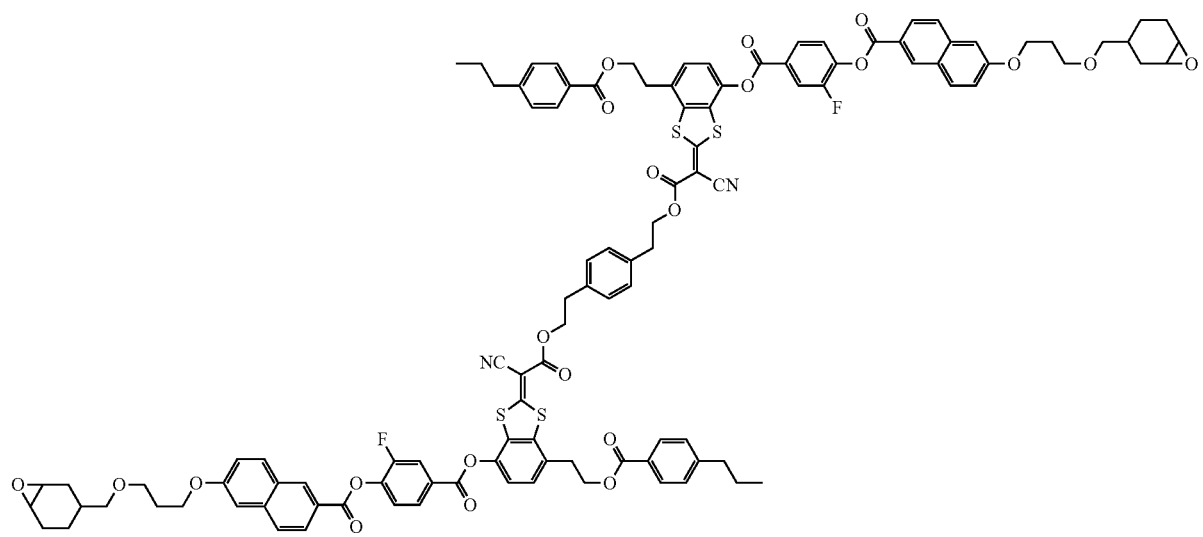
(B2-8)

(B2-9)
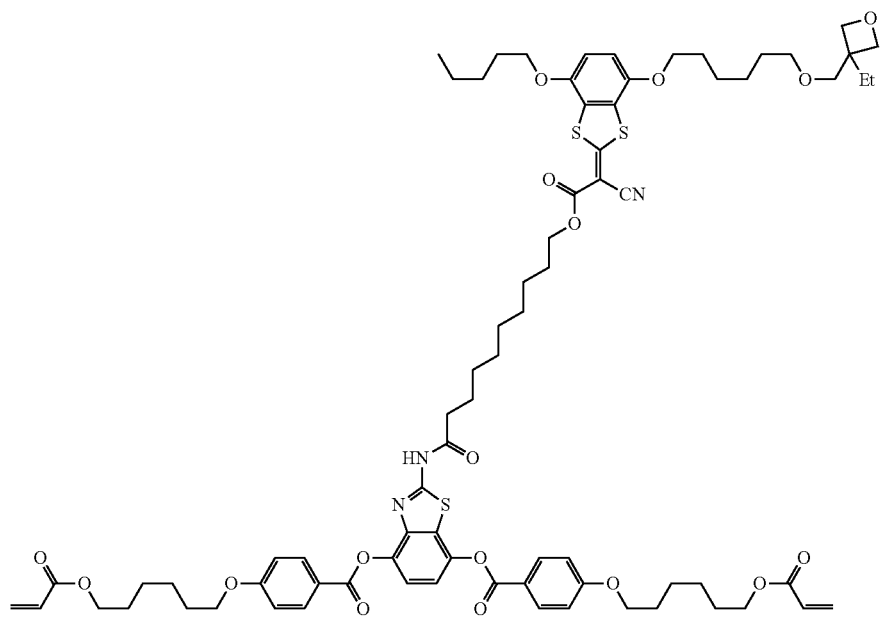
[Chem. 162]
(B2-10)
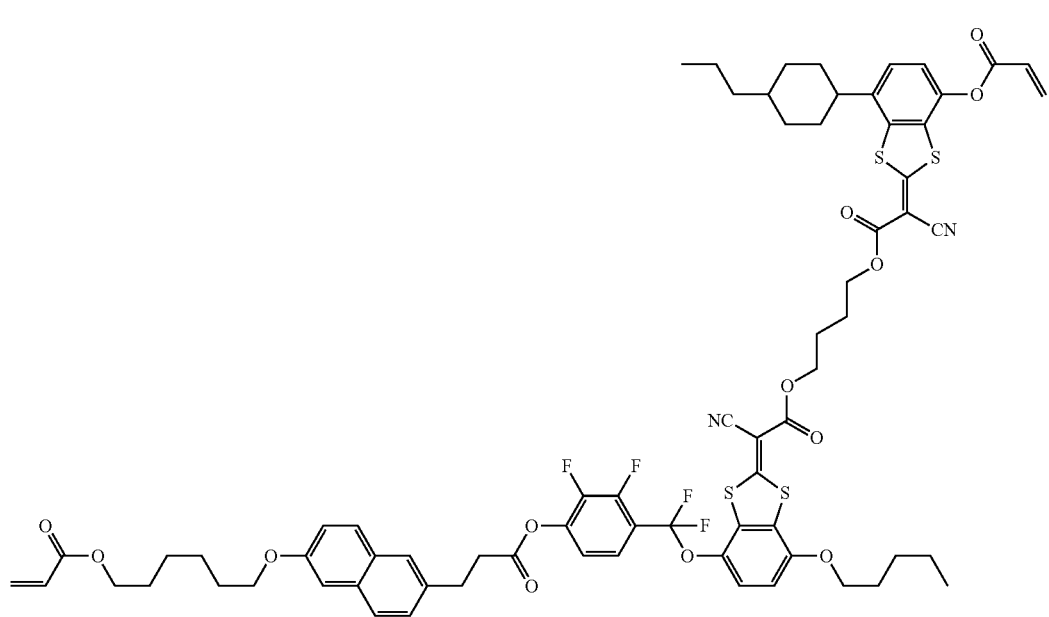

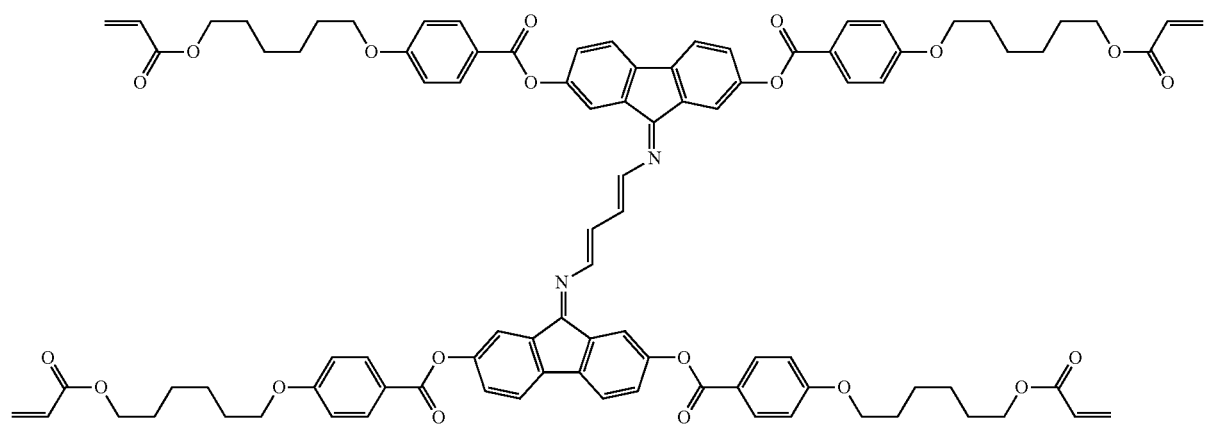
(B2-11)
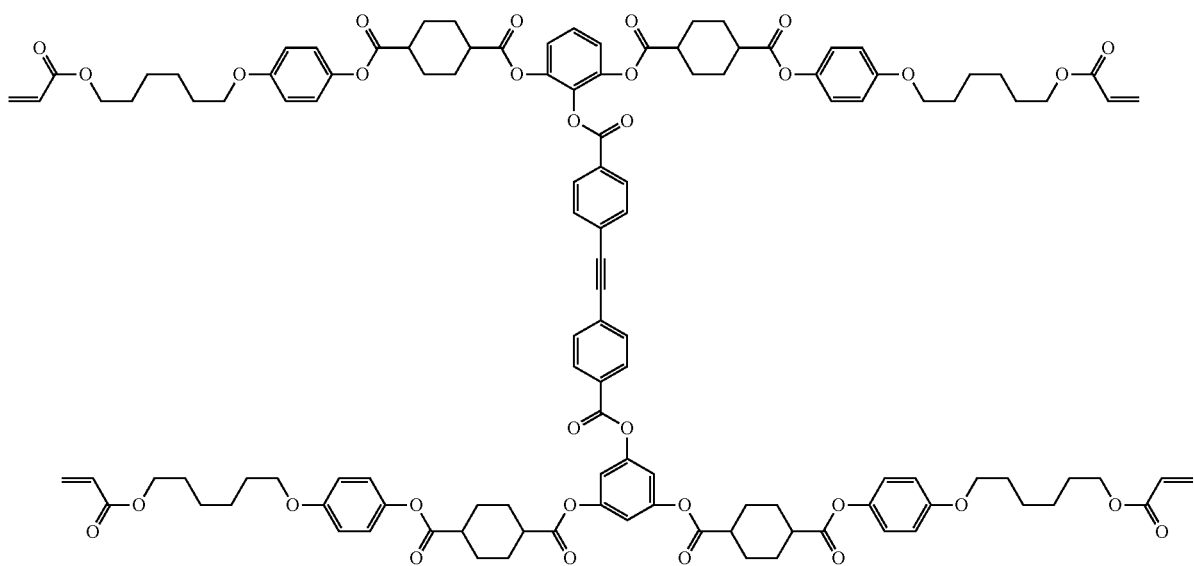
(B2-12)

[Chem. 163]
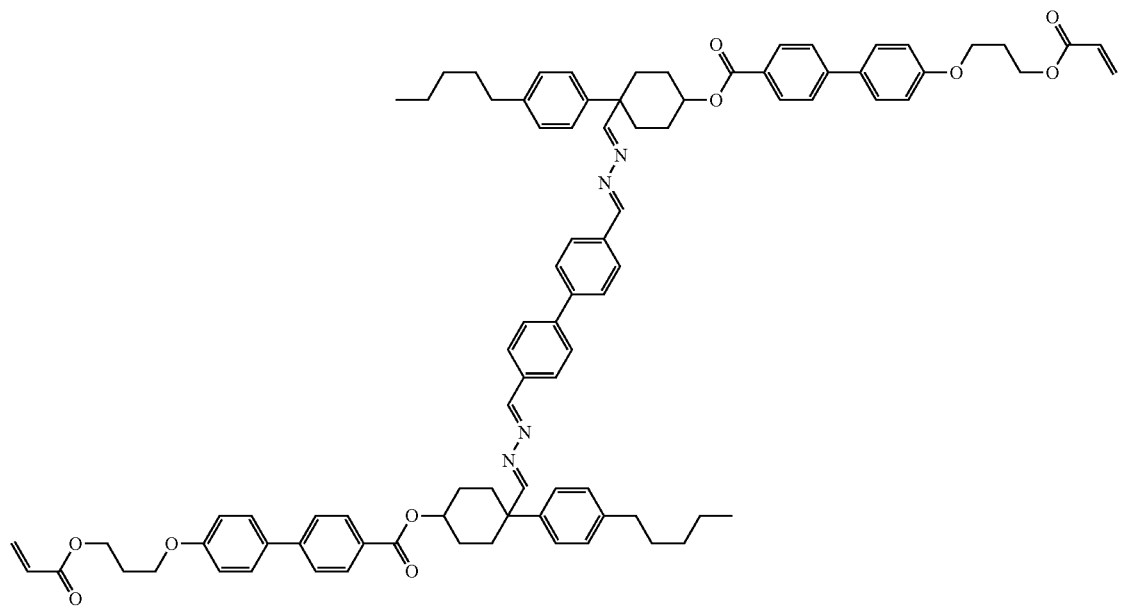
(B2-13)
[Chem. 164]
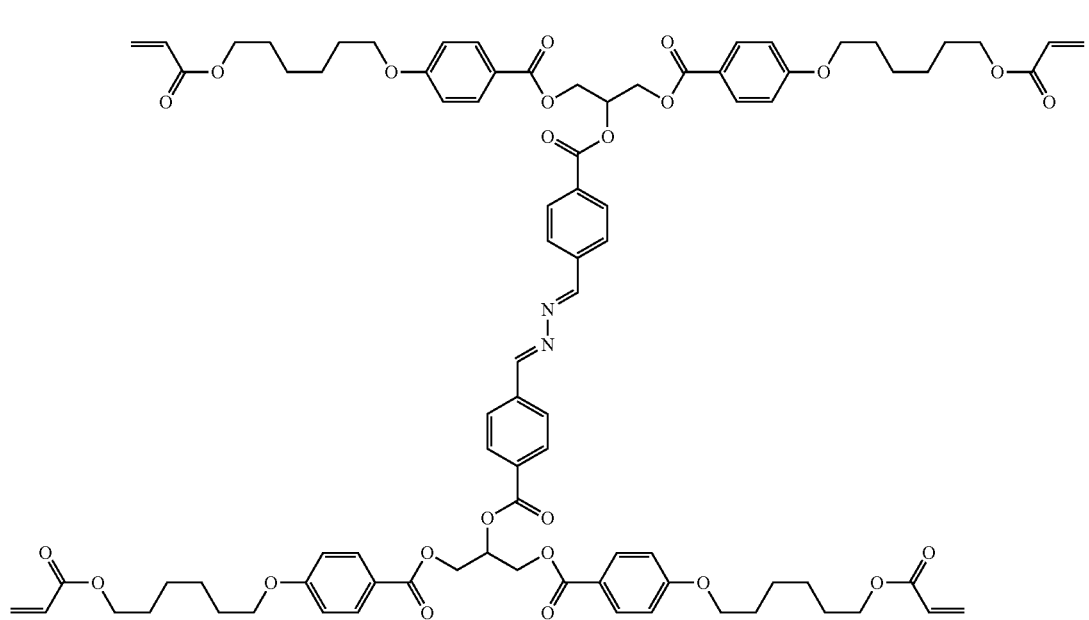
(B3-1)

(B3-2)
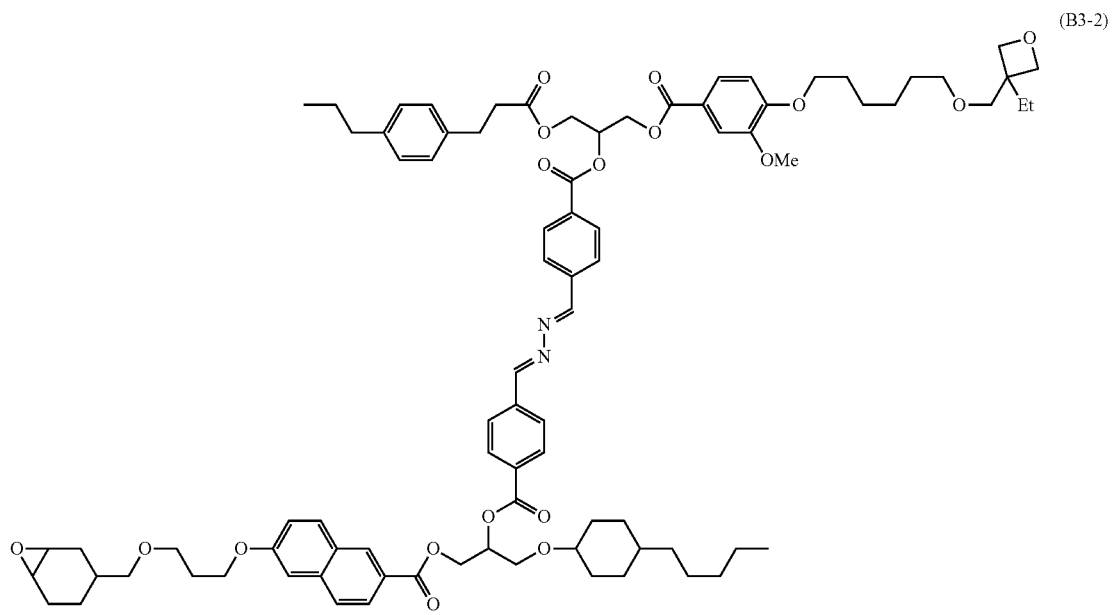
(B3-3)
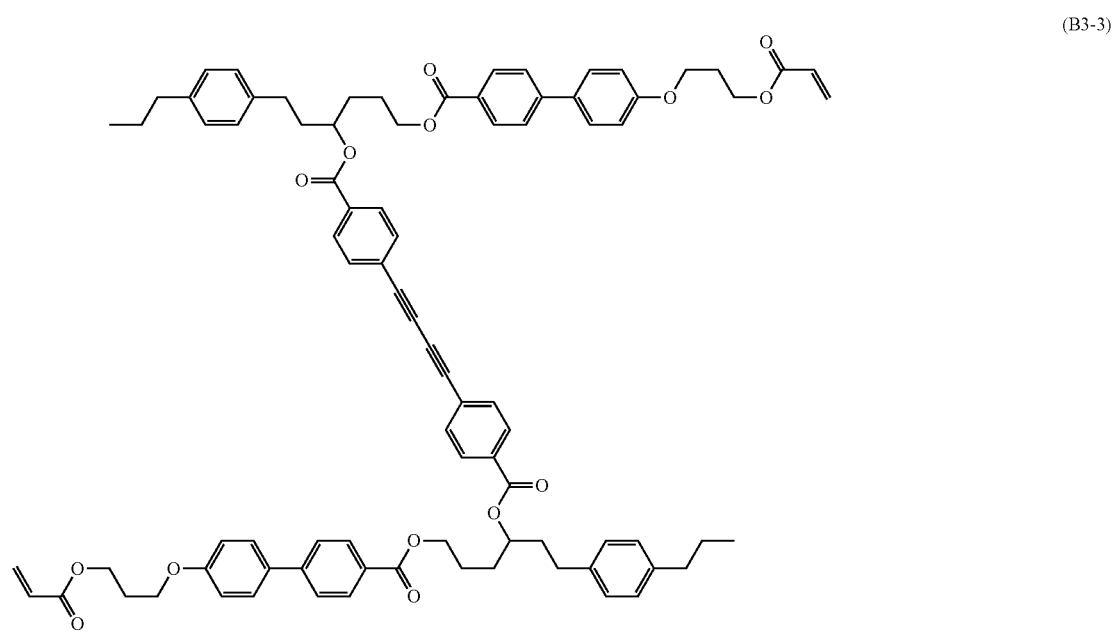

[Chem. 165]
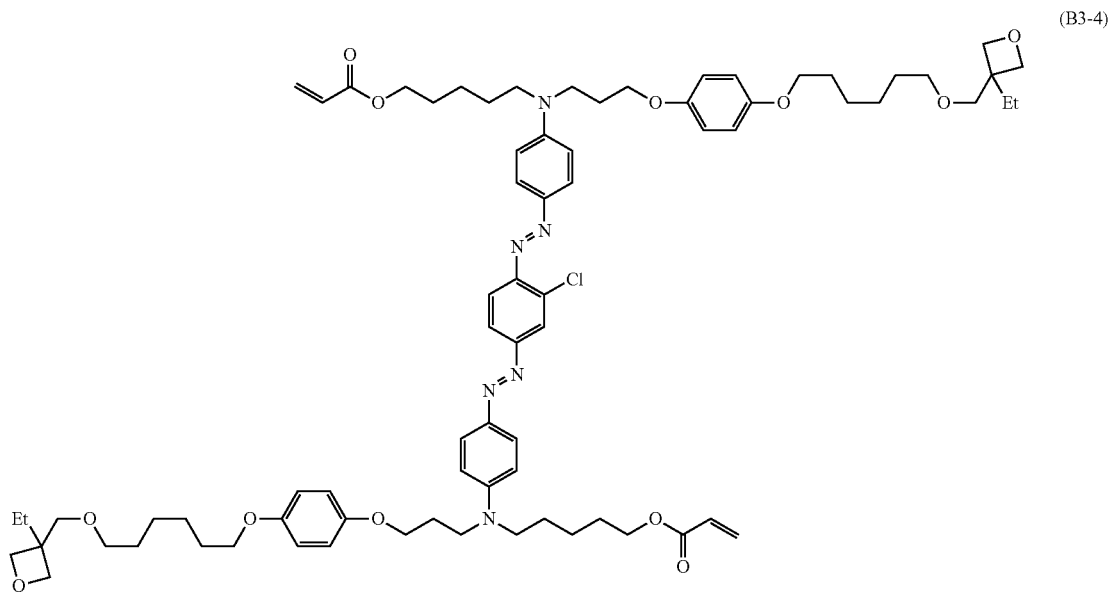
(B3-4)
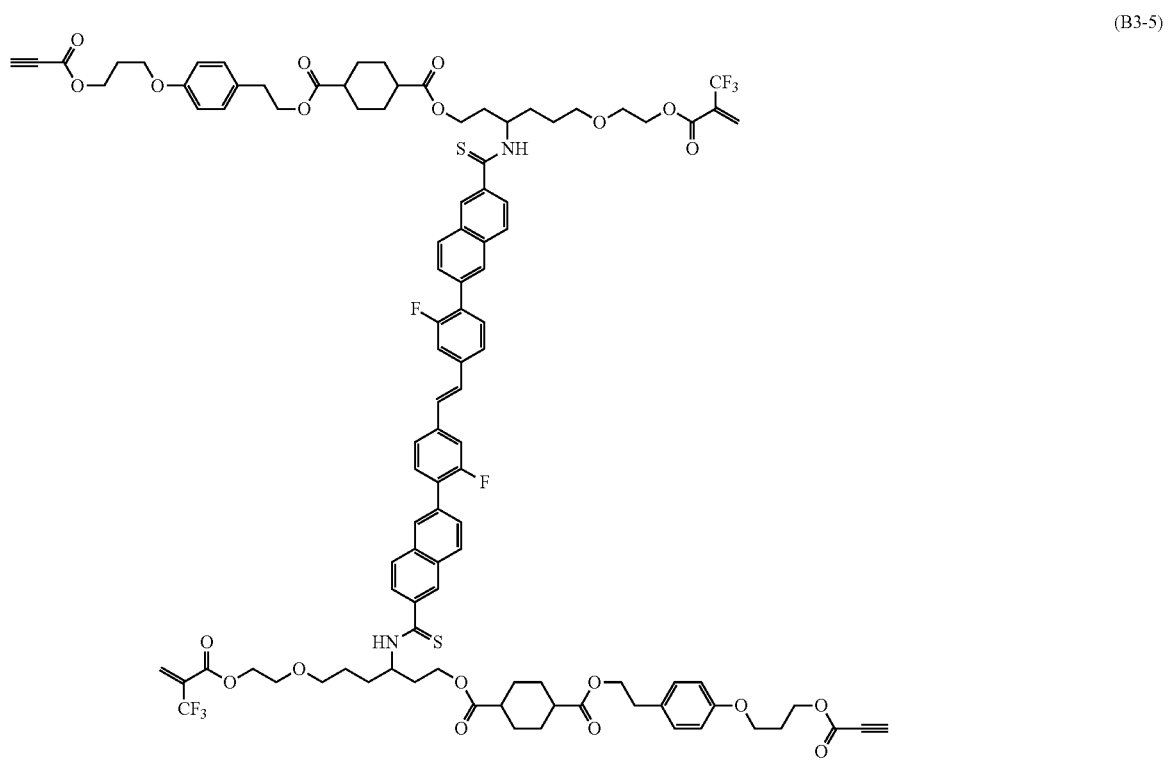
(B3-5)

[Chem. 166]
(C11-1)
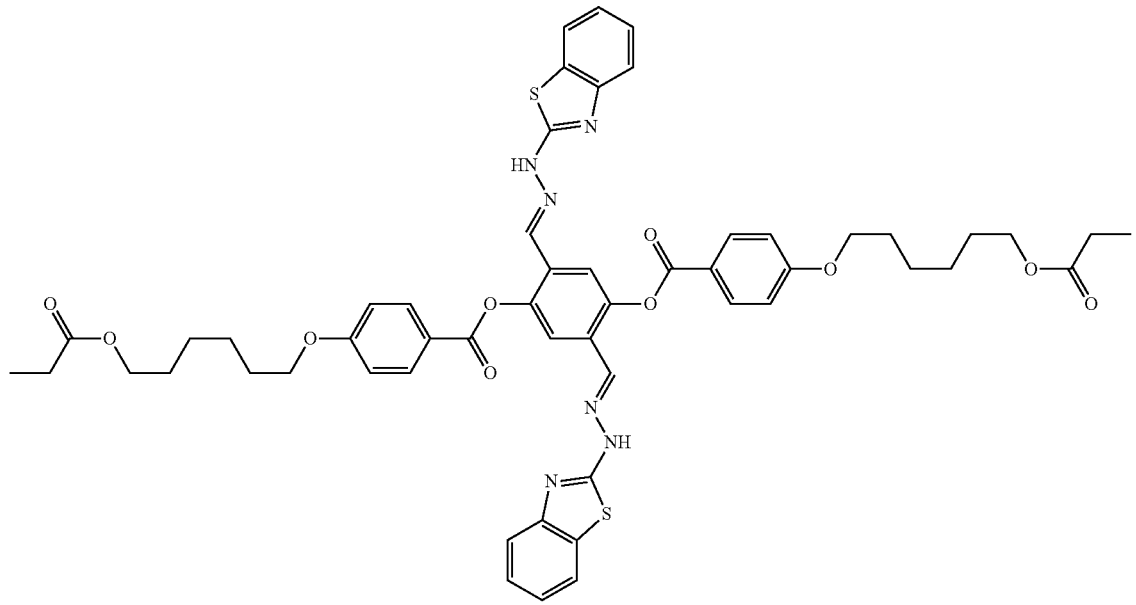
(C11-2)
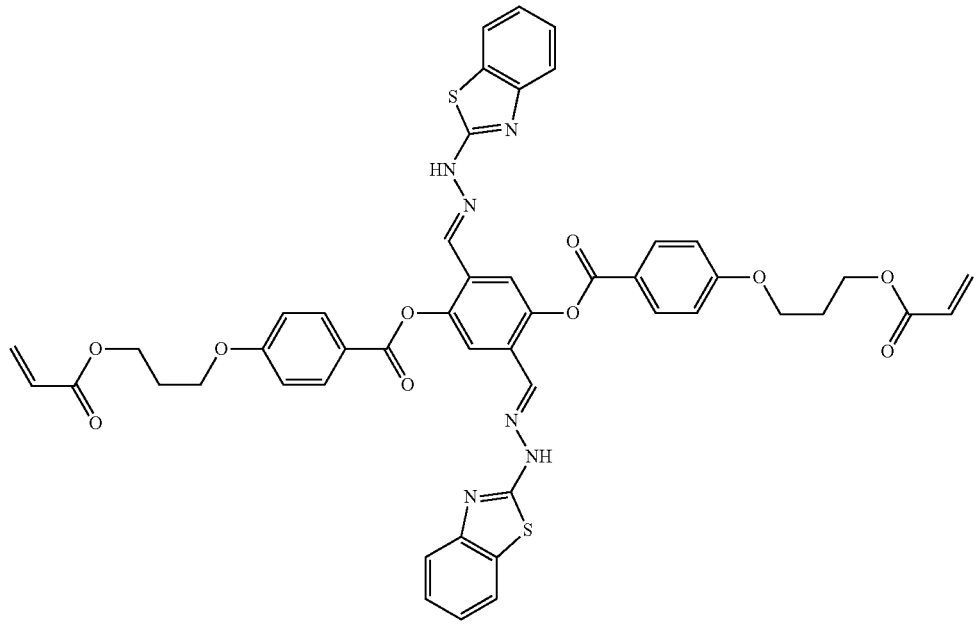

(C11-3)
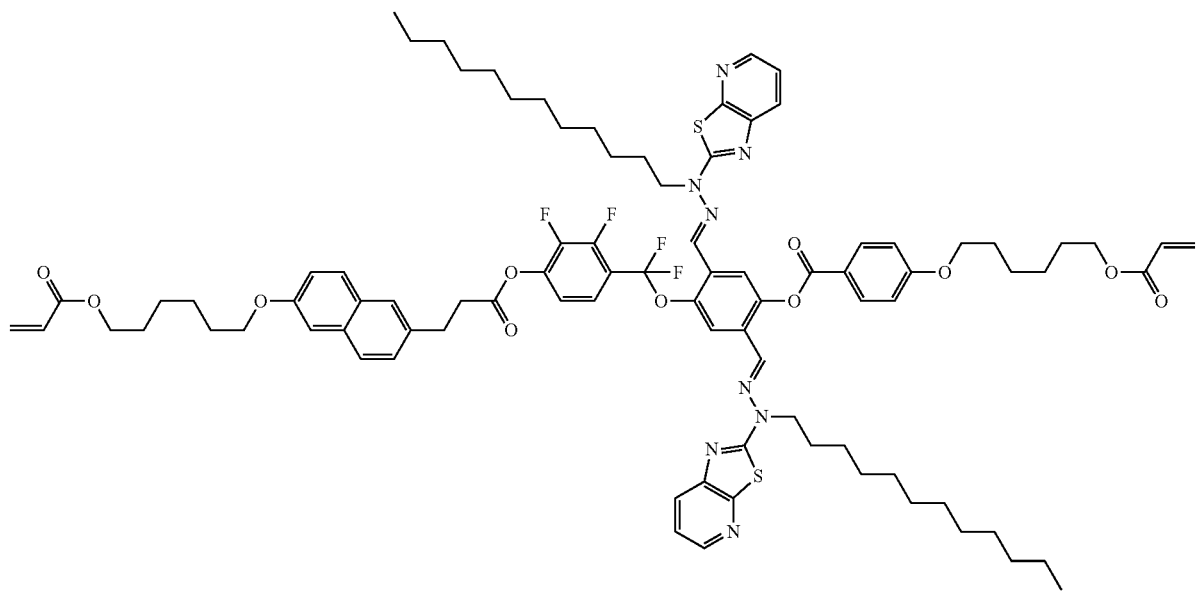
(C11-4)
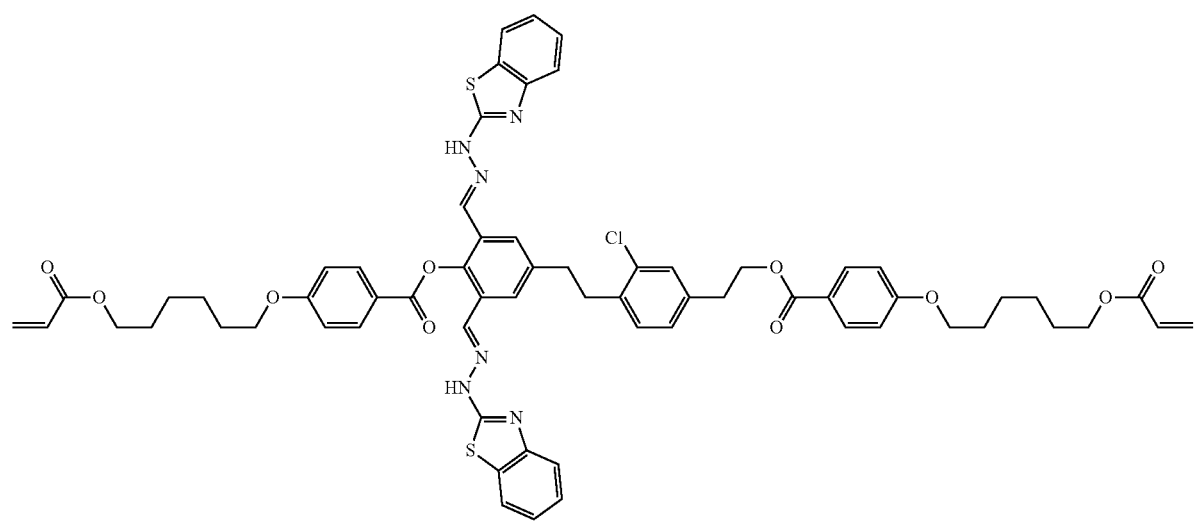

[Chem. 167]
(C11-5)
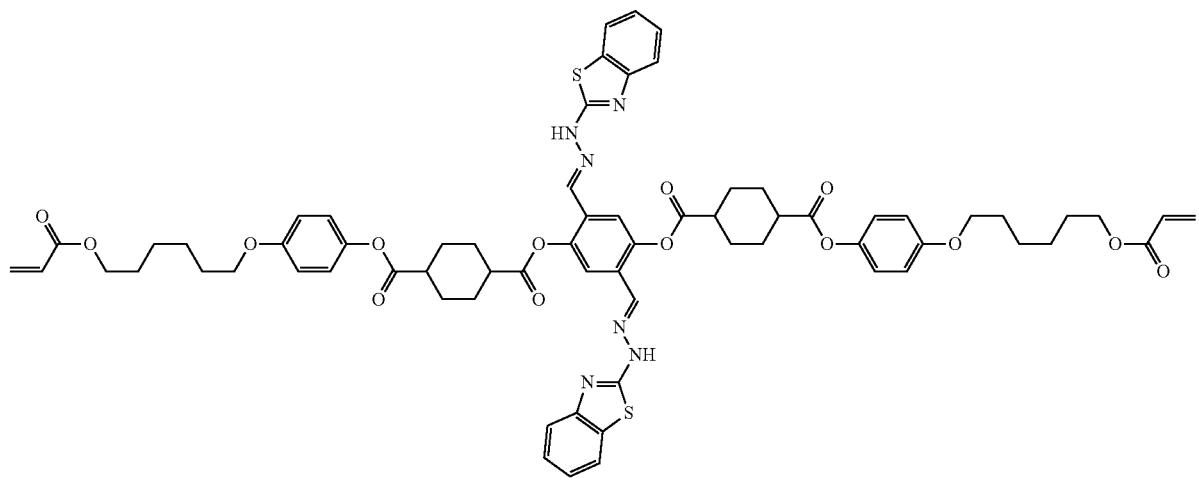
(C11-6)
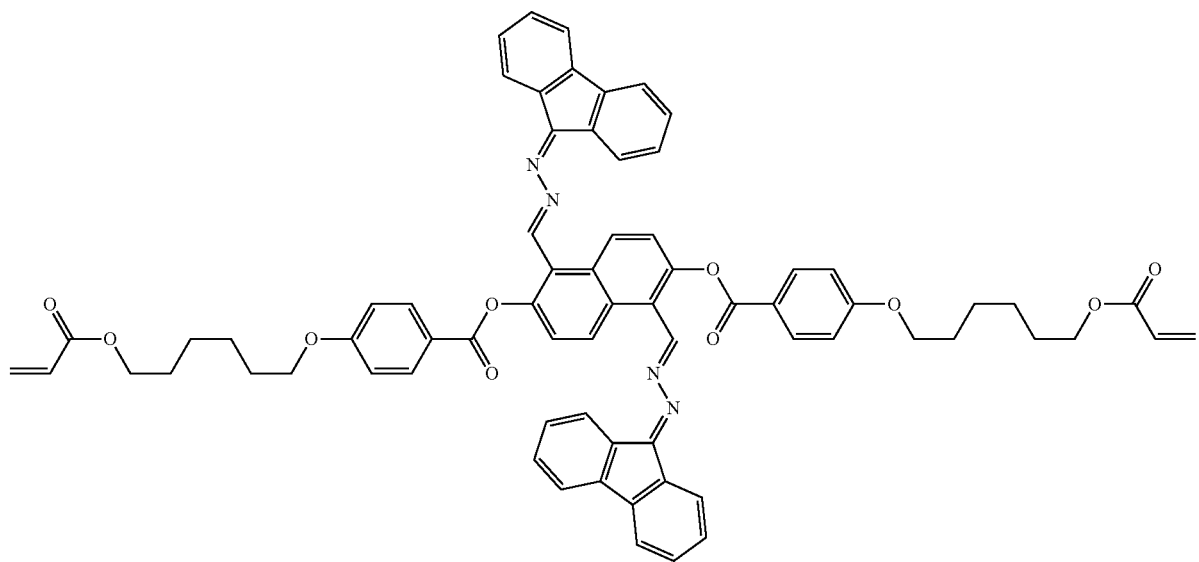

(C11-7)
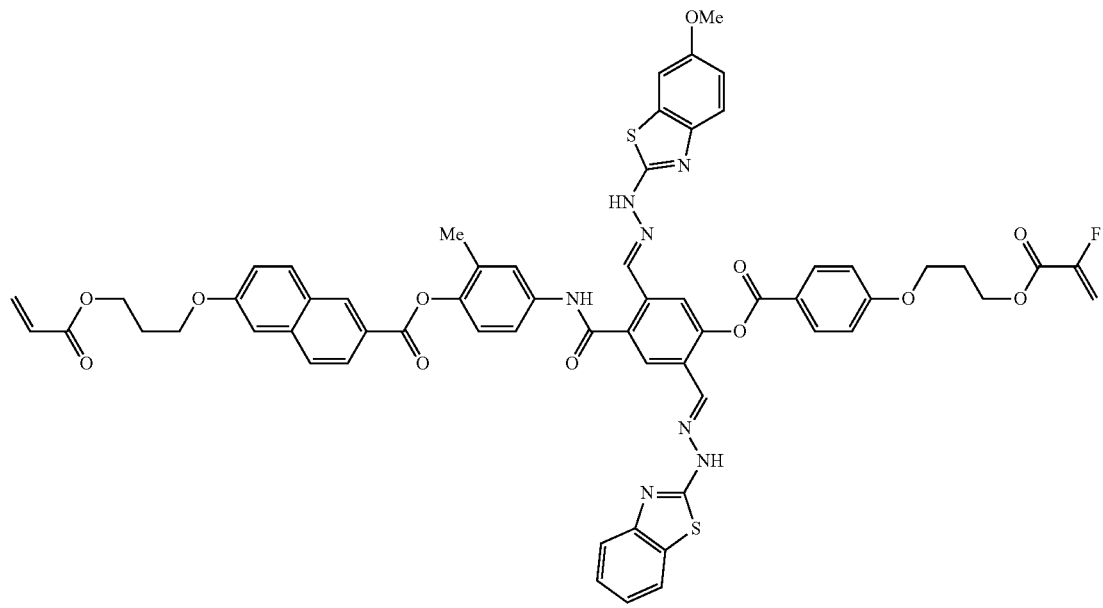
(C11-8)
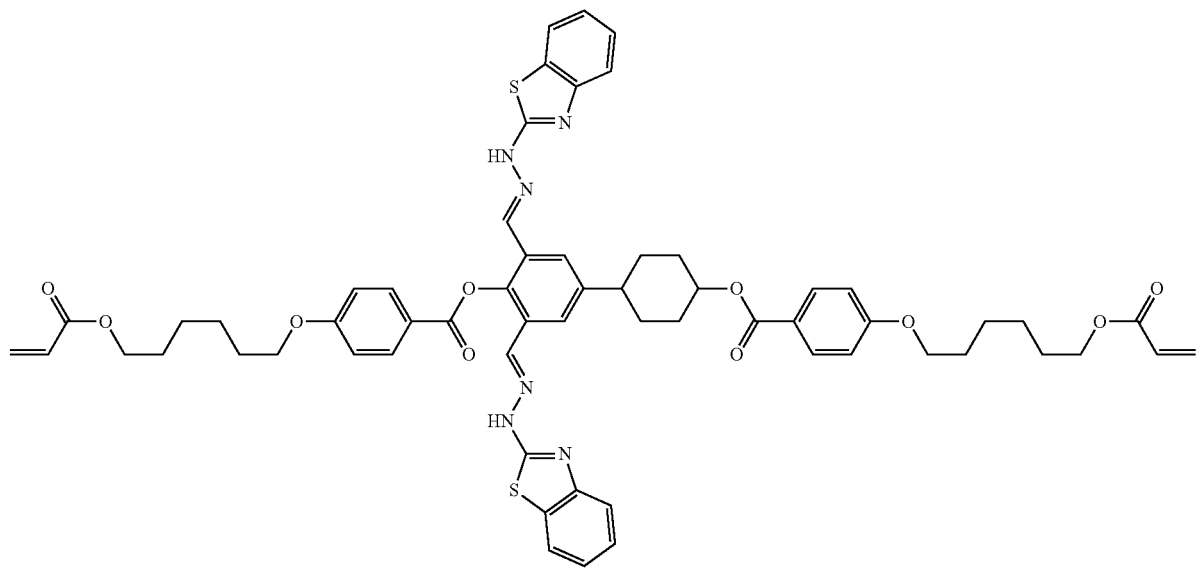

-continued
(C11-9)
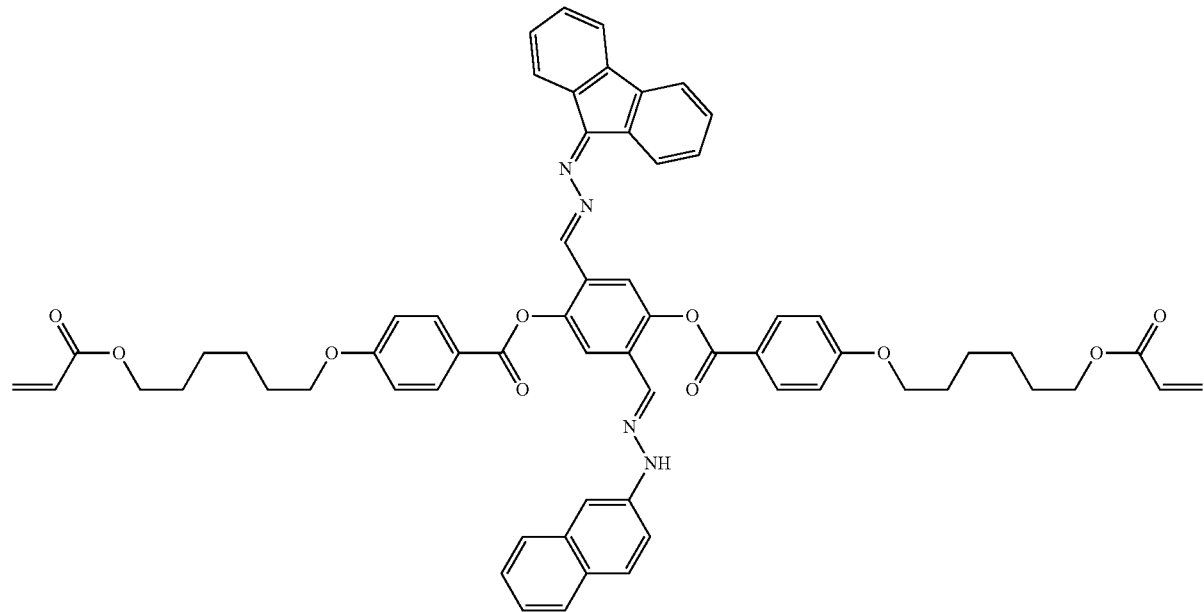
(C11-10)
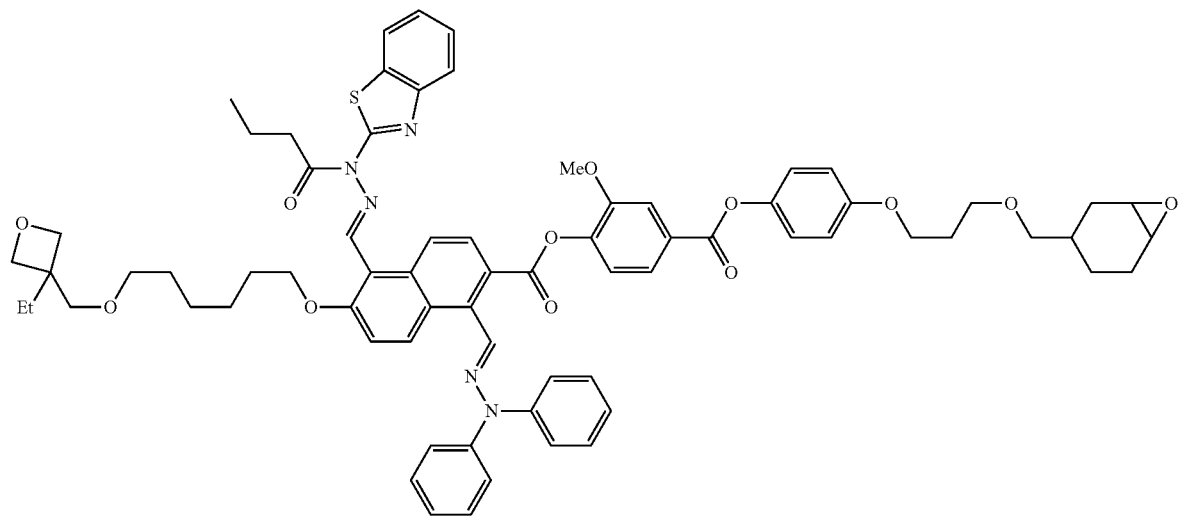

(C11-11)
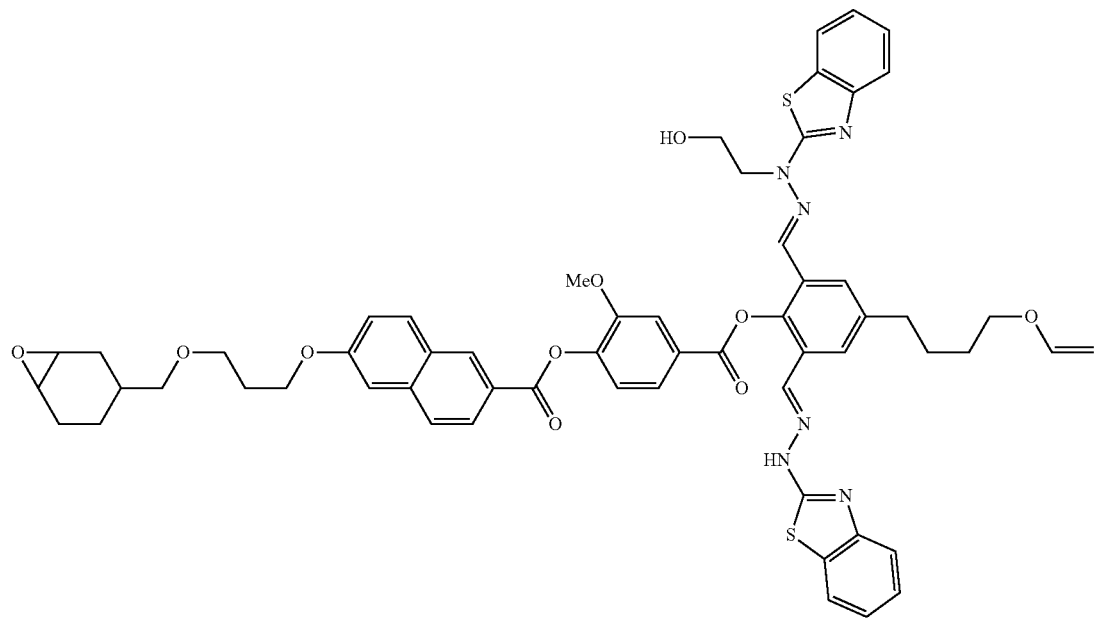
(C11-12)
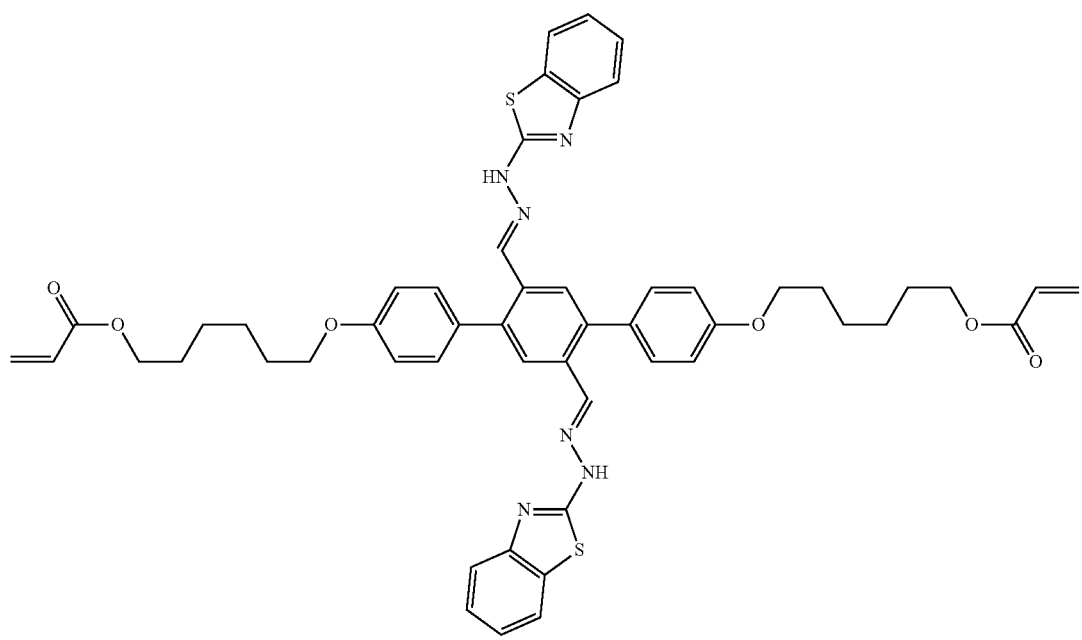

[Chem. 169]
(C11-13)
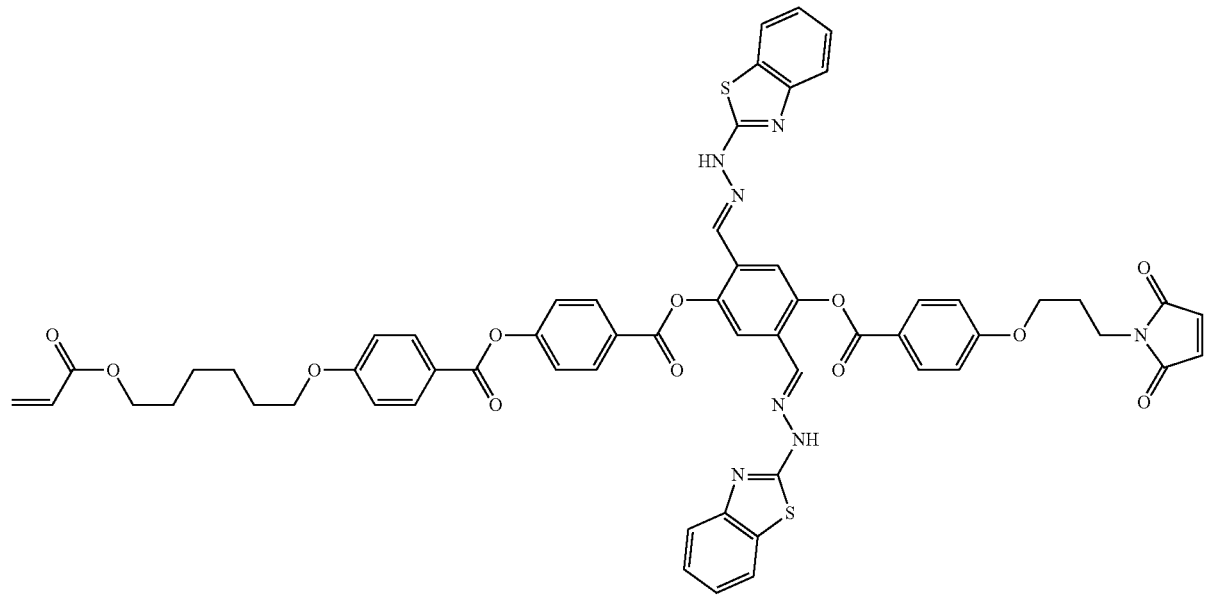
(C11-14)
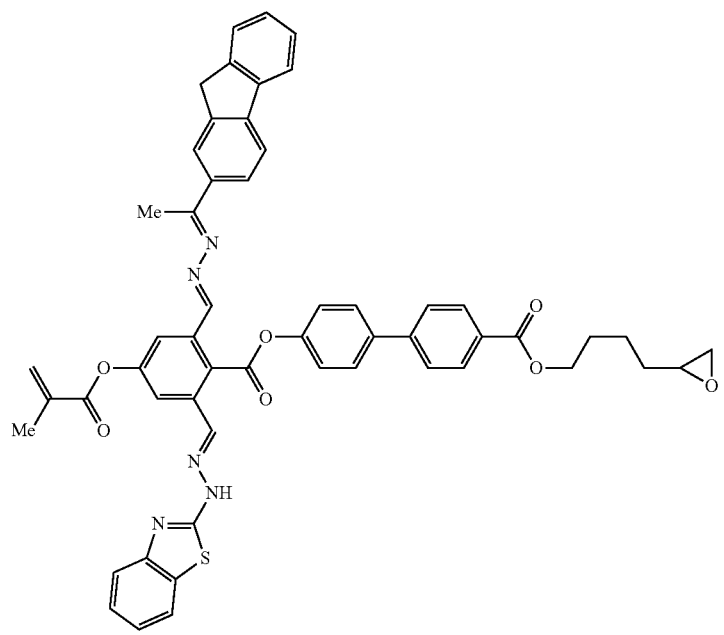

(C11-15)
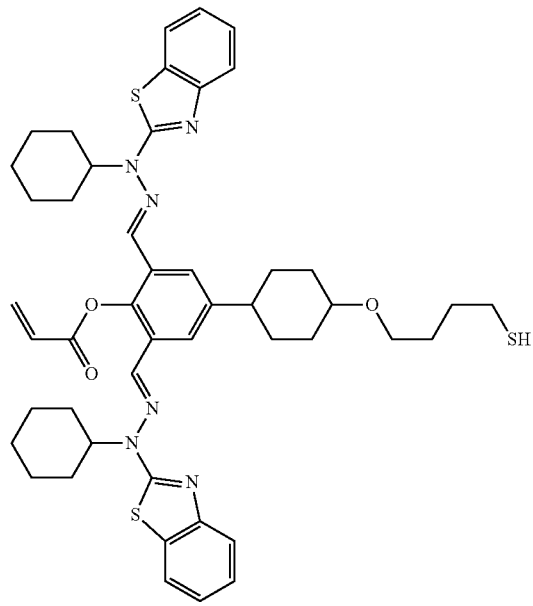
(C11-16)
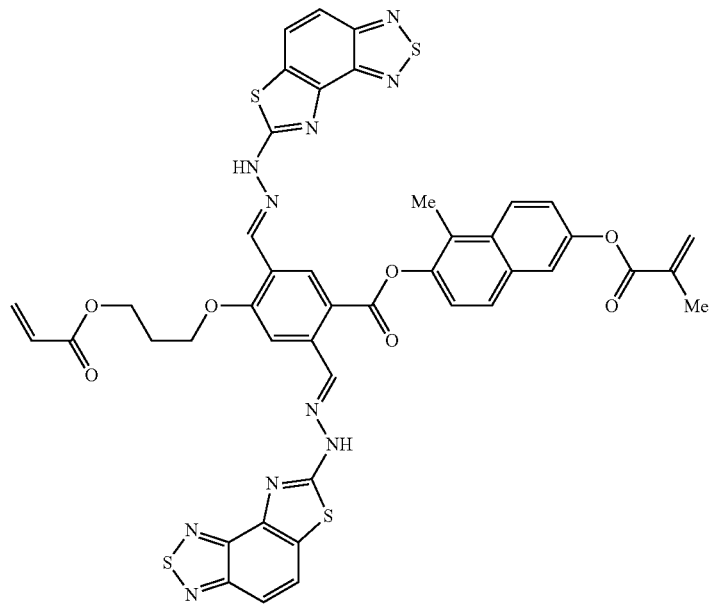

-continued
[Chem. 170]
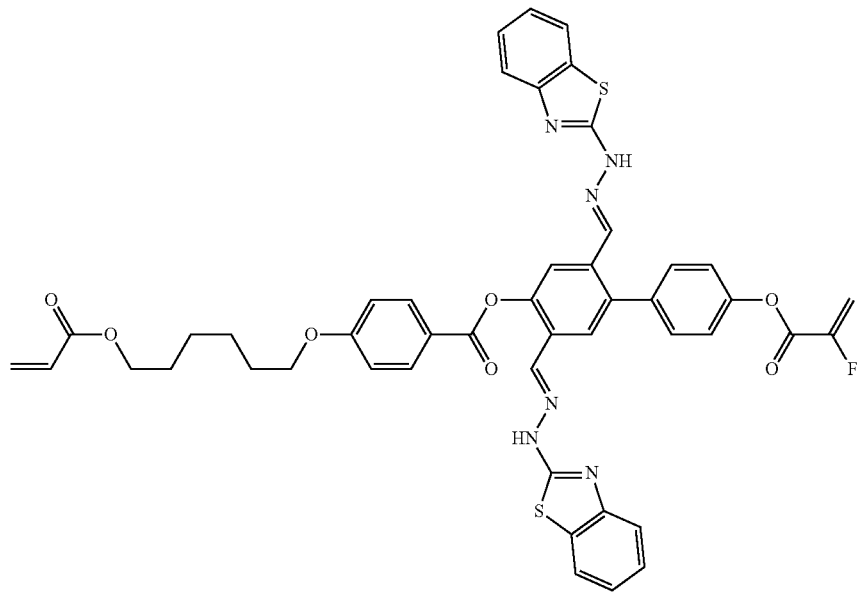
(C11-17)
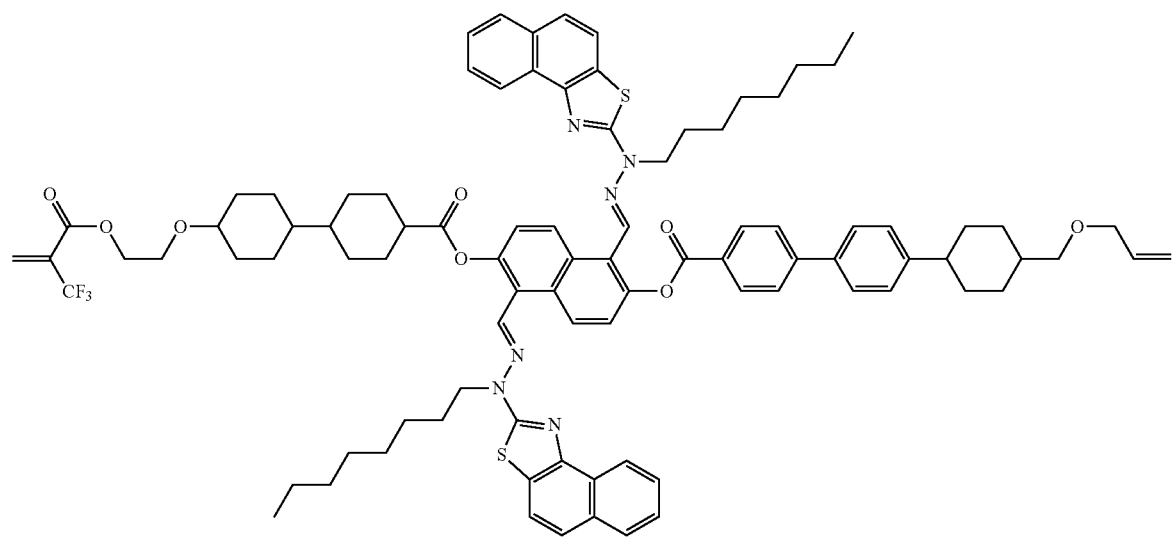
(C11-18)

(C11-19)
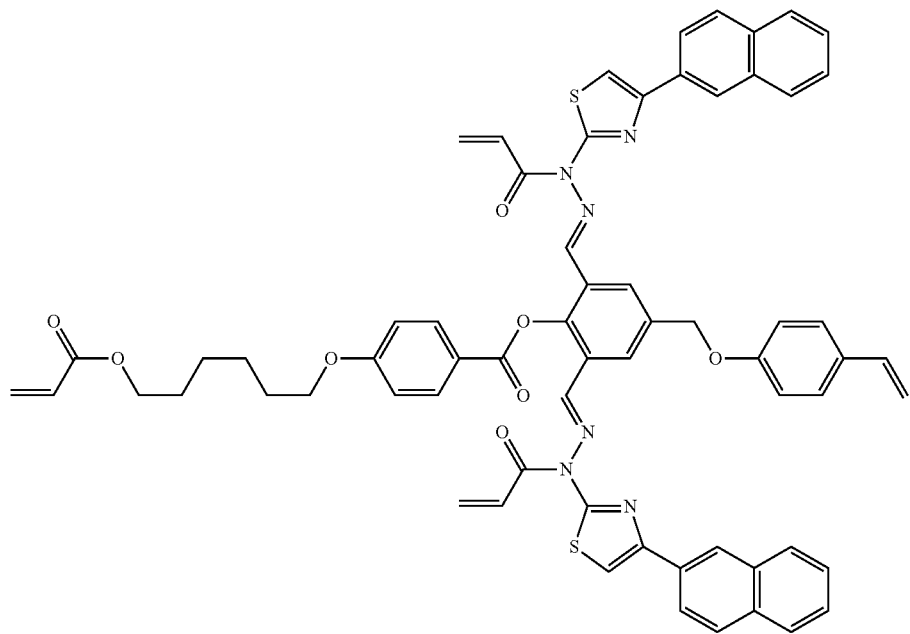
(C11-20)
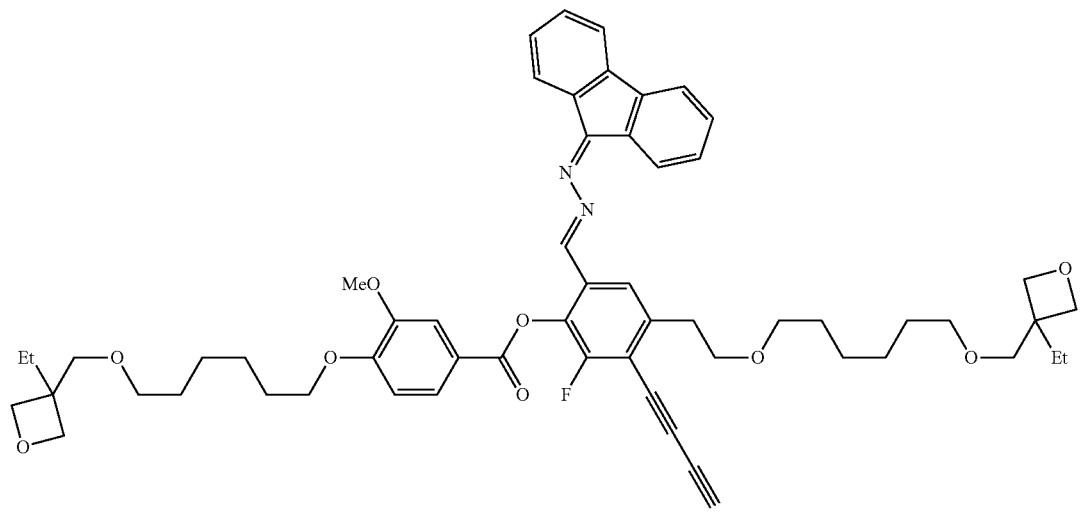

[Chem. 171]
(C12-1)
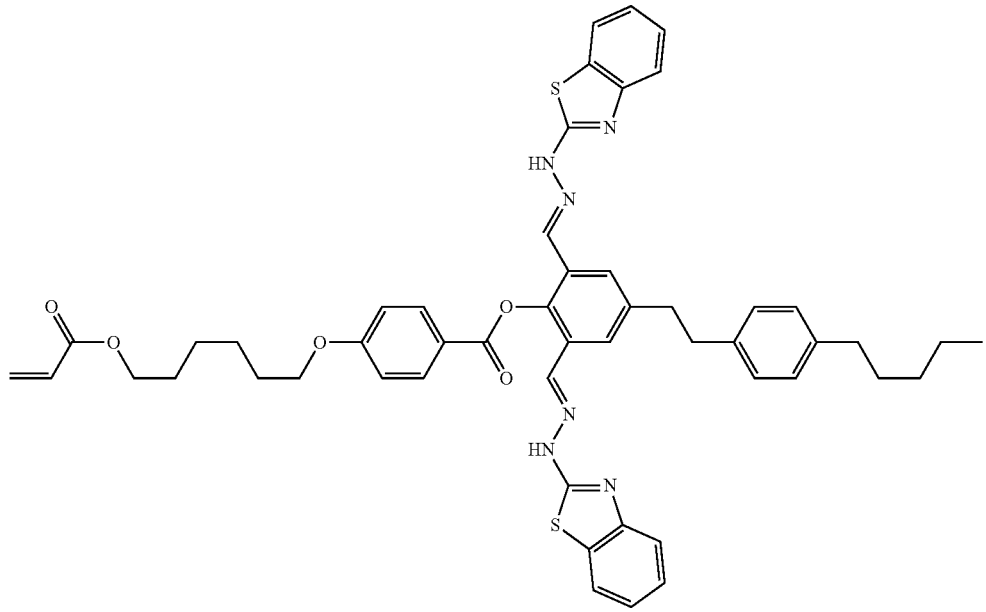
(C12-2)
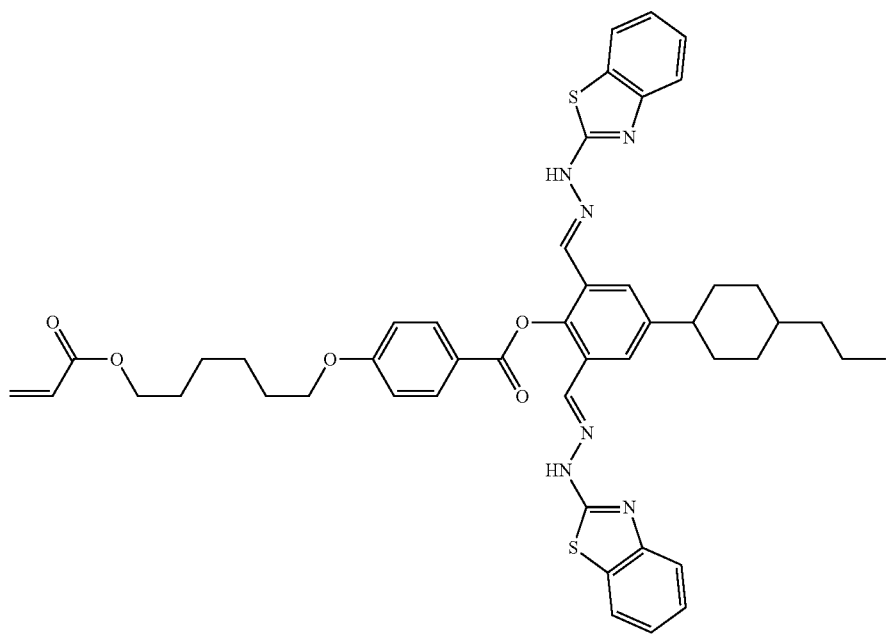

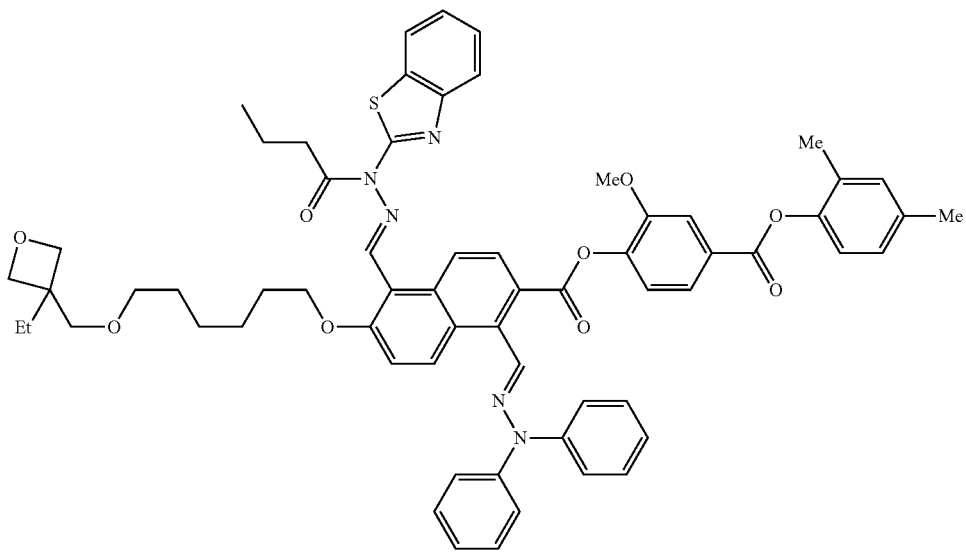
(C12-3)
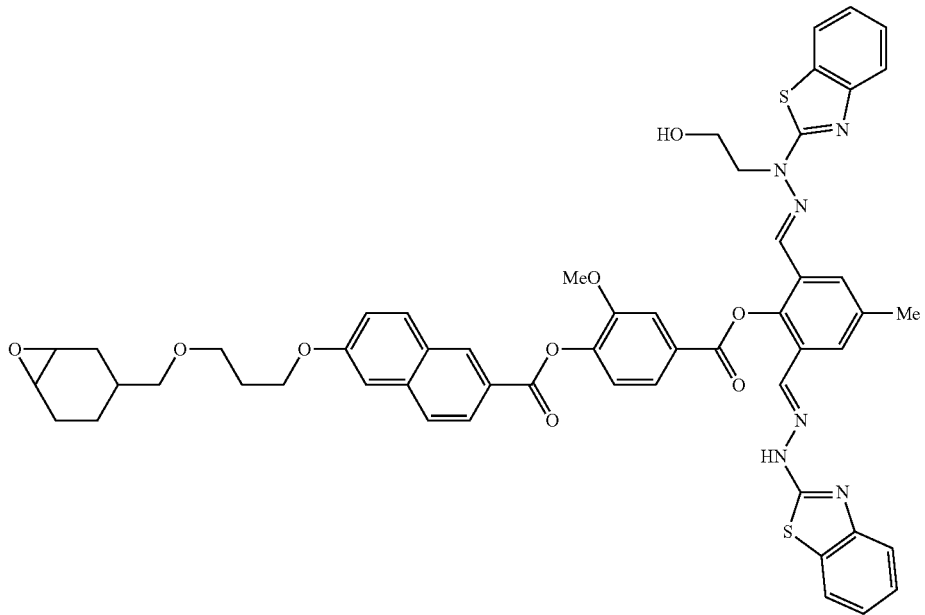
(C12-4)

[Chem. 172]
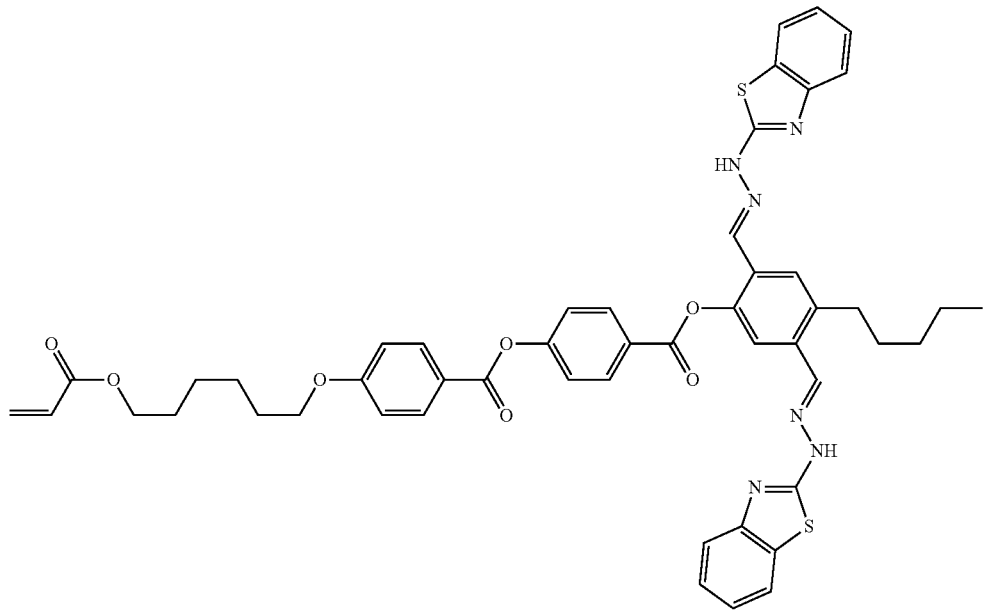
(C12-5)
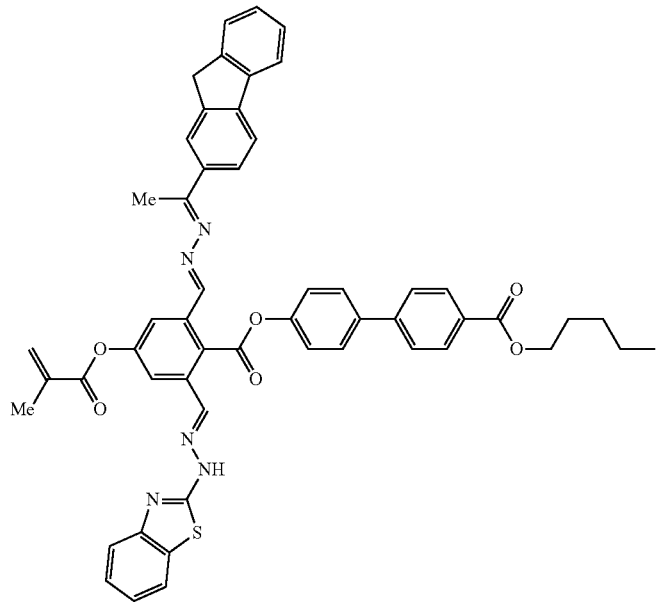
(C12-6)

-continued
(C12-7)
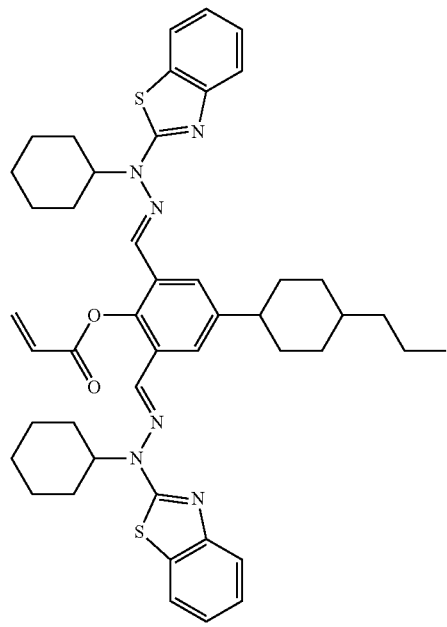
(C12-8)
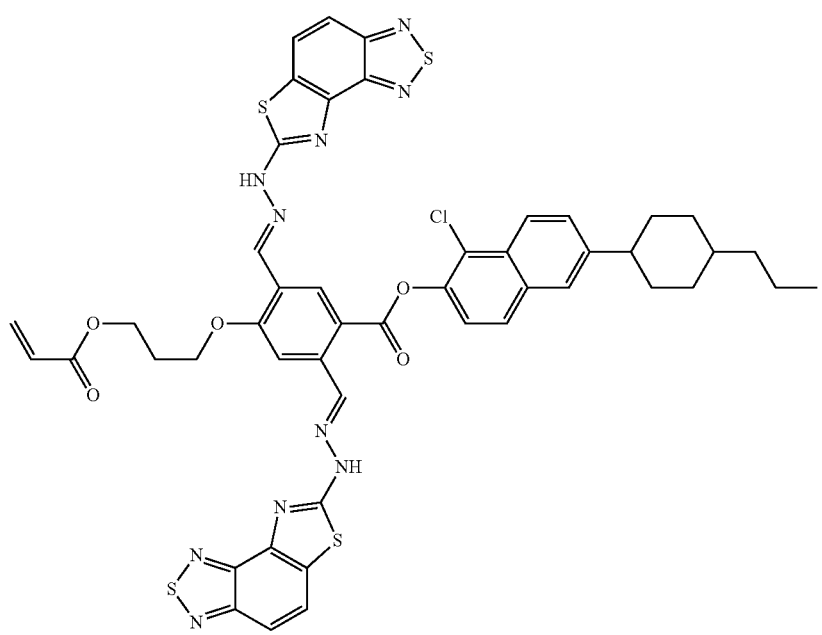

-continued
[Chem. 173]
(C12-9)
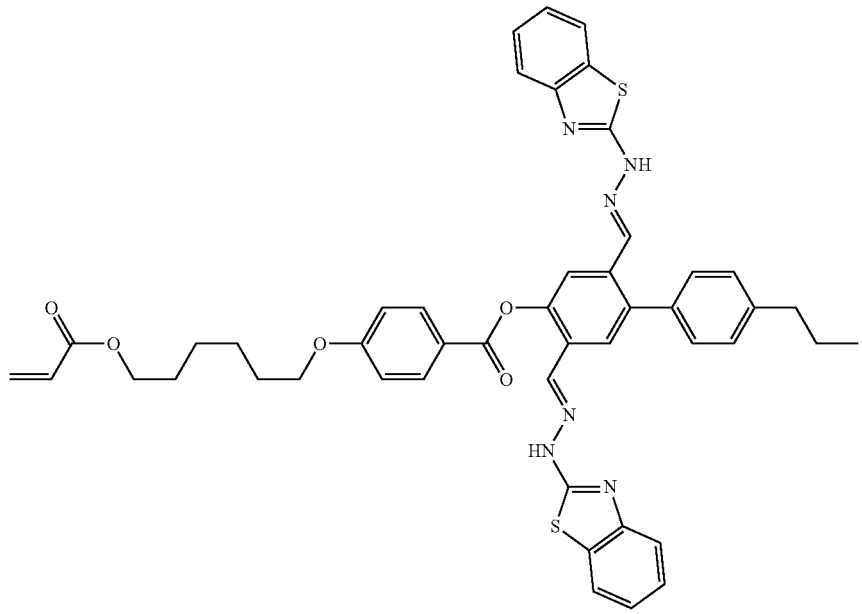
(C12-10)
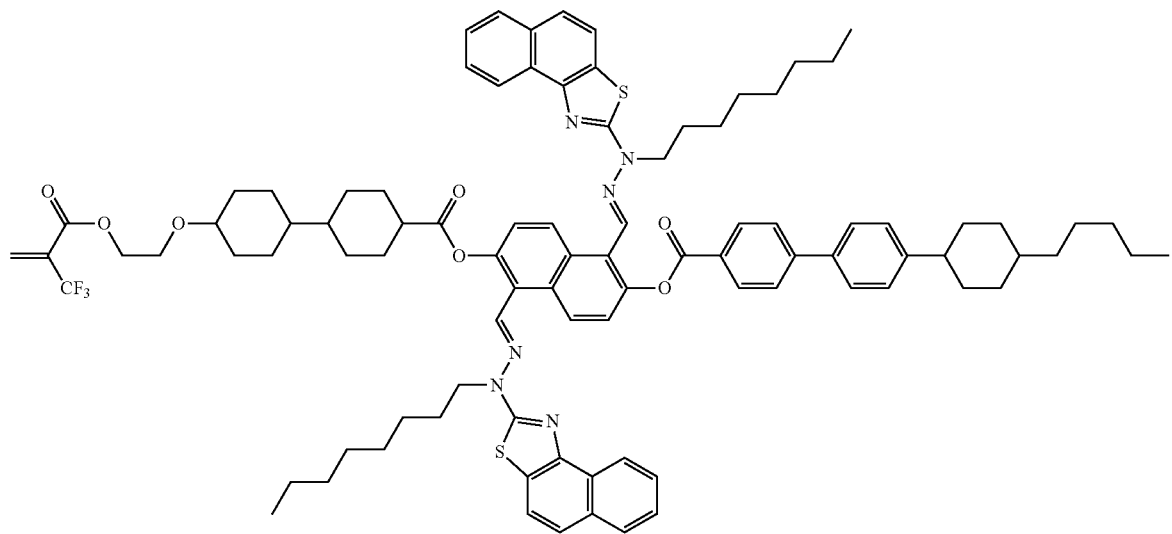

-continued
(C12-11)
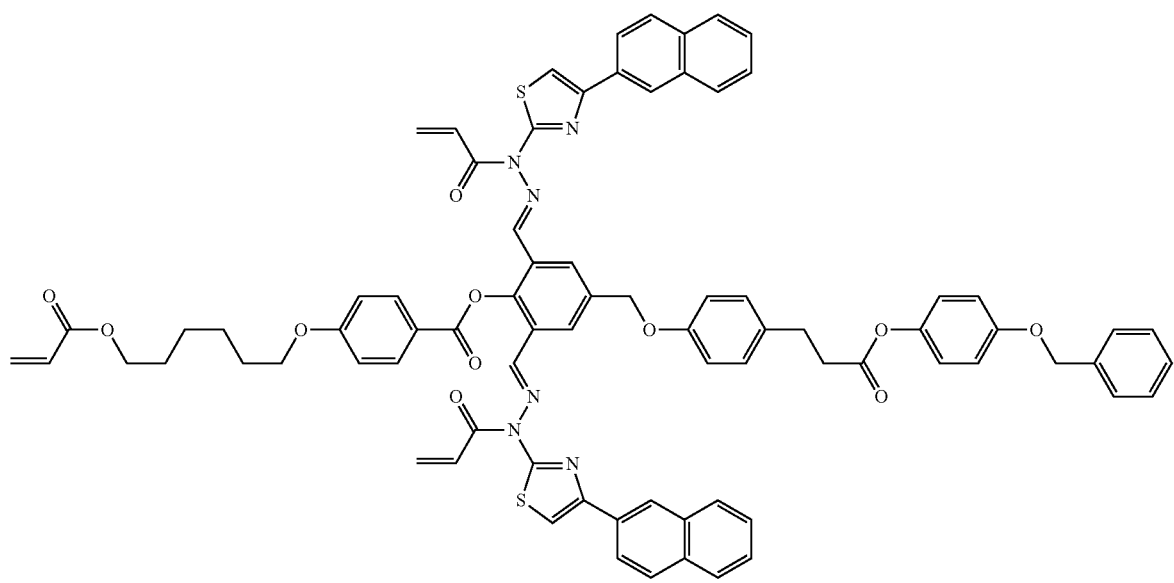
(C12-12)
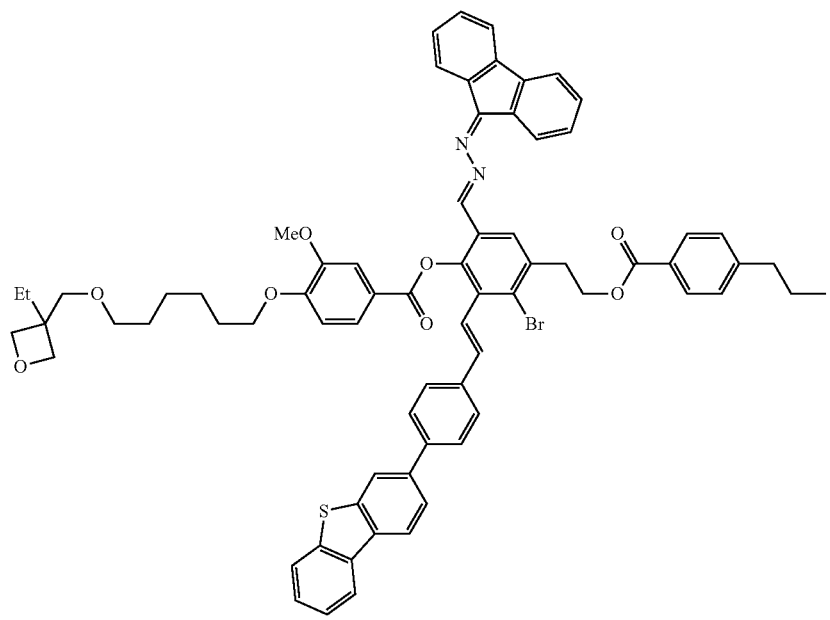

-continued
[Chem. 174]
(C2-1)
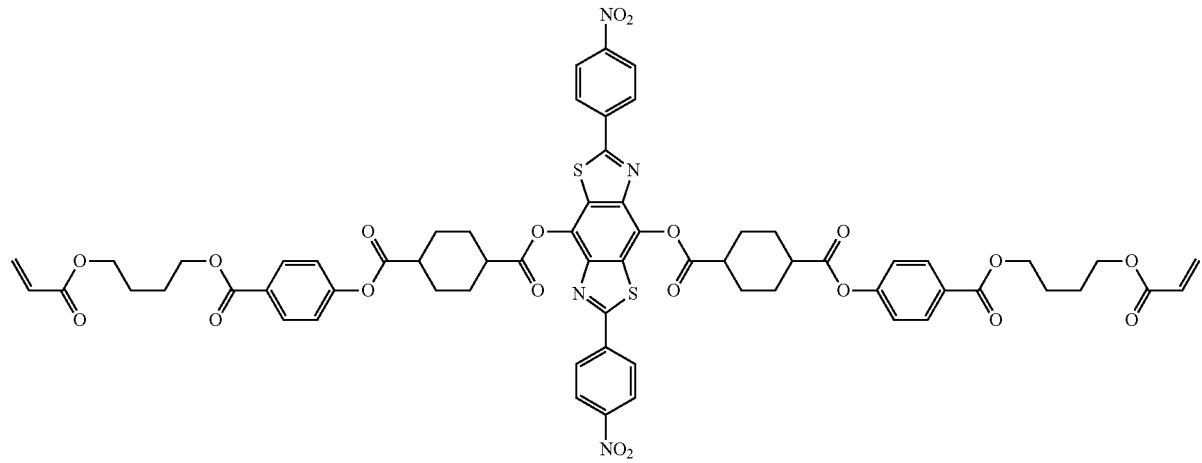
(C2-2)
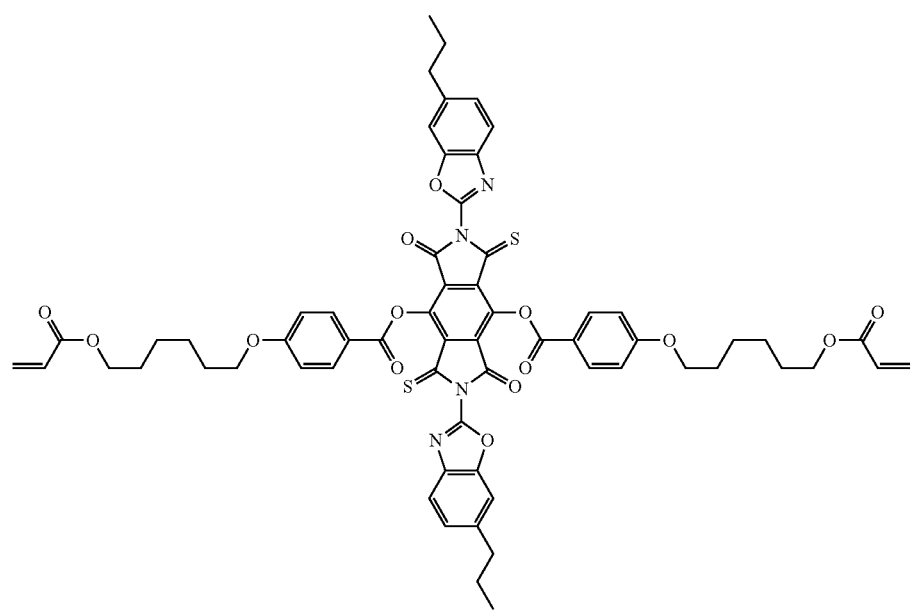

(C2-3)
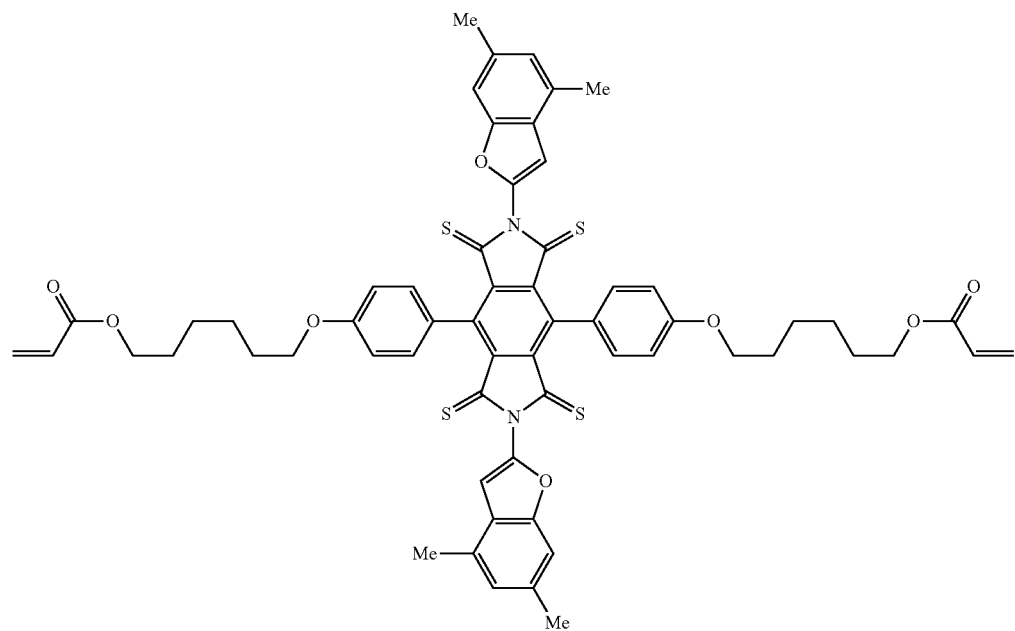
[Chem. 175]
(C2-4)
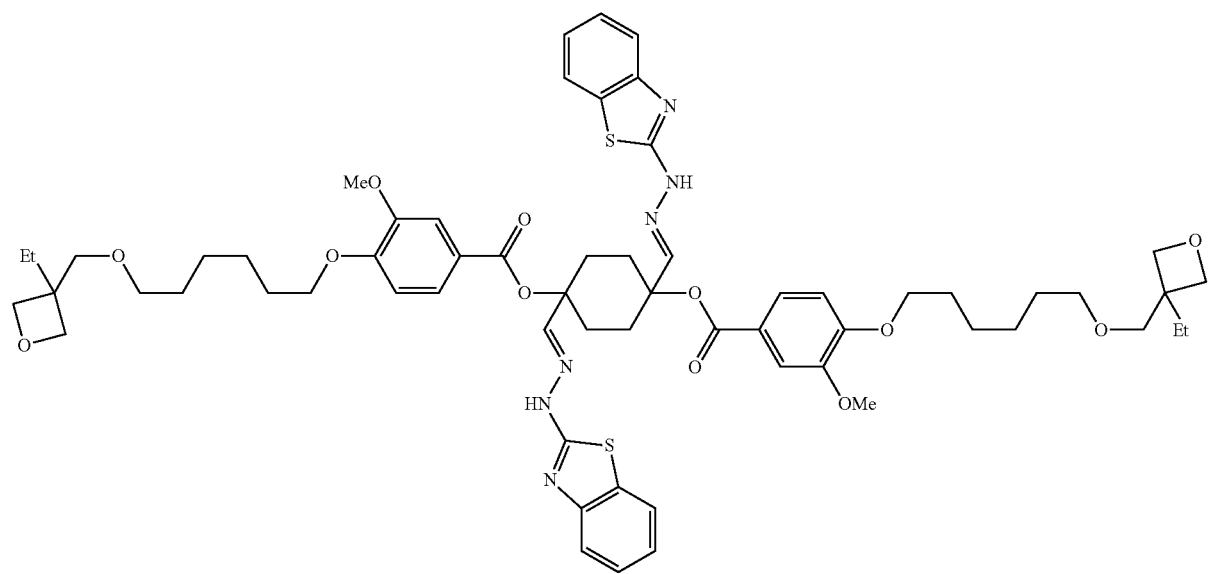

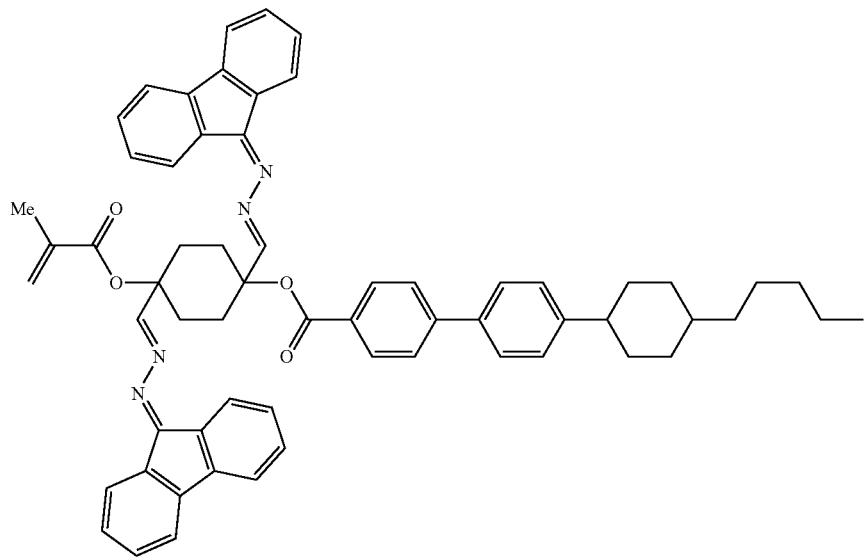
(C2-5)
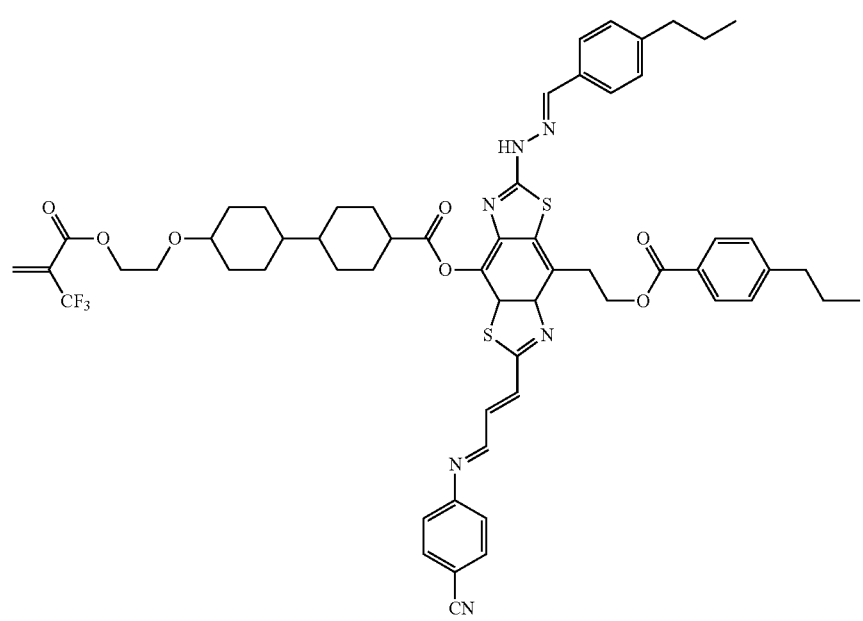
(C2-6)

-continued
(C2-7)
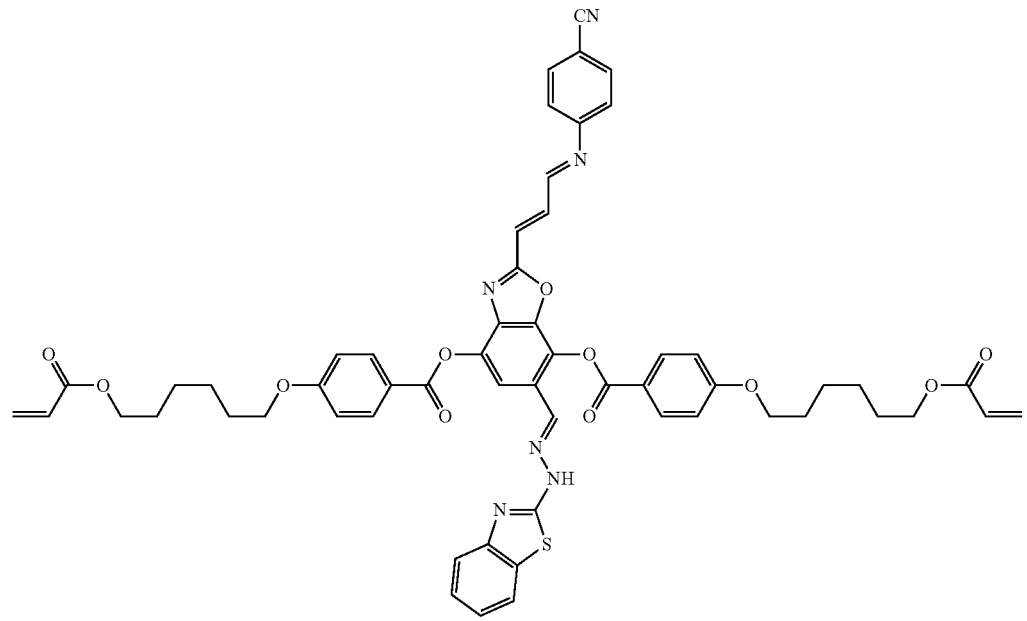
(C2-8)
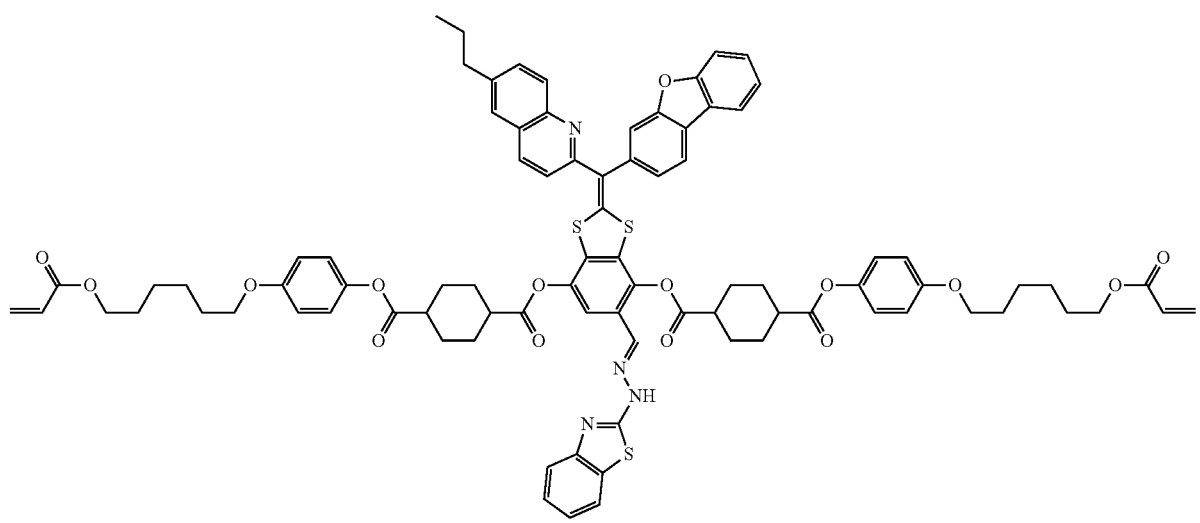

(C2-9)
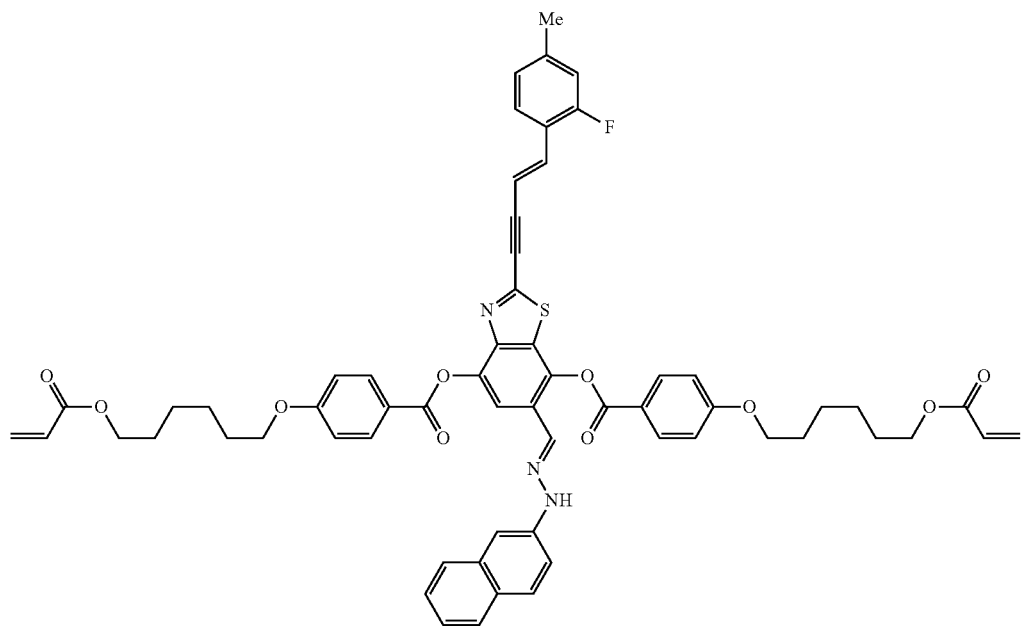
[Chem. 177]
(C2-10)
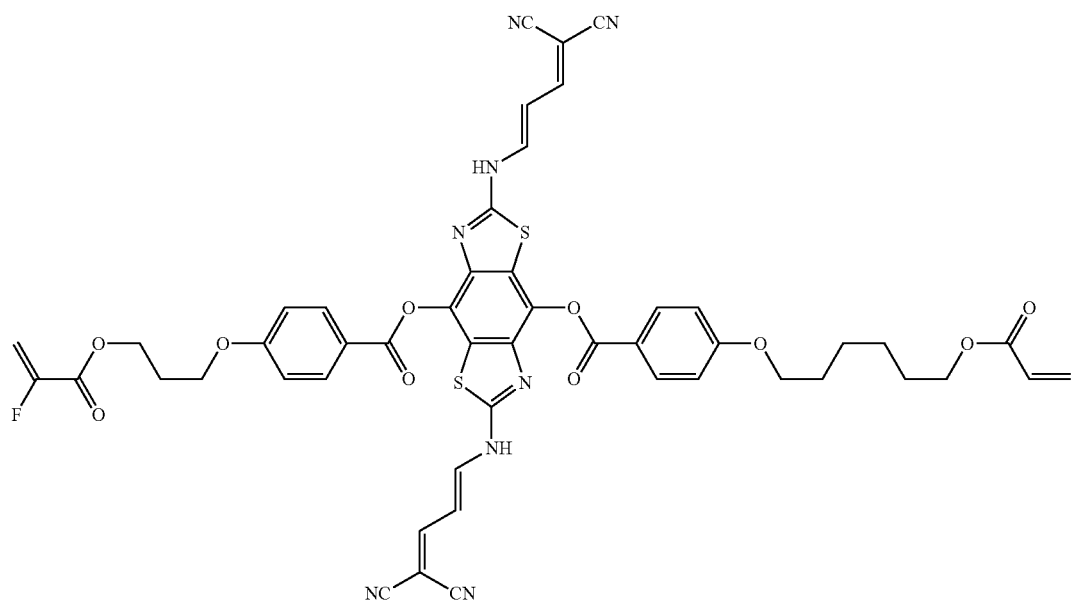

(C2-11)
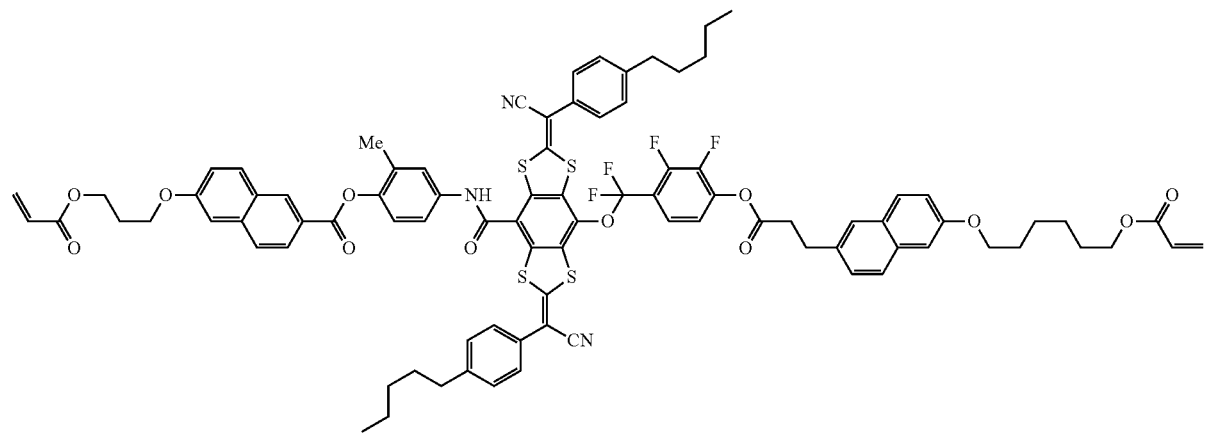
(C2-12)
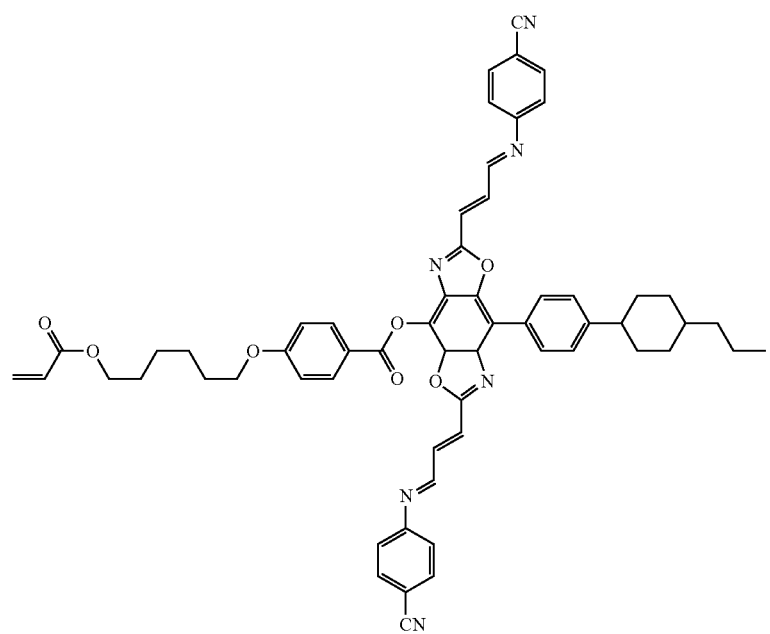

-continued
[Chem. 178]
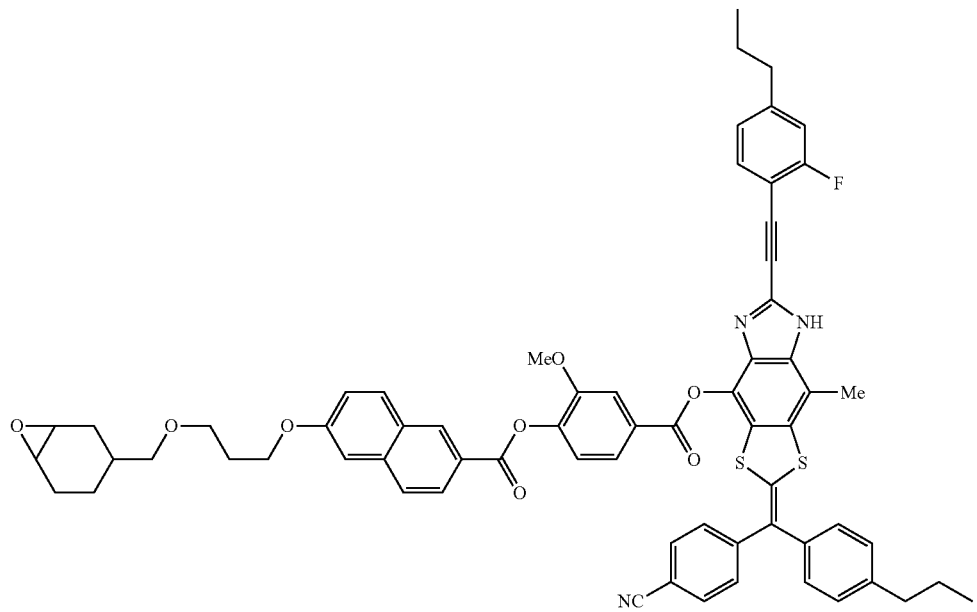
(C2-13)
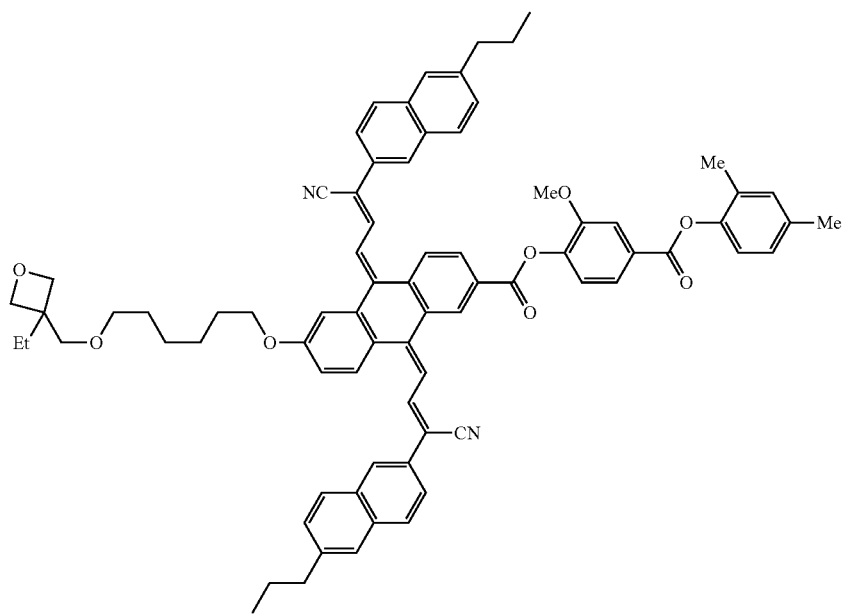
(C2-14)
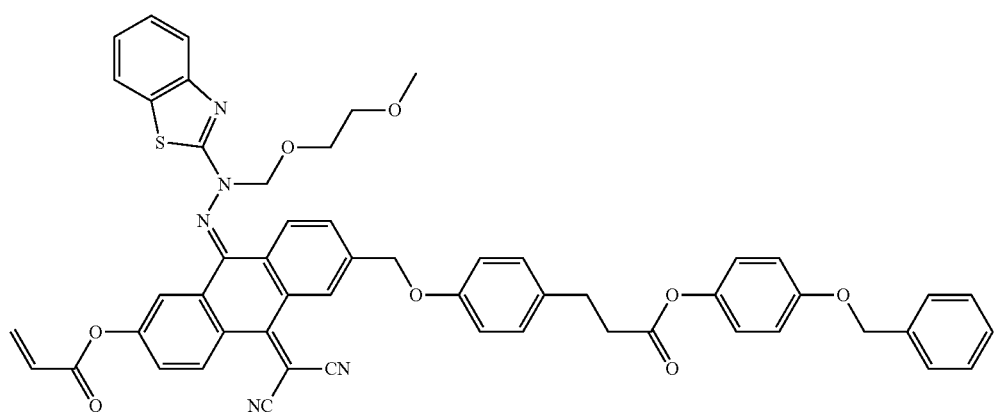
(C2-15)

[Chem. 179]
(C2-16)
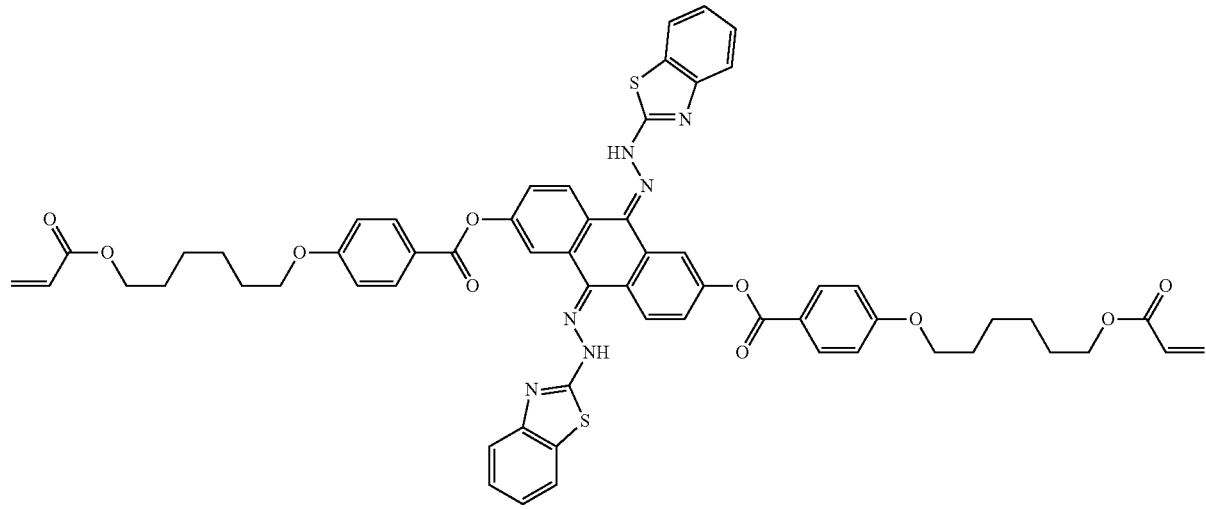
(C2-17)
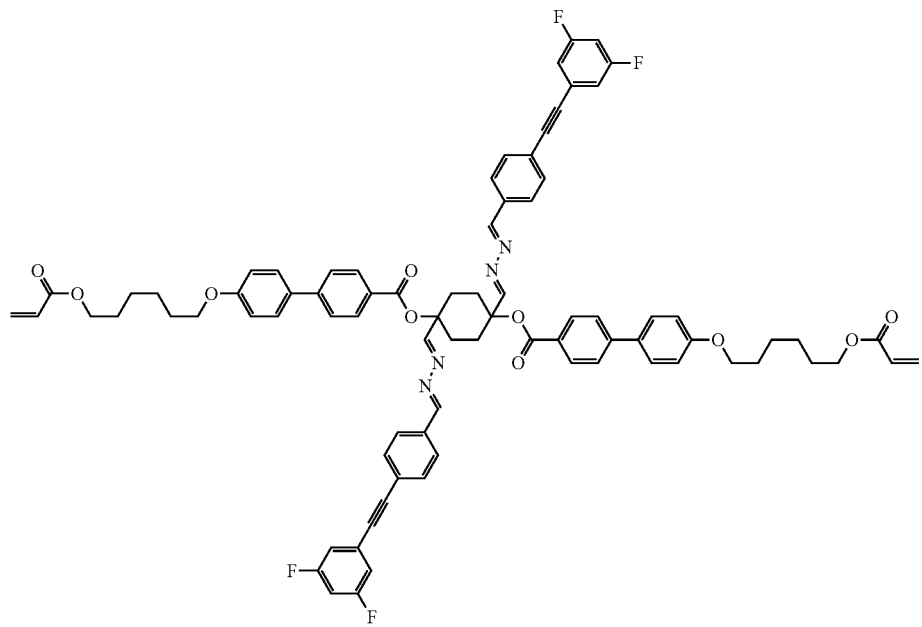

-continued
(C2-18)
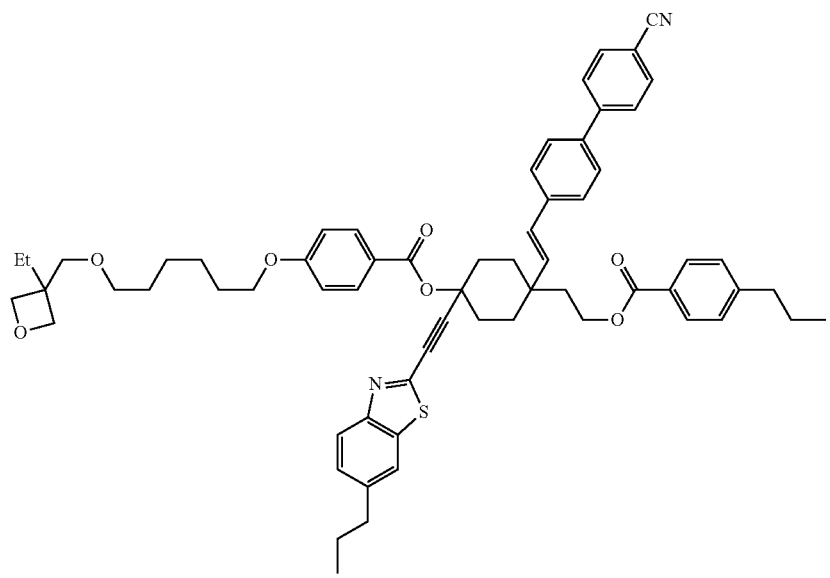
[Chem. 180]
(C3-1)
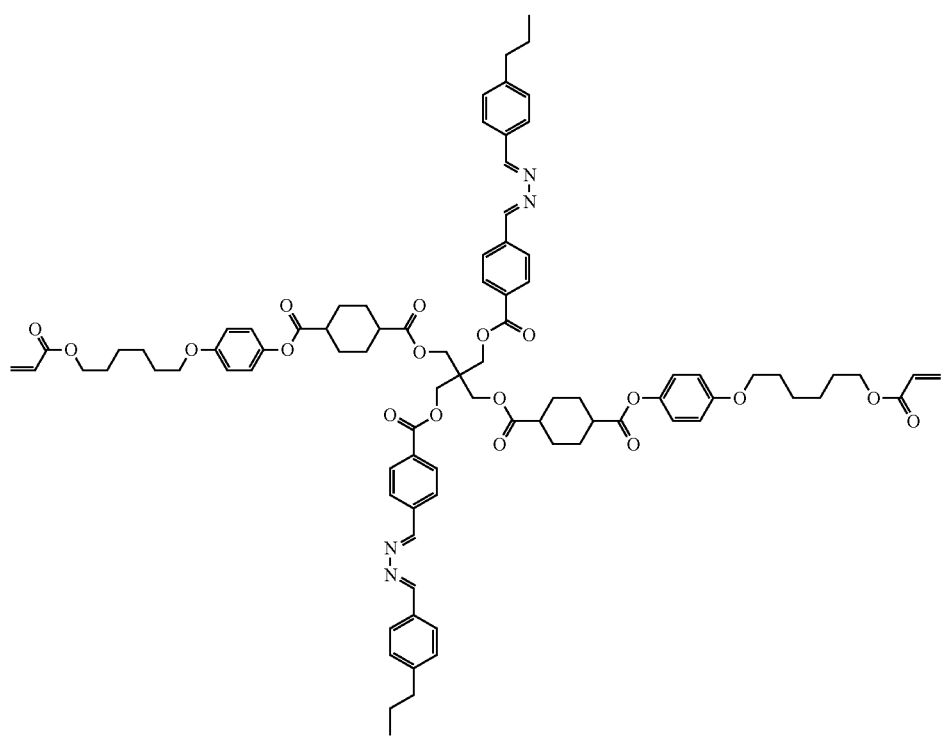

-continued
(C3-2)
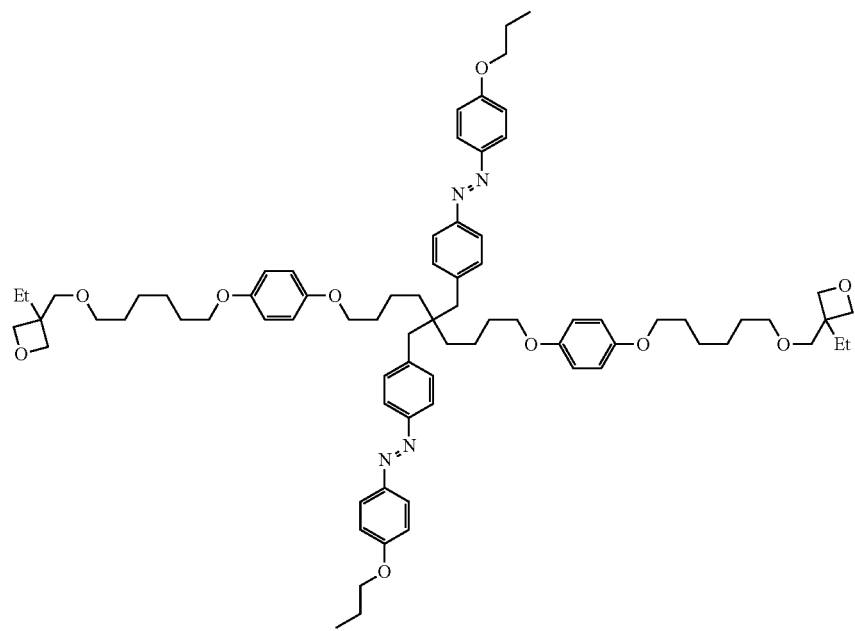
(C3-3)
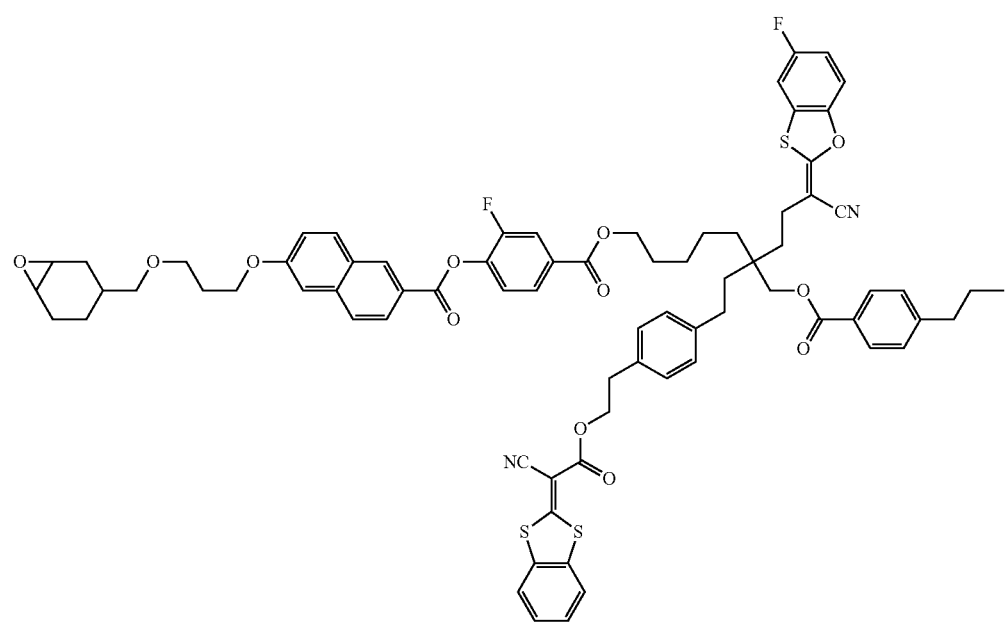

-continued
[Chem. 181]
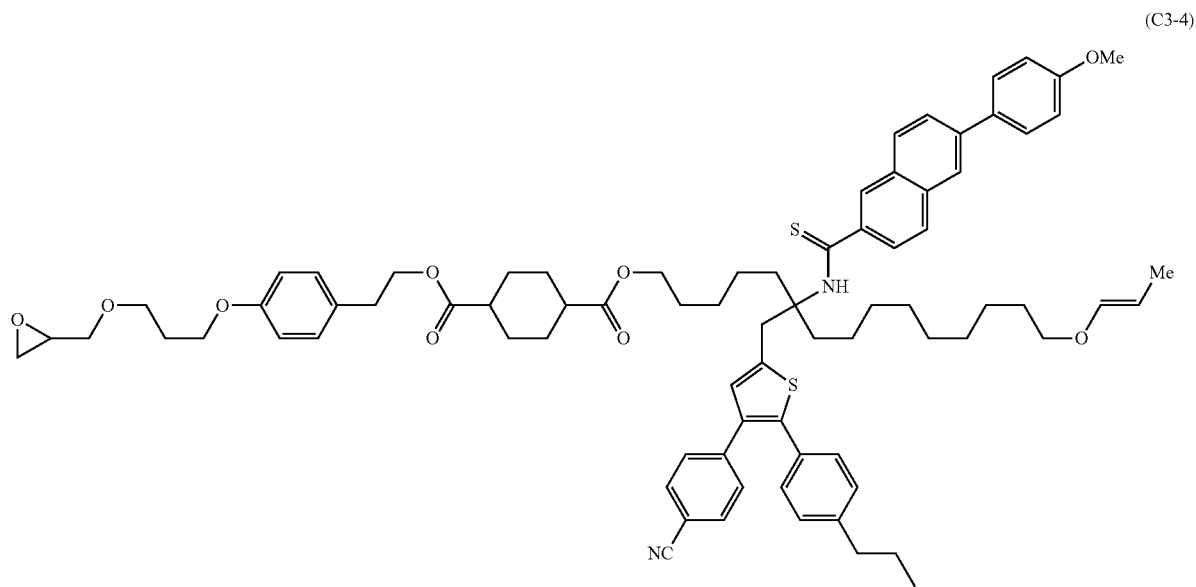
(C3-4)
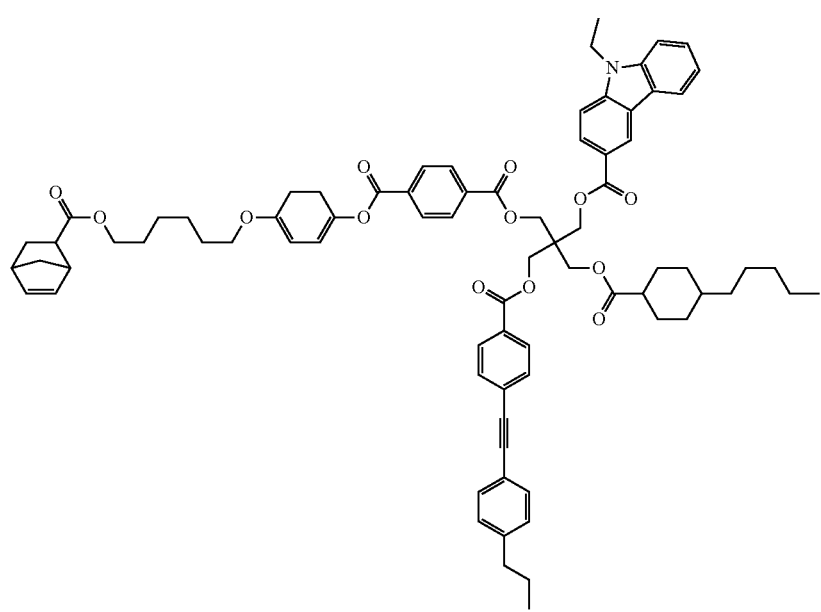
(C3-5)

[Chem. 182]
(D11-1)
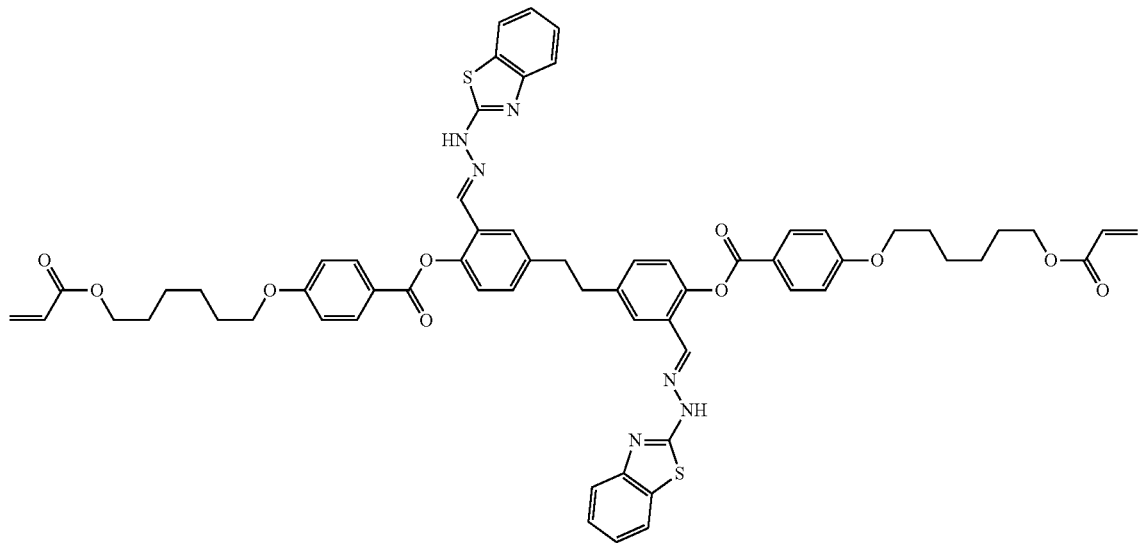
(D11-2)
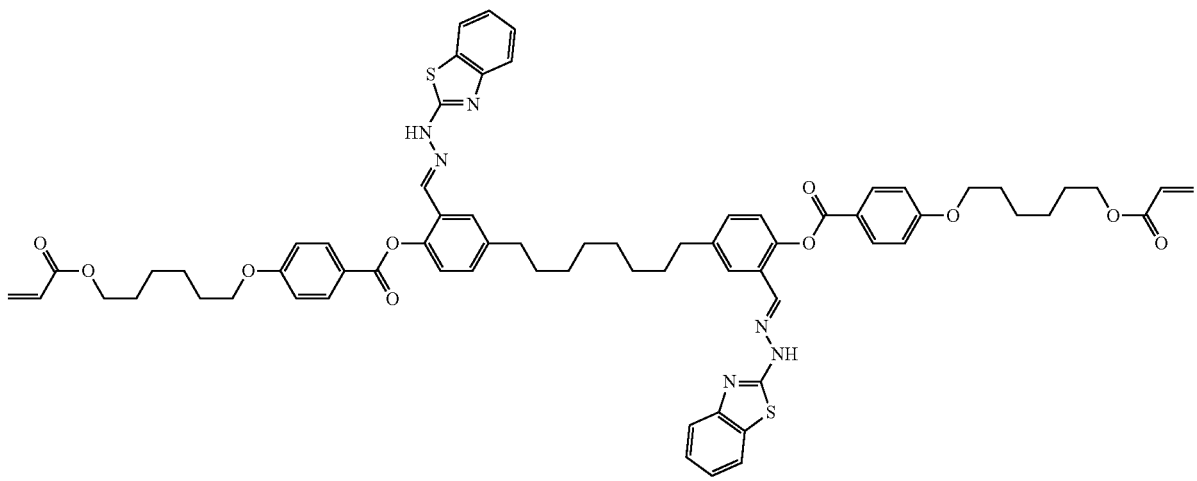
(D11-3)
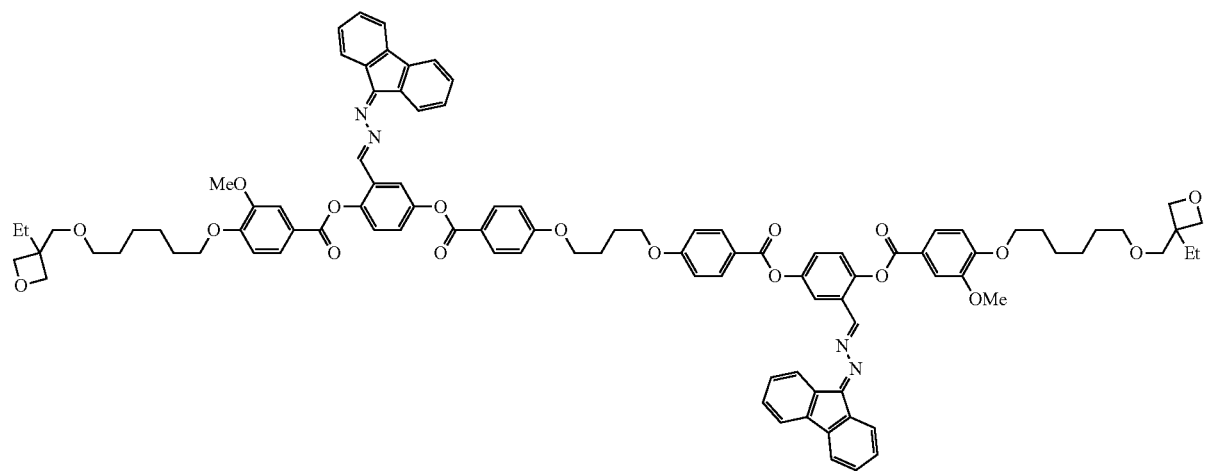

[Chem. 183]
(D11-4)
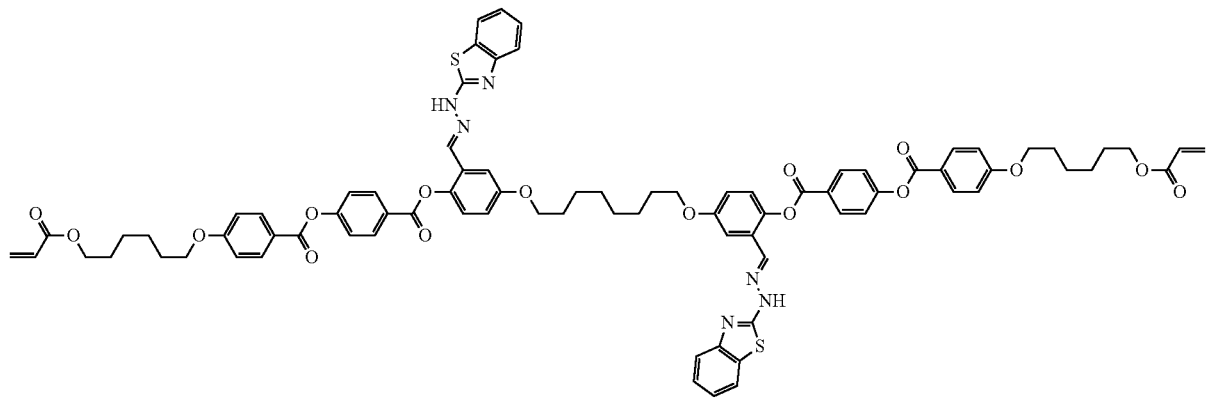
(D11-5)
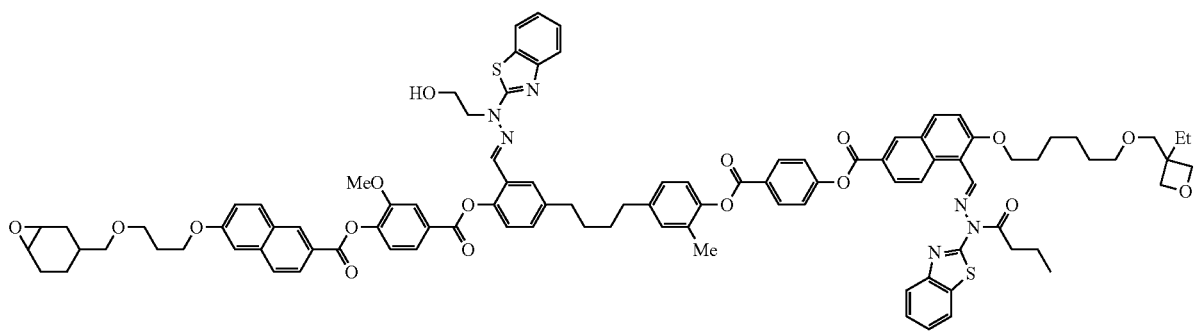
(D11-6)
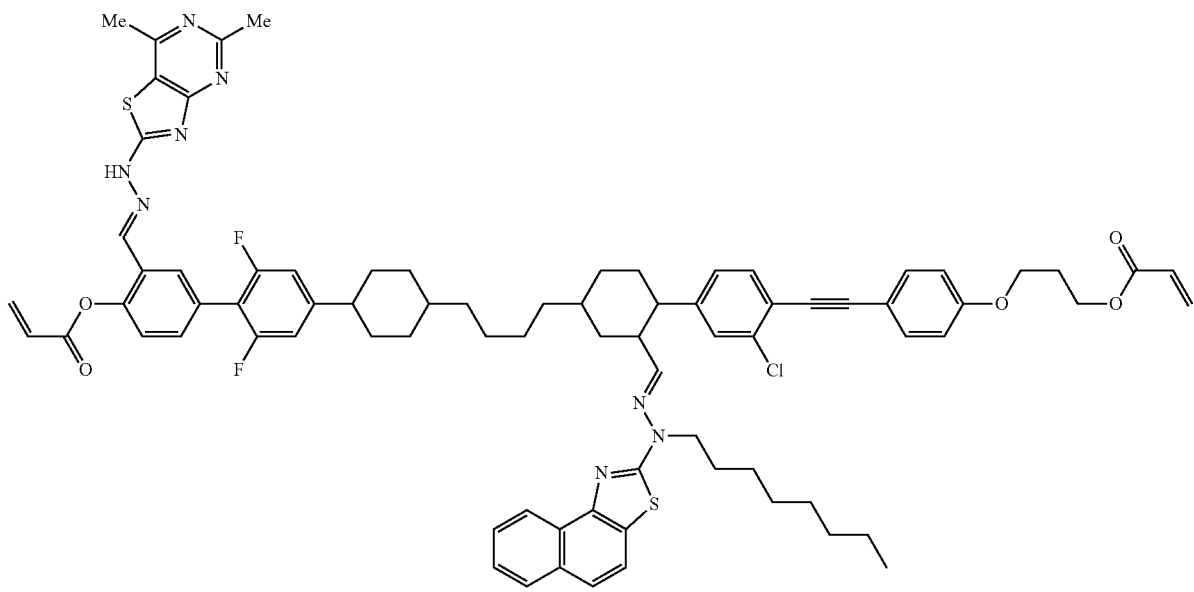

[Chem. 184]
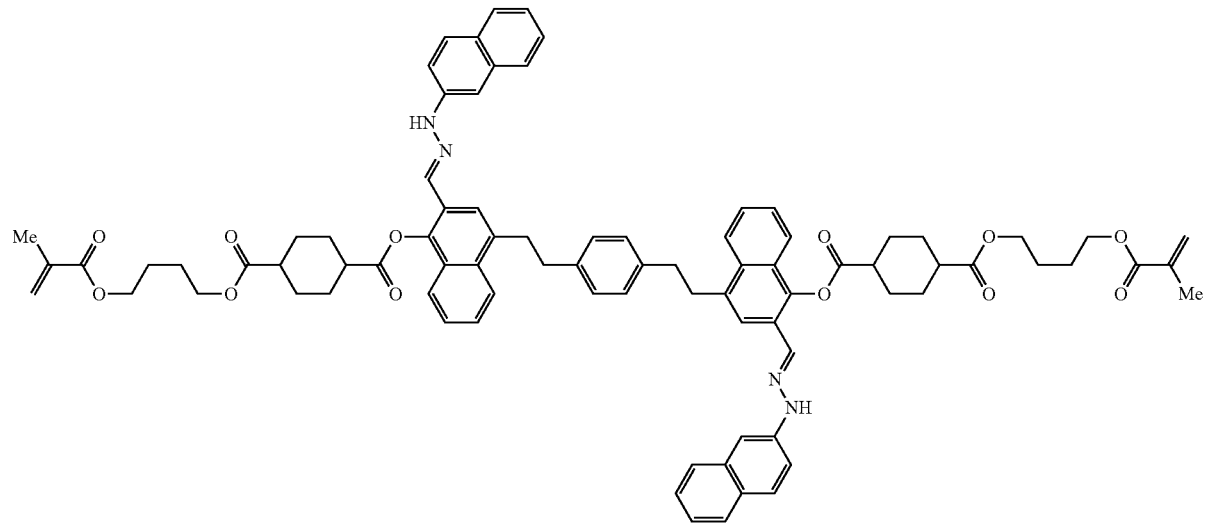
(D11-7)
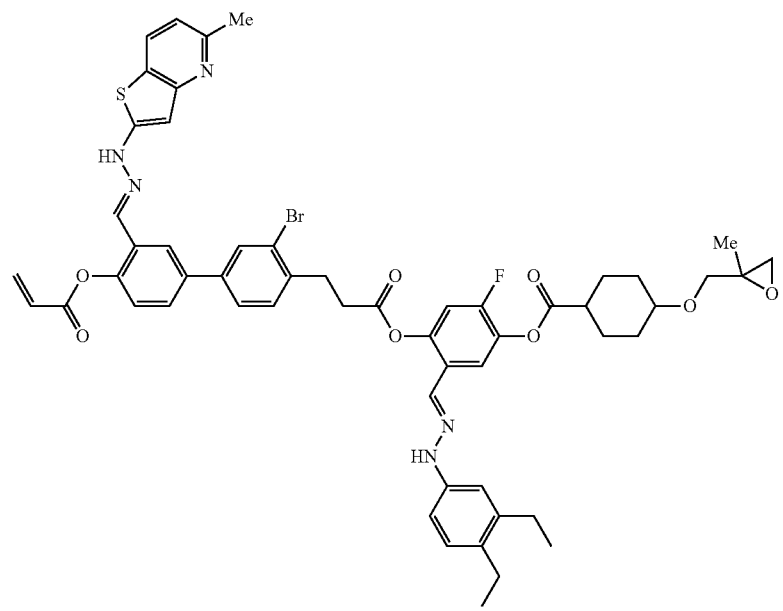
(D11-8)

-continued
(D11-9)
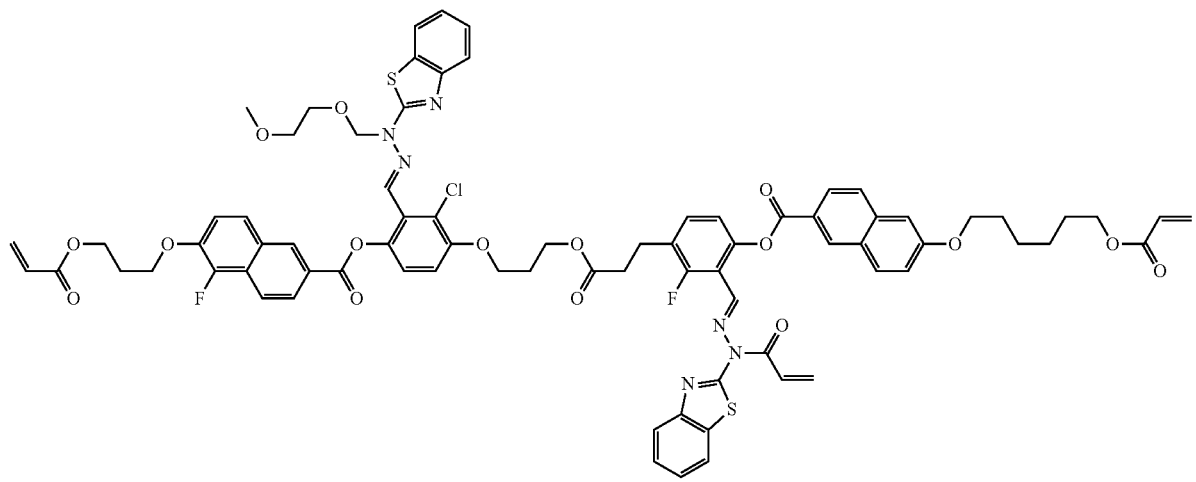
[Chem. 185]
(D11-10)
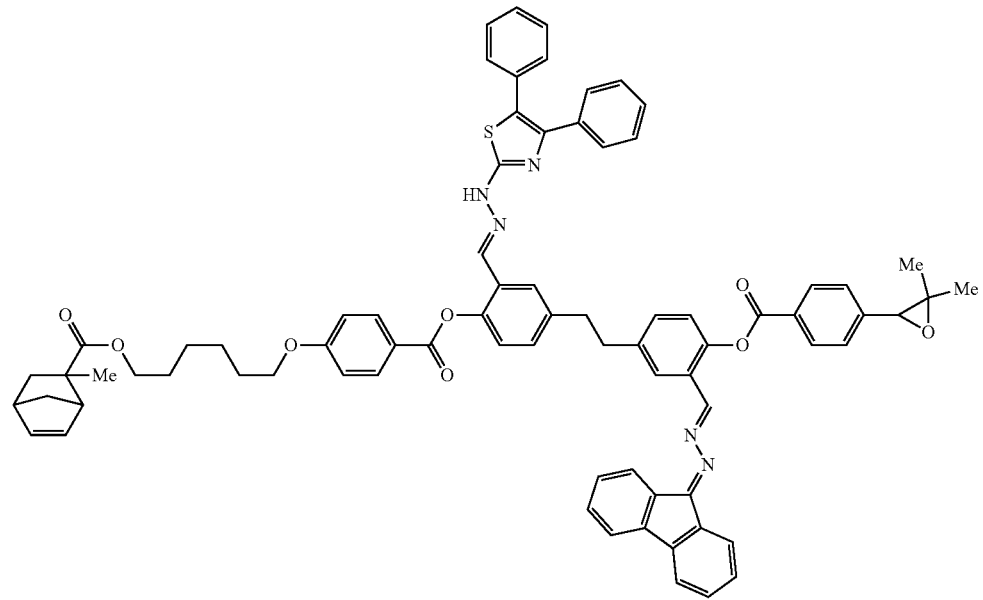

[Chem. 186]
(D12-1)
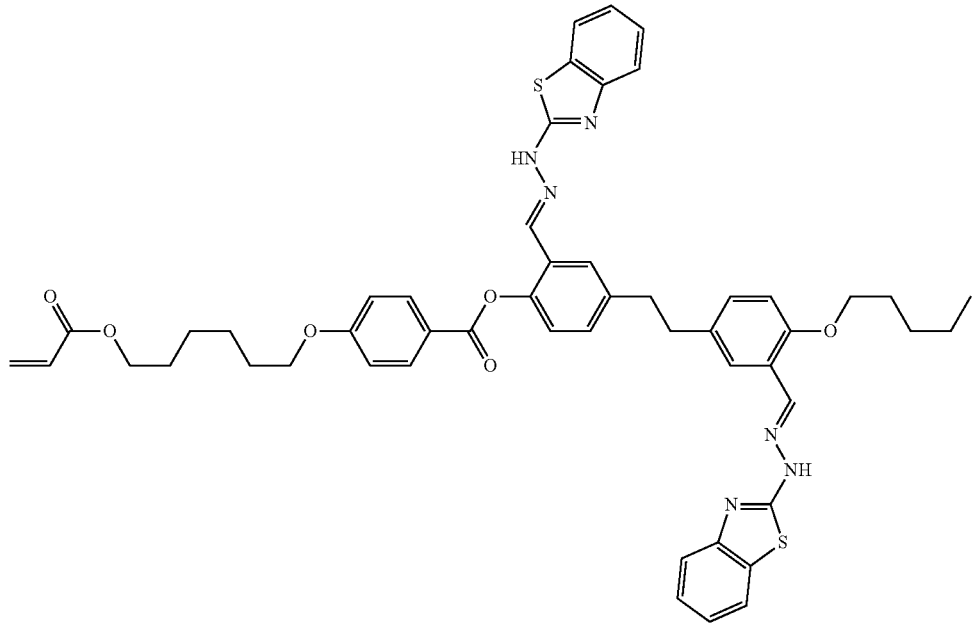
(D12-2)
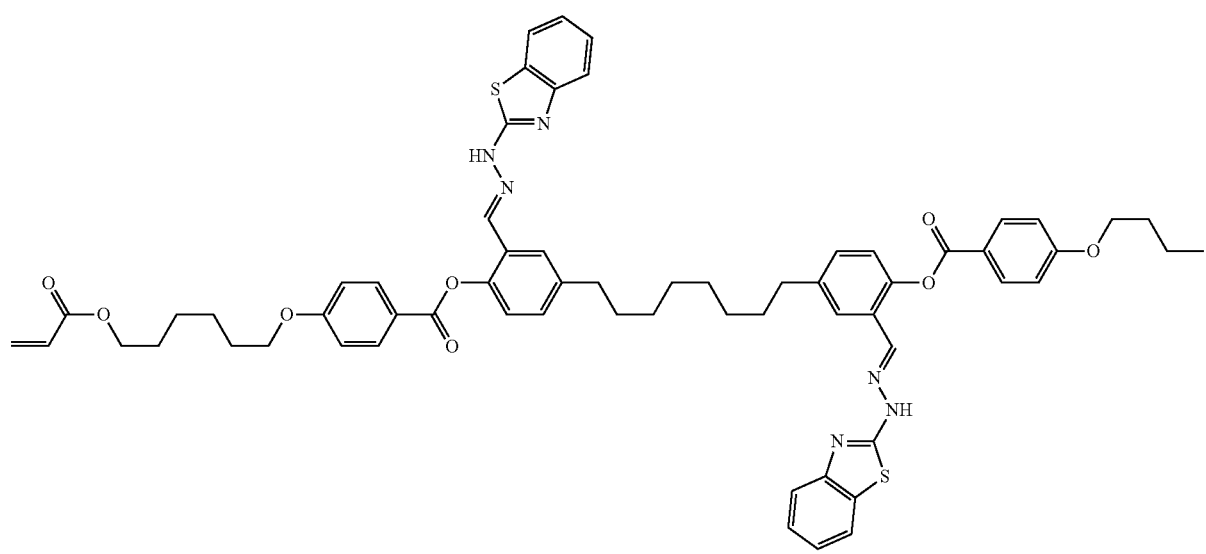

-continued
(D12-3)
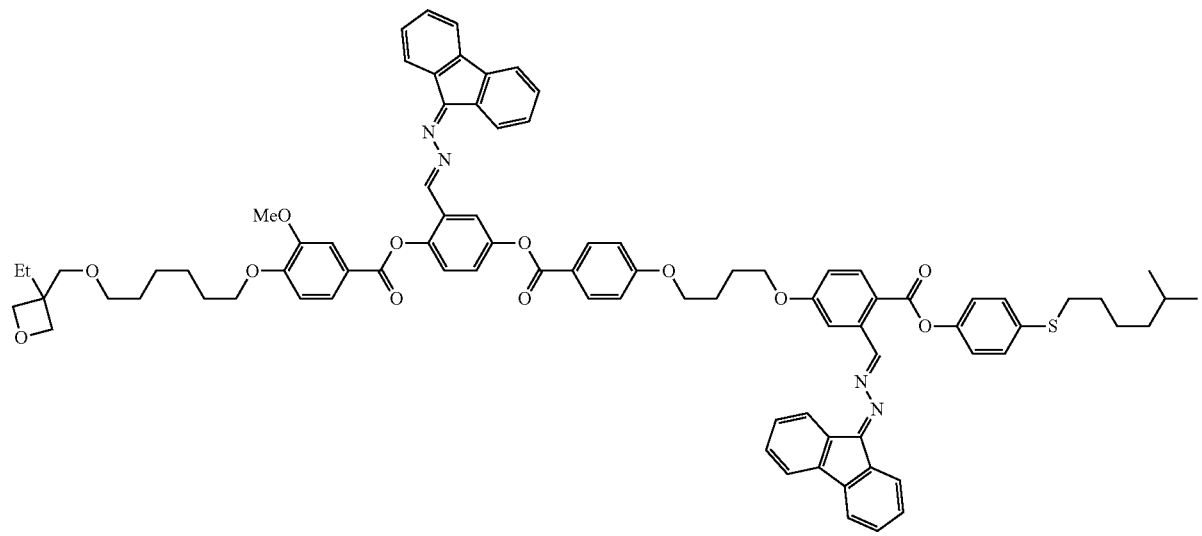
[Chem. 187]
(D12-4)
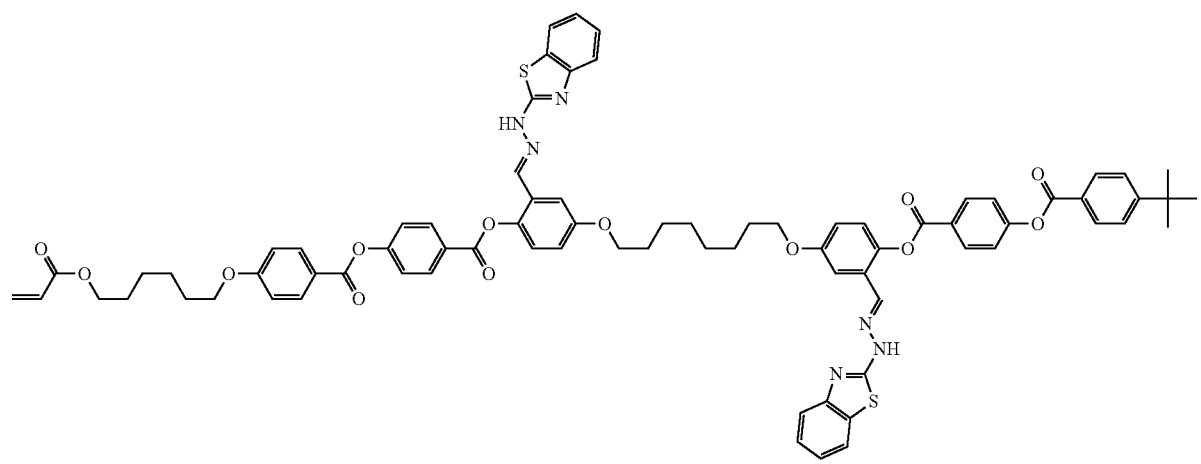
(D12-5)
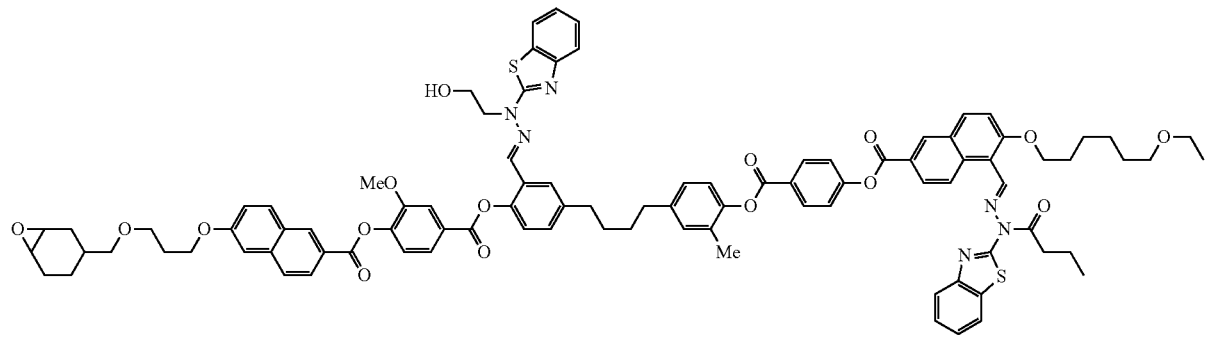

(D12-6)
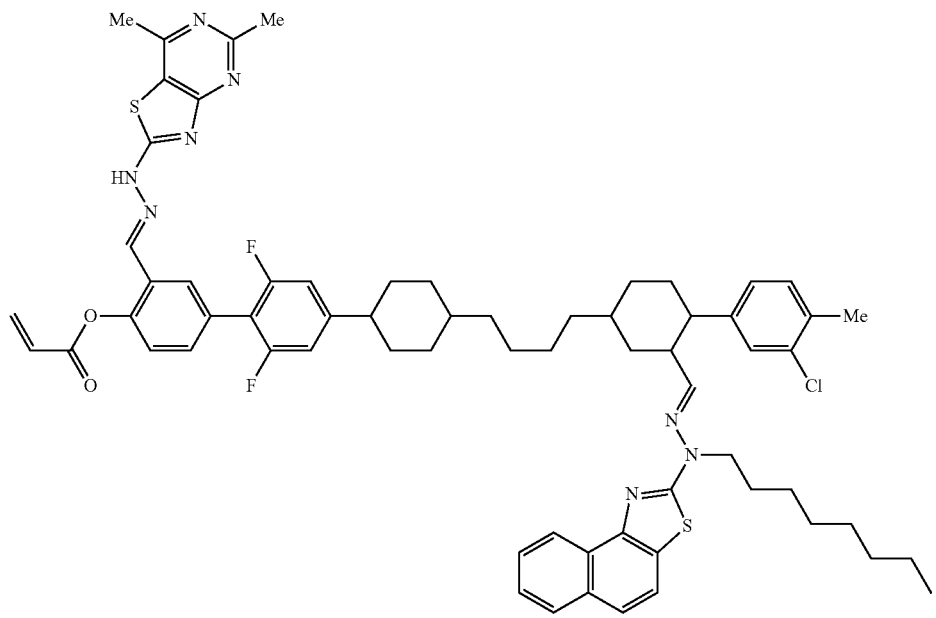
[Chem. 188]
(D12-7)
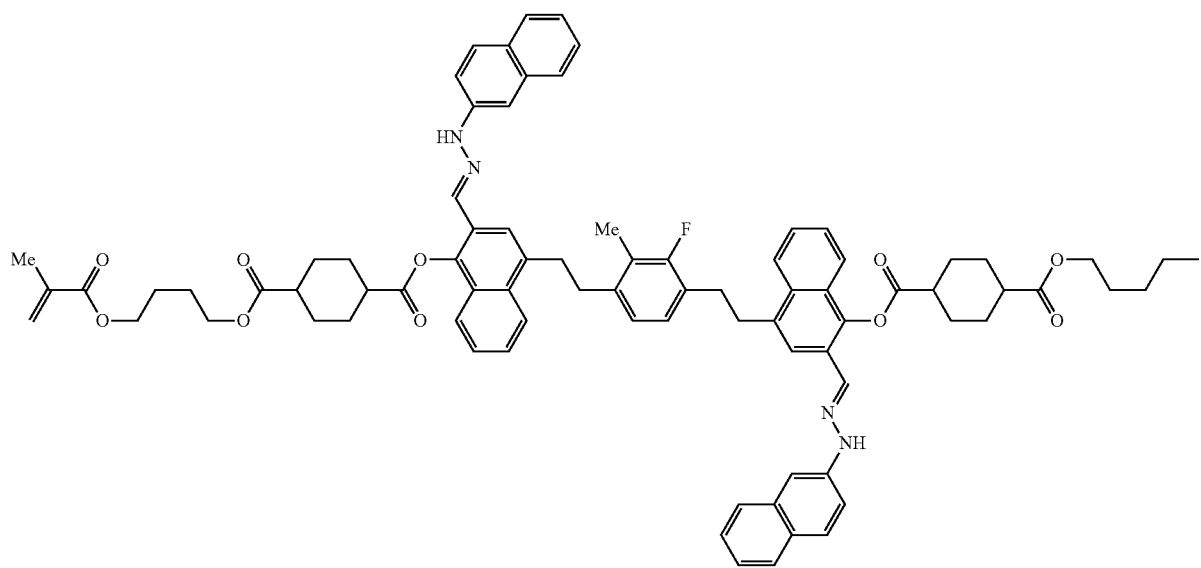

-continued
(D12-8)
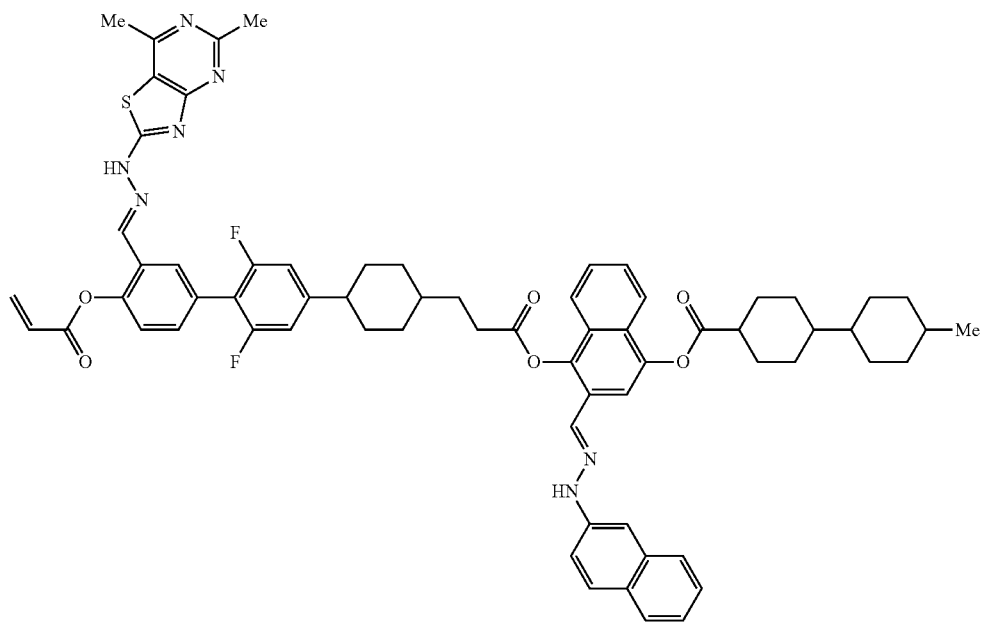
(D12-9)
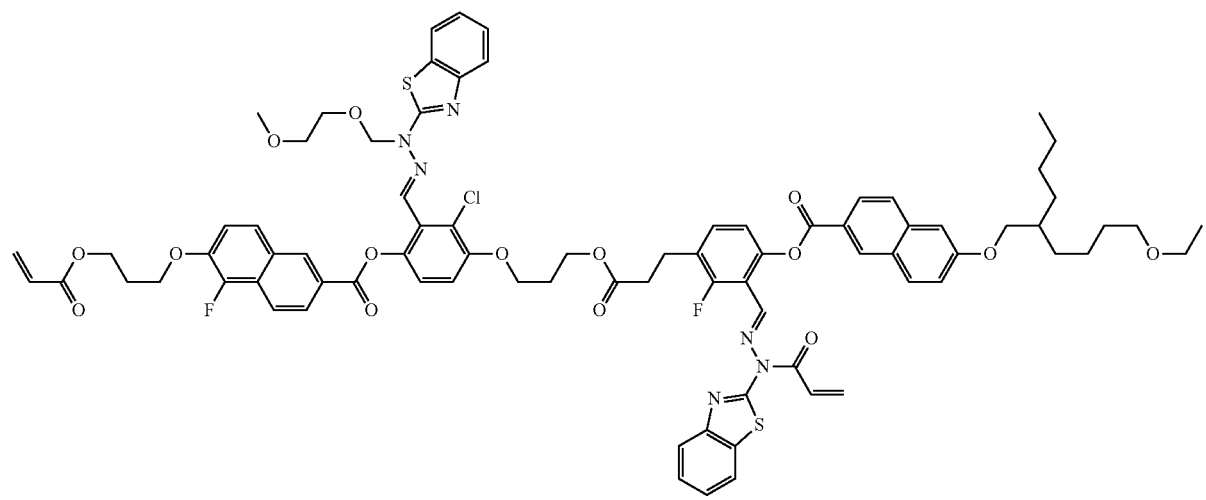

-continued
[Chem. 189]
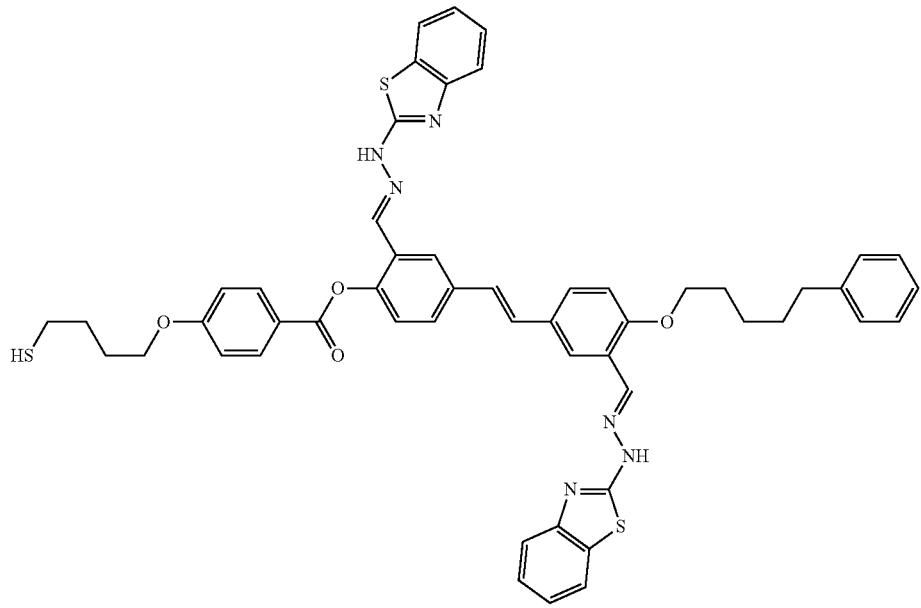
(D12-10)
[Chem. 190]
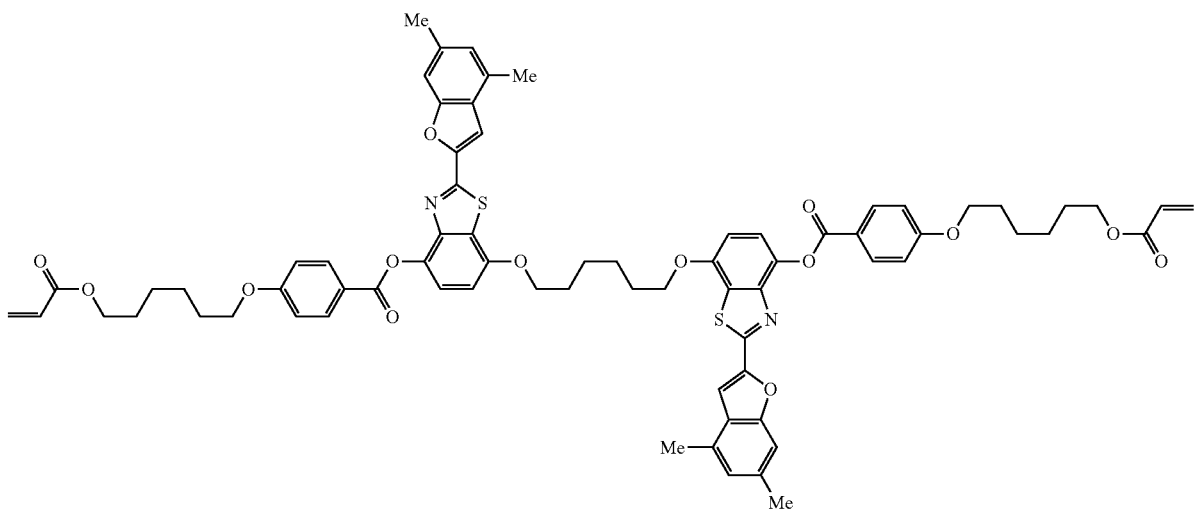
(D2-1)

-continued
(D2-2)
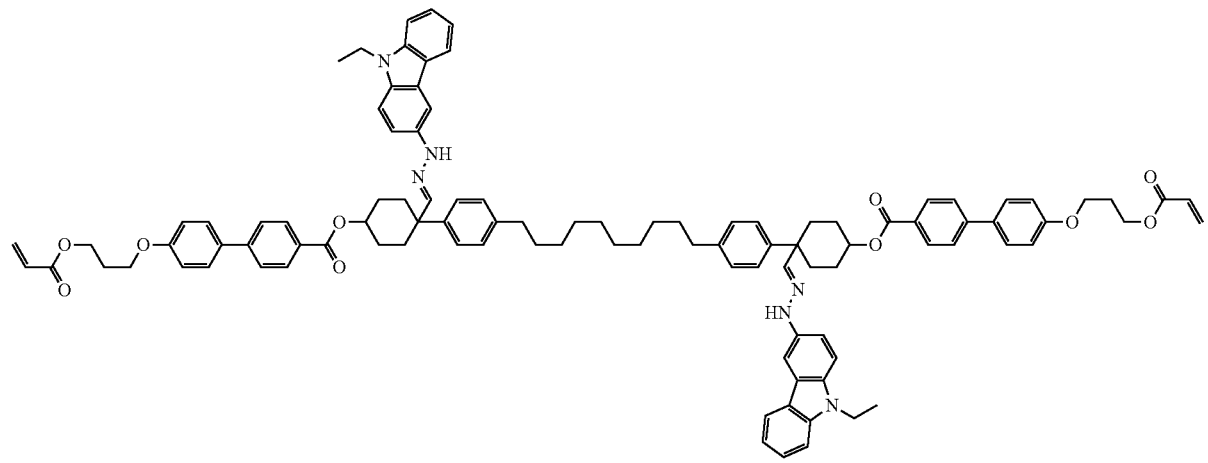
(D2-3)
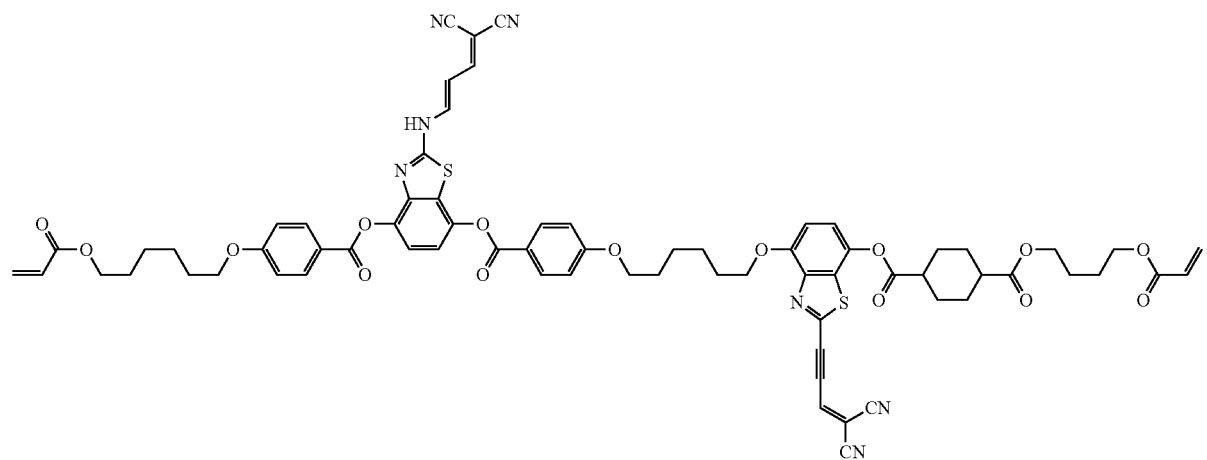
[Chem. 191]
(D2-4)
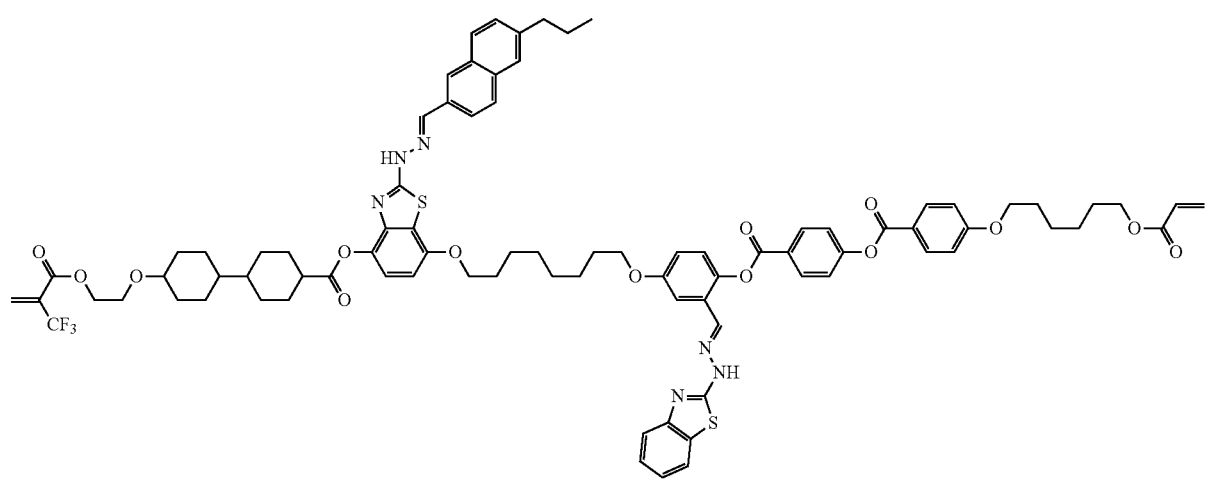

-continued
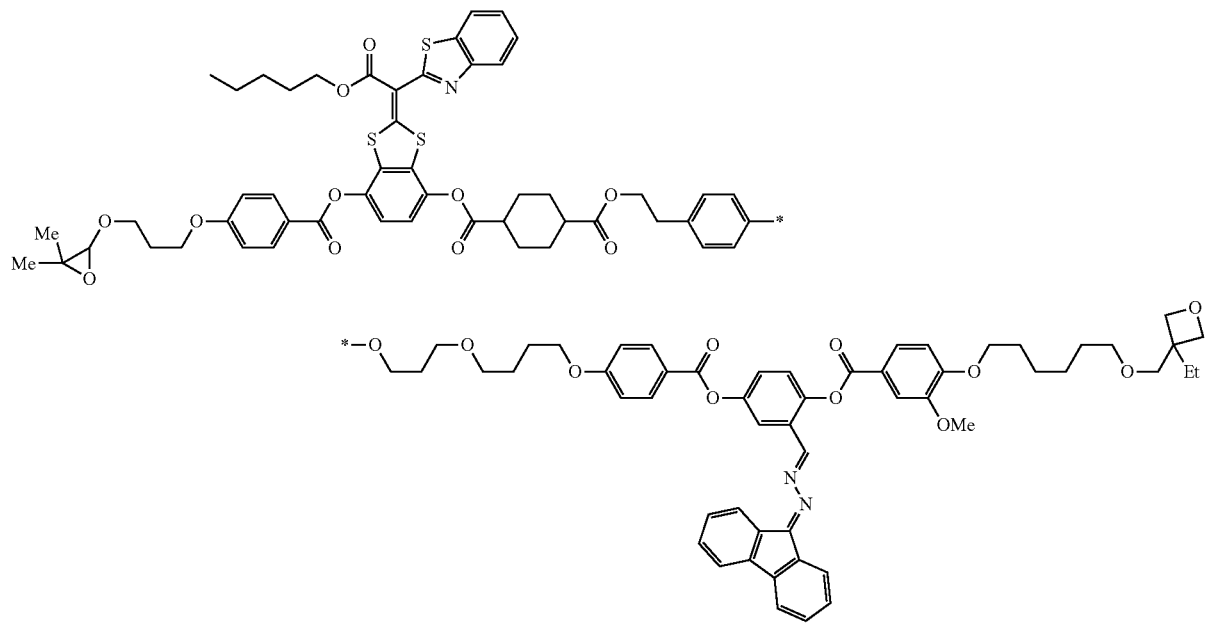
(D2-5)
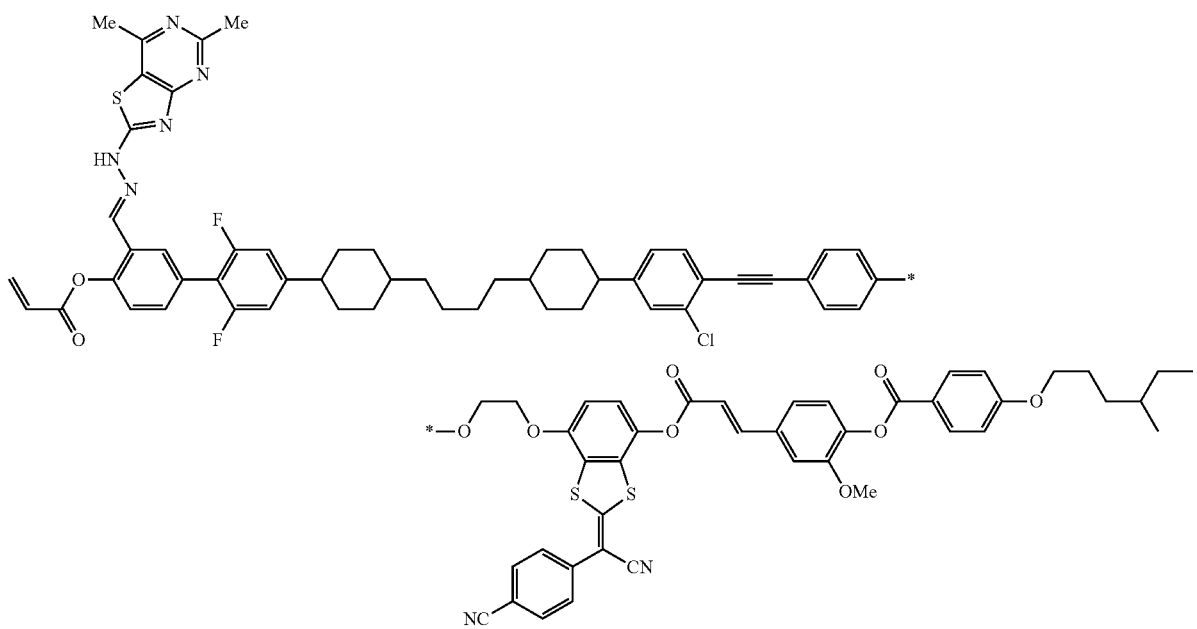
(D2-6)

-continued
[Chem. 192]
(D2-7)
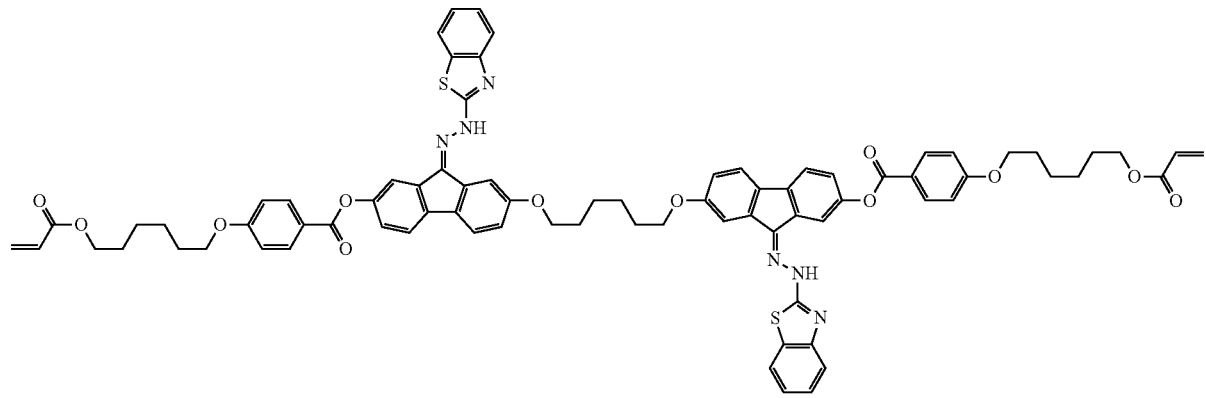
(D2-8)
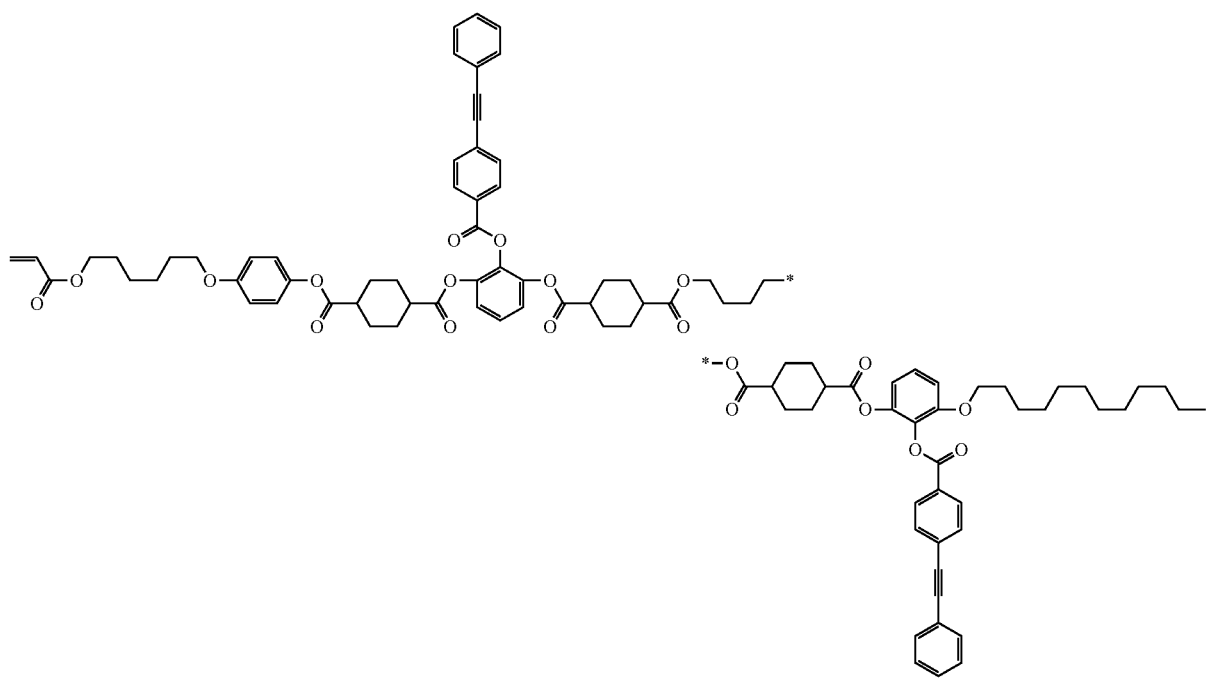
(D2-9)
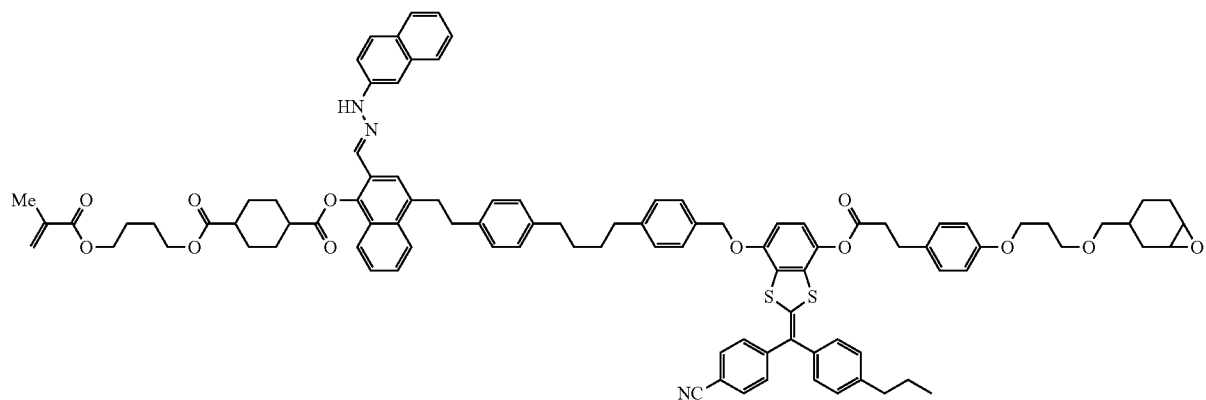

-continued
[Chem. 193]
(D2-10)
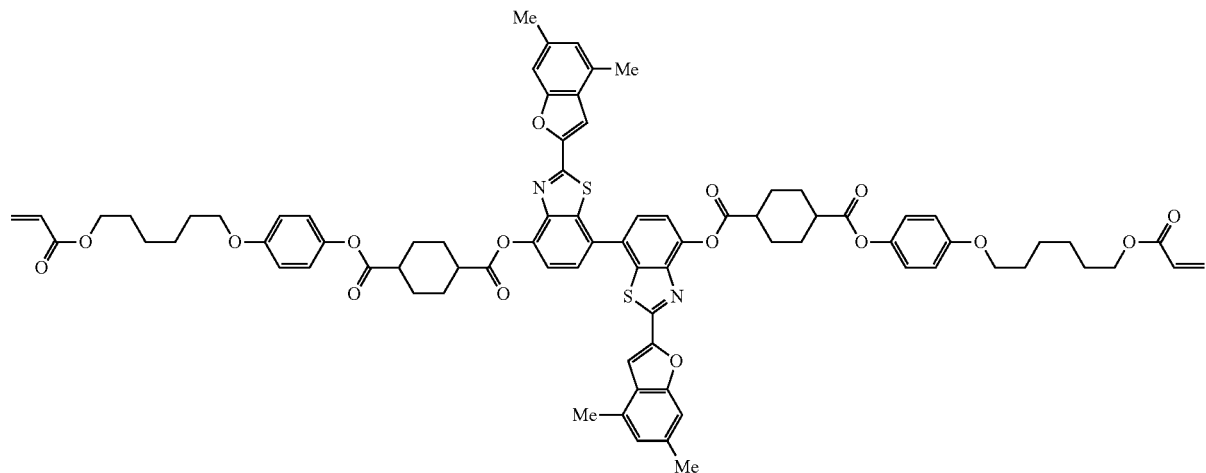
[Chem. 194]
(D3-1)
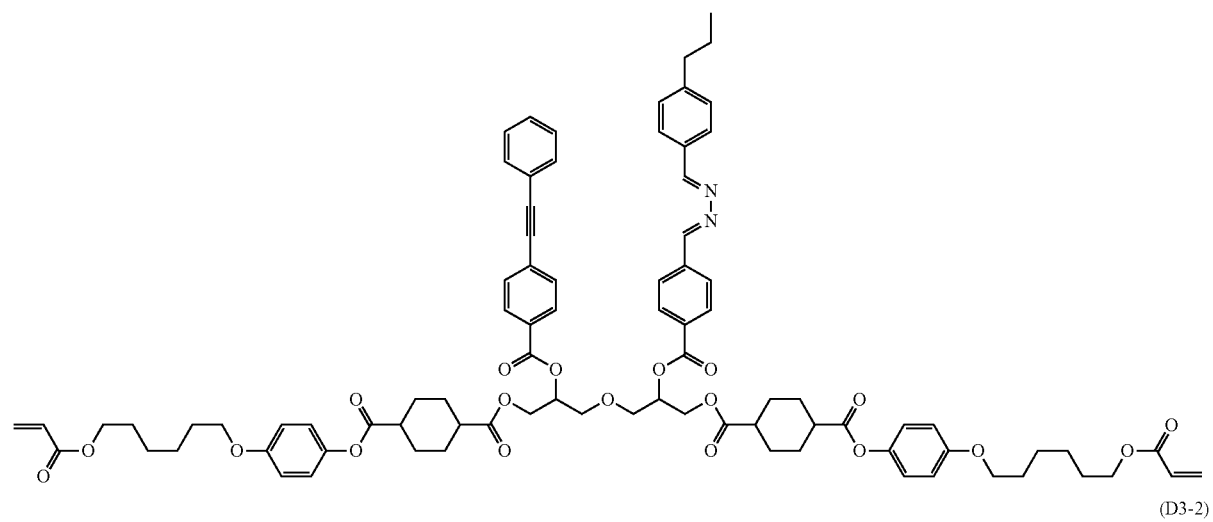
(D3-2)
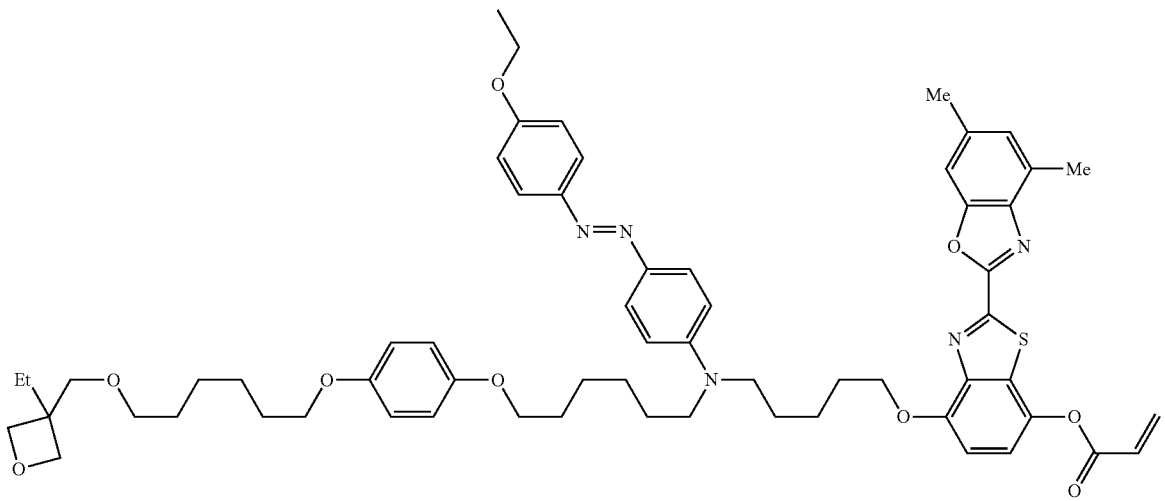

(D3-3)
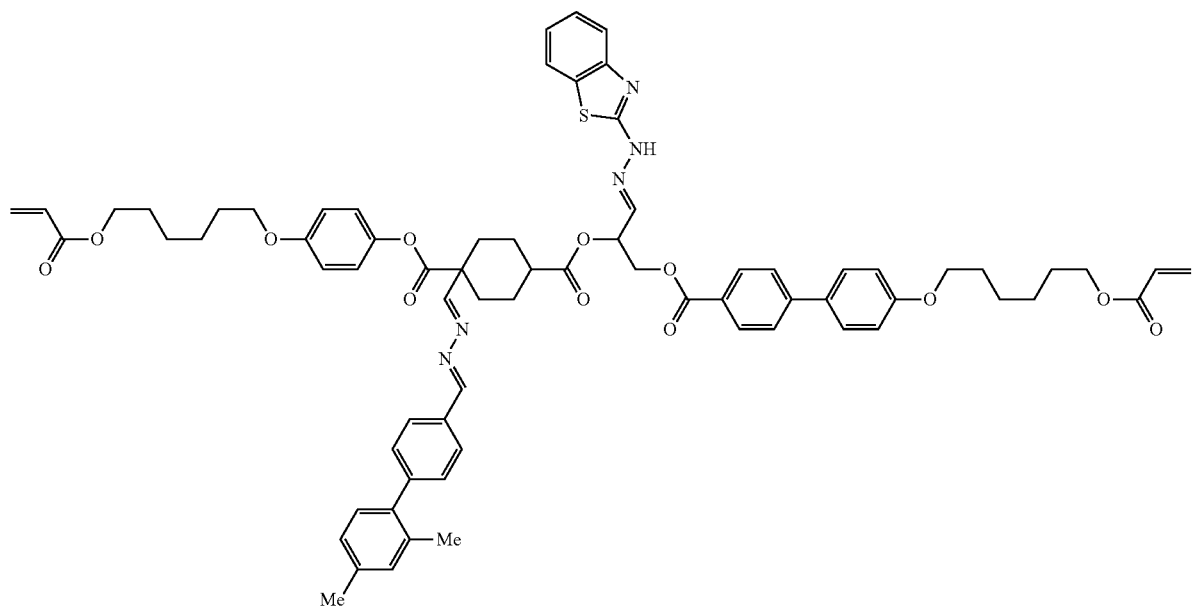
[Chem. 195]
(D3-4)
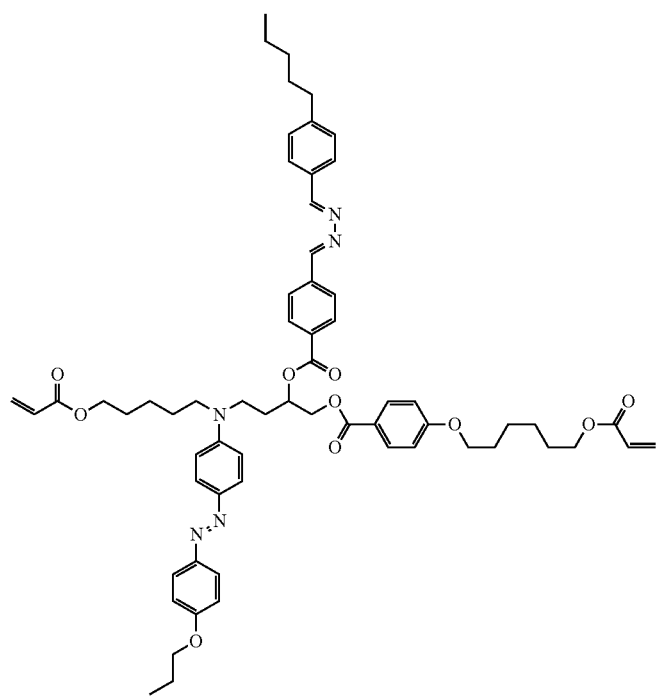

-continued
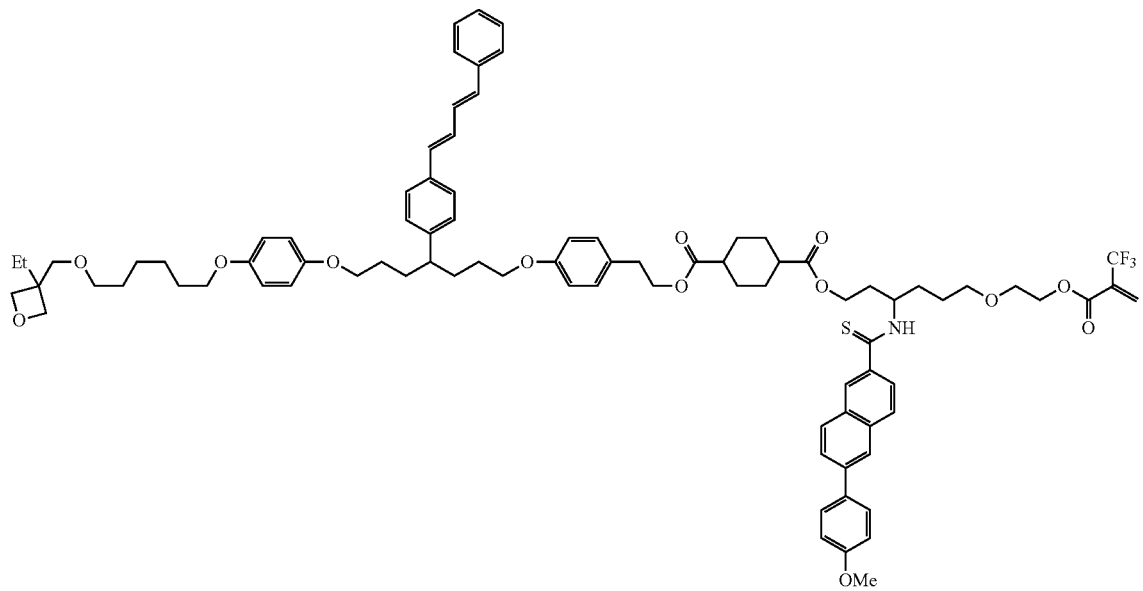
(D3-5)
[Chem. 196]
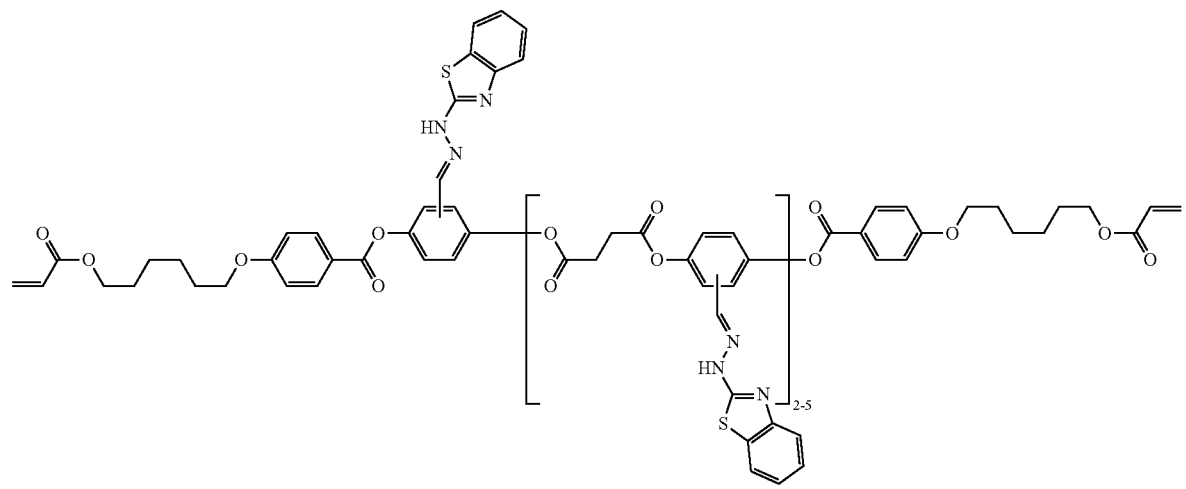
(D4-1)
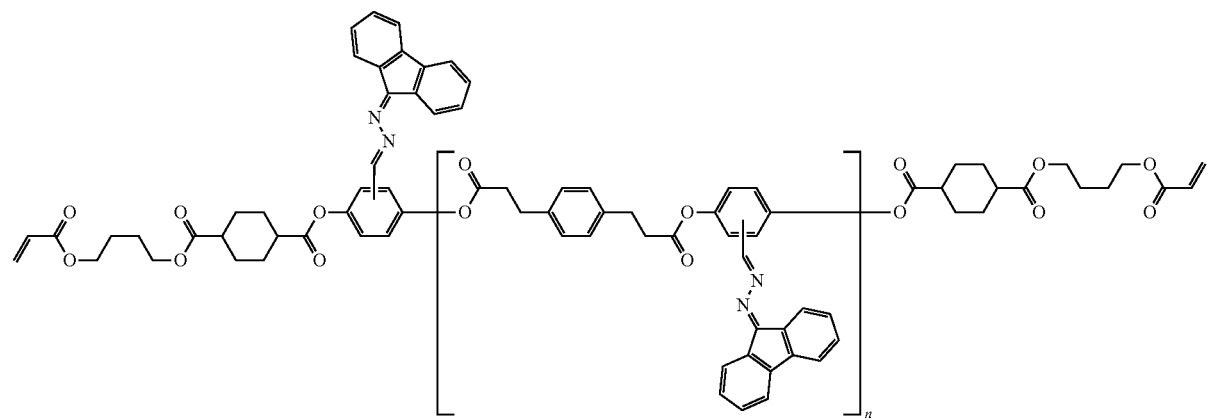
(D4-2)

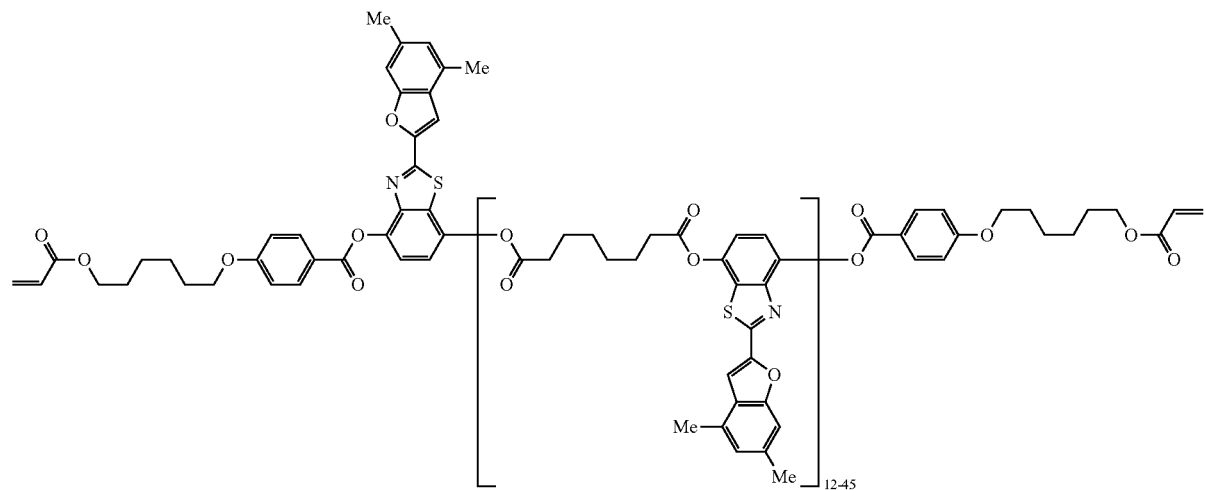
(D4-3)
[Chem. 197]
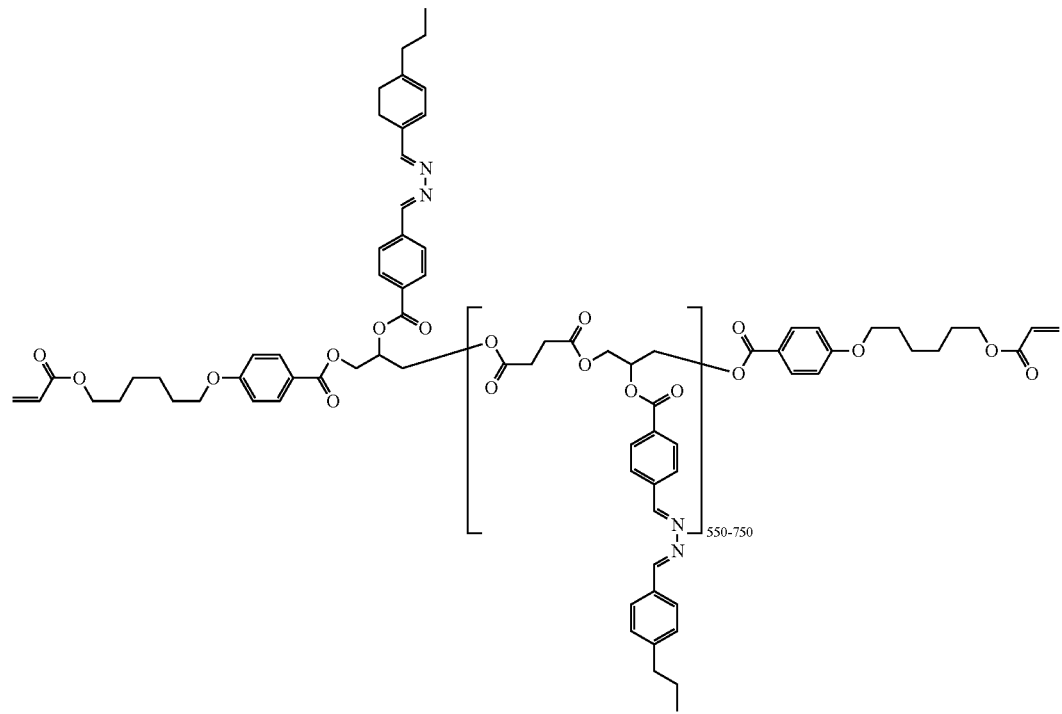
(D4-4)

A compound according to the present invention is preferably used in nematic liquid crystal compositions, smectic liquid crystal compositions, chiral smectic liquid crystal compositions, and cholesteric liquid crystal compositions. A compound outside the scope of the present invention may be added to a liquid crystal composition produced from a reactive compound according to the present invention.

More specifically, another polymerizable compound that can be used in combination with a polymerizable compound according to the present invention is preferably a compound represented by the general formula (X-11)

[Chem. 198]

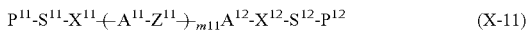
(X-11)

and/or a compound represented by the general formula (X-12).

[Chem. 199]

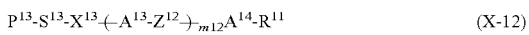
(X-12)

(wherein $P^{11}$, $P^{12}$, and $P^{13}$ independently denote a polymerizable group, $S^{11}$, $S^{12}$, and $S^{13}$ independently denote a single bond or a alkylene group having 1 to 20 carbon atoms, one —$CH_2$— or nonadjacent two or more —$CH_2$—'s may be substituted by —O—, —COO—, —OCO—, or —OCOO—, $X^{11}$, $X^{12}$, and $X^{13}$ independently denote —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —CF=CF—, —C≡C—, or a single bond, $A^{11}$, $A^{12}$, $A^{13}$, and $A^{14}$ independently denote a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, or a 1,3-dioxane-2,5-diyl group, $A^{11}$, $A^{12}$, $A^{13}$, and $A^{14}$ may be independently unsubstituted or substituted by an alkyl group, a halogenated alkyl group, an alkoxy group, a halogenated alkoxy group, a halogen atom, a cyano group, or a nitro group, $R^{11}$ denotes a hydrogen atom, a fluorine atom, a chlorine atom, a bromine atom, an iodine atom, a pentafluorosulfuranyl group, a cyano group, a nitro group, an isocyano group, a thioisocyano group, or a linear or branched alkyl group having 1 to 20 carbon atoms with one —$CH_2$— or nonadjacent two or more —$CH_2$—'s optionally independently substituted by —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, m11 and m12 are 0, 1, 2, or 3, and when m11 and/or m12 is 2 or 3, two or three $A^{11}$'s, $A^{13}$'s, $Z^{11}$'s, and/or $Z^{12}$'s may be the same or different)

Particularly preferably, $P^{11}$, $P^{12}$, and $P^{13}$ denote an acryl group or a methacryl group. More specifically, the compound represented by the general formula (X-11) is preferably a compound represented by the general formula (X-11a),

[Chem. 200]

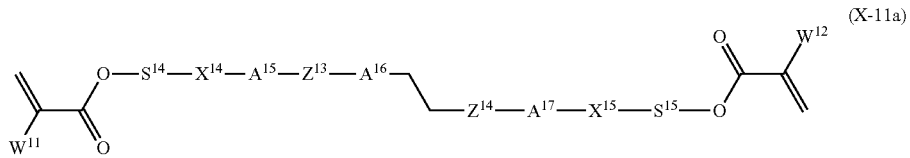
(X-11a)

—OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —CF=CF—, —C≡C—, or a single bond, $Z^{11}$ and $Z^{12}$ independently denote —O—, —S—, —OCH$_2$—, —CH$_2$O—, —COO—, —OCO—, —CO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH$_2$CH$_2$—, —CH$_2$CF$_2$—, —CF$_2$CH$_2$—, —CF$_2$CF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—

(wherein $W^{11}$ and $W^{12}$ independently denote a hydrogen atom or a methyl group, $S^{14}$ and $S^{15}$ independently denote an alkylene group having 2 to 18 carbon atoms, $X^{14}$ and $X^{15}$ independently denote —O—, —COO—, —OCO—, or a single bond, $Z^{13}$ and $Z^{14}$ independently denote —COO— or —OCO—, and $A^{15}$, $A^{16}$, and $A^1$ independently denote a 1,4-phenylene group optionally substituted by a fluorine atom, a chlorine atom, a linear or branched alkyl group having 1 to 4 carbon atoms, or a linear or branched alkoxy group having 1 to 4 carbon atoms)

particularly preferably a compound represented by one of the following formulae (X-11a-1) to (X-11a-4).

[Chem. 201]

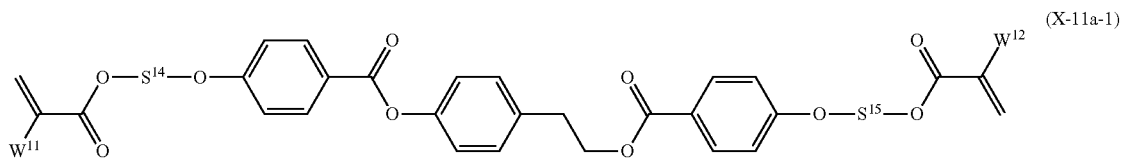
(X-11a-1)

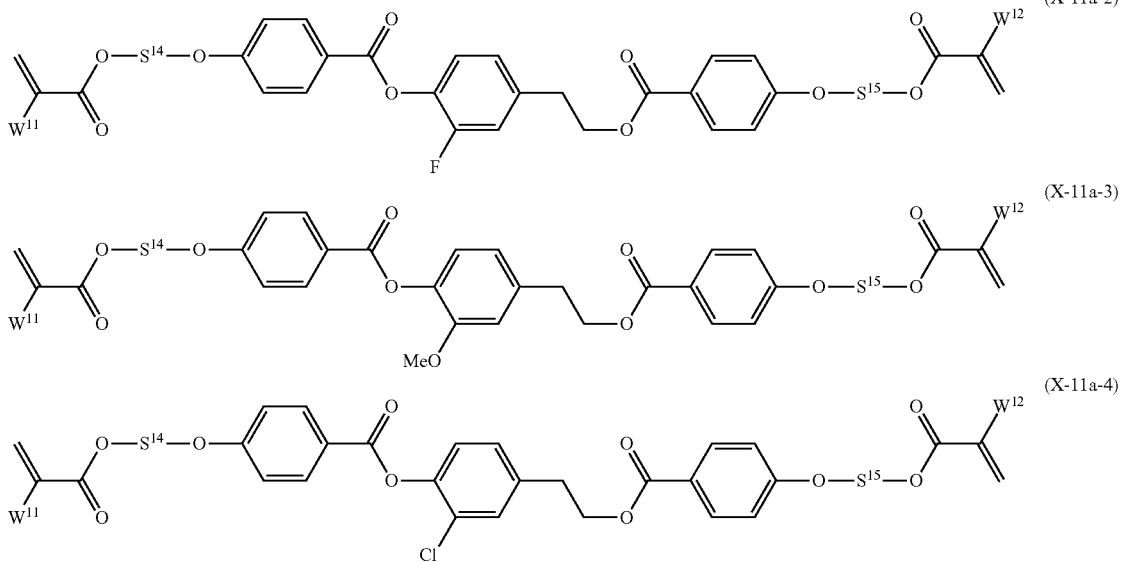

(wherein $W^{11}$, $W^{12}$, $S^{14}$, and $S^{15}$ denote the same as in the general formula (X-11a))

A compound in which $S^{14}$ and $S^{15}$ in the formulae (X-11a-1) to (X-11a-4) independently denote an alkylene group having 2 to 8 carbon atoms is particularly preferred.

Other preferred bifunctional polymerizable compounds include compounds represented by the following general formulae (X-11b-1) to (X-11b-3).

[Chem. 202]

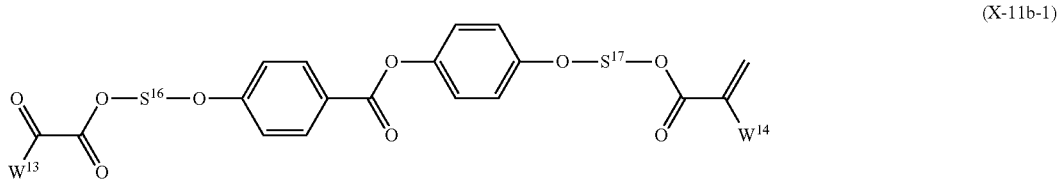

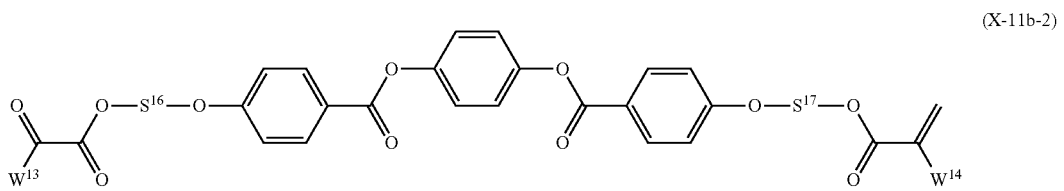

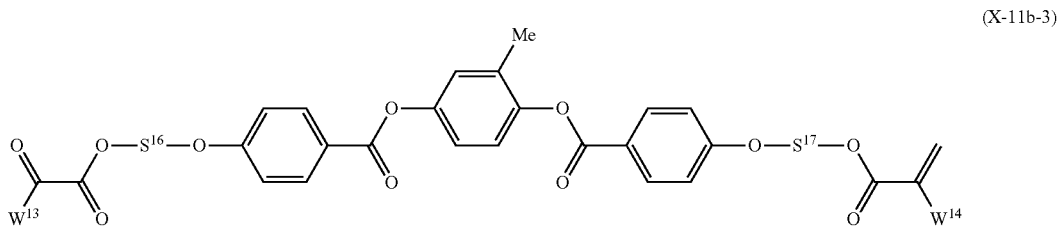

(wherein $W^{13}$ and $W^{14}$ independently denote a hydrogen atom or a methyl group, and $S^{16}$ and $S^{17}$ independently denote an alkylene group having 2 to 18 carbon atoms)

A compound in which $S^{16}$ and $S^{17}$ in the formulae (X-11b-1) to (X-11b-3) independently denote an alkylene group having 2 to 8 carbon atoms is particularly preferred.

More specifically, the compounds represented by the general formula (X-12) include compounds represented by the following general formulae (X-12-1) to (X-12-7).

—CH=CH—COO—, —CH=CH—OCO—, —COO—CH=CH—, —OCO—CH=CH—, —CH=CH—, —CF=CF—, or —C≡C—)

[Chem. 203]

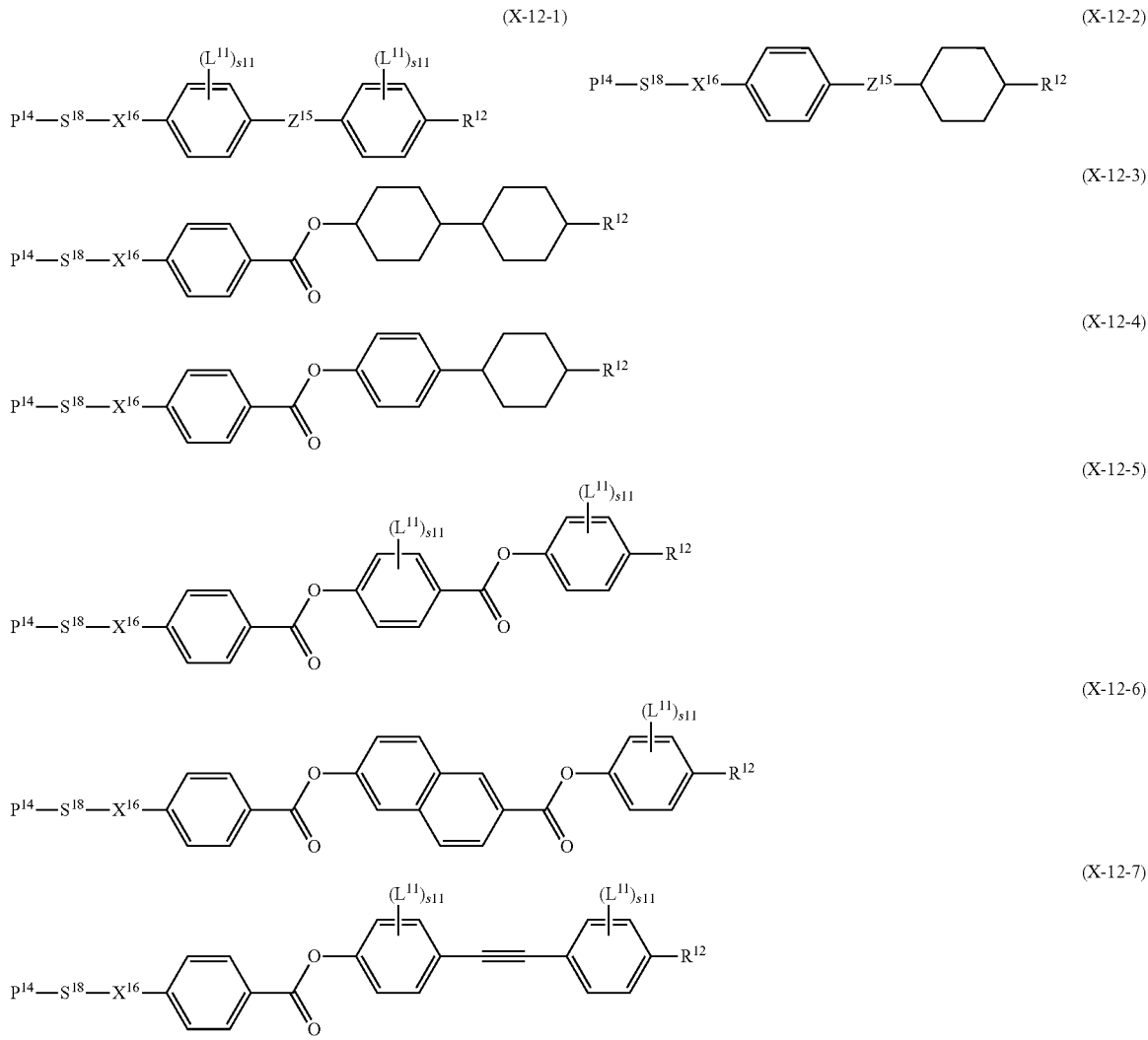

(wherein $P^{14}$ denotes a polymerizable group, $S^{18}$ denotes a single bond or an alkylene group having 1 to 20 carbon atoms, one —CH$_2$— or nonadjacent two or more —CH$_2$—'s may be substituted by —O—, —COO—, —OCO—, or —O—CO—O—, $X^{16}$ denotes a single bond, —O—, —COO—, or —OCO—, $Z^{15}$ denotes a single bond, —COO—, or —OCO—, $L^{11}$ denotes a fluorine atom, a chlorine atom, or a linear or branched alkyl group having 1 to 10 carbon atoms with one —CH$_2$— or nonadjacent two or more —CH$_2$—'s optionally independently substituted by —O—, —COO—, or —OCO—, $s^{11}$ is an integer in the range of 0 to 4, and $R^{12}$ denotes a hydrogen atom, a fluorine atom, a chlorine atom, a cyano group, a nitro group, or a linear or branched alkyl group having 1 to 20 carbon atoms with one —CH$_2$— or nonadjacent two or more —CH$_2$—'s optionally independently substituted by —O—, —S—, —CO—, —COO—, —OCO—, —CO—S—, —S—CO—, —O—CO—O—, —CO—NH—, —NH—CO—, A polymerizable compound having no liquid crystallinity may be added to a polymerizable liquid crystal composition containing a compound according to the present invention, provided that the liquid crystallinity of the composition is not significantly reduced. More specifically, a compound recognized in this technical field as a polymer-forming monomer or a polymer-forming oligomer may be used without limitation. A specific example can be found in "Hikari kouka gijutu deta bukku, zairyo hen (monoma, origoma, hikari jugo kaishizai) (Photo-curing technique data book, Materials Edition (monomer, oligomer, photopolymerization initiator)" (under the supervision of Ichimura Kunihiro and Kato Kiyomi, Technonet).

Although a compound according to the present invention can be polymerized without a photopolymerization initiator, a photopolymerization initiator may be added to the compound in some applications. In such a case, the concentration of a photopolymerization initiator preferably ranges from 0.1% to 15% by mass, more preferably 0.2% to 10% by mass, still more preferably 0.4% to 8% by mass, of a compound according to the present invention. Examples of the photopolymerization initiator include benzoin ethers, benzophenones, acetophenones, benzyl ketals, and acylphosphine oxides. Specific examples of the photopolymerization initiator include 2-methyl-1-(4-methylthiophenyl)-2-morpholinopropan-1-one (IRGACURE 907) and benzoic acid [1-[4-(phenylthio)benzoyl]heptylidene]amino ester (IRGACURE OXE 01). Examples of a thermal polymerization initiator include azo compounds and peroxides. Specific examples of a thermal polymerization initiator include 2,2'-azobis(4-methoxy-2,4-dimethylvaleronitrile) and 2,2'-azobis(isobutyronitrile). These polymerization initiators may be used alone or in combination.

A liquid crystal composition according to the present invention may contain a stabilizer so as to improve storage stability. Examples of the stabilizer to be used include hydroquinones, hydroquinone monoalkyl ethers, tert-butyl-catechols, pyrogallols, thiophenols, nitro compounds, β-naphthylamines, β-naphthols, and nitroso compounds. The amount of stabilizer to be used preferably ranges from 0.005% to 1% by mass, more preferably 0.02% to 0.8% by mass, still more preferably 0.03% to 0.5% by mass, of the composition. These stabilizers may be used alone or in combination. More specifically, the stabilizer is preferably a compound represented by one of the formulae (X-13-1) to (X-13-40).

[Chem. 204]

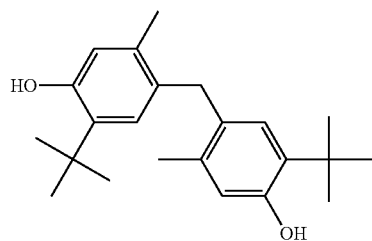
(X-13-1)

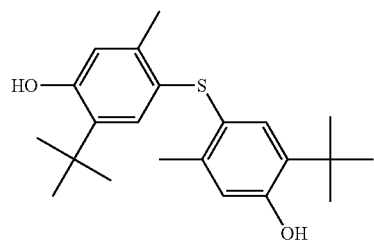
(X-13-2)

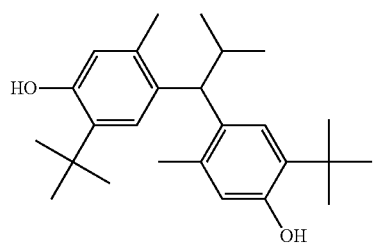
(X-13-3)

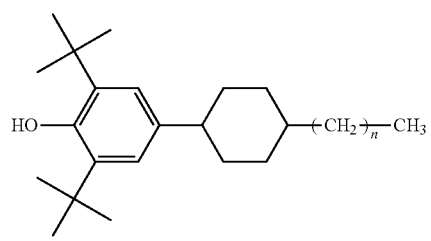
(X-13-4)

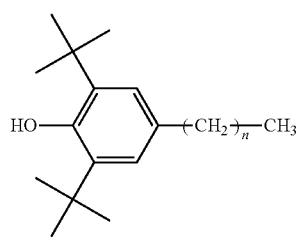
(X-13-5)

[Chem. 205]

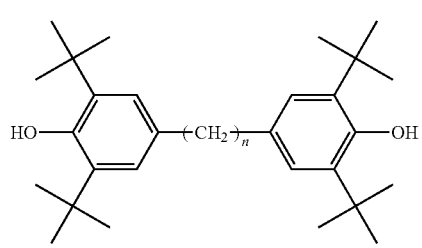
(X-13-6)

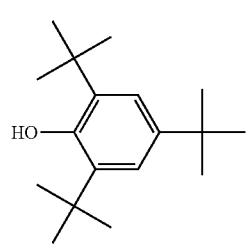
(X-13-7)

-continued
(X-13-8)
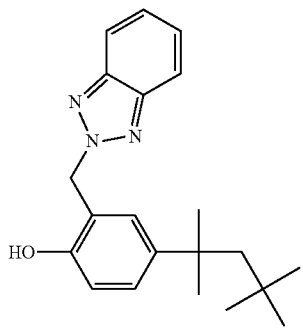
(X-13-9)
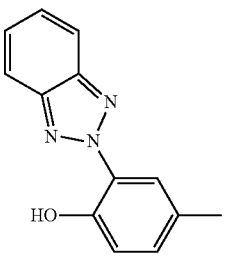
(X-13-10)
[Chem. 206]
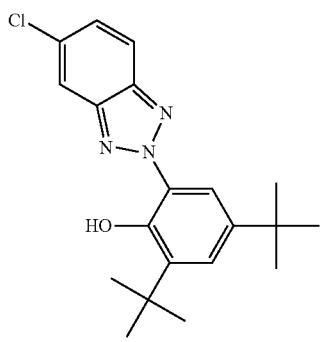
(X-13-11)
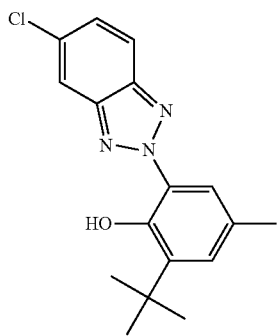
(X-13-12)
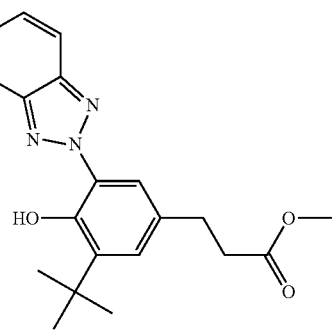
(X-13-13)
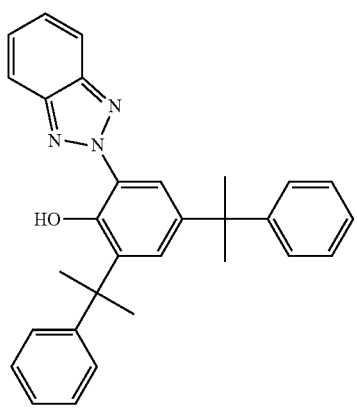
(X-13-14)
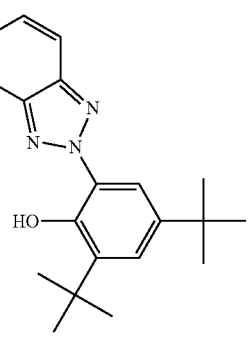

(X-13-15)
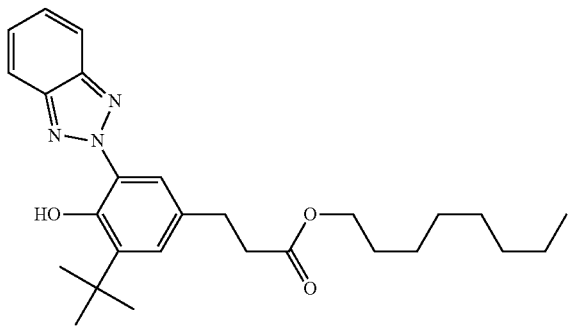
[Chem. 207]
(X-13-16)
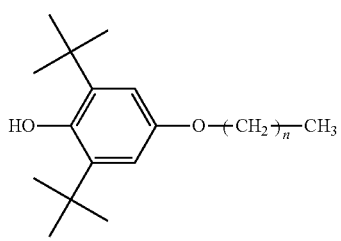
(X-13-17)
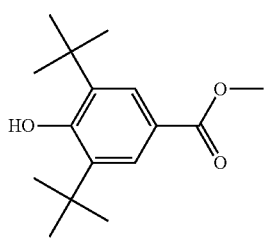
(X-13-18)
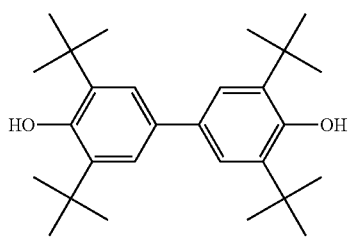
(X-13-19)
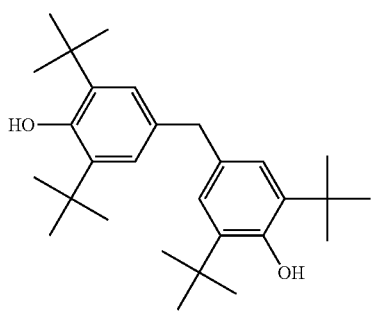
(X-13-20)
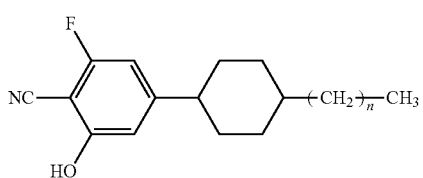
[Chem. 208]
(X-13-21)
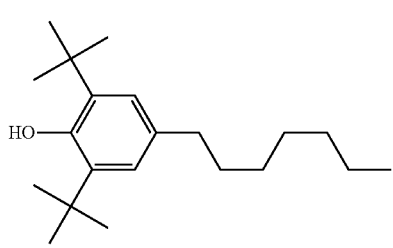
(X-13-22)
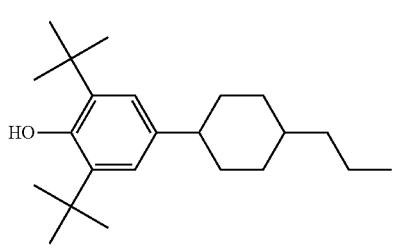
(X-13-23)
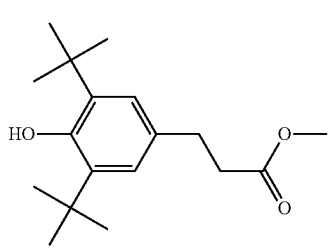
(X-13-24)
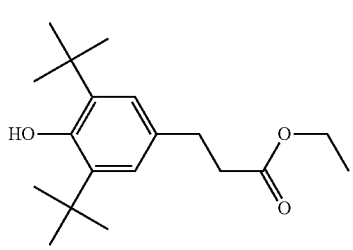

-continued
(X-13-25)
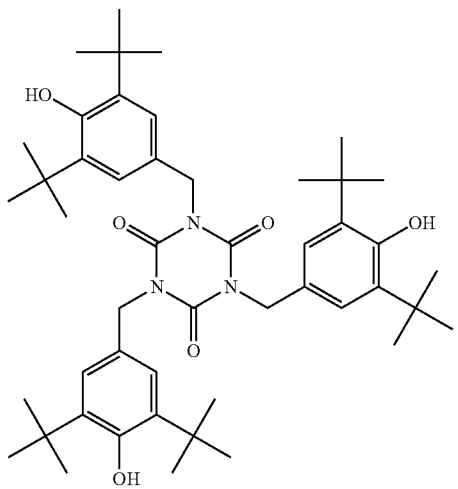
[Chem. 209]
(X-13-26)
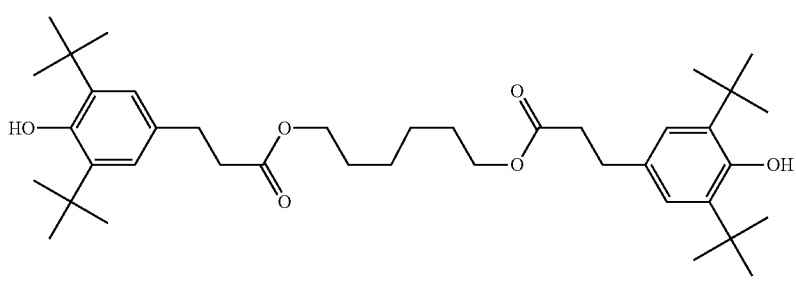
(X-13-27)
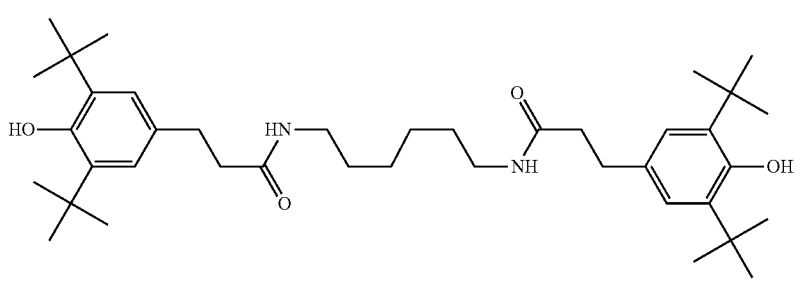
(X-13-28)
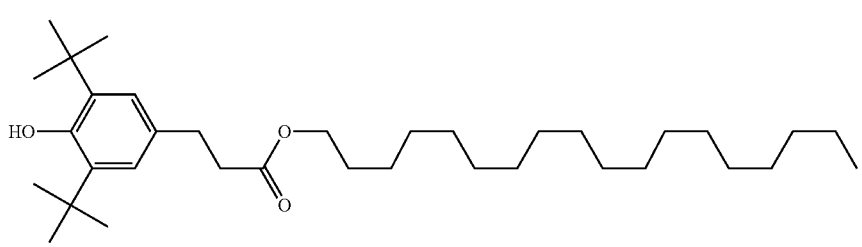

-continued
(X-13-29)
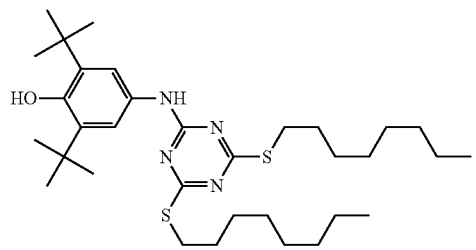
(X-13-30)
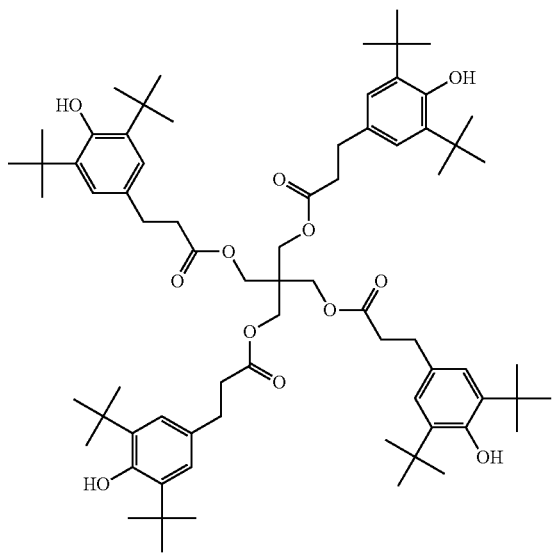
[Chem. 210]
(X-13-31)
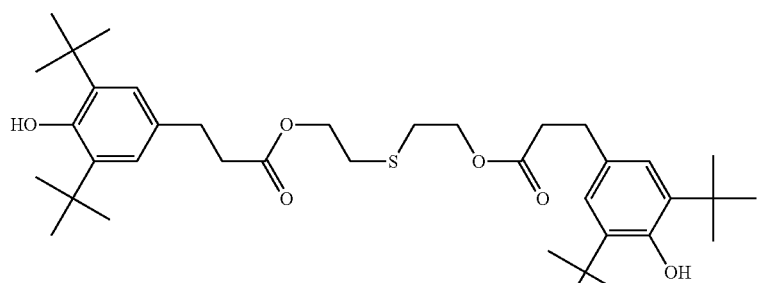
(X-13-32)
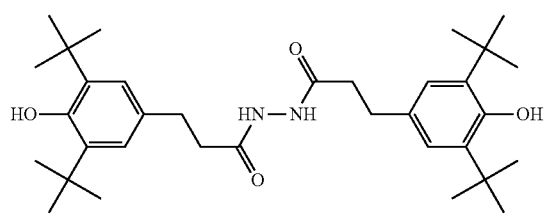
(X-13-33)
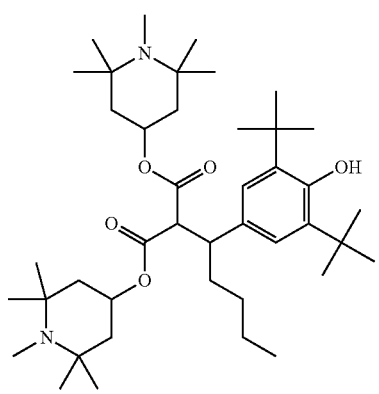
(X-13-34)
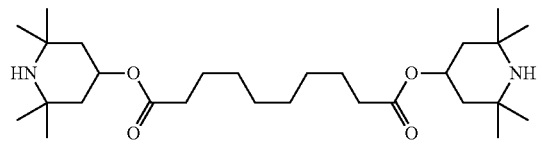
(X-13-35)
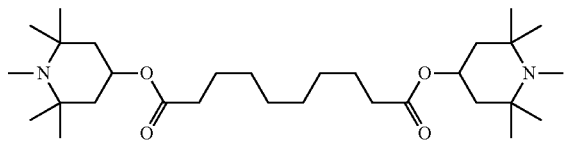

[Chem. 211]

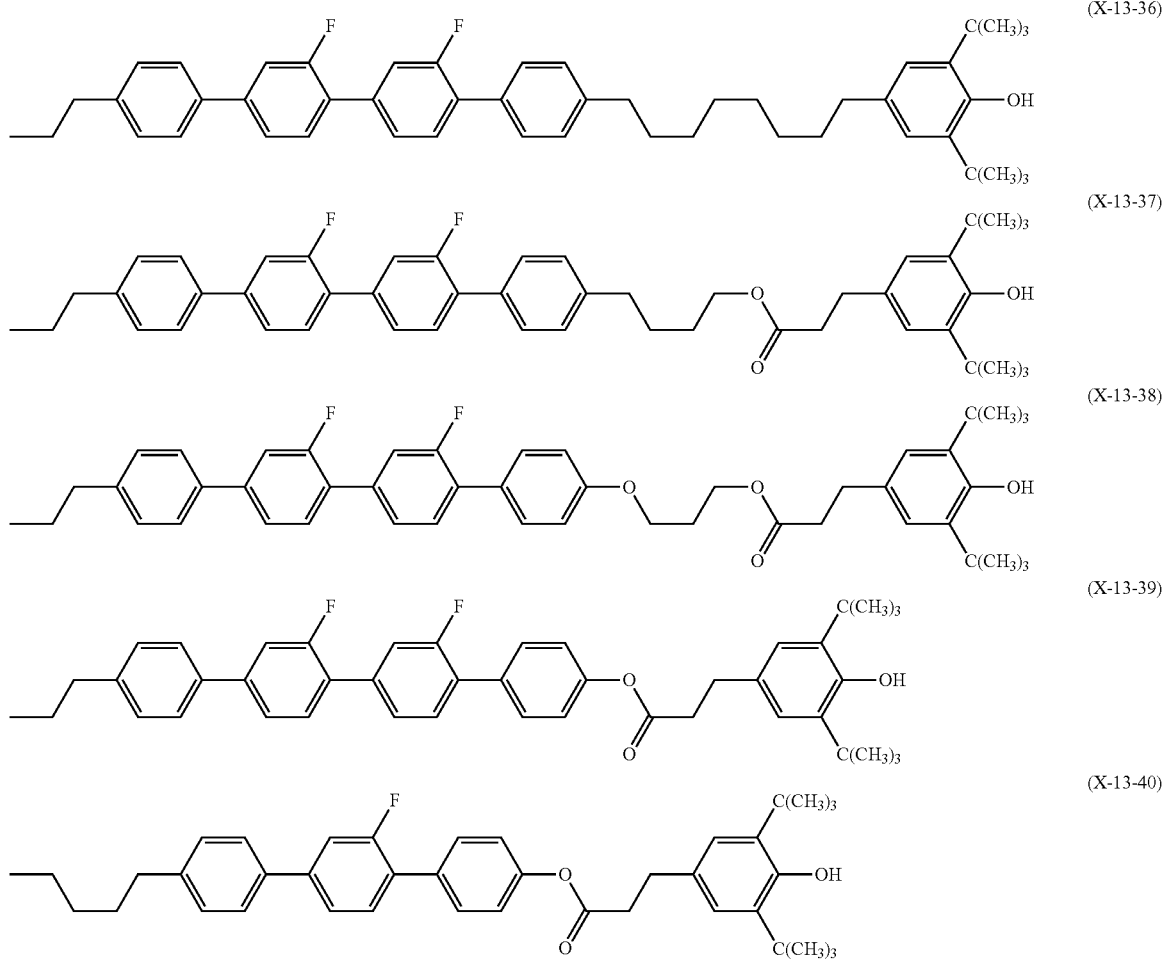

(wherein n is an integer in the range of 0 to 20)

When a polymerizable liquid crystal composition containing a compound according to the present invention is used in applications such as films, optical devices, functional pigments, pharmaceutical agents, cosmetics, coating agents, and synthetic resins, a metal, a metal complex, a colorant, a pigment, a dye, a fluorescent material, a phosphorescent material, a surfactant, a leveling agent, a thixotropic agent, a gelling agent, a polysaccharide, an ultraviolet absorber, an infrared absorber, an antioxidant, an ion-exchange resin, and/or a metal oxide, such as titanium oxide, may be added for each purpose.

A polymer produced by polymerization of a polymerizable liquid crystal composition containing a compound according to the present invention can be utilized in various applications. For example, a polymer produced by polymerization of a polymerizable liquid crystal composition containing a compound according to the present invention without orientation can be utilized as a light scattering plate, a depolarizing plate, or a plate for preventing moire fringes. A polymer produced by polymerization after orientation is also useful for its optical anisotropy. Such an optically anisotropic body can be produced, for example, by placing a polymerizable liquid crystal composition containing a compound according to the present invention on a substrate rubbed with cloth, on a substrate with an organic thin film, on a substrate with an alignment film on which $SiO_2$ is obliquely deposited, or between these substrates, and polymerizing the polymerizable liquid crystal composition.

A method for placing a polymerizable liquid crystal composition on a substrate may be spin coating, die coating, extrusion coating, roll coating, wire bar coating, gravure coating, spray coating, dipping, or printing. For coating, an organic solvent may be added to a polymerizable liquid crystal composition. Examples of the organic solvent include hydrocarbon solvents, halogenated hydrocarbon solvents, ether solvents, alcohol solvents, ketone solvents, ester solvents, and aprotic solvents. For example, hydrocarbon solvents include toluene and hexane, halogenated hydrocarbon solvents include methylene chloride, ether solvents include tetrahydrofuran, acetoxy-2-ethoxyethane, and propylene glycol monomethyl ether acetate, alcohol solvents include methanol, ethanol, and isopropanol, ketone solvents include acetone, methyl ethyl ketone, cyclohexanone, γ-butyl lactone, and N-methylpyrrolidinones, ester solvents include ethyl acetate and cellosolve, and aprotic solvents include dimethylformamide and acetonitrile. These may be used alone or in combination and are appropriately selected in terms of vapor pressure and the solubility of a polymerizable liquid crystal composition. A method for volatilizing an added organic solvent may be natural drying, heat drying, vacuum drying, or vacuum heat drying. In order to further improve the coating performance of a polymerizable liquid crystal material, it is effective to form an intermediate layer, such as a polyimide thin film, on a substrate or to add a leveling agent to the polymerizable liquid crystal material. A method for forming an intermediate layer, such as a polyimide thin film, on a substrate is effective in improving the adhesion between a polymer produced by polymerization of a polymerizable liquid crystal material and the substrate.

Another orientation treatment may utilize the flow-induced orientation of a liquid crystal material or an electric or magnetic field. These orientation methods may be used alone or in combination. An orientation treatment method that can substitute for rubbing may be a photo-alignment method. The substrate may be a flat sheet or may partly have a curved surface. The material of the substrate may be an organic material or an inorganic material. Examples of the organic material serving as a material for a substrate include poly(ethylene terephthalate), polycarbonate, polyimide, polyamide, poly(methyl methacrylate), polystyrene, poly(vinyl chloride), polytetrafluoroethylene, polychlorotrifluoroethylene, polyarylate, polysulfone, cellulose triacetate, cellulose, and poly(ether ether ketone). Examples of the inorganic material include silicon, glass, and calcite.

It is desirable that a polymerizable liquid crystal composition containing a compound according to the present invention be rapidly polymerized. Thus, a polymerization method utilizing irradiation with an active energy beam, such as ultraviolet light or an electron beam, is preferred. When ultraviolet light is used, a polarized or unpolarized light source may be used. When a liquid crystal composition between two substrates is polymerized, at least the substrate to be irradiated must be transparent to an active energy beam. Only a particular portion may be polymerized using a mask during photoirradiation, and then the condition, such as an electric field, a magnetic field, or temperature, may be altered to change the alignment state of an unpolymerized portion, which is then polymerized by irradiation with an active energy beam. The irradiation temperature is preferably in such a range that a polymerizable liquid crystal composition according to the present invention can retain its liquid crystal state. In particular, when an optically anisotropic body is produced by photopolymerization, the polymerization temperature is preferably as close to room temperature as possible, typically 25° C., also in order to prevent unintended thermal polymerization. The active energy beam preferably has an intensity in the range of 0.1 mW/cm$^2$ to 2 W/cm$^2$. At an intensity of 0.1 mW/cm$^2$ or less, photopolymerization takes a long time and has low productivity. At an intensity of 2 W/cm$^2$ or more, a polymerizable liquid crystal compound or a polymerizable liquid crystal composition may deteriorate.

An optically anisotropic body produced by polymerization may be heat-treated to reduce the initial characteristic change and to provide stable characteristics. The heat treatment temperature preferably ranges from 50° C. to 250° C., and the heat-treatment time preferably ranges from 30 seconds to 12 hours.

An optically anisotropic body thus produced may be separated from the substrate before use or may be used in combination with the substrate. An optically anisotropic body may be stacked on another optically anisotropic body or may be attached to another substrate.

EXAMPLES

Although the present invention will be further described in the following examples, the present invention is not limited to these examples. The term "%" with respect to compositions in the following examples and comparative examples refers to "% by mass".

Example 1 Production of a Compound Represented by the Formula (A11-1)

[Chem. 212]

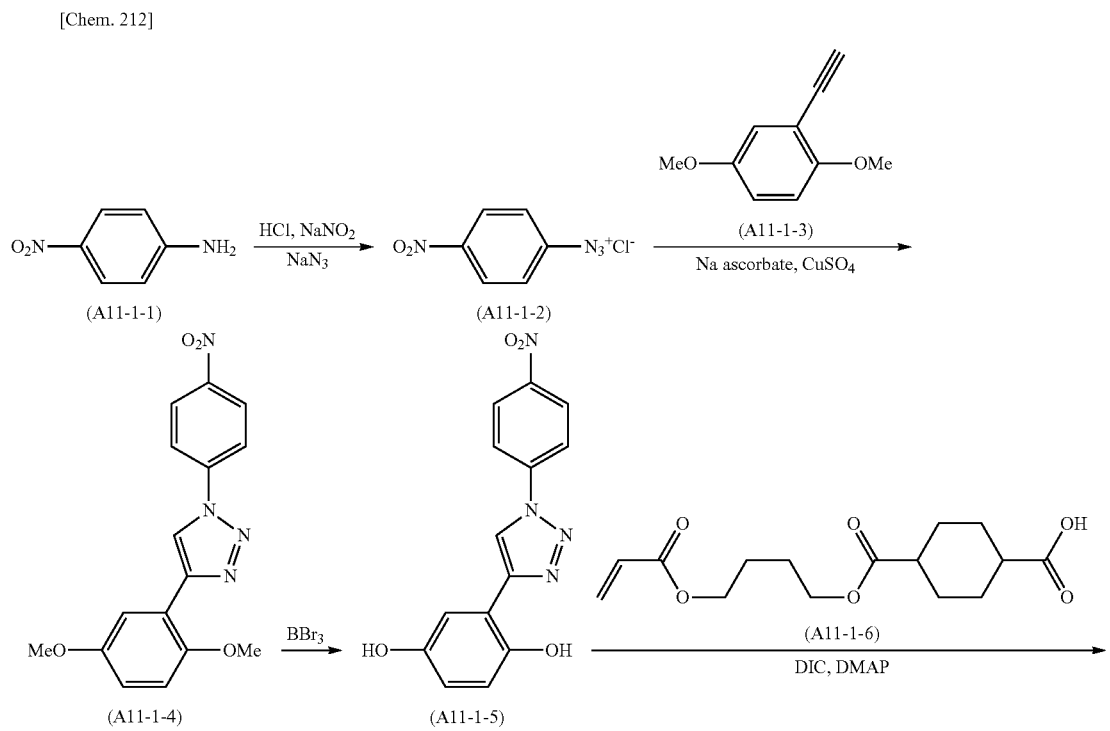

-continued

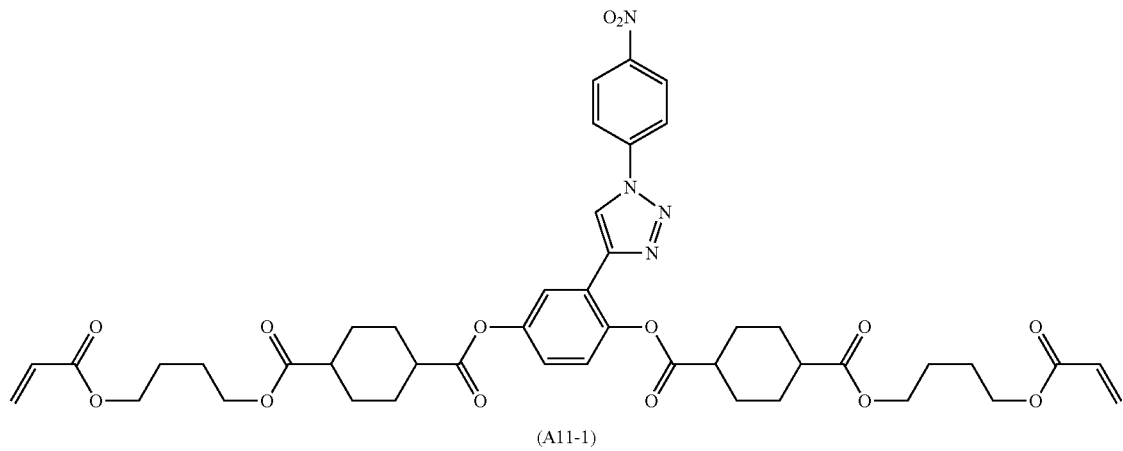

(A11-1)

A reaction vessel was charged with a compound represented by the formula (A11-1-1), water, and hydrochloric acid. Aqueous sodium nitrite was added while ice cooling, and the mixture was stirred. Small amounts of sodium azide were added, and the mixture was stirred at room temperature. Common posttreatment yielded a compound represented by the formula (A11-1-2).

A reaction vessel was charged with the compound represented by the formula (A11-1-2), a compound represented by the formula (A11-1-3), water, and tert-butyl alcohol. Aqueous sodium ascorbate and copper (II) sulfate pentahydrate were added, and the mixture was heated with stirring. After common posttreatment, purification by column chromatography yielded a compound represented by the formula (A11-1-4).

A reaction vessel was charged with the compound represented by the formula (A11-1-4) and dichloromethane. After the addition of boron tribromide and stirring, common posttreatment yielded a compound represented by the formula (A11-1-5).

A compound represented by the formula (A11-1-6) was produced by a method described in Japanese Unexamined Patent Application Publication No. 2010-100541. A reaction vessel was charged with the compound represented by the formula (A11-1-5), the compound represented by the formula (A11-1-6), N,N-dimethylaminopyridine, and dichloromethane. Diisopropyl carbodiimide was added, and the mixture was stirred. After common posttreatment, purification by column chromatography yielded a compound represented by the formula (A11-1).

MS(m/z): 859 [M$^+$+1]

Example 2 Production of a Compound Represented by the Formula (A11-2)

[Chem. 213]

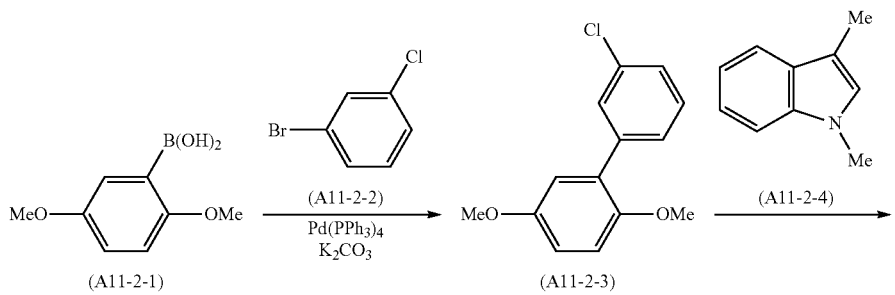

-continued

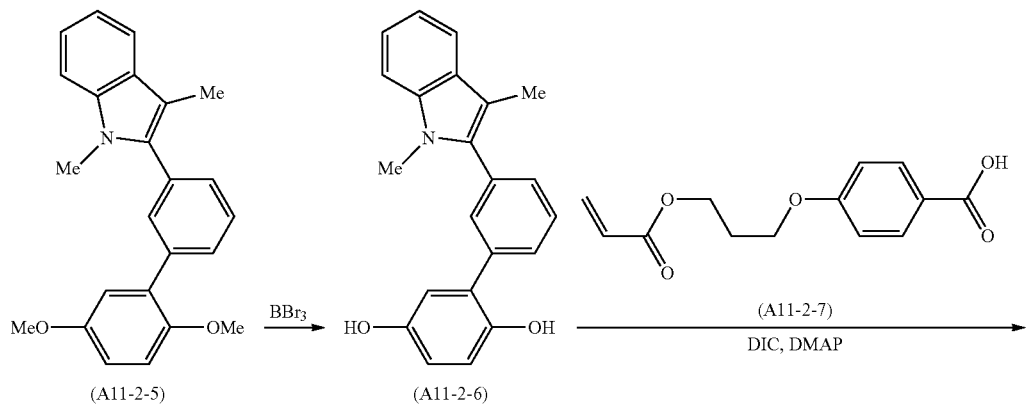

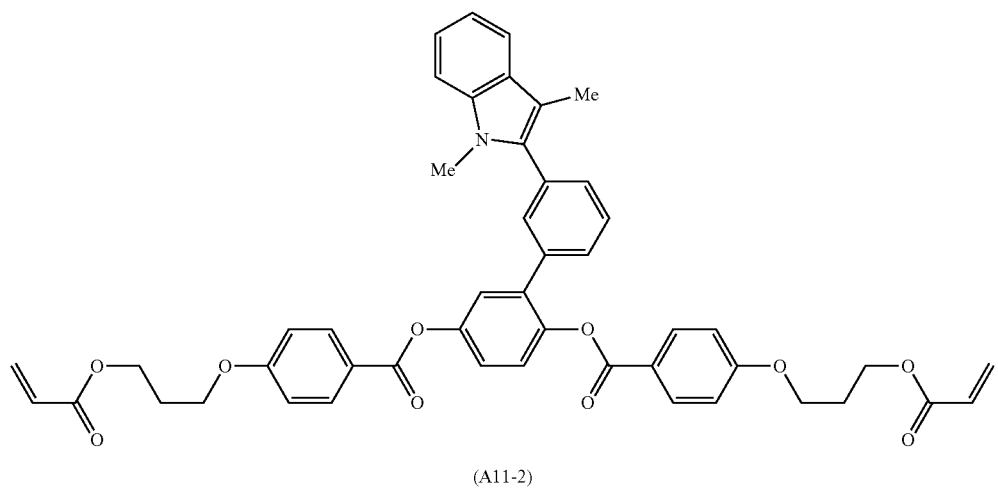

A reaction vessel in an inert atmosphere was charged with a compound represented by the formula (A11-2-1), a compound represented by the formula (A11-2-2), potassium carbonate, tetrakis(triphenylphosphine) palladium (0), tetrahydrofuran, and water, and was heated with stirring. After common posttreatment, purification by column chromatography yielded a compound represented by the formula (A11-2-3).

A reaction vessel in an inert atmosphere was charged with the compound represented by the formula (A11-2-3), a compound represented by the formula (A11-2-4), palladium (II) acetate, (1,1'-biphenyl-2-yl)dicyclohexylphosphine, sodium carbonate, and N,N-dimethylacetamide, and was heated with stirring. After common posttreatment, purification by column chromatography yielded a compound represented by the formula (A11-2-5).

A reaction vessel was charged with the compound represented by the formula (A11-2-5) and dichloromethane. After the addition of boron tribromide and stirring, common posttreatment yielded a compound represented by the formula (A11-2-6).

A reaction vessel was charged with the compound represented by the formula (A11-2-6), a compound represented by the formula (A11-2-7), N,N-dimethylaminopyridine, and dichloromethane. Diisopropyl carbodiimide was added, and the mixture was stirred. After common posttreatment, purification by column chromatography yielded a compound represented by the formula (A11-2).

MS(m/z): 794 [M$^+$+1]

Example 3 Production of a Compound Represented by the Formula (A12-1)

[Chem. 214]

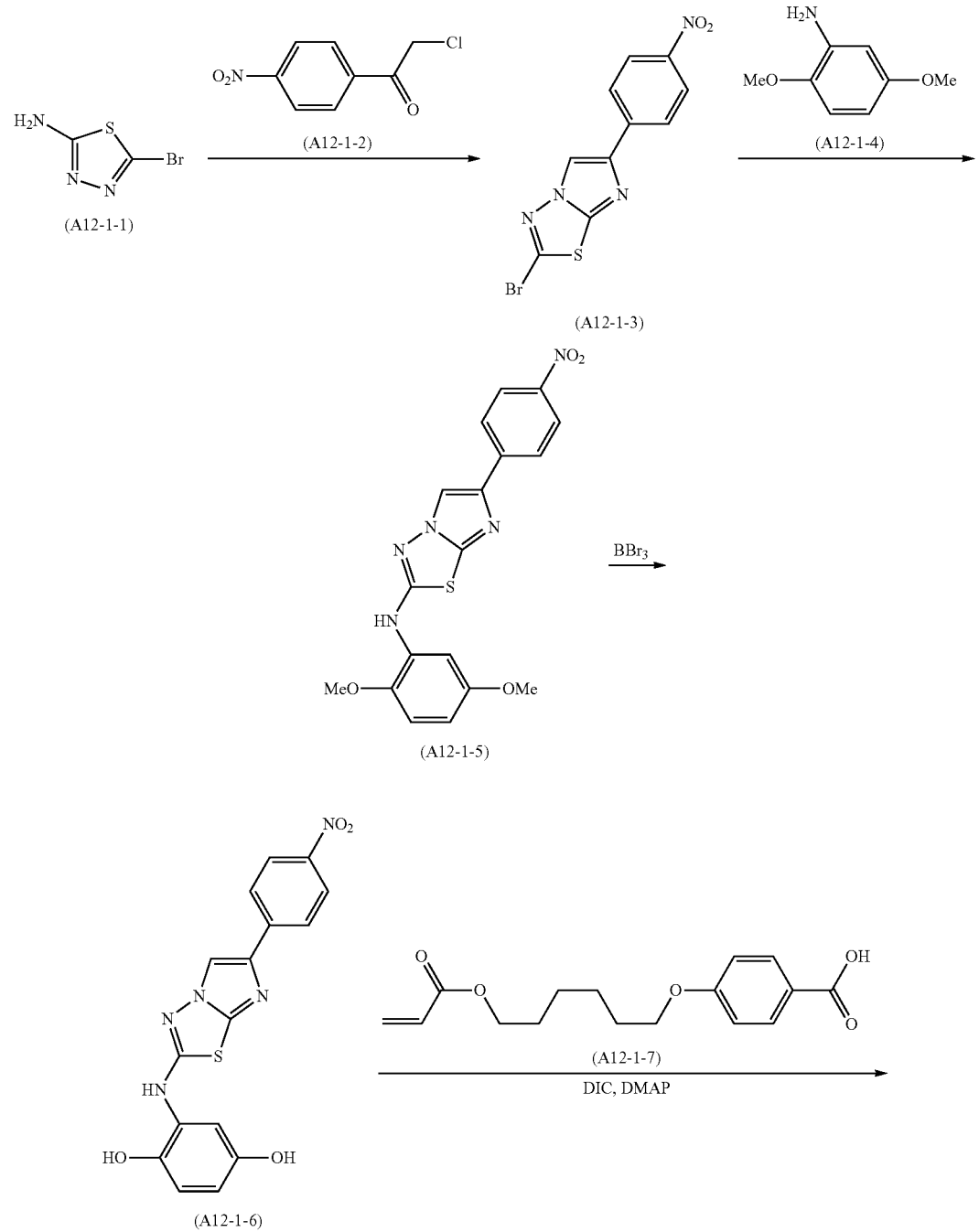

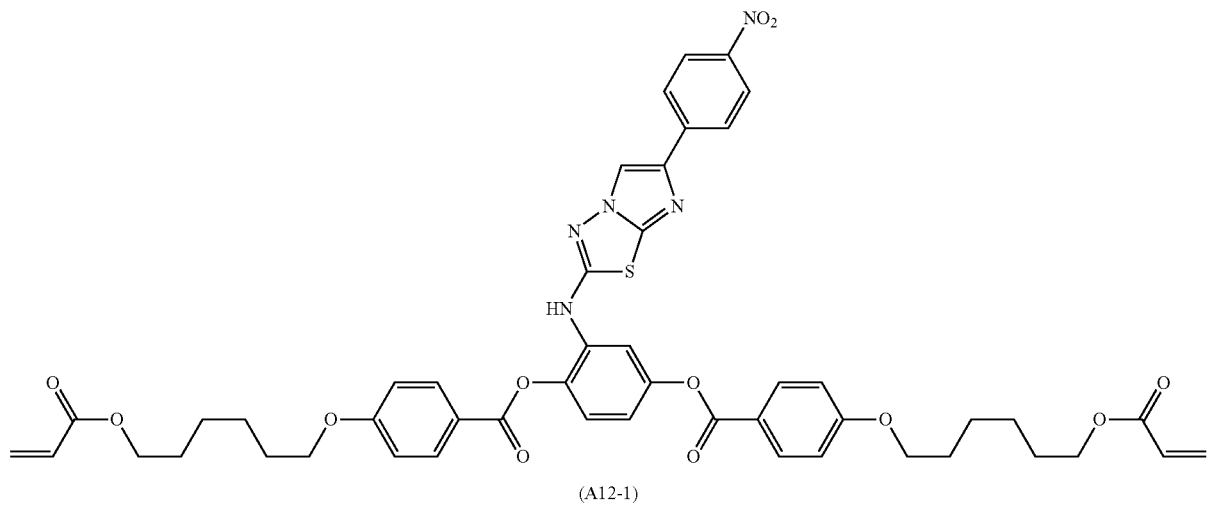 [SMILES: C=CC(=O)OCCCCCCOc1ccc(C(=O)Oc2ccc(OC(=O)c3ccc(OCCCCCCOC(=O)C=C)cc3)c(Nc3nn4cc(-c5ccc([N+](=O)[O-])cc5)nc4s3)c2)cc1]

(A12-1)

A reaction vessel was charged with a compound represented by the formula (A12-1-1), a compound represented by the formula (A12-1-2), and water. After heating with stirring, the mixture was quenched with aqueous sodium hydrogen carbonate. After common posttreatment, purification by column chromatography yielded a compound represented by the formula (A12-1-3).

A reaction vessel was charged with the compound represented by the formula (A12-1-3) and a compound represented by the formula (A12-1-4), and was heated with microwave irradiation. After common posttreatment, purification by column chromatography yielded a compound represented by the formula (A12-1-5).

A reaction vessel was charged with the compound represented by the formula (A12-1-5) and dichloromethane. After the addition of boron tribromide and stirring, common posttreatment yielded a compound represented by the formula (A12-1-6).

A reaction vessel was charged with the compound represented by the formula (A12-1-6), the compound represented by the formula (A12-1-7), N,N-dimethylaminopyridine, and dichloromethane. Diisopropyl carbodiimide was added, and the mixture was stirred. After common posttreatment, purification by column chromatography yielded a compound represented by the formula (A12-1).

MS(m/z): 918 [M$^+$+1]

Example 4 Production of a Compound Represented by the Formula (A13-2)

[Chem. 215]

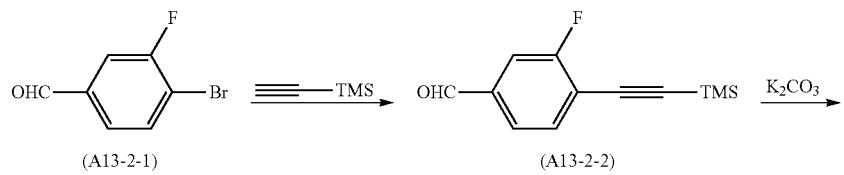

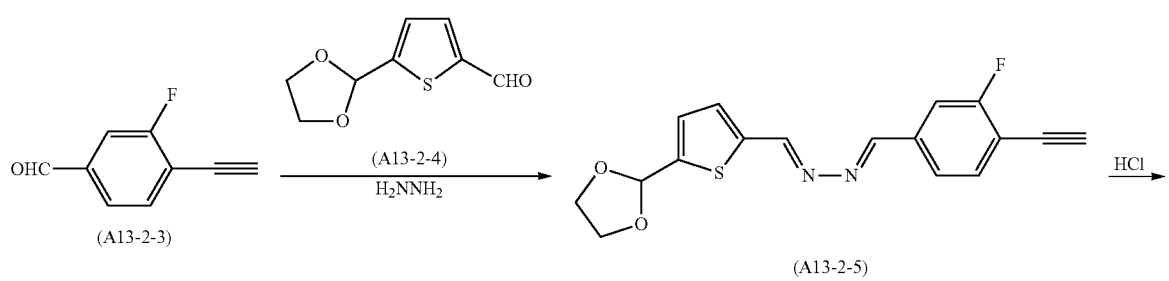

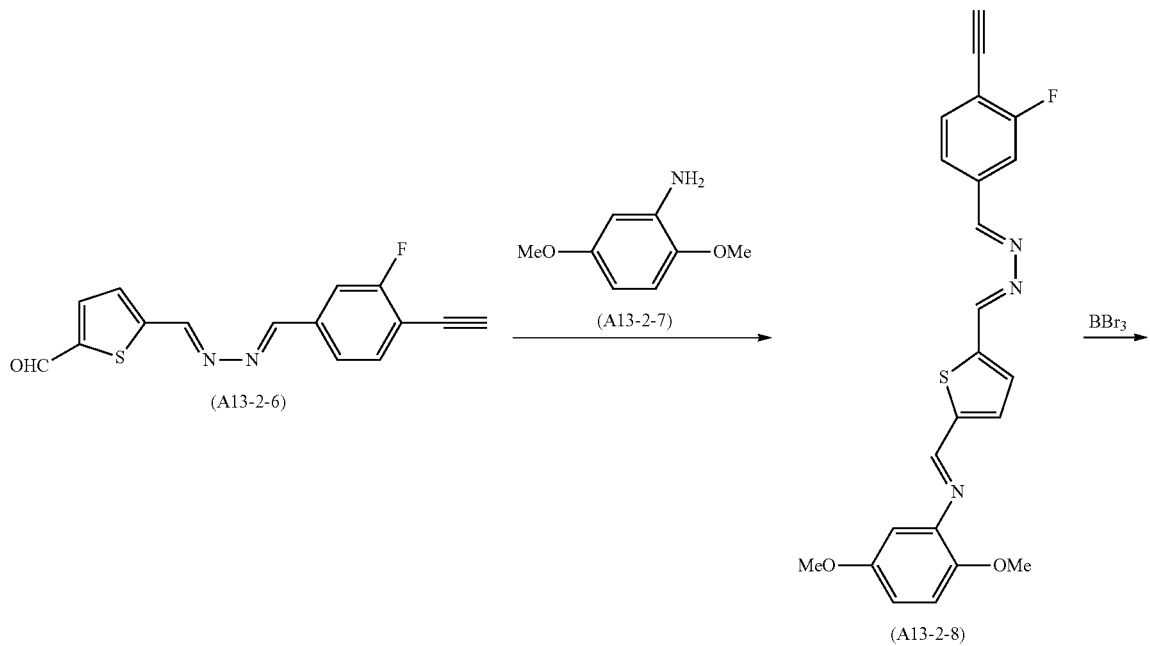
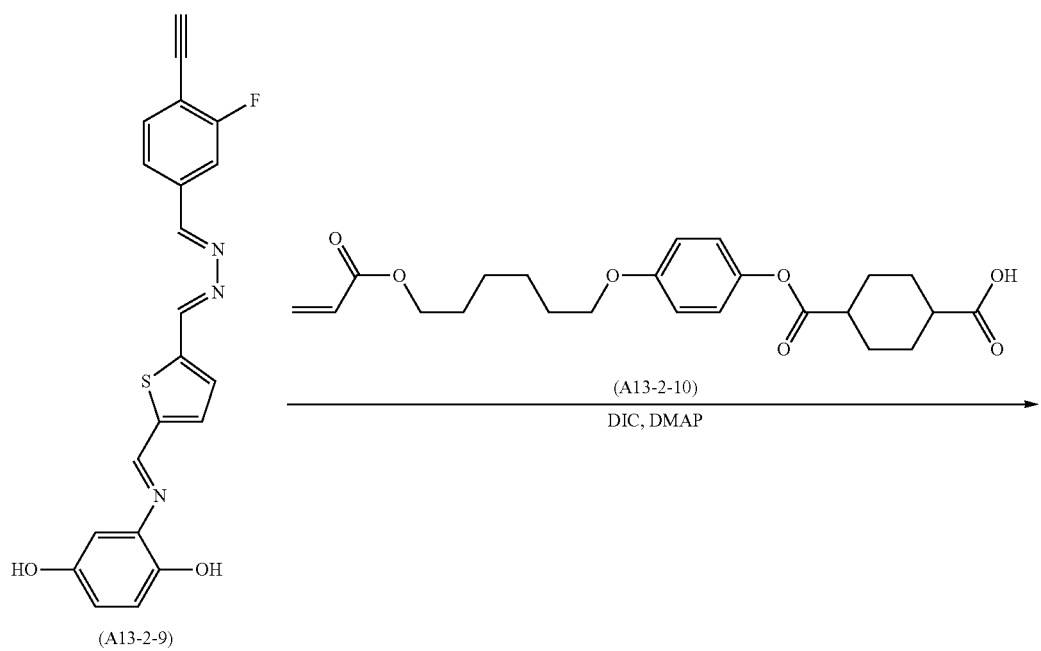

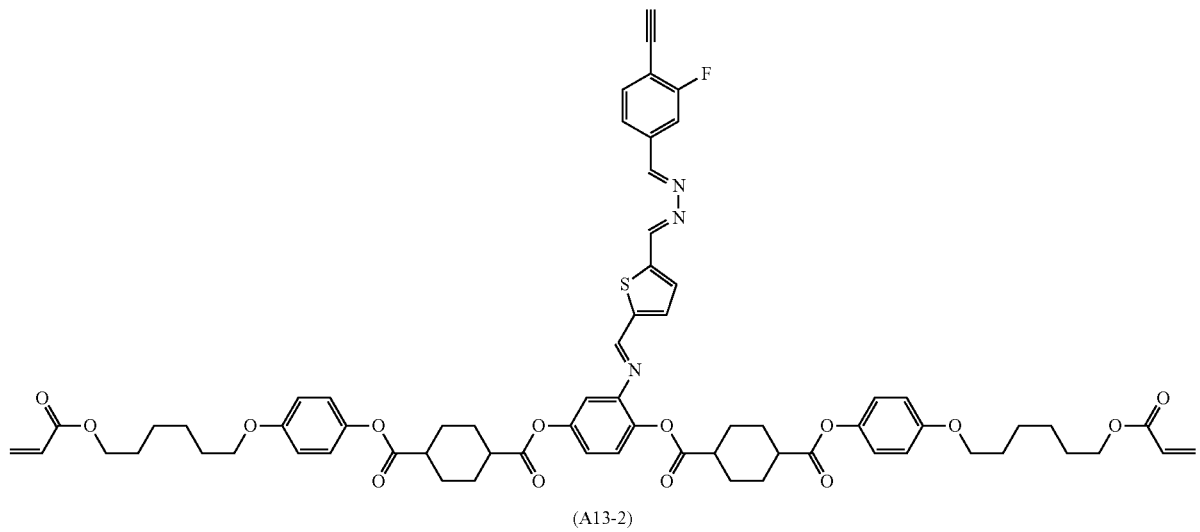 [SMILES: C#Cc1ccc(/C=N/N=C/c2ccc(/C=N/c3cc(OC(=O)C4CCC(C(=O)Oc5ccc(OCCCCCCOC(=O)C=C)cc5)CC4)ccc3OC(=O)C3CCC(C(=O)Oc4ccc(OCCCCCCOC(=O)C=C)cc4)CC3)s2)cc1F]

(A13-2)

A reaction vessel in an inert atmosphere was charged with a compound represented by the formula (A13-2-1), trimethylsilylacetylene, tetrakis(triphenylphosphine) palladium (0), copper (I) iodide, triethylamine, and N,N-dimethylformamide, and was heated with stirring. After common posttreatment, purification by column chromatography yielded a compound represented by the formula (A13-2-2).

A reaction vessel was charged with the compound represented by the formula (A13-2-2), potassium carbonate, and methanol, and was stirred. After common posttreatment, purification by column chromatography yielded a compound represented by the formula (A13-2-3).

A reaction vessel was charged with the compound represented by the formula (A13-2-3), a compound represented by the formula (A13-2-4), hydrazine monohydrate, and ethanol, and was heated with stirring. After common posttreatment, purification by column chromatography yielded a compound represented by the formula (A13-2-5).

A reaction vessel was charged with the compound represented by the formula (A13-2-5), tetrahydrofuran, and hydrochloric acid, and was stirred. After common posttreatment, purification by column chromatography yielded a compound represented by the formula (A13-2-6).

A reaction vessel was charged with the compound represented by the formula (A13-2-6), a compound represented by the formula (A13-2-7), and ethanol, and was stirred. After common posttreatment, purification by column chromatography yielded a compound represented by the formula (A13-2-8).

A reaction vessel was charged with the compound represented by the formula (A13-2-8) and dichloromethane. After the addition of boron tribromide and stirring, common posttreatment yielded a compound represented by the formula (A13-2-9).

A compound represented by the formula (A13-2-10) was produced by a method described in WO 2011/068138 A1. A reaction vessel was charged with the compound represented by the formula (A13-2-9), the compound represented by the formula (A13-2-10), N,N-dimethylaminopyridine, and dichloromethane. Diisopropyl carbodiimide was added, and the mixture was stirred. After common posttreatment, purification by column chromatography yielded a compound represented by the formula (A13-2).

MS(m/z): 1192 [M$^+$+1]

Example 5 Production of a Compound Represented by the Formula (A14-1)

[Chem. 216]

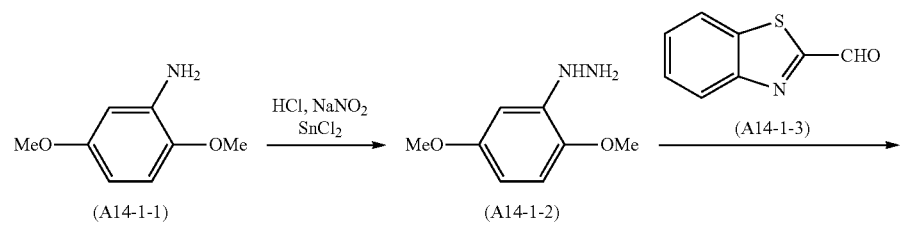

-continued

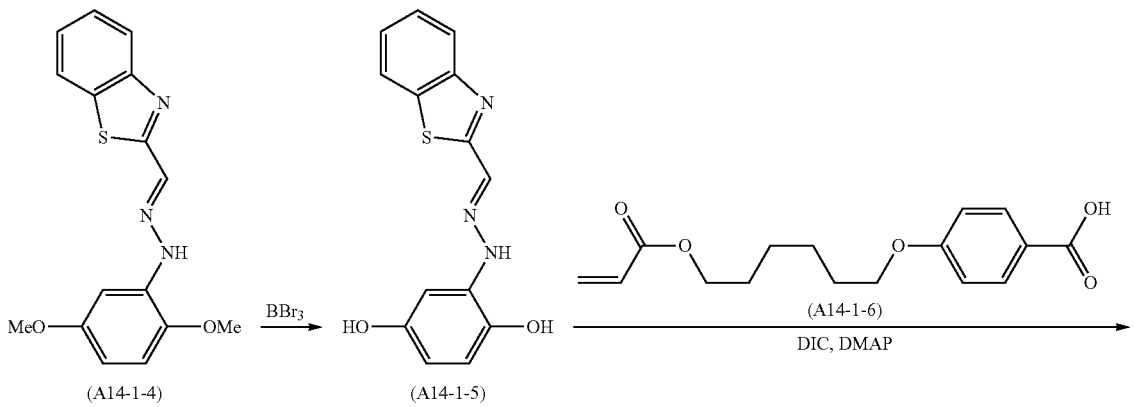

(A14-1-4) → (A14-1-5) BBr₃

(A14-1-6) DIC, DMAP

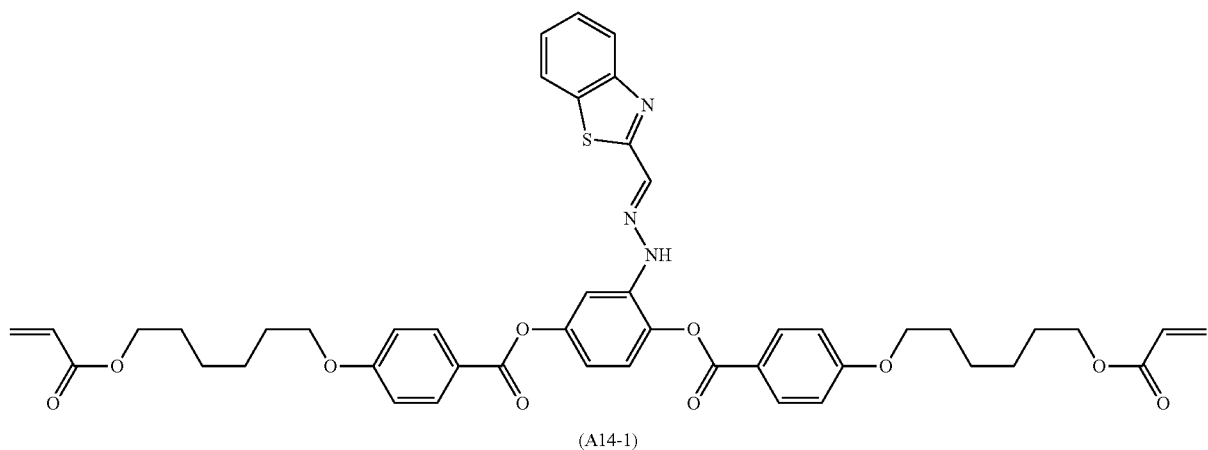

(A14-1)

A reaction vessel was charged with a compound represented by the formula (A14-1-1), acetic acid, and concentrated hydrochloric acid. Aqueous sodium nitrite was added while ice cooling, and the mixture was stirred. A solution of tin (II) chloride dihydrate dissolved in concentrated hydrochloric acid was added dropwise, and the mixture was stirred. Common posttreatment yielded a compound represented by the formula (A14-1-2).

A reaction vessel was charged with the compound represented by the formula (A14-1-2), a compound represented by the formula (A14-1-3), (±)-10-camphorsulfonic acid, and ethanol, and was stirred. After common posttreatment, purification by column chromatography yielded a compound represented by the formula (A14-1-4).

A reaction vessel was charged with the compound represented by the formula (A14-1-4) and dichloromethane. After the addition of boron tribromide and stirring, common posttreatment yielded a compound represented by the formula (A14-1-5).

A reaction vessel was charged with the compound represented by the formula (A14-1-5), a compound represented by the formula (A14-1-6), N,N-dimethylaminopyridine, and dichloromethane. Diisopropyl carbodiimide was added, and the mixture was stirred. After common posttreatment, purification by column chromatography yielded a compound represented by the formula (A14-1).

MS(m/z): 834 [M$^+$+1]

Example 6 Production of a Compound Represented by the Formula (A14-2)

cooling. A solution of a compound represented by the formula (A14-2-2) in pyridine was added dropwise while ice cooling, and the mixture was stirred. After common posttreatment, purification by recrystallization yielded a compound represented by the formula (A14-2-3).

A reaction vessel was charged with the compound represented by the formula (A14-2-3) and dichloromethane. After the addition of boron tribromide and stirring, common posttreatment yielded a compound represented by the formula (A14-2-4).

A compound represented by the formula (A14-2-5) was produced by a method described in Japanese Unexamined Patent Application Publication No. 2010-100541. A reaction vessel was charged with the compound represented by the formula (A14-2-4), the compound represented by the for-

[Chem. 217]

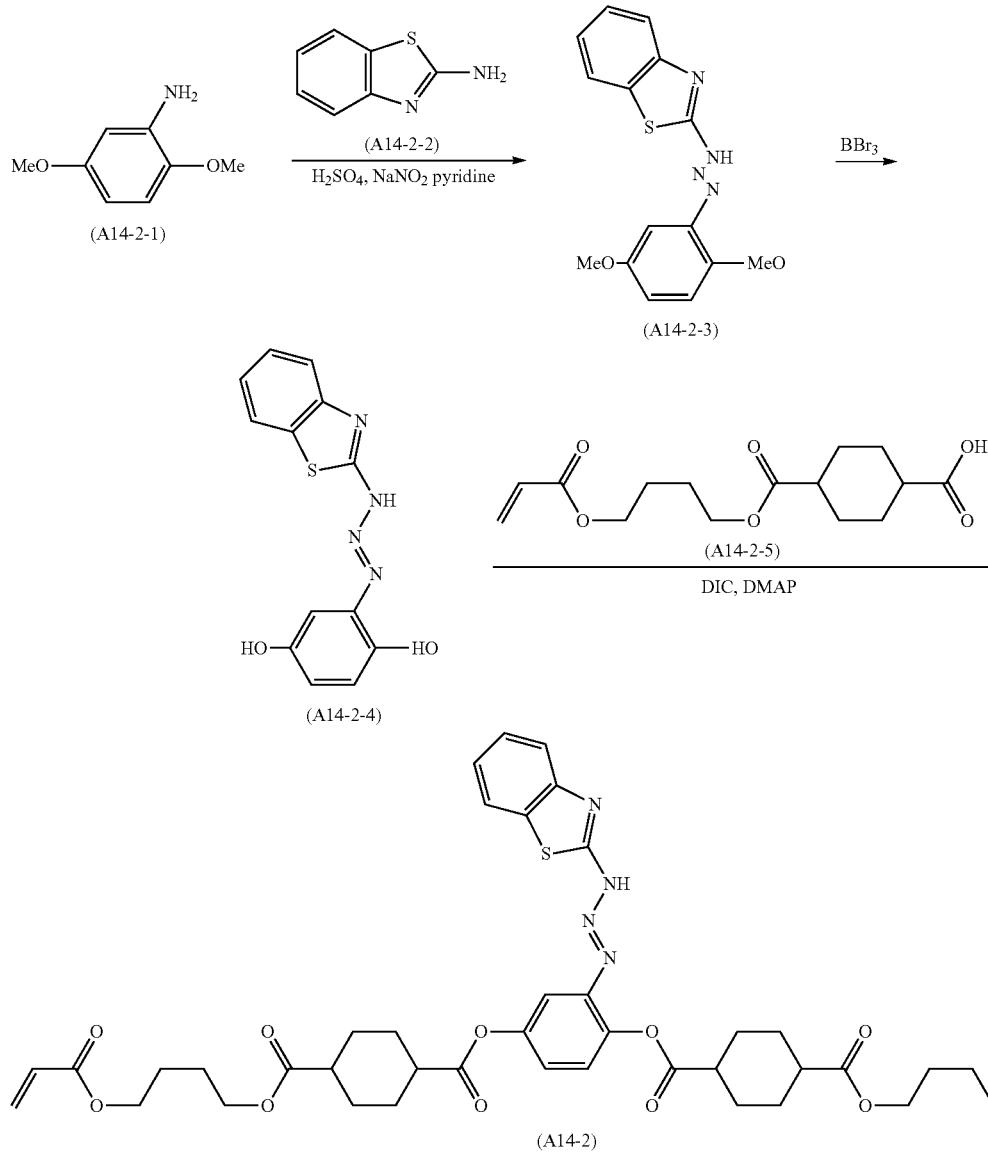

A reaction vessel was charged with a compound represented by the formula (A14-2-1), concentrated sulfuric acid, and water. Aqueous sodium nitrite was added while ice mula (A14-2-5), N,N-dimethylaminopyridine, and dichloromethane. Diisopropyl carbodiimide was added, and the mixture was stirred. After common posttreatment, purification by column chromatography yielded a compound represented by the formula (A14-2).

MS(m/z): 847 [M⁺+1]

Example 7 Production of a Compound Represented by the Formula (A141-1)

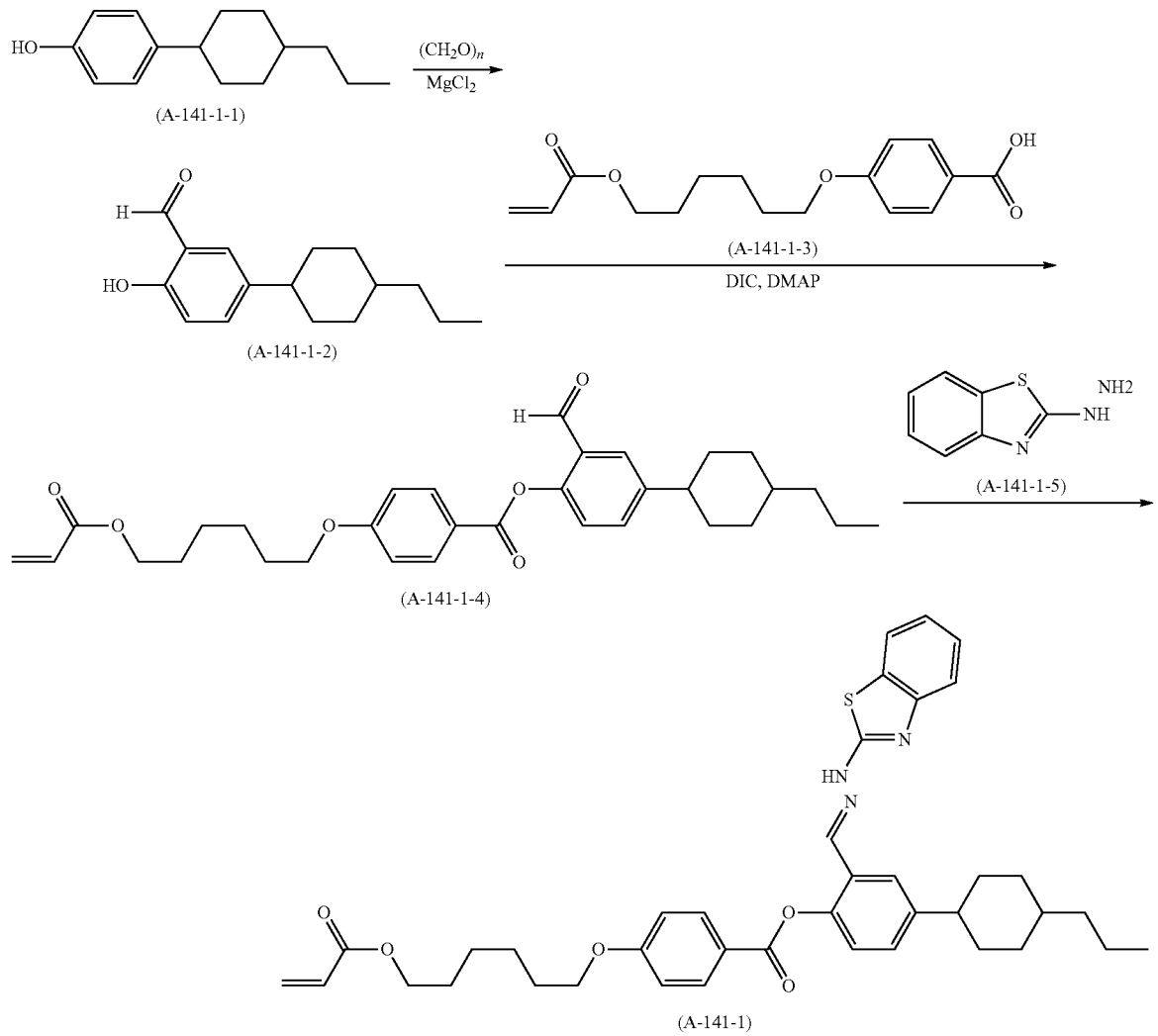

A reaction vessel was charged with 5.00 g of a compound represented by the formula (A-141-1-1), 3.27 g of magnesium chloride, 2.06 g of paraformaldehyde, 20 mL of triethylamine, and 80 mL of acetonitrile. Paraformaldehyde was appropriately added at 60° C. while stirring. The mixture was diluted with ethyl acetate and was washed with hydrochloric acid and saline. Purification by column chromatography yielded 5.36 g of a compound represented by the formula (A-141-1-2).

A reaction vessel was charged with 2.00 g of the compound represented by the formula (A-141-1-2), 2.37 g of a compound represented by the formula (A-141-1-3), 0.05 g of N,N-dimethylaminopyridine, and 30 mL of dichloromethane. 1.23 g of diisopropyl carbodiimide was added dropwise, and the mixture was stirred at room temperature. After a precipitate was filtered out, purification of the filtrate by column chromatography and recrystallization yielded 3.17 g of a compound represented by the formula (A-141-1-4).

A reaction vessel was charged with 2.00 g of the compound represented by the formula (A-141-1-4), 0.63 g of a compound represented by the formula (A-141-1-5), 0.05 g of (±)-10-camphorsulfonic acid, 10 mL of tetrahydrofuran, and 10 mL of ethanol. After stirring, the solvent was distilled off, and the mixture was dispersed and washed in methanol. Purification by column chromatography and recrystallization yielded 1.80 g of a compound represented by the formula (A-141-1).

Transition temperature (heating rate: 5° C./min): C 105 N 150 I

¹H NMR (CDCl₃) δ 0.93 (t, 3H), 1.10 (q, 2H), 1.25 (m, 2H), 1.37 (m, 3H), 1.46-1.59 (m, 6H), 1.74 (quin, 2H), 1.81-1.98 (m, 6H), 2.56 (m, 1H), 4.03 (t, 2H), 4.19 (t, 2H), 5.83 (dd, 1H), 6.13 (dd, 1H), 6.41 (dd, 1H), 6.87 (d, 2H), 7.08 (t, 1H), 7.12 (d, 1H), 7.20 (t, 1H), 7.28 (dd, 1H), 7.45 (dd, 1H), 7.58 (d, 1H), 7.84 (s, 1H), 8.06 (m, 3H) ppm.

MS (m/z): 668 [M⁺+1]

Example 8 Production of a Compound Represented by the Formula (A141-2)
[Chem. 219]
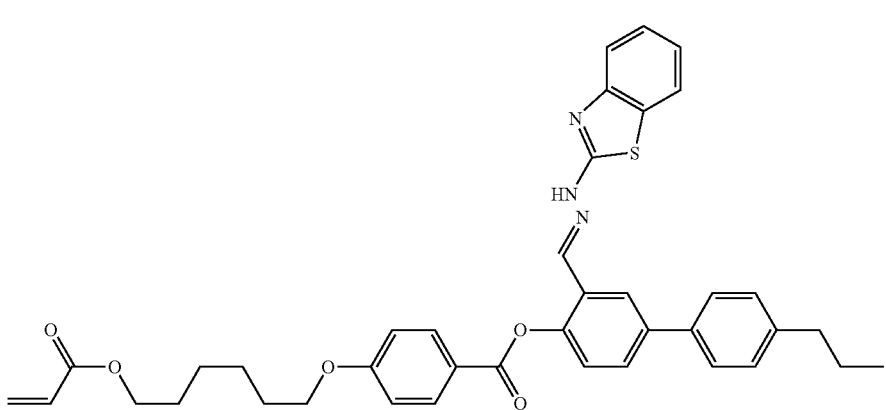
(A141-2)
A compound represented by the formula (A141-2) was produced in the manner described above.
Transition temperature (heating rate: 5° C./min): C 79 N 137 I
$^1$H NMR (CDCl$_3$) δ 1.01 (t, 3H), 1.48 (m, 4H), 1.69-1.79 (m, 6H), 2.67 (t, 2H), 3.95 (m, 2H), 4.18 (t, 2H), 5.83 (dd, 1H), 6.13 (dd, 1H), 6.41 (dd, 1H), 6.83 (m, 2H), 7.03-7.68 (m, 10H), 7.97-8.30 (m, 4H) ppm.
MS (m/z): 662 [M$^+$+1]
Example 9 Production of a Compound Represented by the Formula (A141-3)
[Chem. 220]
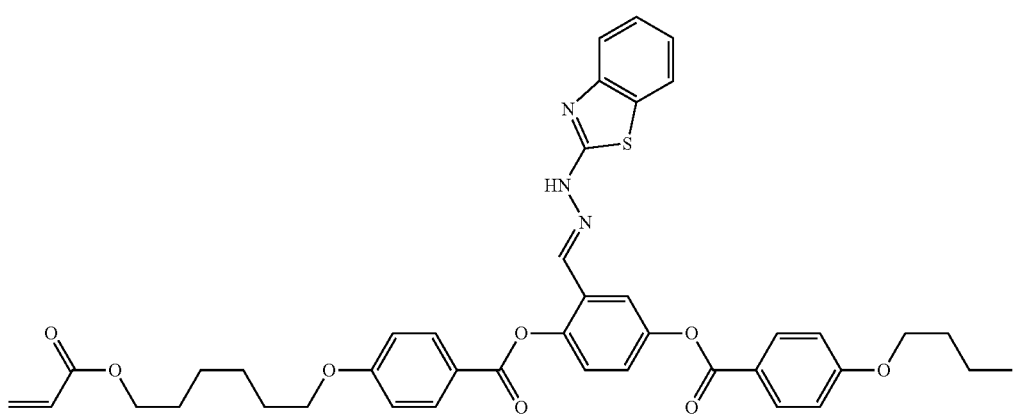
(A141-3)

A compound represented by the formula (A141-3) was produced in the manner described above.

Transition temperature (heating rate: 5° C./min): C 156 N 173 I $^1$H NMR (CDCl$_3$) δ 1.02 (t, 3H), 1.40-1.92 (m, 12H), 4.00 (br, 2H), 4.09 (t, 2H), 4.18 (t, 2H), 5.82 (dd, 1H), 6.13 (dd, 1H), 6.41 (dd, 1H), 6.64-6.13 (m, 14H), 8.19 (d, 2H) ppm.

MS (m/z): 736 [M$^+$+1]

Example 10 Production of a Compound Represented by the Formula (A141-4)

[Chem. 221]

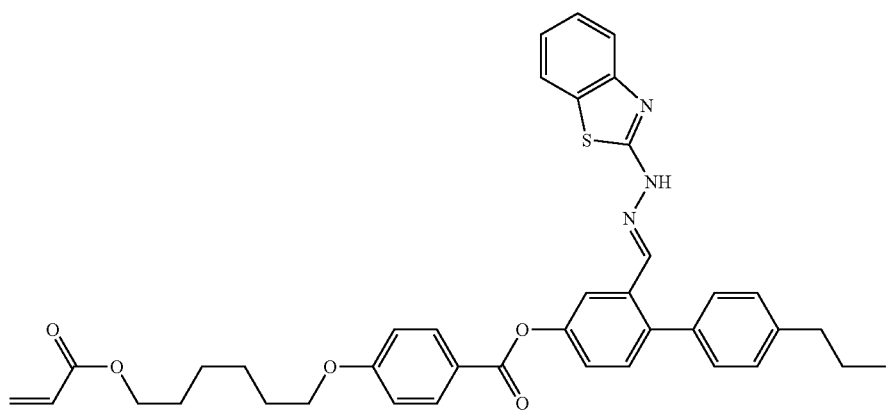

(A141-4)

A compound represented by the formula (A141-4) was produced in the manner described above.

Transition temperature (heating rate: 5° C./min): C 79 N 112 I $^1$H NMR (CDCl$_3$) δ 0.96 (t, 3H), 1.43-1.78 (m, 8H), 1.87 (quin, 2H), 2.60 (t, 2H), 4.08 (t, 2H), 4.20 (t, 2H), 5.83 (dd, 1H), 6.13 (dd, 1H), 6.42 (dd, 1H), 7.01 (d, 2H), 7.09 (t, 1H), 7.17-7.29 (m, 7H), 7.37 (d, 1H), 7.60 (d, 1H), 7.91 (s, 2H), 8.21 (d, 2H) ppm.

MS (m/z): 662 [M$^+$+1]

Example 11 Production of a Compound Represented by the Formula (A141-5)

[Chem. 222]

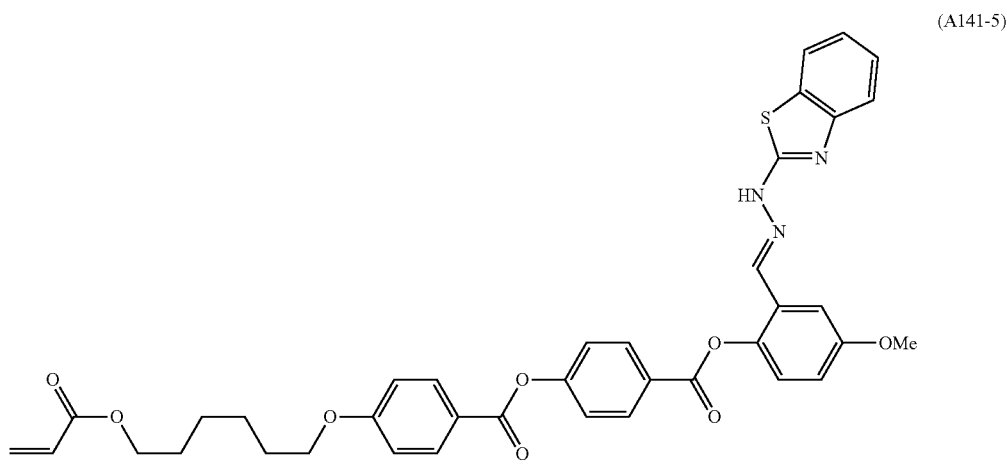

(A141-5)

A compound represented by the formula (A141-5) was produced in the manner described above.

Transition temperature (heating rate: 5° C./min): C 178 N 180 I $^1$H NMR (CDCl$_3$) δ 1.44-1.60 (m, 4H), 1.74 (quin, 2H), 1.86 (quin, 2H), 3.89 (s, 3H), 4.07 (t, 2H), 4.20 (t, 2H), 5.83 (dd, 1H), 6.14 (dd, 1H), 6.42 (dd, 1H), 6.99 (m, 3H), 7.09 (t, 1H), 7.13 (d, 1H), 7.19 (t, 1H), 7.27 (d, 2H), 7.44 (d, 1H), 7.54 (d, 1H), 7.60 (d, 1H), 8.03 (s, 1H), 8.17 (d, 4H) ppm.

MS (m/z): 694 [M$^+$+1]

Example 12 Production of a Compound Represented by the Formula (A141-6)

[Chem. 223]

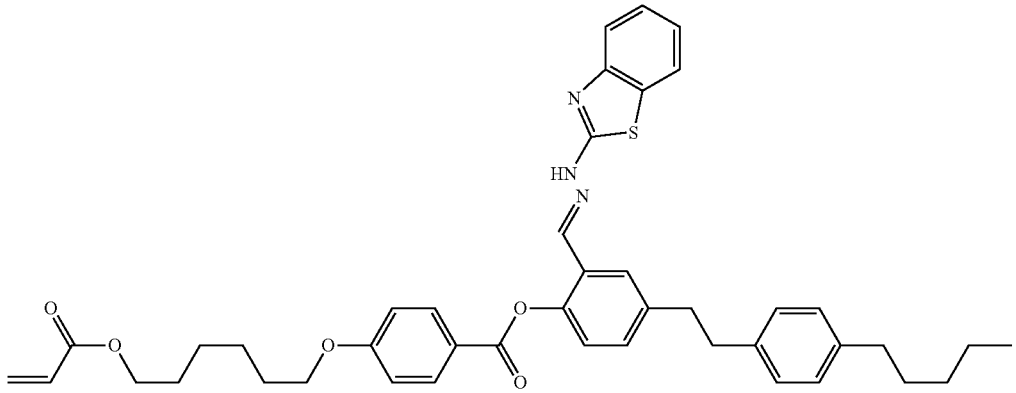

(A141-6)

A compound represented by the formula (A141-6) was produced in the manner described above.

Transition temperature (heating rate: 5° C./min): C 62 N 95 poly $^1$H NMR (CDCl$_3$) δ 0.89 (t, 3H), 1.33 (m, 4H), 1.43-1.57 (m, 2H), 1.61 (quin, 2H), 1.73 (quin, 2H), 1.85 (quin, 2H), 2.59 (t, 2H), 2.97 (m, 4H), 4.03 (t, 2H), 4.19 (m, 2H), 5.83 (dd, 1H), 6.13 (dd, 1H), 6.41 (dd, 1H), 6.87 (d, 2H), 7.04-7.29 (m, 8H), 7.44 (d, 1H), 7.58 (d, 1H), 7.85 (s, 1H), 8.05 (m, 3H) ppm.

MS (m/z): 718 [M$^+$+1]

Example 13 Production of a Compound Represented by the Formula (A141-7)

[Chem. 224]

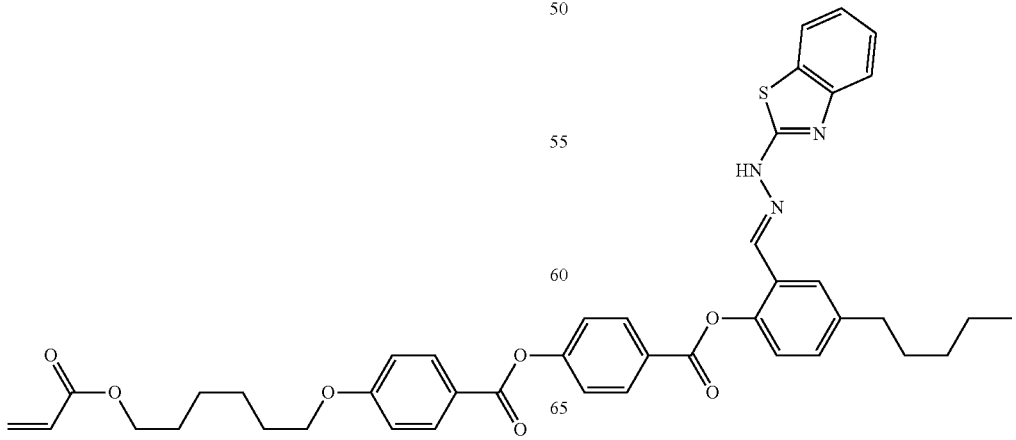

(A141-7)

A compound represented by the formula (A141-7) was produced in the manner described above.

Transition temperature (heating rate: 5° C./min): C 147 N 153 I $^1$H NMR (CDCl$_3$) δ 0.93 (t, 3H), 1.37 (m, 4H), 1.46-1.59 (m, 4H), 1.63-1.78 (m, 4H), 1.86 (quin, 2H), 2.68 (t, 2H), 4.07 (t, 2H), 4.19 (t, 2H), 5.84 (dd, 1H), 6.14 (dd, 1H), 6.42 (dd, 1H), 7.00 (d, 2H), 7.09 (t, 1H), 7.12 (d, 1H), 7.19 (t, 1H), 7.23-7.33 (m, 3H), 7.45 (d, 1H), 7.61 (d, 1H), 7.80 (d, 1H), 8.07 (s, 1H), 8.14-8.23 (m, 4H) ppm.

MS (m/z): 734 [M$^+$+1]

Example 14 Production of a Compound Represented by the Formula (A141-8)

[Chem. 225]

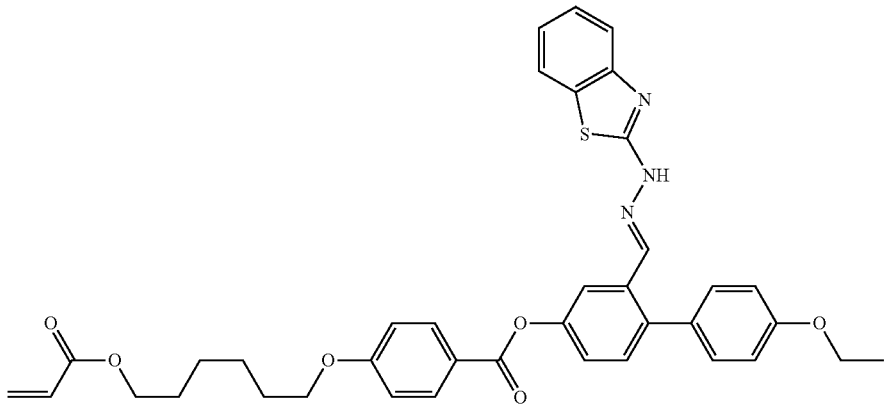

(A141-8)

A compound represented by the formula (A141-8) was produced in the manner described above.

Transition temperature (heating rate: 5° C./min): C 169 N 178 I $^1$H NMR (CDCl$_3$) δ 1.43 (t, 3H), 1.47-1.60 (m, 4H), 1.75 (quin, 2H), 1.87 (m, 2H), 3.99 (q, 2H), 4.08 (t, 2H), 4.20 (t, 2H), 5.83 (dd, 1H), 6.14 (dd, 1H), 6.42 (dd, 1H), 6.85 (d, 2H), 7.01 (d, 2H), 7.08 (t, 1H), 7.14 (t, 1H), 7.20 (t, 3H), 7.25 (dd, 1H), 7.35 (d, 1H), 7.60 (d, 1H), 7.90 (d, 1H), 7.94 (s, 1H) 8.21 (d, 2H) ppm.

MS (m/z): 664 [M$^+$+1]

Example 15 Production of a Compound Represented by the Formula (A141-9)

[Chem. 226]

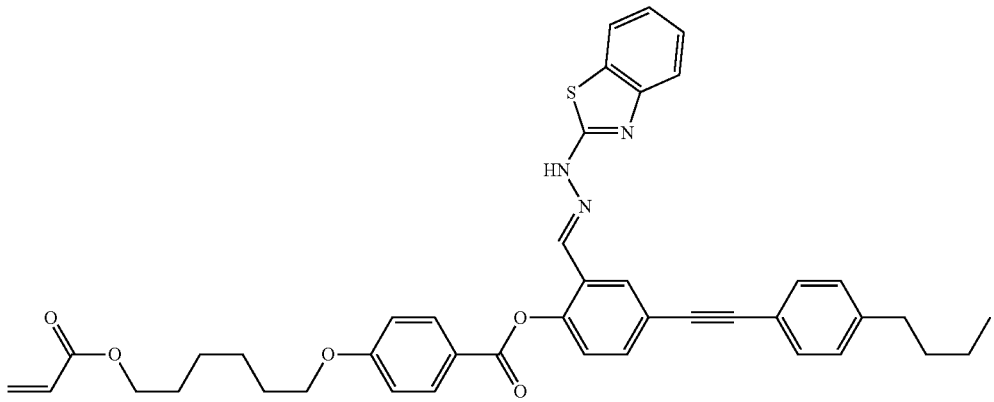

(A141-9)

A compound represented by the formula (A141-9) was produced in the manner described above.

Transition temperature (heating rate: 5° C./min): C 98 N 157 I $^1$H NMR (CDCl$_3$) δ 0.94 (t, 3H), 1.31-1.76 (m, 12H), 2.66 (t, 2H), 3.89 (t, 2H), 4.12 (t, 2H), 5.80 (dd, 1H), 6.13 (dd, 1H), 6.41 (dd, 1H), 6.50-8.20 (m, 16H) ppm.

MS (m/z): 700 [M$^+$+1]

Example 16 Production of a Compound Represented by the Formula (A141-10)

[Chem. 227]

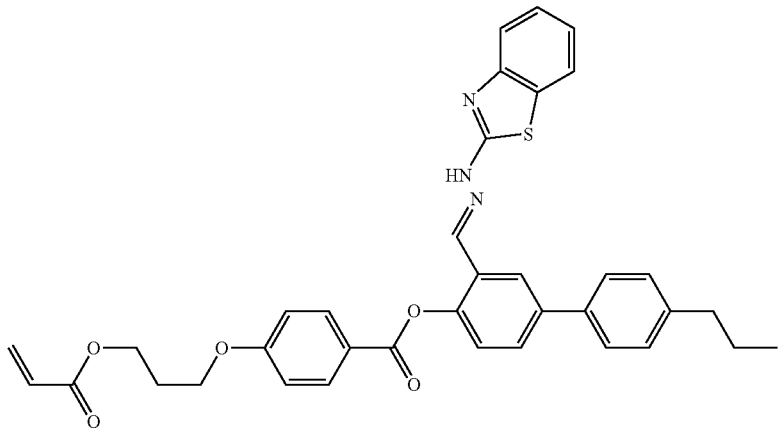

(A141-10)

A compound represented by the formula (A141-10) was produced in the manner described above.

Transition temperature (heating rate: 5° C./min): C 164 I $^1$H NMR (DMSO-d$_6$) δ 0.94 (t, 3H), 1.65 (q, 2H), 2.15 (t, 2H), 2.63 (t, 2H), 4.22 (t, 2H), 4.30 (t, 2H), 5.96 (d, 1H), 6.20 (q, 1H), 6.36 (d, 1H), 7.10 (t, 1H), 7.18 (d, 2H), 7.28 (t, 1H), 7.35 (d, 2H), 7.52 (d, 2H), 7.63 (d, 2H), 7.23 (t, 2H), 8.15 (t, 3H), 8.25 (s, 1H) ppm.

MS (m/z): 620 [M$^+$+1]

Example 17 Production of a Compound Represented by the Formula (A141-11)

[Chem. 228]

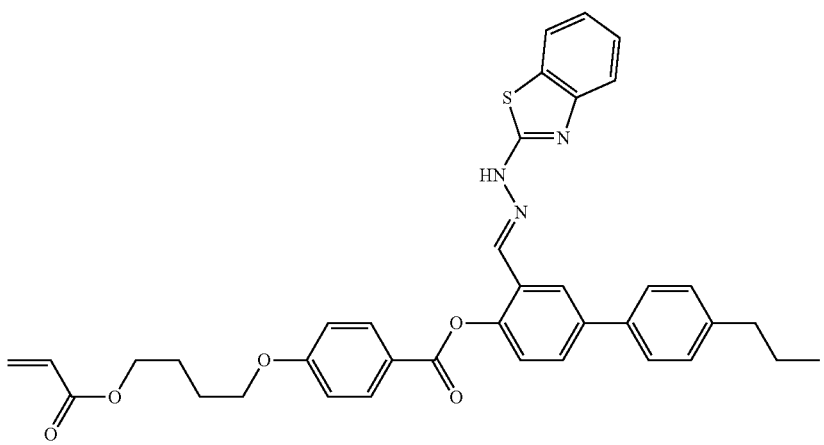

(A141-11)

A compound represented by the formula (A141-11) was produced in the manner described above.

Transition temperature (heating rate: 5° C./min): C 155 N 158 I $^1$H NMR (CDCl$_3$) δ 1.02 (t, 3H), 1.73 (q, 3H), 1.86 (m, 4H), 2.68 (t, 2H), 3.96 (m, 2H), 4.24 (m, 2H), 5.85 (d, 1H), 6.14 (dd, 1H), 6.43 (d, 1H), 6.80 (m, 2H), 7.08-7.33 (m, 5H), 7.44 (m, 1H), 7.59 (m, 4H), 8.01 (m, 2H), 8.23 (m, 2H) ppm.

MS (m/z): 634 [M$^+$+1]

Example 18 Production of a Compound Represented by the Formula (A141-12)

[Chem. 229]

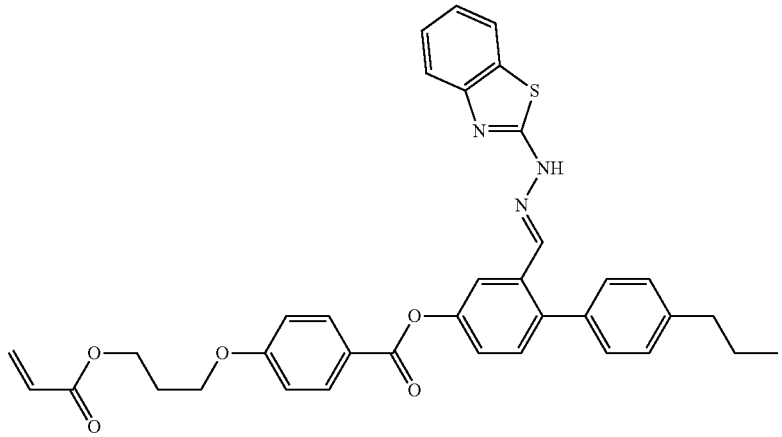

(A141-12)

A compound represented by the formula (A141-12) was produced in the manner described above.

Transition temperature (heating rate: 5° C./min): C 154 I $^1$H NMR (CDCl$_3$) δ 0.95 (tt, 3H), 1.63 (m, 2H), 2.24 (quin, 2H), 2.59 (m, 2H), 4.19 (t, 2H), 4.41 (t, 2H), 5.85 (dd, 1H), 6.14 (dd, 1H), 6.43 (dd, 1H), 7.02 (d, 2H), 7.09-7.28 (m, 8H), 7.37 (d, 1H), 7.60 (d, 1H), 7.91 (m, 2H), 8.22 (d, 2H) ppm.

MS (m/z): 620 [M$^+$+1]

Example 19 Production of a Compound Represented by the Formula (A141-13)

[Chem. 230]

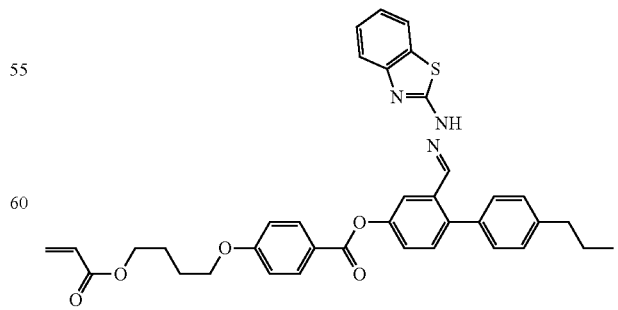

(A141-13)

A compound represented by the formula (A141-13) was produced in the manner described above.

Transition temperature (heating rate: 5° C./min): C 146 N 149 I $^1$H NMR (CDCl$_3$) δ 0.95 (t, 3H), 1.63 (m, 2H), 1.93 (m, 4H), 2.58 (t, 2H), 4.12 (t, 2H), 4.28 (t, 2H), 5.85 (dd, 1H), 6.14 (dd, 1H), 6.43 (dd, 1H), 7.01 (d, 2H), 7.07-7.29 (m, 8H), 7.36 (d, 1H), 7.60 (d, 1H), 7.91 (m, 2H), 8.21 (d, 2H) ppm.

MS (m/z): 634 [M$^+$+1]

Example 20 Production of a Compound Represented by the Formula (A141-14)

[Chem. 231]

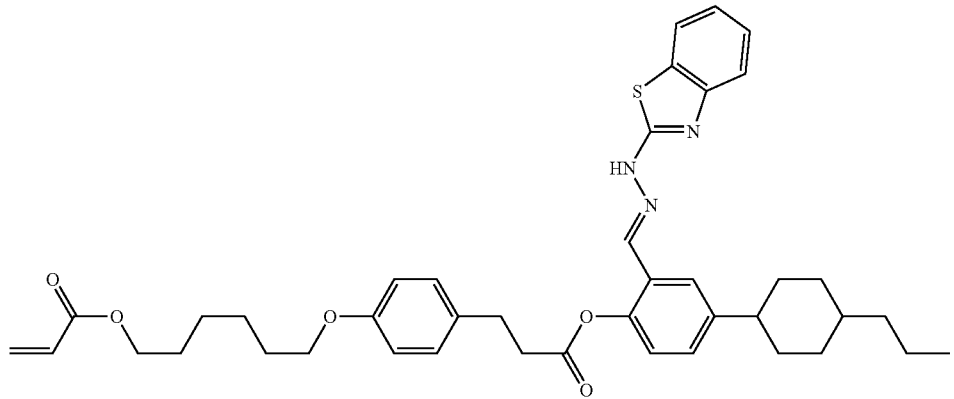

(A141-14)

A compound represented by the formula (A141-14) was produced in the manner described above.

Transition temperature (heating rate, cooling rate: 5° C./min): C 128 (N 80) I $^1$H NMR (CDCl$_3$) δ 0.92 (t, 3H), 1.07 (m, 2H), 1.20-1.50 (m, 11H), 1.66 (quin, 2H), 1.78 (quin, 2H), 1.89 (m, 4H), 2.51 (tt, 1H), 2.73 (t, 2H), 2.91 (t, 2H), 3.95 (t, 2H), 4.14 (t, 2H), 5.81 (dd, 1H), 6.12 (dd, 1H), 6.39 (dd, 1H), 6.85 (d, 2H), 6.93 (d, 1H), 7.09 (d, 2H), 7.14 (t, 1H), 7.21 (dd, 1H), 7.33 (t, 1H), 7.54 (d, 1H), 7.58 (s, 1H), 7.66 (d, 1H), 7.80 (d, 1H) ppm.

MS (m/z): 696 [M$^+$+1]

Example 21 Production of a Compound Represented by the Formula (A141-15)

[Chem. 232]

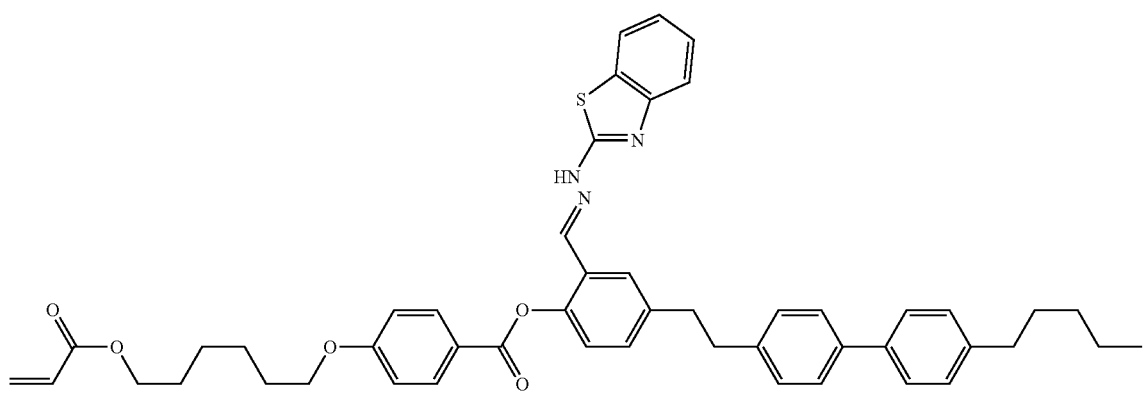

(A141-15)

A compound represented by the formula (A141-15) was produced in the manner described above.

MS (m/z): 794 [M$^+$+1]

Example 22 Production of a Compound Represented by the Formula (A141-16)

[Chem. 233]

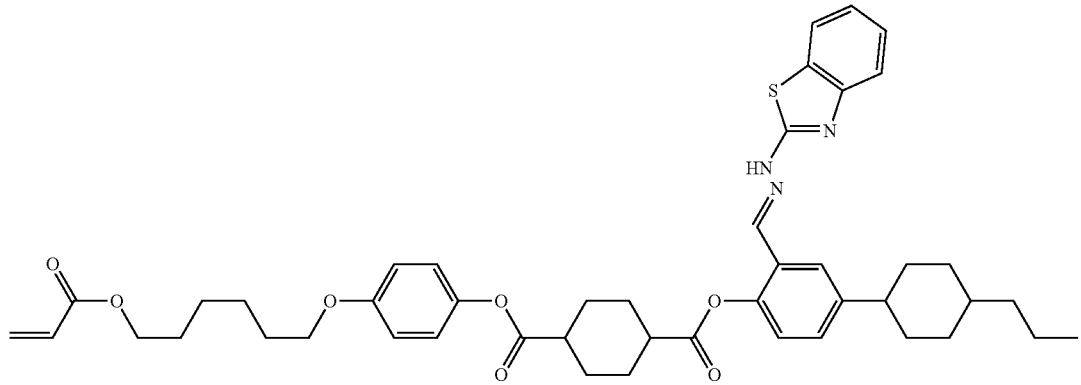

(A141-16)

A compound represented by the formula (A141-16) was produced in the manner described above.

Transition temperature (heating rate: 5° C./min): C 117 N 220 I $^1$H NMR (CDCl$_3$) δ 0.92 (t, 3H), 1.07 (q, 2H), 1.24-2.06 (m, 27H), 2.35 (m, 2H), 2.55 (t, 1H), 3.95 (t, 2H), 4.18 (t, 2H), 5.83 (dd, 1H), 6.13 (dd, 1H), 6.42 (dd, 1H), 6.88 (d, 2H), 6.98 (m, 3H), 7.19-7.26 (m, 2H), 7.35 (m, 1H), 7.51 (m, 1H), 7.68 (m, 1H), 7.89 (m, 1H), 8.08 (m, 1H) ppm.

MS (m/z): 794 [M$^+$+1]

Example 23 Production of a Compound Represented by the Formula (A141-17)

[Chem. 234]

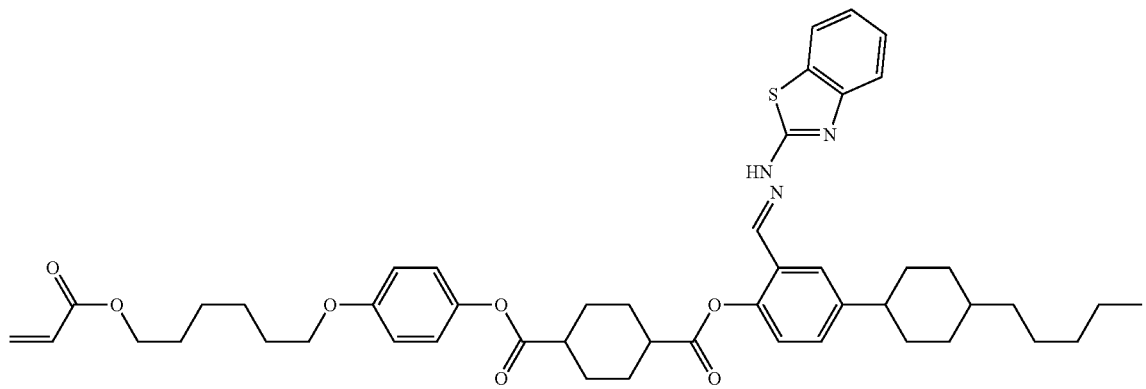

(A141-17)

A compound represented by the formula (A141-17) was produced in the manner described above.
Transition temperature (heating rate: 5° C./min): C 90 S 156 N $^1$H NMR (CDCl$_3$) δ 0.92 (t, 3H), 1.09 (m, 2H), 1.31 (m, 13H), 1.48 (m, 6H), 1.74 (t, 3H), 1.81 (t, 3H), 1.93 (m, 6H), 2.54 (t, 1H), 2.72 (t, 1H), 3.94 (t, 2H), 4.18 (t, 2H), 5.81 (d, 1H), 6.13 (q, 1H), 6.41 (d, 1H), 6.41 (d, 1H), 6.88 (d, 2H), 6.96 (d, 2H), 7.20 (t, 1H), 7.26 (d, 1H), 7.45 (d, 1H), 7.57 (d, 1H), 7.84 (s, 1H), 8.07 (d, 3H) ppm.

MS (m/z): 822 [M$^+$+1]

Example 24 Production of a Compound Represented by the Formula (A141-18)

[Chem. 235]

(A141-18)

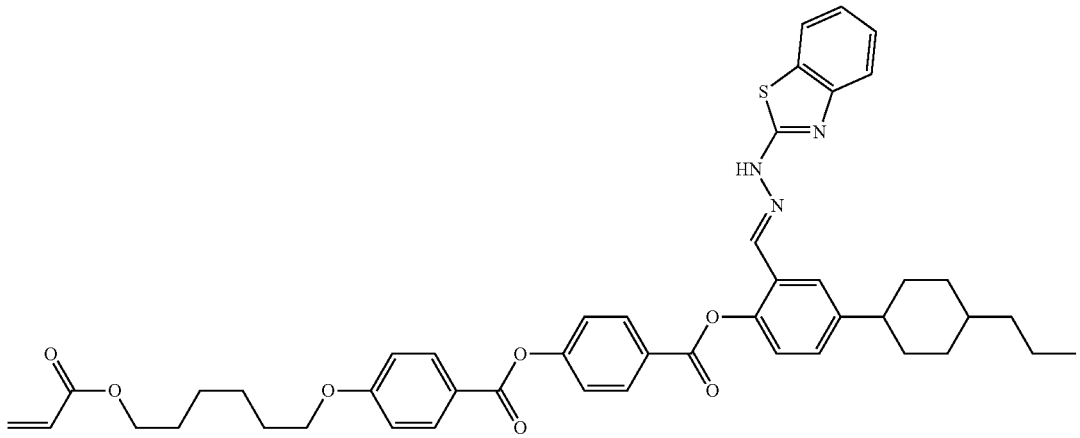

A compound represented by the formula (A141-18) was produced in the manner described above.
Transition temperature (heating rate: 5° C./min): C 64-77 N>220 I $^1$H NMR (CDCl$_3$) δ 0.92 (t, 3H), 1.07 (q, 2H), 1.23 (m, 2H), 1.37 (m, 3H), 1.48-1.60 (m, 6H), 1.74 (quin, 2H), 1.83-1.90 (m, 4H), 1.97 (d, 2H), 2.56 (tt, 1H), 4.07 (t, 2H), 4.19 (t, 2H), 5.83 (dd, 1H), 6.13 (dd, 1H), 6.42 (dd, 1H), 7.00 (d, 2H), 7.11 (q, 1H), 7.12 (d, 1H), 7.19-7.31 (m, 4H), 7.46 (d, 1H), 7.61 (d, 1H), 7.85 (d, 1H), 8.09 (s, 1H), 8.17 (m, 4H) ppm.

MS (m/z): 788 [M$^+$+1]

Example 25 Production of a Compound Represented by the Formula (A141-19)

[Chem. 236]

(A141-19)

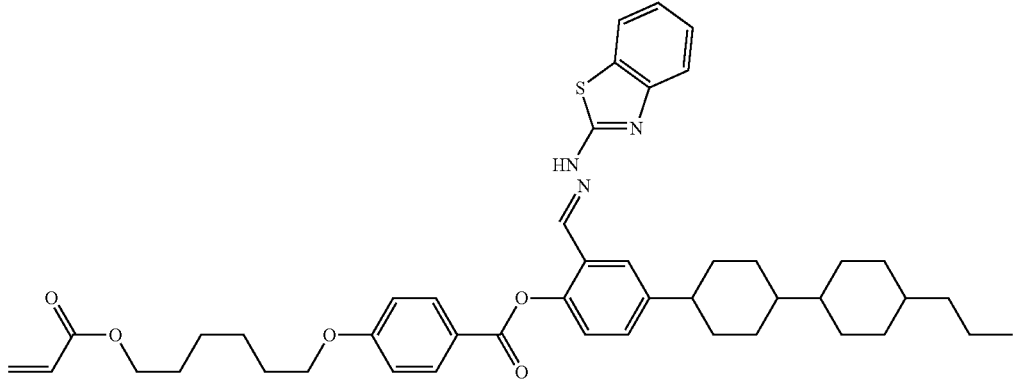

A compound represented by the formula (A141-19) was produced in the manner described above.

Transition temperature (heating rate: 5° C./min): C 190 N 260 I $^1$H NMR (CDCl$_3$) δ 0.89 (t, 1H), 1.05 (t, 2H), 1.31 (q, 2H), 1.50 (m, 6H), 1.74, (m, 15H), 2.54 (t, 1H), 4.03 (t, 2H), 4.19 (t, 2H), 5.81 (d, 1H), 6.13 (q, 1H), 6.41 (d, 1H), 6.43 (d, 1H), 7.09 (d, 2H), 7.11 (d, 2H), 7.20 (t, 1H), 7.26 (d, 1H), 7.45 (d, 1H), 7.57 (d, 1H), 7.84 (s, 1H), 8.07 (d, 3H) ppm.

MS (m/z): 750 [M$^+$+1]

Example 26 Production of a Compound Represented by the Formula (A141-20)

[Chem. 237]

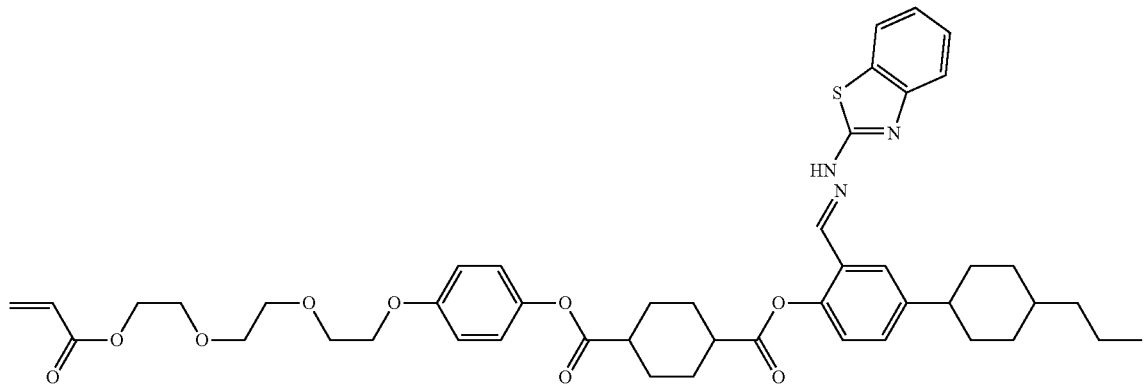

(A141-20)

A compound represented by the formula (A141-20) was produced in the manner described above.

Transition temperature (heating rate: 5° C./min): C 75-108 N 180 I $^1$H NMR (CDCl$_3$) δ 0.94 (t, 3H), 1.10 (m, 2H), 1.25 (m, 2H), 1.29-1.57 (m, 11H), 1.80-2.08 (m, 6H), 2.30 (m, 2H), 2.54 (m, 1H), 3.67-3.78 (m, 6H), 3.85 (t, 2H), 4.11 (t, 2H), 4.32 (t, 2H), 5.84 (dd, 1H), 6.15 (dd, 1H), 6.40 (dd, 1H), 6.82-7.00 (m, 4H), 7.08-7.60 (m, 4H), 7.65-8.10 (m, 3H), 8.40 (s, 1H), 11.6 (s, 1H) ppm.

LCMS: 826 [M+1]

Example 27 Production of a Compound Represented by the Formula (A141-21)

[Chem. 238]

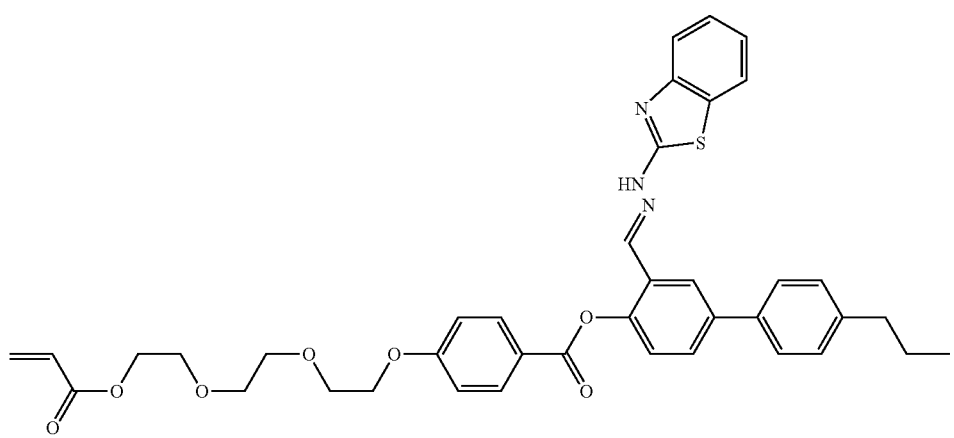

(A141-21)

A compound represented by the formula (A141-21) was produced in the manner described above.

Transition temperature (heating rate: 5° C./min): C 89-123 I $^1$H NMR (CDCl$_3$) δ 1.05 (t, 3H), 1.70 (m, 2H), 2.70 (t, 2H), 3.58-3.73 (m, 6H), 3.75 (t, 2H), 4.02 (t, 2H), 4.27 (t, 2H), 5.84 (dd, 1H), 6.12 (dd, 1H), 6.42 (dd, 1H), 6.65 (d, 2H), 7.00 (d, 2H), 7.15-7.45 (m, 5H), 7.51-7.70 (m, 5H), 7.78 (dd, 1H), 8.17 (s, 1H), 11.7 (s, 1H) ppm.

LCMS: 694 [M+1]

Example 28 Production of a Compound Represented by the Formula (A141-22)

[Chem. 239]

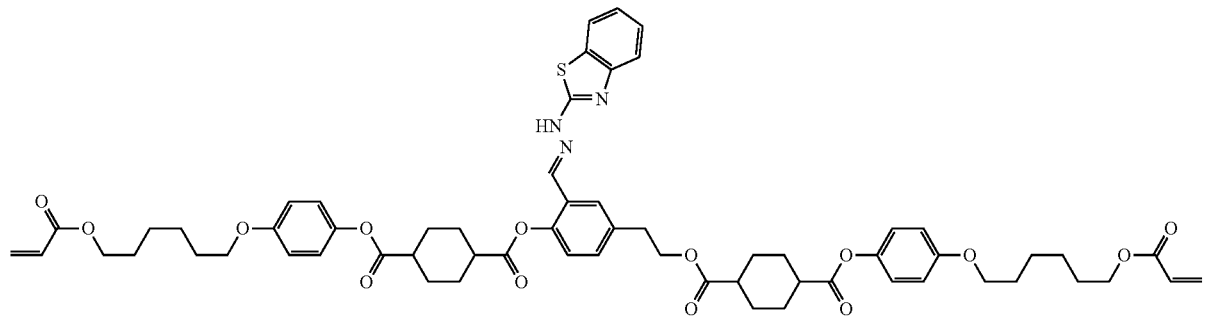

(A141-22)

A compound represented by the formula (A141-22) was produced in the manner described above.

Transition temperature: C? N 150 I $^1$H NMR (CDCl$_3$) δ 1.40-1.82 (m, 24H), 2.04-2.20 (m, 8H), 2.35-2.49 (m, 4H), 3.02 (t, 2H), 3.92 (t, 2H), 3.95 (t, 2H), 4.17 (t, 2H), 4.18 (t, 2H), 4.36 (t, 2H), 5.82 (dd, 1H), 5.82 (dd, 1H), 6.12 (dd, 1H), 6.13 (dd, 1H), 6.40 (dd, 1H), 6.40 (dd, 1H), 6.82-6.90 (m, 6H), 6.97-7.04 (m, 3H), 7.17 (m, 1H), 7.26 (m, 1H), 7.35 (t, 1H), 7.49 (d, 1H), 7.69 (d, 1H), 7.93 (s, 1H), 8.07 (s, 1H) ppm.

Example 29 Production of a Compound Represented by the Formula (A141-23)

[Chem. 240]

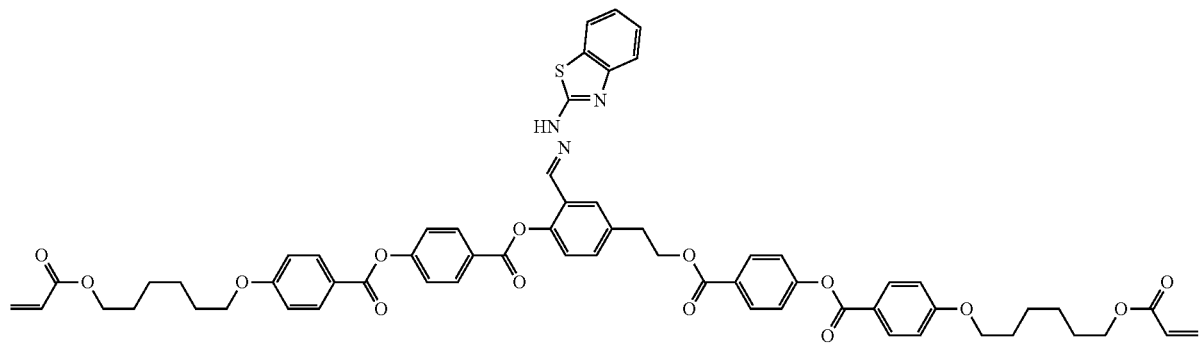

(A141-23)

A compound represented by the formula (A141-23) was produced in the manner described above.

Transition temperature: C 145 N 207 I $^1$H NMR (CDCl$_3$) δ 1.47-1.87 (m, 16H), 3.17 (t, 2H), 4.05 (t, 2H), 4.06 (t, 2H), 4.18 (t, 2H), 4.19 (t, 2H), 4.62 (t, 2H), 5.82 (dd, 1H), 5.82 (dd, 1H), 6.13 (dd, 1H), 6.13 (dd, 1H), 6.41 (dd, 1H), 6.41 (dd, 1H), 6.96 (m, 4H), 7.09 (m, 1H), 7.19-7.38 (m, 7H), 7.45 (d, 1H), 7.61 (d, 1H), 7.96 (m, 1H), 8.05-8.18 (m, 7H), 8.22 (d, 2H) ppm.

Example 30 Production of a Compound Represented by the Formula (A141-24)

[Chem. 241]

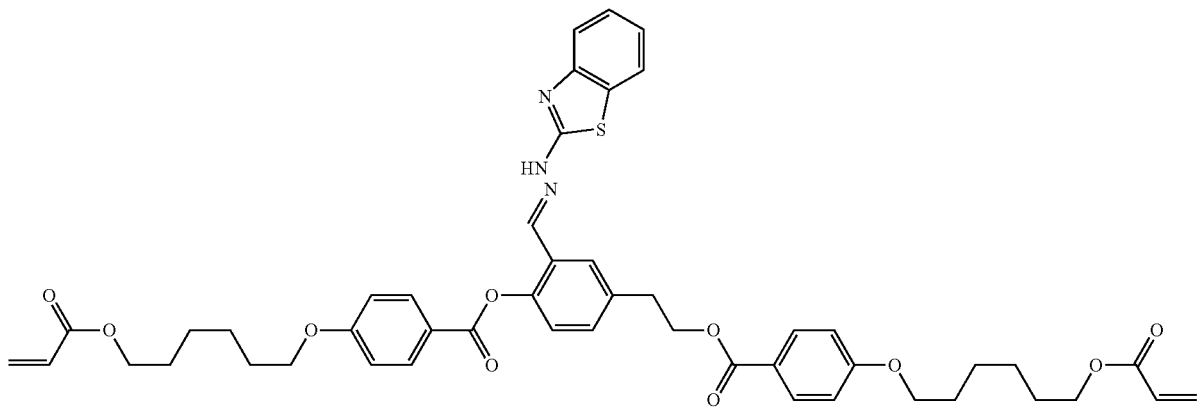

(A141-24)

A compound represented by the formula (A141-24) was produced in the manner described above.

Transition temperature: S 60 I $^1$H NMR (CDCl$_3$) δ: 1.40-1.60 (p, 8H), 1.6 (br, 1H), 1.65-1.80 (p, 4H), 1.80-1.97 (p, 4H), 3.15 (t, 2H), 4.01 (t, 2H), 4.17 (t, 2H), 4.31 (t, 2H), 4.40 (t, 2H), 4.57 (t, 2H), 5.81-5.85 (d+d, 2H), 6.08-6.18 (m, 2H), 6.37-6.46 (d+d, 2H), 6.87 (d, 2H), 6.96 (d, 2H), 7.12-7.18 (m, 2H), 7.34 (d, 1H), 7.48 (d, 1H), 7.58 (d, 1H), 7.99-8.02 (s+d, 5H), 8.12 (d, 2H) ppm.

LC-MS: m/z 862.60 [M+]

Example 31 Production of a Compound Represented by the Formula (A141-25)

[Chem. 242]

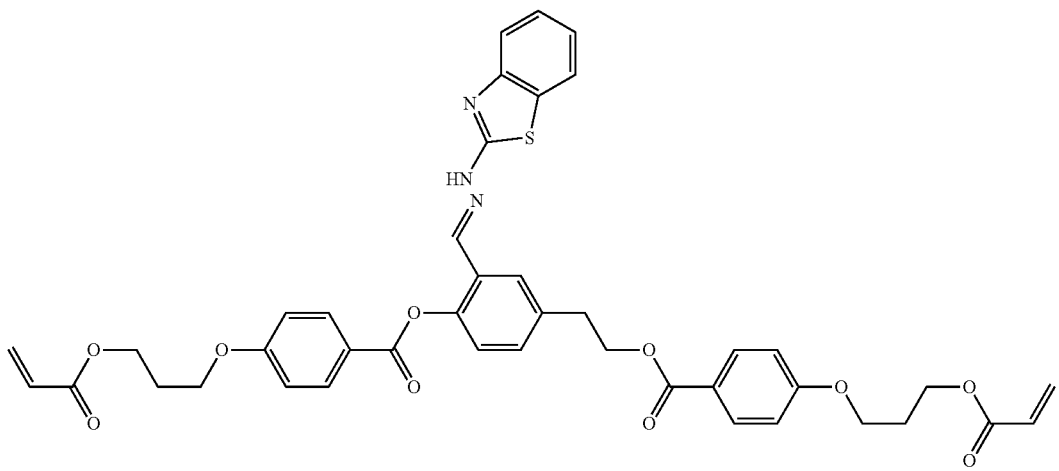

(A141-25)

A compound represented by the formula (A141-25) was produced in the manner described above.

Transition temperature: C 118 I $^1$H NMR (CDCl$_3$) δ 2.11 (quin, 2H), 2.22 (quin, 2H), 3.15 (t, 2H), 4.01 (t, 2H), 4.14 (t, 2H), 4.31 (t, 2H), 4.40 (t, 2H), 4.57 (t, 2H), 5.83 (m, 2H), 6.13 (m, 2H), 6.41 (m, 2H), 6.88 (m, 4H), 7.09 (m, 1H), 7.16-7.23 (m, 2H), 7.34 (m, 1H), 7.45 (m, 1H), 7.55 (m, 1H), 7.97-8.09 (m, 6H) ppm.

Example 32 Production of a Compound Represented by the Formula (A141-26)

[Chem. 243]

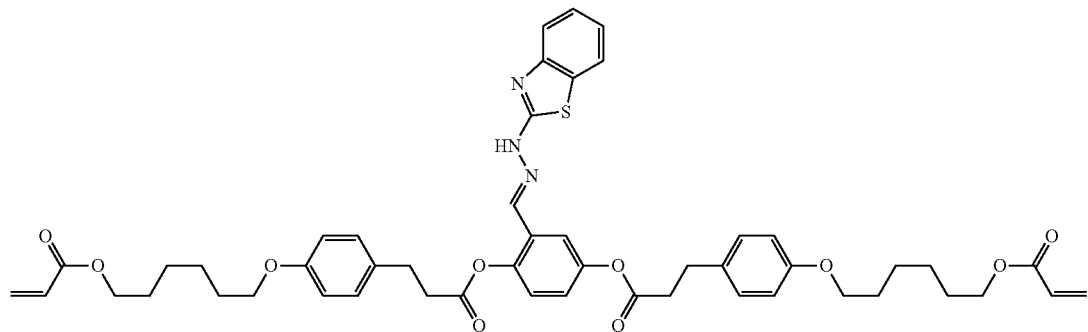

(A141-26)

A compound represented by the formula (A141-26) was produced in the manner described above.

Transition temperature: C 61-67 (N 40) I $^1$H NMR (CDCl$_3$) δ 1.42-1.82 (m, 16H), 2.83-3.09 (m, 8H), 3.97 (m, 4H), 4.17 (m, 4H), 5.84 (d, 2H), 6.15 (dd, 2H), 6.43 (d, 2H), 6.86-6.92 (m, 4H), 7.04 (m, 2H), 7.15-7.23 (m, 5H), 7.36 (t, 1H), 7.42 (s, 1H), 7.57 (d, 1H), 7.68 (m, 2H) ppm.

Example 33 Production of a Compound Represented by the Formula (A141-27)

[Chem. 244]

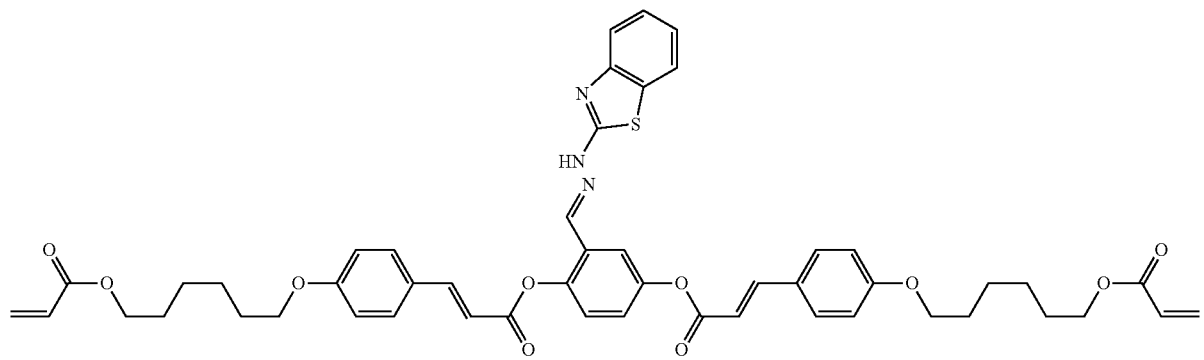

(A141-27)

A compound represented by the formula (A141-27) was produced in the manner described above.

Transition temperature: C 106 S 196 N 203 I $^1$H NMR (CDCl$_3$) δ: 1.41-1.61 (p, 8H), 1.65-1.80 (p, 4H), 1.7 (br, 1H), 1.80-1.97 (p, 4H), 4.02 (t, 2H), 4.17 (t, 2H), 5.82 (d, 2H), 6.10-6.18 (dd, 2H), 6.39-6.44 (s+d, 3H), 6.93 (dd, 4H), 7.09 (t, 2H), 7.23 (s, 1H), 7.30 (d, 1H), 7.43 (d, 1H), 7.50-7.58 (p, 4H), 7.75-7.89 (p, 3H), 8.10 (s, 1H) ppm.

LC-MS: m/z 885.61 [M+]

Example 34 Production of a Compound Represented by the Formula (A141-28)

[Chem. 245]

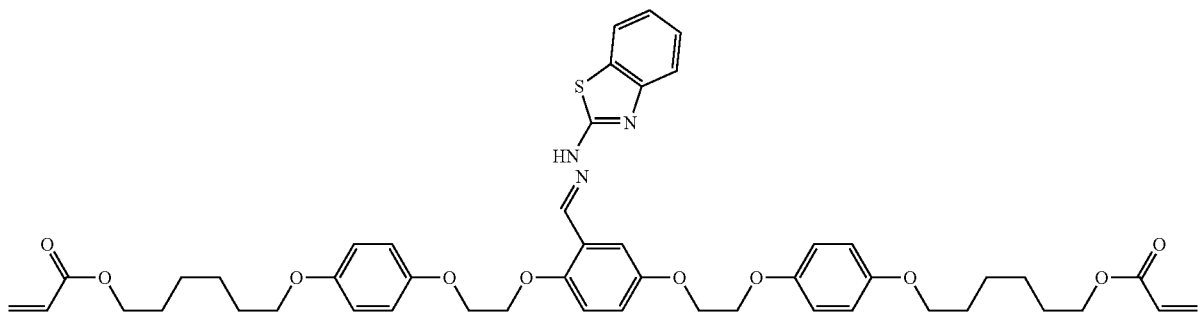

(A141-28)

A compound represented by the formula (A141-28) was produced in the manner described above.

Transition temperature: C 141 I $^1$H NMR (CDCl$_3$) δ 1.41-1.50 (m, 8H), 1.64-1.81 (m, 8H), 3.88 (t, 2H), 3.91 (t, 2H), 4.16 (m, 6H), 4.26-4.35 (m, 6H), 5.81 (dd, 1H), 5.81 (dd, 1H), 6.12 (dd, 1H), 6.12 (dd, 1H), 6.40 (dd, 1H), 6.40 (dd, 1H), 6.79-6.98 (m, 10H), 7.13 (t, 1H), 7.32 (t, 1H), 7.58 (m, 2H), 7.65 (d, 1H), 8.22 (s, 1H) ppm.

Example 35 Production of a Compound Represented by the Formula (A141-29)

[Chem. 246]

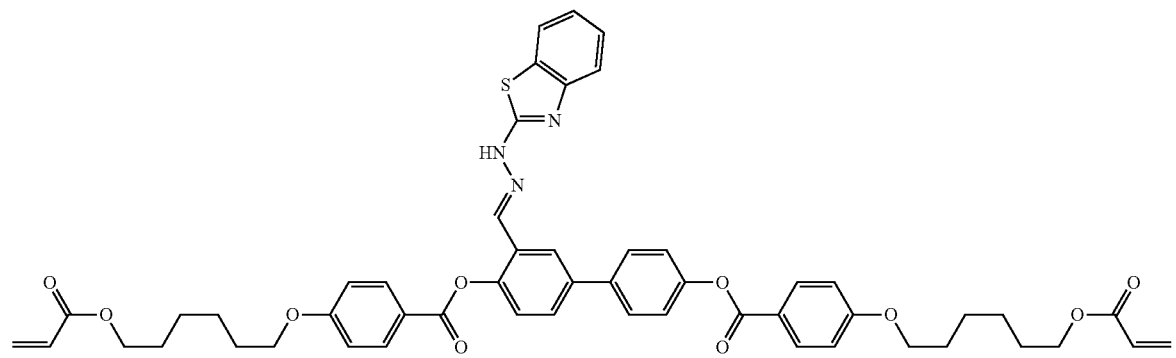

(A141-29)

A compound represented by the formula (A141-29) was produced in the manner described above.

Phase transition temperature (heating stage): C 180 N>220 I $^1$H NMR (CDCl$_3$): 1.42-1.60 (m, 8H), 1.68-1.91 (m, 8H), 3.95 (m, 2H), 4.07 (t, 2H), 4.16-4.22 (m, 4H), 5.83 (dd, 2H), 6.09-6.18 (m, 2H), 6.42 (dd, 2H), 6.82 (br, 2H), 7.00 (d, 2H), 7.09 (br, 1H), 7.21 (br, 1H), 7.33 (m, 3H), 7.45 (br, 1H), 7.62 (m, 2H), 7.70 (d, 2H), 8.02 (br, 2H), 8.19 (d, 3H), 8.25 (br, 1H) ppm.

Example 36 Production of a Compound Represented by the Formula (A141-30)

[Chem. 247]

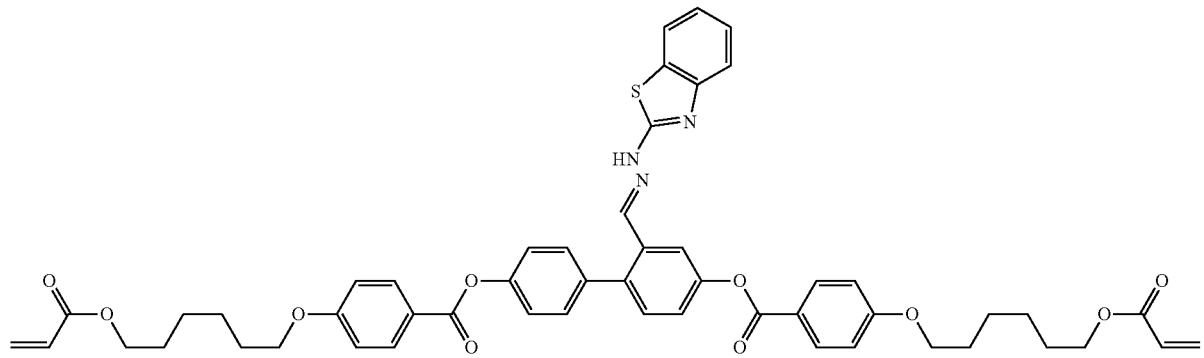

(A141-30)

A compound represented by the formula (A141-30) was produced in the manner described above.

Phase transition temperature (heating stage): C 107 N 217 I $^1$H NMR (CDCl$_3$): 1.52 (m, 8H), 1.74 (quin, 4H), 1.86 (quin, 4H), 4.07 (td, 4H), 4.20 (td, 4H), 5.84 (d, 2H), 6.14 (dd, 2H), 6.42 (d, 2H), 6.99 (d, 4H), 7.11 (t, 1H), 7.21-7.40 (m, 8H), 7.62 (d, 1H), 7.93 (m, 2H), 8.19 (dd, 4H) ppm.

Example 37 Production of a Compound Represented by the Formula (A141-31)

[Chem. 248]

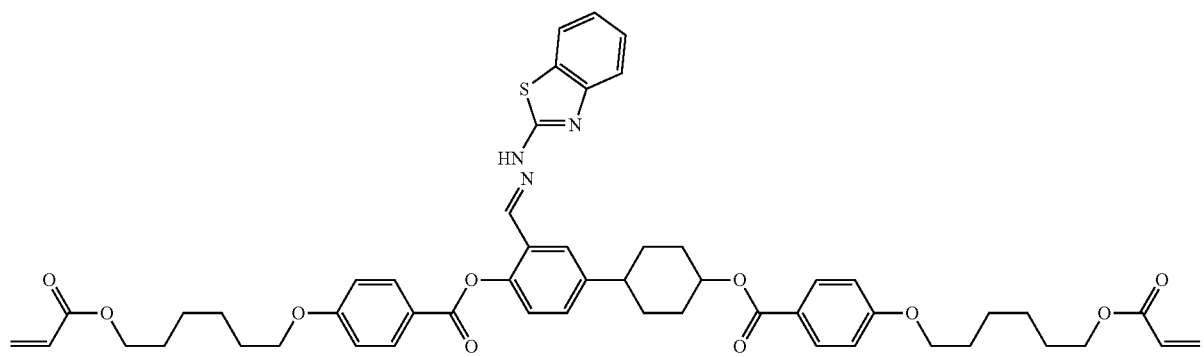

(A141-31)

A compound represented by the formula (A141-31) was produced in the manner described above.

Phase transition temperature (heating stage): C 60-80 N 206 I $^1$H NMR (CDCl$_3$): 1.44-1.60 (m, 9H), 1.66-1.90 (m, 13H), 2.07 (m, 2H), 2.29 (m, 2H), 2.68 (m, 1H), 4.03 (td, 4H), 4.19 (td, 4H), 5.07 (m, 1H), 5.84 (dt, 2H), 6.13 (dd, 2H), 6.42 (dd, 2H), 6.86 (d, 2H), 6.93 (d, 2H), 7.06-7.22 (m, 3H), 7.30 (dd, 1H), 7.45 (d, 1H), 7.63 (d, 1H), 7.90 (s, 1H), 8.04 (m, 4H), 8.11 (s, 1H) ppm.

Example 38 Production of a Compound Represented by the Formula (A141-32)

[Chem. 249]

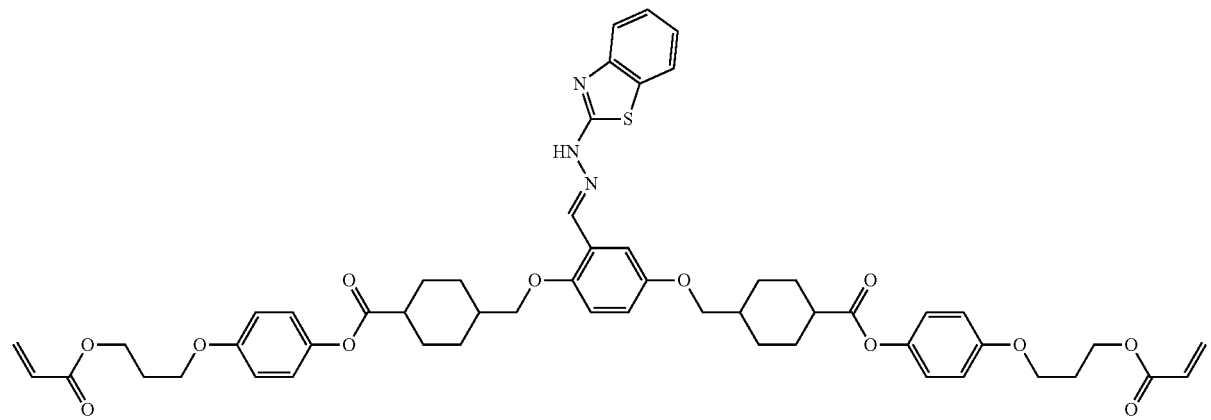

(A141-32)

A compound represented by the formula (A141-32) was produced in the manner described above.

Transition temperature (heating rate: 5° C./min) C 155 N>220 I $^1$H NMR (CDCl$_3$) δ 1.12 (q, 2H), 1.26 (q, 2H), 1.50 (q, 2H), 1.67 (qd, 2H), 1.91-2.27 (m, 14H), 2.43 (t, 1H), 2.56 (tt, 2H), 3.77 (d, 2H), 3.88 (d, 2H), 4.09 (t, 4H), 4.40 (t, 4H), 5.88 (d, 2H), 6.17 (ddd, 2H), 6.45 (d, 2H), 6.85 (d, 1H), 6.92 (m, 5H), 7.02 (d, 4H), 7.19 (t, 1H), 7.37 (t, 1H), 7.59 (m, 2H), 7.71 (d, 1H), 8.44 (s, 1H) ppm.

Example 39 Production of a Compound Represented by the Formula (A141-33)

[Chem. 250]

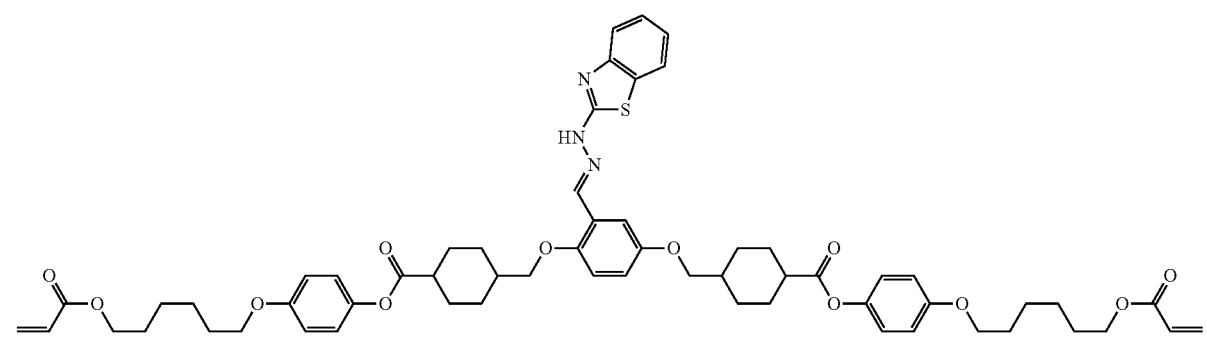

(A141-33)

A compound represented by the formula (A141-33) was produced in the manner described above.

Transition temperature (heating rate: 5° C./min) C 90-110 N 182-187 I $^1$H NMR (CDCl$_3$) δ 1.07 (q, 2H), 1.24 (q, 2H), 1.47-1.90 (m, 24H), 2.09 (m, 4H), 2.22 (d, 2H), 2.39 (t, 1H), 2.53 (t, 1H), 3.74 (d, 2H), 3.85 (d, 2H), 3.94 (td, 4H), 4.17 (td, 4H), 5.82 (d, 2H), 6.13 (dd, 2H), 6.40 (d, 2H), 6.80-6.99 (m, 6H), 6.98 (d, 4H), 7.16 (t, 1H), 7.33 (t, 1H), 7.55 (m, 2H), 7.67 (d, 1H), 8.40 (s, 1H) ppm.

Example 40 Production of a Compound Represented by the Formula (A142-1)

[Chem. 251]

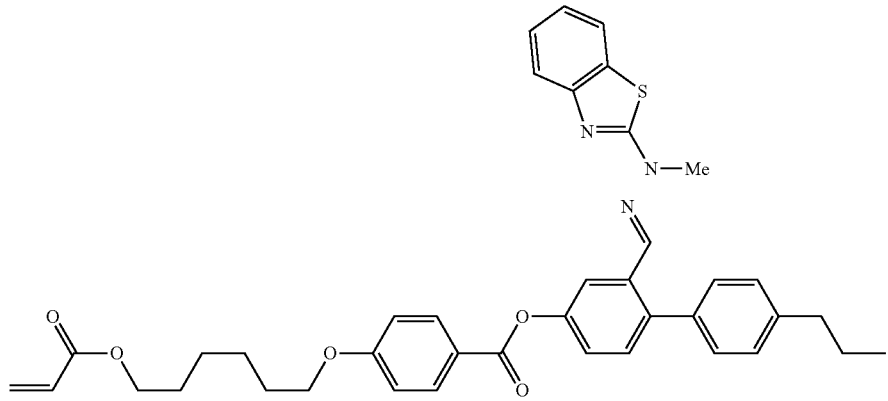

(A142-1)

A compound represented by the formula (A142-1) was produced in the manner described above.

Transition temperature (heating rate, cooling rate: 5° C./min): C 128 (N 80) I $^1$H NMR (CDCl$_3$) δ 1.00 (t, 3H), 1.47-1.60 (m, 4H), 1.73 (m, 4H), 1.87 (quin, 2H), 2.67 (t, 2H), 3.55 (s, 3H), 4.08 (t, 2H), 4.20 (t, 2H), 5.84 (dd, 1H), 6.14 (dd, 1H), 6.42 (dd, 1H), 7.02 (d, 2H), 7.13 (t, 1H), 7.25-7.33 (m, 6H), 7.39 (d, 1H), 7.62 (dd, 2H), 7.69 (s, 1H), 7.93 (d, 1H), 8.22 (d, 2H) ppm.

MS (m/z): 696 [M$^+$+1]

Example 41 Production of a Compound Represented by the Formula (A142-2)

[Chem. 252]

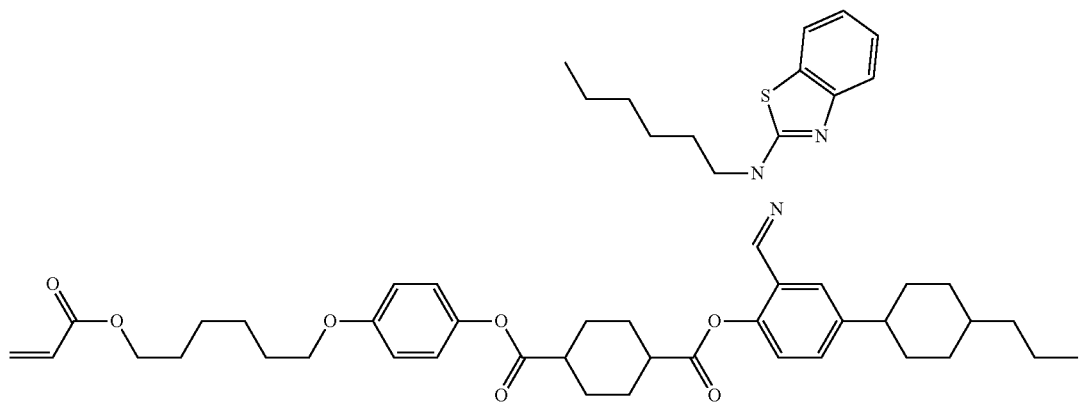

(A142-2)

A compound represented by the formula (A142-2) was produced in the manner described above.

Transition temperature (heating rate: 5° C./min): C 117-122 N 146 I $^1$H NMR (CDCl$_3$) δ 0.91 (m, 6H), 1.10 (q, 2H), 1.23-1.56 (m, 18H), 1.68-1.81 (m, 9H), 1.94 (t, 4H), 2.32 (m, 4H), 2.56-2.70 (m, 3H), 3.94 (t, 2H), 4.18 (t, 2H), 4.29 (t, 2H), 5.82 (dd, 1H), 6.13 (dd, 1H), 6.40 (dd, 1H), 6.89 (d, 2H), 6.99 (m, 3H), 7.16 (t, 1H), 7.23 (dd, 1H), 7.34 (t, 1H), 7.66-7.72 (m, 3H), 7.90 (d, 1H) ppm.

MS (m/z): 878 [M$^+$+1]

Example 42 Production of a Compound Represented by the Formula (A142-3)

[Chem. 253]

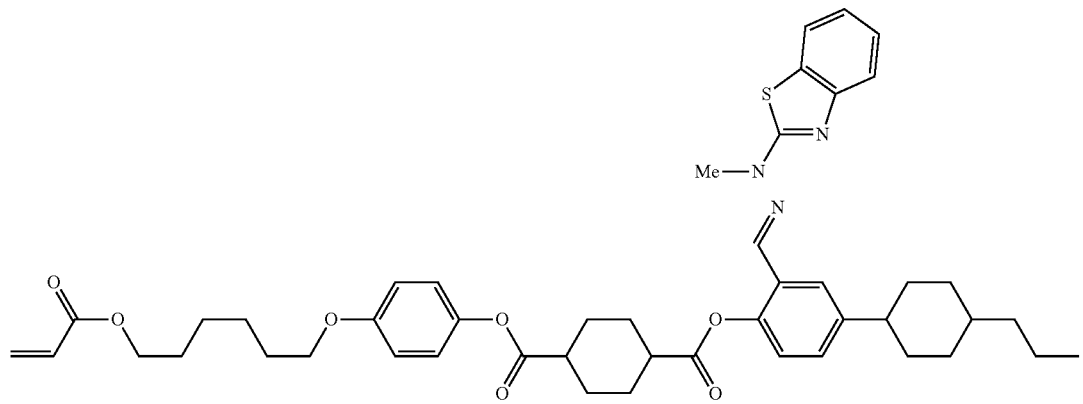

(A142-3)

A compound represented by the formula (A142-3) was produced in the manner described above.

Transition temperature (heating rate: 5° C./min): C 147-156 N 173 I $^1$H NMR (CDCl$_3$) δ 0.92 (t, 3H), 1.11 (q, 2H), 1.25 (m, 2H), 1.37-1.55 (m, 9H), 1.71 (m, 6H), 1.78 (m, 2H), 1.94 (m, 4H), 2.33 (m, 4H), 2.56 (m, 2H), 2.70 (m, 1H), 3.72 (s, 3H), 3.94 (t, 2H), 4.17 (t, 2H), 5.82 (dd, 1H), 6.13 (dd, 1H), 6.40 (dd, 1H), 6.88 (d, 2H), 6.98 (m, 3H), 7.17 (t, 1H), 7.24 (dd, 1H), 7.35 (t, 1H), 7.66-7.72 (m, 3H), 7.88 (d, 1H) ppm.

MS (m/z): 808 [M$^+$+1]

Example 43 Production of a Compound Represented by the Formula (A142-4)

[Chem. 254]

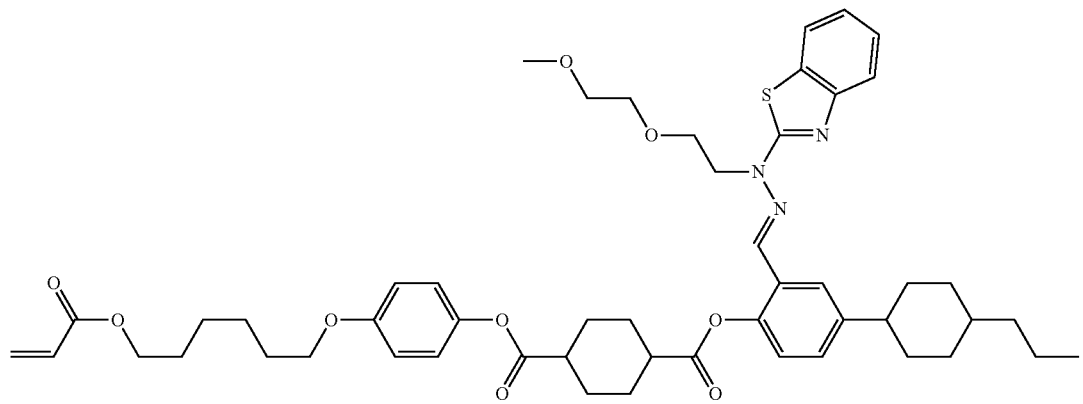

(A142-4)

A compound represented by the formula (A142-4) was produced in the manner described above.

Transition temperature (heating rate: 5° C./min): C 106 N 125 I $^1$H NMR (CDCl$_3$) δ 0.92 (t, 3H), 1.05-1.83 (m, 22H), 1.93 (t, 5H), 2.33 (m, 4H), 2.55 (m, 2H), 2.71 (m, 1H), 3.30 (s, 3H), 3.62 (m, 2H), 3.85 (t, 2H), 3.94 (t, 2H), 4.17 (t, 2H), 4.48 (t, 2H), 5.82 (dd, 1H), 6.12 (dd, 1H), 6.40 (dd, 1H), 6.88 (d, 2H), 6.99 (m, 3H), 7.17 (t, 1H), 7.23 (dd, 1H), 7.34 (t, 1H), 7.66 (d, 1H), 7.71 (d, 1H), 7.89 (d, 1H), 8.02 (s, 1H) ppm.

Example 44 Production of a Compound Represented by the Formula (A142-5)

[Chem. 255]

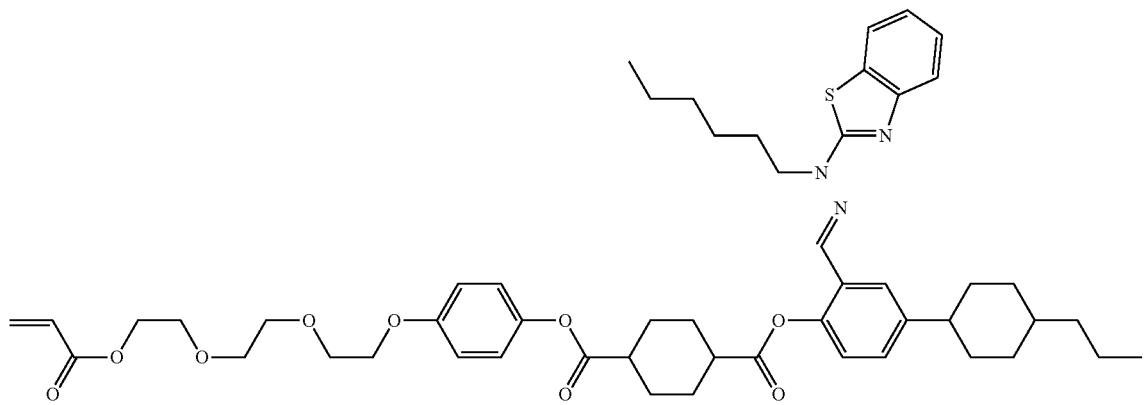

(A142-5)

A compound represented by the formula (A142-5) was produced in the manner described above.

Transition temperature (heating rate: 5° C./min): C 131 I $^1$H NMR (CDCl$_3$) δ 0.88-0.94 (m, 6H), 1.10 (m, 2H), 1.22-1.52 (m, 13H), 1.72 (m, 6H), 1.94 (t, 4H), 2.32 (m, 4H), 2.53-2.62 (m, 3H), 3.69-3.77 (m, 6H), 3.86 (t, 2H), 4.12 (t, 2H), 4.27-4.34 (m, 4H), 5.83 (dd, 1H), 6.16 (dd, 1H), 6.43 (dd, 1H), 6.91 (d, 2H), 6.97-7.02 (m, 3H), 7.16 (t, 1H), 7.23 (dd, 1H), 7.33 (t, 1H), 6.66-7.72 (m, 3H), 7.90 (d, 1H) ppm.

LCMS: 910 [M+1]

Example 45 Production of a Compound Represented by the Formula (A142-6)

[Chem. 256]

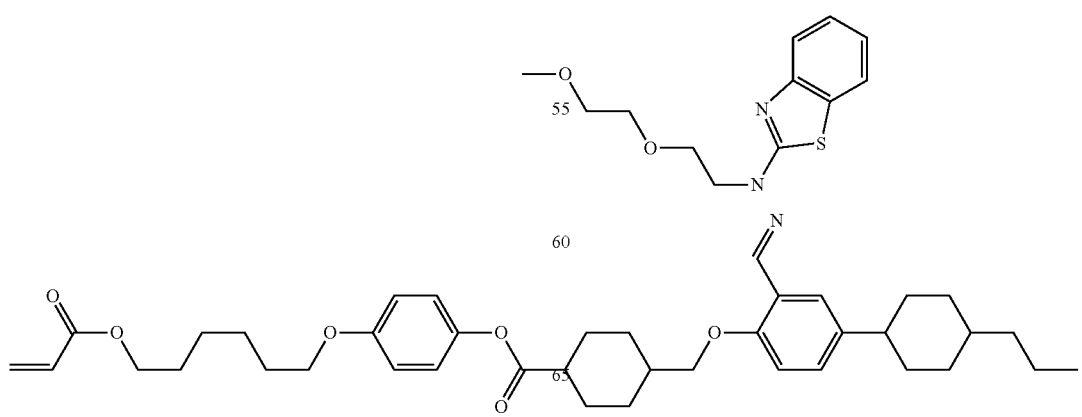

(A142-6)

A compound represented by the formula (A142-6) was produced in the manner described above.

Transition temperature (heating rate: 5° C./min, cooling rate: 5° C./min): C 101-105 (N 82) I $^1$H NMR (CDCl$_3$) δ 0.92 (t, 3H), 1.08-1.91 (m, 26H), 2.06 (d, 2H), 2.24 (d, 2H), 2.51 (m, 2H), 3.30 (s, 3H), 3.51 (dd, 2H), 3.67 (dd, 2H), 3.87 (quin, 4H), 3.94 (t, 2H), 4.17 (t, 2H), 4.54 (t, 2H), 5.82 (dd, 1H), 6.12 (dd, 1H), 6.40 (dd, 1H), 6.86 (m, 3H), 6.97 (m, 2H), 7.16 (m, 2H), 7.32 (t, 1H), 7.65 (d, 1H), 7.70 (d, 1H), 7.82 (d, 1H), 8.36 (s, 1H) ppm.

Example 46 Production of a Compound Represented by the Formula (A142-7)

[Chem. 257]

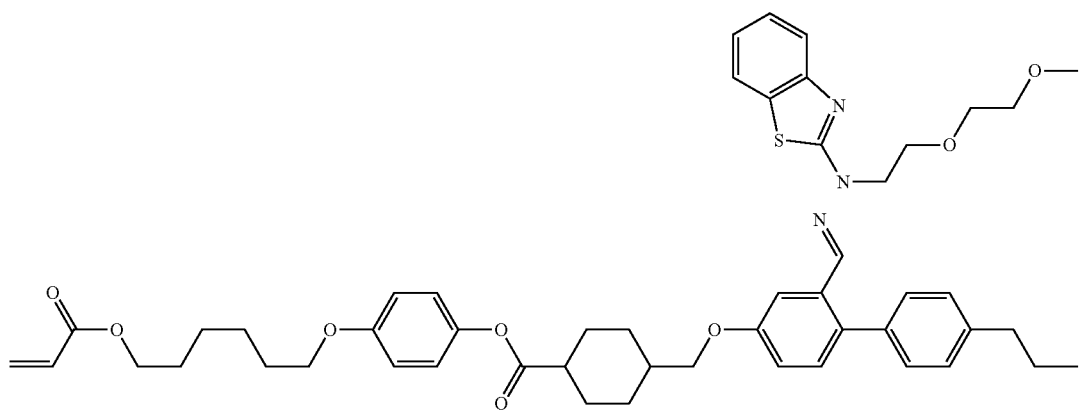

(A142-7)

A compound represented by the formula (A142-7) was produced in the manner described above.

Transition temperature (heating rate: 5° C./min): C 67-100 I $^1$H NMR (CDCl$_3$) δ 1.00 (t, 3H), 1.28 (m, 2H), 1.45-1.81 (m, 12H), 1.97 (br, 1H), 2.13 (m, 2H), 2.26 (m, 2H), 2.57 (tt, 1H), 2.65 (t, 2H), 3.27 (s, 3H), 3.37 (m, 2H), 3.50 (m, 2H), 3.70 (t, 2H), 3.95 (q, 4H), 4.17 (t, 2H), 4.33 (t, 2H), 5.82 (dd, 1H), 6.12 (dd, 1H), 6.40 (dd, 1H), 6.87 (d, 2H), 6.98 (m, 3H), 7.15 (t, 1H), 7.25 (m, 5H), 7.32 (t, 1H), 7.64 (m, 2H), 7.69 (d, 1H), 7.91 (s, 1H) ppm.

Example 47 Production of a Compound Represented by the Formula (A142-8)

[Chem. 258]

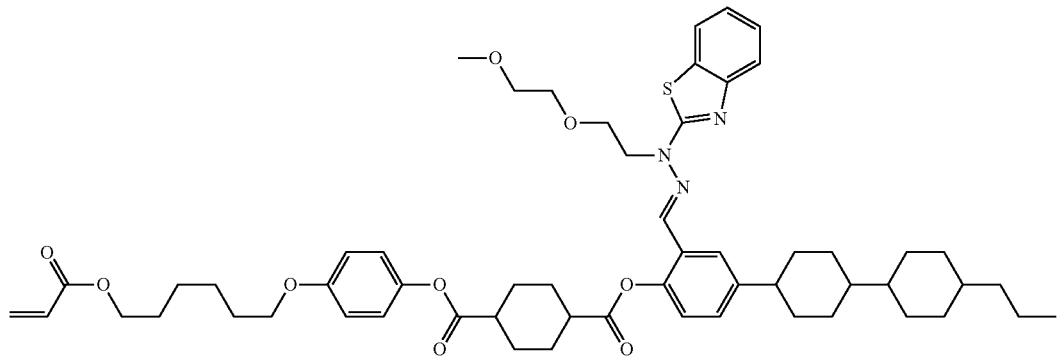

(A142-8)

A compound represented by the formula (A142-8) was produced in the manner described above.

$^1$H NMR (CDCl$_3$) δ 0.92 (t, 3H), 1.05-1.83 (m, 32H), 1.93 (t, 5H), 2.33 (m, 4H), 2.55 (m, 2H), 2.71 (m, 1H), 3.30 (s, 3H), 3.62 (m, 2H), 3.85 (t, 2H), 3.94 (t, 2H), 4.17 (t, 2H), 4.48 (t, 2H), 5.82 (dd, 1H), 6.12 (dd, 1H), 6.40 (dd, 1H), 6.88 (d, 2H), 6.99 (m, 3H), 7.17 (t, 1H), 7.23 (dd, 1H), 7.34 (t, 1H), 7.66 (d, 1H), 7.71 (d, 1H), 7.89 (d, 1H), 8.02 (s, 1H) ppm.

LCMS: 978 [M+1]

Example 48 Production of a Compound Represented by the Formula (A142-9)

[Chem. 259]

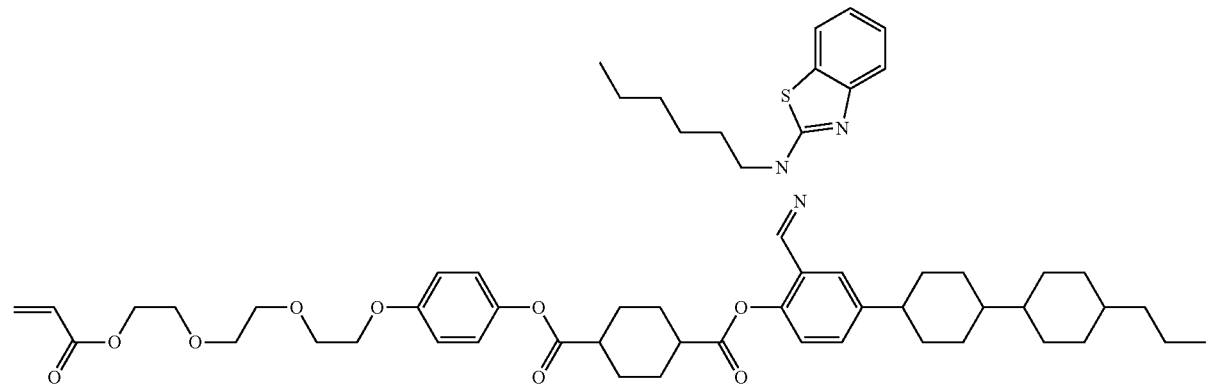

(A142-9)

A compound represented by the formula (A142-9) was produced in the manner described above.

Transition temperature (heating rate: 5° C./min): C 90 S 218 N 265 I $^1$H NMR (CDCl$_3$) δ 0.88 (m, 6H), 1.01-1.19 (m, 8H), 1.32-1.45 (m, 6H), 1.71-1.76 (m, 6H), 1.88-1.99 (m, 3H), 2.17 (m, 12H), 2.31 (m, 4H), 2.53 (m, 2H), 2.67 (m, 1H), 3.70-3.76 (m, 6H), 3.85 (t, 2H), 4.11 (t, 2H), 4.31 (m, 4H), 5.82 (d, 2H), 6.15 (q, 2H), 6.43 (d, 2H), 6.92 (m, 5H), 7.14-7.26 (m, 2H), 7.33 (t, 1H), 7.68 (m, 3H), 7.88 (s, 1H) ppm.

Example 49 Production of a Compound Represented by the Formula (A142-10)

[Chem. 260]

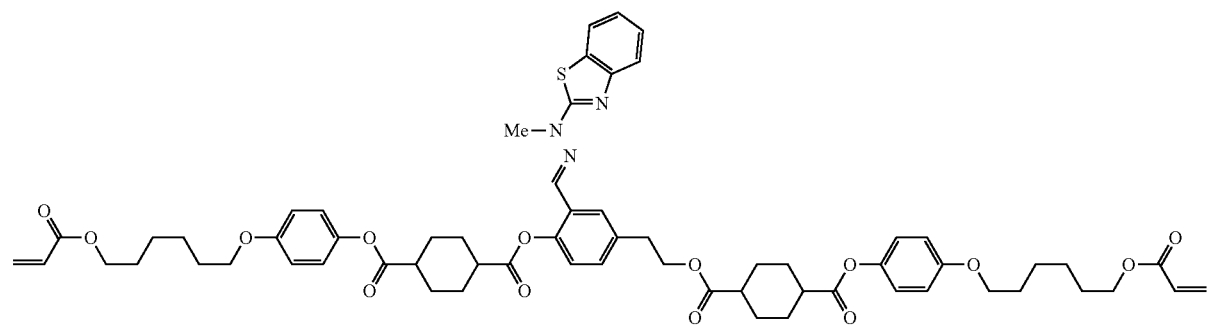

(A142-10)

A compound represented by the formula (A142-10) was produced in the manner described above.

Transition temperature: C 113-123 (N 113) I $^1$H NMR (CDCl$_3$) δ 1.40-1.82 (m, 24H), 2.09-2.17 (m, 4H), 2.33 (m, 5H), 2.47 (m, 1H), 2.61 (m, 1H), 2.71 (m, 1H), 3.03 (t, 2H), 3.74 (s, 3H), 3.93 (t, 2H), 3.94 (t, 2H), 4.17 (t, 2H), 4.17 (t, 2H), 4.37 (t, 2H), 5.82 (m, 2H), 6.12 (m, 2H), 6.40 (m, 2H), 6.83-6.90 (m, 6H), 6.98 (d, 2H), 7.04 (d, 1H), 7.16 (t, 1H), 7.25 (m, 1H), 7.34 (t, 1H), 7.66-7.71 (m, 3H), 7.91 (d, 1H) ppm.

Example 50 Production of a Compound Represented by the Formula (A142-11)

[Chem. 261]

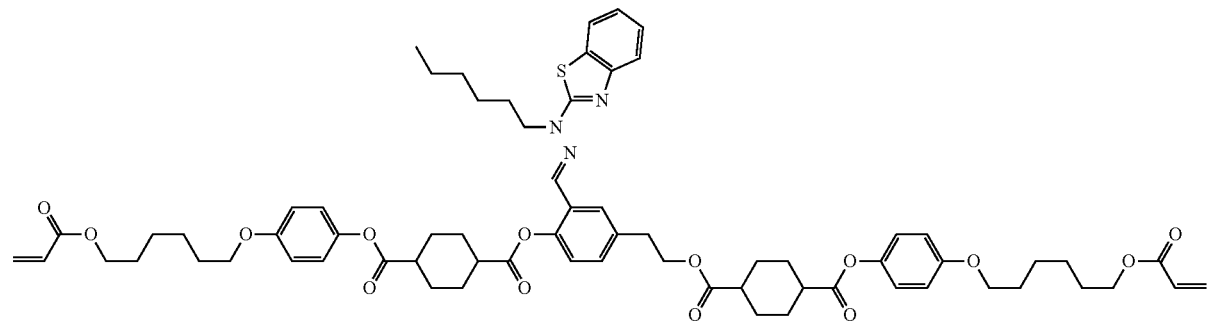

(A142-11)

A compound represented by the formula (A142-11) was produced in the manner described above.

Transition temperature: C 134-139 (N 102) I $^1$H NMR (CDCl$_3$) δ 0.89 (t, 3H), 1.32-1.56 (m, 18H), 1.70-1.81 (m, 14H), 2.09-2.17 (m, 4H), 2.33 (m, 5H), 2.46 (m, 1H), 2.59 (m, 1H), 2.69 (m, 1H), 3.03 (t, 2H), 3.93 (t, 2H), 3.94 (t, 2H), 4.17 (t, 2H), 4.17 (t, 2H), 4.30 (t, 2H), 4.37 (t, 2H), 5.81 (dd, 1H), 5.82 (dd, 1H), 6.12 (dd, 1H), 6.13 (dd, 1H), 6.40 (dd, 1H), 6.40 (dd, 1H), 6.83-6.89 (m, 6H), 6.98 (d, 2H), 7.05 (d, 1H), 7.15 (t, 1H), 7.24 (dd, 1H), 7.33 (t, 1H), 7.68 (dd, 2H), 7.71 (s, 1H), 7.93 (d, 1H) ppm.

Example 51 Production of a Compound Represented by the Formula (A142-12)

[Chem. 262]

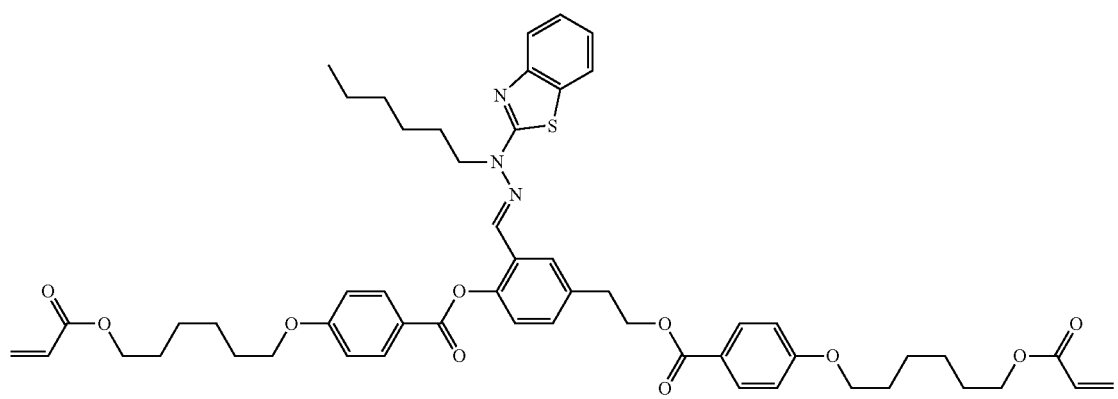

(A142-12)

A compound represented by the formula (A142-12) was produced in the manner described above.

Transition temperature: C 60-65 I $^1$H NMR (CDCl$_3$) δ 0.78 (t, 3H), 1.11-1.18 (m, 6H), 1.42-1.59 (m, 10H), 1.68-1.77 (m, 6H), 1.86 (quin, 2H), 3.17 (t, 2H), 3.86 (t, 2H), 4.06 (t, 2H), 4.15-4.21 (m, 6H), 4.58 (t, 2H), 5.82 (dd, 1H), 5.82 (dd, 1H), 6.13 (dd, 1H), 6.13 (dd, 1H), 6.40 (dd, 1H), 6.40 (dd, 1H), 6.84 (d, 2H), 7.00 (d, 2H), 7.14 (t, 1H), 7.18 (d, 1H), 7.29-7.35 (m, 2H), 7.63 (m, 2H), 7.76 (s, 1H), 8.00-8.04 (m, 3H), 8.18 (d, 2H) ppm.

Example 52 Production of a Compound Represented by the Formula (A142-13)

[Chem. 263]

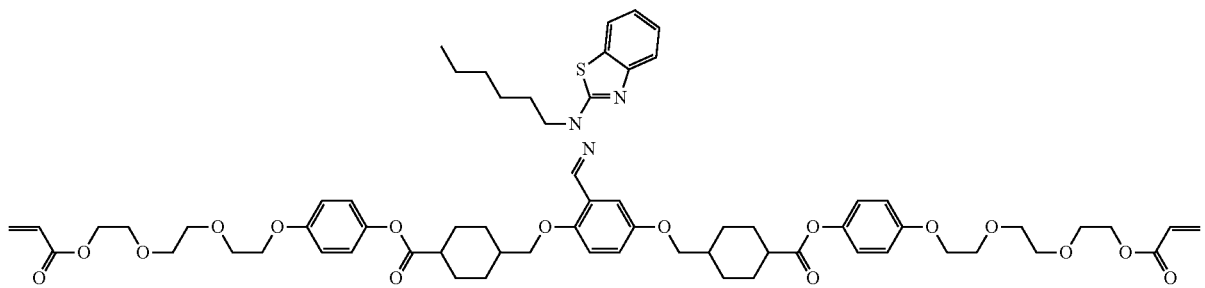

(A142-13)

A compound represented by the formula (A142-13) was produced in the manner described above.

Transition temperature (heating rate: 5° C./min): C 77 S 90 N 109 I $^1$H NMR (CDCl$_3$) δ 0.89 (t, 3H), 1.20-1.35 (m, 10H), 1.61-1.69 (m, 6H), 1.78 (m, 2H), 1.90 (m, 2H), 2.07 (t, 4H), 2.23 (d, 4H), 2.50 (m, 2H), 3.69-3.76 (m, 12H), 3.83-3.87 (m, 8H), 4.11 (t, 4H), 4.32 (t, 6H), 5.82 (d, 2H), 6.15 (q, 2H), 6.42 (d, 2H), 6.83-6.98 (m, 10H), 7.13 (t, 1H), 7.32 (t, 1H), 7.53 (t, 1H), 7.66 (t, 2H), 8.13 (s, 1H) ppm.

Example 53 Production of a Compound Represented by the Formula (A142-14)

[Chem. 264]

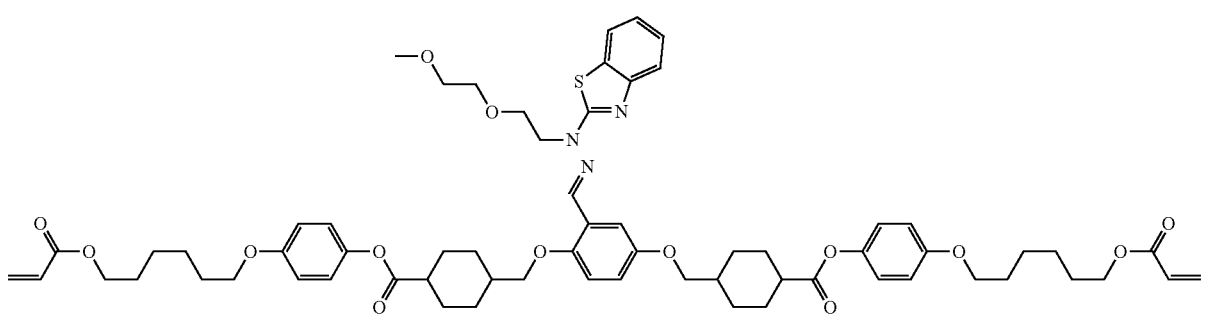

(A142-14)

A compound represented by the formula (A142-14) was produced in the manner described above.

Transition temperature (heating rate: 5° C./min): C 85 N 128 I $^1$H NMR (CDCl$_3$) δ 1.22-1.28 (m, 4H), 1.44-1.47 (m, 8H), 1.60-1.82 (m, 12H), 1.90 (m, 2H), 2.07 (t, 4H), 2.24 (d, 4H), 2.53 (m, 2H), 3.30 (s, 3H), 3.50 (t, 2H), 3.66 (t, 2H), 3.85-3.89 (m, 6H), 3.93 (t, 4H), 4.17 (t, 4H), 4.53 (t, 2H), 5.82 (d, 2H), 6.13 (q, 2H), 6.40 (d, 2H), 6.83-6.90 (m, 6H), 6.95-6.98 (m, 4H), 7.14 (t, 1H), 7.32 (t, 1H), 7.52 (t, 1H), 7.67 (t, 2H), 8.33 (s, 1H) ppm.

Example 54 Production of a Compound Represented by the Formula (A142-15)

[Chem. 265]

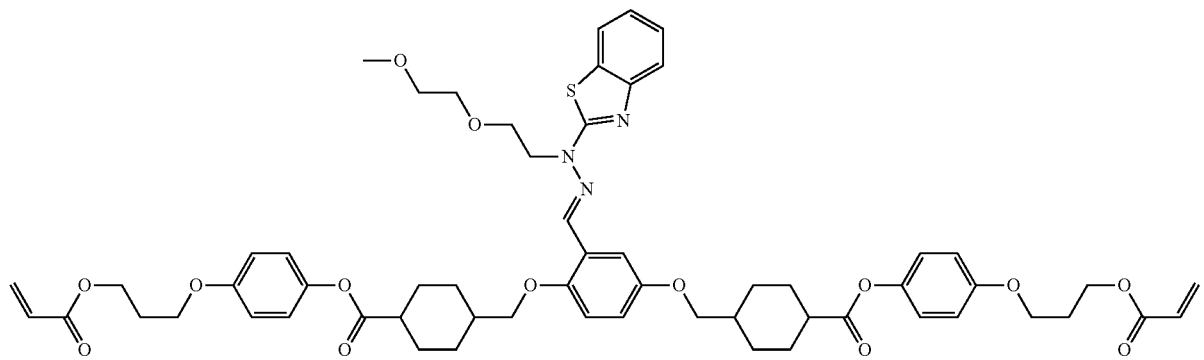

A compound represented by the formula (A142-15) was produced in the manner described above.

Transition temperature (heating rate: 5° C./min): C 89-95 N 145 I $^1$H NMR (CDCl$_3$) δ 1.24 (m, 4H), 1.65 (m, 4H), 1.91 (m, 2H), 2.05-2.25 (m, 12H), 2.55 (m, 2H), 3.30 (s, 3H), 3.51 (m, 2H), 3.67 (m, 2H), 3.84-3.89 (m, 6H), 4.05 (t, 4H), 4.36 (t, 4H), 4.54 (t, 2H), 5.84 (dd, 2H), 6.13 (dd, 2H), 6.41 (dd, 2H), 6.84-6.89 (m, 6H), 6.97-7.00 (m, 4H), 7.14 (t, 1H), 7.33 (t, 1H), 7.52 (d, 1H), 7.67 (dd, 2H), 8.34 (s, 1H) ppm.

Example 55 Production of a Compound Represented by the Formula (A143-1)

[Chem. 266]

(A143-1)

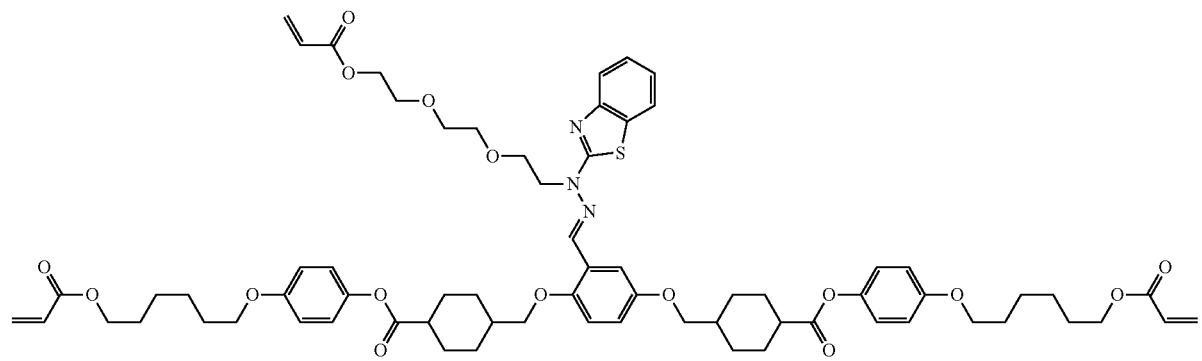

A compound represented by the formula (A143-1) was produced in the manner described above.

Transition temperature (heating rate: 5° C./min) C 71 N 115 I $^{1}$H NMR (CDCl$_{3}$) δ 1.19-1.29 (m, 4H), 1.41-1.82 (m, 22H), 1.91 (m, 2H), 2.08 (m, 4H), 2.24 (m, 4H), 2.53 (m, 2H), 3.62 (m, 3H), 3.67 (m, 2H), 3.84-3.90 (m, 5H), 3.94 (t, 4H), 4.15-4.19 (m, 6H), 4.53 (t, 2H), 5.76 (dd, 1H), 5.82 (dd, 2H), 6.08 (dd, 1H), 6.12 (dd, 2H), 6.37 (dd, 1H), 6.40 (dd, 2H), 6.84-6.90 (m, 6H), 6.95-6.98 (m, 4H), 7.14 (t, 1H), 7.32 (t, 1H), 7.53 (d, 1H), 7.65 (d, 1H), 7.69 (d, 1H), 8.34 (s, 1H) ppm.

LCMS: 1244 [M+1]

Example 56 Production of a Compound Represented by the Formula (A143-2)

[Chem. 267]

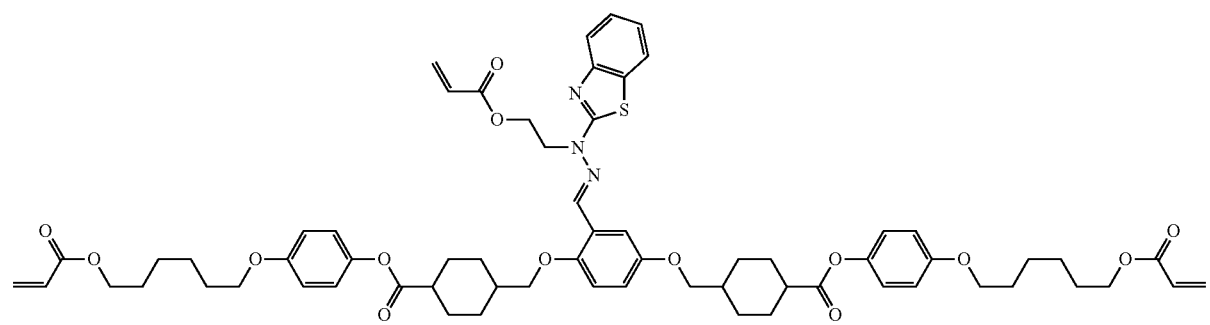

(A143-2)

A compound represented by the formula (A143-2) was produced in the manner described above.

Transition temperature (heating rate: 5° C./min) C 122 N 142 I $^{1}$H NMR (CDCl$_{3}$) δ 1.24 (m, 4H), 1.48 (m, 8H), 1.60-1.83 (m, 12H), 1.93 (m, 2H), 2.08 (t, 4H), 2.23 (m, 4H), 2.54 (m, 2H), 3.86 (dd, 4H), 3.94 (t, 4H), 4.17 (t, 4H), 4.53 (t, 2H), 4.65 (t, 2H), 5.78 (dd, 1H), 5.82 (dd, 2H), 6.08 (dd, 1H), 6.12 (dd, 2H), 6.39 (dd, 1H), 6.40 (dd, 2H), 6.88 (m, 6H), 6.97 (dd, 4H), 7.16 (t, 1H), 7.34 (t, 1H), 7.54 (d, 1H), 7.66 (d, 1H), 7.70 (d, 1H), 8.36 (s, 1H) ppm.

LCMS: 1156 [M+1]

Example 57 Production of a Compound Represented by the Formula (A144-1)

[Chem. 268]

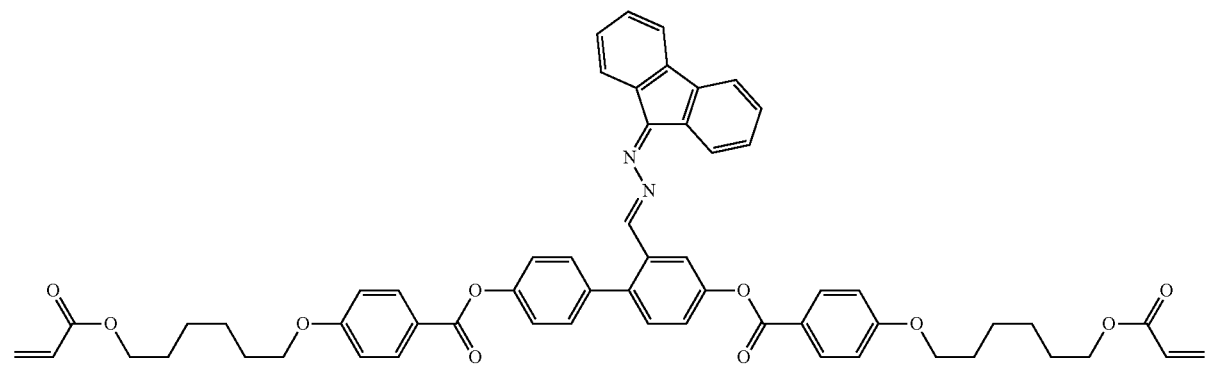

(A144-1)

A compound represented by the formula (A144-1) was produced in the manner described above.
Phase transition temperature (heating stage): C 113 N 171 I
$^1$H NMR (CDCl$_3$): 1.48-1.59 (m, 8H), 1.74 (m, 4H), 1.85 (m, 4H), 4.07 (q, 4H), 4.19 (td, 4H), 5.84 (d, 2H), 6.14 (ddd, 2H), 6.42 (dt, 2H), 7.00 (q, 4H), 7.30 (m, 4H), 7.39-7.46 (m, 5H), 7.51 (d, 1H), 7.61 (dd, 2H), 7.85 (d, 1H), 6.17 (d, 2H), 8.22-8.25 (m, 3H), 8.39 (d, 1H), 8.57 (s, 1H) ppm.
Example 58 Production of a Compound Represented by the Formula (A15-1)
[Chem. 269]
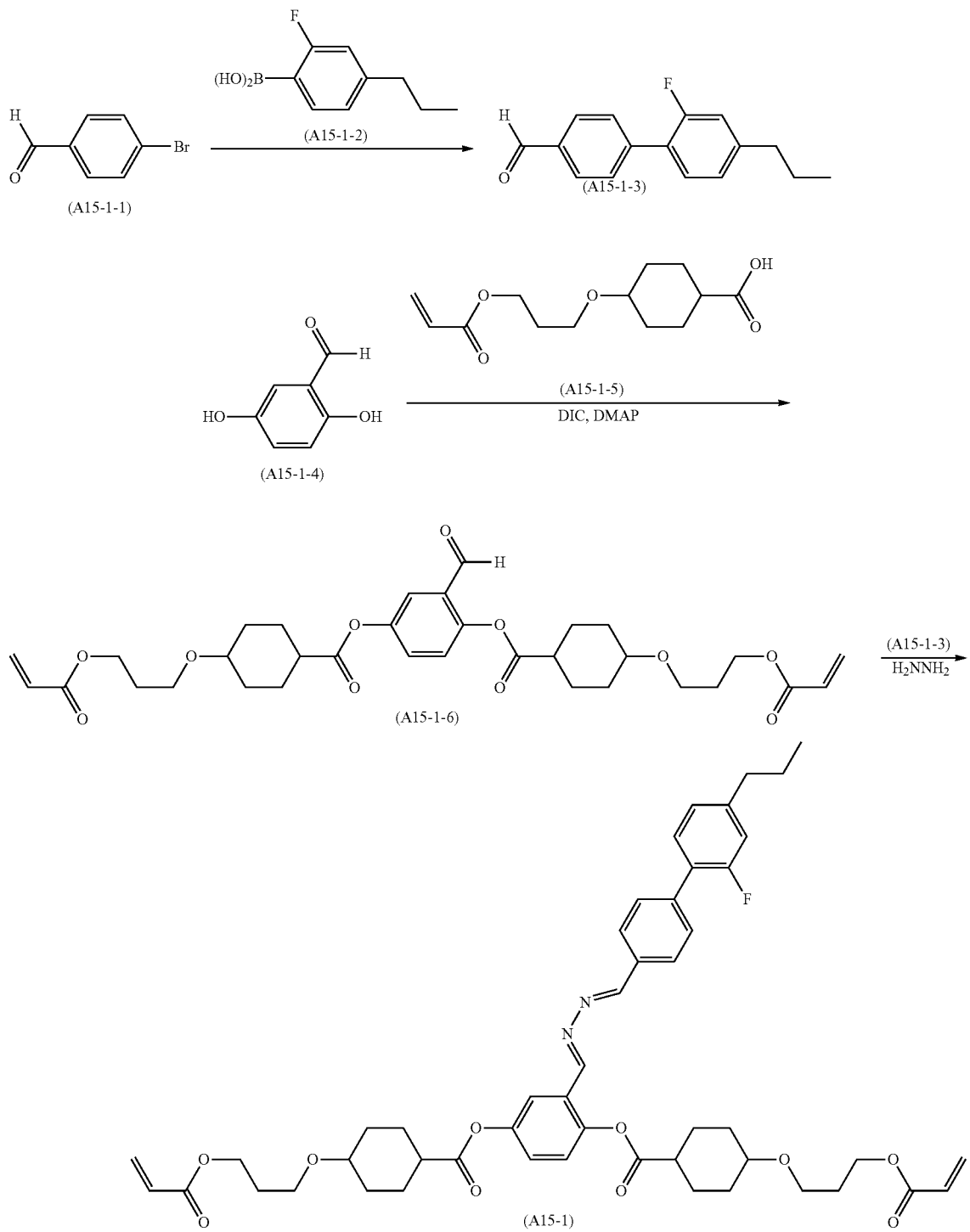

A reaction vessel was charged with a compound represented by the formula (A15-1-1), a compound represented by the formula (A15-1-2), potassium carbonate, ethanol, and tetrakis(triphenylphosphine) palladium (0), and was heated with stirring. After common posttreatment, purification by column chromatography and recrystallization yielded a compound represented by the formula (A15-1-3).

A reaction vessel was charged with a compound represented by the formula (A15-1-4), a compound represented by the formula (A15-1-5), N,N-dimethylaminopyridine, and dichloromethane. Diisopropyl carbodiimide was added, and the mixture was stirred. After common posttreatment, purification by column chromatography and recrystallization yielded a compound represented by the formula (A15-1-6).

A reaction vessel was charged with the compound represented by the formula (A15-1-6), the compound represented by the formula (A15-1-3), hydrazine monohydrate, and ethanol, and was heated with stirring. After common posttreatment, purification by column chromatography yielded a compound represented by the formula (A15-1).

MS(m/z): 853 [M$^+$+1]

Example 59 Production of a Compound Represented by the Formula (A2-3)

[Chem. 270]

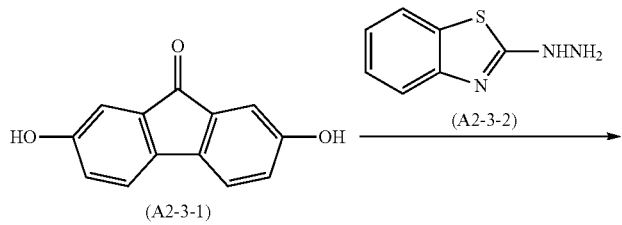

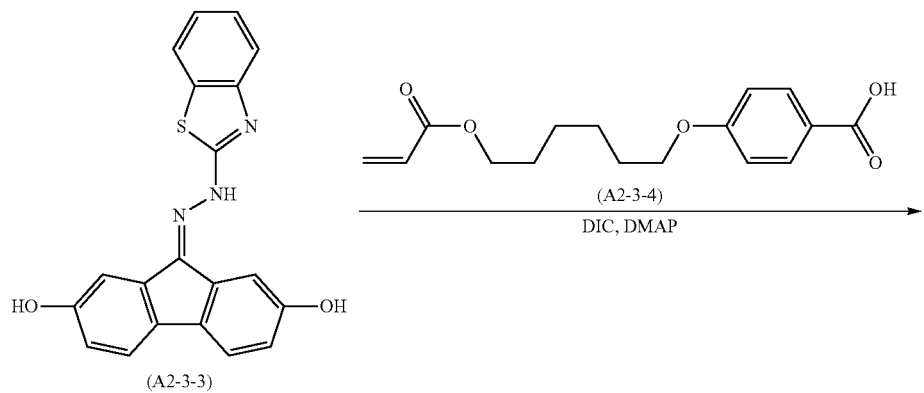

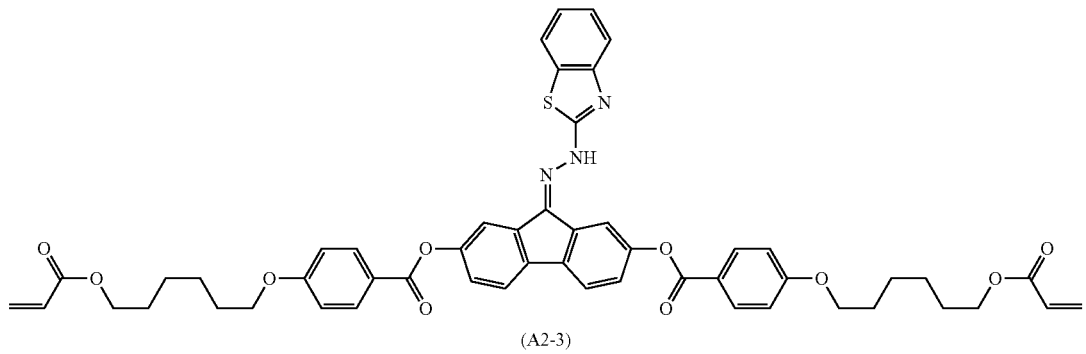

A reaction vessel was charged with a compound represented by the formula (A2-3-1), a compound represented by the formula (A2-3-1), tetrahydrofuran, ethanol, and was stirred. After common posttreatment, purification by column chromatography and recrystallization yielded a compound represented by the formula (A2-3-3).

A reaction vessel was charged with the compound represented by the formula (A2-3-3), the compound represented by the formula (A2-3-4), N,N-dimethylaminopyridine, and dichloromethane. Diisopropyl carbodiimide was added, and the mixture was stirred. After common posttreatment, purification by column chromatography and recrystallization yielded a compound represented by the formula (A2-3).

MS (m/z): 908 [M$^+$+1]

Example 60 Production of a Compound Represented by the Formula (A2-5)

[Chem. 271]

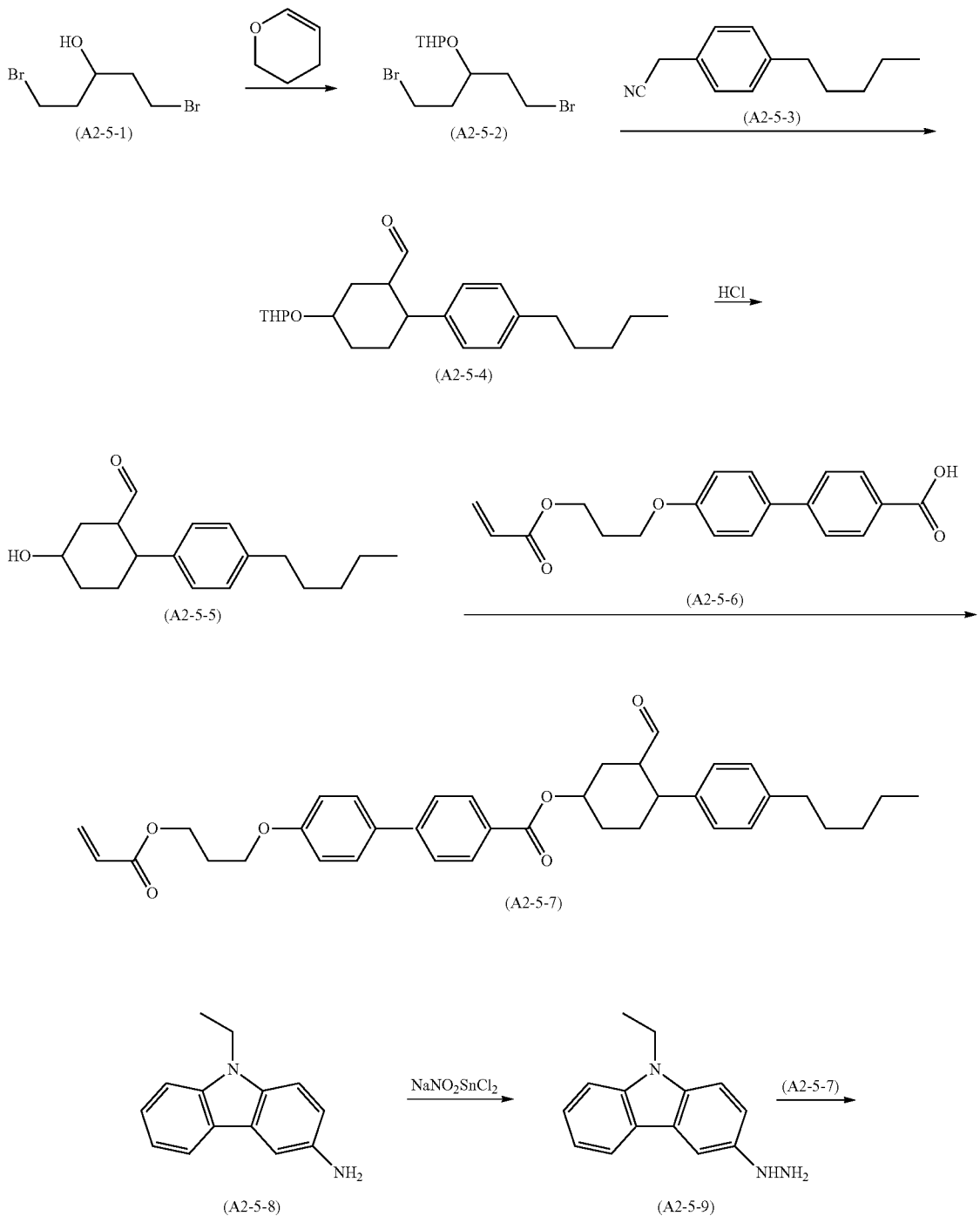

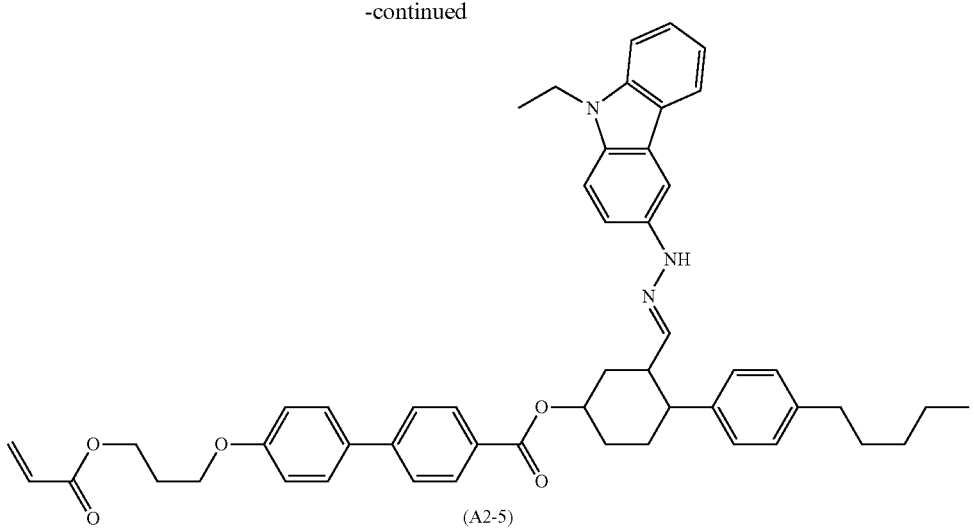

(A2-5)

A reaction vessel was charged with a compound represented by the formula (A2-5-1), pyridinium p-toluenesulfonate, and dichloromethane. After 3,4-dihydro-2H-pyran was added dropwise, the mixture was stirred. After common posttreatment, purification by column chromatography yielded a compound represented by the formula (A2-5-2).

A compound represented by the formula (A2-5-4) was produced in the same manner as in a method described in Journal of the American Chemical Society, Vol. 135, No. 34, pp. 12576-12579.

A reaction vessel was charged with the compound represented by the formula (A2-5-4), tetrahydrofuran, methanol, and concentrated hydrochloric acid, and was stirred. After common posttreatment, purification by column chromatography yielded a compound represented by the formula (A2-5-5).

A compound represented by the formula (A2-5-6) was produced in the same manner as in a method described in Example 9 of WO 2012/144331 A1. A reaction vessel was charged with the compound represented by the formula (A2-5-5), the compound represented by the formula (A2-5-6), N,N-dimethylaminopyridine, and dichloromethane. Diisopropyl carbodiimide was added, and the mixture was stirred. After common posttreatment, purification by column chromatography and recrystallization yielded a compound represented by the formula (A2-5-7).

A reaction vessel was charged with a compound represented by the formula (A2-5-8), acetic acid, and concentrated hydrochloric acid. Aqueous sodium nitrite was added dropwise while ice cooling, and the mixture was stirred. A solution of tin (II) chloride in concentrated hydrochloric acid was added dropwise while ice cooling, and the mixture was stirred. After common posttreatment, purification by column chromatography and recrystallization yielded a compound represented by the formula (A2-5-9).

A reaction vessel was charged with the compound represented by the formula (A2-5-9), the compound represented by the formula (A2-5-7), (±)-10-camphorsulfonic acid, tetrahydrofuran, and ethanol, and was stirred. After common posttreatment, purification by column chromatography and recrystallization yielded a compound represented by the formula (A2-5).

MS(m/z): 790 [M$^+$+1]

Example 61 Production of a Compound Represented by the Formula (A3-1)

[Chem. 272]

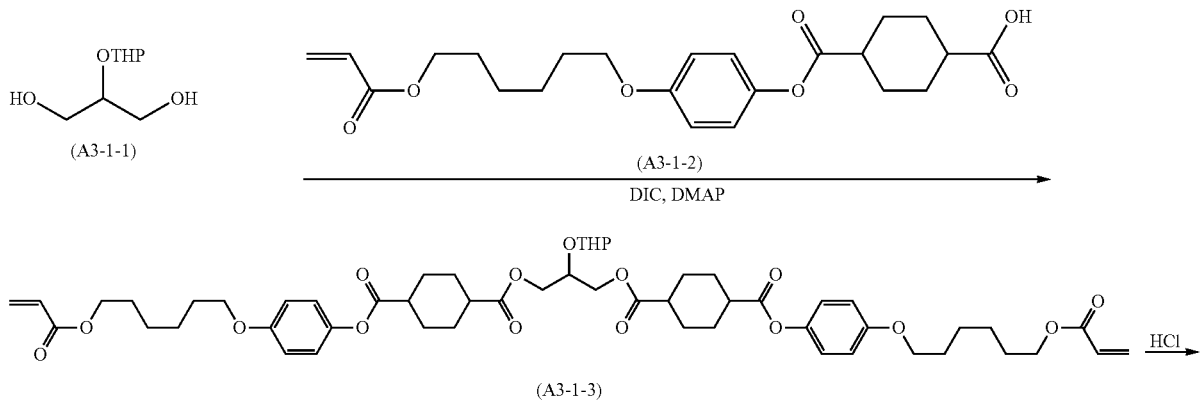

-continued

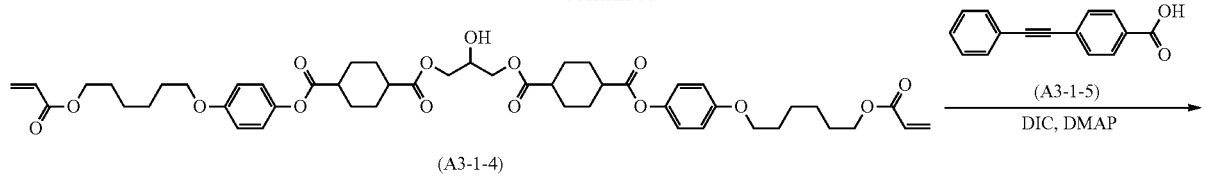

(A3-1-4)

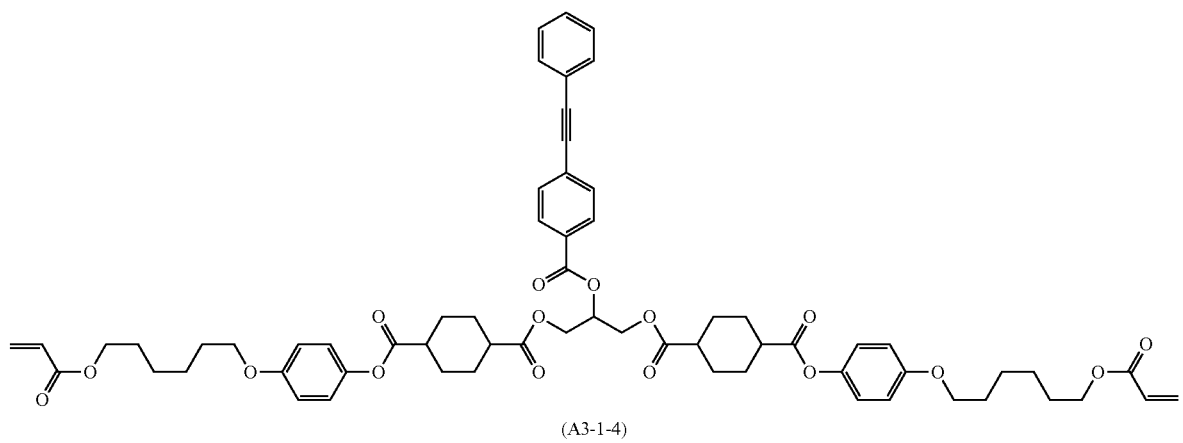

(A3-1-4)

A compound represented by the formula (A3-1-1) was produced by a method described in Journal of Medicinal Chemistry, Vol. 54, No. 23, pp. 8085-8098. A compound represented by the formula (A3-1-2) was produced by a method described in WO 2011/068138 A1. A reaction vessel was charged with the compound represented by the formula (A3-1-1), the compound represented by the formula (A3-1-2), N,N-dimethylaminopyridine, and dichloromethane. Diisopropyl carbodiimide was added, and the mixture was stirred. After common posttreatment, purification by column chromatography yielded a compound represented by the formula (A3-1-3).

A reaction vessel was charged with the compound represented by the formula (A3-1-3), tetrahydrofuran, methanol, and concentrated hydrochloric acid, and was stirred. After common posttreatment, purification by column chromatography yielded a compound represented by the formula (A3-1-4).

A reaction vessel was charged with the compound represented by the formula (A3-1-4), a compound represented by the formula (A3-1-5), N,N-dimethylaminopyridine, and dichloromethane. Diisopropyl carbodiimide was added, and the mixture was stirred. After common posttreatment, purification by column chromatography yielded a compound represented by the formula (A3-1).

MS(m/z): 1097 [M$^+$+1]

Example 62 Production of a Compound Represented by the Formula (B11-1)

[Chem. 273]

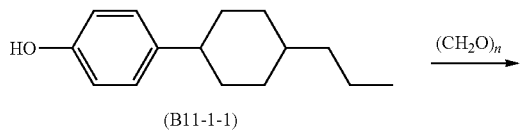

(B11-1-1)

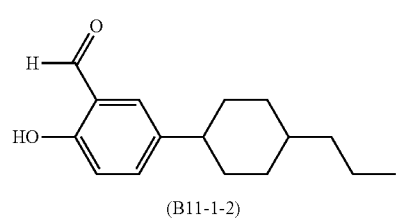

(B11-1-2)

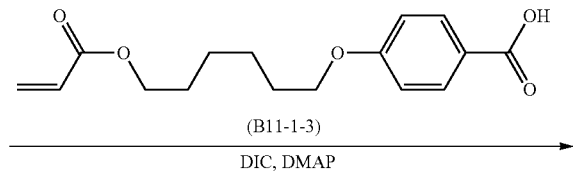

(B11-1-3)

DIC, DMAP

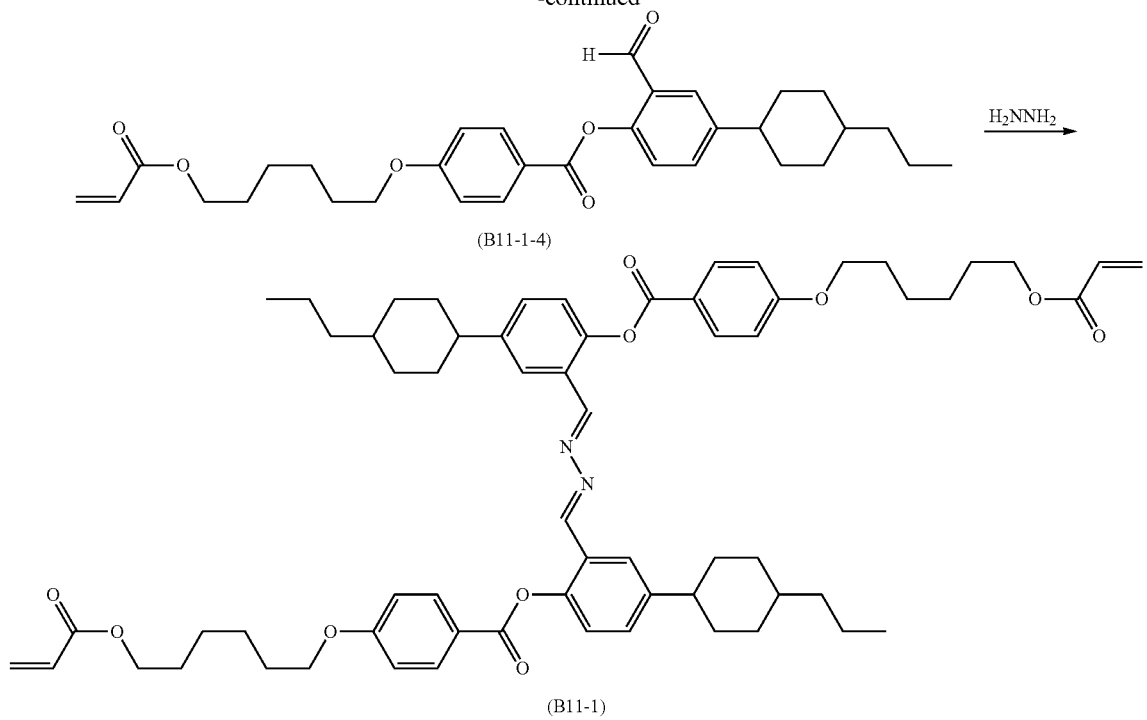

A reaction vessel was charged with a compound represented by the formula (B11-1-1), paraformaldehyde, magnesium chloride, triethylamine, and acetonitrile, and was heated with stirring. After common posttreatment, purification by column chromatography yielded a compound represented by the formula (B11-1-2).

A reaction vessel was charged with the compound represented by the formula (B11-1-2), a compound represented by the formula (B11-1-3), N,N-dimethylaminopyridine, and dichloromethane. Diisopropyl carbodiimide was added, and the mixture was stirred. After common posttreatment, purification by column chromatography and recrystallization yielded a compound represented by the formula (B11-1-4).

A reaction vessel was charged with the compound represented by the formula (B11-1-4), hydrazine monohydrate, and ethanol, and was heated with stirring. After common posttreatment, purification by column chromatography and recrystallization yielded a compound represented by the formula (B11-1).

MS(m/z): 1037 [M$^+$+1]

Example 63 Production of a Compound Represented by the Formula (B11-8)

[Chem. 274]

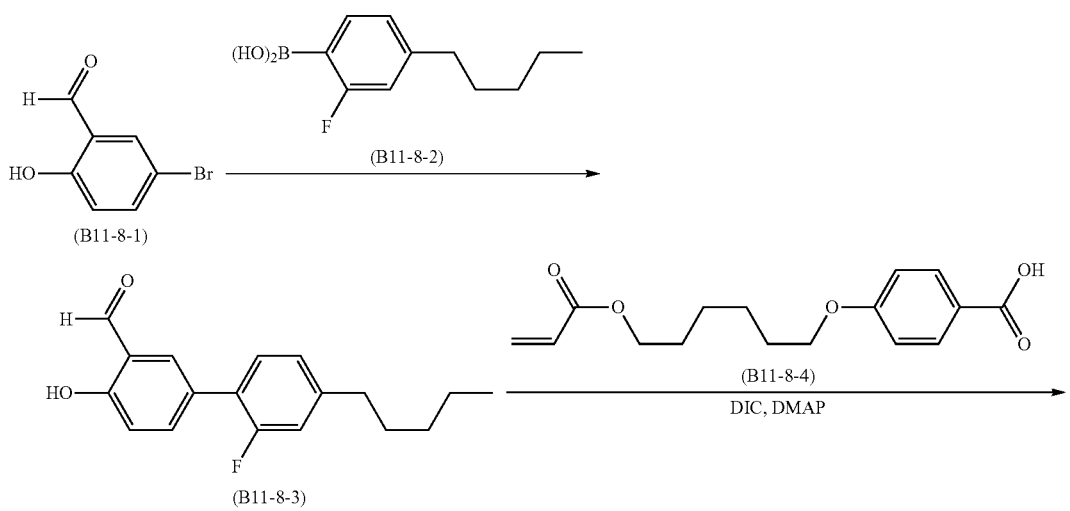

-continued

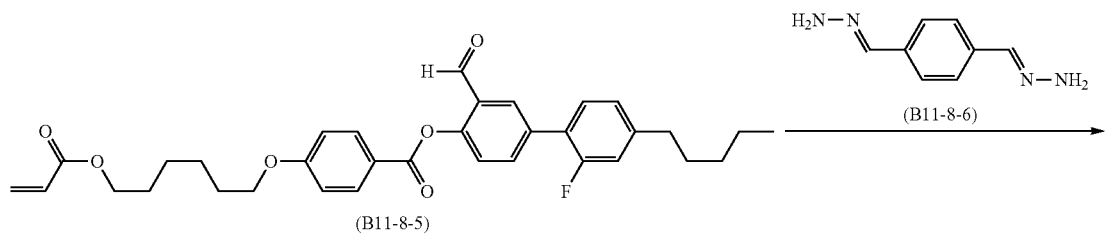

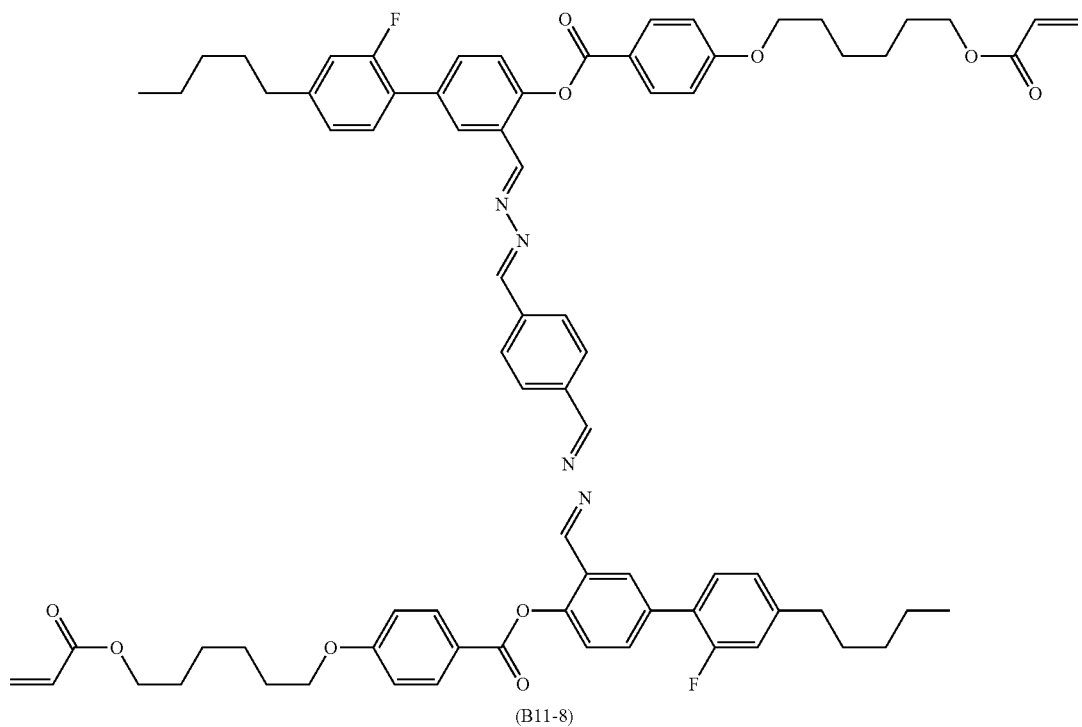

A reaction vessel was charged with a compound represented by the formula (B11-8-1), a compound represented by the formula (B11-8-2), potassium carbonate, ethanol, and tetrakis(triphenylphosphine) palladium (0), and was heated with stirring. After common posttreatment, purification by column chromatography and recrystallization yielded a compound represented by the formula (B11-8-3).

A reaction vessel was charged with the compound represented by the formula (B11-8-3), a compound represented by the formula (B11-8-4), N,N-dimethylaminopyridine, and dichloromethane. Diisopropyl carbodiimide was added, and the mixture was stirred. After common posttreatment, purification by column chromatography and recrystallization yielded a compound represented by the formula (B11-8-5).

A compound represented by the formula (B11-8-6) was produced by a method described in Oriental Journal of Chemistry, Vol. 27, No. 2, pp. 517-522. A reaction vessel was charged with the compound represented by the formula (B11-8-5), the compound represented by the formula (B11-8-6), and ethanol, and was heated with stirring. After common posttreatment, purification by column chromatography and recrystallization yielded a compound represented by the formula (B11-8).
MS(m/z): 1247 [M$^+$+1]
Example 64 Production of a Compound Represented by the Formula (B2-2)
[Chem. 275]
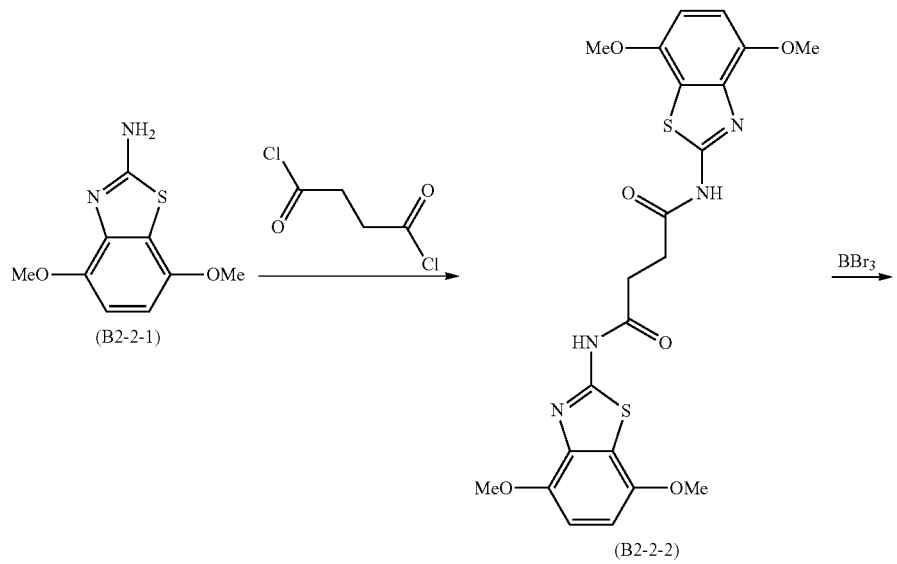
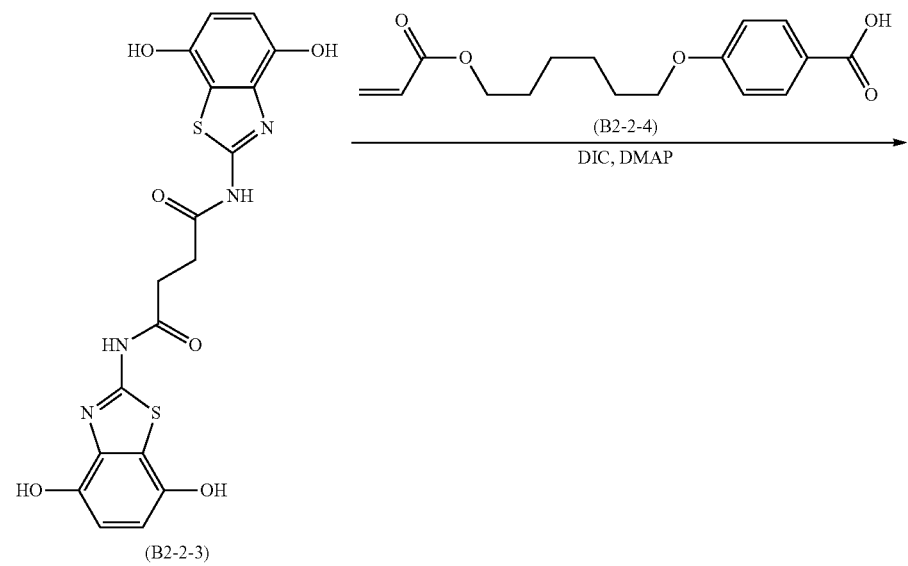

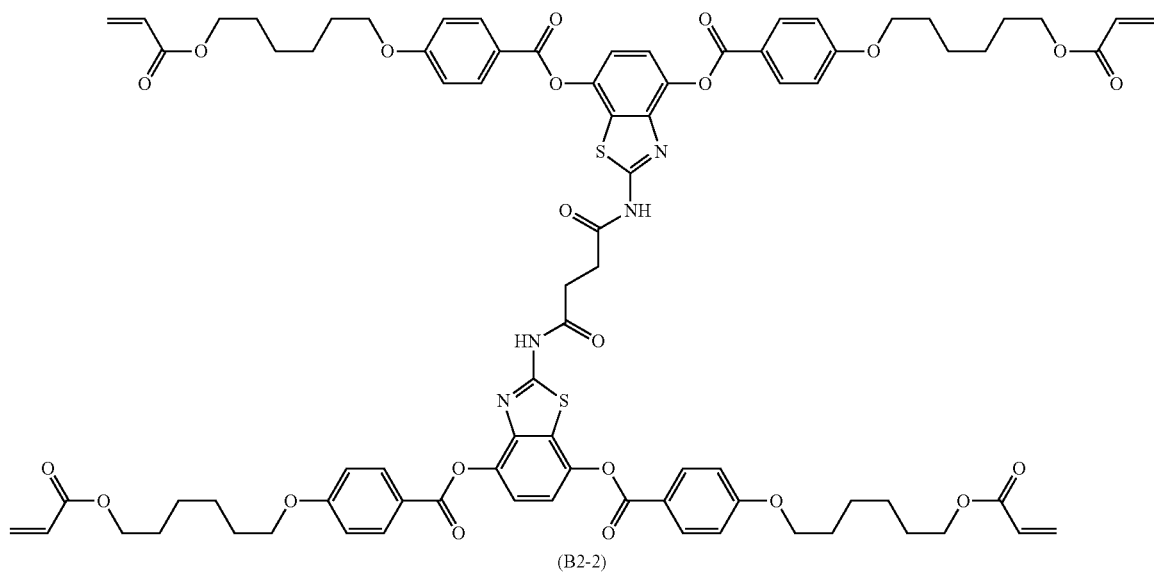

(B2-2)

A compound represented by the formula (B2-2-1) was produced by a method described in WO 2002/047762 A1. A reaction vessel was charged with the compound represented by the formula (B2-2-1), triethylamine, dichloromethane, and succinyl chloride, and was stirred. After common posttreatment, purification by column chromatography and recrystallization yielded a compound represented by the formula (B2-2-2).

A reaction vessel was charged with the compound represented by the formula (B2-2-2) and dichloromethane. Boron tribromide was added while cooling to −78° C., and the mixture was stirred. After common posttreatment, purification by column chromatography and recrystallization yielded a compound represented by the formula (B2-2-3).

A reaction vessel was charged with the compound represented by the formula (B2-2-3), a compound represented by the formula (B2-2-4), N,N-dimethylaminopyridine, and dichloromethane. Diisopropyl carbodiimide was added, and the mixture was stirred. After common posttreatment, purification by column chromatography and recrystallization yielded a compound represented by the formula (B2-2).

MS(m/z): 1543 [M$^+$+1]

Example 65 Production of a Compound Represented by the Formula (B2-6)

[Chem. 276]

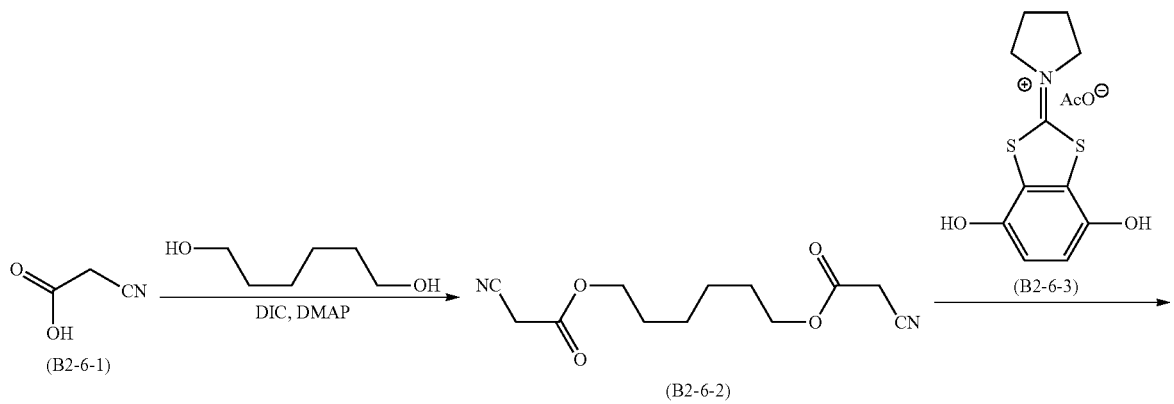

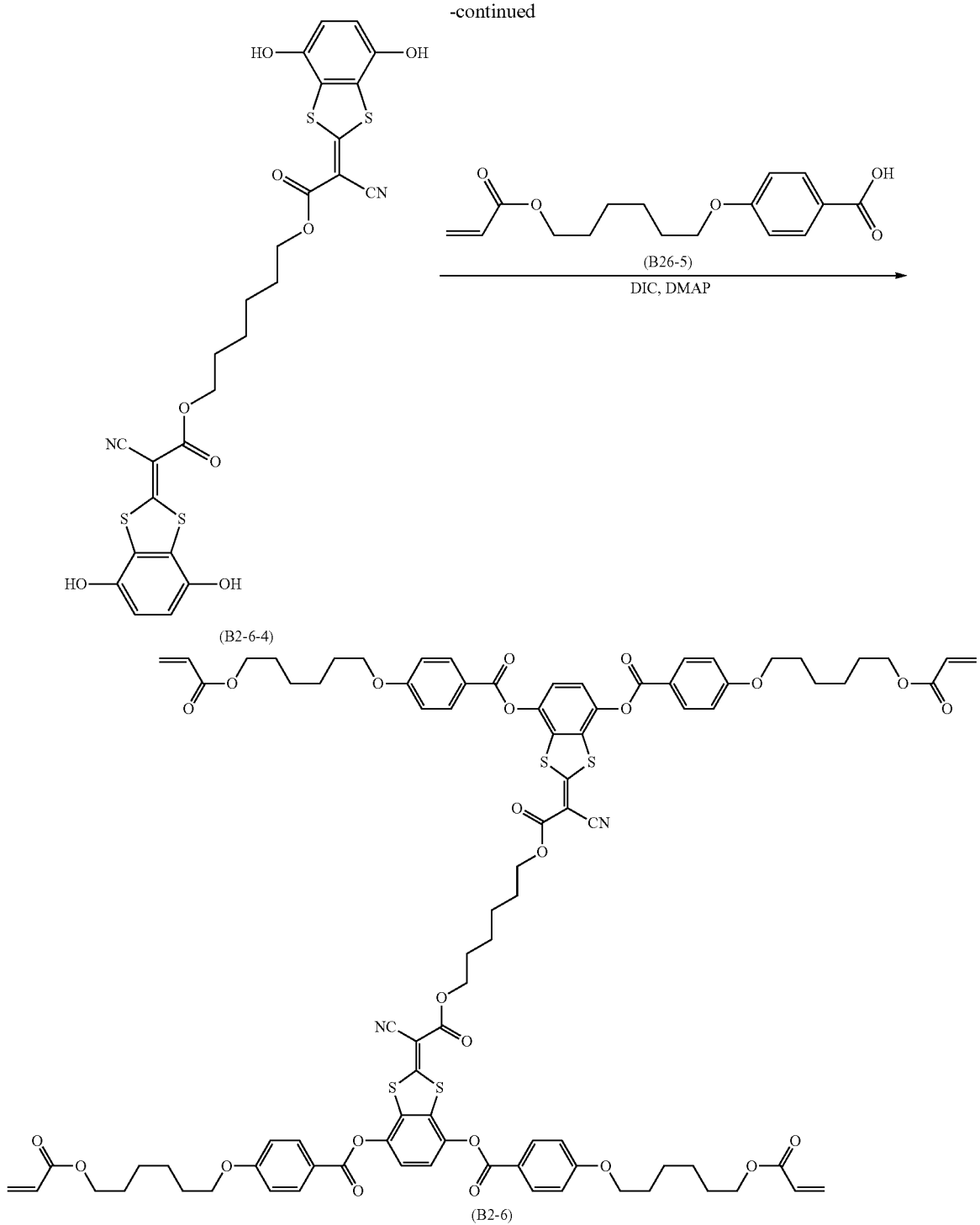

A reaction vessel was charged with a compound represented by the formula (B2-6-1), 1,6-hexanediol, N,N-dimethylaminopyridine, and dichloromethane. Diisopropyl carbodiimide was added, and the mixture was stirred. After common posttreatment, purification by column chromatography yielded a compound represented by the formula (B2-6-2).

A compound represented by the formula (B2-6-3) was produced by a method described in Journal of Chemical Crystallography, Vol. 27, No. 9, pp. 515-526. A reaction vessel was charged with the compound represented by the formula (B2-6-3), N-methylpyrrolidinone, and the compound represented by the formula (B2-6-2), and was heated with stirring. After common posttreatment, purification by column chromatography and recrystallization yielded a compound represented by the formula (B2-6-4).

A reaction vessel was charged with the compound represented by the formula (B2-6-4), a compound represented by the formula (B2-6-5), N,N-dimethylaminopyridine, and dichloromethane. Diisopropyl carbodiimide was added, and the mixture was stirred. After common posttreatment, purification by column chromatography and recrystallization yielded a compound represented by the formula (B2-6).
MS(m/z): 1713 [M+ +1]
Example 66 Production of a Compound Represented by the Formula (B2-13)
[Chem. 277]
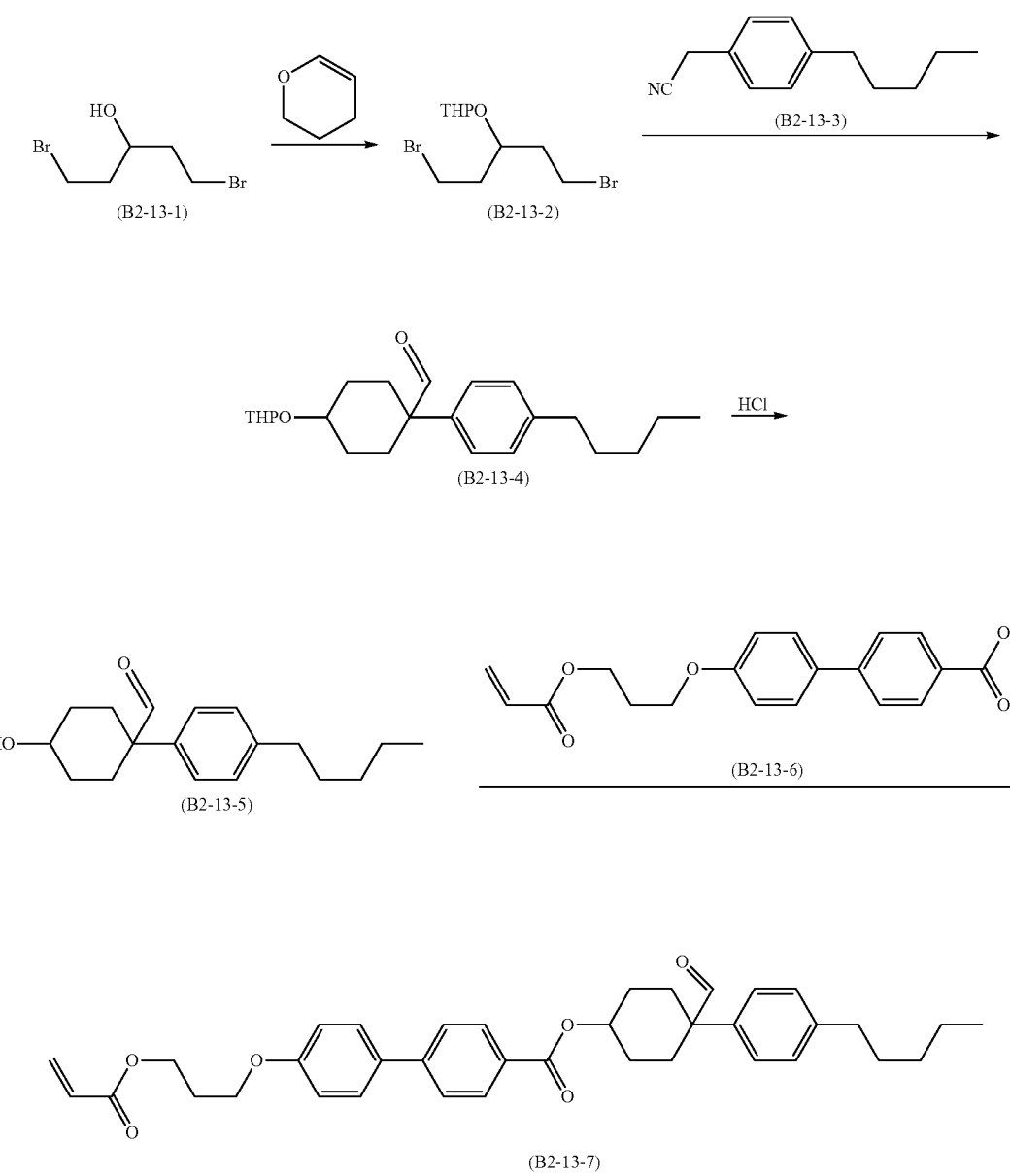
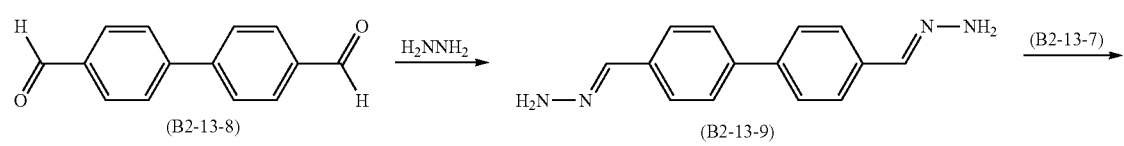

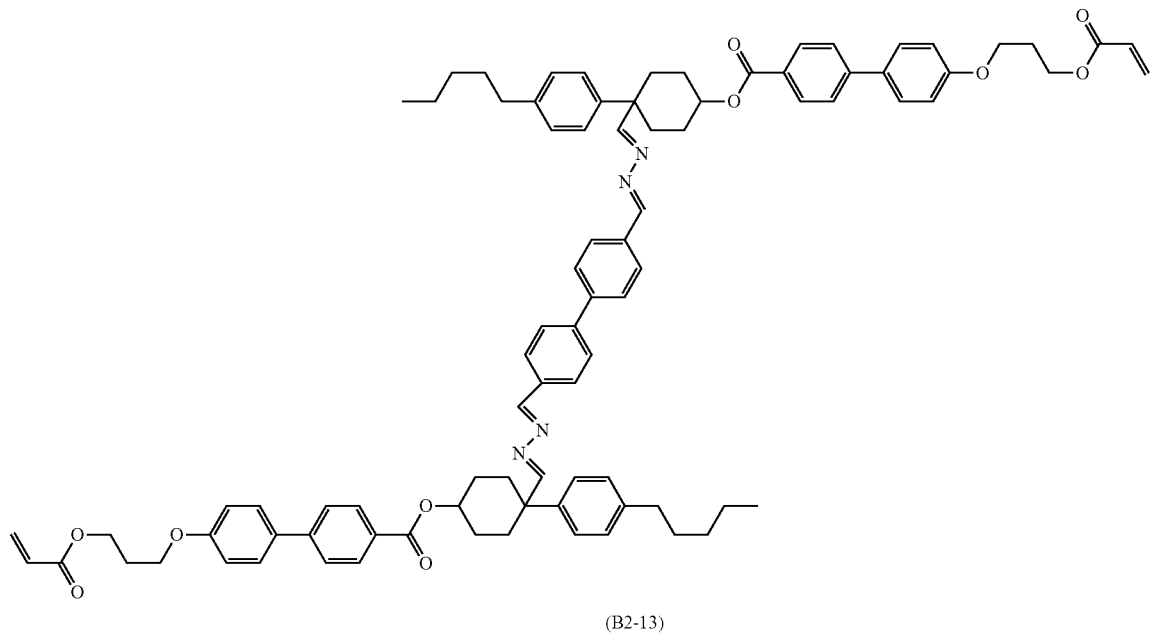

(B2-13)

A reaction vessel was charged with a compound represented by the formula (B2-13-1), pyridinium p-toluenesulfonate, and dichloromethane. After 3,4-dihydro-2H-pyran was added dropwise, the mixture was stirred. After common posttreatment, purification by column chromatography yielded a compound represented by the formula (B2-13-2).

A compound represented by the formula (B2-13-4) was produced in the same manner as in a method described in Journal of the American Chemical Society, Vol. 135, No. 34, pp. 12576-12579.

A reaction vessel was charged with the compound represented by the formula (B2-13-4), tetrahydrofuran, methanol, and concentrated hydrochloric acid, and was stirred. After common posttreatment, purification by column chromatography yielded a compound represented by the formula (B2-13-5).

A compound represented by the formula (B2-13-6) was produced in the same manner as in a method described in Example 9 of WO 2012/144331 A1. A reaction vessel was charged with the compound represented by the formula (B2-13-5), the compound represented by the formula (B2-13-6), N,N-dimethylaminopyridine, and dichloromethane. Diisopropyl carbodiimide was added, and the mixture was stirred. After common posttreatment, purification by column chromatography and recrystallization yielded a compound represented by the formula (B2-13-7).

A reaction vessel was charged with a compound represented by the formula (B2-13-8), hydrazine monohydrate, and ethanol, and was heated with stirring. After common posttreatment, purification by column chromatography and recrystallization yielded a compound represented by the formula (B2-13-9).

A reaction vessel was charged with the compound represented by the formula (B2-13-9), the compound represented by the formula (B2-13-7), (±)-10-camphorsulfonic acid, tetrahydrofuran, and ethanol, and was stirred. After common posttreatment, purification by column chromatography and recrystallization yielded a compound represented by the formula (B2-13).

MS(m/z): 1367 [M$^+$+1]

Example 67 Production of a Compound Represented by the Formula (B3-1)

[Chem. 278]

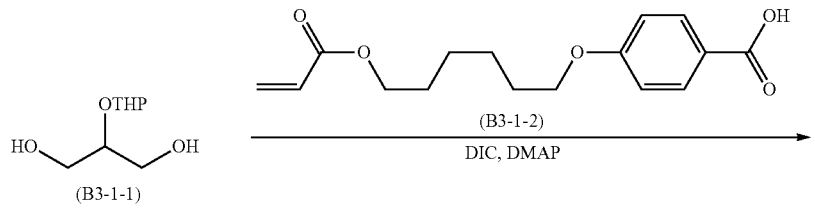

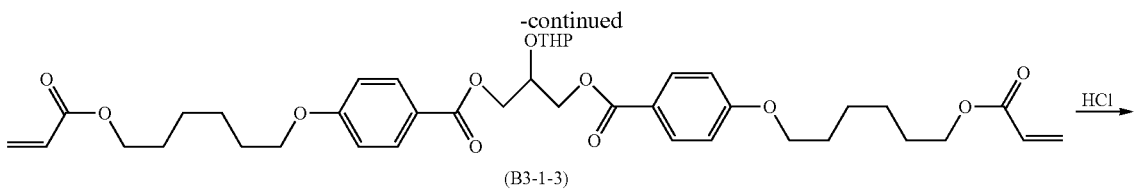

(B3-1-3)

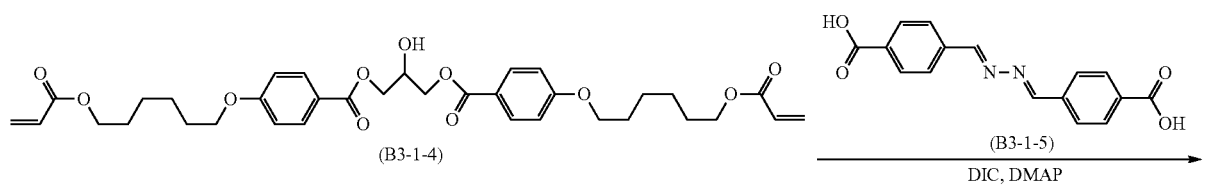

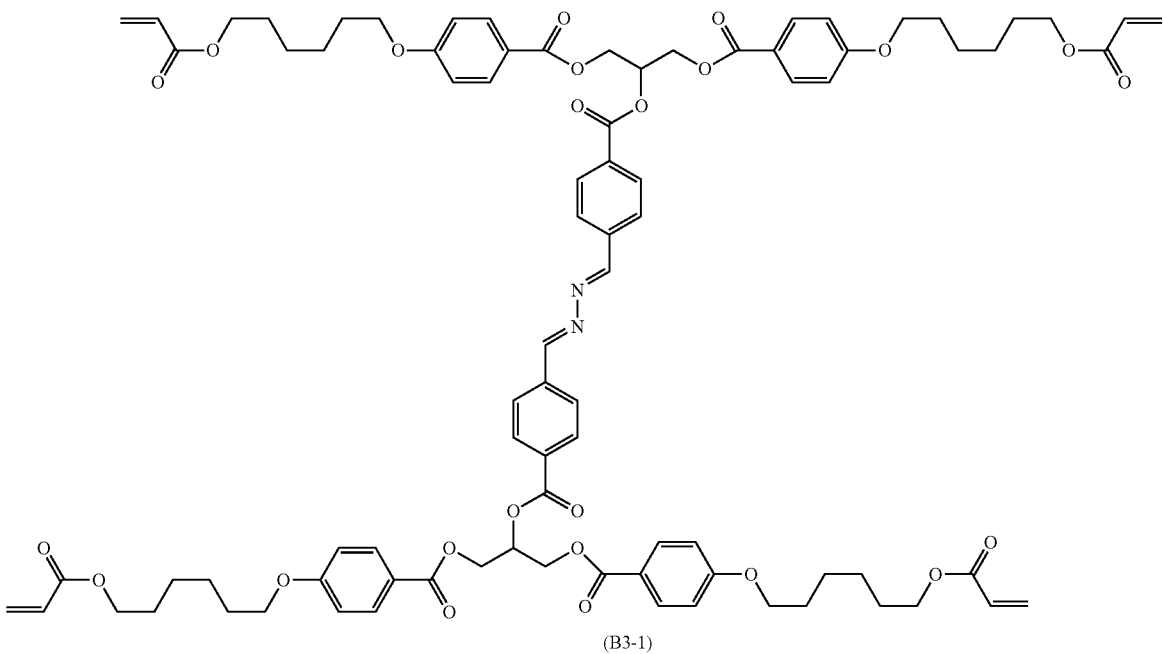

(B3-1)

A compound represented by the formula (B3-1-1) was produced by a method described in Journal of Medicinal Chemistry, Vol. 54, No. 23, pp. 8085-8098. A reaction vessel was charged with the compound represented by the formula (B3-1-1), a compound represented by the formula (B3-1-2), N,N-dimethylaminopyridine, and dichloromethane. Diisopropyl carbodiimide was added, and the mixture was stirred. After common posttreatment, purification by column chromatography yielded a compound represented by the formula (B3-1-3).

A reaction vessel was charged with the compound represented by the formula (B3-1-3), tetrahydrofuran, methanol, and concentrated hydrochloric acid, and was stirred. After common posttreatment, purification by column chromatography yielded a compound represented by the formula (B3-1-4).

A compound represented by the formula (B3-1-5) was produced by a method described in Acta Chimica Slovenica, Vol. 49, No. 3, pp. 605-611. A reaction vessel was charged with the compound represented by the formula (B3-1-4), the compound represented by the formula (B3-1-5), N,N-dimethylaminopyridine, and dichloromethane. Diisopropyl carbodiimide was added, and the mixture was stirred. After common posttreatment, purification by column chromatography yielded a compound represented by the formula (B3-1).
MS(m/z): 1541 [M$^+$+1]
Example 68 Production of a Compound Represented by the Formula (C11-2)
[Chem. 279]
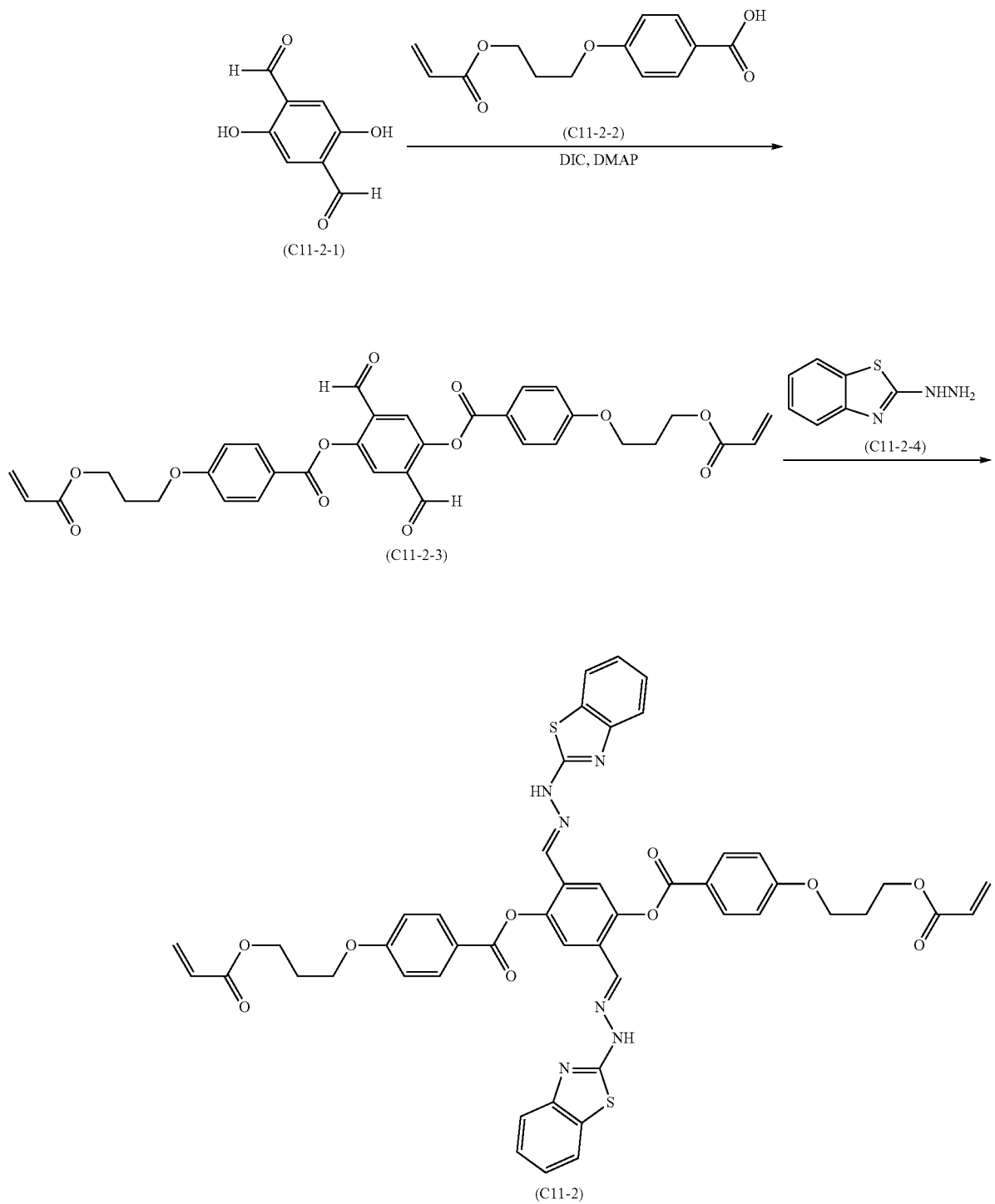

A compound represented by the formula (C11-2-1) was produced by a method described in Tetrahedron Letters, Vol. 54, No. 26, pp. 3419-3423. A reaction vessel was charged with the compound represented by the formula (C11-2-1), a compound represented by the formula (C11-2-2), N,N-dimethylaminopyridine, and dichloromethane. Diisopropyl carbodiimide was added, and the mixture was stirred. After common posttreatment, purification by column chromatography and recrystallization yielded a compound represented by the formula (C11-2-3).

A reaction vessel was charged with the compound represented by the formula (C11-2-3), a compound represented by the formula (C11-2-4), (±)-10-camphorsulfonic acid, tetrahydrofuran, and ethanol, and was stirred. After common posttreatment, purification by column chromatography and recrystallization yielded a compound represented by the formula (C11-2).

MS(m/z): 925 [M$^+$+1]

Example 69 Production of a Compound Represented by the Formula (C12-1)

[Chem. 280]

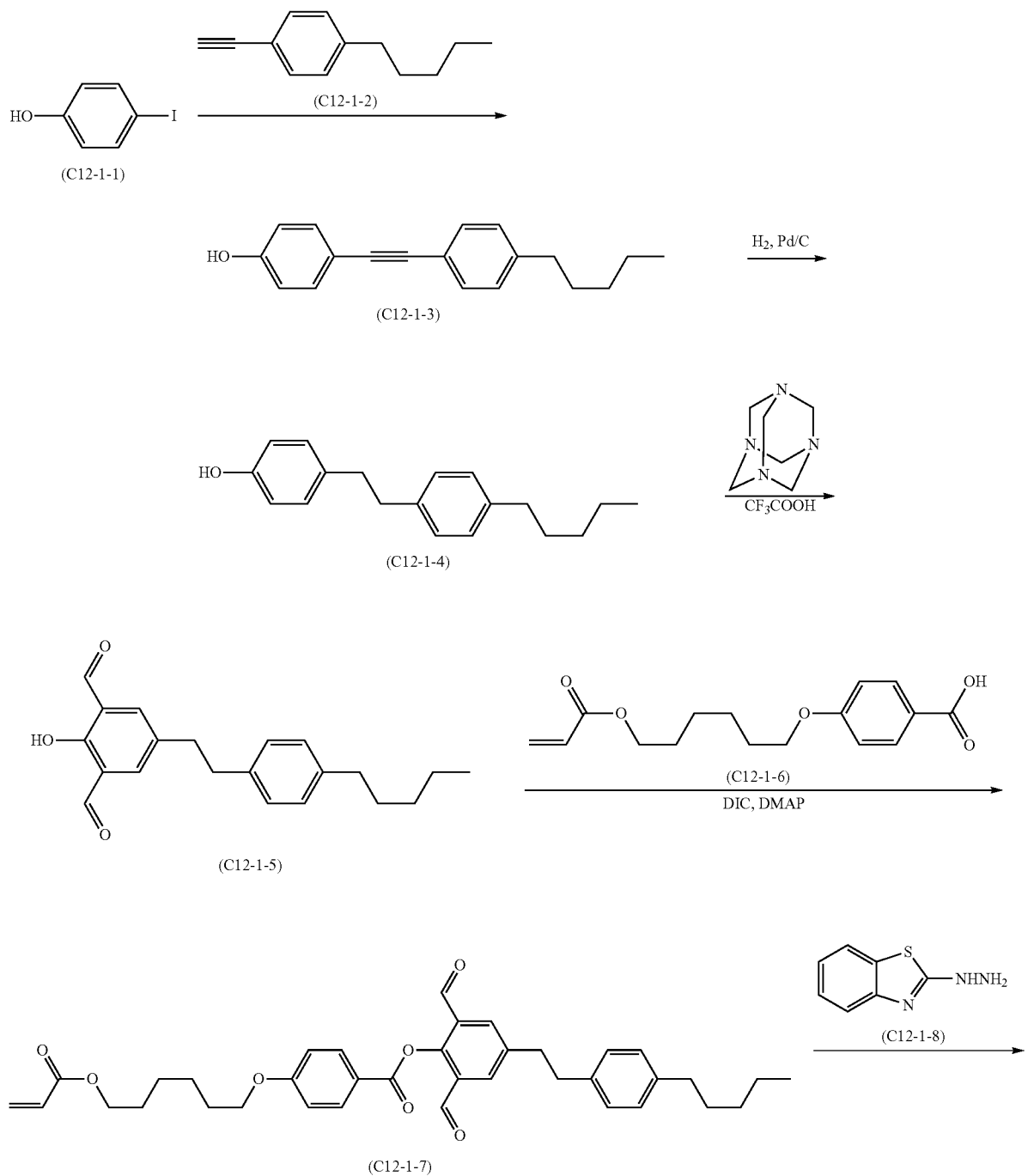

-continued

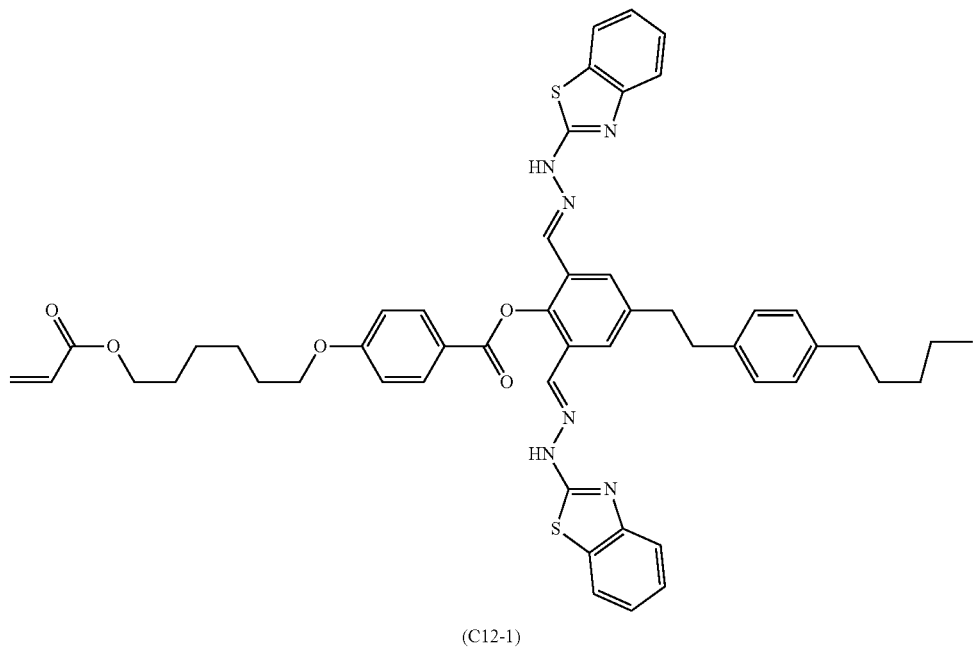

(C12-1)

A reaction vessel in an inert atmosphere was charged with a compound represented by the formula (C12-1-1), a compound represented by the formula (C12-1-2), copper (I) iodide, triethylamine, N,N-dimethylformamide, and tetrakis (triphenylphosphine) palladium (0), and was heated with stirring. After common posttreatment, purification by column chromatography and recrystallization yielded a compound represented by the formula (C12-1-3).

A reaction vessel was charged with the compound represented by the formula (C12-1-3), tetrahydrofuran, and 5% palladium carbon, and was stirred in a hydrogen atmosphere. After the catalyst was removed, purification by column chromatography and recrystallization yielded a compound represented by the formula (C12-1-4).

A reaction vessel was charged with the compound represented by the formula (C12-1-4), hexamethylenetetramine, and trifluoroacetic acid, and was heated with stirring. A reaction liquid was poured into 4 N hydrochloric acid, and precipitated solid was filtered. Purification by column chromatography and recrystallization yielded a compound represented by the formula (C12-1-5).

A reaction vessel was charged with the compound represented by the formula (C12-1-5), a compound represented by the formula (C12-1-6), N,N-dimethylaminopyridine, and dichloromethane. Diisopropyl carbodiimide was added, and the mixture was stirred. After common posttreatment, purification by column chromatography and recrystallization yielded a compound represented by the formula (C12-1-7).

A reaction vessel was charged with the compound represented by the formula (C12-1-7), a compound represented by the formula (C12-1-8), (±)-10-camphorsulfonic acid, tetrahydrofuran, and ethanol, and was stirred. After common posttreatment, purification by column chromatography and recrystallization yielded a compound represented by the formula (C12-1).

MS(m/z): 893 [M$^+$+1]

Example 70 Production of a Compound Represented by the Formula (C2-1)

[Chem. 281]

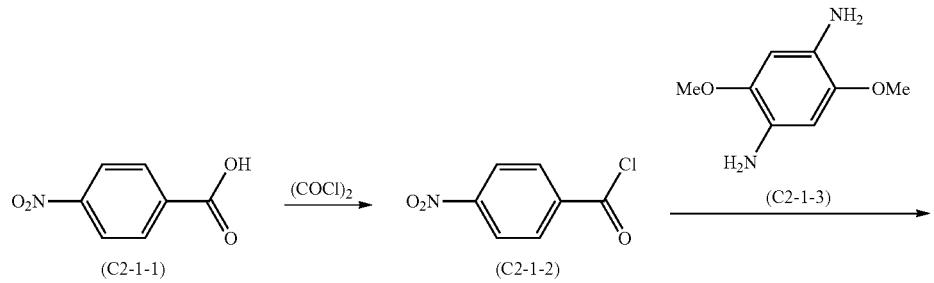

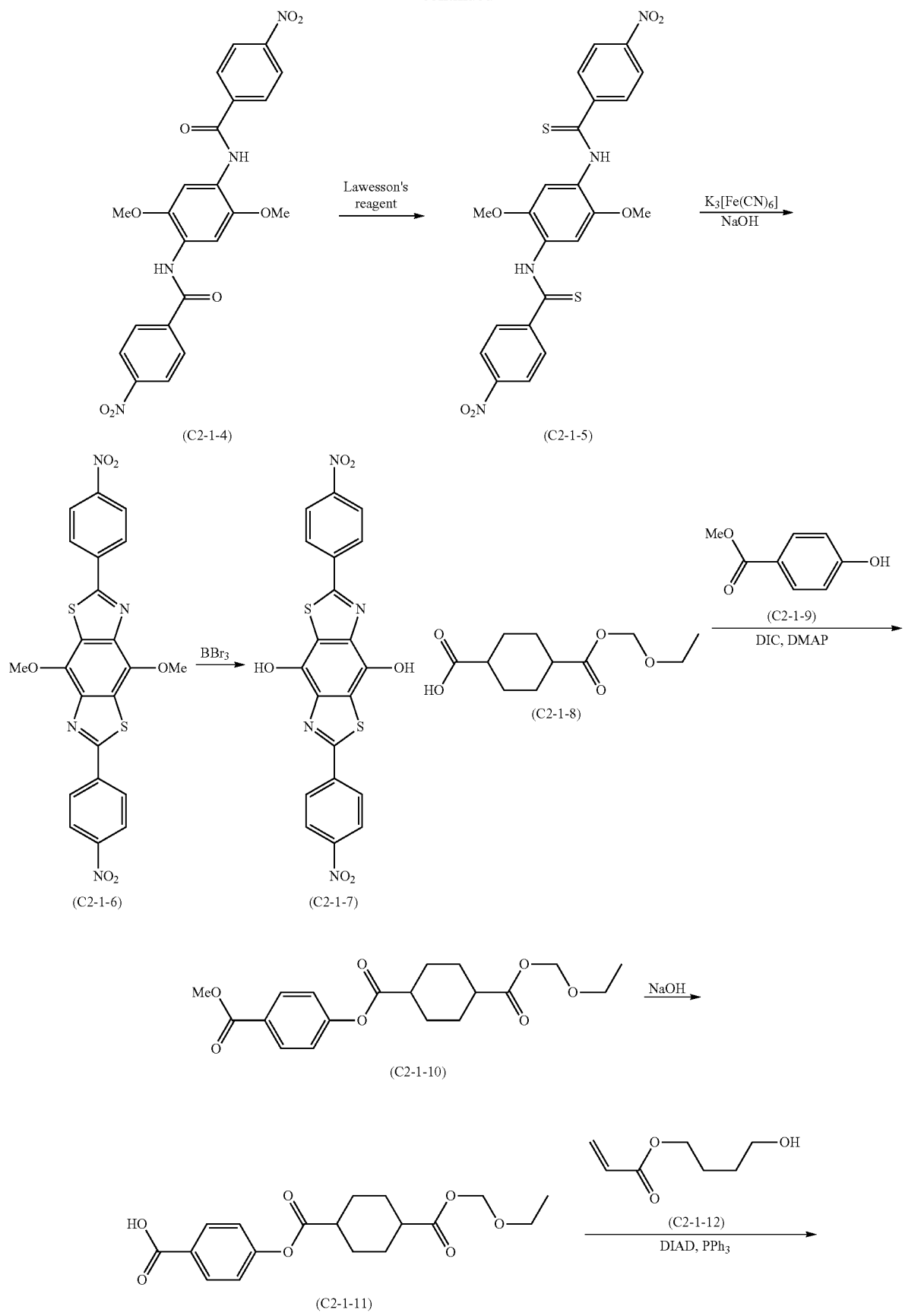

-continued

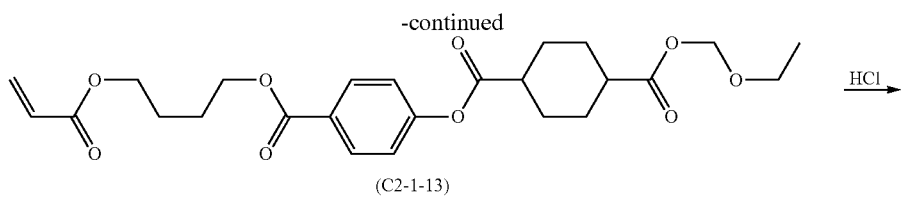

(C2-1-13)

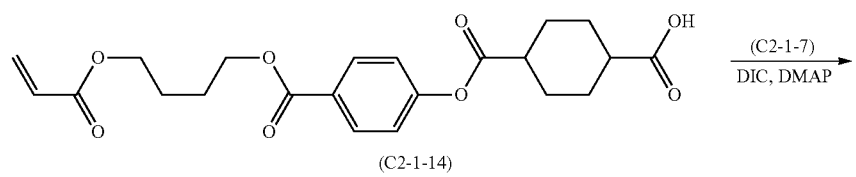

(C2-1-14)

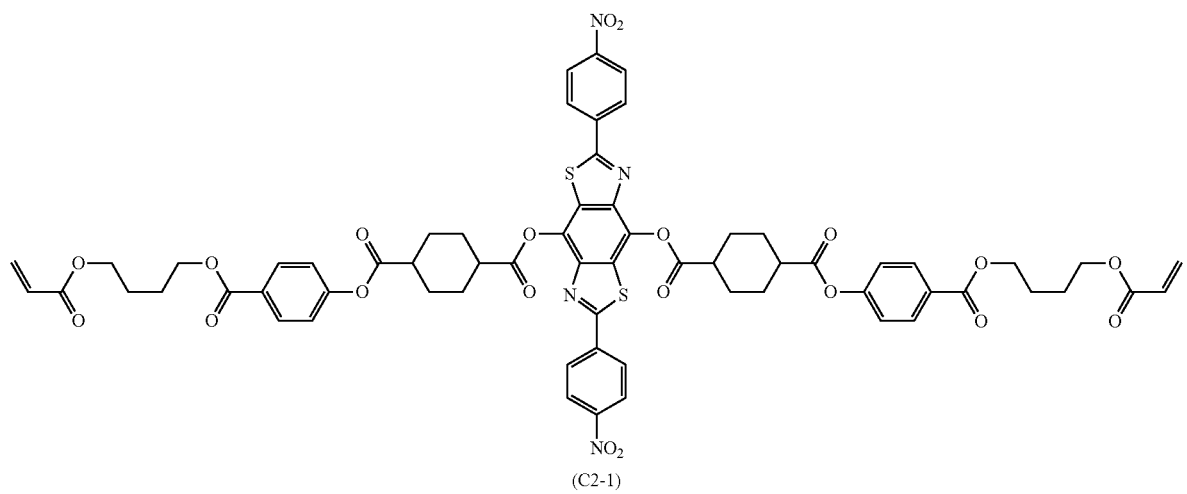

(C2-1)

A reaction vessel was charged with a compound represented by the formula (C2-1-1), oxalylchloride, 1,3-dimethyl-2-imidazolidinone, and chloroform, and was stirred. The solvent was distilled off, thereby yielding a compound represented by the formula (C2-1-2).

A compound represented by the formula (C2-1-3) was produced by a method described in Journal of Organic Chemistry, Vol. 72, No. 8, pp. 2897-2905. A reaction vessel was charged with the compound represented by the formula (C2-1-2), the compound represented by the formula (C2-1-3), triethylamine, and chloroform, and was stirred. After common posttreatment, purification by column chromatography and recrystallization yielded a compound represented by the formula (C2-1-4).

A reaction vessel was charged with the compound represented by the formula (C2-1-4), Lawesson's reagent, and toluene, and was heated with stirring. After common posttreatment, purification by column chromatography and recrystallization yielded a compound represented by the formula (C2-1-5).

A reaction vessel was charged with the compound represented by the formula (C2-1-5) and aqueous sodium hydroxide. Aqueous potassium ferricyanide was added, and the mixture was stirred. The solid was filtered and washed, thereby yielding a compound represented by the formula (C2-1-6).

A reaction vessel was charged with the compound represented by the formula (C2-1-6) and dichloromethane. Boron tribromide was added while ice cooling, and the mixture was stirred. After common posttreatment, purification by column chromatography and recrystallization yielded a compound represented by the formula (C2-1-7).

A compound represented by the formula (C2-1-8) was produced by a method described in Japanese Unexamined Patent Application Publication No. 2010-126651. A reaction vessel was charged with the compound represented by the formula (C2-1-8), a compound represented by the formula (C2-1-9), N,N-dimethylaminopyridine, and dichloromethane. Diisopropyl carbodiimide was added, and the mixture was stirred. After common posttreatment, purification by column chromatography yielded a compound represented by the formula (C2-1-10).

A reaction vessel was charged with the compound represented by the formula (C2-1-10), methanol, and aqueous sodium hydroxide, and was heated with stirring. After neutralization and common posttreatment, purification by recrystallization yielded a compound represented by the formula (C2-1-11).

A reaction vessel was charged with the compound represented by the formula (C2-1-11), a compound represented by the formula (C2-1-12), triphenylphosphine, and tetrahydrofuran. Diisopropyl azodicarboxylate was added while ice cooling, and the mixture was stirred. After common posttreatment, purification by column chromatography yielded a compound represented by the formula (C2-1-13).

A reaction vessel was charged with the compound represented by the formula (C2-1-13), tetrahydrofuran, methanol, and concentrated hydrochloric acid, and was stirred. After common posttreatment, purification by column chromatography and recrystallization yielded a compound represented by the formula (C2-1-14).

A reaction vessel was charged with the compound represented by the formula (C2-1-7), the compound represented by the formula (C2-1-14), N,N-dimethylaminopyridine, and dichloromethane. Diisopropyl carbodiimide was added, and the mixture was stirred. After common posttreatment, purification by column chromatography and recrystallization yielded a compound represented by the formula (C2-1).

MS(m/z): 1267 [M$^+$+1]

Example 71 Production of a Compound Represented by the Formula (C2-4)

[Chem. 282]

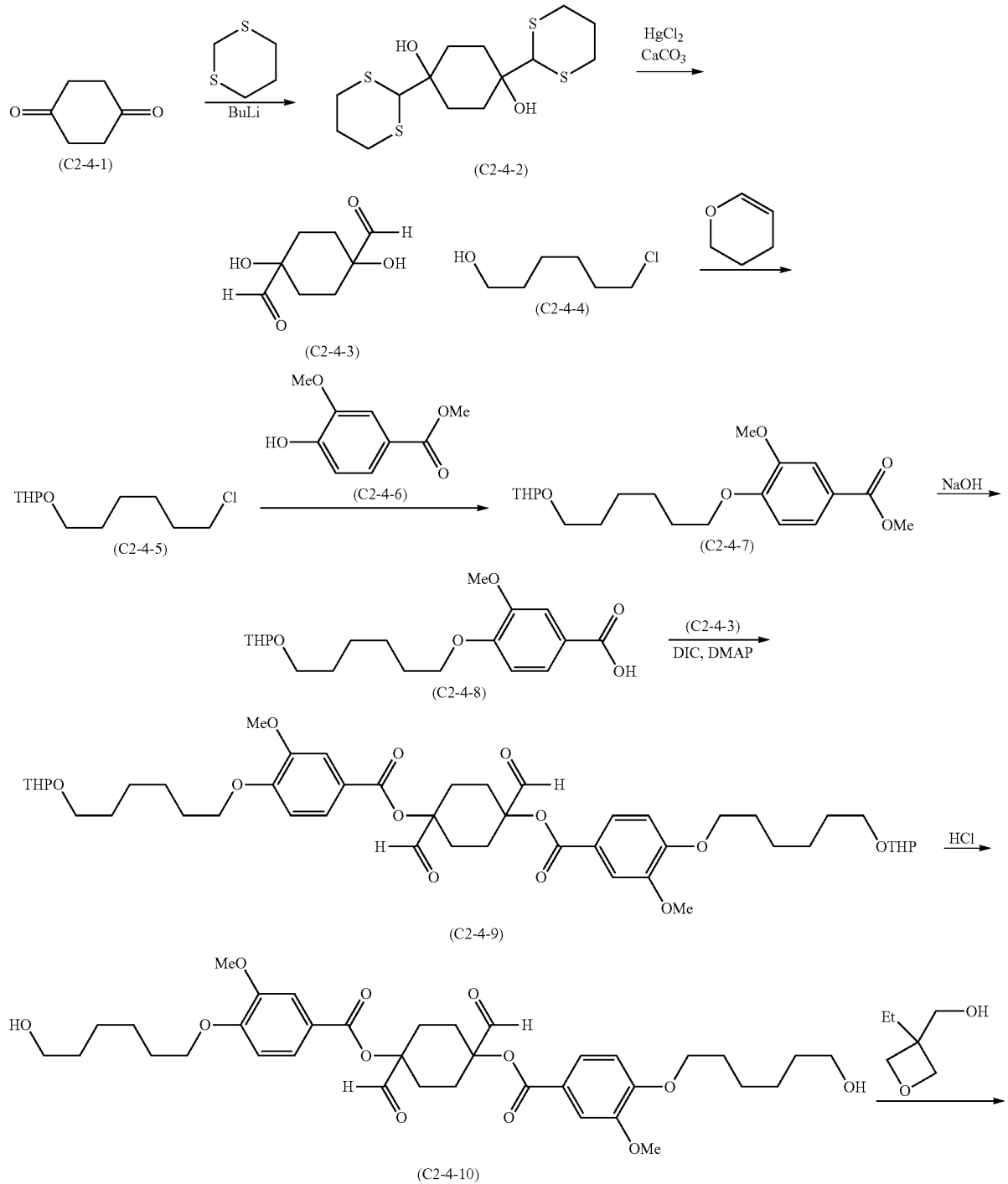

-continued

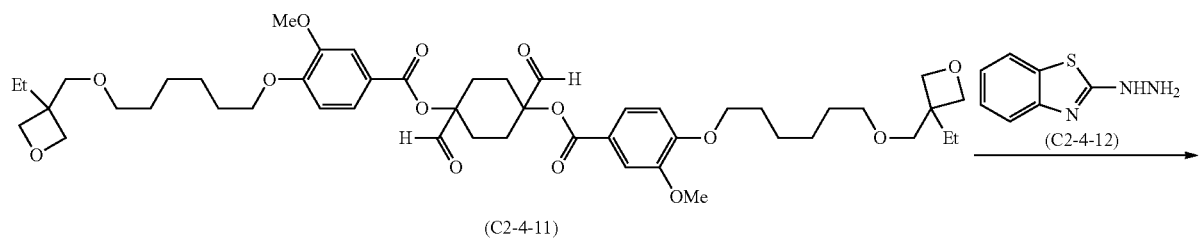

(C2-4-11)

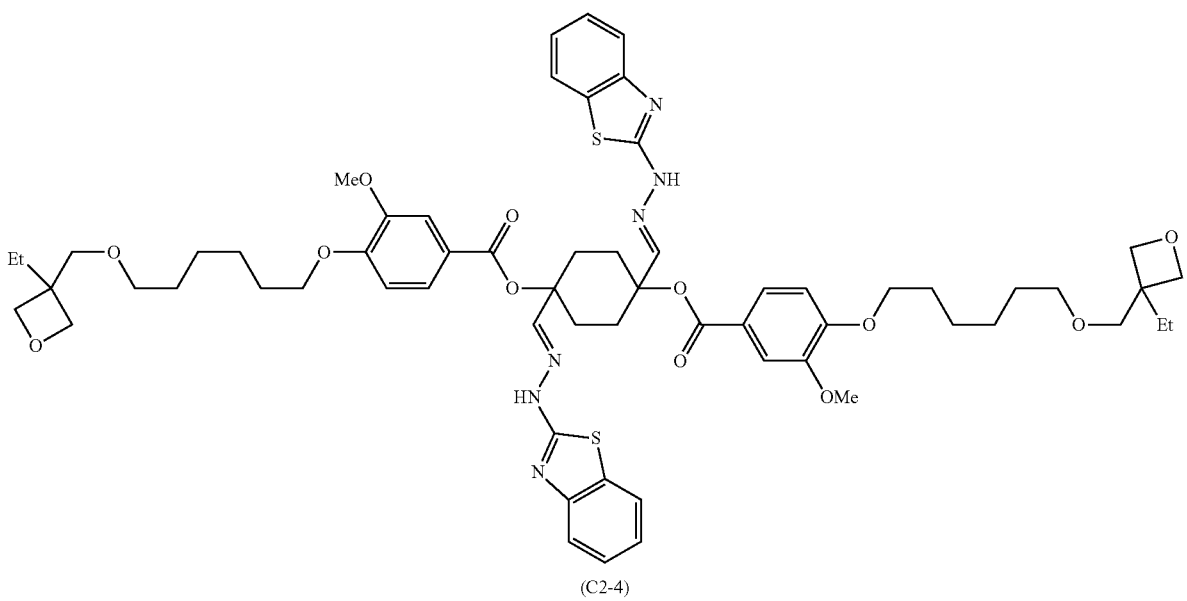

(C2-4)

A reaction vessel was charged with 1,3-dithiane and tetrahydrofuran. After cooling to −78° C., a butyllithium/hexane solution was added dropwise. After stirring at −25° C., a solution of a compound represented by the formula (C2-4-1) in tetrahydrofuran was added dropwise, and the mixture was further stirred at room temperature. After common posttreatment, purification by column chromatography yielded a compound represented by the formula (C2-4-2).

A reaction vessel was charged with the compound represented by the formula (C2-4-2), tetrahydrofuran, acetonitrile, water, mercury (II) chloride, and calcium carbonate, and was heated with stirring. After a precipitate was removed, purification by column chromatography yielded a compound represented by the formula (C2-4-3).

A reaction vessel was charged with a compound represented by the formula (C2-4-4), 3,4-dihydro-2H-pyran, pyridinium p-toluenesulfonate, and dichloromethane, and was stirred. After common posttreatment, purification by column chromatography yielded a compound represented by the formula (C2-4-5).

A reaction vessel was charged with the compound represented by the formula (C2-4-5), a compound represented by the formula (C2-4-6), cesium carbonate, and dimethyl sulfoxide, and was heated with stirring. After common posttreatment, purification by column chromatography yielded a compound represented by the formula (C2-4-7).

A reaction vessel was charged with the compound represented by the formula (C2-4-7), methanol, and aqueous sodium hydroxide, and was heated with stirring. After neutralization and common posttreatment, purification by column chromatography yielded a compound represented by the formula (C2-4-8).

A reaction vessel was charged with the compound represented by the formula (C2-4-8), the compound represented by the formula (C2-4-3), N,N-dimethylaminopyridine, and dichloromethane. Diisopropyl carbodiimide was added, and the mixture was stirred. After common posttreatment, purification by column chromatography yielded a compound represented by the formula (C2-4-9).

A reaction vessel was charged with the compound represented by the formula (C2-4-9), tetrahydrofuran, methanol, and concentrated hydrochloric acid, and was stirred. After common posttreatment, purification by column chromatography yielded a compound represented by the formula (C2-4-10).

A reaction vessel was charged with the compound represented by the formula (C2-4-10), 3-ethyl-3-oxetane methanol, triphenylphosphine, and tetrahydrofuran. Diisopropyl azodicarboxylate was added while ice cooling, and the mixture was stirred. After common posttreatment, purification by column chromatography yielded a compound represented by the formula (C2-4-11).

A reaction vessel was charged with the compound represented by the formula (C2-4-11), a compound represented by the formula (C2-4-12), (±)-10-camphorsulfonic acid, tetrahydrofuran, and ethanol, and was stirred. After common posttreatment, purification by column chromatography and recrystallization yielded a compound represented by the formula (C2-4).

MS(m/z): 1163 [M⁺+1]

Example 72 Production of a Compound Represented by the Formula (C2-16)

[Chem. 283]

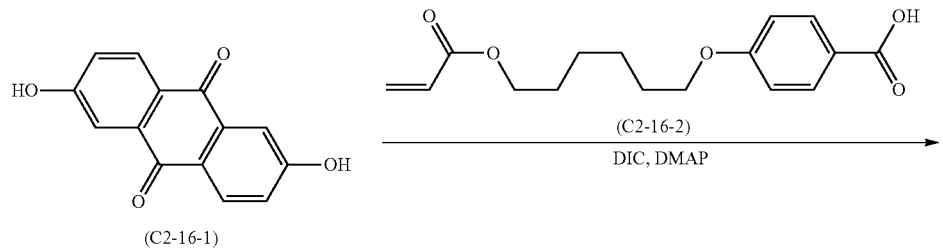

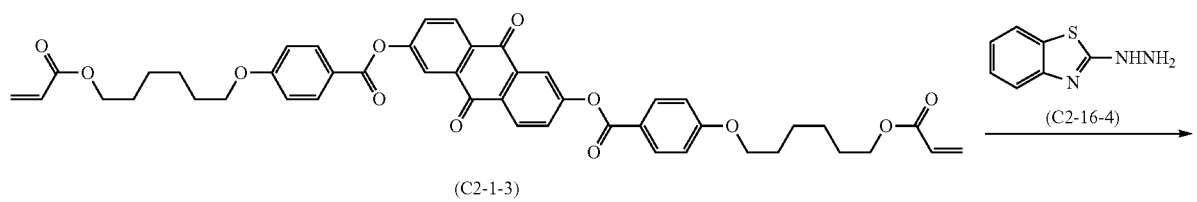

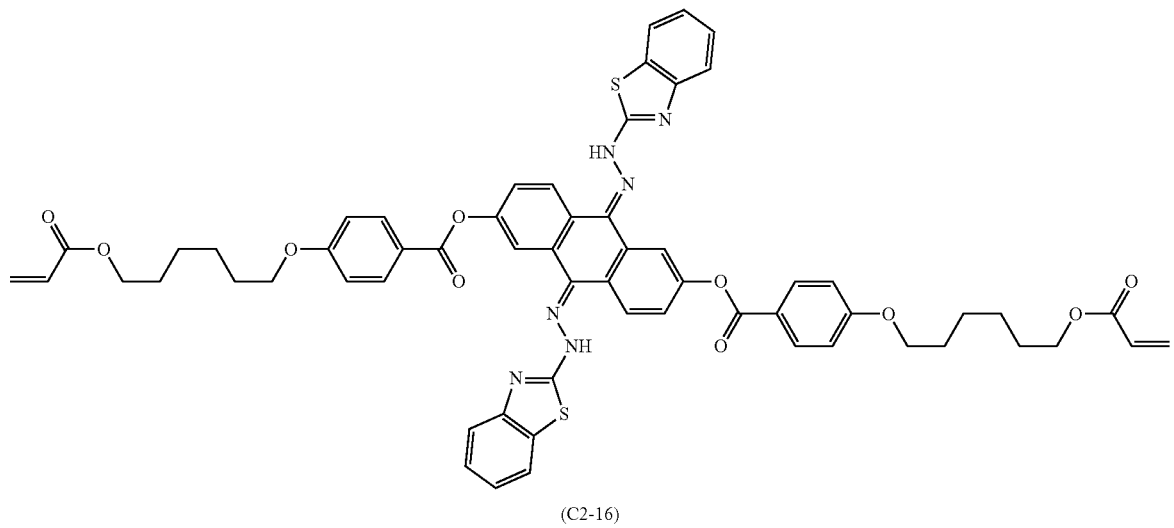

A reaction vessel was charged with a compound represented by the formula (C2-16-1), a compound represented by the formula (C2-16-2), N,N-dimethylaminopyridine, and dichloromethane. Diisopropyl carbodiimide was added, and the mixture was stirred. After common posttreatment, purification by column chromatography and recrystallization yielded a compound represented by the formula (C2-16-3).

A reaction vessel was charged with the compound represented by the formula (C2-16-3), a compound represented by the formula (C2-16-4), (±)-10-camphorsulfonic acid, tetrahydrofuran, and ethanol, and was stirred. After common posttreatment, purification by column chromatography and recrystallization yielded a compound represented by the formula (C2-16).

MS(m/z): 1083 [M$^+$+1]

Example 73 Production of a Compound Represented by the Formula (C3-1)

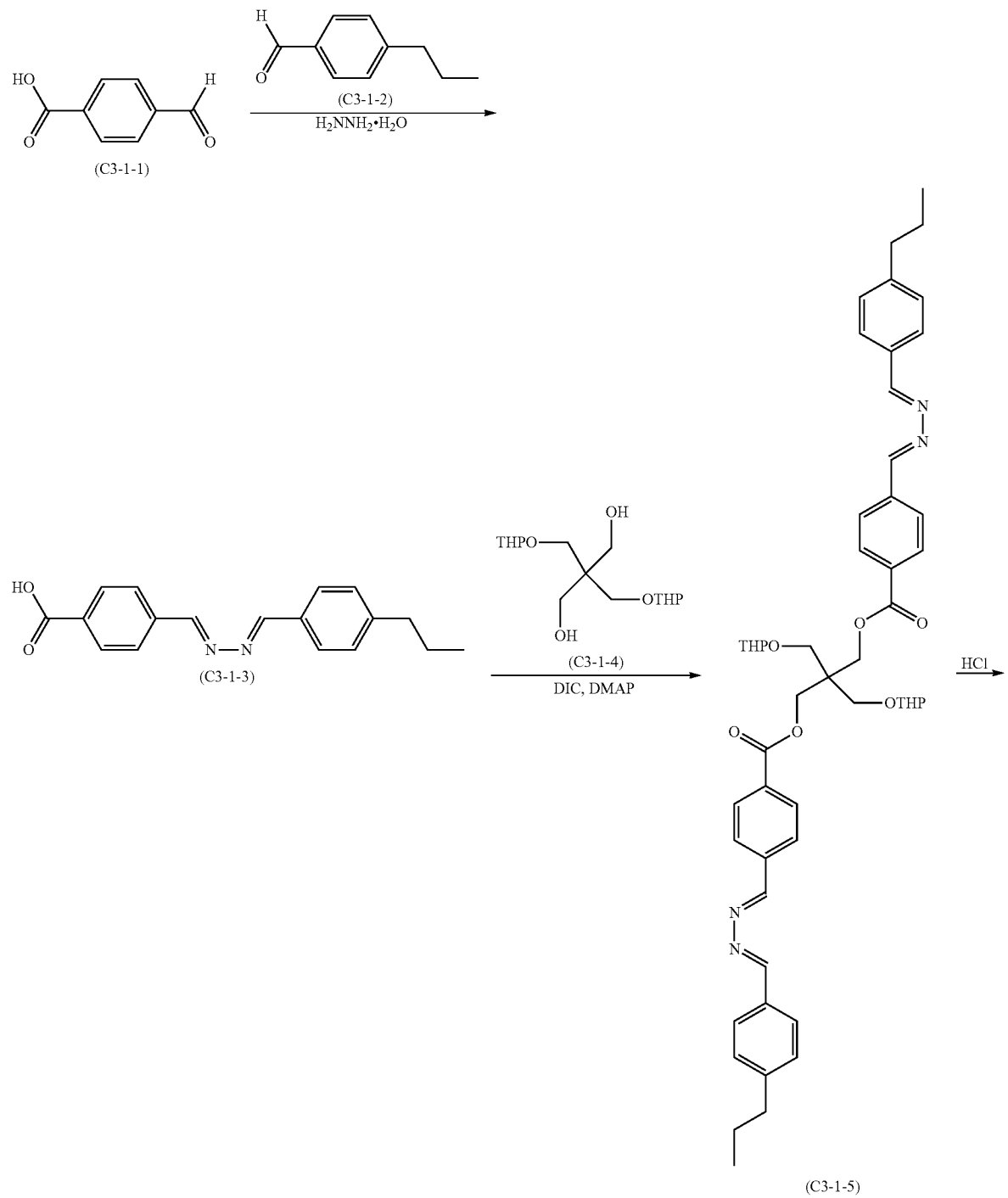

[Chem. 284]

-continued
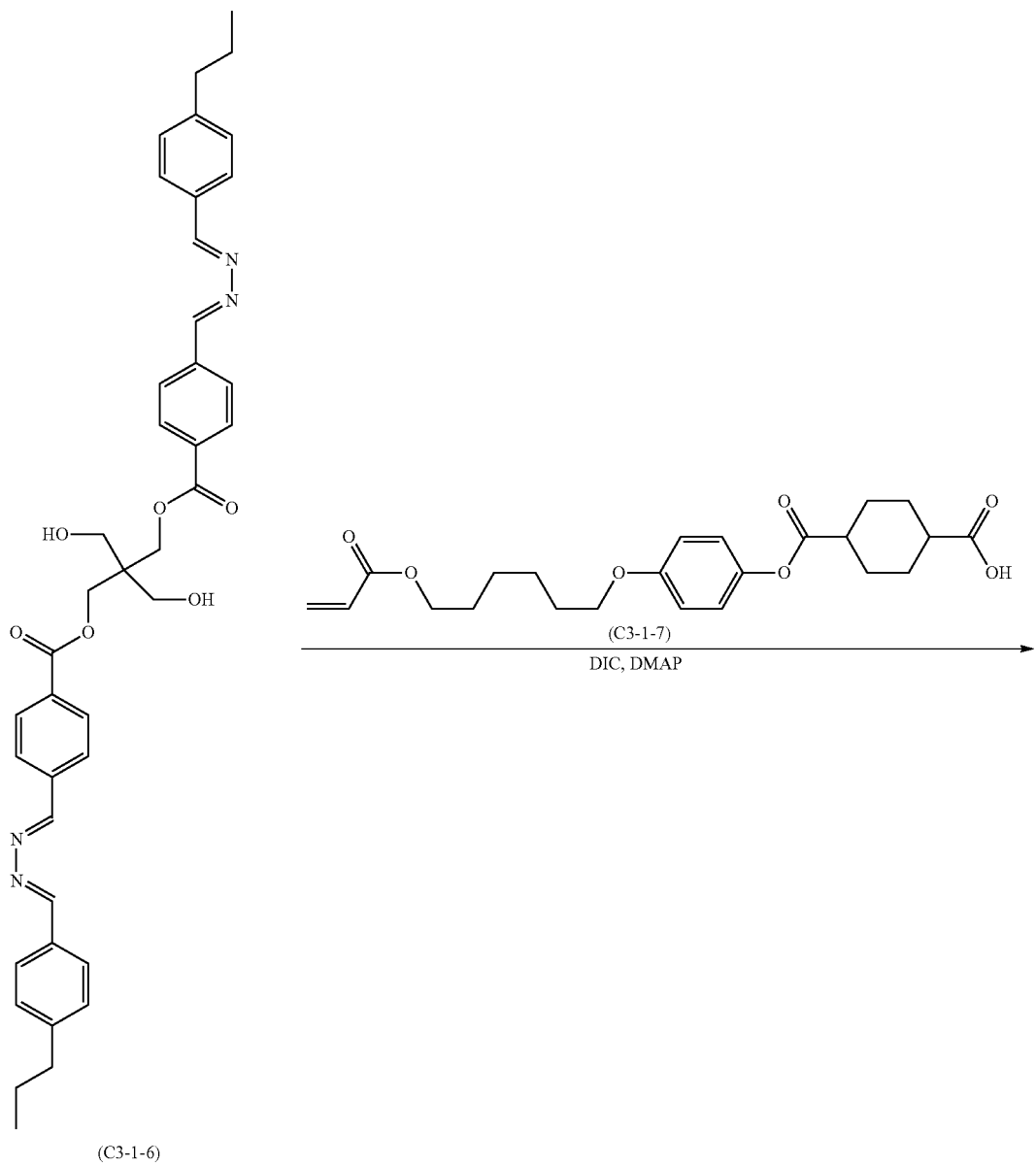 [SMILES: CCCc1ccc(/C=N/N=C/c2ccc(C(=O)OCC(CO)(CO)COC(=O)c3ccc(/C=N/N=C/c4ccc(CCC)cc4)cc3)cc2)cc1 ; C=CC(=O)OCCCCCCOc1ccc(OC(=O)C2CCC(C(=O)O)CC2)cc1]

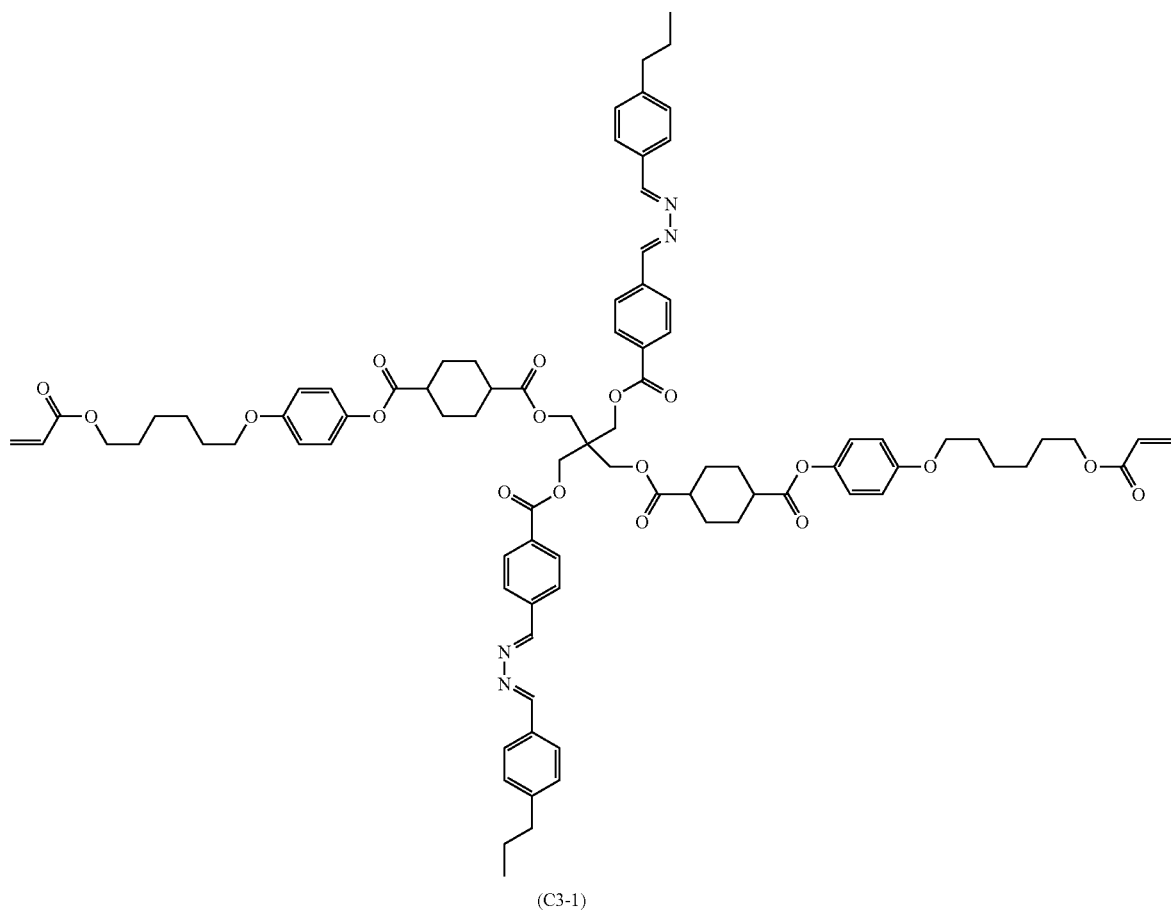

(C3-1)

A reaction vessel was charged with a compound represented by the formula (C3-1-1), a compound represented by the formula (C3-1-2), hydrazine monohydrate, and ethanol, and was heated with stirring. After common posttreatment, purification by column chromatography and recrystallization yielded a compound represented by the formula (C3-1-3).

A compound represented by the formula (C3-1-4) was produced by a method described in WO 2009/080147 A1. A reaction vessel was charged with the compound represented by the formula (C3-1-3), the compound represented by the formula (C3-1-4), N,N-dimethylaminopyridine, and dichloromethane. Diisopropyl carbodiimide was added, and the mixture was stirred. After common posttreatment, purification by column chromatography yielded a compound represented by the formula (C3-1-5).

A reaction vessel was charged with the compound represented by the formula (C3-1-5), tetrahydrofuran, methanol, and concentrated hydrochloric acid, and was stirred. After common posttreatment, purification by column chromatography yielded a compound represented by the formula (C3-1-6).

A compound represented by the formula (C3-1-7) was produced by a method described in WO 2011/068138 A1. A reaction vessel was charged with the compound represented by the formula (C3-1-6), the compound represented by the formula (C3-1-7), N,N-dimethylaminopyridine, and dichloromethane. Diisopropyl carbodiimide was added, and the mixture was stirred. After common posttreatment, purification by column chromatography yielded a compound represented by the formula (C3-1).

MS(m/z): 1489 [M$^+$+1]

Example 74 Production of a Compound Represented by the Formula (D11-1)

[Chem. 285]

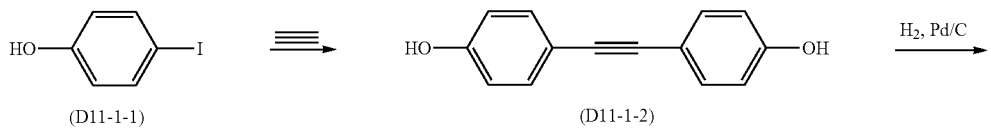

(D11-1-1)      (D11-1-2)

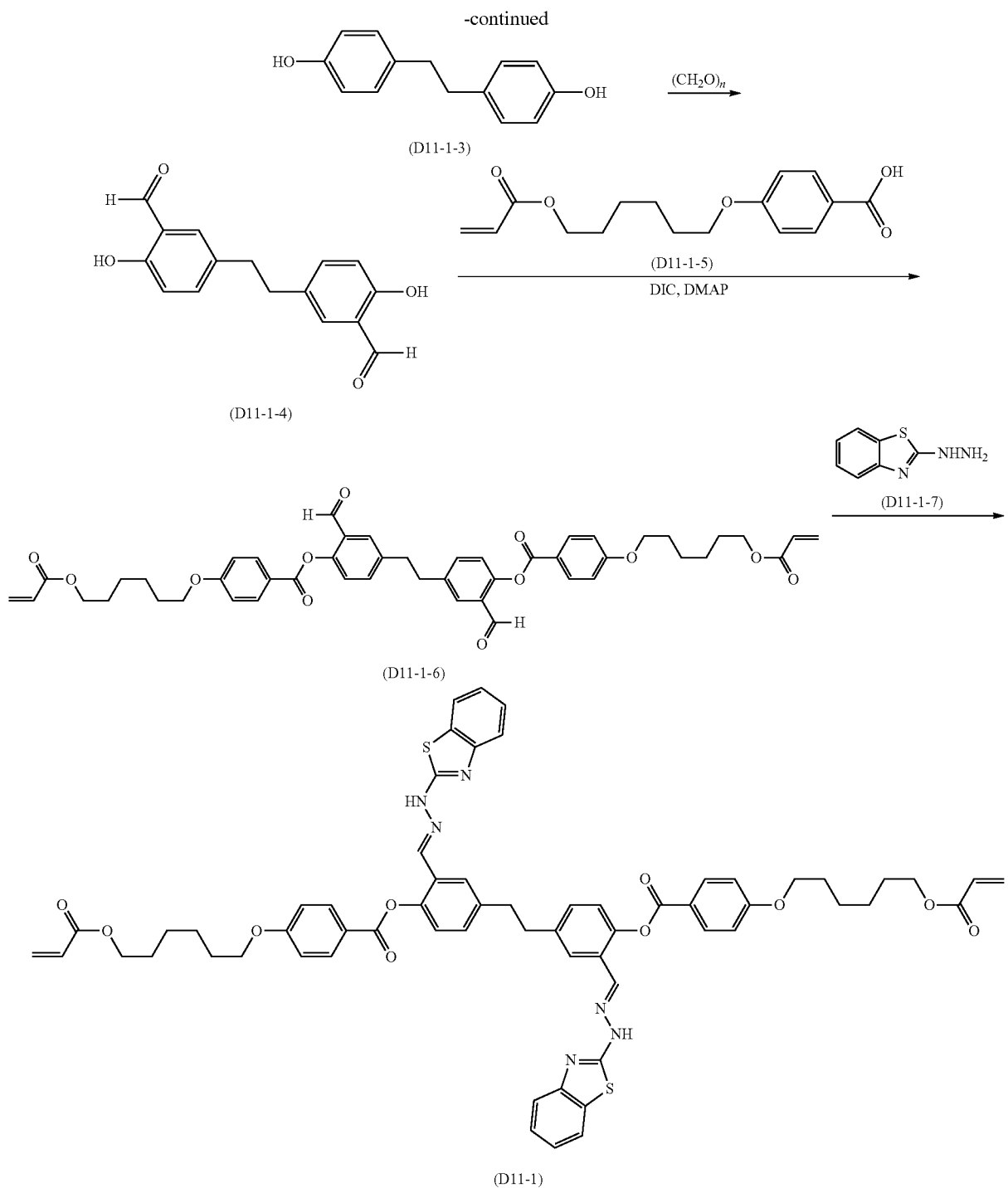

A reaction vessel in an inert atmosphere was charged with a compound represented by the formula (D11-1-1), copper (I) iodide, triethylamine, N,N-dimethylformamide, tetrakis (triphenylphosphine) palladium (0). Acetylene was introduced during heating. After common posttreatment, purification by column chromatography and recrystallization yielded a compound represented by the formula (D11-1-2).

A reaction vessel was charged with the compound represented by the formula (D11-1-2), tetrahydrofuran, and 5% palladium carbon. After stirring in a hydrogen atmosphere, the catalyst was removed. Purification by column chromatography yielded a compound represented by the formula (D11-1-3).

A reaction vessel was charged with the compound represented by the formula (D11-1-3), magnesium chloride, triethylamine, acetonitrile, paraformaldehyde, and was heated with stirring. After common posttreatment, purification by column chromatography yielded a compound represented by the formula (D11-1-4).

A reaction vessel was charged with the compound represented by the formula (D11-1-4), a compound represented by the formula (D11-1-5), N,N-dimethylaminopyridine, and dichloromethane. Diisopropyl carbodiimide was added, and the mixture was stirred. After common posttreatment, purification by column chromatography and recrystallization yielded a compound represented by the formula (D11-1-6).

A reaction vessel was charged with the compound represented by the formula (D11-1-6), a compound represented by the formula (D11-1-7), (±)-10-camphorsulfonic acid, tetrahydrofuran, and ethanol, and was stirred. After common posttreatment, purification by column chromatography and recrystallization yielded a compound represented by the formula (D11-1).

MS(m/z): 1113 [M$^+$+1]

Example 75 Production of a Compound Represented by the Formula (D12-1)

[Chem. 286]

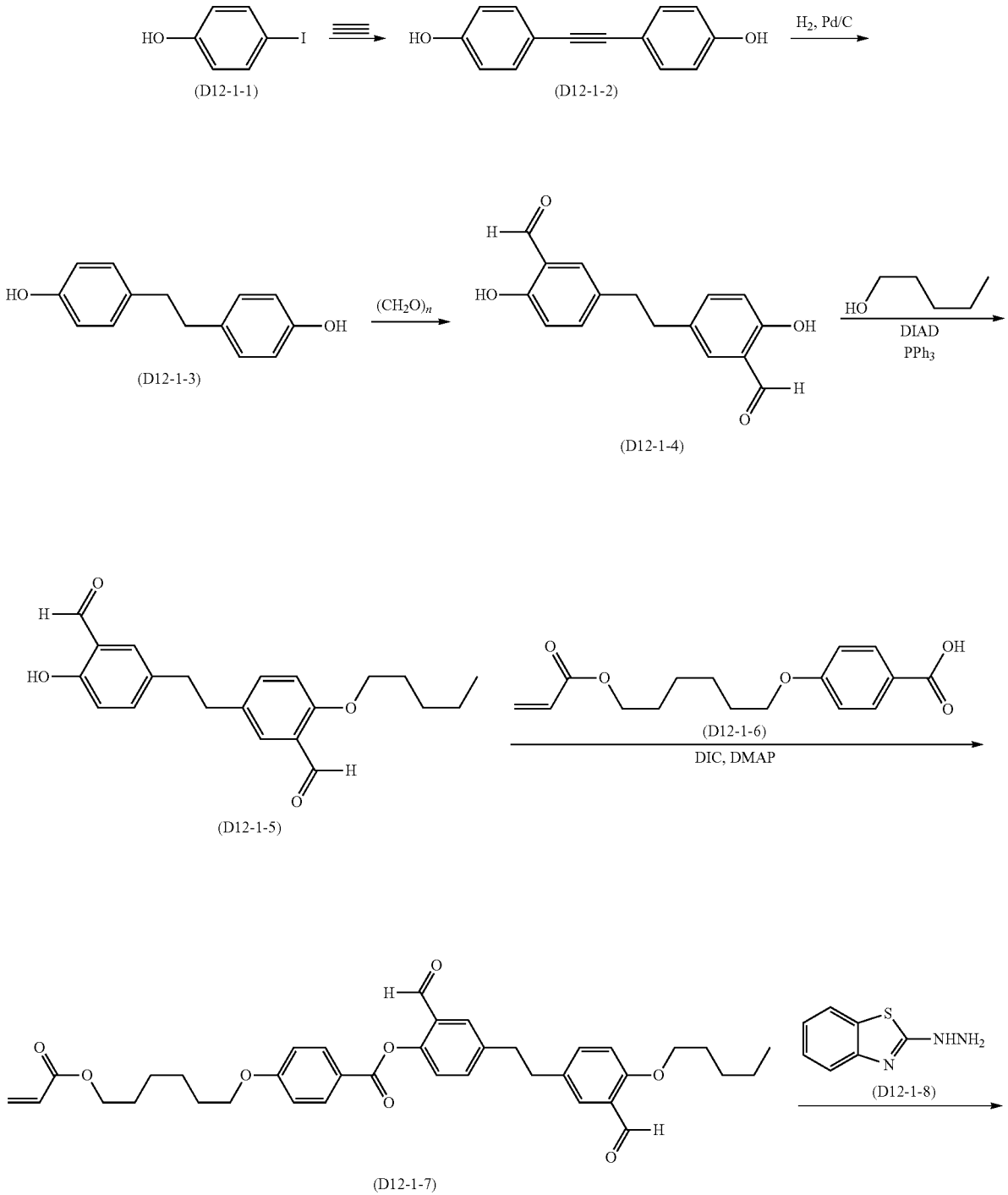

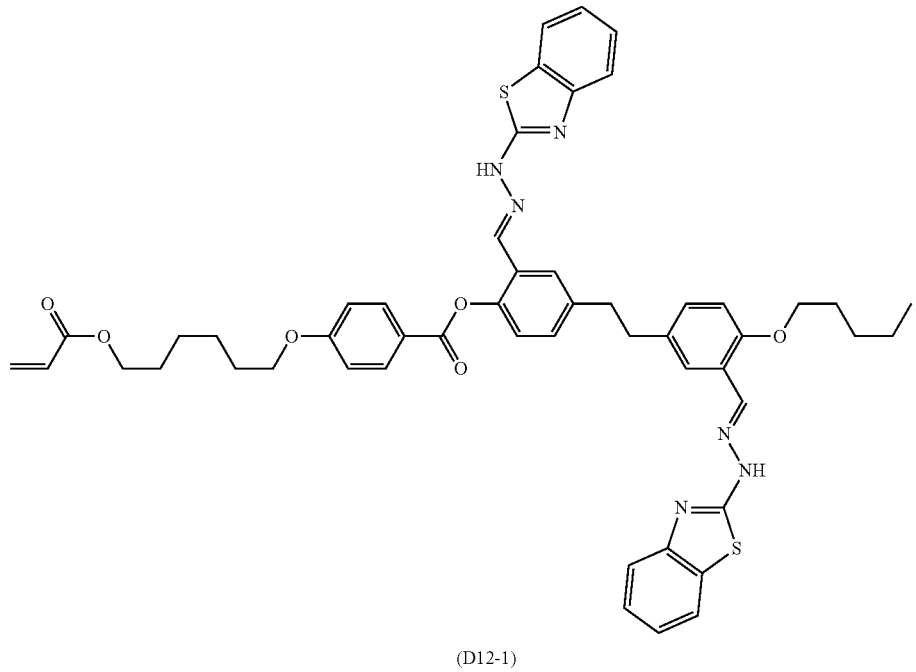

(D12-1)

A reaction vessel in an inert atmosphere was charged with a compound represented by the formula (D12-1-1), copper (I) iodide, triethylamine, N,N-dimethylformamide, and tetrakis(triphenylphosphine) palladium (0). Acetylene was introduced during heating. After common posttreatment, purification by column chromatography and recrystallization yielded a compound represented by the formula (D12-1-2).

A reaction vessel was charged with the compound represented by the formula (D12-1-2), tetrahydrofuran, and 5% palladium carbon. After stirring in a hydrogen atmosphere, the catalyst was removed. Purification by column chromatography yielded a compound represented by the formula (D12-1-3).

A reaction vessel was charged with the compound represented by the formula (D12-1-3), magnesium chloride, triethylamine, acetonitrile, paraformaldehyde, and was heated with stirring. After common posttreatment, purification by column chromatography yielded a compound represented by the formula (D12-1-4).

A reaction vessel was charged with the compound represented by the formula (D12-1-4), 1-pentanol, triphenylphosphine, and tetrahydrofuran. Diisopropyl azodicarboxylate was added dropwise while ice cooling, and the mixture was stirred. After common posttreatment, purification by column chromatography yielded a compound represented by the formula (D12-1-5).

A reaction vessel was charged with the compound represented by the formula (D12-1-5), a compound represented by the formula (D12-1-6), N,N-dimethylaminopyridine, and dichloromethane. Diisopropyl carbodiimide was added, and the mixture was stirred. After common posttreatment, purification by column chromatography and recrystallization yielded a compound represented by the formula (D12-1-7).

A reaction vessel was charged with the compound represented by the formula (D12-1-7), a compound represented by the formula (D12-1-8), (±)-10-camphorsulfonic acid, tetrahydrofuran, and ethanol, and was stirred. After common posttreatment, purification by column chromatography and recrystallization yielded a compound represented by the formula (D12-1).

MS(m/z): 909 [M$^+$+1]

Example 76 Production of a Compound Represented by the Formula (D2-1)

[Chem. 287]

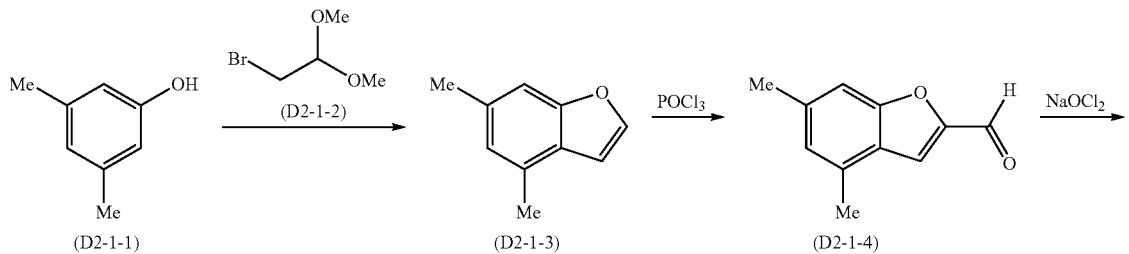

-continued
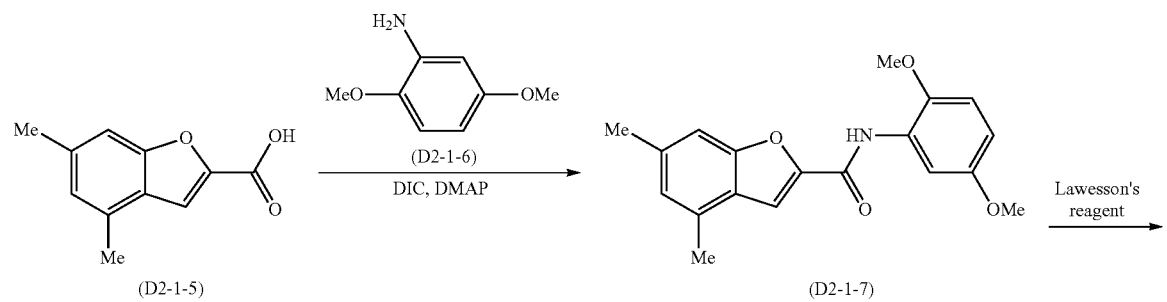
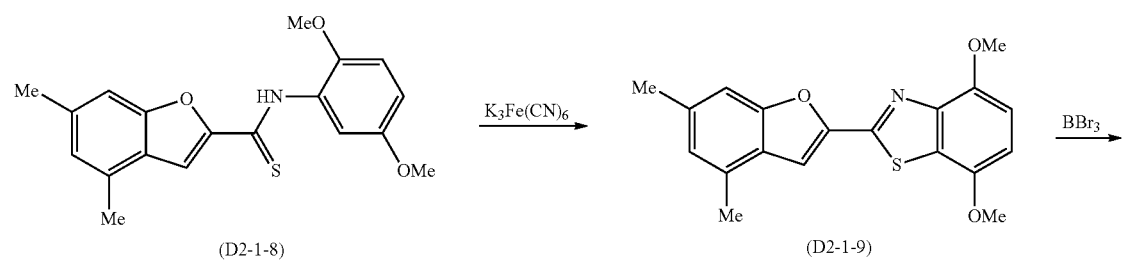
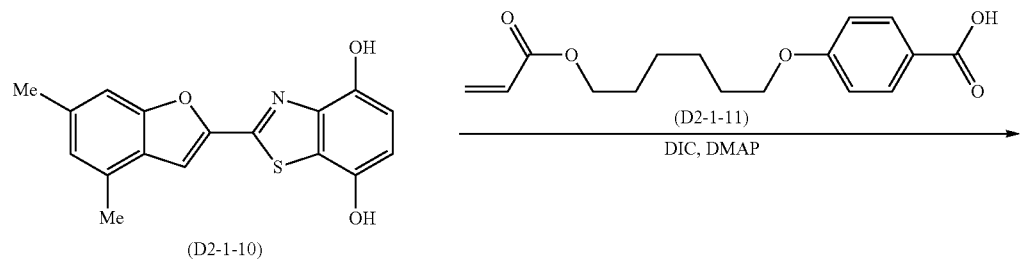
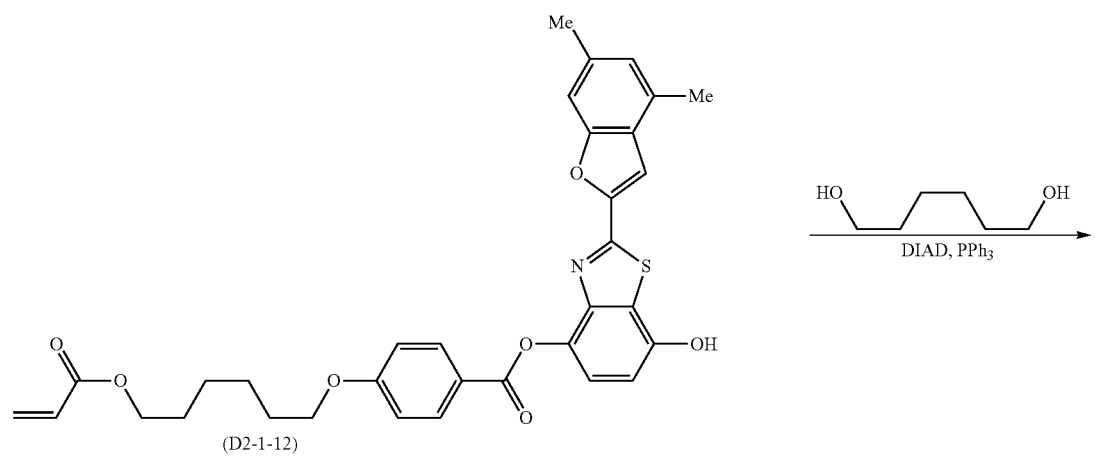

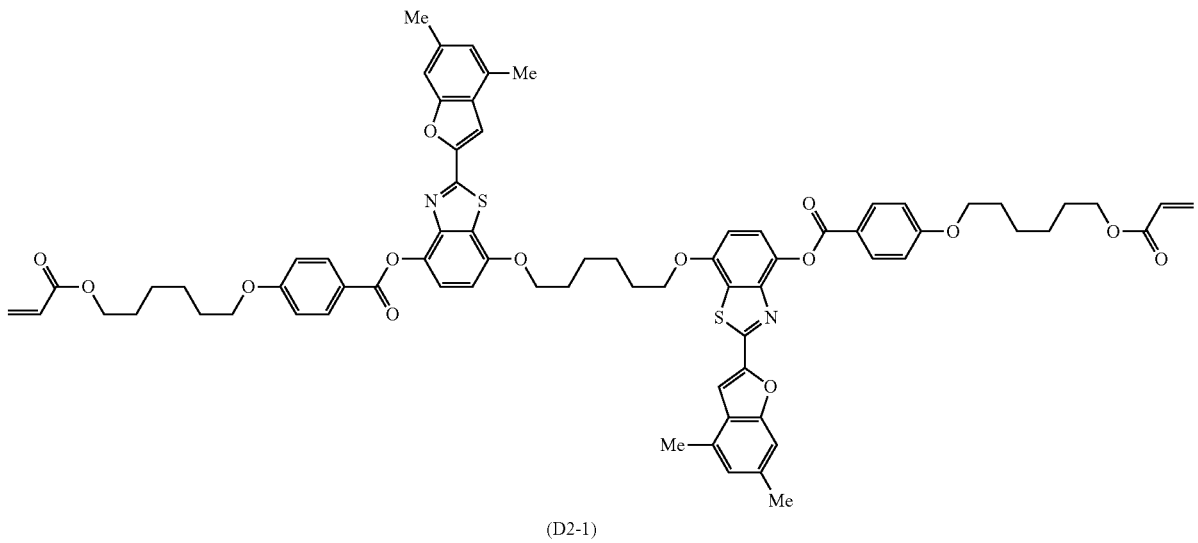 [SMILES: C=CC(=O)OCCCCCCOc1ccc(C(=O)Oc2ccc(OCCCCCCOc3ccc(OC(=O)c4ccc(OCCCCCCOC(=O)C=C)cc4)c4nc(-c5cc6c(C)cc(C)cc6o5)sc34)c3sc(-c4cc5c(C)cc(C)cc5o4)nc23)cc1 ; "(D2-1)"]

(D2-1)

A reaction vessel was charged with a compound represented by the formula (D2-1-1) and N,N-dimethylacetamide. Sodium hydroxide was added while ice cooling, and the mixture was stirred. A compound represented by the formula (D2-1-2) was added, and the mixture was heated with stirring. Another reaction vessel was charged with orthophosphoric acid and toluene. During heating with stirring, the reaction liquid was added, and the mixture was further heated with stirring. After common posttreatment, purification by column chromatography yielded a compound represented by the formula (D2-1-3).

A reaction vessel was charged with the compound represented by the formula (D2-1-3), N,N-dimethylformamide, and phosphorus oxychloride, and was heated with stirring. After common posttreatment, purification by column chromatography and recrystallization yielded a compound represented by the formula (D2-1-4).

A reaction vessel was charged with the compound represented by the formula (D2-1-4), amidosulfuric acid, and water. Aqueous sodium chlorite was added, and the mixture was stirred. After common posttreatment, purification by column chromatography and recrystallization yielded a compound represented by the formula (D2-1-5).

A reaction vessel was charged with the compound represented by the formula (D2-1-5), a compound represented by the formula (D2-1-6), N,N-dimethylaminopyridine, and dichloromethane. Diisopropyl carbodiimide was added, and the mixture was stirred. After common posttreatment, purification by column chromatography and recrystallization yielded a compound represented by the formula (D2-1-7).

A reaction vessel was charged with the compound represented by the formula (D2-1-7), Lawesson's reagent, and toluene, and was heated with stirring. After common posttreatment, purification by column chromatography and recrystallization yielded a compound represented by the formula (D2-1-8).

A reaction vessel was charged with the compound represented by the formula (D2-1-8) and aqueous sodium hydroxide. Aqueous potassium ferricyanide was added, and the mixture was heated with stirring. A precipitate was filtered, dispersed, and washed, thereby yielding a compound represented by the formula (D2-1-9).

A reaction vessel was charged with the compound represented by the formula (D2-1-9) and dichloromethane. Boron tribromide was added, and the mixture was stirred. After common posttreatment, purification by column chromatography and recrystallization yielded a compound represented by the formula (D2-1-10).

A reaction vessel was charged with the compound represented by the formula (D2-1-10), a compound represented by the formula (D2-1-11), N,N-dimethylaminopyridine, and dichloromethane. Diisopropyl carbodiimide was added, and the mixture was stirred. After common posttreatment, purification by column chromatography and recrystallization yielded a compound represented by the formula (D2-1-12).

A reaction vessel was charged with the compound represented by the formula (D2-1-12), 1,6-hexanediol, triphenylphosphine, and tetrahydrofuran. Diisopropyl azodicarboxylate was added while ice cooling, and the mixture was stirred. After common posttreatment, purification by column chromatography and recrystallization yielded a compound represented by the formula (D2-1).
MS(m/z): 1253 [M$^+$+1]
Example 77 Production of a Mixture Represented by the Formula (D3-1)
[Chem. 288]
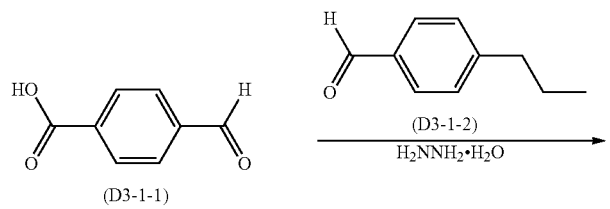
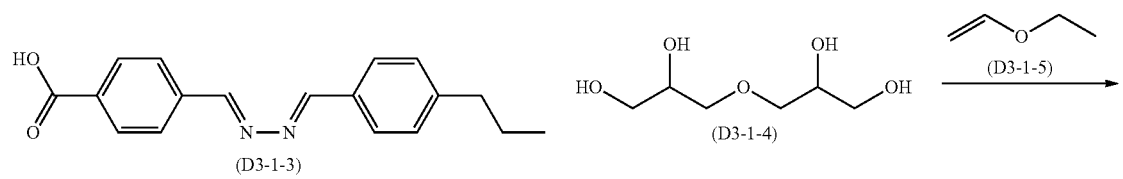
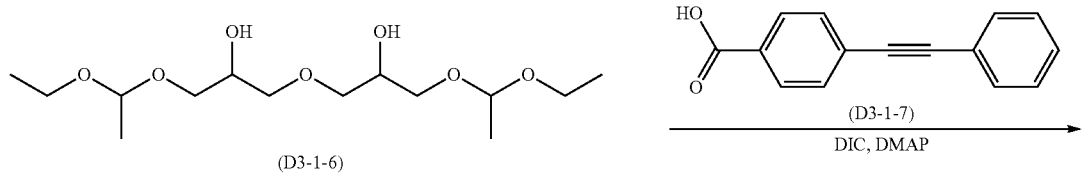
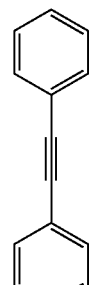

-continued
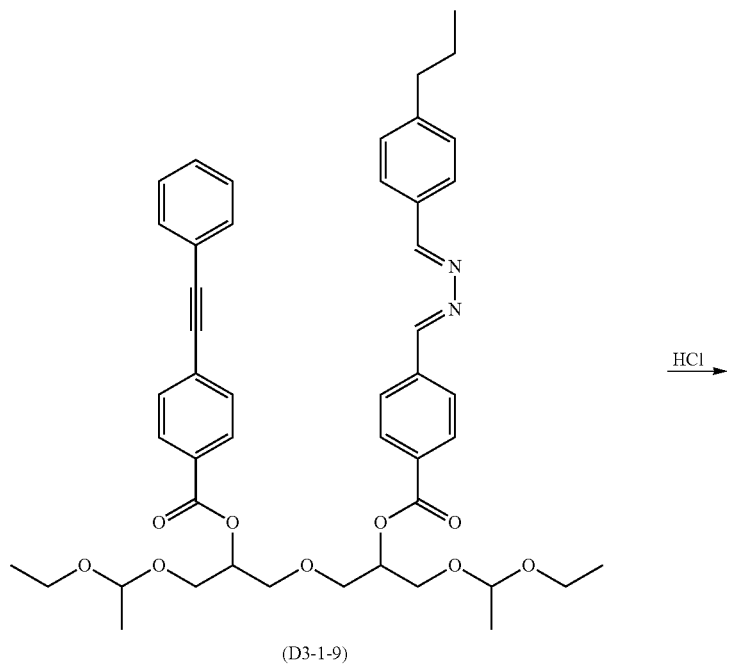
(D3-1-9)
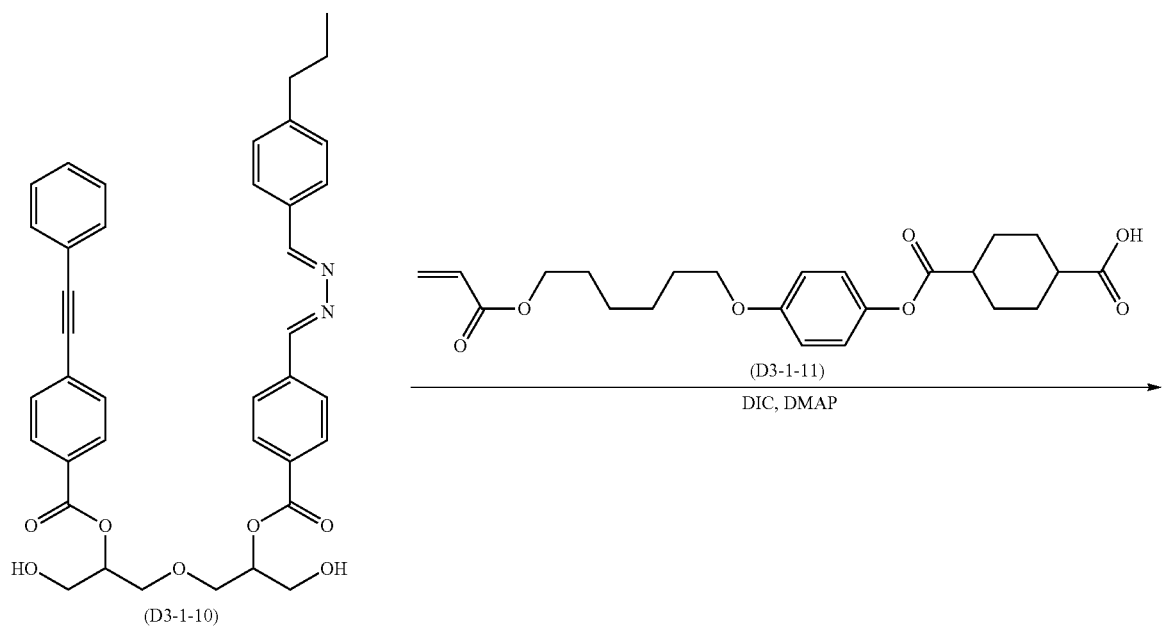

-continued

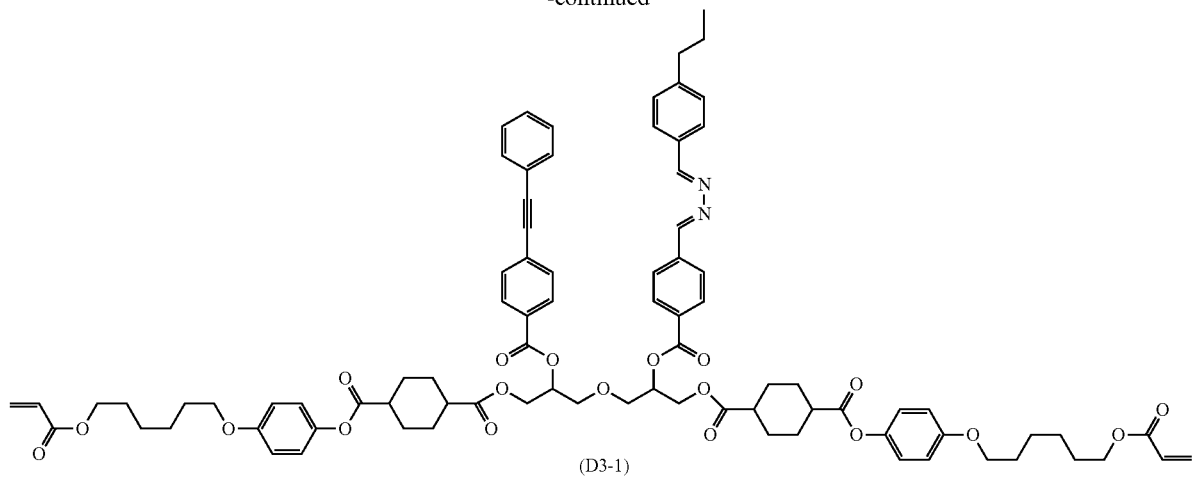

(D3-1)

A reaction vessel was charged with a compound represented by the formula (D3-1-1), a compound represented by the formula (D3-1-2), hydrazine monohydrate, and ethanol, and was heated with stirring. After common posttreatment, purification by column chromatography and recrystallization yielded a compound represented by the formula (D3-1-3).

A compound represented by formula (D3-1-4) and a compound represented by the formula (D3-1-5) were allowed to react in the same manner as in a method described in Journal of the American Chemical Society, No. 103, Vol. 9, pp. 2427-2428, thereby yielding a compound represented by the formula (D3-1-6).

A reaction vessel was charged with the compound represented by the formula (D3-1-6), a compound represented by the formula (D3-1-7), N,N-dimethylaminopyridine, and dichloromethane. Diisopropyl carbodiimide was added, and the mixture was stirred. After common posttreatment, purification by column chromatography yielded a compound represented by the formula (D3-1-8).

A reaction vessel was charged with the compound represented by the formula (D3-1-8), the compound represented by the formula (D3-1-3), N,N-dimethylaminopyridine, and dichloromethane. Diisopropyl carbodiimide was added, and the mixture was stirred. After common posttreatment, purification by column chromatography yielded a compound represented by the formula (D3-1-9).

A reaction vessel was charged with the compound represented by the formula (D3-1-9) and tetrahydrofuran. 0.5 N hydrochloric acid was added at 0° C., and the mixture was stirred. After common posttreatment, purification by column chromatography yielded a compound represented by the formula (D3-1-10).

A compound represented by the formula (D3-1-11) was produced by a method described in WO 2011/068138 A1. A reaction vessel was charged with the compound represented by the formula (D3-1-10), the compound represented by the formula (D3-1-11), N,N-dimethylaminopyridine, and dichloromethane. Diisopropyl carbodiimide was added, and the mixture was stirred. After common posttreatment, purification by column chromatography yielded a compound represented by the formula (D3-1).

MS(m/z): 1447 [M$^+$+1]

Example 78 Production of a Mixture Represented by the Formula (D4-2)

[Chem. 289]

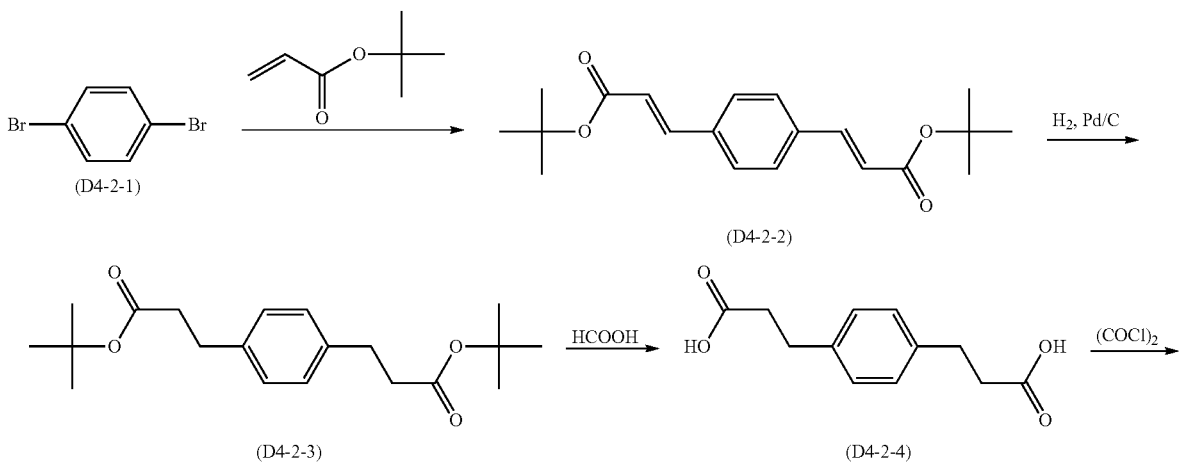

-continued
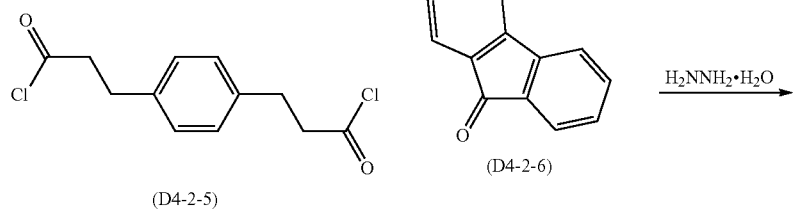
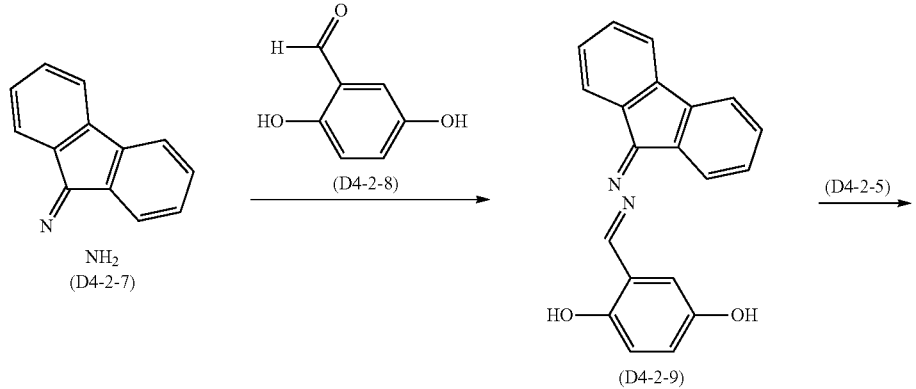
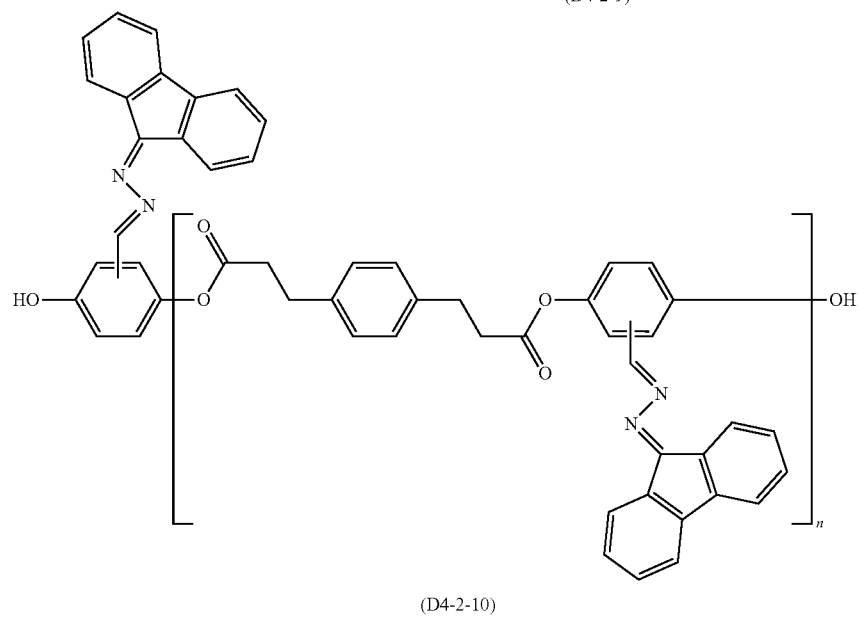
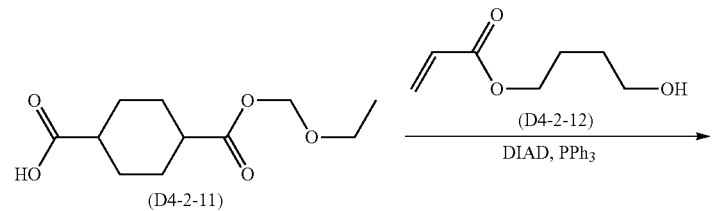
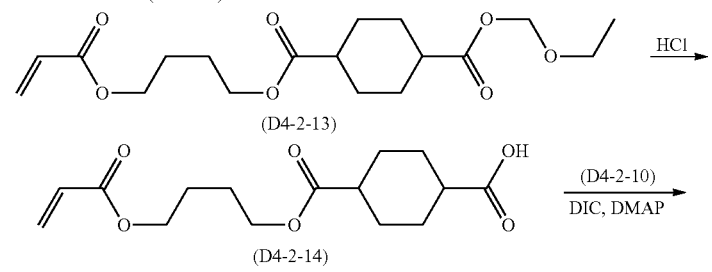

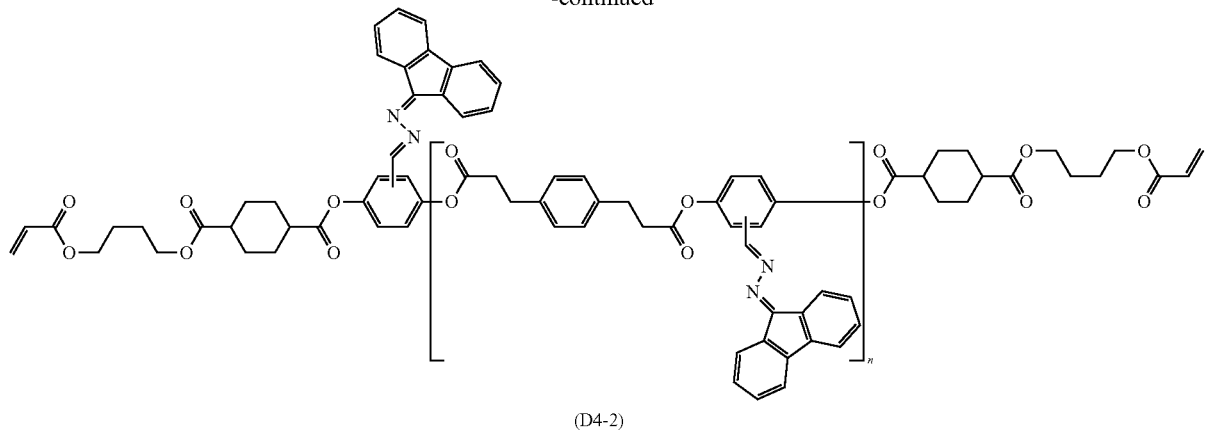

(D4-2)

A reaction vessel in an inert atmosphere was charged with a compound represented by the formula (D4-2-1), tert-butyl acrylate, potassium carbonate, N,N-dimethylacetamide, and palladium (II) acetate, and was heated with stirring. After common posttreatment, purification by column chromatography yielded a compound represented by the formula (D4-2-2).

A reaction vessel was charged with the compound represented by the formula (D4-2-2), 5% palladium carbon, and tetrahydrofuran. After stirring in a hydrogen atmosphere, the catalyst was removed. Purification by column chromatography yielded a compound represented by the formula (D4-2-3).

A reaction vessel was charged with the compound represented by the formula (D4-2-3), dichloromethane, and formic acid, and was heated with stirring. After common posttreatment, purification by column chromatography yielded a compound represented by the formula (D4-2-4).

A reaction vessel was charged with the compound represented by the formula (D4-2-4), dichloromethane, oxalyl chloride, and pyridine, and was stirred. The solvent was distilled off, thereby yielding a compound represented by the formula (D4-2-5).

A reaction vessel was charged with a compound represented by the formula (D4-2-6), hydrazine monohydrate, ethanol, and tetrahydrofuran, and was stirred. After common posttreatment, purification by recrystallization yielded a compound represented by the formula (D4-2-7).

A reaction vessel was charged with the compound represented by the formula (D4-2-7), a compound represented by the formula (D4-2-8), tetrahydrofuran, and ethanol, and was stirred. After the solvent was distilled off, purification by recrystallization yielded a compound represented by the formula (D4-2-9).

A reaction vessel was charged with the compound represented by the formula (D4-2-9), tetrahydrofuran, and triethylamine. A solution of the compound represented by the formula (D4-2-5) in tetrahydrofuran was added, and the mixture was stirred. After common posttreatment, dispersion and washing yielded a mixture represented by the formula (D4-2-10).

A compound represented by the formula (D4-2-11) was produced by a method described in Japanese Unexamined Patent Application Publication No. 2010-126651. A reaction vessel was charged with the compound represented by the formula (D4-2-11), a compound represented by the formula (D4-2-12), triphenylphosphine, and tetrahydrofuran. Diisopropyl azodicarboxylate was added while ice cooling, and the mixture was stirred. After common posttreatment, purification by column chromatography yielded a compound represented by the formula (D4-2-13).

A reaction vessel was charged with the compound represented by the formula (D4-2-13), tetrahydrofuran, methanol, and concentrated hydrochloric acid, and was stirred. After common posttreatment, purification by column chromatography yielded a compound represented by the formula (D4-2-14).

A reaction vessel was charged with the compound represented by the formula (D4-2-14), the mixture represented by the formula (D4-2-10), N,N-dimethylaminopyridine, and dichloromethane. Diisopropyl carbodiimide was added, and the mixture was stirred. After common posttreatment, dispersion and washing yielded a mixture represented by the formula (D4-2).

Mw=271,000, Mn=114,000, Mw/Mn=2.4

Compounds represented by the formulae (A11-1) to (D4-4) were produced by a known method in the same manner as in Examples 1 to 78.

Examples 79 to 345

The compounds represented by the formulae (A11-1) to (D4-4) according to the present invention were tested.

In order to evaluate storage stability, the stable storage concentrations of the compounds were measured. A compound to be tested was added to a mother liquid crystal at a concentration of 5% to 25% in increments of 5% to prepare compositions. The compositions were left to stand at 18.8° C. for 10 weeks. The maximum concentration of the compound that caused no crystal precipitation was considered to be the stable storage concentration. This means that a compound having a higher maximum concentration has a higher stable storage concentration and causes no crystal precipitation during storage for extended periods.

A liquid crystal composition composed of a compound (X-1) described in Japanese Unexamined Patent Application Publication (Translation of PCT Application) No. 2002-539182: 30%, a compound (X-2) described in Japanese Unexamined Patent Application Publication No. 2007-119415: 30%, and a compound (X-3) described in Japanese Unexamined Patent Application Publication No. 2003-183226: 40% was used as a mother liquid crystal (X) in the measurement of stable storage concentration. Table 1 shows the results.

[Chem. 290]
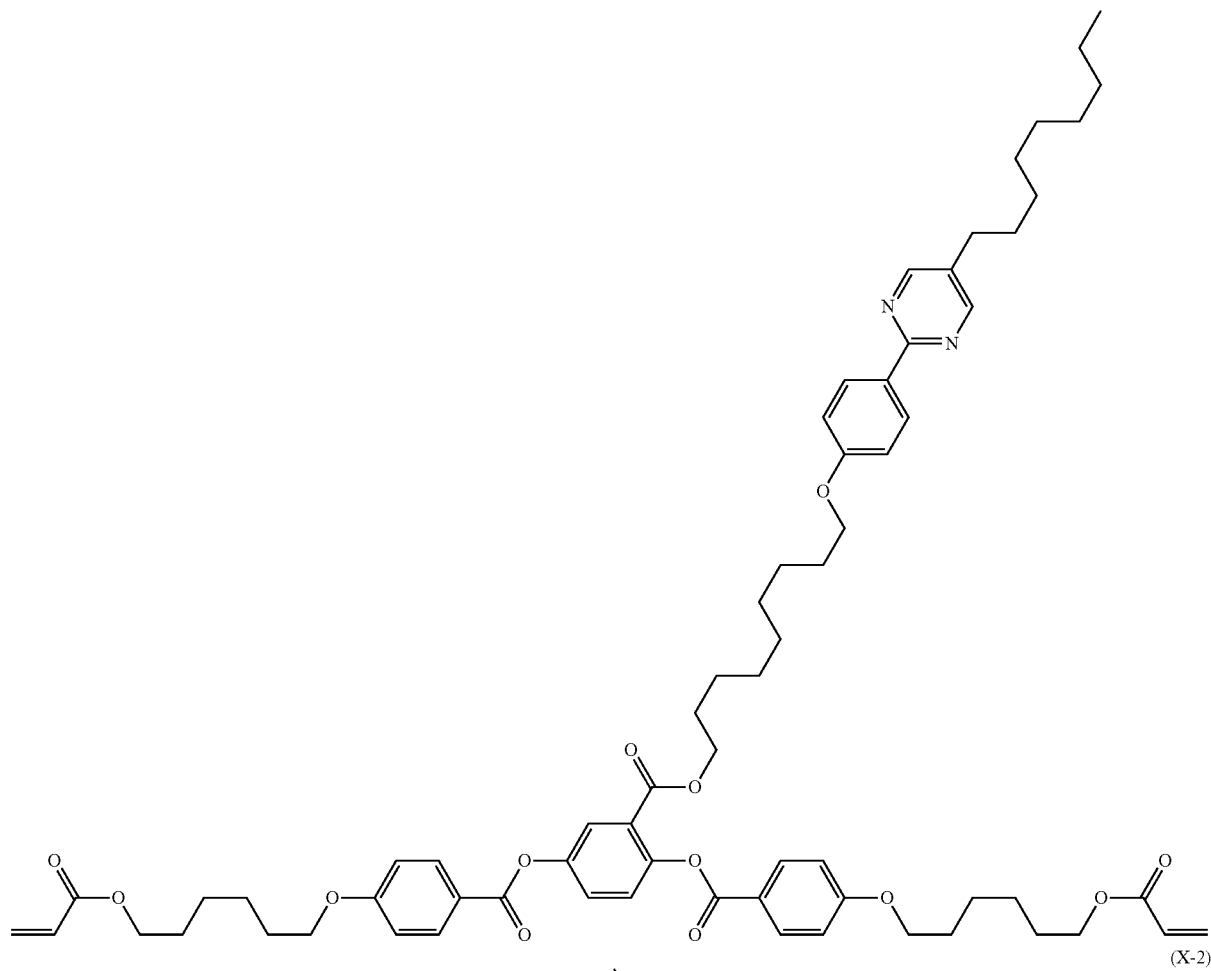
(X-1)
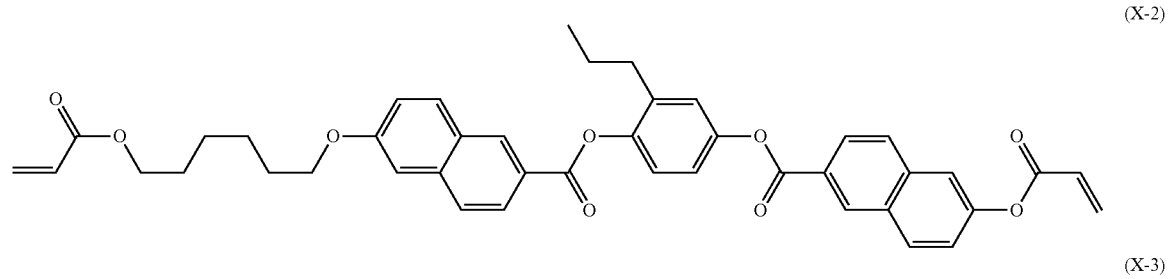
(X-2)
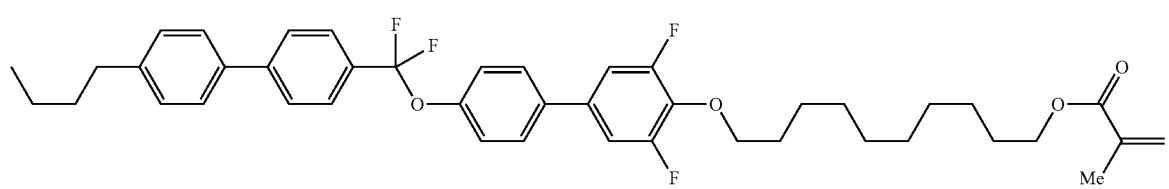
(X-3)
| | Test compound | Storage stability |
|---|---|---|
| Example 79 (Example 1) | Compound of the invention (A11-1) | 15% |
| Example 80 (Example 2) | Compound of the invention (A11-2) | 15% |
| Example 81 | Compound of the invention (A11-3) | 10% |
| Example 82 | Compound of the invention (A11-4) | 10% |
| Example 83 | Compound of the invention (A11-5) | 10% |
| Example 84 | Compound of the invention (A11-6) | 10% |

TABLE 1-continued

| Test compound | | Storage stability |
|---|---|---|
| Example 85 | Compound of the invention (A11-7) | 10% |
| Example 86 | Compound of the invention (A11-8) | 10% |
| Example 87 | Compound of the invention (A11-9) | 10% |
| Example 88 | Compound of the invention (A11-10) | 10% |
| Example 89 | Compound of the invention (A11-11) | 10% |
| Example 90 | Compound of the invention (A11-12) | 10% |
| Example 91 | Compound of the invention (A11-13) | 10% |
| Example 92 | Compound of the invention (A11-14) | 10% |
| Example 93 | Compound of the invention (A11-15) | 10% |

TABLE 2

| Test compound | | Storage stability |
|---|---|---|
| Example 94 (Example 3) | Compound of the invention (A12-1) | 25% |
| Example 95 | Compound of the invention (A12-2) | 25% |
| Example 96 | Compound of the invention (A12-3) | 25% |
| Example 97 | Compound of the invention (A12-4) | 25% |
| Example 98 | Compound of the invention (A12-5) | 25% |
| Example 99 | Compound of the invention (A12-6) | 20% |
| Example 100 | Compound of the invention (A12-7) | 20% |
| Example 101 | Compound of the invention (A12-8) | 20% |
| Example 102 | Compound of the invention (A12-9) | 20% |
| Example 103 | Compound of the invention (A12-10) | 20% |
| Example 104 | Compound of the invention (A12-11) | 20% |
| Example 105 | Compound of the invention (A12-12) | 20% |
| Example 106 | Compound of the invention (A12-13) | 20% |
| Example 107 | Compound of the invention (A12-14) | 20% |
| Example 108 | Compound of the invention (A12-15) | 20% |
| Example 109 | Compound of the invention (A12-16) | 20% |
| Example 110 | Compound of the invention (A12-17) | 20% |
| Example 111 | Compound of the invention (A12-18) | 20% |

TABLE 3

| Test compound | | Storage stability |
|---|---|---|
| Example 112 | Compound of the invention (A13-1) | 15% |
| Example 113 (Example 4) | Compound of the invention (A13-2) | 15% |
| Example 114 | Compound of the invention (A13-3) | 15% |
| Example 115 | Compound of the invention (A13-4) | 15% |
| Example 116 | Compound of the invention (A13-5) | 10% |
| Example 117 | Compound of the invention (A13-6) | 10% |
| Example 118 | Compound of the invention (A13-7) | 10% |
| Example 119 | Compound of the invention (A13-8) | 10% |
| Example 120 | Compound of the invention (A13-9) | 10% |
| Example 121 | Compound of the invention (A13-10) | 10% |

TABLE 4

| Test compound | | Storage stability |
|---|---|---|
| Example 122 (Example 5) | Compound of the invention (A14-1) | 25% |
| Example 123 (Example 6) | Compound of the invention (A14-2) | 25% |
| Example 124 | Compound of the invention (A14-3) | 25% |
| Example 125 | Compound of the invention (A14-4) | 20% |
| Example 126 | Compound of the invention (A14-5) | 20% |
| Example 127 | Compound of the invention (A14-6) | 25% |
| Example 128 | Compound of the invention (A14-7) | 20% |
| Example 129 | Compound of the invention (A14-8) | 20% |
| Example 130 | Compound of the invention (A14-9) | 20% |
| Example 131 | Compound of the invention (A14-10) | 20% |
| Example 132 | Compound of the invention (A14-11) | 20% |
| Example 133 | Compound of the invention (A14-12) | 20% |

TABLE 4-continued

| Test compound | | Storage stability |
|---|---|---|
| Example 134 | Compound of the invention (A14-13) | 20% |
| Example 135 | Compound of the invention (A14-14) | 20% |
| Example 136 | Compound of the invention (A14-15) | 20% |

TABLE 5

| Test compound | | Storage stability |
|---|---|---|
| Example 137 (Example 7) | Compound of the invention (A141-1) | 20% |
| Example 138 (Example 8) | Compound of the invention (A141-2) | 20% |
| Example 139 (Example 9) | Compound of the invention (A141-3) | 20% |
| Example 140 (Example 10) | Compound of the invention (A141-4) | 20% |
| Example 141 (Example 11) | Compound of the invention (A141-5) | 20% |
| Example 142 (Example 12) | Compound of the invention (A141-6) | 20% |
| Example 143 (Example 13) | Compound of the invention (A141-7) | 20% |
| Example 144 (Example 14) | Compound of the invention (A141-8) | 20% |
| Example 145 (Example 15) | Compound of the invention (A141-9) | 20% |
| Example 146 (Example 16) | Compound of the invention (A141-10) | 20% |
| Example 147 (Example 17) | Compound of the invention (A141-11) | 20% |
| Example 148 (Example 18) | Compound of the invention (A141-12) | 20% |
| Example 149 (Example 19) | Compound of the invention (A141-13) | 20% |
| Example 150 (Example 20) | Compound of the invention (A141-14) | 20% |
| Example 151 (Example 21) | Compound of the invention (A141-15) | 20% |
| Example 152 (Example 22) | Compound of the invention (A141-16) | 20% |
| Example 153 (Example 23) | Compound of the invention (A141-17) | 20% |
| Example 154 (Example 24) | Compound of the invention (A141-18) | 20% |
| Example 155 (Example 25) | Compound of the invention (A141-19) | 20% |
| Example 156 (Example 26) | Compound of the invention (A141-20) | 20% |

TABLE 6

| Test compound | | Storage stability |
|---|---|---|
| Example 157 (Example 27) | Compound of the invention (A141-21) | 20% |
| Example 158 (Example 28) | Compound of the invention (A141-22) | 20% |
| Example 159 (Example 29) | Compound of the invention (A141-23) | 20% |
| Example 160 (Example 30) | Compound of the invention (A141-24) | 20% |
| Example 161 (Example 31) | Compound of the invention (A141-25) | 20% |
| Example 162 (Example 32) | Compound of the invention (A141-26) | 20% |
| Example 163 (Example 33) | Compound of the invention (A141-27) | 20% |
| Example 164 (Example 34) | Compound of the invention (A141-28) | 20% |

TABLE 6-continued

| | Test compound | Storage stability |
|---|---|---|
| Example 165 (Example 35) | Compound of the invention (A141-29) | 20% |
| Example 166 (Example 36) | Compound of the invention (A141-30) | 20% |
| Example 167 (Example 37) | Compound of the invention (A141-31) | 20% |
| Example 168 (Example 38) | Compound of the invention (A141-32) | 20% |
| Example 169 (Example 39) | Compound of the invention (A141-33) | 20% |

TABLE 7

| | Test compound | Storage stability |
|---|---|---|
| Example 170 (Example 40) | Compound of the invention (A142-1) | 20% |
| Example 171 (Example 41) | Compound of the invention (A142-2) | 20% |
| Example 172 (Example 42) | Compound of the invention (A142-3) | 20% |
| Example 173 (Example 43) | Compound of the invention (A142-4) | 20% |
| Example 174 (Example 44) | Compound of the invention (A142-5) | 20% |
| Example 175 (Example 45) | Compound of the invention (A142-6) | 20% |
| Example 176 (Example 46) | Compound of the invention (A142-7) | 20% |
| Example 177 (Example 47) | Compound of the invention (A142-8) | 20% |
| Example 178 (Example 48) | Compound of the invention (A142-9) | 20% |
| Example 179 (Example 49) | Compound of the invention (A142-10) | 20% |
| Example 180 (Example 50) | Compound of the invention (A142-11) | 20% |
| Example 181 (Example 51) | Compound of the invention (A142-12) | 20% |
| Example 182 (Example 52) | Compound of the invention (A142-13) | 20% |
| Example 183 (Example 53) | Compound of the invention (A142-14) | 20% |
| Example 184 (Example 54) | Compound of the invention (A142-15) | 20% |

TABLE 8

| | Test compound | Storage stability |
|---|---|---|
| Example 185 (Example 55) | Compound of the invention (A143-1) | 20% |
| Example 186 (Example 56) | Compound of the invention (A143-2) | 20% |
| Example 187 (Example 57) | Compound of the invention (A144-1) | 20% |

TABLE 9

| | Test compound | Storage stability |
|---|---|---|
| Example 188 (Example 58) | Compound of the invention (A15-1) | 15% |
| Example 189 | Compound of the invention (A15-2) | 15% |
| Example 190 | Compound of the invention (A15-3) | 15% |
| Example 191 | Compound of the invention (A15-4) | 15% |
| Example 192 | Compound of the invention (A15-5) | 10% |

TABLE 9-continued

| | Test compound | Storage stability |
|---|---|---|
| Example 193 | Compound of the invention (A15-6) | 15% |
| Example 194 | Compound of the invention (A15-7) | 15% |
| Example 195 | Compound of the invention (A15-8) | 10% |
| Example 196 | Compound of the invention (A15-9) | 10% |
| Example 197 | Compound of the invention (A15-10) | 10% |
| Example 198 | Compound of the invention (A15-11) | 10% |
| Example 199 | Compound of the invention (A15-12) | 10% |
| Example 200 | Compound of the invention (A15-13) | 10% |
| Example 201 | Compound of the invention (A15-14) | 10% |
| Example 202 | Compound of the invention (A15-15) | 10% |

TABLE 10

| | Test compound | Storage stability |
|---|---|---|
| Example 203 | Compound of the invention (A2-1) | 5% |
| Example 204 | Compound of the invention (A2-2) | 5% |
| Example 205 (Example 59) | Compound of the invention (A2-3) | 5% |
| Example 206 | Compound of the invention (A2-4) | 5% |
| Example 207 (Example 60) | Compound of the invention (A2-5) | 5% |
| Example 208 | Compound of the invention (A2-6) | 5% |
| Example 209 | Compound of the invention (A2-7) | 5% |
| Example 210 | Compound of the invention (A2-8) | 5% |
| Example 211 | Compound of the invention (A2-9) | 5% |
| Example 212 | Compound of the invention (A2-10) | 5% |
| Example 213 (Example 61) | Compound of the invention (A3-1) | 25% |
| Example 214 | Compound of the invention (A3-2) | 25% |
| Example 215 | Compound of the invention (A3-3) | 20% |
| Example 216 | Compound of the invention (A3-4) | 20% |
| Example 217 | Compound of the invention (A3-5) | 20% |

TABLE 11

| | Test compound | Storage stability |
|---|---|---|
| Example 218 (Example 62) | Compound of the invention (B11-1) | 5% |
| Example 219 | Compound of the invention (B11-2) | 5% |
| Example 220 | Compound of the invention (B11-3) | 5% |
| Example 221 | Compound of the invention (B11-4) | 5% |
| Example 222 | Compound of the invention (B11-5) | 5% |
| Example 223 | Compound of the invention (B11-6) | 5% |
| Example 224 | Compound of the invention (B11-7) | 5% |
| Example 225 (Example 63) | Compound of the invention (B11-8) | 5% |
| Example 226 | Compound of the invention (B11-9) | 5% |
| Example 227 | Compound of the invention (B11-10) | 5% |
| Example 228 | Compound of the invention (B11-11) | 5% |
| Example 229 | Compound of the invention (B11-12) | 5% |
| Example 230 | Compound of the invention (B11-13) | 5% |
| Example 231 | Compound of the invention (B11-14) | 5% |
| Example 232 | Compound of the invention (B11-15) | 5% |
| Example 233 | Compound of the invention (B11-16) | 5% |

TABLE 12

| | Test compound | Storage stability |
|---|---|---|
| Example 234 | Compound of the invention (B2-1) | 5% |
| Example 235 (Example 64) | Compound of the invention (B2-2) | 5% |
| Example 236 | Compound of the invention (B2-3) | 5% |
| Example 237 | Compound of the invention (B2-4) | 5% |

TABLE 12-continued

| | Test compound | Storage stability |
|---|---|---|
| Example 238 | Compound of the invention (B2-5) | 5% |
| Example 239 (Example 65) | Compound of the invention (B2-6) | 5% |
| Example 240 | Compound of the invention (B2-7) | 5% |
| Example 241 | Compound of the invention (B2-8) | 5% |
| Example 242 | Compound of the invention (B2-9) | 5% |
| Example 243 | Compound of the invention (B2-10) | 5% |
| Example 244 | Compound of the invention (B2-11) | 5% |
| Example 245 | Compound of the invention (B2-12) | 5% |
| Example 246 (Example 66) | Compound of the invention (B2-13) | 5% |
| Example 247 (Example 67) | Compound of the invention (B3-1) | 5% |
| Example 248 | Compound of the invention (B3-2) | 5% |
| Example 249 | Compound of the invention (B3-3) | 5% |
| Example 250 | Compound of the invention (B3-4) | 5% |
| Example 251 | Compound of the invention (B3-5) | 5% |

TABLE 13

| | Test compound | Storage stability |
|---|---|---|
| Example 252 | Compound of the invention (C11-1) | 5% |
| Example 253 (Example 68) | Compound of the invention (C11-2) | 5% |
| Example 254 | Compound of the invention (C11-3) | 5% |
| Example 255 | Compound of the invention (C11-4) | 5% |
| Example 256 | Compound of the invention (C11-5) | 5% |
| Example 257 | Compound of the invention (C11-6) | 5% |
| Example 258 | Compound of the invention (C11-7) | 5% |
| Example 259 | Compound of the invention (C11-8) | 5% |
| Example 260 | Compound of the invention (C11-9) | 5% |
| Example 261 | Compound of the invention (C11-10) | 5% |
| Example 262 | Compound of the invention (C11-11) | 5% |
| Example 263 | Compound of the invention (C11-12) | 5% |
| Example 264 | Compound of the invention (C11-13) | 5% |
| Example 265 | Compound of the invention (C11-14) | 5% |
| Example 266 | Compound of the invention (C11-15) | 5% |
| Example 267 | Compound of the invention (C11-16) | 5% |
| Example 268 | Compound of the invention (C11-17) | 5% |
| Example 269 | Compound of the invention (C11-18) | 5% |
| Example 270 | Compound of the invention (C11-19) | 5% |
| Example 271 | Compound of the invention (C11-20) | 5% |

TABLE 14

| | Test compound | Storage stability |
|---|---|---|
| Example 272 (Example 69) | Compound of the invention (C12-1) | 5% |
| Example 273 | Compound of the invention (C12-2) | 5% |
| Example 274 | Compound of the invention (C12-3) | 5% |
| Example 275 | Compound of the invention (C12-4) | 5% |
| Example 276 | Compound of the invention (C12-5) | 5% |
| Example 277 | Compound of the invention (C12-6) | 5% |
| Example 278 | Compound of the invention (C12-7) | 5% |
| Example 279 | Compound of the invention (C12-8) | 5% |
| Example 280 | Compound of the invention (C12-9) | 5% |
| Example 281 | Compound of the invention (C12-10) | 5% |
| Example 282 | Compound of the invention (C12-11) | 5% |
| Example 283 | Compound of the invention (C12-12) | 5% |

TABLE 15

| | Test compound | Storage stability |
|---|---|---|
| Example 284 (Example 70) | Compound of the invention (C2-1) | 25% |
| Example 285 | Compound of the invention (C2-2) | 25% |
| Example 286 | Compound of the invention (C2-3) | 25% |
| Example 287 (Example 71) | Compound of the invention (C2-4) | 25% |
| Example 288 | Compound of the invention (C2-5) | 20% |
| Example 289 | Compound of the invention (C2-6) | 20% |
| Example 290 | Compound of the invention (C2-7) | 20% |
| Example 291 | Compound of the invention (C2-8) | 20% |
| Example 292 | Compound of the invention (C2-9) | 20% |
| Example 293 | Compound of the invention (C2-10) | 20% |
| Example 294 | Compound of the invention (C2-11) | 20% |
| Example 295 | Compound of the invention (C2-12) | 20% |
| Example 296 | Compound of the invention (C2-13) | 20% |
| Example 297 | Compound of the invention (C2-14) | 20% |
| Example 298 | Compound of the invention (C2-15) | 20% |
| Example 299 (Example 72) | Compound of the invention (C2-16) | 20% |
| Example 300 | Compound of the invention (C2-17) | 20% |
| Example 301 | Compound of the invention (C2-18) | 20% |
| Example 302 (Example 73) | Compound of the invention (C3-1) | 5% |
| Example 303 | Compound of the invention (C3-2) | 5% |
| Example 304 | Compound of the invention (C3-3) | 5% |
| Example 305 | Compound of the invention (C3-4) | 5% |
| Example 306 | Compound of the invention (C3-5) | 5% |

TABLE 16

| | Test compound | Storage stability |
|---|---|---|
| Example 307 (Example 74) | Compound of the invention (D11-1) | 25% |
| Example 308 | Compound of the invention (D11-2) | 25% |
| Example 309 | Compound of the invention (D11-3) | 25% |
| Example 310 | Compound of the invention (D11-4) | 25% |
| Example 311 | Compound of the invention (D11-5) | 20% |
| Example 312 | Compound of the invention (D11-6) | 20% |
| Example 313 | Compound of the invention (D11-7) | 20% |
| Example 314 | Compound of the invention (D11-8) | 20% |
| Example 315 | Compound of the invention (D11-9) | 20% |
| Example 316 | Compound of the invention (D11-10) | 20% |

TABLE 17

| | Test compound | Storage stability |
|---|---|---|
| Example 317 (Example 75) | Compound of the invention (D12-1) | 15% |
| Example 318 | Compound of the invention (D12-2) | 15% |
| Example 319 | Compound of the invention (D12-3) | 10% |
| Example 320 | Compound of the invention (D12-4) | 10% |
| Example 321 | Compound of the invention (D12-5) | 10% |
| Example 322 | Compound of the invention (D12-6) | 10% |
| Example 323 | Compound of the invention (D12-7) | 10% |
| Example 324 | Compound of the invention (D12-8) | 10% |
| Example 325 | Compound of the invention (D12-9) | 10% |
| Example 326 | Compound of the invention (D12-10) | 10% |

TABLE 18

| Test compound | | Storage stability |
|---|---|---|
| Example 327 (Example 76) | Compound of the invention (D2-1) | 5% |
| Example 328 | Compound of the invention (D2-2) | 5% |
| Example 329 | Compound of the invention (D2-3) | 5% |
| Example 330 | Compound of the invention (D2-4) | 5% |
| Example 331 | Compound of the invention (D2-5) | 5% |
| Example 332 | Compound of the invention (D2-6) | 5% |
| Example 333 | Compound of the invention (D2-7) | 5% |
| Example 334 | Compound of the invention (D2-8) | 5% |
| Example 335 | Compound of the invention (D2-9) | 5% |
| Example 336 | Compound of the invention (D2-10) | 5% |

TABLE 19

| Test compound | | Storage stability |
|---|---|---|
| Example 337 (Example 77) | Compound of the invention (D3-1) | 5% |
| Example 338 | Compound of the invention (D3-2) | 5% |
| Example 339 | Compound of the invention (D3-3) | 5% |
| Example 340 | Compound of the invention (D3-4) | 5% |
| Example 341 | Compound of the invention (D3-5) | 5% |
| Example 342 | Compound of the invention (D4-1) | 5% |
| Example 343 (Example 78) | Compound of the invention (D4-2) | 5% |
| Example 344 | Compound of the invention (D4-3) | 5% |
| Example 345 | Compound of the invention (D4-4) | 5% |

The tables show that the compounds of Examples 79 to 345 according to the present invention have a high maximum concentration at which no crystal precipitation occurs and have high storage stability.

Examples 346 to 612

A polyimide solution for an alignment film was applied to a glass substrate with a thickness of 0.7 mm by spin coating, was dried at 100° C. for 10 minutes, and was baked at 200° C. for 60 minutes to form a coating film. The coating film was rubbed. Rubbing was performed with a commercially available rubbing machine.

25% of a compound to be tested was added to the mother liquid crystal (X) to prepare a composition. 1% of a photopolymerization initiator Irgacure 907 (manufactured by BASF), 0.1% of 4-methoxyphenol, and 80% of chloroform were added to the composition to prepare a coating liquid. The coating liquid was applied to a rubbed glass substrate by spin coating. The coating liquid was dried at 80° C. for 1 minute and at 120° C. for 1 minute. Ultraviolet irradiation with a high-pressure mercury lamp at an intensity of 40 mW/cm$^2$ for 25 seconds formed a film to be tested. 20 films containing a compound to be tested were formed. The following tables list the example numbers of the films and their corresponding compounds to be tested.

TABLE 20

| Film | Test compound used |
|---|---|
| Example 346 | Compound of the invention (A11-1) |
| Example 347 | Compound of the invention (A11-2) |
| Example 348 | Compound of the invention (A11-3) |
| Example 349 | Compound of the invention (A11-4) |
| Example 350 | Compound of the invention (A11-5) |
| Example 351 | Compound of the invention (A11-6) |
| Example 352 | Compound of the invention (A11-7) |
| Example 353 | Compound of the invention (A11-8) |
| Example 354 | Compound of the invention (A11-9) |
| Example 355 | Compound of the invention (A11-10) |
| Example 356 | Compound of the invention (A11-11) |
| Example 357 | Compound of the invention (A11-12) |
| Example 358 | Compound of the invention (A11-13) |
| Example 359 | Compound of the invention (A11-14) |
| Example 360 | Compound of the invention (A11-15) |

TABLE 21

| Film | Test compound used |
|---|---|
| Example 361 | Compound of the invention (A12-1) |
| Example 362 | Compound of the invention (A12-2) |
| Example 363 | Compound of the invention (A12-3) |
| Example 364 | Compound of the invention (A12-4) |
| Example 365 | Compound of the invention (A12-5) |
| Example 366 | Compound of the invention (A12-6) |
| Example 367 | Compound of the invention (A12-7) |
| Example 368 | Compound of the invention (A12-8) |
| Example 369 | Compound of the invention (A12-9) |
| Example 370 | Compound of the invention (A12-10) |
| Example 371 | Compound of the invention (A12-11) |
| Example 372 | Compound of the invention (A12-12) |
| Example 373 | Compound of the invention (A12-13) |
| Example 374 | Compound of the invention (A12-14) |
| Example 375 | Compound of the invention (A12-15) |
| Example 376 | Compound of the invention (A12-16) |
| Example 377 | Compound of the invention (A12-17) |
| Example 378 | Compound of the invention (A12-18) |

TABLE 22

| Film | Test compound used |
|---|---|
| Example 379 | Compound of the invention (A13-1) |
| Example 380 | Compound of the invention (A13-2) |
| Example 381 | Compound of the invention (A13-3) |
| Example 382 | Compound of the invention (A13-4) |
| Example 383 | Compound of the invention (A13-5) |
| Example 384 | Compound of the invention (A13-6) |
| Example 385 | Compound of the invention (A13-7) |
| Example 386 | Compound of the invention (A13-8) |
| Example 387 | Compound of the invention (A13-9) |
| Example 388 | Compound of the invention (A13-10) |

TABLE 23

| Film | Test compound used |
|---|---|
| Example 389 | Compound of the invention (A14-1) |
| Example 390 | Compound of the invention (A14-2) |
| Example 391 | Compound of the invention (A14-3) |
| Example 392 | Compound of the invention (A14-4) |
| Example 393 | Compound of the invention (A14-5) |
| Example 394 | Compound of the invention (A14-6) |
| Example 395 | Compound of the invention (A14-7) |
| Example 396 | Compound of the invention (A14-8) |
| Example 397 | Compound of the invention (A14-9) |
| Example 398 | Compound of the invention (A14-10) |
| Example 399 | Compound of the invention (A14-11) |
| Example 400 | Compound of the invention (A14-12) |
| Example 401 | Compound of the invention (A14-13) |
| Example 402 | Compound of the invention (A14-14) |
| Example 403 | Compound of the invention (A14-15) |

TABLE 24

| Film | Test compound used |
| --- | --- |
| Example 404 | Compound of the invention (A141-1) |
| Example 405 | Compound of the invention (A141-2) |
| Example 406 | Compound of the invention (A141-3) |
| Example 407 | Compound of the invention (A141-4) |
| Example 408 | Compound of the invention (A141-5) |
| Example 409 | Compound of the invention (A141-6) |
| Example 410 | Compound of the invention (A141-7) |
| Example 411 | Compound of the invention (A141-8) |
| Example 412 | Compound of the invention (A141-9) |
| Example 413 | Compound of the invention (A141-10) |
| Example 414 | Compound of the invention (A141-11) |
| Example 415 | Compound of the invention (A141-12) |
| Example 416 | Compound of the invention (A141-13) |
| Example 417 | Compound of the invention (A141-14) |
| Example 418 | Compound of the invention (A141-15) |
| Example 419 | Compound of the invention (A141-16) |
| Example 420 | Compound of the invention (A141-17) |
| Example 421 | Compound of the invention (A141-18) |
| Example 422 | Compound of the invention (A141-19) |
| Example 423 | Compound of the invention (A141-20) |

TABLE 25

| Film | Test compound used |
| --- | --- |
| Example 424 | Compound of the invention (A141-21) |
| Example 425 | Compound of the invention (A141-22) |
| Example 426 | Compound of the invention (A141-23) |
| Example 427 | Compound of the invention (A141-24) |
| Example 428 | Compound of the invention (A141-25) |
| Example 429 | Compound of the invention (A141-26) |
| Example 430 | Compound of the invention (A141-27) |
| Example 431 | Compound of the invention (A141-28) |
| Example 432 | Compound of the invention (A141-29) |
| Example 433 | Compound of the invention (A141-30) |
| Example 434 | Compound of the invention (A141-31) |
| Example 435 | Compound of the invention (A141-32) |
| Example 436 | Compound of the invention (A141-33) |

TABLE 26

| Film | Test compound used |
| --- | --- |
| Example 437 | Compound of the invention (A142-1) |
| Example 438 | Compound of the invention (A142-2) |
| Example 439 | Compound of the invention (A142-3) |
| Example 440 | Compound of the invention (A142-4) |
| Example 441 | Compound of the invention (A142-5) |
| Example 442 | Compound of the invention (A142-6) |
| Example 443 | Compound of the invention (A142-7) |
| Example 444 | Compound of the invention (A142-8) |
| Example 445 | Compound of the invention (A142-9) |
| Example 446 | Compound of the invention (A142-10) |
| Example 447 | Compound of the invention (A142-11) |
| Example 448 | Compound of the invention (A142-12) |
| Example 449 | Compound of the invention (A142-13) |
| Example 450 | Compound of the invention (A142-14) |
| Example 451 | Compound of the invention (A142-15) |

TABLE 27

| Film | Test compound used |
| --- | --- |
| Example 452 | Compound of the invention (A143-1) |
| Example 453 | Compound of the invention (A143-2) |
| Example 454 | Compound of the invention (A144-1) |

TABLE 28

| Film | Test compound used |
| --- | --- |
| Example 455 | Compound of the invention (A15-1) |
| Example 456 | Compound of the invention (A15-2) |
| Example 457 | Compound of the invention (A15-3) |
| Example 458 | Compound of the invention (A15-4) |
| Example 459 | Compound of the invention (A15-5) |
| Example 460 | Compound of the invention (A15-6) |
| Example 461 | Compound of the invention (A15-7) |
| Example 462 | Compound of the invention (A15-8) |
| Example 463 | Compound of the invention (A15-9) |
| Example 464 | Compound of the invention (A15-10) |
| Example 465 | Compound of the invention (A15-11) |
| Example 466 | Compound of the invention (A15-12) |
| Example 467 | Compound of the invention (A15-13) |
| Example 468 | Compound of the invention (A15-14) |
| Example 469 | Compound of the invention (A15-15) |

TABLE 29

| Film | Test compound used |
| --- | --- |
| Example 470 | Compound of the invention (A2-1) |
| Example 471 | Compound of the invention (A2-2) |
| Example 472 | Compound of the invention (A2-3) |
| Example 473 | Compound of the invention (A2-4) |
| Example 474 | Compound of the invention (A2-5) |
| Example 475 | Compound of the invention (A2-6) |
| Example 476 | Compound of the invention (A2-7) |
| Example 477 | Compound of the invention (A2-8) |
| Example 478 | Compound of the invention (A2-9) |
| Example 479 | Compound of the invention (A2-10) |
| Example 480 | Compound of the invention (A3-1) |
| Example 481 | Compound of the invention (A3-2) |
| Example 482 | Compound of the invention (A3-3) |
| Example 483 | Compound of the invention (A3-4) |
| Example 484 | Compound of the invention (A3-5) |

TABLE 30

| Film | Test compound used |
| --- | --- |
| Example 485 | Compound of the invention (B11-1) |
| Example 486 | Compound of the invention (B11-2) |
| Example 487 | Compound of the invention (B11-3) |
| Example 488 | Compound of the invention (B11-4) |
| Example 489 | Compound of the invention (B11-5) |
| Example 490 | Compound of the invention (B11-6) |
| Example 491 | Compound of the invention (B11-7) |
| Example 492 | Compound of the invention (B11-8) |
| Example 493 | Compound of the invention (B11-9) |
| Example 494 | Compound of the invention (B11-10) |
| Example 495 | Compound of the invention (B11-11) |
| Example 496 | Compound of the invention (B11-12) |
| Example 497 | Compound of the invention (B11-13) |
| Example 498 | Compound of the invention (B11-14) |
| Example 499 | Compound of the invention (B11-15) |
| Example 500 | Compound of the invention (B11-16) |

TABLE 31

| Film | Test compound used |
| --- | --- |
| Example 501 | Compound of the invention (B2-1) |
| Example 502 | Compound of the invention (B2-2) |
| Example 503 | Compound of the invention (B2-3) |
| Example 504 | Compound of the invention (B2-4) |
| Example 505 | Compound of the invention (B2-5) |
| Example 506 | Compound of the invention (B2-6) |
| Example 507 | Compound of the invention (B2-7) |
| Example 508 | Compound of the invention (B2-8) |
| Example 509 | Compound of the invention (B2-9) |
| Example 510 | Compound of the invention (B2-10) |

TABLE 31-continued

| Film | Test compound used |
| --- | --- |
| Example 511 | Compound of the invention (B2-11) |
| Example 512 | Compound of the invention (B2-12) |
| Example 513 | Compound of the invention (B2-13) |
| Example 514 | Compound of the invention (B3-1) |
| Example 515 | Compound of the invention (B3-2) |
| Example 516 | Compound of the invention (B3-3) |
| Example 517 | Compound of the invention (B3-4) |
| Example 518 | Compound of the invention (B3-5) |

TABLE 32

| Film | Test compound used |
| --- | --- |
| Example 519 | Compound of the invention (C11-1) |
| Example 520 | Compound of the invention (C11-2) |
| Example 521 | Compound of the invention (C11-3) |
| Example 522 | Compound of the invention (C11-4) |
| Example 523 | Compound of the invention (C11-5) |
| Example 524 | Compound of the invention (C11-6) |
| Example 525 | Compound of the invention (C11-7) |
| Example 526 | Compound of the invention (C11-8) |
| Example 527 | Compound of the invention (C11-9) |
| Example 528 | Compound of the invention (C11-10) |
| Example 529 | Compound of the invention (C11-11) |
| Example 530 | Compound of the invention (C11-12) |
| Example 531 | Compound of the invention (C11-13) |
| Example 532 | Compound of the invention (C11-14) |
| Example 533 | Compound of the invention (C11-15) |
| Example 534 | Compound of the invention (C11-16) |
| Example 535 | Compound of the invention (C11-17) |
| Example 536 | Compound of the invention (C11-18) |
| Example 537 | Compound of the invention (C11-19) |
| Example 538 | Compound of the invention (C11-20) |

TABLE 33

| Film | Test compound used |
| --- | --- |
| Example 539 | Compound of the invention (C12-1) |
| Example 540 | Compound of the invention (C12-2) |
| Example 541 | Compound of the invention (C12-3) |
| Example 542 | Compound of the invention (C12-4) |
| Example 543 | Compound of the invention (C12-5) |
| Example 544 | Compound of the invention (C12-6) |
| Example 545 | Compound of the invention (C12-7) |
| Example 546 | Compound of the invention (C12-8) |
| Example 547 | Compound of the invention (C12-9) |
| Example 548 | Compound of the invention (C12-10) |
| Example 549 | Compound of the invention (C12-11) |
| Example 550 | Compound of the invention (C12-12) |

TABLE 34

| Film | Test compound used |
| --- | --- |
| Example 551 | Compound of the invention (C2-1) |
| Example 552 | Compound of the invention (C2-2) |
| Example 553 | Compound of the invention (C2-3) |
| Example 554 | Compound of the invention (C2-4) |
| Example 555 | Compound of the invention (C2-5) |
| Example 556 | Compound of the invention (C2-6) |
| Example 557 | Compound of the invention (C2-7) |
| Example 558 | Compound of the invention (C2-8) |
| Example 559 | Compound of the invention (C2-9) |
| Example 560 | Compound of the invention (C2-10) |
| Example 561 | Compound of the invention (C2-11) |
| Example 562 | Compound of the invention (C2-12) |
| Example 563 | Compound of the invention (C2-13) |
| Example 564 | Compound of the invention (C2-14) |
| Example 565 | Compound of the invention (C2-15) |
| Example 566 | Compound of the invention (C2-16) |

TABLE 34-continued

| Film | Test compound used |
| --- | --- |
| Example 567 | Compound of the invention (C2-17) |
| Example 568 | Compound of the invention (C2-18) |
| Example 569 | Compound of the invention (C3-1) |
| Example 570 | Compound of the invention (C3-2) |
| Example 571 | Compound of the invention (C3-3) |
| Example 572 | Compound of the invention (C3-4) |
| Example 573 | Compound of the invention (C3-5) |

TABLE 35

| Film | Test compound used |
| --- | --- |
| Example 574 | Compound of the invention (D11-1) |
| Example 575 | Compound of the invention (D11-2) |
| Example 576 | Compound of the invention (D11-3) |
| Example 577 | Compound of the invention (D11-4) |
| Example 578 | Compound of the invention (D11-5) |
| Example 579 | Compound of the invention (D11-6) |
| Example 580 | Compound of the invention (D11-7) |
| Example 581 | Compound of the invention (D11-8) |
| Example 582 | Compound of the invention (D11-9) |
| Example 583 | Compound of the invention (D11-10) |

TABLE 36

| Film | Test compound used |
| --- | --- |
| Example 584 | Compound of the invention (D12-1) |
| Example 585 | Compound of the invention (D12-2) |
| Example 586 | Compound of the invention (D12-3) |
| Example 587 | Compound of the invention (D12-4) |
| Example 588 | Compound of the invention (D12-5) |
| Example 589 | Compound of the invention (D12-6) |
| Example 590 | Compound of the invention (D12-7) |
| Example 591 | Compound of the invention (D12-8) |
| Example 592 | Compound of the invention (D12-9) |
| Example 593 | Compound of the invention (D12-10) |

TABLE 37

| Film | Test compound used |
| --- | --- |
| Example 594 | Compound of the invention (D2-1) |
| Example 595 | Compound of the invention (D2-2) |
| Example 596 | Compound of the invention (D2-3) |
| Example 597 | Compound of the invention (D2-4) |
| Example 598 | Compound of the invention (D2-5) |
| Example 599 | Compound of the invention (D2-6) |
| Example 600 | Compound of the invention (D2-7) |
| Example 601 | Compound of the invention (D2-8) |
| Example 602 | Compound of the invention (D2-9) |
| Example 603 | Compound of the invention (D2-10) |

TABLE 38

| Film | Test compound used |
| --- | --- |
| Example 604 | Compound of the invention (D3-1) |
| Example 605 | Compound of the invention (D3-2) |
| Example 606 | Compound of the invention (D3-3) |
| Example 607 | Compound of the invention (D3-4) |
| Example 608 | Compound of the invention (D3-5) |
| Example 609 | Compound of the invention (D4-1) |
| Example 610 | Compound of the invention (D4-2) |
| Example 611 | Compound of the invention (D4-3) |
| Example 612 | Compound of the invention (D4-4) |

The haze, thickness uniformity, nonuniform orientation, surface hardness, and adhesiveness of 10 of the 20 films were measured. The following tables show the results.

<Haze>

The haze, which is calculated using the following formula (wherein Td denotes diffuse transmittance, and Tt denotes the total light transmittance), was measured with a haze meter (NHD 2000 manufactured by Nippon Denshoku Industries Co., Ltd.). Five measurements of each of the 10 films were averaged.

Haze (%)=$Td/Tt$×100

<Film Thickness Uniformity>

A value (%) was calculated by dividing the difference between the maximum film thickness and the minimum film thickness by the average film thickness. The thickness of each of the 10 films was measured at 25 positions with an interference thickness meter (FE-3000 manufactured by Otsuka Electronics Co., Ltd.).

<Nonuniform Orientation>

Nonuniform orientation was determined by polarized light microscopy. The number of orientation defects observed in each of the 10 films was summed up.

<Surface Hardness>

The pencil hardness (JIS K 5400) of each of the 10 films was measured at 5 positions.

<Adhesiveness>

The 10 films were subjected to a cross-cut tape test (JIS K 5400). The average (%) of the number of removed squares was determined in each of the 10 films.

TABLE 39

| Film | Haze | Thickness uniformity | Non-uniform orientation | Surface hardness | Adhesiveness |
| --- | --- | --- | --- | --- | --- |
| Example 346 | 1.6 | 1.1 | 3 | F | 1.1 |
| Example 347 | 1.5 | 1.1 | 3 | F | 1.1 |
| Example 348 | 1.8 | 1.8 | 5 | F | 1.5 |
| Example 349 | 1.9 | 1.9 | 6 | F | 1.6 |
| Example 350 | 1.8 | 1.8 | 5 | F | 1.8 |
| Example 351 | 1.7 | 1.6 | 5 | F | 2.0 |
| Example 352 | 2.0 | 1.9 | 5 | F | 1.9 |
| Example 353 | 1.7 | 1.4 | 6 | F | 1.8 |
| Example 354 | 1.9 | 1.4 | 4 | F | 1.7 |
| Example 355 | 1.9 | 1.5 | 5 | F | 1.8 |
| Example 356 | 1.8 | 2.0 | 6 | F | 1.7 |
| Example 357 | 1.7 | 1.8 | 5 | F | 1.6 |
| Example 358 | 2.0 | 1.7 | 5 | F | 1.4 |
| Example 359 | 1.9 | 1.6 | 5 | F | 1.6 |
| Example 360 | 1.8 | 1.5 | 6 | F | 1.5 |

TABLE 40

| Film | Haze | Thickness uniformity | Non-uniform orientation | Surface hardness | Adhesiveness |
| --- | --- | --- | --- | --- | --- |
| Example 361 | 1.6 | 1.1 | 0 | HB | 1.1 |
| Example 362 | 1.6 | 1.1 | 0 | HB | 1.1 |
| Example 363 | 1.6 | 1.1 | 0 | HB | 1.1 |
| Example 364 | 1.6 | 1.2 | 0 | HB | 1.1 |
| Example 365 | 1.7 | 1.3 | 1 | HB | 1.2 |
| Example 366 | 1.9 | 1.5 | 2 | HB | 1.5 |
| Example 367 | 2.0 | 1.8 | 2 | HB | 1.6 |
| Example 368 | 1.8 | 1.7 | 2 | HB | 1.5 |
| Example 369 | 1.9 | 1.9 | 2 | HB | 1.8 |
| Example 370 | 1.9 | 2.0 | 2 | HB | 1.7 |
| Example 371 | 2.0 | 1.7 | 2 | HB | 1.5 |
| Example 372 | 1.8 | 1.8 | 2 | HB | 1.6 |
| Example 373 | 2.0 | 1.6 | 2 | HB | 1.8 |

TABLE 40-continued

| Film | Haze | Thickness uniformity | Non-uniform orientation | Surface hardness | Adhesiveness |
| --- | --- | --- | --- | --- | --- |
| Example 374 | 1.9 | 1.8 | 2 | HB | 2.0 |
| Example 375 | 1.9 | 2.0 | 2 | HB | 1.9 |
| Example 376 | 1.6 | 2.0 | 0 | HB | 1.1 |
| Example 377 | 1.6 | 2.0 | 0 | HB | 1.1 |
| Example 378 | 1.6 | 2.0 | 0 | HB | 1.1 |

TABLE 41

| Film | Haze | Thickness uniformity | Non-uniform orientation | Surface hardness | Adhesiveness |
| --- | --- | --- | --- | --- | --- |
| Example 379 | 1.6 | 0.5 | 3 | HB | 0 |
| Example 380 | 1.6 | 0.5 | 3 | HB | 0 |
| Example 381 | 1.6 | 0.5 | 3 | HB | 0 |
| Example 382 | 1.7 | 0.7 | 4 | HB | 0.1 |
| Example 383 | 1.8 | 0.9 | 6 | HB | 0.2 |
| Example 384 | 1.8 | 1.0 | 6 | HB | 0.2 |
| Example 385 | 1.9 | 0.8 | 6 | HB | 0.2 |
| Example 386 | 1.8 | 0.9 | 6 | HB | 0.2 |
| Example 387 | 2.0 | 0.9 | 5 | HB | 0.2 |
| Example 388 | 1.9 | 0.9 | 5 | HB | 0.2 |

TABLE 42

| Film | Haze | Thickness uniformity | Non-uniform orientation | Surface hardness | Adhesiveness |
| --- | --- | --- | --- | --- | --- |
| Example 389 | 0.2 | 1.1 | 3 | HB | 1.1 |
| Example 390 | 0.2 | 1.2 | 3 | HB | 1.1 |
| Example 391 | 0.3 | 1.1 | 3 | HB | 1.1 |
| Example 392 | 0.7 | 1.8 | 6 | HB | 1.8 |
| Example 393 | 0.6 | 1.7 | 6 | HB | 1.8 |
| Example 394 | 0.4 | 1.1 | 3 | HB | 1.1 |
| Example 395 | 0.7 | 1.9 | 5 | HB | 1.7 |
| Example 396 | 0.8 | 1.7 | 5 | HB | 1.7 |
| Example 397 | 0.9 | 2.0 | 6 | HB | 1.7 |
| Example 398 | 1.0 | 1.9 | 5 | HB | 1.8 |
| Example 399 | 0.8 | 1.7 | 5 | HB | 1.9 |
| Example 400 | 0.9 | 1.6 | 6 | HB | 2.0 |
| Example 401 | 0.8 | 1.5 | 6 | HB | 1.7 |
| Example 402 | 0.6 | 1.8 | 5 | HB | 1.8 |
| Example 403 | 0.7 | 1.7 | 5 | HB | 1.8 |

TABLE 43

| Film | Haze | Thickness uniformity | Non-uniform orientation | Surface hardness | Adhesiveness |
| --- | --- | --- | --- | --- | --- |
| Example 404 | 0.2 | 1.1 | 3 | HB | 1.1 |
| Example 405 | 0.3 | 1.1 | 3 | HB | 1.1 |
| Example 406 | 0.4 | 1.1 | 3 | HB | 1.1 |
| Example 407 | 0.2 | 1.1 | 3 | HB | 1.1 |
| Example 408 | 0.3 | 1.1 | 3 | HB | 1.1 |
| Example 409 | 0.4 | 1.1 | 3 | HB | 1.1 |
| Example 410 | 0.2 | 1.1 | 3 | HB | 1.1 |
| Example 411 | 0.2 | 1.1 | 3 | HB | 1.1 |
| Example 412 | 0.3 | 1.1 | 3 | HB | 1.1 |
| Example 413 | 0.4 | 1.1 | 3 | HB | 1.1 |
| Example 414 | 0.2 | 1.1 | 3 | HB | 1.1 |
| Example 415 | 0.3 | 1.1 | 3 | HB | 1.1 |
| Example 416 | 0.2 | 1.1 | 3 | HB | 1.1 |
| Example 417 | 0.3 | 1.1 | 3 | HB | 1.1 |
| Example 418 | 0.4 | 1.1 | 3 | HB | 1.1 |
| Example 419 | 0.2 | 1.1 | 3 | HB | 1.1 |
| Example 420 | 0.2 | 1.1 | 3 | HB | 1.1 |
| Example 421 | 0.4 | 1.1 | 3 | HB | 1.1 |

TABLE 43-continued

| Film | Haze | Thickness uniformity | Non-uniform orientation | Surface hardness | Adhesiveness |
|---|---|---|---|---|---|
| Example 422 | 0.2 | 1.1 | 3 | HB | 1.1 |
| Example 423 | 0.3 | 1.1 | 3 | HB | 1.1 |

TABLE 44

| Film | Haze | Thickness uniformity | Non-uniform orientation | Surface hardness | Adhesiveness |
|---|---|---|---|---|---|
| Example 424 | 0.2 | 1.1 | 3 | HB | 1.1 |
| Example 425 | 0.3 | 1.1 | 3 | HB | 1.1 |
| Example 426 | 0.4 | 1.1 | 3 | HB | 1.1 |
| Example 427 | 0.2 | 1.1 | 3 | HB | 1.1 |
| Example 428 | 0.3 | 1.1 | 3 | HB | 1.1 |
| Example 429 | 0.2 | 1.1 | 3 | HB | 1.1 |
| Example 430 | 0.3 | 1.1 | 3 | HB | 1.1 |
| Example 431 | 0.4 | 1.1 | 3 | HB | 1.1 |
| Example 432 | 0.2 | 1.1 | 3 | HB | 1.1 |
| Example 433 | 0.3 | 1.1 | 3 | HB | 1.1 |
| Example 434 | 0.4 | 1.1 | 3 | HB | 1.1 |
| Example 435 | 0.2 | 1.1 | 3 | HB | 1.1 |
| Example 436 | 0.3 | 1.1 | 3 | HB | 1.1 |

TABLE 45

| Film | Haze | Thickness uniformity | Non-uniform orientation | Surface hardness | Adhesiveness |
|---|---|---|---|---|---|
| Example 437 | 0.3 | 1.1 | 3 | HB | 1.1 |
| Example 438 | 0.2 | 1.1 | 3 | HB | 1.1 |
| Example 439 | 0.3 | 1.1 | 3 | HB | 1.1 |
| Example 440 | 0.4 | 1.1 | 3 | HB | 1.1 |
| Example 441 | 0.2 | 1.1 | 3 | HB | 1.1 |
| Example 442 | 0.3 | 1.1 | 3 | HB | 1.1 |
| Example 443 | 0.2 | 1.1 | 3 | HB | 1.1 |
| Example 444 | 0.3 | 1.1 | 3 | HB | 1.1 |
| Example 445 | 0.4 | 1.1 | 3 | HB | 1.1 |
| Example 446 | 0.2 | 1.1 | 3 | HB | 1.1 |
| Example 447 | 0.4 | 1.1 | 3 | HB | 1.1 |
| Example 448 | 0.2 | 1.1 | 3 | HB | 1.1 |
| Example 449 | 0.3 | 1.1 | 3 | HB | 1.1 |
| Example 450 | 0.3 | 1.1 | 3 | HB | 1.1 |
| Example 451 | 0.4 | 1.1 | 3 | HB | 1.1 |

TABLE 46

| Film | Haze | Thickness uniformity | Non-uniform orientation | Surface hardness | Adhesiveness |
|---|---|---|---|---|---|
| Example 452 | 0.2 | 1.1 | 3 | HB | 1.1 |
| Example 453 | 0.3 | 1.1 | 3 | HB | 1.1 |
| Example 454 | 0.4 | 1.1 | 3 | HB | 1.1 |

TABLE 47

| Film | Haze | Thickness uniformity | Nonuniform orientation | Surface hardness | Adhesiveness |
|---|---|---|---|---|---|
| Example 455 | 0.2 | 0.5 | 3 | HB | 1.1 |
| Example 456 | 0.2 | 0.5 | 3 | HB | 1.1 |
| Example 457 | 0.3 | 0.7 | 4 | HB | 1.3 |
| Example 458 | 0.4 | 0.6 | 5 | HB | 1.3 |
| Example 459 | 0.7 | 0.9 | 6 | HB | 1.8 |
| Example 460 | 0.3 | 0.6 | 4 | HB | 1.4 |
| Example 461 | 0.4 | 0.7 | 4 | HB | 1.4 |

TABLE 47-continued

| Film | Haze | Thickness uniformity | Nonuniform orientation | Surface hardness | Adhesiveness |
|---|---|---|---|---|---|
| Example 462 | 0.8 | 1.0 | 6 | HB | 1.9 |
| Example 463 | 0.9 | 0.8 | 6 | HB | 2.0 |
| Example 464 | 1.0 | 0.9 | 6 | HB | 1.8 |
| Example 465 | 0.8 | 0.9 | 6 | HB | 1.9 |
| Example 466 | 0.9 | 0.8 | 6 | HB | 2.0 |
| Example 467 | 0.8 | 0.9 | 6 | HB | 1.7 |
| Example 468 | 0.6 | 1.0 | 6 | HB | 1.8 |
| Example 469 | 0.7 | 1.0 | 6 | HB | 1.8 |

TABLE 48

| Film | Haze | Thickness uniformity | Nonuniform orientation | Surface hardness | Adhesiveness |
|---|---|---|---|---|---|
| Example 470 | 1.6 | 2.1 | 7 | B | 1.1 |
| Example 471 | 1.6 | 2.2 | 7 | B | 1.1 |
| Example 472 | 1.6 | 2.1 | 7 | B | 1.1 |
| Example 473 | 1.6 | 2.1 | 7 | B | 1.2 |
| Example 474 | 1.6 | 2.2 | 7 | B | 1.2 |
| Example 475 | 2.0 | 2.8 | 10 | B | 1.5 |
| Example 476 | 1.8 | 2.9 | 10 | B | 1.6 |
| Example 477 | 1.7 | 2.7 | 8 | B | 1.6 |
| Example 478 | 1.8 | 3.0 | 9 | B | 1.8 |
| Example 479 | 1.9 | 2.7 | 9 | B | 1.8 |
| Example 480 | 1.6 | 0.5 | 7 | B | 1.1 |
| Example 481 | 1.6 | 0.5 | 7 | B | 1.1 |
| Example 482 | 2.0 | 0.8 | 9 | B | 1.6 |
| Example 483 | 1.9 | 0.9 | 9 | B | 1.8 |
| Example 484 | 1.8 | 1.0 | 10 | B | 1.9 |

TABLE 49

| Film | Haze | Thickness uniformity | Nonuniform orientation | Surface hardness | Adhesiveness |
|---|---|---|---|---|---|
| Example 485 | 2.1 | 2.1 | 0 | F | 0.3 |
| Example 486 | 2.1 | 2.2 | 0 | F | 0.3 |
| Example 487 | 2.5 | 2.6 | 2 | F | 0.6 |
| Example 488 | 2.6 | 2.7 | 2 | F | 0.9 |
| Example 489 | 2.4 | 3.0 | 2 | F | 0.7 |
| Example 490 | 2.7 | 2.7 | 2 | F | 0.7 |
| Example 491 | 2.1 | 2.1 | 0 | F | 0.3 |
| Example 492 | 2.2 | 2.3 | 1 | F | 0.4 |
| Example 493 | 3.0 | 2.8 | 2 | F | 1.0 |
| Example 494 | 2.1 | 2.2 | 0 | F | 0.3 |
| Example 495 | 2.9 | 2.7 | 2 | F | 0.7 |
| Example 496 | 2.7 | 2.8 | 2 | F | 0.8 |
| Example 497 | 2.6 | 2.9 | 2 | F | 0.8 |
| Example 498 | 2.4 | 3.0 | 2 | F | 0.7 |
| Example 499 | 2.8 | 2.7 | 2 | F | 0.7 |
| Example 500 | 2.8 | 2.8 | 2 | F | 0.6 |

TABLE 50

| Film | Haze | Thickness uniformity | Nonuniform orientation | Surface hardness | Adhesiveness |
|---|---|---|---|---|---|
| Example 501 | 2.2 | 2.3 | 8 | F | 0.1 |
| Example 502 | 2.1 | 2.1 | 7 | F | 0 |
| Example 503 | 2.2 | 2.3 | 8 | F | 0.1 |
| Example 504 | 2.5 | 2.7 | 10 | F | 0.2 |
| Example 505 | 2.8 | 2.9 | 9 | F | 0.2 |
| Example 506 | 2.8 | 2.9 | 9 | F | 0.2 |
| Example 507 | 2.9 | 3.0 | 10 | F | 0.2 |
| Example 508 | 2.7 | 2.8 | 9 | F | 0.2 |
| Example 509 | 3.0 | 2.7 | 9 | F | 0.2 |
| Example 510 | 2.8 | 2.6 | 9 | F | 0.2 |
| Example 511 | 2.7 | 2.8 | 10 | F | 0.2 |
| Example 512 | 3.0 | 2.7 | 10 | F | 0.2 |
| Example 513 | 2.8 | 2.6 | 9 | F | 0.2 |

TABLE 50-continued

| Film | Haze | Thickness uniformity | Nonuniform orientation | Surface hardness | Adhesiveness |
|---|---|---|---|---|---|
| Example 514 | 1.6 | 1.1 | 7 | B | 0 |
| Example 515 | 1.9 | 2.0 | 9 | B | 0.2 |
| Example 516 | 1.8 | 1.9 | 8 | B | 0.2 |
| Example 517 | 2.0 | 1.7 | 9 | B | 0.2 |
| Example 518 | 1.8 | 1.8 | 10 | B | 0.2 |

TABLE 51

| Film | Haze | Thickness uniformity | Nonuniform orientation | Surface hardness | Adhesiveness |
|---|---|---|---|---|---|
| Example 519 | 0.2 | 0.5 | 7 | B | 1.1 |
| Example 520 | 0.2 | 0.5 | 7 | B | 1.1 |
| Example 521 | 1.2 | 0.9 | 10 | B | 1.6 |
| Example 522 | 0.9 | 1.0 | 9 | B | 1.7 |
| Example 523 | 0.2 | 0.5 | 7 | B | 1.1 |
| Example 524 | 0.2 | 0.5 | 7 | B | 1.1 |
| Example 525 | 0.8 | 1.0 | 9 | B | 1.7 |
| Example 526 | 1.0 | 0.9 | 10 | B | 1.5 |
| Example 527 | 0.2 | 0.5 | 7 | B | 1.1 |
| Example 528 | 0.7 | 0.9 | 9 | B | 1.8 |
| Example 529 | 1.0 | 0.8 | 9 | B | 1.8 |
| Example 530 | 0.4 | 0.6 | 8 | B | 1.2 |
| Example 531 | 1.1 | 0.8 | 10 | B | 1.7 |
| Example 532 | 0.8 | 0.9 | 10 | B | 2.0 |
| Example 533 | 1.1 | 1.0 | 10 | B | 1.9 |
| Example 534 | 1.2 | 0.7 | 9 | B | 1.9 |
| Example 535 | 0.8 | 0.8 | 8 | B | 1.8 |
| Example 536 | 0.9 | 0.7 | 8 | B | 1.8 |
| Example 537 | 1.5 | 0.8 | 8 | B | 1.9 |
| Example 538 | 1.4 | 0.9 | 9 | B | 1.8 |

TABLE 52

| Film | Haze | Thickness uniformity | Nonuniform orientation | Surface hardness | Adhesiveness |
|---|---|---|---|---|---|
| Example 539 | 2.1 | 0.5 | 7 | F | 0.3 |
| Example 540 | 2.1 | 0.5 | 7 | F | 0.3 |
| Example 541 | 2.5 | 1.0 | 9 | F | 0.9 |
| Example 542 | 2.4 | 0.8 | 10 | F | 0.7 |
| Example 543 | 2.5 | 0.9 | 9 | F | 0.8 |
| Example 544 | 2.7 | 0.8 | 9 | F | 0.5 |
| Example 545 | 2.6 | 0.8 | 9 | F | 0.8 |
| Example 546 | 2.7 | 0.7 | 9 | F | 0.9 |
| Example 547 | 2.5 | 0.8 | 9 | F | 1.0 |
| Example 548 | 2.8 | 0.9 | 10 | F | 0.9 |
| Example 549 | 2.8 | 0.9 | 10 | F | 0.8 |
| Example 550 | 2.9 | 1.0 | 10 | F | 0.7 |

TABLE 53

| Film | Haze | Thickness uniformity | Nonuniform orientation | Surface hardness | Adhesiveness |
|---|---|---|---|---|---|
| Example 551 | 2.1 | 2.1 | 7 | HB | 1.1 |
| Example 552 | 2.2 | 2.3 | 8 | HB | 1.3 |
| Example 553 | 2.2 | 2.3 | 8 | HB | 1.3 |
| Example 554 | 2.2 | 2.3 | 8 | HB | 1.2 |
| Example 555 | 2.5 | 3.0 | 9 | HB | 1.8 |
| Example 556 | 2.7 | 2.8 | 9 | HB | 1.9 |
| Example 557 | 2.6 | 2.9 | 9 | HB | 2.0 |
| Example 558 | 2.7 | 2.7 | 9 | HB | 1.8 |
| Example 559 | 2.5 | 2.6 | 9 | HB | 1.7 |
| Example 560 | 2.8 | 2.8 | 10 | HB | 1.8 |
| Example 561 | 2.8 | 2.7 | 10 | HB | 1.9 |
| Example 562 | 2.9 | 2.9 | 10 | HB | 2.0 |
| Example 563 | 2.8 | 2.8 | 10 | HB | 1.7 |
| Example 564 | 2.8 | 2.7 | 10 | HB | 1.7 |
| Example 565 | 2.9 | 2.9 | 10 | HB | 1.9 |

TABLE 53-continued

| Film | Haze | Thickness uniformity | Nonuniform orientation | Surface hardness | Adhesiveness |
|---|---|---|---|---|---|
| Example 566 | 2.8 | 2.8 | 10 | HB | 1.8 |
| Example 567 | 2.8 | 2.7 | 10 | HB | 1.9 |
| Example 568 | 2.9 | 2.9 | 10 | HB | 1.8 |
| Example 569 | 1.6 | 2.1 | 7 | F | 1.1 |
| Example 570 | 1.9 | 2.4 | 10 | F | 1.9 |
| Example 571 | 2.0 | 2.6 | 9 | F | 1.8 |
| Example 572 | 1.8 | 2.8 | 9 | F | 2.0 |
| Example 573 | 1.7 | 2.2 | 8 | F | 1.3 |

TABLE 54

| Film | Haze | Thickness uniformity | Nonuniform orientation | Surface hardness | Adhesiveness |
|---|---|---|---|---|---|
| Example 574 | 2.1 | 2.1 | 7 | B | 0 |
| Example 575 | 2.1 | 2.1 | 7 | B | 0 |
| Example 576 | 2.3 | 2.3 | 8 | B | 0.1 |
| Example 577 | 2.3 | 2.3 | 8 | B | 0.1 |
| Example 578 | 2.5 | 2.6 | 10 | B | 0.2 |
| Example 579 | 2.8 | 2.8 | 10 | B | 0.2 |
| Example 580 | 2.7 | 3.0 | 10 | B | 0.2 |
| Example 581 | 2.6 | 2.7 | 9 | B | 0.2 |
| Example 582 | 2.8 | 2.6 | 9 | B | 0.2 |
| Example 583 | 2.7 | 2.9 | 9 | B | 0.2 |

TABLE 55

| Film | Haze | Thickness uniformity | Nonuniform orientation | Surface hardness | Adhesiveness |
|---|---|---|---|---|---|
| Example 584 | 2.1 | 0.5 | 0 | B | 0.3 |
| Example 585 | 2.3 | 0.6 | 1 | B | 0.4 |
| Example 586 | 2.5 | 1.0 | 2 | B | 0.7 |
| Example 587 | 2.7 | 0.9 | 2 | B | 0.8 |
| Example 588 | 2.6 | 0.9 | 2 | B | 0.8 |
| Example 589 | 2.6 | 0.8 | 2 | B | 0.8 |
| Example 590 | 2.9 | 0.8 | 2 | B | 0.8 |
| Example 591 | 3.0 | 0.9 | 2 | B | 0.9 |
| Example 592 | 2.8 | 0.7 | 2 | B | 0.7 |
| Example 593 | 2.9 | 0.8 | 2 | B | 0.9 |

TABLE 56

| Film | Haze | Thickness uniformity | Nonuniform orientation | Surface hardness | Adhesiveness |
|---|---|---|---|---|---|
| Example 594 | 0.2 | 2.1 | 7 | B | 0 |
| Example 595 | 0.3 | 2.3 | 8 | B | 0.1 |
| Example 596 | 0.7 | 2.9 | 9 | B | 0.2 |
| Example 597 | 0.8 | 2.8 | 10 | B | 0.2 |
| Example 598 | 0.6 | 2.7 | 10 | B | 0.2 |
| Example 599 | 0.8 | 2.8 | 9 | B | 0.2 |
| Example 600 | 0.9 | 2.9 | 10 | B | 0.2 |
| Example 601 | 0.7 | 2.9 | 9 | B | 0.2 |
| Example 602 | 0.9 | 3.0 | 10 | B | 0.2 |
| Example 603 | 0.3 | 2.3 | 8 | B | 0.1 |

TABLE 57

| Film | Haze | Thickness uniformity | Nonuniform orientation | Surface hardness | Adhesiveness |
|---|---|---|---|---|---|
| Example 604 | 0.2 | 2.1 | 3 | F | 1.1 |
| Example 605 | 0.8 | 2.8 | 6 | F | 1.9 |
| Example 606 | 0.9 | 2.6 | 6 | F | 1.7 |
| Example 607 | 0.9 | 2.7 | 5 | F | 1.8 |
| Example 608 | 1.0 | 2.9 | 5 | F | 1.8 |
| Example 609 | 0.2 | 1.1 | 7 | B | 1.1 |

TABLE 57-continued

| Film | Haze | Thickness uniformity | Nonuniform orientation | Surface hardness | Adhesiveness |
|---|---|---|---|---|---|
| Example 610 | 0.4 | 1.3 | 8 | B | 1.3 |
| Example 611 | 0.9 | 1.9 | 10 | B | 1.9 |
| Example 612 | 1.2 | 1.8 | 9 | B | 1.9 |

The tables show that the films according to the present invention had a low haze, high thickness uniformity, low occurrence of nonuniform orientation, high surface hardness, and high adhesiveness.

The remaining 10 of the 20 films were then irradiated with 100 J of light at 50 mW/cm$^2$ and at 25° C. in a xenon lamp irradiation tester (Atlas Suntest XLS). The films were visually inspected for appearances, such as discoloration and detachment, and were microscopically inspected for orientation defects. The following tables show the results.

<Appearances>

In visual inspection of the 10 films, no discoloration and no detachment was rated A+. Slight discoloration but no detachment was rated A−. Slight discoloration and detachment in 0.2% or less of the whole was rated B+. Slight discoloration and 0.3% to 1.0% detachment was rated B−. Slight discoloration and 1.1% to 2.0% detachment was rated C+. Slight discoloration and 2.1% or more detachment was rated C−. Some strong discoloration was rated D.

<Orientation Defects>

The total number of orientation defects was measured by polarized light microscopy in each of the 10 films.

TABLE 58

| Film | Appearances | Orientation defects |
|---|---|---|
| Example 346 | A+ | 3 |
| Example 347 | A+ | 3 |
| Example 348 | A− | 5 |
| Example 349 | A− | 5 |
| Example 350 | A− | 5 |
| Example 351 | A− | 5 |
| Example 352 | A− | 4 |
| Example 353 | A− | 4 |
| Example 354 | A− | 5 |
| Example 355 | A− | 5 |
| Example 356 | A− | 5 |
| Example 357 | A− | 4 |
| Example 358 | A− | 5 |
| Example 359 | A− | 4 |
| Example 360 | A− | 5 |

TABLE 59

| Film | Appearances | Orientation defects |
|---|---|---|
| Example 361 | C+ | 0 |
| Example 362 | C+ | 0 |
| Example 363 | C+ | 0 |
| Example 364 | C+ | 0 |
| Example 365 | C+ | 1 |
| Example 366 | C− | 2 |
| Example 367 | C− | 2 |
| Example 368 | C− | 2 |
| Example 369 | C− | 2 |
| Example 370 | C− | 2 |
| Example 371 | C− | 2 |
| Example 372 | C− | 2 |
| Example 373 | C− | 2 |
| Example 374 | C− | 2 |
| Example 375 | C− | 2 |

TABLE 59-continued

| Film | Appearances | Orientation defects |
|---|---|---|
| Example 376 | C− | 2 |
| Example 377 | C− | 2 |
| Example 378 | C− | 2 |

TABLE 60

| Film | Appearances | Orientation defects |
|---|---|---|
| Example 379 | C+ | 3 |
| Example 380 | C+ | 3 |
| Example 381 | C+ | 3 |
| Example 382 | C+ | 4 |
| Example 383 | C− | 5 |
| Example 384 | C− | 5 |
| Example 385 | C− | 5 |
| Example 386 | C− | 5 |
| Example 387 | C− | 5 |
| Example 388 | C− | 5 |

TABLE 61

| Film | Appearances | Orientation defects |
|---|---|---|
| Example 389 | C+ | 0 |
| Example 390 | C+ | 0 |
| Example 391 | C+ | 0 |
| Example 392 | C− | 2 |
| Example 393 | C− | 2 |
| Example 394 | C+ | 0 |
| Example 395 | C− | 2 |
| Example 396 | C− | 2 |
| Example 397 | C− | 2 |
| Example 398 | C− | 2 |
| Example 399 | C− | 2 |
| Example 400 | C− | 2 |
| Example 401 | C− | 2 |
| Example 402 | C− | 2 |
| Example 403 | C− | 2 |

TABLE 62

| Film | Appearances | Orientation defects |
|---|---|---|
| Example 404 | C+ | 0 |
| Example 405 | C+ | 0 |
| Example 406 | C+ | 0 |
| Example 407 | C+ | 0 |
| Example 408 | C+ | 0 |
| Example 409 | C+ | 0 |
| Example 410 | C+ | 0 |
| Example 411 | C+ | 0 |
| Example 412 | C+ | 0 |
| Example 413 | C+ | 0 |
| Example 414 | C+ | 0 |
| Example 415 | C+ | 0 |
| Example 416 | C+ | 0 |
| Example 417 | C+ | 0 |
| Example 418 | C+ | 0 |
| Example 419 | C+ | 0 |
| Example 420 | C+ | 0 |
| Example 421 | C+ | 0 |
| Example 422 | C+ | 0 |
| Example 423 | C+ | 0 |

TABLE 63

| Film | Appearances | Orientation defects |
| --- | --- | --- |
| Example 424 | C+ | 0 |
| Example 425 | C+ | 0 |
| Example 426 | C+ | 0 |
| Example 427 | C+ | 0 |
| Example 428 | C+ | 0 |
| Example 429 | C+ | 0 |
| Example 430 | C+ | 0 |
| Example 431 | C+ | 0 |
| Example 432 | C+ | 0 |
| Example 433 | C+ | 0 |
| Example 434 | C+ | 0 |
| Example 435 | C+ | 0 |
| Example 436 | C+ | 0 |

TABLE 64

| Film | Appearances | Orientation defects |
| --- | --- | --- |
| Example 437 | C+ | 0 |
| Example 438 | C+ | 0 |
| Example 439 | C+ | 0 |
| Example 440 | C+ | 0 |
| Example 441 | C+ | 0 |
| Example 442 | C+ | 0 |
| Example 443 | C+ | 0 |
| Example 444 | C+ | 0 |
| Example 445 | C+ | 0 |
| Example 446 | C+ | 0 |
| Example 447 | C+ | 0 |
| Example 448 | C+ | 0 |
| Example 449 | C+ | 0 |
| Example 450 | C+ | 0 |
| Example 451 | C+ | 0 |

TABLE 65

| Film | Appearances | Orientation defects |
| --- | --- | --- |
| Example 452 | C+ | 0 |
| Example 453 | C+ | 0 |
| Example 454 | C+ | 0 |

TABLE 66

| Film | Appearances | Orientation defects |
| --- | --- | --- |
| Example 455 | C+ | 6 |
| Example 456 | C+ | 6 |
| Example 457 | C+ | 7 |
| Example 458 | C+ | 7 |
| Example 459 | C− | 9 |
| Example 460 | C+ | 7 |
| Example 461 | C+ | 7 |
| Example 462 | C− | 8 |
| Example 463 | C− | 8 |
| Example 464 | C− | 9 |
| Example 465 | C− | 9 |
| Example 466 | C− | 8 |
| Example 467 | C− | 10 |
| Example 468 | C− | 8 |
| Example 469 | C− | 9 |

TABLE 67

| Film | Appearances | Orientation defects |
| --- | --- | --- |
| Example 470 | A+ | 0 |
| Example 471 | A+ | 0 |
| Example 472 | A+ | 0 |

TABLE 67-continued

| Film | Appearances | Orientation defects |
| --- | --- | --- |
| Example 473 | A+ | 0 |
| Example 474 | A+ | 0 |
| Example 475 | A− | 2 |
| Example 476 | A− | 2 |
| Example 477 | A− | 2 |
| Example 478 | A− | 2 |
| Example 479 | A− | 2 |
| Example 480 | B+ | 0 |
| Example 481 | B+ | 0 |
| Example 482 | B− | 2 |
| Example 483 | B− | 2 |
| Example 484 | B− | 2 |

TABLE 68

| Film | Appearances | Orientation defects |
| --- | --- | --- |
| Example 485 | C+ | 6 |
| Example 486 | C+ | 6 |
| Example 487 | C− | 9 |
| Example 488 | C− | 10 |
| Example 489 | C− | 10 |
| Example 490 | C− | 9 |
| Example 491 | C+ | 6 |
| Example 492 | C+ | 7 |
| Example 493 | C− | 9 |
| Example 494 | C+ | 6 |
| Example 495 | C− | 9 |
| Example 496 | C− | 8 |
| Example 497 | C− | 8 |
| Example 498 | C− | 8 |
| Example 499 | C− | 9 |
| Example 500 | C− | 9 |

TABLE 69

| Film | Appearances | Orientation defects |
| --- | --- | --- |
| Example 501 | C+ | 7 |
| Example 502 | C+ | 6 |
| Example 503 | C+ | 7 |
| Example 504 | C− | 9 |
| Example 505 | C− | 8 |
| Example 506 | C− | 8 |
| Example 507 | C− | 8 |
| Example 508 | C− | 9 |
| Example 509 | C− | 7 |
| Example 510 | C− | 9 |
| Example 511 | C− | 8 |
| Example 512 | C− | 9 |
| Example 513 | C− | 8 |
| Example 514 | A+ | 6 |
| Example 515 | A− | 10 |
| Example 516 | A− | 9 |
| Example 517 | A− | 8 |
| Example 518 | A− | 9 |

TABLE 70

| Film | Appearances | Orientation defects |
| --- | --- | --- |
| Example 519 | B+ | 0 |
| Example 520 | B+ | 0 |
| Example 521 | B− | 2 |
| Example 522 | B− | 2 |
| Example 523 | B+ | 0 |
| Example 524 | B+ | 0 |
| Example 525 | B− | 2 |
| Example 526 | B− | 2 |
| Example 527 | B+ | 0 |
| Example 528 | B− | 2 |

TABLE 70-continued

| Film | Appearances | Orientation defects |
|---|---|---|
| Example 529 | B− | 2 |
| Example 530 | B+ | 1 |
| Example 531 | B− | 2 |
| Example 532 | B− | 2 |
| Example 533 | B− | 2 |
| Example 534 | B− | 2 |
| Example 535 | B− | 2 |
| Example 536 | B− | 2 |
| Example 537 | B− | 2 |
| Example 538 | B− | 2 |

TABLE 71

| Film | Appearances | Orientation defects |
|---|---|---|
| Example 539 | C+ | 6 |
| Example 540 | C+ | 6 |
| Example 541 | C− | 9 |
| Example 542 | C− | 10 |
| Example 543 | C− | 8 |
| Example 544 | C− | 8 |
| Example 545 | C− | 9 |
| Example 546 | C− | 9 |
| Example 547 | C− | 10 |
| Example 548 | C− | 9 |
| Example 549 | C− | 8 |
| Example 550 | C− | 9 |

TABLE 72

| Film | Appearances | Orientation defects |
|---|---|---|
| Example 551 | C+ | 0 |
| Example 552 | C+ | 1 |
| Example 553 | C+ | 1 |
| Example 554 | C+ | 1 |
| Example 555 | C− | 2 |
| Example 556 | C− | 2 |
| Example 557 | C− | 2 |
| Example 558 | C− | 2 |
| Example 559 | C− | 2 |
| Example 560 | C− | 2 |
| Example 561 | C− | 2 |
| Example 562 | C− | 2 |
| Example 563 | C− | 2 |
| Example 564 | C− | 2 |
| Example 565 | C− | 2 |
| Example 566 | C− | 2 |
| Example 567 | C− | 2 |
| Example 568 | C− | 2 |
| Example 569 | C+ | 0 |
| Example 570 | C− | 2 |
| Example 571 | C− | 2 |
| Example 572 | C− | 2 |
| Example 573 | C+ | 1 |

TABLE 73

| Film | Appearances | Orientation defects |
|---|---|---|
| Example 574 | A+ | 6 |
| Example 575 | A+ | 6 |
| Example 576 | A+ | 7 |
| Example 577 | A+ | 7 |
| Example 578 | A− | 9 |
| Example 579 | A− | 9 |
| Example 580 | A− | 10 |
| Example 581 | A− | 8 |
| Example 582 | A− | 8 |
| Example 583 | A− | 9 |

TABLE 74

| Film | Appearances | Orientation defects |
|---|---|---|
| Example 584 | C+ | 6 |
| Example 585 | C+ | 7 |
| Example 586 | C− | 9 |
| Example 587 | C− | 9 |
| Example 588 | C− | 10 |
| Example 589 | C− | 8 |
| Example 590 | C− | 9 |
| Example 591 | C− | 10 |
| Example 592 | C− | 8 |
| Example 593 | C− | 9 |

TABLE 75

| Film | Appearances | Orientation defects |
|---|---|---|
| Example 594 | B+ | 6 |
| Example 595 | B+ | 7 |
| Example 596 | B− | 9 |
| Example 597 | B− | 9 |
| Example 598 | B− | 10 |
| Example 599 | B− | 8 |
| Example 600 | B− | 9 |
| Example 601 | B− | 10 |
| Example 602 | B− | 8 |
| Example 603 | B+ | 7 |

TABLE 76

| Film | Appearances | Orientation defects |
|---|---|---|
| Example 604 | C+ | 6 |
| Example 605 | C− | 8 |
| Example 606 | C− | 9 |
| Example 607 | C− | 9 |
| Example 608 | C− | 10 |
| Example 609 | A+ | 0 |
| Example 610 | A+ | 1 |
| Example 611 | A− | 2 |
| Example 612 | A− | 2 |

The tables show that the compounds according to the present invention provide good appearances and fewer orientation defects after photoirradiation.

These results show that a compound according to the present invention in a polymerizable composition has high storage stability, and an optically anisotropic body produced from a composition containing a compound according to the present invention has low haze, high thickness uniformity, low occurrence of nonuniform orientation, high surface hardness, high adhesiveness, and good appearances and fewer orientation defects even after ultraviolet irradiation. Thus, a compound according to the present invention is useful as a constituent of a polymerizable composition. An optically anisotropic body produced from a polymerizable liquid crystal composition containing a compound according to the present invention is useful in applications such as optical films.

The invention claimed is:
1. A reverse dispersion compound represented by formula (I-z2-A-1),

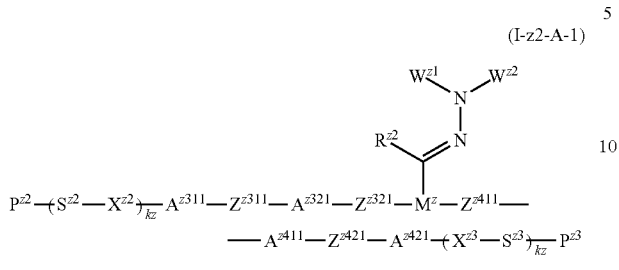

(I-z2-A-1)

wherein $M^z$ denotes a group selected from the following formulae (M-z-1) to (M-z-2)

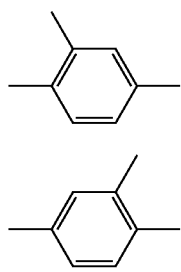

(M-z-1)

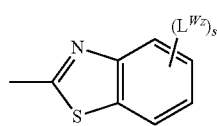

(M-z-2)

$R^{z2}$ denotes a hydrogen atom,
$W^{z1}$ denotes the following formula (W-a-5), (W-a-5)

in the formula (W-a-5), s is an integer in the range of 0 to 4,
$L^{Wz}$ denotes a fluorine atom, a chlorine atom, a bromine atom, an iodine atom, a pentafluorosulfuranyl group, a nitro group, a cyano group, an isocyano group, an amino group, a hydroxy group, a mercapto group, a methylamino group, a dimethylamino group, a diethylamino group, a diisopropylamino group, a trimethylsilyl group, a dimethylsilyl group, a thioisocyano group, a linear alkyl group having 1 to 20 carbon atoms with one —CH$_2$— or nonadjacent two or more —CH$_2$—'s optionally independently substituted by —O—, —S—, —CO—, —COO—, —OCO—, —CO—S—, —S—CO—, —O—CO—O—, —CO—NH—, or —NH—CO—, or a branched alkyl group having 3 to 20 carbon atoms with one —CH$_2$— or nonadjacent two or more —CH$_2$—'s optionally independently substituted by —O—, —S—, —CO—, —COO—, —OCO—, —CO—S—, —S—CO—, —O—CO—O—, —CO—NH—, or —NH—CO—, and any hydrogen atom of the alkyl group may be substituted by a fluorine atom, and a plurality of $L^{Wz}$'s, if present at all, may be the same or different,
$W^{z21}$ denotes a group selected from a linear alkyl group having 1 to 20 carbon atoms with one —CH$_2$— or nonadjacent two or more —CH$_2$—'s optionally independently substituted by —O—, or a branched alkyl group having 3 to 20 carbon atoms with one —CH$_2$— or nonadjacent two or more —CH$_2$—'s optionally independently substituted by —O—,
$P^{z2}$ and $P^{z3}$ independently denote a group selected from the formulae (P-1) to (P-20),

(P-1)

(P-2)

(P-3)

(P-4)

(P-5)

(P-6)

(P-7)

(P-8)

(P-9)

(P-10)

(P-11)

(P-12)

(P-13)

-continued

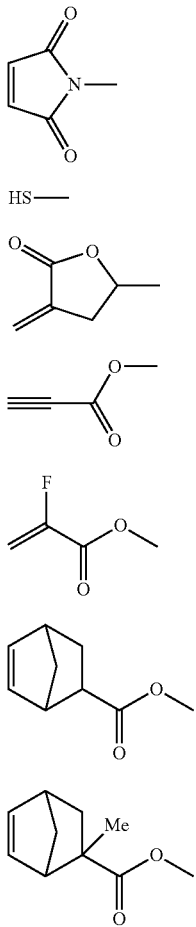

(P-14)
(P-15)
(P-16)
(P-17)
(P-18)
(P-19)
(P-20)

$S^{z2}$ and $S^{z3}$ independently denote an alkylene group having 1 to 20 carbon atoms with one —$CH_2$— or nonadjacent two or more —$CH_2$—'s optionally independently substituted by —O—, —COO—, —OCO—, —OCO—O—, —CO—NH—, —NH—CO—, —CH=CH—, or —C≡C—, if present at all, may be the same or different, $X^{z2}$ and $X^{z3}$ independently denote —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH— OCO—, —COO—CH=CH—, —OCO— CH=CH—, —COO—$CH_2CH_2$—, —OCO— $CH_2CH_2$—, —$CH_2CH_2$—COO—, —$CH_2CH_2$— OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C—, or a single bond, a plurality of X's, if present at all, may be the same or different, provided that $P^{z2}$-($S^{z2}$-$X^{z2}$)$_{kz}$- and $P^{z3}$-($S^{z3}$-$X^{z3}$)$_{kz}$- have no —O—O— bond, $A^{z311}$ and $A^{z421}$ independently denote a 1,4-phenylene group, the group may be unsubstituted or substituted by one or more substituents $L^{z11}$'s, $L^{z11}$ denotes a fluorine atom, a chlorine atom, a linear alkyl group having 1 to 20 carbon atoms with one —$CH_2$— or nonadjacent two or more —$CH_2$—'s optionally independently substituted by —O—, —CO—, —COO—, or —OCO—, any hydrogen atom of the alkyl group may be substituted by a fluorine atom, or a branched alkyl group having 3 to 20 carbon atoms with one —$CH_2$— or nonadjacent two or more —$CH_2$—'s optionally independently substituted by —O—, —CO—, —COO—, or —OCO—, any hydrogen atom of the alkyl group may be substituted by a fluorine atom, $A^{z321}$ and $A^{z411}$ denote a 1,4-cyclohexylene group, $Z^{z311}$ and $Z^{z421}$ independently denote —$OCH_2$—, —$CH_2O$—, —COO—, or —OCO—, $Z^{z321}$ and $Z^{z411}$ independently denote —$OCH_2$— or —$CH_2O$—, kz is an integer in the range of 0 to 8.

2. The compound according to claim 1, wherein $P^{z2}$ and $P^{z3}$ in the formula (I-z2-A-1) independently denote a group selected from the formulae (P-1) to (P-2).

3. The compound according to claim 1, wherein $S^{z2}$ and $S^{z3}$ in the formula (I-z2-A-1) independently denotes an alkylene group having 1 to 20 carbon atoms with one —$CH_2$— or nonadjacent two or more —$CH_2$—'s optionally independently substituted by —O—.

4. A composition comprising the compound according to claim 1.

5. A liquid crystal composition comprising the compound according to claim 1.

6. A method for producing a polymer, the method comprising:
providing the composition according to claim 4; and polymerizing the composition.

7. A method for producing an optically anisotropic body, the method comprising:
providing the composition according to claim 4;
polymerizing the composition.

* * * * *